(12) United States Patent
Iavarone et al.

(10) Patent No.: US 12,006,503 B2
(45) Date of Patent: Jun. 11, 2024

(54) FUSION PROTEINS AND METHODS THEREOF

(71) Applicant: The Trustees of Columbia University in the City of New York, New York, NY (US)

(72) Inventors: Antonio Iavarone, New York, NY (US); Anna Lasorella, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 782 days.

(21) Appl. No.: 16/899,312

(22) Filed: Jun. 11, 2020

(65) Prior Publication Data
US 2020/0300860 A1 Sep. 24, 2020

Related U.S. Application Data

(60) Continuation of application No. 16/508,021, filed on Jul. 10, 2019, which is a division of application No. 14/604,530, filed on Jan. 23, 2015, now abandoned, which is a continuation-in-part of application No. PCT/US2013/051888, filed on Jul. 24, 2013.

(60) Provisional application No. 62/096,311, filed on Dec. 23, 2014, provisional application No. 61/675,006, filed on Jul. 24, 2012.

(51) Int. Cl.
| | |
|---|---|
| *G01N 33/53* | (2006.01) |
| *C07K 14/47* | (2006.01) |
| *C07K 14/71* | (2006.01) |
| *C07K 14/82* | (2006.01) |
| *C07K 16/18* | (2006.01) |
| *C07K 16/28* | (2006.01) |
| *C12N 9/12* | (2006.01) |
| *C12N 15/62* | (2006.01) |
| *C12Q 1/6886* | (2018.01) |
| *G01N 33/574* | (2006.01) |

(52) U.S. Cl.
CPC ............. *C12N 15/62* (2013.01); *C07K 14/47* (2013.01); *C07K 14/71* (2013.01); *C07K 14/82* (2013.01); *C07K 16/18* (2013.01); *C07K 16/2863* (2013.01); *C12N 9/12* (2013.01); *C12Q 1/6886* (2013.01); *G01N 33/57492* (2013.01); *C07K 2319/00* (2013.01); *C07K 2319/73* (2013.01); *C12Q 2600/158* (2013.01); *G01N 2333/91205* (2013.01)

(58) Field of Classification Search
None
See application file for complete search history.

(56) References Cited

U.S. PATENT DOCUMENTS

| | | |
|---|---|---|
| 5,783,683 A | 7/1998 | Morrison |
| 6,844,168 B1 | 1/2005 | Keifer et al. |
| 8,399,442 B2 | 3/2013 | Berdini et al. |
| 8,895,745 B2 | 11/2014 | Berdini et al. |
| 9,481,911 B2 | 11/2016 | Suzuki et al. |
| 2006/0275794 A1 | 12/2006 | Carrino et al. |
| 2007/0039076 A1 | 2/2007 | Boukharov et al. |
| 2007/0059711 A1 | 3/2007 | Slominski et al. |
| 2008/0312248 A1 | 12/2008 | Bold et al. |
| 2011/0053787 A1 | 3/2011 | Brulliard et al. |
| 2011/0105337 A1 | 5/2011 | Krizman |
| 2011/0195848 A1 | 8/2011 | Roopra et al. |
| 2011/0287974 A1 | 11/2011 | Benvenisty et al. |
| 2016/0108380 A1 | 4/2016 | Iavarone et al. |
| 2020/0033353 A1 | 1/2020 | Iavarone et al. |
| 2020/0174003 A1 | 6/2020 | Iavarone et al. |
| 2020/0300860 A1 | 9/2020 | Iavarone et al. |

FOREIGN PATENT DOCUMENTS

| | | |
|---|---|---|
| CN | 104379740 A | 2/2015 |
| EP | 2824181 | 1/2015 |
| JP | 2012-052147 A | 3/2012 |
| WO | WO-1999035159 A1 | 7/1999 |
| WO | WO-2008070179 A2 | 6/2008 |
| WO | WO-2008075068 A2 | 6/2008 |
| WO | WO-2008/077165 | 7/2008 |
| WO | WO-2008/149521 A1 | 12/2008 |
| WO | WO-2010/111367 A1 | 9/2010 |
| WO | WO-2010129509 A1 | 11/2010 |
| WO | WO-2011111367 A1 | 9/2011 |
| WO | WO-2013129369 A1 | 9/2013 |
| WO | WO-2013133351 A1 | 9/2013 |
| WO | WO-2014017797 A1 | 1/2014 |
| WO | WO-2014018673 A2 | 1/2014 |
| WO | WO-2014113729 | 7/2014 |
| WO | WO-2014/130890 A1 | 8/2014 |
| WO | WO-2014151734 A1 | 9/2014 |
| WO | WO-2016105517 A1 | 6/2016 |

OTHER PUBLICATIONS

Dienstmann, R. et al., "Genomic aberrations in the FGFR pathway: opportunities for targeted therapies in solid tumors", Annals of Oncology, 25:552-563, 2014, published online Nov. 20, 2013 (12 pages).
European Partial Search Report issued in European Patent Application 20197862.4, dated Jan. 29, 2021 (17 pages).
Ablain, J., et al., "The Drug-Induced Degradation of Oncoproteins: An Unexpected Achilles' Heel of Cancer Cells?" Cancer Discov., vol. 1, No. 2, pp. 117-127 (2011).
Bahleda, R., et al., "Phase 1 study of JNJ-42756493, a pan-fibroblast growth factor receptor (FGFR) inhibitor, in patients with advanced solid tumors," J. Clin. Oncol., vol. 32, Supp., Abstr., 2501, 4 pages (2014).

(Continued)

*Primary Examiner* — Michael D Pak
(74) *Attorney, Agent, or Firm* — Wilmer Cutler Pickering Hale and Dorr LLP

(57) ABSTRACT

The invention discloses oncogenic fusion proteins. The invention provides methods for treating gene-fusion based cancers.

24 Claims, 108 Drawing Sheets
(44 of 108 Drawing Sheet(s) Filed in Color)
Specification includes a Sequence Listing.

(56) References Cited

OTHER PUBLICATIONS

Bass, A. I., et al., "Genomic sequencing of colorectal adenocarcinomas identifies a recurrent VTI1A-TCF7L2 fusion," Nat. Genet., vol. 43, No. 10, pp. 964-968 (2011).
Borad, MJ, et al., "Integrated Genomic Characterization Reveals Novel, Therapeutically Relevant Drug Targets in FGFR and EGFR Pathways in Sporadic Intrahepatic Cholangiocarcinoma," PLoS Genetics, vol. 10, No. 2, e1004135 (2014).
Brennan, C. W., et al., "The somatic genomic landscape of glioblastoma," Cell, vol. 155, pp. 462-477 (2013).
Bulusu, K. C., et al., "canSAR: updated cancer research and drug discovery knowledgebase," Nucleic Acids Res., vol. 42, pp. D1040-D1047 (2014).
Cahill, D. P., et al., "Genetic instability and darwinian selection in tumours," Trends Cell. Biol., vol. 9, pp. M57-M60 (1999).
Capelletti, M., et al., "Identification of Recurrent FGFR3-TACC3 Fusion Oncogenes from Lung Adenocarcinoma," Clin. Cancer Res., vol. 20, No. 24, pp. 6551-6558 (2014).
Carro, M. S., et al., "The transcriptional network for mesenchymal transformation of brain tumours," Nature, vol. 463, No. 7279, pp. 318-325, 23 pages (2010).
Cohen et al., "IDH1 and IDH2 Mutations in Gliomas," Author Manuscript, published in final edited form as: Current Neurology and Neuroscience Reports, vol. 13, No. 5, 13 pages (2013).
Coschi, C. H., and Dick, F. A., "Chromosome instability and deregulated proliferation: an unavoidable duo," Cell. Mol. Life Sci., vol. 69, pp. 2009-2024 (2012).
Di Stefano, A. L. et al., "Detection, characterization and inhibition of FGFRTACC fusions in IDH wild type glioma," Clin. Cancer Res., vol. 21, No. 14, pp. 3307-3317 (2015).
Druker, Brian J., "Perspectives on the development of imatinib and the future of cancer research," Nature Medicine, vol. 15, pp. 1149-1152 (2009).
Ene, C. I. and Fine, H. A., "Many tumors in one: a daunting therapeutic prospect," Cancer Cell, vol. 20, pp. 695-697 (2011).
Extended European Search Report for European Patent Application No. 13823252.5 dated Jan. 13, 2016 (7 pages).
Extended European Search Report dated Oct. 25, 2018 for European Patent Application No. 15873797.3 (23 pages).
Frampton et al., "Development and validation of a clinical cancer genomic profiling test based on massively parallel DNA sequencing," Nature Biotechnology, 31(11), 38 pages (2013).
Furnari, F. B., et al., "Malignant astrocytic glioma: genetics, biology, and paths to treatment," Genes Development, vol. 21, pp. 2683-2710 (2007).
Gavine, P. R., et al., "AZD4547: An Orally Bioavailable, Potent, and Selective Inhibitor of the Fibroblast Growth Factor Receptor Tyrosine Kinase Family," Cancer Research, vol. 72, pp. 2045-2056 (2012).
GenBank Accession No. AF095791 "*Homo sapiens* TACC2 protein (TACC2) mRNA, complete cds," accessed Dec. 21, 2016 <http://wwwncbi.nlm.nih.gov/nuccore/af095791> (2 pages).
GenBank Accession No. AF049910, "*Homo sapiens* TACC1 (TACC1) mRNA, complete CDS," accessed Dec. 21, 2016 <http://wwwncbi.nlm.nih.gov/nuccore/af049910> (3 pages).
GenBank Accession No. AF093543, "*Homo sapiens* transforming acidic coiled-coil containing protein 3 (TACC3) mRNA, complete CDS," accessed Dec. 21, 2016 <http://wwwncbi.nlm.nih.gov/nuccore/af093543>(2 pages).
Gerber, D. E., and Minna, J. D., "ALK inhibition for non-small cell lung cancer: from discovery to therapy in record time," Cancer Cell, vol. 18, pp. 548-551 (2010).
Gergely, F., et al., The TACC domain identifies a family of centrosomal proteins that can interact with microtubules. Proc. Natl. Acad. Sci. USA 97, 14352-14357 (2000).
Goldman M., et al., "The UCSC Cancer Genomics Browser: update 2013," Nucleic Acids Research, vol. 41, pp. D949-D954 (2013).
Gonzalez-Aguilar, A., et al., "Recurrent mutations of MYD88 and TBLIXRI in primary central nervous system lymphomas," Clinical Cancer Research, vol. 18, pp. 5203-5211 (2012).
Gordon, D. J., et al., "Causes and consequences of aneuploidy in cancer," Nature Reviews Genetics, vol. 13, pp. 189-203 (2012).
Greulich and Pollock, "Targeting mutant fibroblast growth factor receptors in cancer," Trends in Molecular Medicine 17(5), pp. 283-292 (2011).
Guagnano, V., et al., "Discovery of 3-(2,6-dichloro-3,5-dimethoxyphenyl)-1-{ 6-[ 4-( 4-ethyl-piperazin-1-yl)-phenylamin o ]-pyrimidin-4-yl }-1-methyl-urea (NVP-BGJ398), a potent and selective inhibitor of the fibroblast growth factor receptor family of receptor tyrosine kinase," J. Med. Chem., vol. 54, pp. 7066-7083 (2011).
Guasch et al., "Bp12 Stem Cell Myeloproliferative Disorder: the FOP-Fibroblast Growth Factor Receptor 1 Fusion Protein of the t(6;8) Translocation Induces Cell Survival Mediated by Mitogen-Activated Protein Kinase and Phosphatidylinositol 3-Kinase/Akt/mTOR Pathways", Mol. Cell. Biol. vol. 21, No. 23, pp. B129-B142 (2001).
Hoang-Xuan, K., et al., "Molecular heterogeneity of oligodendrogliomas suggests alternative pathways in tumor progression," Neurology, vol. 57, pp. 1278-1281 (2001).
Holland, A. I. and Cleveland, D. W., "Boveri revisited: chromosomal instability, aneuploidy and tumorigenesis," Nat. Rev. Mol. Cell. Biol., vol. 10, No. 7, pp. 478-487 (2009).
Hood, F. E. and Royle, S. J., "Pulling it together: The mitotic function of TACC3," Bioarchitecture, vol. 1, pp. 105-109 (2011).
Houillier, C., et al., "Prognostic impact of molecular markers in a series of 220 primary glioblastomas," Cancer, vol. 106, pp. 2218-2223 (2006).
Idbaih, A., et al., "BAC array CGH distinguishes mutually exclusive alterations that define clinicogenetic subtypes of gliomas," International Journal of Cancer, vol. 122, No. 8, pp. 1778-1786 (2008).
Idbaih, A., et al., "Epidermal growth factor receptor extracellular domain mutations in primary glioblastoma," Neuropathology and Applied Neurobiology, vol. 35, No. 2, pp. 208-213, 11 pages (2009).
Iglewicz, B. and Hoaglin, D. C., "How to detect and handle outliers," The ASQC Basic References in Quality Control: Statistical Techniques, 4 pages—Cover Page, Copyright Page and Table of Contents Only (1993).
Inda, M. M., et al., "Tumor heterogeneity is an active process maintained by a mutant EGFR-induced cytokine circuit in glioblastoma," Genes Dev., vol. 24, No. 16, pp. 1731-1745, 11 pages (2010).
International Search Report for International Patent Application No. PCT/US2013/051888 dated Feb. 28, 2014 (7 pages).
International Search Report for International Patent Application No. PCT/US2015/000270 dated May 13, 2016 (6 pages).
J0754258, GenBank Accession No. J0754258, TSA: Lingulodinium polyedrum Locus_74488_Transcript_ 1/1.Lipo mRNA sequence, Apr. 25, 2012 [online]. [Retrieved on Feb. 3, 2014]. Retrieved from the internet: <www.ncbi.nlm.nih.gov/nuccore/J0754258>.
Javle et al., "Molecular characterization of gallbladder cancer using somatic mutation profiling," Human Pathology, 45, pp. 701-708 (2014).
Johnson, D. E. and Williams, E. T., "Structural and functional diversity in the FGF receptor multigene family," Adv. Cancer Res., vol. 60, pp. 1-41 (1993).
Zheng et al., "A survey of intragenic breakpoints in glioblastoma identifies a distinct subset associated with poor survival," Genes & Development, 27, pp. 1462-1472 (2013).
Katoh et al., Recombination cluster around FGFR2-WDR11-HTPAPL locus on human chromosome 10q26, International Journal of Molecular Medicine, vol. 11, pp. 579-583 (2003).
Keats et al., "In multiple myeloma, t(4;14)(p16;q32) is an adverse prognostic factor irrespective of FGFR3 expression", Blood, vol. 101, No. 4, pp. 1520-1529 (2003).
Kindich, R., et al., "Application of a modified real-time PCR technique for relative gene copy number quantification to the determination of the relationship between NKX3 .1 loss and MYC gain in prostate cancer," Clin. Chem., vol. 51, No. 3, pp. 649-652 (2005).
Krejci, P., et al., "NF449 Is a Novel Inhibitor of Fibroblast Growth Factor Receptor 3 (FGFR3) Signaling Active in Chondrocytes and Multiple Myeloma Cells," Journal of Biological Chemistry, vol. 285, No. 27, pp. 20644-20653 (2010).

(56) References Cited

OTHER PUBLICATIONS

La Rosa et al., "Immunohistochemical detection of fibroblast growth factor receptors in normal endocrine cells and related tumors of the digestive system," Applied Immunohistochemistry & Molecular Morphology, vol. 9, No. 4, pp. 319-328 (2001).
Labussiere, M., et al., "Combined analysis of TERT, EGFR and IDH status define distinct prognostic glioblastoma classes," Neurology, vol. 83, pp. 1200-1206 (2014).
Lauffart et al., "Molecular cloning, genomic structure and interactions of the putative breast tumor suppressor TACC2," Genomics, vol. B1, No. 2, pp. 192-201 (2003).
Law, M., et al., "Comparison of cerebral blood volume and vascular permeability from dynamic susceptibility contrast-enhanced perfusion MR imaging with glioma grade," AJNR Am. J. Neuroradiol., vol. 25, pp. 746-755 (2004).
Lee, J., et al., "Tumor stem cells derived from glioblastomas cultured in bFGF and EGF more closely mirror the phenotype and genotype of primary tumors than do serum-cultured cell lines," Cancer Cell, vol. 9, pp. 391-403 (2006).
Lengauer, C., et al., "Genetic instabilities in human cancers," Nature, vol. 396, No. 6712, pp. 643-649 (1998).
Lengauer, C., et al., "Genetic instability in colorectal cancers," Nature, vol. 386, No. 6625, pp. 623-627 (1997).
Li, H. and Durbin, R., "Fast and accurate short read alignment with Burrows-Wheeler transform," Bioinformatics, vol. 25, No. 14, pp. 1754-1760 (2009).
Lo, Hui-Wen, "EGFR-targeted therapy in malignant glioma: novel aspects and mechanisms of drug resistance," Curr. Mol. Pharmacol., vol. 3, No. 1, pp. 37-52, 28 pages (2010).
Majewski, I. J., et al., "Identification of recurrent FGFR3 fusion genes in lung cancer through kinome-centred RNA sequencing," J. Pathol., vol. 230, pp. 270-276 (2013).
Marumoto, T., et al., "Development of a novel mouse glioma model using lentiviral vectors," Nat. Med., vol. 15, No. 1, pp. 110-116 (2009).
Mayer, R. J. and Walker, J. H., "Immunochemical Methods In Cell and Molecular Biology," Academic Press, London, 9 pages—Cover Page, Copyright Page, Table of Contents Only (1987).
Medves, S. and Demoulin, J. B., "Tyrosine kinase gene fusions in cancer: translating mechanisms into targeted therapies," J. Cell Mol. Med., vol. 16, pp. 237-248 (2012).
Mitelman, F., et al., "The impact of translocations and gene fusions on cancer causation," Nat. Rev. Cancer, vol. 7, pp. 233-245 (2007).
Mohammadi, M., et al., "Crystal structure of an angiogenesis inhibitor bound to the FGF receptor tyrosine kinase domain," EMBO J., vol. 17, pp. 5896-5904 (1998).
Morganella, S., et al., "VEGA: variational segmentation for copy number detection," Bioinformatics, vol. 26, pp. 3020-3027 (2010).
Morrison, R., et al., "Growth Factor Receptor Gene Expression and Immunoreactivity are Elevated in Human Glioblastoma Multiforme," Cancer Research vol. 54, Issue 10, 2794-2799 (1994).
Ohgaki, H. and Kleihues, P., "Population-based studies on incidence, survival rates, and genetic alterations in astrocytic and ligodendroglial gliomas," J. Neuropathol. Exp. Neurol., vol. 64, pp. 479-489 (2010).
Olshen, A. B., et al., "Circular binary segmentation for the analysis of array-based DNA copy number data," Biostatistics, vol. 5, pp. 557-572 (2004).
Omuro A. and DeAngelis L. M., "Glioblastoma and other malignant gliomas: a clinical review," JAMA, vol. 310, No. 17, pp. 1842-1850 (2013).
Parker, B. C., et al., "The tumorigenic FGFR3-TACC3 gene fusion escapes miR-99a regulation in glioblastoma," J. Clin. Invest., vol. 123, pp. 855-865 (2013).
Peset, I. and Vernos, I., "The TACC proteins: TACC-ling microtubule dynamics and centrosome function," Trends Cell. Biol., vol. 18, pp. 379-388 (2008).
Prensner, J.R. and Chinnaiyan, A.M., "Oncogenic gene fusions in epithelial carcinomas," Curr. Opin. Genet. Dev., vol. 19, pp. 82-91 (2009).

Quillien, V., et al., "Comparative assessment of 5 methods (methylation-specific polymerase chain reaction, MethyLight, pyrosequencing, methylation-sensitive high-resolution melting, and immunohistochemistry) to analyze 06-methylguanine-DNA-methyltranferase in a series of 100 glioblastoma patients," Cancer, vol. 118, pp. 4201-4211 (2012).
Reardon, D. A., et al., "Phase 2 trial of erlotinib plus sirolimus in adults with recurrent glioblastoma," J. Neurooncol., vol. 96, pp. 219-230 (2010).
Reiter et al., "Consistent Fusion of ZNF198 to the Fibroblast Growth Factor Receptor-1 in the t(8;13)(p11;q12) Myeloproliferative Syndrome," Blood, vol. 92, No. 5, pp. 1735-1742 (1998).
Reyes-Botero, G., et al., "Molecular analysis of diffuse intrinsic brainstem gliomas in adults," J. Neurooncol., vol. 116, pp. 405-411 (2014).
Ross et al., "New Routes to Targeted Therapy of Intrahepatic Cholangiocarcinomas Revealed by Next-Generation Sequencing," The Oncologist, 19, pp. 235-242 (2014).
Salah et al. "Neurologic Manifestations of Glioblastoma Multiforme, Medscape," (<http://emedicine.medscape.com/article/1156220-overview>) Updated: Nov. 9, 2015 (4 pages).
Sanson, M., et al., "Isocitrate dehydrogenase 1 codon 132 mutation is an important prognostic biomarker in gliomas," J. Clin. Oncol., vol. 27, pp. 4150-4154 (2009).
Seal, R. L., et al., "genenames.org: the HGNC resources in 2011," Nucleic Acids Res., vol. 39, pp. D514-D519 (2011).
Shah, N, et al., "Exploration of the Gene Fusion Landscape of .Glioblastoma Using Transcriptome Sequencing and Copy Number Data," BMC Genomics, vol. 14, 15 pages (2013).
Sheltzer, J.M. and Amon, A., "The aneuploidy paradox: costs and benefits of an incorrect karyotype," Trends Genet., vol. 27, pp. 446-453 (2011).
Singh, D., et al., "Transforming fusions of FGFR and TACC genes in human glioblastoma," Science, vol. 337, pp. 1231-1235 (2012).
Snuderl, M., et al., "Mosaic amplification of multiple receptor tyrosine kinase genes in glioblastoma," Cancer Cell, vol. 20, pp. 810-817 (2011).
Solomon, D.A., Kim, T., Diaz-Martinez, L.A., Fair, J., Elkahloun, A.G., Harris, B.T., Toretsky, I.A., Rosenberg, S.A., Shukla, N., Ladanyi, M., et al. (2011). Mutational inactivation of STAG2 causes aneuploidy in human cancer. Science 333, 1039-1043.
Somaiah et al., "Molecular Targeted Agents and Biologic Therapies for Lung Cancer," Journal of Thoracic Oncology 6(11), Supplement 4, pp. S1758-S1785 (2011).
Sottoriva, A., et al., "Intratumor heterogeneity in human glioblastoma reflects cancer evolutionary dynamics," Proc. Natl. Acad. Sci. USA, vol. 110, pp. 4009-4014 (2013).
Squires, M., et al., "Potent, selective inhibitors of fibroblast growth factor receptor define fibroblast growth factor dependence in preclinical cancer models," Mol. Cancer Ther., vol. 10, pp. 1542-1552 (2011).
Stephens, P. J., et al., "Complex landscapes of somatic rearrangement in human breast cancer genomes," Nature, vol. 462, pp. 1005-1010 (2009).
Still, I. H., et al., "The third member of the transforming acidic coiled coil-containing gene family, TACC3, maps in 4p16, close to translocation breakpoints in multiple myeloma, and is upregulated in various cancer cell lines," Genomics, vol. 58, pp. 165-170 (1999).
Stransky, N., et al., "The landscape of kinase fusions in cancer," Nat. Commun., vol. 5, 10 pages (2014).
Stupp, R., et al., "Radiotherapy plus concomitant and adjuvant temozolomide for glioblastoma," N. Engl. J. Med., vol. 352, pp. 987-996 (2005).
Supplementary Partial European Search Report dated Jun. 18, 2018 for European Patent Application No. 15873797.3 (21 pages).
The Cancer Genome Atlas Research Network, "Comprehensive genomic characterization defines human glioblastoma genes and core pathways," Nature, vol. 455, pp. 1061-1068 (2008).
Thompson et al., "A Gene Encoding a Fibroblast Growth Factor Receptor Isolated from the Huntington Disease Gene Region of Human Chromosome 4," Genomics, 11, pp. 1133-1142 (1991).
Thompson et al., "Human novel growth factor receptor mRNA, 3' cds," GenBank Accession No. M64347.1, 2 pages (1994).

(56) References Cited

OTHER PUBLICATIONS

Thompson, S. L., et al., "Mechanisms of chromosomal instability," Curr. Biol., vol. 20, pp. R285-R295 (2010).
Tomlins, S. A., et al., "Distinct classes of chromosomal rearrangements create oncogenic ETS gene fusions in prostate cancer," Nature, vol. 448, pp. 595-599 (2007).
Tomlins, S. A., et al., "Recurrent fusion of TMPRSS2 and ETS transcription factor genes in prostate cancer," Science, vol. 310, pp. 644-648 (2005).
Turner, N., and Grose, R., "Fibroblast growth factor signalling: from development to cancer," Nat. Rev. Cancer, vol. 10, pp. 116-129 (2010).
Van den Bent, M. J., et al., "Randomized phase II trial of erlotinib versus temozolomide or carmustine in recurrent glioblastoma: EORTC brain tumor group study 26034," J. Clin. Oncol., vol. 27, pp. 1268-1274 (2009).
Vilella, A. I., et al., "EnsemblCompara GeneTrees: Complete, duplication-aware phylogenetic trees in vertebrates," Genome Res., vol. 19, pp. 327-335 (2009).
Wang, K., et al., "PennCNV: an integrated hidden Markov model designed for high-resolution copy number variation detection in whole-genome SNP genotyping data," Genome Res., vol. 17, pp. 1665-1674 (2007).
Wang, R., et al., "FGFRI/3 Tyrosine Kinase Fusions Define a Unique Molecular Subtype of Non-Small Cell Lung Cancer, " Clin. Cancer Res., vol. 20, pp. 4107-4114 (2014).
Wang, X. S., et al., "An integrative approach to reveal driver gene fusions from paired-end sequencing data in cancer," Nat. Biotechnol., vol. 27, No. 11, pp. 1005-1011 (2009).
Weathers, S.P. and Gilbert, M. R., "Advances in treating glioblastoma," F1OOO Prime Rep., pp. 1-9 (2014).
Weaver, B. A. and Cleveland, D.W., "The role of aneuploidy in promoting and suppressing tumors," J. Cell. Biol., vol. 185, pp. 935-937 (2009).
Wen, P. Y., et al., "Updated response assessment criteria for high-grade gliomas: response assessment in neuro-oncology working group," J. Clin. Oncol., vol. 28, pp. 1963-1972 (2010).
Wesche, J., et al., "Fibroblast growth factors and their receptors in cancer," Biochem. J., vol. 437, pp. 199-213 (2011).
Williams, S. V., et al., "Onocogenic FGFR3 gene fusions in bladder cancer," Hum. Mol. Genet., vol. 22, pp. 795-803 (2013).
Wu, Y. M., et al., "Identification of targetable FGFR gene fusions in diverse cancers," Cancer Discov., vol. 3, pp. 636-647 (2013).
Wurdak, H., et al., "A small molecule accelerates neuronal differentiation in the adult rat," PNAS, vol. 107, No. 38, pp. 16542-16547 (2010).
Yan, H., et al., "IDHI and IDH2 mutations in gliomas," New Engl. J. Med., vol. 360, pp. 765-773 (2009).
Zhang, J., et al., "Whole-genome sequencing identifies genetic alterations in pediatric low-grade gliomas," Nat. Genet. vol. 45, pp. 602-612 (2013).
Zhao, G., et al., "A Novel, Selective Inhibitor of Fibroblast Growth Factor Receptors That Shows a Potent Broad Spectrum of Antitumor Activity in Several Tumor Xenograft Models," Mol. Cancer Ther., vol. 10, No. 11, pp. 2200-2210 (2011).
Zhao, X., et al., "The HECT-domain ubiquitin ligase Huwe 1 controls neural differentiation and proliferation by destabilizing the N-Myc oncoprotein," Nature Cell Biology, vol. 10, No. 6, pp. 643-653 (2008).
Zhao, X., et al., "The N-Myc-DLL3 cascade is suppressed by the ubiquitin ligase Huwel to inhibit proliferation and promote neurogenesis in the developing brain," Dev. Cell, vol. 17, pp. 210-221 (2009).
Examination Report for European Patent Application No. 13823252. 5, dated Nov. 30, 2017 (6 pages).
Schuelke, "An economic method for the fluorescent labeling of PCR fragments", Nature Biotechnology, 18:233-234, Feb. 2000 (2 pages).
Tomlinson, et al., "Alternative Splicing of Fibroblast Growth Factor Receptor 3 Produces a Secreted Isoform That Inhibits Fibroblast Growth Factor-Induced Proliferation and Is Repressed in Urothelial Carcinoma Cell Lines", Cancer Res., 65(22):10441-10449, Nov. 15, 2005 (9 pages).
Annex I to Third Party Observations filed Oct. 19, 2018 in EP13823252.5 provided as D4 in Opposition to EP2877854 (2 pages).
Heid, et al., "Real Time Quantitative PCR", Genome Methods, Cold Spring Harbor Laboratory Press, Cold Spring, New York, 6:986-994, 1996 (10 pages).
Opposition filed in European Patent Application No. 13823252.5, dated Jun. 13, 2023 (50 pages).
Rodriguez-Tome, et al., "RHdb: the Radiation Hybrid database", Nucleic Acids Research, 29(1):165-166, 2001 (2 pages).
Sambrook, et al., excerpts from "Northern Hybridization", in Molecular Cloning: A Laboratory Manual, Third Edition, vol. 1, Cold Spring Harbor Laboratory Press, Cold Spring Harbor, New York, pp. 7.21-7.27, 7.42-7.45, 2001 (12 pages).
Sequence alignments between SEQ ID No. 2 of WO2013133351, EP2824181A1, JP2012-052147 and SEQ ID No. 161 of [U.S. Appl. No. 16/508,021] and SEQ ID No. 4 of WO2013133351, EP2824181A1, JP2012-052147 and SEQ ID No. 160 of [U.S. Appl. No. 16/508,021] provided as D5 in Opposition to EP2877854 dated Jun. 7, 2023 (3 pages).
Singh, et al. "Transforming Fusions of FGFR and TACC Genes in Human Glioblastoma", Author Manuscript published in final edited form as Science, 337(6099):1231-1235, Sep. 7, 2012 (10 pages).
Wang, et al., "Technical Advance: RNAscope: A Novel in Situ RNA Analysis Platform for Formalin-Fixed, Paraffin-Embedded Tissues", Journal of Molecular Diagnostics, 14(1):22-29, Jan. 2012 (8 pages).
Chesi, et al., "Frequent translocation t(4;14)(p16.3;q32.3) in multiple myeloma is associated with increased expression and activating mutations of fibroblast growth factor receptor 3", Author Manuscript published in final edited form as Nat Genet, 16(3):260-264, doi:10.1038/ng0797-260, Jul. 1997 (12 pages).
European Extended Search Report issued in EP20197862.4, dated Apr. 30, 2021 (15 pages).
Ueno, N. et al., "Enhanced Expression of Fibroblast Growth Factor Receptor 3 IIIc Promotes Human Esophageal Carcinoma Cell Proliferation", Journal Histochemistry & Cytochemistry, 64(1):7-17, DOI:10.1369/0022155415616161, 2016 (11 pages).
European Partial Search Report issued in European Patent Application No. 21173909.9; dated Nov. 18, 2021 (17 pages).

NM_000142
FGFR3

```
                5'
Reference:   C  W  H  A  A  P  S  Q  R  P  T  F  K  Q  L  V  E  D  L  D  R  V  L  T  V  T  S
             GTGCTGGCATGCCGGCGCCCTCCCAGACGCCCACCTTCAAGCAGCTGGTGGTGGAGGACCTGGACCGTGTCCTTACCGTGACGTC
SplitReads:
                                                                                            C
                                                                                           TC
                                                                                          GTC
                                                                                         CGTC
                                                                                        GACGTC
                                                                                       TGACGTC
                                                                                      GTGACGTC   Cont. on
                                                                                     CGTGACGTC     on
                                                                                    CCGTGACGTC   FIG.1B-2
                                                                                   CTTACCGTGACGTC
                                                                                  GTCCTTACCGTGACGTC
                                                                                 TGTCCTTACCGTGACGTC
                                                                                GTGTCCTTACCGTGACGTC
                                                                               CGTGTCCTTACCGTGACGTC
                                                                              ACCGTGTCCTTACCGTGACGTC
                                                                             GACCGTGTCCTTACCGTGACGTC
                                                                            GGACCGTGTCCTTACCGTGACGTC
                                                                           CTGGACCGTGTCCTTACCGTGACGTC
                                                                          CCTGGACCGTGTCCTTACCGTGACGTC
                                                                         GACCTGGACCGTGTCCTTACCGTGACGTC
                                                                        GGACCTGGACCGTGTCCTTACCGTGACGTC
                                                                       AGGACCTGGACCGTGTCCTTACCGTGACGTC
                                                                      GAGGACCTGGACCGTGTCCTTACCGTGACGTC
                                                                     GGAGGACCTGGACCGTGTCCTTACCGTGACGTC
                                                                    TGGAGGACCTGGACCGTGTCCTTACCGTGACGTC
                                                                   GTGGAGGACCTGGACCGTGTCCTTACCGTGACGTC
                                                                  GCTGGAGGACCTGGACCGTGTCCTTACCGTGACGTC
                                                                 TGGTGCAGGACCTGGACCGTGTCCTTACCGTGACGTC
```

NM_006342
TACC3

2530 1751                                                                                                    3'
T D   F K E S A L R K Q S L Y L K F D P L L R D S P G R P V P V A
CACCGAC TTTAAGGAGTCGGCCTTGAGGAAGCAGTCCTTATACCTCAAGTTCGACCCCCTCCTGAGGGACAGTCCTGGTAGACCAGTGCCCGTGGCC

C TTTAAGGAGTCGGCCTTGAGGAAGCAGTCCTTATACCTCAAGTTCGACCCCCTCCTGAGGGACAGTCCTGGTAGACCAGTGCCCGTGGCC
    AC TTTAAGGAGTCGGCCTTGAGGAAGCAGTCCTTATACCTCAAGTTCGACCCCCTCCTGAGGGACAGTCCTGGTAGACCAGTGCCCGTGGG
   GAC TTTAAGGAGTCGGCCTTGAGGAAGCAGTCCTTATACCTCAAGTTCGACCCCCTCCTGAGGGACAGTCCTGGTAGACCAGTGCCCGTGG
  CGAC TTTAAGGAGTCGGCCTTGAGGAAGCAGTCCTTATACCTCAAGTTCGACCCCCTCCTGAGGGACAGTCCTGGTAGACCAGTGCCCGTT
 CCGAC TTTAAGGAGTCGGCCTTGAGGAAGCAGTCCTTATACCTCAAGTTCGACCCCCTCCTGAGGGACAGTCCTGGTAGACCAGTGCCCGG
ACCGAC TTTAAGGAGTCGGCCTTGAGGAAGCAGTCCTTATACCTCAAGTTCGACCCCCTCCTGAGGGACAGTCCTGGTAGACCAGTGCCCC
CACCGAC TTTAAGGAGTCGGCCTTGAGGAAGCAGTCCTTATACCTCAAGTTCGACCCCCTCCTGAGGGACAGTCCTGGTAGACCAGTGCCC
CACCGAC TTTAAGGAGTCGGCCTTGAGGAAGCAGTCCTTATACCTCAAGTTCGACCCCCTCCTGAGGGACAGTCCTGGTAGACCAGTGCC
CACCGAC TTTAAGGAGTCGGCCTTGAGGAAGCAGTCCTTATACCTCAAGTTCGACCCCCTCCTGAGGGACAGTCCTGGTAGACCAGTGG
CACCGAC TTTAAGGAGTCGGCCTTGAGGAAGCAGTCCTTATACCTCAAGTTCGACCCCCTCCTGAGGGACAGTCCTGGTAGACCACTT
CACCGAC TTTAAGGAGTCGGCCTTGAGGAAGCAGTCCTTATACCTCAAGTTCGACCCCCTCCTGAGGGACAGTCCTGGTAGACCAGG
CACCGAC TTTAAGGAGTCGGCCTTGAGGAAGCAGTCCTTATACCTCAAGTTCGACCCCCTCCTGAGGGACAGTCCTGGTAGACG
CACCGAC TTTAAGGAGTCGGCCTTGAGGAAGCAGTCCTTATACCTCAAGTTCGACCCCCTCCTGAGGGACAGTCCTGGTAGACC
CACCGAC TTTAAGGAGTCGGCCTTGAGGAAGCAGTCCTTATACCTCAAGTTCGACCCCCTCCTGAGGGACAGTCCTGGTAGAA
CACCGAC TTTAAGGAGTCGGCCTTGAGGAAGCAGTCCTTATACCTCAAGTTCGACCCCCTCCTGAGGGACAGTCCTGGTAGG
CACCGAC TTTAAGGAGTCGGCCTTGAGGAAGCAGTCCTTATACCTCAAGTTCGACCCCCTCCTGAGGGACAGTCCTGGTAA
CACCGAC TTTAAGGAGTCGGCCTTGAGGAAGCAGTCCTTATACCTCAAGTTCGACCCCCTCCTGAGGGACAGTCCTT
CACCGAC TTTAAGGAGTCGGCCTTGAGGAAGCAGTCCTTATACCTCAAGTTCGACCCCCTCCTGAGGGACAGTT
CACCGAC TTTAAGGAGTCGGCCTTGAGGAAGCAGTCCTTATACCTCAAGTTCGACCCCCTCCTGAGGGACAGG
CACCGAC TTTAAGGAGTCGGCCTTGAGGAAGCAGTCCTTATACCTCAAGTTCGACCCCCTCCTGAGGGACAA
CACCGAC TTTAAGGAGTCGGCCTTGAGGAAGCAGTCCTTATACCTCAAGTTCGACCCCCTCCTGAGGGACC
CACCGAC TTTAAGGAGTCGGCCTTGAGGAAGCAGTCCTTATACCTCAAGTTCGACCCCCTCCTGAGGGG
CACCGAC TTTAAGGAGTCGGCCTTGAGGAAGCAGTCCTTATACCTCAAGTTCGACCCCCTCCTGAGGG
CACCGAC TTTAAGGAGTCGGCCTTGAGGAAGCAGTCCTTATACCTCAAGTTCGACCCCCTCCTGAGG
CACCGAC TTTAAGGAGTCGGCCTTGAGGAAGCAGTCCTTATACCTCAAGTTCGACCCCCTCCTGG
CACCGAC TTTAAGGAGTCGGCCTTGAGGAAGCAGTCCTTATACCTCAAGTTCGACCCCCTCCTT
CACCGAC TTTAAGGAGTCGGCCTTGAGGAAGCAGTCCTTATACCTCAAGTTCGACCCCCTCC
CACCGAC TTTAAGGAGTCGGCCTTGAGGAAGCAGTCCTTATACCTCAAGTTCGACCCCCTT
CACCGAC TTTAAGGAGTCGGCCTTGAGGAAGCAGTCCTTATACCTCAAGTTCGACCCCCC
CACCGAC TTTAAGGAGTCGGCCTTGAGGAAGCAGTCCTTATACCTCAAGTTCGACCCCC
CACCGAC TTTAAGGAGTCGGCCTTGAGGAAGCAGTCCTTATACCTCAAGTTCGACCCC
CACCGAC TTTAAGGAGTCGGCCTTGAGGAAGCAGTCCTTATACCTCAAGTTCGACCC
CACCGAC TTTAAGGAGTCGGCCTTGAGGAAGCAGTCCTTATACCTCAAGTTCGACC
CACCGAC TTTAAGGAGTCGGCCTTGAGGAAGCAGTCCTTATACCTCAAGTTCGAC
CACCGAC TTTAAGGAGTCGGCCTTGAGGAAGCAGTCCTTATACCTCAAGTTCGA
CACCGAC TTTAAGGAGTCGGCCTTGAGGAAGCAGTCCTTATACCTCAAGTTCG

Cont. from FIG.1B-1

Cont. FROM FIG.1B-1

```
                              CTGGTGGAGGACCTGGACCGTGTCCTTACCGTGACGTC
                             GCTGGTGGAGGACCTGGACCGTGTCCTTACCGTGACGTC
                            AGCTGGTGGAGGACCTGGACCGTGTCCTTACCGTGACGTC
                           CAGCTGGTGGAGGACCTGGACCGTGTCCTTACCGTGACGTC
                          GCAGCTGGTGGAGGACCTGGACCGTGTCCTTACCGTGACGTC
                         AGCAGCTGGTGGAGGACCTGGACCGTGTCCTTACCGTGACGTC
                        AAGCAGCTGGTGGAGGACCTGGACCGTGTCCTTACCGTGACGTC
                       CAAGCAGCTGGTGGAGGACCTGGACCGTGTCCTTACCGTGACGTC
                      TCAAGCAGCTGGTGGAGGACCTGGACCGTGTCCTTACCGTGACGTC
                     TTCAAGCAGCTGGTGGAGGACCTGGACCGTGTCCTTACCGTGACGTC
                    CTTCAAGCAGCTGGTGGAGGACCTGGACCGTGTCCTTACCGTGACGTC
                   CCTTCAAGCAGCTGGTGGAGGACCTGGACCGTGTCCTTACCGTGACGTC
                  ACCTTCAAGCAGCTGGTGGAGGACCTGGACCGTGTCCTTACCGTGACGTC
                 CACCTTCAAGCAGCTGGTGGAGGACCTGGACCGTGTCCTTACCGTGACGTC
                CCACCTTCAAGCAGCTGGTGGAGGACCTGGACCGTGTCCTTACCGTGACGTC
               CCCACCTTCAAGCAGCTGGTGGAGGACCTGGACCGTGTCCTTACCGTGACGTC
              GCCCACCTTCAAGCAGCTGGTGGAGGACCTGGACCGTGTCCTTACCGTGACGTC
             AGGCCCACCTTCAAGCAGCTGGTGGAGGACCTGGACCGTGTCCTTACCGTGACGTC
            GAGGCCCACCTTCAAGCAGCTGGTGGAGGACCTGGACCGTGTCCTTACCGTGACGTC
           AGAGGCCCACCTTCAAGCAGCTGGTGGAGGACCTGGACCGTGTCCTTACCGTGACGTC
          CAGAGGCCCACCTTCAAGCAGCTGGTGGAGGACCTGGACCGTGTCCTTACCGTGACGTC
         CCAGAGGCCCACCTTCAAGCAGCTGGTGGAGGACCTGGACCGTGTCCTTACCGTGACGTC
        CCCAGAGGCCCACCTTCAAGCAGCTGGTGGAGGACCTGGACCGTGTCCTTACCGTGACGTC
       TCCCAGAGGCCCACCTTCAAGCAGCTGGTGGAGGACCTGGACCGTGTCCTTACCGTGACGTC
      CTCCCAGAGGCCCACCTTCAAGCAGCTGGTGGAGGACCTGGACCGTGTCCTTACCGTGACGTC
     CCTCCCAGAGGCCCACCTTCAAGCAGCTGGTGGAGGACCTGGACCGTGTCCTTACCGTGACGTC
    CCCTCCCAGAGGCCCACCTTCAAGCAGCTGGTGGAGGACCTGGACCGTGTCCTTACCGTGACGTC
   GCCCTCCCAGAGGCCCACCTTCAAGCAGCTGGTGGAGGACCTGGACCGTGTCCTTACCGTGACGTC
  CGCCCTCCCAGAGGCCCACCTTCAAGCAGCTGGTGGAGGACCTGGACCGTGTCCTTACCGTGACGTC
 CCGCCCTCCCAGAGGCCCACCTTCAAGCAGCTGGTGGAGGACCTGGACCGTGTCCTTACCGTGACGTC
GCCGCCCTCCCAGAGGCCCACCTTCAAGCAGCTGGTGGAGGACCTGGACCGTGTCCTTACCGTGACGTC
TGCCGCCCTCCCAGAGGCCCACCTTCAAGCAGCTGGTGGAGGACCTGGACCGTGTCCTTACCGTGACGTC
ATGCCGCCCTCCCAGAGGCCCACCTTCAAGCAGCTGGTGGAGGACCTGGACCGTGTCCTTACCGTGACGTC
CATGCCGCCCTCCCAGAGGCCCACCTTCAAGCAGCTGGTGGAGGACCTGGACCGTGTCCTTACCGTGACGTC
GCATGCCGCCCTCCCAGAGGCCCACCTTCAAGCAGCTGGTGGAGGACCTGGACCGTGTCCTTACCGTGACGTC
GCCATGCCGCCCTCCCAGAGGCCCACCTTCAAGCAGCTGGTGGAGGACCTGGACCGTGTCCTTACCGTGACGTC
TGGCATGCCGCCCTCCCAGAGGCCCACCTTCAAGCAGCTGGTGGAGGACCTGGACCGTGTCCTTACCGTGACGTC
CTGGCATGCCGCCCTCCCAGAGGCCCACCTTCAAGCAGCTGGTGGAGGACCTGGACCGTGTCCTTACCGTGACGTC
GCTGGCATGCCGCCCTCCCAGAGGCCCACCTTCAAGCAGCTGGTGGAGGACCTGGACCGTGTCCTTACCGTGACGTC
TGCTGGCATGCCGCCCTCCCAGAGGCCCACCTTCAAGCAGCTGGTGGAGGACCTGGACCGTGTCCTTACCGTGACGTC
GTGCTGGCATGCCGCCCTCCCAGAGGCCCACCTTCAAGCAGCTGGTGGAGGACCTGGACCGTGTCCTTACCGTGACGTC
```

Cont. FROM FIG.1B-2

CACCGAC TTTAAGGAGTCGGCCTTGAGGAAGCAGTCCTTATACCTCTAATCA
CACCGAC TTTAAGGAGTCGGCCTTGAGGAAGCAGTCCTTATACCTCAAGTT
CACCGAC TTTAAGGAGTCGGCCTTGAGGAAGCAGTCCTTATACCTCAAGT
CACCGAC TTTAAGGAGTCGGCCTTGAGGAAGCAGTCCTTATACCTCAAG
CACCGAC TTTAAGGAGTCGGCCTTGAGGAAGCAGTCCTTATACCTCAA
CACCGAC TTTAAGGAGTCGGCCTTGAGGAAGCAGTCCTTATACCTCA
CACCGAC TTTAAGGAGTCGGCCTTGAGGAAGCAGTCCTTATACCTC
CACCGAC TTTAAGGAGTCGGCCTTGAGGAAGCAGTCCTTATACCT
CACCGAC TTTAAGGAGTCGGCCTTGAGGAAGCAGTCCTTATACC
CACCGAC TTTAAGGAGTCGGCCTTGAGGAAGCAGTCCTTATAC
CACCGAC TTTAAGGAGTCGGCCTTGAGGAAGCAGTCCTTATA
CACCGAC TTTAAGGAGTCGGCCTTGAGGAAGCAGTCCTTAT
CACCGAC TTTAAGGAGTCGGCCTTGAGGAAGCAGTCCTTA
CACCGAC TTTAAGGAGTCGGCCTTGAGGAAGCAGTCCTT
CACCGAC TTTAAGGAGTCGGCCTTGAGGAAGCAGTCCT
CACCGAC TTTAAGGAGTCGGCCTTGAGGAAGCAGTCC
CACCGAC TTTAAGGAGTCGGCCTTGAGGAAGCAGT
CACCGAC TTTAAGGAGTCGGCCTTGAGGAAGCAG
CACCGAC TTTAAGGAGTCGGCCTTGAGGAAGCA
CACCGAC TTTAAGGAGTCGGCCTTGAGGAAGC
CACCGAC TTTAAGGAGTCGGCCTTGAGGAAG
CACCGAC TTTAAGGAGTCGGCCTTGAGGAA
CACCGAC TTTAAGGAGTCGGCCTTGAGGA
CACCGAC TTTAAGGAGTCGGCCTTGAGG
CACCGAC TTTAAGGAGTCGGCCTTGAG
CACCGAC TTTAAGGAGTCGGCCTTGA
CACCGAC TTTAAGGAGTCGGCCTTG
CACCGAC TTTAAGGAGTCGGCC
CACCGAC TTTAAGGAGTCGGC
CACCGAC TTTAAGGAGTCGG
CACCGAC TTTAAGGAGTCG
CACCGAC TTTAAGGAGTC
CACCGAC TTTAAGGAGT
CACCGAC TTTAAGGAG
CACCGAC TTTAAGGA
CACCGAC TTTAAGG
CACCGAC TTTAAG
CACCGAC TTTAA
CACCGAC TTTA
CACCGAC TTT
CACCGAC TT

Cont. from FIG.1B-3

FIG.1B-4

MGAPACALALCVAVAIVAGASSESLGTEQRVVGRAAEVPGPEPGQQEQLVFGSGDAVELSCPPPG
GGPMGPTVWVKDGTGLVPSERVLVGPQRLQVLNASHEDSGAYSCRQRLTQRVLCHFSVRVTDAPS
SGDDEDGEDEAEDTGVDTGAPYWTRPERMDKKLLAVPAANTVRFRCPAAGNPTPSISWLKNGREF
RGEHRIGGIKLRHQQWSLVMESVVPSDRGNYTCVVENKFGSIRQTYTLDVLERSPHRPILQAGLP
ANQTAVLGSDVEFHCKVYSDAQPHIQWLKHVEVNGSKVGPDGTPYVTVLKTAGANTTDKELEVLS
LHNVTFEDAGEYTCLAGNSIGFSHHSAWLVVLPAEEELVEADEAGSVYAGILSYGVGFFLFILVV
AAVTLCRLRSPPKKGLGSPTVHKISRFPLKRQVSLESNASMSSNTPLVRIARLSSGEGPTLANVS
ELELPADPKWELSRARLTLGKPLGEGCFGQVVMAEAIGIDKDRAAKPVTVAVKMLKDDATDKDLS
DLVSEMEMMKMIGKHKNIINLLGACTQGGPLYVLVEYAAKGNLREFLRARRPPGLDYSFDTCKPP
EEQLTFKDLVSCAYQVARGMEYLASQKCIHRDLAARNVLVTEDNVMKIADFGLARDVHNLDYYKK
TTNGRLPVKWMAPEALFDRVYTHQSDVWSFGVLLWEIFTLGGSPYPGIPVEELFKLLKEGHRMDK
PANCTHDLYMIMRECWHAAPSQRPTFKQLVEDLDRVLTVTSTDFKESALRKQSLYLKFDPLLRDS
PGRPVPVATETSSMHGANETPSGRPREAKLVEFDFLGALDIPVPGPPPGVPAPGGPPLSTGPIVD
LLQYSQKDLDAVVKATQEENRELRSRCEELHGKNLELGKIMDRFEEVVYQAMEEVQKQKELSKAE
IQKVLKEKDQLTTDLNSMEKSFSDLFKRFEKQKEVIEGYRKNEESLKKCVEDYLARITQEGQRYQ
ALKAHAEEKLQLANEEIAQVRSKAQAEALALQASLRKEQMRIQSLEKTVEQKTKENEELTRICDD
LISKMEKI

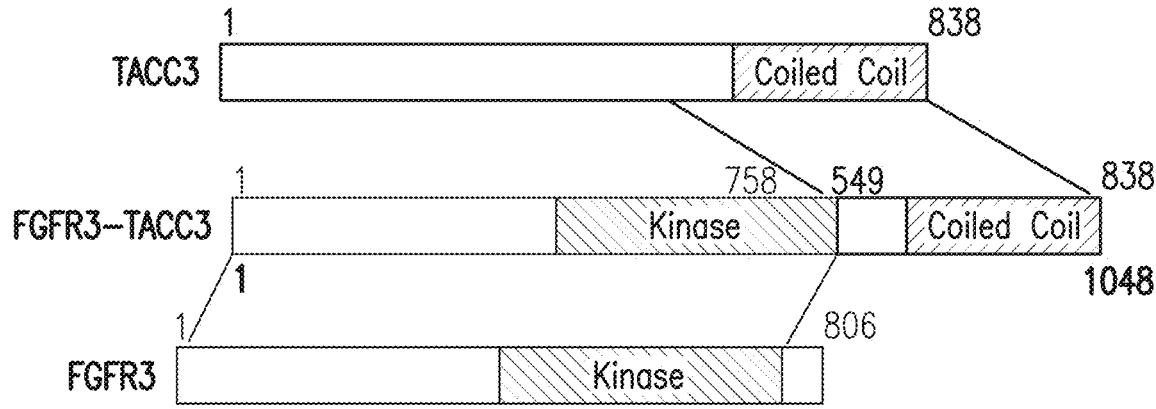

FIG.1D

TCGA-27-1835

FGFR3: Intron 16
1778595

5' CATCCTGCCCCCAGAGTGCTGAGGTGCTGAGGTCAGGGAGGCCTTCTGGGGCAGGAGGTGCTGCCA

R: GGCTCTGCCA
F: ACACAGCCTGGGGCACAGCCTGGGCACAGAGGTGCTGTGCCA
R: CGCACAGCCTGGGCACAGCCTGGGCACAGAGGTGCTGTGCCA
R: TTCCTGGGCACAGCCTGGGCACAGAGGTGCTGTGCCA
R: CTTCCTGGGCACAGCCTGGGCACAGAGGTGCTGTGCCA
R: GGCTTCCTGGGCACAGCCTGGGCACAGAGGTGCTGTGCCA
R: GGTGTGGGGCCGGCCCTTCTGGGCACAGCCTGGGCACAGAGGTGCTGTGCCA
R: GGTGTGGGGCCGGCCCTTCTGGGCACAGCCTGGGCACAGAGGTGCTGTGCCA
R: TGCTGCAGGTGCTGAGGTGCTGAGGTCAGGGAGGCCTTCTGGGCACAGCCTGGGCACAGAGGTGCTGTGCCA
R: AGTGCTGCAGGTGCTGAGGTGCTGAGGTCAGGGAGGCCTTCTGGGCACAGCCTGGGCACAGAGGTGCTGTGCCA
R: CCCAGAGTGCTGCAGGTGCTGAGGTGCTGAGGTCAGGGAGGCCTTCTGGGCACAGCCTGGGCACAGAGGTGCTGTGCCA
R: CCTGCCCCCAGAGTGCTGCAGGTGCTGAGGTGCTGAGGTCAGGGAGGCCTTCTGGGCACAGCCTGGGCACAGAGGTGCTGTGCCA

TACC3: Intron 10
1709397 3'

AGGTCCCTGAGGTCCAGGCTTCCACCCAGTCCACCAGTGCTGCCACCAGCCTCCCCGGAGACTCTCC
AGGTCCCTGAGGTCCAGGCTTCCACCCAGTGTCCACCAGTCAGCCTT
AGGTCCCTGAGGTCCAGGCTTCCACCCAGTGTCCCGGCACTCAGCCTT
AGGTCCCTGAGGTCCAGGCTTCCACCCAGTGTCCCGGCACTCAGCCTT
AGGTCCCTGAGGTCCAGGCTTCCACCCAGTGTCCCGGCAGTCAA
AGGTCCCTGAGGTCCAGGCTTCCACCCAGTGTCCCGGCAGTCAA
AGGTCCCTGAGGTCCAGGCTTCCACCAGCCAGTGTCCC
AGGTCCCTGAGGTCCAGGCTTCCACCCAGCCAGTGTCCC
AGGTCCCTGAGGTCCAGGCTTCCACCCAGCCAGTGTCCC
AGGTCCCTGAGGGTCCAGGCTTCC
AGGTCCCTGAGGTCCAGGCTTCC
AGGTCCCTGAGGGTCCAGGTCCAA
AGGTCCCTGAGGGTCC
AGG

TCGA-19-5958

FGFR3: Intron 16
1778539

5' GTGCTGGGCTGTGGCCTGGTGCCACCGGCTATGCCCCTCCCCGTGCCCTCCCCGGCTCCCCGGCCTCCCCACATCCTGCCCCCAGAGTGC

R: AGAGTGC
R: GGCCATCCTGCCCCCAGAGTGC
R: TCCCCCTGCCGTGCCCGGCCATCCTGCCCCCAGAGTGC

TACC3: Intron 7
1707202 3'

CGGGGCTAAGGGCCCAGGGAGGGAGGTCACCTGCACACTGCACACTCCACCGCACACCCCCAGGTCACCGCACACTCCCACCGCACACCCGGTCACCCG
AGGGGGCTAAGGGCCCAGGGAGGGAGGTCACCTGCACACTGCACACTCCACCGCACACCCCCAGGTCACCGCACACTCCCACCGCACACCCGGTCACCCG
AGGGGGCTAAGGGCCCAGGGAGGGAGGTCACCTGCACACTGCACACTCCACCGCACACCCGCCAGGTCACCCG
AGGGGGCTAAGGGCCCAGGGAGGGAGGTCACCTGCACACTCC

| Cell line | Metaphases inspected | Cells with segregation defects (%±SD) | Metaphases with misaligned chromosomes (%±SD) | Anaphases with lagging chromosomes (%±SD) | Anaphases/telophases with chromosome bridges (%±SD) |
|---|---|---|---|---|---|
| Rat1A Vector | 150 | 9.5±3.8 | 2.3±1.7 | 2.4±0.9 | 5.4±2.4 |
| Rat1A FGFR3-TACC3 | 150 | 27.4±3.9 | 8.0±2.6 | 8.0±1.0 | 11.2±0.7 |
| Rat1A FGFR1-TACC1 | 100 | 45.5±3.1 | 5±2.8 | 10±1.4 | 31.5±4.9 |

FIG.4F

| Cell line | Number of cells counted | Percent aneuploidy | Range | Mean number | Average variation from mean number | p- value |
|---|---|---|---|---|---|---|
| Vector | 100 | 8 | 42-46 | 45.85 | 0.28 | |
| FGFR3-TACC3 | 100 | 42 | 28-48 | 42.24 | 3.33 | $p = <0.001$ |

FIG. 5D

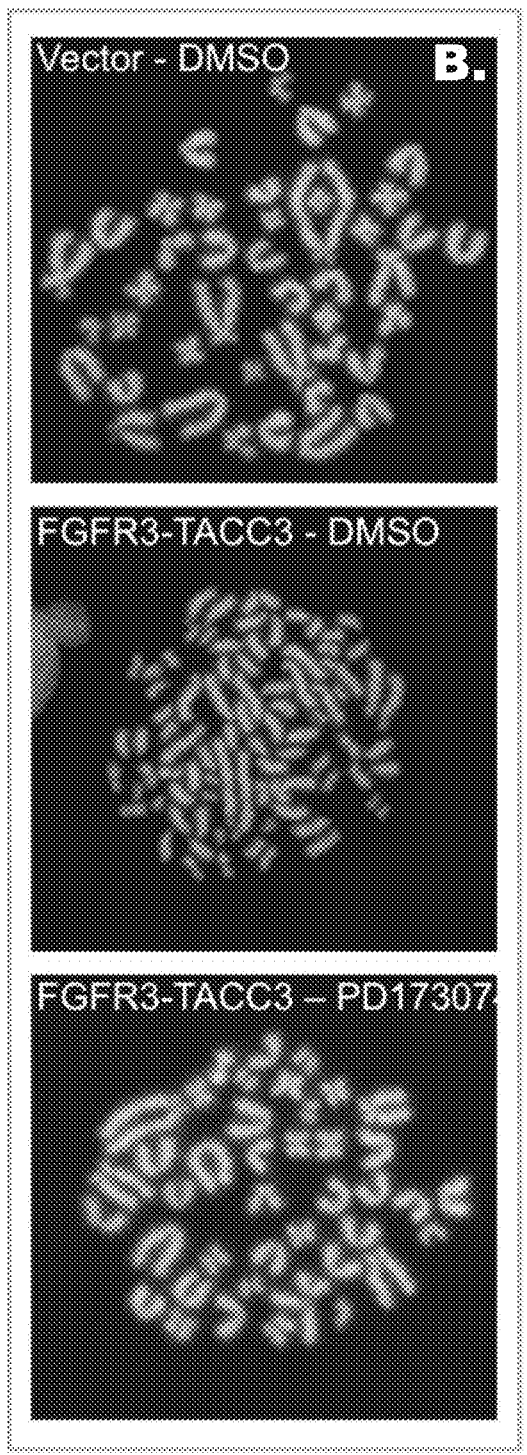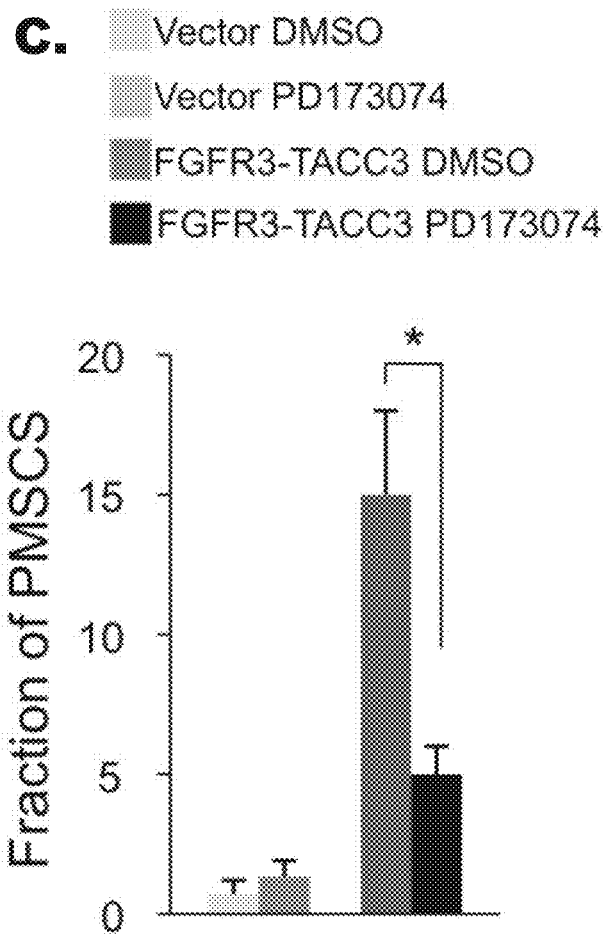
FIGS. 6B-C

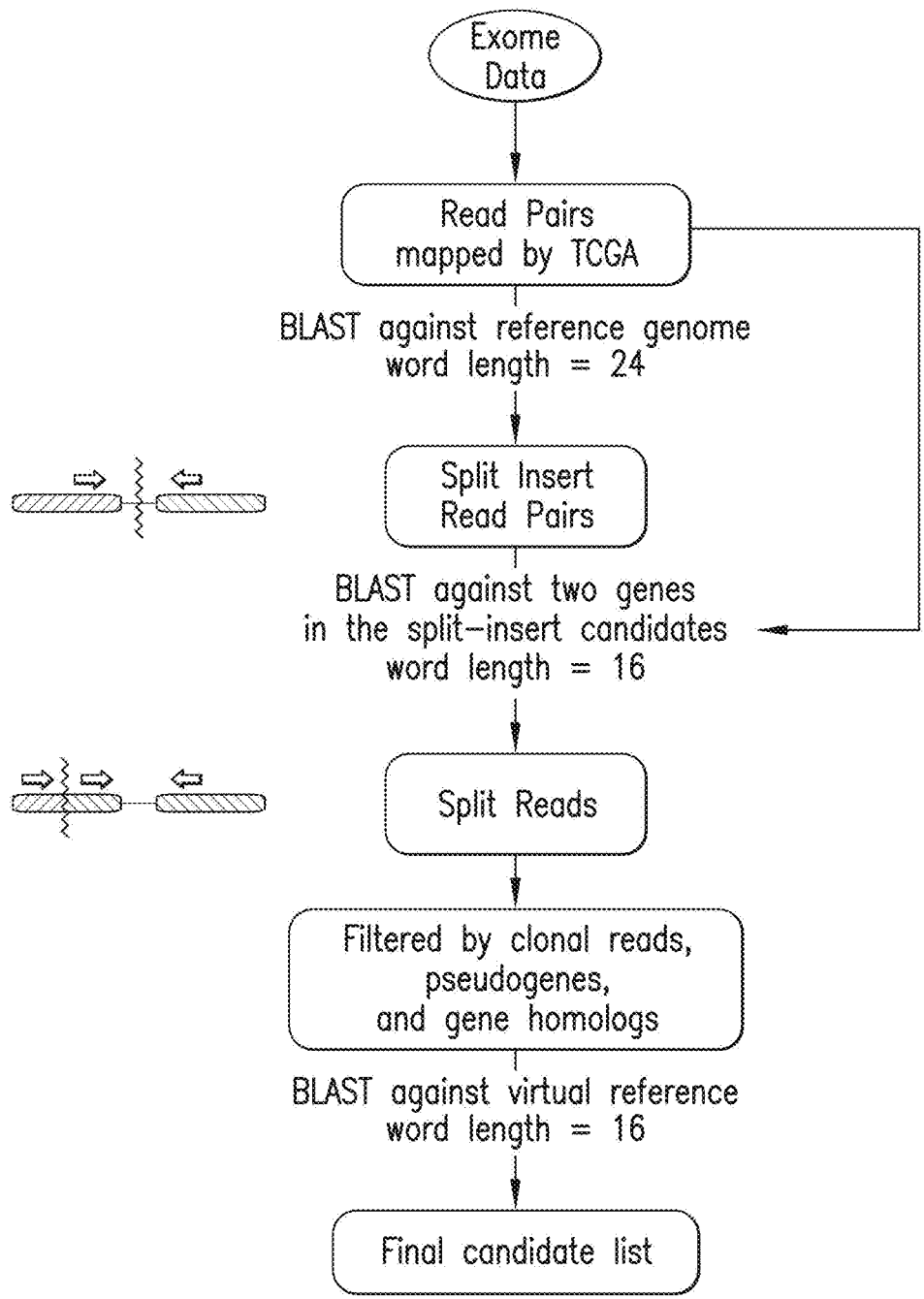
FIG. 8 - CONT.

ST8SIA4-PAM GSC-0517

PIGU-NCOA6 GSC-0308

NM_000937
POLR2A

Reference: 5'
G G G P P S G D S A C P L R T I K R V Q F G V L S P D
CGGGGGTGGCCCCCCCTCGGGGACAGCGCATGCCCGCTGCGCACCATCAAGAGAGTCCAGTTCGGAGTCCTGAGTCCGGA SplitReads:

```
                                                                                A
                                                                               GA
                                                                              GGA
                                                                             CGGA
                                                                            CCGGA
                                                                           TCCGGA
                                                                          GTCCGGA
                                                                         AGTCCGGA
                                                                        GAGTCCGGA
                                                                       TGAGTCCGGA
                                                                      CTGAGTCCGGA
                                                                     CCTGAGTCCGGA
                                                                    TCCTGAGTCCGGA
                                                                   GTCCTGAGTCCGGA
                                                                  AGTCCTGAGTCCGGA
                                                                 GAGTCCTGAGTCCGGA
                                                                GGAGTCCTGAGTCCGGA
                                                               CGGAGTCCTGAGTCCGGA
                                                              TCGGAGTCCTGAGTCCGGA
                                                             TTCGGAGTCCTGAGTCCGGA
                                                            GTTCGGAGTCCTGAGTCCGGA
                                                           CAGTTCGGAGTCCTGAGTCCGGA
                                                          CCAGTTCGGAGTCCTGAGTCCGGA
                                                         TCCAGTTCGGAGTCCTGAGTCCGGA
                                                        GTCCAGTTCGGAGTCCTGAGTCCGGA
                                                       GACTCCAGTTCGGAGTCCTGAGTCCGGA
                                                      AGACTCCAGTTCGGAGTCCTGAGTCCGGA
                                                     GAGAGTCCAGTTCGGAGTCCTGAGTCCGGA
                                                    AGAGAGTCCAGTTCGGAGTCCTGAGTCCGGA
                                                   AAGAGAGTCCAGTTCGGAGTCCTGAGTCCGGA
                                                  CAAGAGAGTCCAGTTCGGAGTCCTGAGTCCGGA
                                                 TCAAGAGAGTCCAGTTCGGAGTCCTGAGTCCGGA
                                                ATCAAGAGAGTCCAGTTCGGAGTCCTGAGTCCGGA
                                               CACCATCAAGAGAGTCCAGTTCGGAGTCCTGAGTCCGGA
                                              CGGCACCATCAAGAGAGTCCAGTTCGGAGTCCTGAGTCCGGA
                                             GCGCACCATCAAGAGAGTCCAGTTCGGAGTCCTGAGTCCGGA
                                            GCCCGCTGCGCACCATCAAGAGAGTCCAGTTCGGAGTCCTGAGTCCGGA
                                           CGCATGCCCGCTGCGCACCATCAAGAGAGTCCAGTTCGGAGTCCTGAGTCCGGA
                                          GCGCATGCCCGCTGCGCACCATCAAGAGAGTCCAGTTCGGAGTCCTGAGTCCGGA
                                         AGCGCATGCCCGCTGCGCACCATCAAGAGAGTCCAGTTCGGAGTCCTGAGTCCGGA
                                        CAGCGCATGCCCGCTGCGCACCATCAAGAGAGTCCAGTTCGGAGTCCTGAGTCCGGA
                                       GGGACAGCGCATGCCCGCTGCGCACCATCAAGAGAGTCCAGTTCGGAGTCCTGAGTCCGGA
                                      CGGGGACAGCGCATGCCCGCTGCGCACCATCAAGAGAGTCCAGTTCGGAGTCCTGAGTCCGGA
                                     CCCCCCTCGGGGACAGCGCATGCCCGCTGCGCACCATCAAGAGAGTCCAGTTCGGAGTCCTGAGTCCGGA
                                    CCCCCCCTCGGGGACAGCGCATGCCCGCTGCGCACCATCAAGAGAGTCCAGTTCGGAGTCCTGAGTCCGGA
                                   GGCCCCCCCTCGGGGACAGCGCATGCCCGCTGCGCACCATCAAGAGAGTCCAGTTCGGAGTCCTGAGTCCGGA
                                  GGGTGGCCCCCCCTCGGGGACAGCGCATGCCCGCTGCGCACCATCAAGAGAGTCCAGTTCGGAGTCCTGAGTCCGGA
                                 CGGGGGTGGCCCCCCCTCGGGGACAGCGCATGCCCGCTGCGCACCATCAAGAGAGTCCAGTTCGGAGTCCTGAGTCCGGA
```

NM_001143990
WRAP53

```
           479 798                                                                                                  3'
           E L  V P V L R M V E G D T I Y D Y C W Y S L M S S A Q P D T S X
           TGAACTG GTCCCTGTCCTTCGAATGGTGGAAGGTGATACCATCTATGATTACTGCTGGTATTCTCTGATGTCCTCAGCCCAGCCAGACACCTCCT

TG GTCCCTGTCCTTCGAATGGTGGAAGGTGATACCATCTATGATTACTGCTGGTATTCTCTGATGTCCTCAGCCCAGCCAGACACCTCCT
               CTG GTCCCTGTCCTTCGAATGGTGGAAGGTGATACCATCTATGATTACTGCTGGTATTCTCTGATGTCCTCAGCCCAGCCAGACACCTCC
              ACTG GTCCCTGTCCTTCGAATGGTGGAAGGTGATACCATCTATGATTACTGCTGGTATTCTCTGATGTCCTCAGCCCAGCCAGACACCAC
             AACTG GTCCCTGTCCTTCGAATGGTGGAAGGTGATACCATCTATGATTACTGCTGGTATTCTCTGATGTCCTCAGCCCAGCCAGACACCT
            GAACTG GTCCCTGTCCTTCGAATGGTGGAAGGTGATACCATCTATGATTACTGCTGGTATTCTCTGATGTCCTCAGCCCAGCCAGACACC
           TGAACTG GTCCCTGTCCTTCGAATGGTGGAAGGTGATACCATCTATGATTACTGCTGGTATTCTCTGATGTCCTCAGCCCAGCCAGACAC
           TGAACTG GTCCCTGTCCTTCGAATGGTGGAAGGTGATACCATCTATGATTACTGCTGGTATTCTCTGATGTCCTCAGCCCAGCCAGACACC
           TGAACTG GTCCCTGTCCTTCGAATGGTGGAAGGTGATACCATCTATGATTACTGCTGGTATTCTCTGATGTCCTCAGCCCAGCCAGAC
           TGAACTG GTCCCTGTCCTTCGAATGGTGGAAGGTGATACCATCTATGATTACTGCTGGTATTCTCTGATGTCCTCAGCCCAGCCAGA
           TGAACTG GTCCCTGTCCTTCGAATGGTGGAAGGTGATACCATCTATGATTACTGCTGGTATTCTCTGATGTCCTCAGCCCAGCCAG
           TGAACTG GTCCCTGTCCTTCGAATGGTGGAAGGTGATACCATCTATGATTACTGCTGGTATTCTCTGATGTCCTCAGCCCAGCCA
           TGAACTG GTCCCTGTCCTTCGAATGGTGGAAGGTGATACCATCTATGATTACTGCTGGTATTCTCTGATGTCCTCAGCCCAGCC
           TGAACTG GTCCCTGTCCTTCGAATGGTGGAAGGTGATACCATCTATGATTACTGCTGGTATTCTCTGATGTCCTCAGCCCAGC
           TGAACTG GTCCCTGTCCTTCGAATGGTGGAAGGTGATACCATCTATGATTACTGCTGGTATTCTCTGATGTCCTCAGCCCAG
           TGAACTG GTCCCTGTCCTTCGAATGGTGGAAGGTGATACCATCTATGATTACTGCTGGTATTCTCTGATGTCCTCAGCCCA
           TGAACTG GTCCCTGTCCTTCGAATGGTGGAAGGTGATACCATCTATGATTACTGCTGGTATTCTCTGATGTCCTCAGCCC
           TGAACTG GTCCCTGTCCTTCGAATGGTGGAAGGTGATACCATCTATGATTACTGCTGGTATTCTCTGATGTCCTCAGCC
           TGAACTG GTCCCTGTCCTTCGAATGGTGGAAGGTGATACCATCTATGATTACTGCTGGTATTCTCTGATGTCCTCAGC
           TGAACTG GTCCCTGTCCTTCGAATGGTGGAAGGTGATACCATCTATGATTACTGCTGGTATTCTCTGATGTCCTCAG
           TGAACTG GTCCCTGTCCTTCGAATGGTGGAAGGTGATACCATCTATGATTACTGCTGGTATTCTCTGATGTCCTCA
           TGAACTG GTCCCTGTCCTTCGAATGGTGGAAGGTGATACCATCTATGATTACTGCTGGTATTCTCTGATGTCCTC
Cont.      TGAACTG GTCCCTGTCCTTCGAATGGTGGAAGGTGATACCATCTATGATTACTGCTGGTATTCTCTGATGTCCT
From       TGAACTG GTCCCTGTCCTTCGAATGGTGGAAGGTGATACCATCTATGATTACTGCTGGTATTCTCTGATGTCC
FIG.9E-1   TGAACTG GTCCCTGTCCTTCGAATGGTGGAAGGTGATACCATCTATGATTACTGCTGGTATTCTCTGATGTC
           TGAACTG GTCCCTGTCCTTCGAATGGTGGAAGGTGATACCATCTATGATTACTGCTGGTATTCTCTGATGT
           TGAACTG GTCCCTGTCCTTCGAATGGTGGAAGGTGATACCATCTATGATTACTGCTGGTATTCTCTGATG
           TGAACTG GTCCCTGTCCTTCGAATGGTGGAAGGTGATACCATCTATGATTACTGCTGGTATTCTCTGAT
           TGAACTG GTCCCTGTCCTTCGAATGGTGGAAGGTGATACCATCTATGATTACTGCTGGTATTCTCTGA
           TGAACTG GTCCCTGTCCTTCGAATGGTGGAAGGTGATACCATCTATGATTACTGCTGGTATTCTCTG
           TGAACTG GTCCCTGTCCTTCGAATGGTGGAAGGTGATACCATCTATGATTACTGCTGGTATTCTCT
           TGAACTG GTCCCTGTCCTTCGAATGGTGGAAGGTGATACCATCTATGATTACTGCTGGTATTCTC
           TGAACTG GTCCCTGTCCTTCGAATGGTGGAAGGTGATACCATCTATGATTACTGCTGGTATTCT
           TGAACTG GTCCCTGTCCTTCGAATGGTGGAAGGTGATACCATCTATGATTACTGCTGGTATT
           TGAACTG GTCCCTGTCCTTCGAATGGTGGAAGGTGATACCATCTATGATTACTGCTGGTAT
           TGAACTG GTCCCTGTCCTTCGAATGGTGGAAGGTGATACCATCTATGATTACTGCTGGTA
           TGAACTG GTCCCTGTCCTTCGAATGGTGGAAGGTGATACCATCTATGATTACTGCTGGT
           TGAACTG GTCCCTGTCCTTCGAATGGTGGAAGGTGATACCATCTATGATTACTGCGG
           TGAACTG GTCCCTGTCCTTCGAATGGTGGAAGGTGATACCATCTATGATTACTGCTG
           TGAACTG GTCCCTGTCCTTCGAATGGTGGAAGGTGATACCATCTATGATTACTGCT
           TGAACTG GTCCCTGTCCTTCGAATGGTGGAAGGTGATACCATCTATGATTACTGC
           TGAACTG GTCCCTGTCCTTCGAATGGTGGAAGGTGATACCATCTATGATTA
           TGAACTG GTCCCTGTCCTTCGAATGGTGGAAGGTGATACCATCTATGAT
           TGAACTG GTCCCTGTCCTTCGAATGGTGGAAGGTGATACCATCTATGA
           TGAACTG GTCCCTGTCCTTCGAATGGTGGAAGGTGATACCA
           TGAACTG GTCCCTGTCCTTCGAATGGTGGAAGGTGA
           TGAACTG GTCCCTGTCCTTCGAATGGTGGAAGGTG
           TGAACTG GTCCCTGTCCTTCGAATGGTGGAAGGT
           TGAACTG GTCCCTGTCCTTCGAATGGTGGAAGG
           TGAACTG GTCCCTGTCCTTCGAATGGTGG
           TGAACTG GTCCCTGTCCTTCGAATGG
           TGAACTG GTCCCTGTCCTT
           TGAACTG GTCCCTGTCCT
           TGAACTG GTCCCTGTC
           TGAACTG GTCC
           TGAACTG GT
```

FIG.9E-2

NM_001206540
CAPZB

Reference: 5'  Q L D C A L D L M R R L P P Q Q I E K N L S D L I D
GCAGC-TGGACTGTGCCTTGGACCTAATGAGGCGCCTGCCTCCCCAGCAAATCGAGAAAAACCTCAGCGACCTGATCGAC SplitReads:

```
                                                                              C
                                                                             AC
                                                                            GCC
                                                                           CCAC
                                                                          GCGAC
                                                                         GATCGAC
                                                                        ACCTGATCGAC
                                                                       CGACCTGATCGAC
                                                                      CTCAGCGACCTGATCGAC
                                                                     AAAAACCTCAGCGACCTGATCGAC
                                                                    GAAAAACCTCAGCGACCTGATCGAC
                                                                   AGAAAAACCTCAGCGACCTGATCGAC
                                                                  CGAGAAAAACCTCAGCGACCTGATCGAC
                                                                 TCGAGAAAAACCTCAGCGACCTGATCGAC
                                                                ATCGAGAAAAACCTCAGCGACCTGATCGAC
                                                               AATCGAGAAAAACCTCAGCGACCTGATCGAC
                                                              AAATCGAGAAAAACCTCAGCGACCTGATCGAC
                                                             CAAATCGAGAAAAACCTCAGCGACCTGATCGAC
                                                            GCAAATCGAGAAAAACCTCAGCGACCTGATCGAC
                                                           AGCAAATCGAGAAAAACCTCAGCGACCTGATCGAC
                                                          CAGCAAATCGAGAAAAACCTCAGCGACCTGATCGAC
                                                         CCCAGCAAATCGAGAAAAACCTCAGCGACCTGATCGAC
                                                        CTCCCCAGCAAATCGAGAAAAACCTCAGCGACCTGATCGAC
                                                       CCTCCCCAGCAAATCGAGAAAAACCTCAGCGACCTGATCGAC
                                                      GCCTCCCCAGCAAATCGAGAAAAACCTCAGCGACCTGATCGAC
                                                     TGCCTCCCCAGCAAATCGAGAAAAACCTCAGCGACCTGATCGAC
                                                    CTGCCTCCCCAGCAAATCGAGAAAAACCTCAGCGACCTGATCGAC
                                                   CCTGCCTCCCCAGCAAATCGAGAAAAACCTCAGCGACCTGATCGAC
                                                  CGCCTGCCTCCCCAGCAAATCGAGAAAAACCTCAGCGACCTGATCGAC
                                                 GGGCGCCTGCCTCCCCAGCAAATCGAGAAAAACCTCAGCGACCTGATCGAC
                                                GCGGCGCCTGCCTCCCCAGCAAATCGAGAAAAACCTCAGCGACCTGATCGAC
                                               TGAGGCGCCTGCCTCCCCAGCAAATCGAGAAAAACCTCAGCGACCTGATCGAC
                                              ATGAGGCGCCTGCCTCCCCAGCAAATCGAGAAAAACCTCAGCGACCTGATCGAC
                                             AATGAGGCGCCTGCCTCCCCAGCAAATCGAGAAAAACCTCAGCGACCTGATCGAC
                                            TAATGAGGCGCCTGCCTCCCCAGCAAATCGAGAAAAACCTCAGCGACCTGATCGAC
                                           GACCTAATGAGGCGCCTGCCTCCCCAGCAAATCGAGAAAAACCTCAGCGACCTGATCGAC
                                          TTGGACCTAATGAGGCGCCTGCCTCCCCAGCAAATCGAGAAAAACCTCAGCGACCTGATCGAC
                                         CTTGGACCTAATGAGGCGCCTGCCTCCCCAGCAAATCGAGAAAAACCTCAGCGACCTGATCGAC
                                        GCCTTGGACCTAATGAGGCGCCTGCCTCCCCAGCAAATCGAGAAAAACCTCAGCGACCTGATCGAC
                                       GTGCCTTGGACCTAATGAGGCGCCTGCCTCCCCAGCAAATCGAGAAAAACCTCAGCGACCTGATCGAC
                                      ACTGTGCCTTGGACCTAATGAGGCGCCTGCCTCCCCAGCAAATCGAGAAAAACCTCAGCGACCTGATCGAC
                                     GACTGTGCCTTGGACCTAATGAGGCGCCTGCCTCCCCAGCAAATCGAGAAAAACCTCAGCGACCTGATCGAC
                                    CATGGACTGTGCCTTGGACCTAATGAGGCGCCTGCCTCCCCAGCAAATCGAGAAAAACCTCAGCGACCTGATCGAC
                                    GC--TGGACTGTGCCTTGGACCTAATGAGGCGCCTGCCTCCCCAGCAAATCGAGAAAAACCTCAGCGACCTGATCGAC
                                   AGC--TGGACTGTGCCTTGGACCTAATGAGGCGCCTGCCTCCCCAGCAAATCGAGAAAAACCTCAGCGACCTGATCGAC
                                  GCAGC--TGGACTGTGCCTTGGACCTAATGAGGCGCCTGCCTCCCCAGCAAATCGAGAAAAACCTCAGCGACCTGATCGAC
```

```
                        NM_020/65
227 12110               UBR4                                                    3'
 L   D  V  P  V  E  A  L  T  T  V  K  P  Y  C  N  E  I  H  A  Q  A  Q  L  W  L  K  R  D  P
CTG GATGTCCCCGTTGAGGCCCTCACCACGTGAAGCCATACTGCAATGAGATCCATGCCCAGGCTCAACTGTGGCTCAAGAGAGACCCCA

TG GATGTCCCCGTTGAGGCCCTCACCACGTGAAGCCATACTGCAATGAGATCCATGCCCAGGCTCAACTGTGGCTCAAGAGAGACCCCA
CTG GATGTCCCCGTTGAGGCCCTCACCACGTGAAGCCATACTGCAATGAGATCCATGCCCAGGCTCAACTGTGGCTCAAGAGAGACCCC
AAG GATGTCCCCGTTGAGGCCCTCACCACGTGAAGCCATACTGCAATGAGATCCATGCCCAGGCTCAACTGTGGCTCAAGAGAGACCT
CTG GATGTCCCCGTTGAGGCCCTCACCACGTGAAGCCATACTGCAATGAGATCCATGCCCAGGCTCAACTGTGGCTCAAGAGAGACC
CTG GATGTCCCCGTTGAGGCCCTCACCACGTGAAGCCATACTGCAATGAGATCCATGCCCAGGCTCAACTGTGGCTCAAGAGAGAC
CTT GATGTCCCCGTTGAGGCCCTCACCACGTGAAGCCATACTGCAATGAGATCCATGCCCAGGCTCAACTGTGGCTCAAGAGAGA
CTG GATGTCCCCGTTGAGGCCCTCACCACGTGAAGCCATACTGCAATGAGATCCATGCCCAGGCTCAACTGTGGCTCAAGAGAG
CTG GATGTCCCCGTTGAGGCCCTCACCACGTGAAGCCATACTGCAATGAGATCCATGCCCAGGCTCAACTGTGGCTCAAGAG
CTG GATGTCCCCGTTGAGGCCCTCACCACGTGAAGCCATACTGCAATGAGATCCATGCCCAGGCTCAACTGTGGCTCA
CTG GATGTCCCCGTTGAGGCCCTCACCACGTGAAGCCATACTGCAATGAGATCCATGCCCAGGCTCAACTGTGGCT
CTG GATGTCCCCGTTGAGGCCCTCACCACGTGAAGCCATACTGCAATGAGATCCATGCCCAGGCTCAACTG
CTG GATGTCCCCGTTGAGGCCCTCACCACGTGAAGCCATACTGCAATGAGATCCATGCCCAGGCTC
CTG GATGTCCCCGTTGAGGCCCTCACCACGTGAAGCCATACTGCAATGAGATCCATGCCCAGGC
CTG GATGTCCCCGTTGAGGCCCTCACCACGTGAAGCCATACTGCAATGAGATCCATGCCCAGG
CTG GATGTCCCCGTTGAGGCCCTCACCACGTGAAGCCATACTGCAATGAGATCCATGCCCA
CTG GATGTCCCCGTTGAGGCCCTCACCACGTGAAGCCATACTGCAATGAGATCCATGCCC
CTG GATGTCCCCGTTGAGGCCCTCACCACGTGAAGCCATACTGCAATGAGATCCATGCC
CTG GATGTCCCCGTTGAGGCCCTCACCACGTGAAGCCATACTGCAATGAGATCCATGC
CTG GATGTCCCCGTTGAGGCCCTCACCACGTGAAGCCATACTGCAATGAGATCCATG
CTG GATGTCCCCGTTGAGGCCCTCACCACGTGAAGCCATACTGCAATGAGATCCA
CTG GATGTCCCCGTTGAGGCCCTCACCACGTGAAGCCATACTGCAATGAGATCC
CTG GATGTCCCCGTTGAGGCCCTCACCACGTGAAGCCATACTGCAATGAGATC
CTG GATGTCCCCGTTGAGGCCCTCACCACGTGAAGCCATACTGCAATGAG
CTG GATGTCCCCGTTGAGGCCCTCACCACGTGAAGCCATACTGCAATG
CTG GATGTCCCCGTTGAGGCCCTCACCACGTGAAGCCATACTGCAAT
CTG GATGTCCCCGTTGAGGCCCTCACCACGTGAAGCCATACTGCAA
CTG GATGTCCCCGTTGAGGCCCTCACCACGTGAAGCCATACTGCA
CTG GATGTCCCCGTTGAGGCCCTCACCACGTGAAGCCATACTGC
CTG GATGTCCCCGTTGAGGCCCTCACCACGTGAAGCCATACTG
CTG GATGTCCCCGTTGAGGCCCTCACCACGTGAAGCCATAC
CTG GATGTCCCCGTTGAGGCCCTCACCACGTGAAGCCAT
CTG GATGTCCCCGTTGAGGCCCTCACCACGTGAAGCC
CTG GATGTCCCCGTTGAGGCCCTCACCACGTGAAGC
CTG GATGTCCCCGTTGAGGCCCTCACCACGTGAAG
CTG GATGTCCCCGTTGAGGCCCTCACCACGTGAA
CTG GATGTCCCCGTTGAGGCCCTCACCACGTGA
CTG GATGTCCCCGTTGAGGCCCTCACCACG
CTG GATGTCCCCGTTGAGGCCCTCACC
CTG GATGTCCCCGTTGAGGCCCTCAC
CTG GATGTCCCCGTTGAGGCCCTC
CTG GATGTCCCCGTTGAGGCCC
CTG GATGTCCCCGTTGAGG
CTG GATGTCCCCGTCGAG
CTG GATGTCCCCGA
CTG GATGTCCCCG
CTG GATGTCCCGG
CTG GATGTCCCC
```

Cont. From FIG.9E-3

FIG.9E-4

NM_005668
ST8SIA4
Reference: 5' E W V N A L I L K N K L K V R T A Y P S L R L I H A
SpiltReads: GGAGTGGGTTAATGCATTAATCCTTAAGAATAAACTGAAAGTGCGAACTGCCTATCCGTCATTGAGACTTATTCATGC

```
                                                                              GC
                                                                             TGC
                                                                            ATGC
                                                                           CATGC
                                                                          TCATGC
                                                                        TATTCATGC
                                                                       CTTATTCATGC    Cont.
                                                                      ACTTATTCATGC     On
                                                                   GAGACTTATTCATGC   FIG.9E-6
                                                                   TGACACTTATTCATGC
                                                                  TTGAGACTTATTCATGC
                                                                GTCATTGAGACTTATTCATGC
                                                               CCGTCATTGAGACTTATTCATGC
                                                              TATCCGTCATTGAGACTTATTCATGC
                                                             CTATCCGTCATTGAGACTTATTCATGC
                                                            CCTATCCGTCATTGAGACTTATTCATGC
                                                           GCCTATCCGTCATTGAGACTTATTCATGC
                                                     TGAAAGTGCGAACTGCCTATCCGTCATTGAGACTTATTCATGC
                                                    CTGAAAGTGCGAACTGCCTATCCGTCATTGAGACTTATTCATGC
                                                  AAACTGAAAGTGCGAACTGCCTATCCGTCATTGAGACTTATTCATGC
                                                 TAAACTGAAAGTGCGAACTGCCTATCCGTCATTGAGACTTATTCATGC
                                           ATTAATCCTTAAGAATAAACTGAAAGTGCGAACTGCCTATCCGTCATTGAGACTTATTCATGC
                                          GCATTAATCCTTAAGAATAAACTGAAAGTGCGAACTGCCTATCCGTCATTGAGACTTATTCATGC
                                     GGAGTGGGTTAATGCATTAATCCTTAAGAATAAACTGAAAGTGCGAACTGCCTATCCGTCATTGAGACTTATTCATGC
```

NM_080476
PIGU

Reference: 5' H D F V L C C Q V Y L C H Q Q H P H C F L H F D Y D K
ACACGATTTTGTCTTGTGTTGCCAAGTCTACCTGTGCCATCAACAACACCCTCATTGCTTTCTTCATTTTGACTACGATA SplitReads:
```
                                                                          ATA
                                                       TTGCTTTCTTCATTTTGACTACGATA
                                                   CCTCATTGCTTTCTTCATTTTGACTACGATA
                                                  CCCTCATTGCTTTCTTCATTTTGACTACGATA
                                                 CACCCTCATTGCTTTCTTCATTTTGACTACGATA
                                              CAACACCCTCATTGCTTTCTTCATTTTGACTACGATA
                                           CAACAACACCCTCATTGCTTTCTTCATTTTGACTACGATA
                                          ATCAACAACACCCTCATTGCTTTCTTCATTTTGACTACGATA
                                         CATCAACAACACCCTCATTGCTTTCTTCATTTTGACTACGATA
                                       GTGCCATCAACAACACCCTCATTGCTTTCTTCATTTTGACTACGATA
                                    GTCTACCTGTGCCATCAACAACACCCTCATTGCTTTCTTCATTTTGACTACGATA
                                  CAAGTCTACCTGTGCCATCAACAACACCCTCATTGCTTTCTTCATTTTGACTACGATA
                                 CCAAGTCTACCTGTGCCATCAACAACACCCTCATTGCTTTCTTCATTTTGACTACGATA
                           GTCTTGTGTTGCCAAGTCTACCTGTGCCATCAACAACACCCTCATTGCTTTCTTCATTTTGACTACGATA
                         TTTTCTTGTGTTGCCAAGTCTACCTGTGCCATCAACAACACCCTCATTGCTTTCTTCATTTTGACTACGATA
                        ATTTTGTCTTGTGTTGCCAAGTCTACCTGTGCCATCAACAACACCCTCATTGCTTTCTTCATTTTGACTACGATA
                       ACACGATTTTGTCTTGTGTTGCCAAGTCTACCTGTGCCATCAACAACACCCTCATTGCTTTCTTCATTTTGACTACGATA
```

Cont. on FIG.9E-8

NM_000874
IFNAR2

Reference: 5' L E H S D E Q A V I K S P L K C T L L P P G Q E S
ATTTAGAGCACAGTGATGAGCAAGCAGTAATAAAGTCTCCCTTAAAATGCACCCTCCTTCCACCACCTGGCCAGGAA SplitReads:
```
                                                                              G
                         CAGTAATAAAGTCTCCCTTAAAATGCACCCTCCTTCCACCACCTGGCCAGGAA
                  GTGATGAGCAAGCAGTAATAAAGTCTCCCTTAAAATGCACCCTCCTTCCACCACCTGGCCAGGAA
                ACAGTGATGAGCAAGCAGTAATAAAGTCTCCCTTAAAATGCACCCTCCTTCCACCACCTGGCCAGGAA
           ATTTAGAGCACAGTGATGAGCAAGCAGTAATAAAGTCTCCCTTAAAATGCACCCTCCTTCCACCACCTGGCCAGGAA
```

FIG.9E-7

```
                                    NM_014071
        729 6471                      NCOA6                                                  3'
        R H N Q C G A I Q A K K I Q V N K Q D C D L I L G N V C X
        AAAG ACATAACCAGTGCGGTGCAATCCAAGCGAAGAAAATCCAAGTAAACAAGCAGGACTGCGACTTGATACTTGGAAATGTGTGTG

AAAG ACATAACCAGTGCGGTGCAATCCAAGCGAAGAAAATCCAAGTAAACAAGCAGGACTGCGACTTGATACTTGGAAATGTGTGTG
        AAAG ACATAACCAGTGCGGTGCAATCCAAGCGAAGAAAATCCAAGTAAACAAGCAGGACTGCGA
        AAAG ACATAACCAGTGCGGTGCAATCCAAGCGAAGAAAATCCAAGTAAACAAGCAGGAC
        AAAG ACATAACCAGTGCGGTGCAATCCAAGCGAAGAAAATCCAAGTAAACAAGCAGGA
        AAAG ACATAACCAGTGCGGTGCAATCCAAGCGAAGAAAATCCAAGTAAACAAGCAG
        AAAG ACATAACCAGTGCGGTGCAATCCAAGCGAAGAAAATCCAAGTAAACAAG
        AAAG ACATAACCAGTGCGGTGCAATCCAAGCGAAGAAAATCCAAGTAAAC
        AAAG ACATAACCAGTGCGGTGCAATCCAAGCGAAGAAAATCCAAGTAA
        AAAG ACATAACCAGTGCGGTGCAATCCAAGCGAAGAAAATCCAAGTA
        AAAG ACATAACCAGTGCGGTGCAATCCAAGCGAAGAAAATCCA
        AAAG ACATAACCAGTGCGGTGCAATCCAAGCGAAG
        AAAG ACATAACCAGTGCGGTGCAATCCAAGCG
        AAAG ACATAACCAGTGCGGTGCAATCCAAGC
Cont.   AAAG ACATAACCAGTGCGGT
From    AAAG ACATAACCAGTGCG
FIG.9E-7 AAAG ACATAACCAGT
        AAAG ACATAA NM_000628
        1083 149                     IL10RB                                                  3'
        A L G M V P P P E N V R M N S V N F K N I L Q W E S P A F X
        TCAG CATTGGGAATGGTACCACCTCCCGAAAATGTCAGAATGAATTCTGTTAATTTCAAGAACATTCTACAGTGGGAGTCACCTGCTTTTGC AG CATTGGGAATGGTACCACCTCCCGAAAATGTCAGAATGAATTCTGTTAATTTCAAGAACATTCTACAGTGGGAGTCACCTGCTTTTGC
        TCAG CATTGGGAATGGTACCACCTCCCGAAAATGTCAGAATGAATTCTGTTAATTTCAAGAACATTCTACAGTGGGAGTCACCTGCTTTT
        TCAG CATTGGGAATGGTACCACCTCCCGAAAATGTCAGAA
        TCAG CATTGGGAATGGTACCACCTCCCG
        TCAG CATTGGGAATGGTACCACCAA
        TCAG CATTGGGAATGG
```

FIG.9E-8

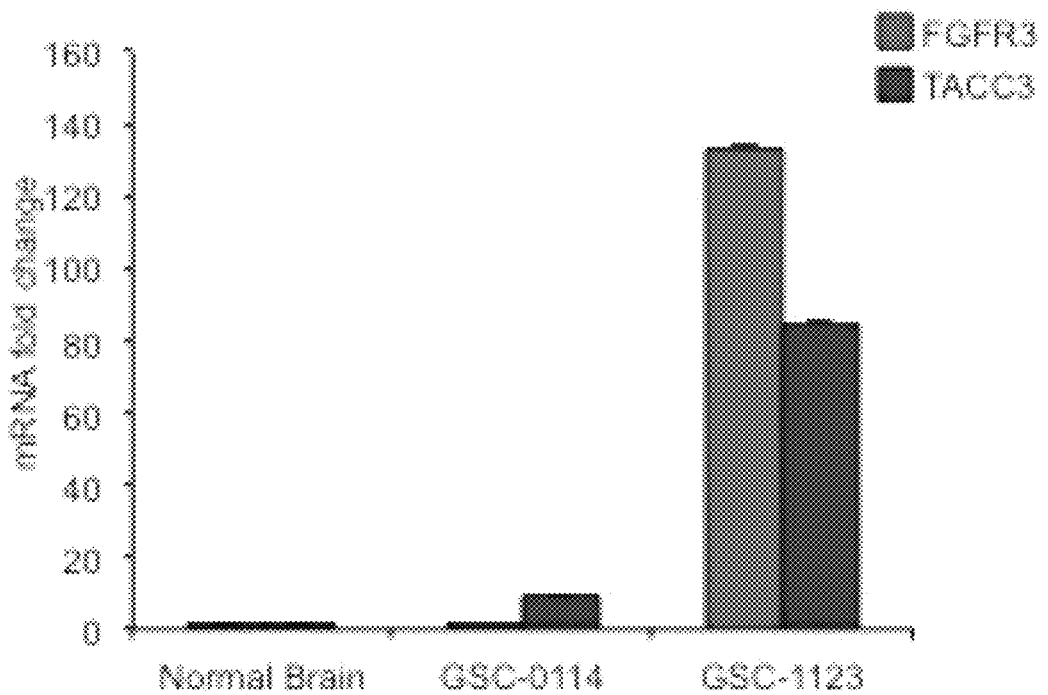
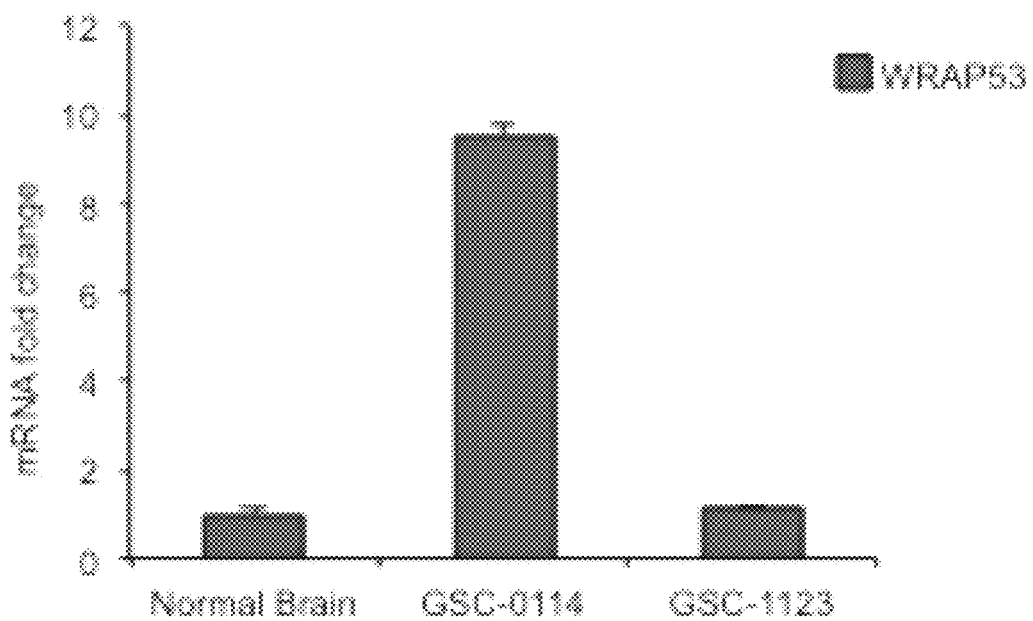
FIG. 10B

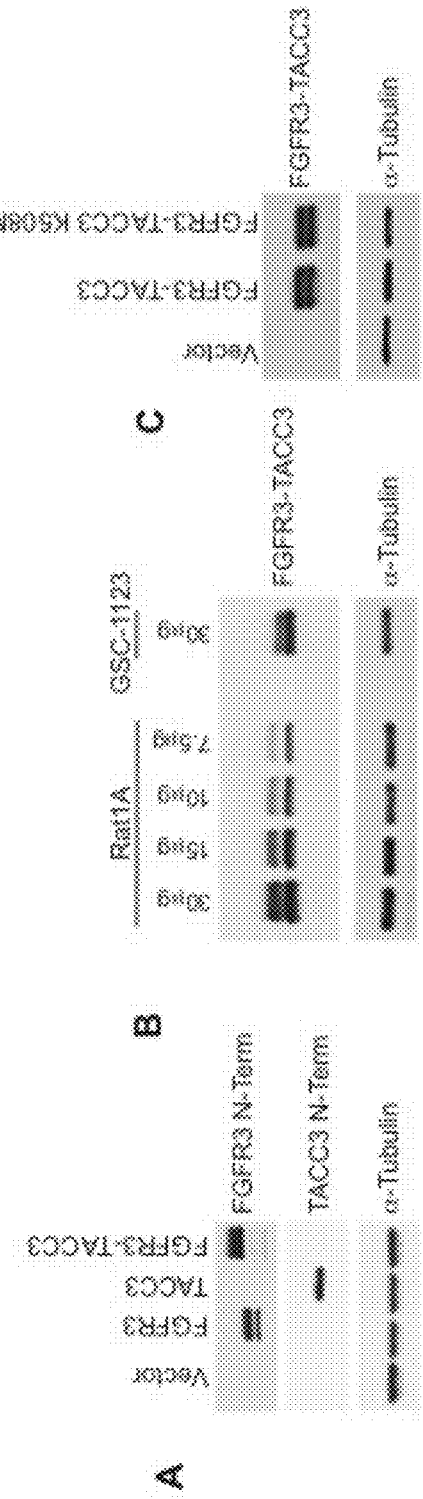
FIGS. 11A-C

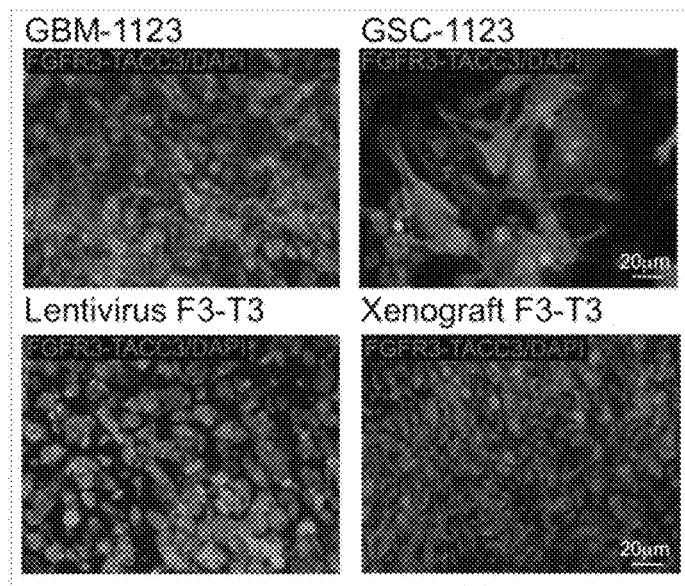
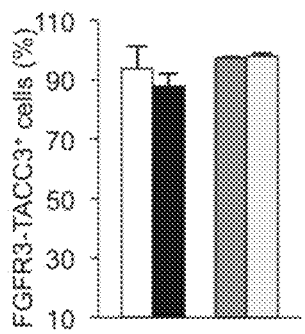
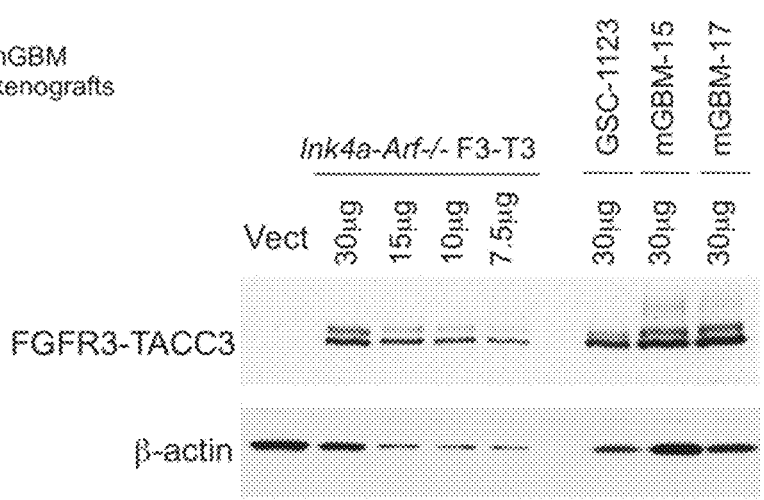
FIGS. 11D-F

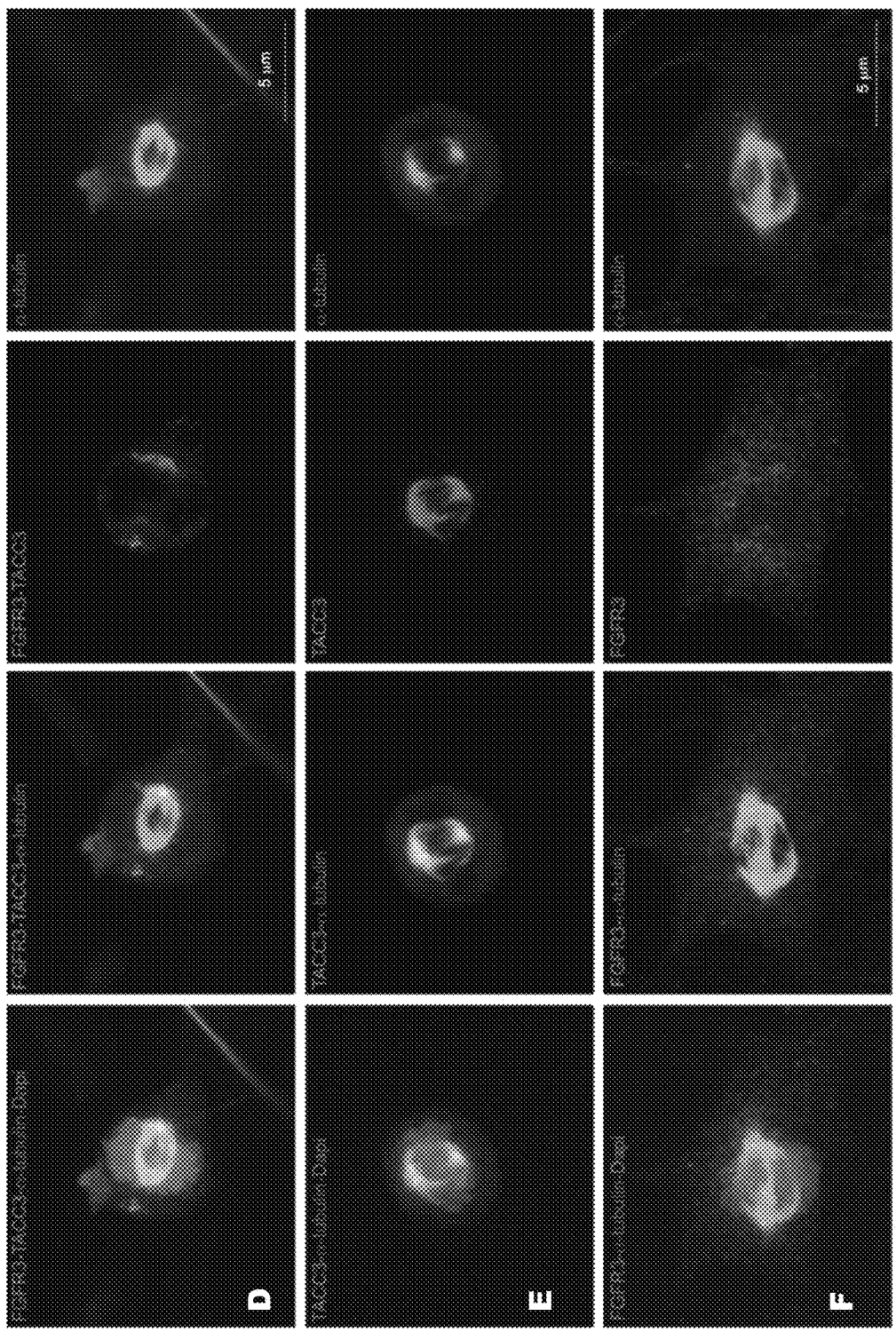
FIGS. 12D-F

| Cell line | Metaphases inspected | Cells with segregation defects (%±SD) | Metaphases with misaligned chromosomes (%±SD) | Anaphases with lagging chromosomes (%±SD) | Anaphases/telophases with chromosome bridges (%±SD) |
|---|---|---|---|---|---|
| Ink4A,ARF-/- Vector | 100 | 7.3±1.5 | 2.2±1.5 | 2.0±0.7 | 3.3±0.6 |
| Ink4A,ARF-/- F3-T3 Fusion | 100 | 18.3±1.5 | 8.0±1.1 | 6.5±1.3 | 11.2±0.7 |

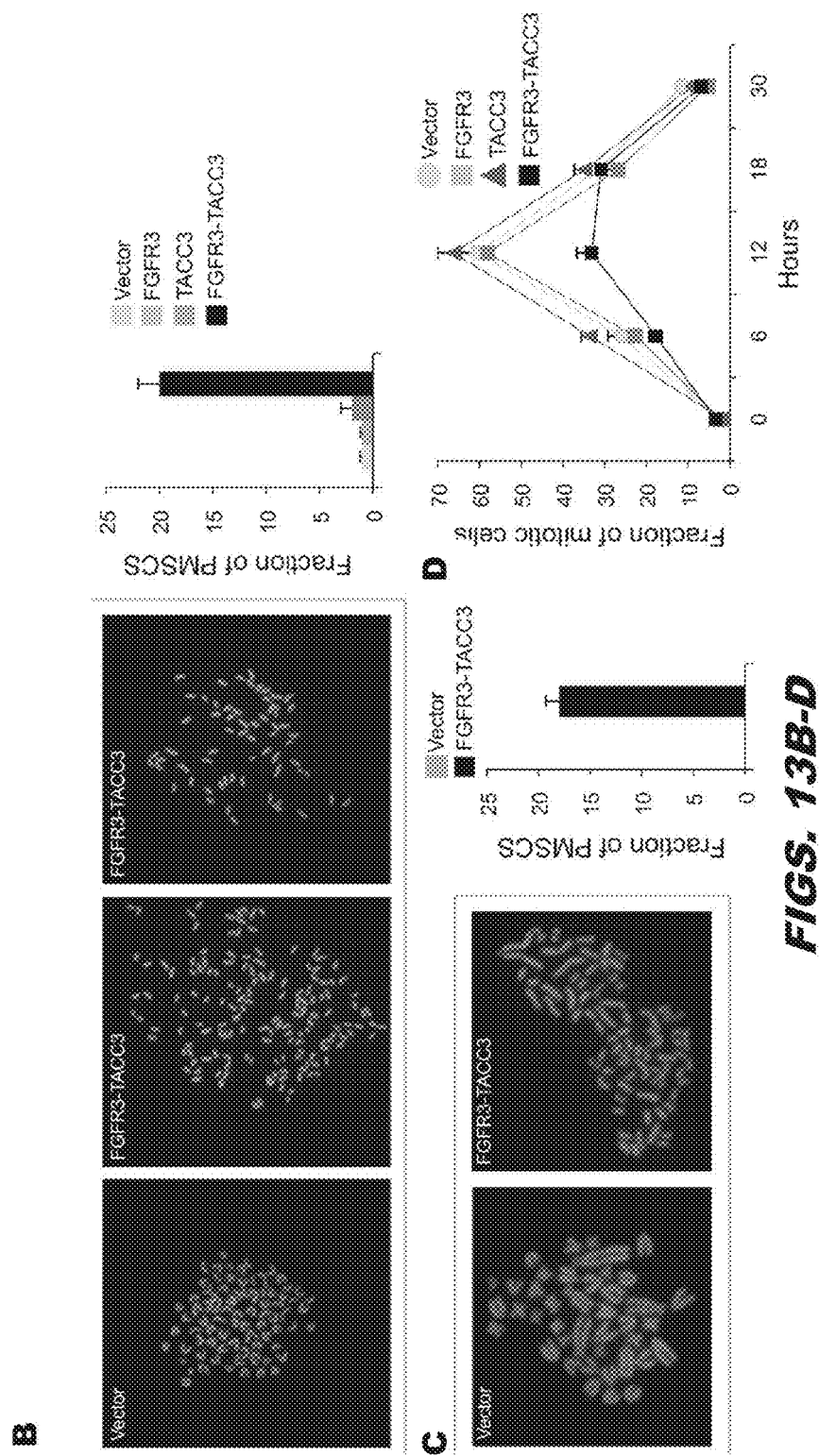
FIGS. 13B-D

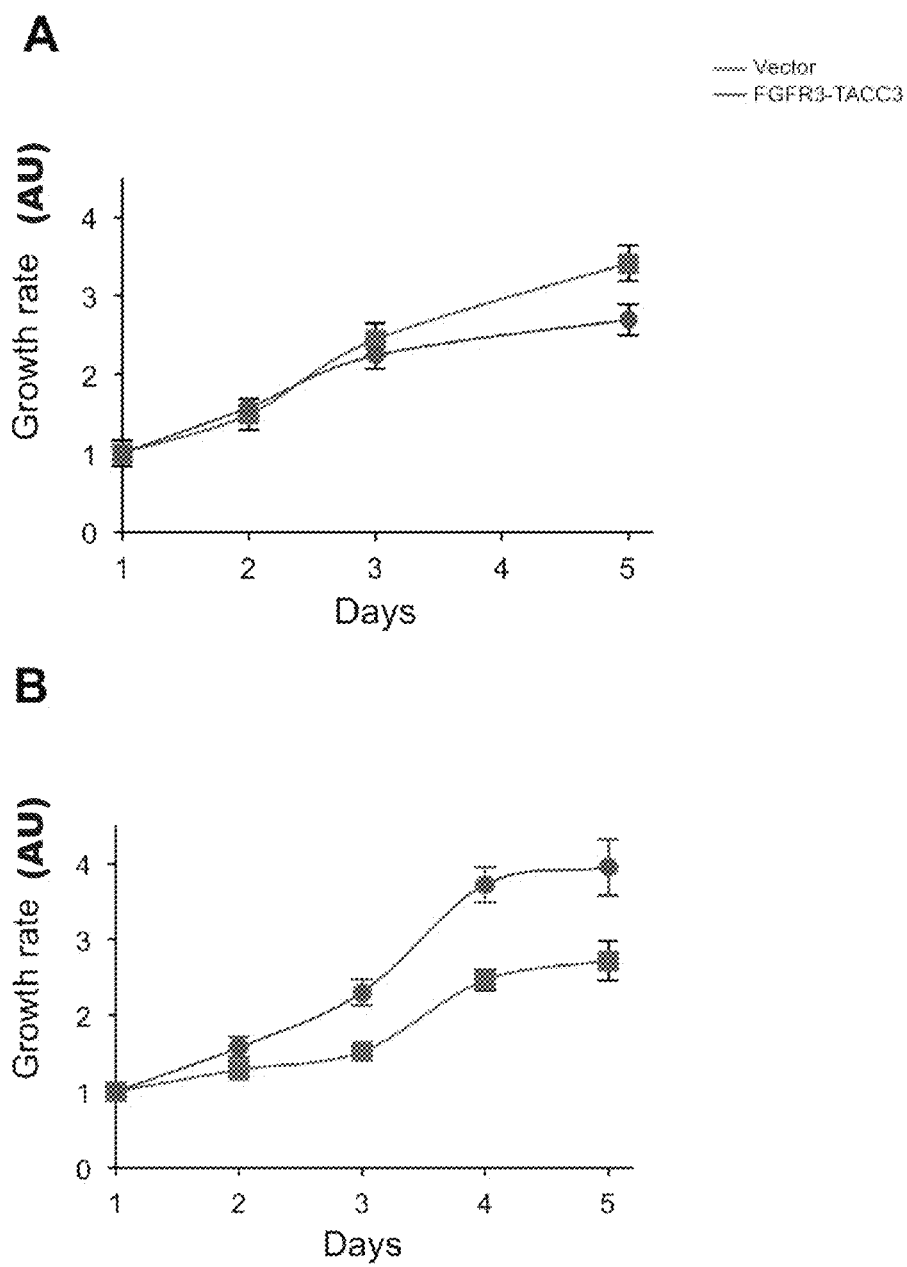
*FIG. 14A-B*

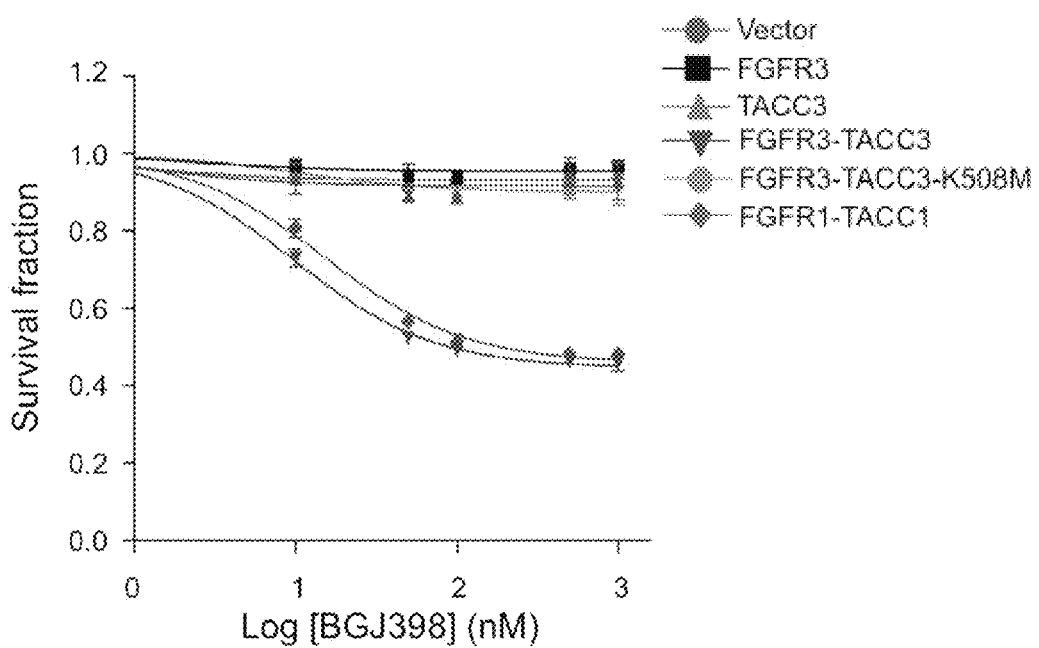
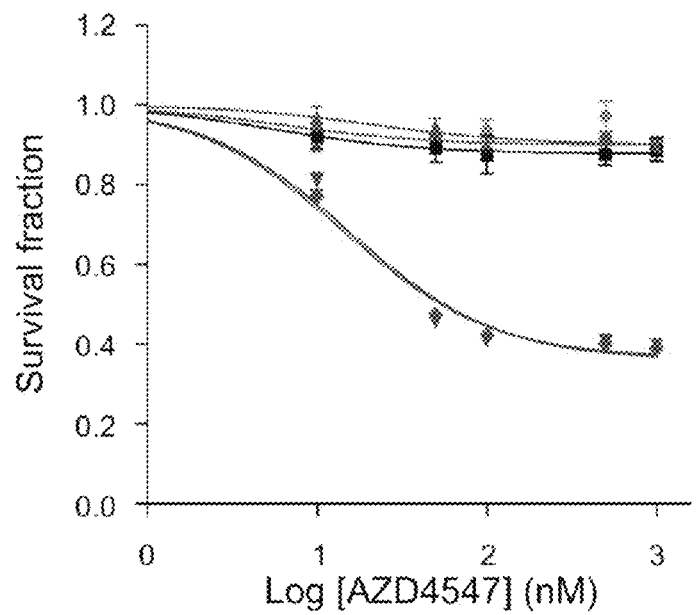
FIG. 14C-D

MGAPACALALCVAVAIVAGASSESLGTEQRVVGRAAEVPGPEPGQQEQLVFCSGDAVELSCPPPGGGPMGPTVWKDCTGLVPSERVLVGPQRLQV
LNASHEDSGAYSCRQRLTQRVLCHFSVRVTDAPSGDDEDGEDEAEDTGVDTGAPYWTRPERMDKKLLAVPAANTVRFRCPAAGNPTPSISWLKNG
REFRGEHRIGGIKLRHQQWSLVMESVVPSDRGNYTCVENKFGSIRQTYTLDVLERSPHRPILQAGLPANQIAVLGSDVEFHCKVYSDAQPHIQWL
KHVEVNGSKVGPDGTPYYTVLKTAGANTTDKELELVLSLHNVTFEDAGEYTCLAGNSIGFSHHSAWLVVLPAEEELVEADEAGSVYAGILSYGVGFF
LFILVVAAVTLCRLRSPPKKGLGSPTVHKISRFPLKRQVSLESNASMSSNTPLVRIARLSSGEGPTLANVSELELPADPKWELSRARLTLGKPLGE
GCFGQVVMAEAIGIDKDRAAKPVTVAVKMLKDDATDKDLSDLVSEMEMMKMIGKHKNIINLLGACTQGGPLYVLVEYAAKGNLREFLRARRPPGLD
YSFDTCKPPEEQLTFKDLVSCAYQVARGMEYLASQKCIHRDLAARNVLVTEDNVMKIADFGLARDVHNLDYYKKTTNGRLPVKWMAPEALFDRVYT
HQSDVWSFGVLLWEIFTLGGSPYPGIPVEELFKLLKEGHRMDKPANCTHDLYMIMRECWHAAPSQRPTFKQLVEDLDRVLTVTSTDFKESALRKQS
LYLKFDPLLRDSPGRPVPVATETSSMHGANETPSGRPREAKLVEFDFLGALDIPVPGPPGVPAPGGPPLSTGPIVDLLQYSQKDLDAVVKATQEE
NRELRSRCEELHGKNLELGKIMDRFEEVVYQAMEEVQKQKELSKAEIQKVLKEKDQLTTDLNSMEKSFSDLFKRFEKQKEVIEGYRKNEESLKKCV
EDYLARITQEGQRYQALKAHAEEKLQLANEEIAQVRSKAQAEALQASLRKEQMRIQSLEKTVEQKTKENEELTRICDDLISKMEKI

FIG.25

A
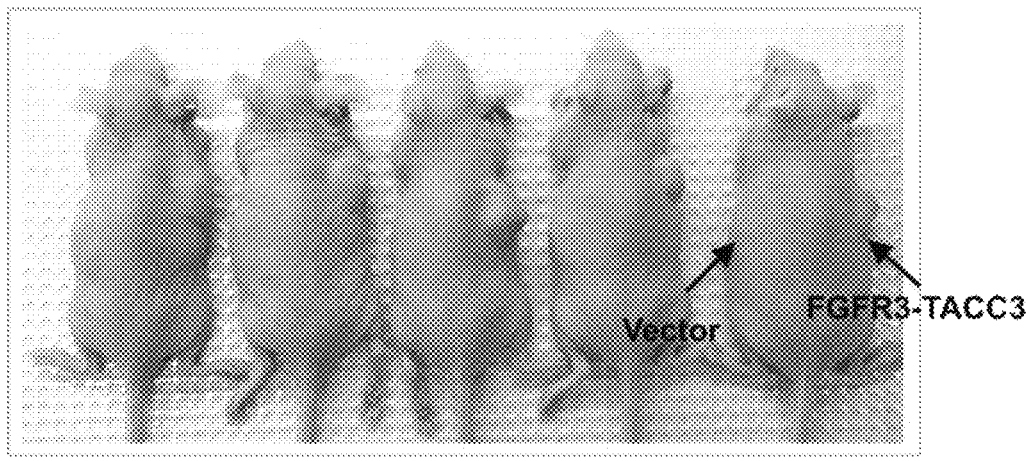
B
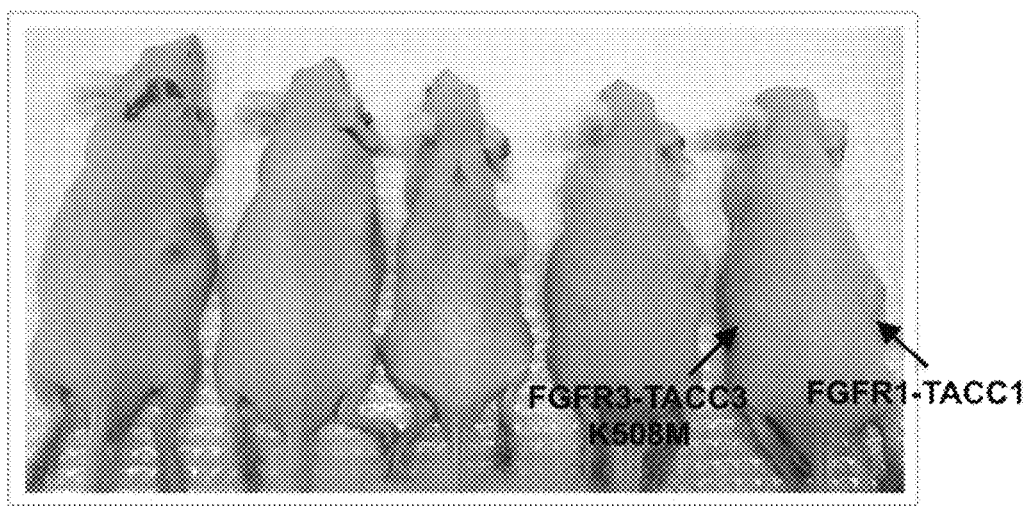
*FIG. 27A-B*

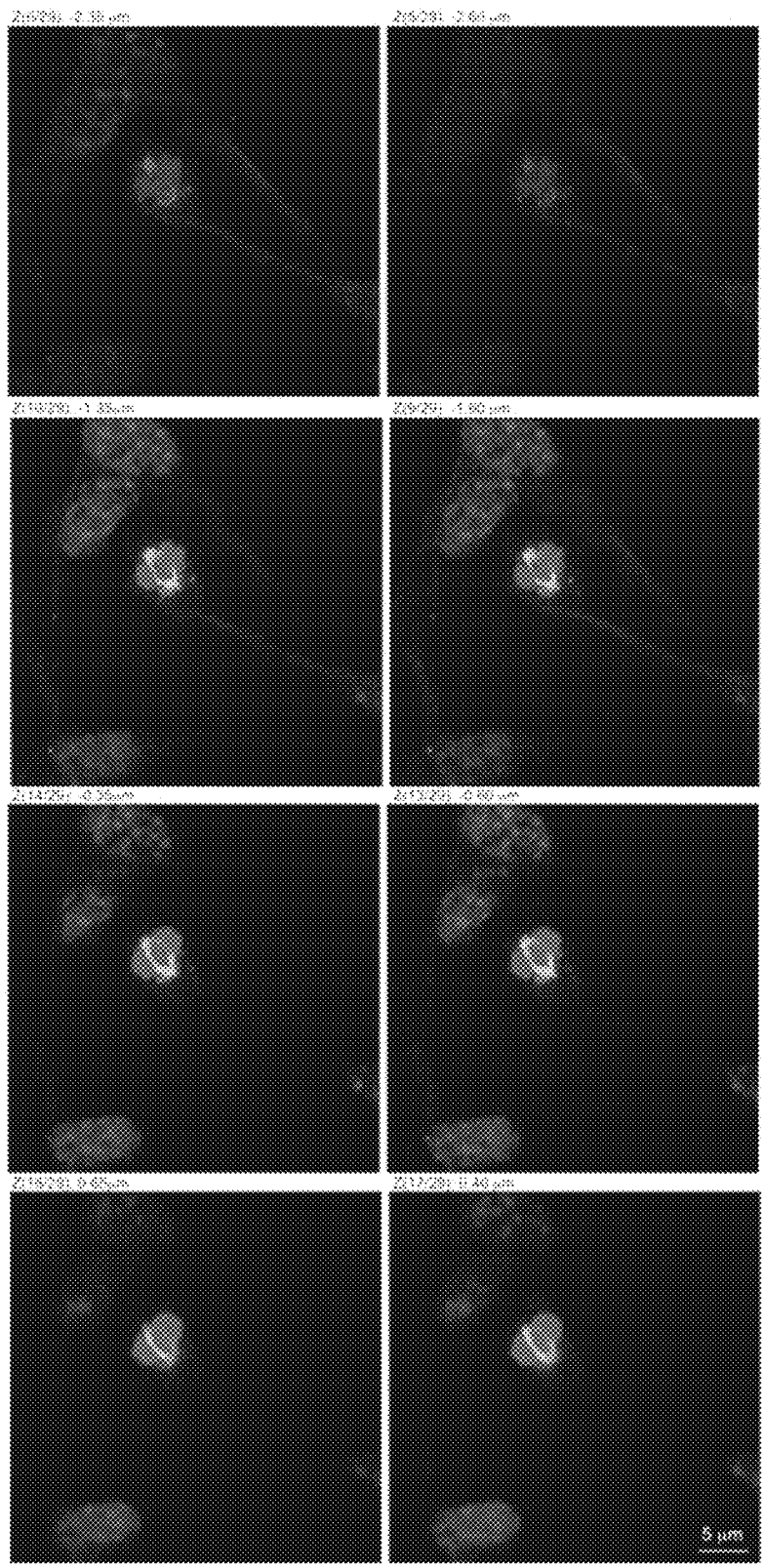
*FIG. 29 – Cont.*

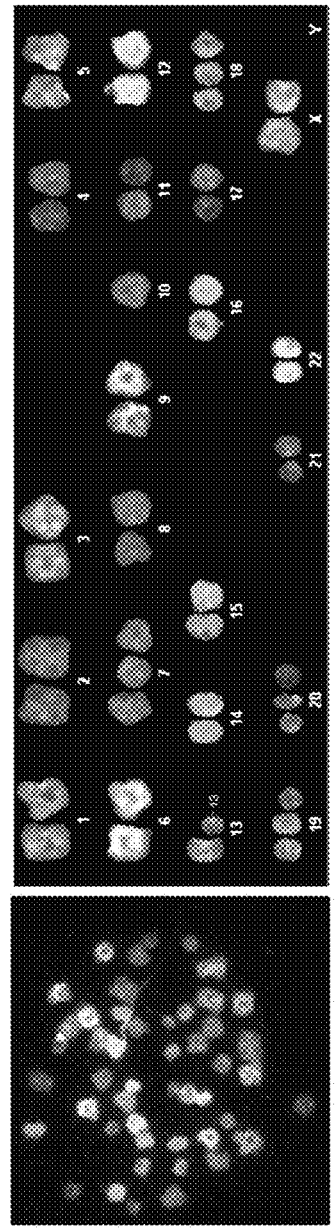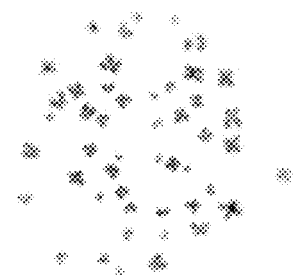
FIG. 30

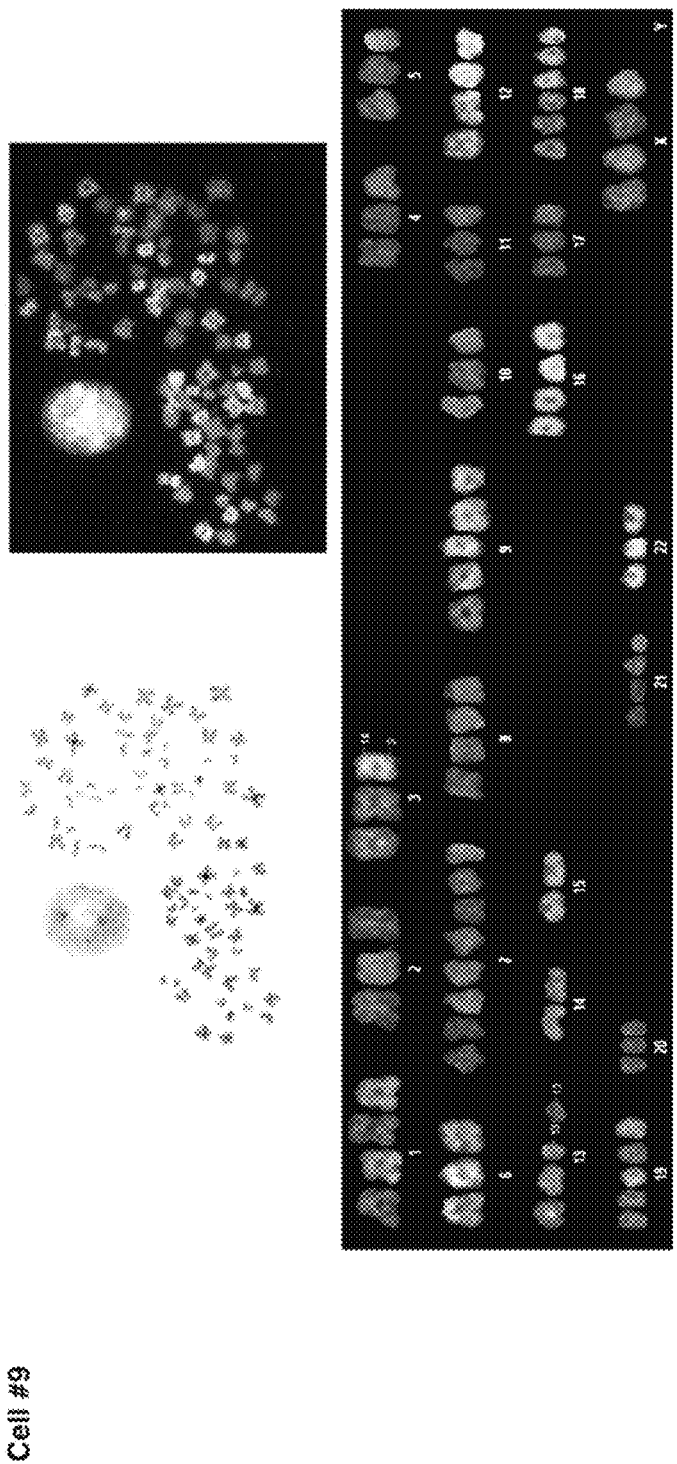
FIG. 30 – CONT.
Cell #9

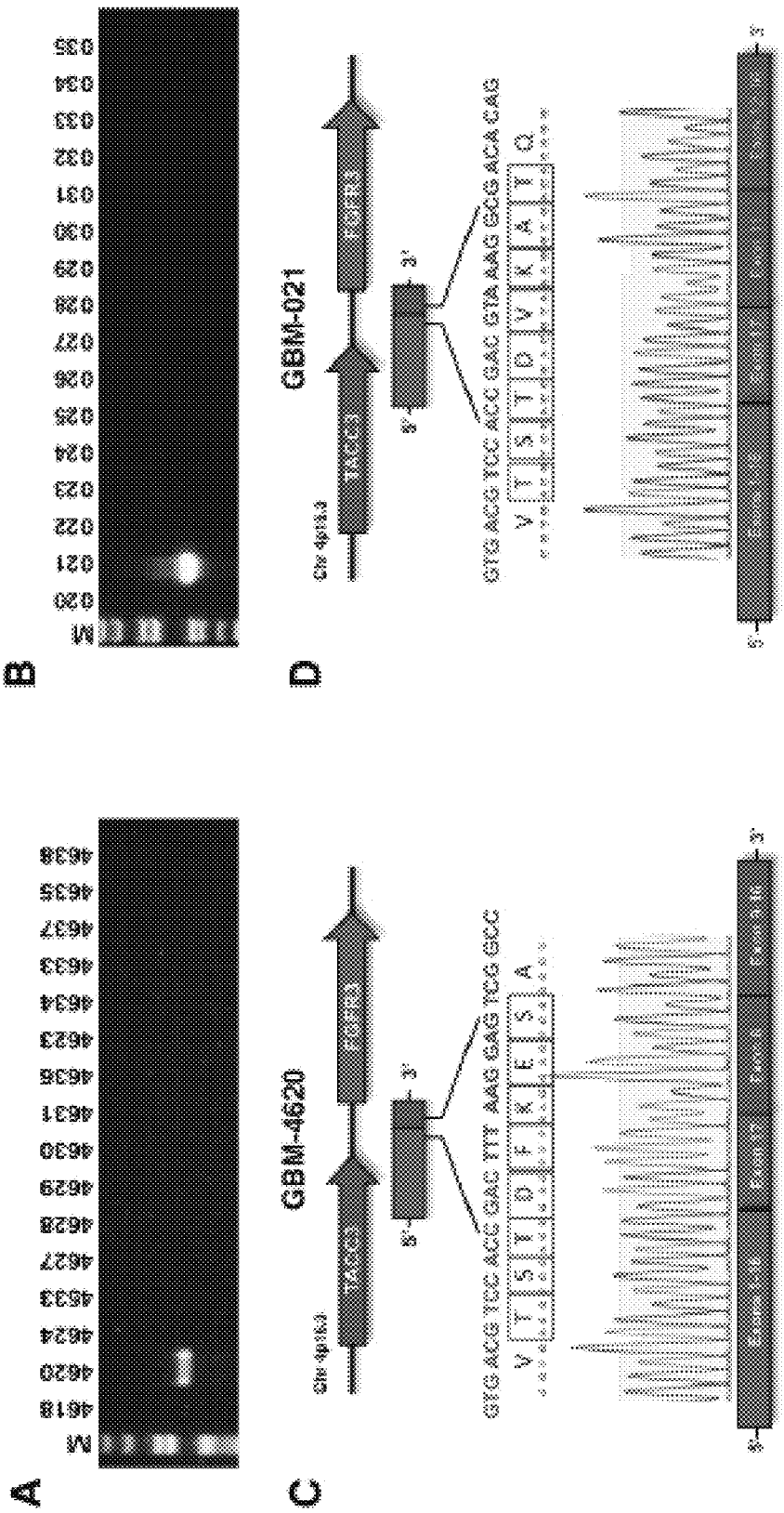
FIGS. 37A-D

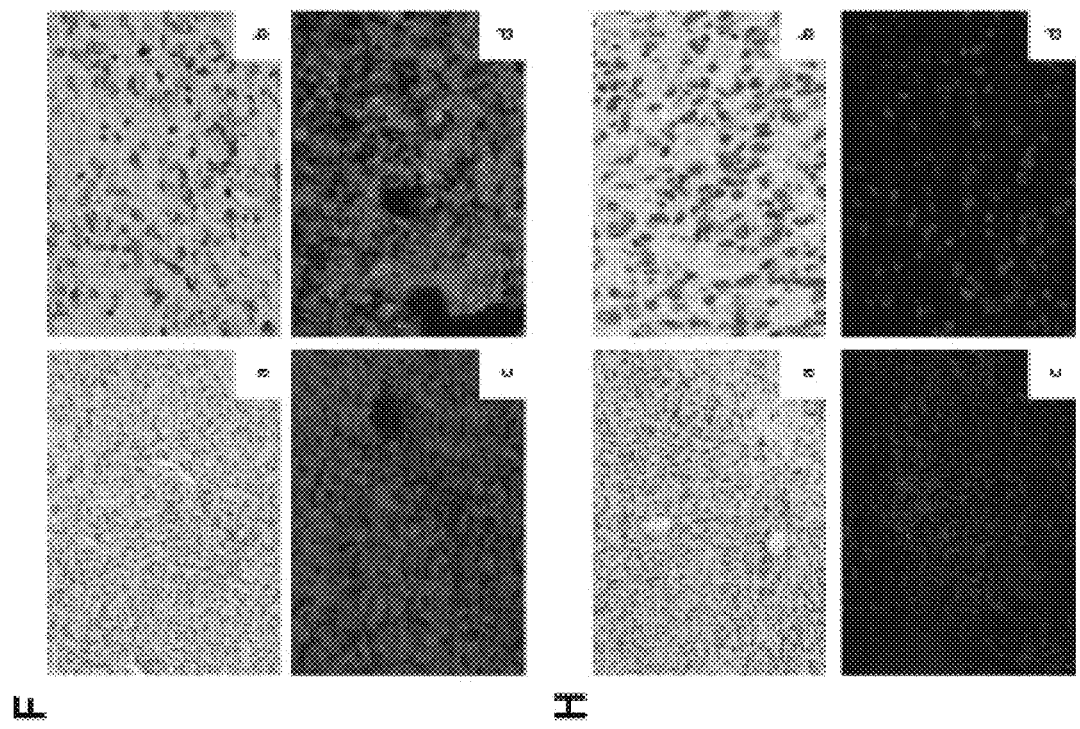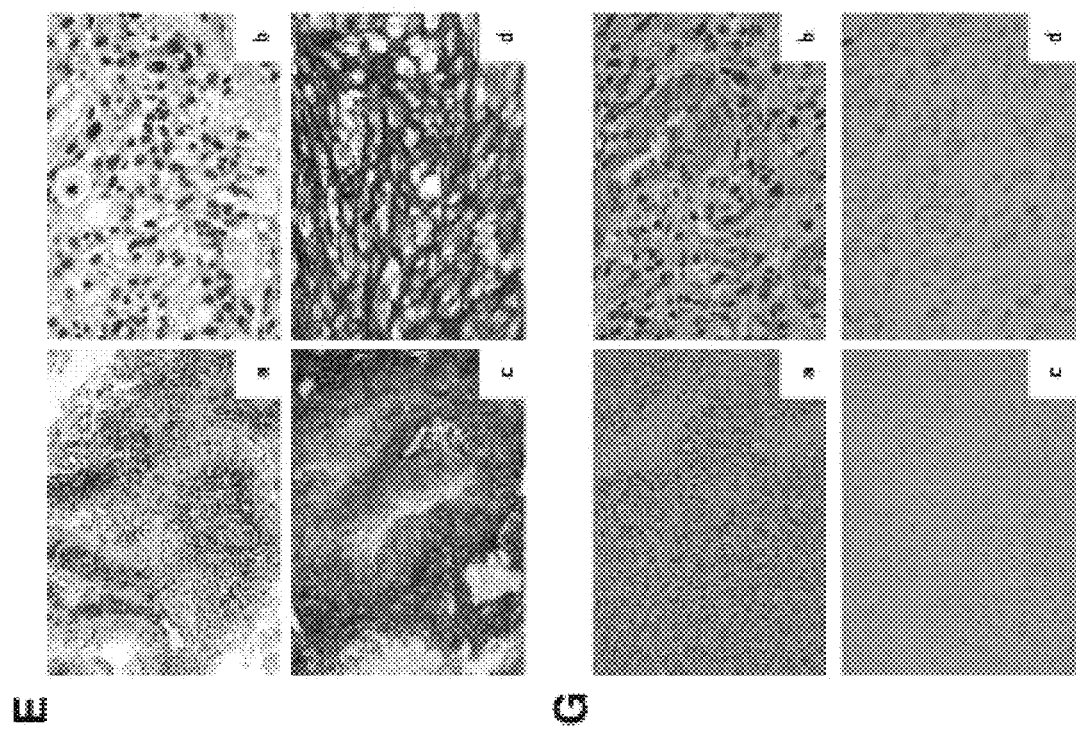
FIGS. 37E-H

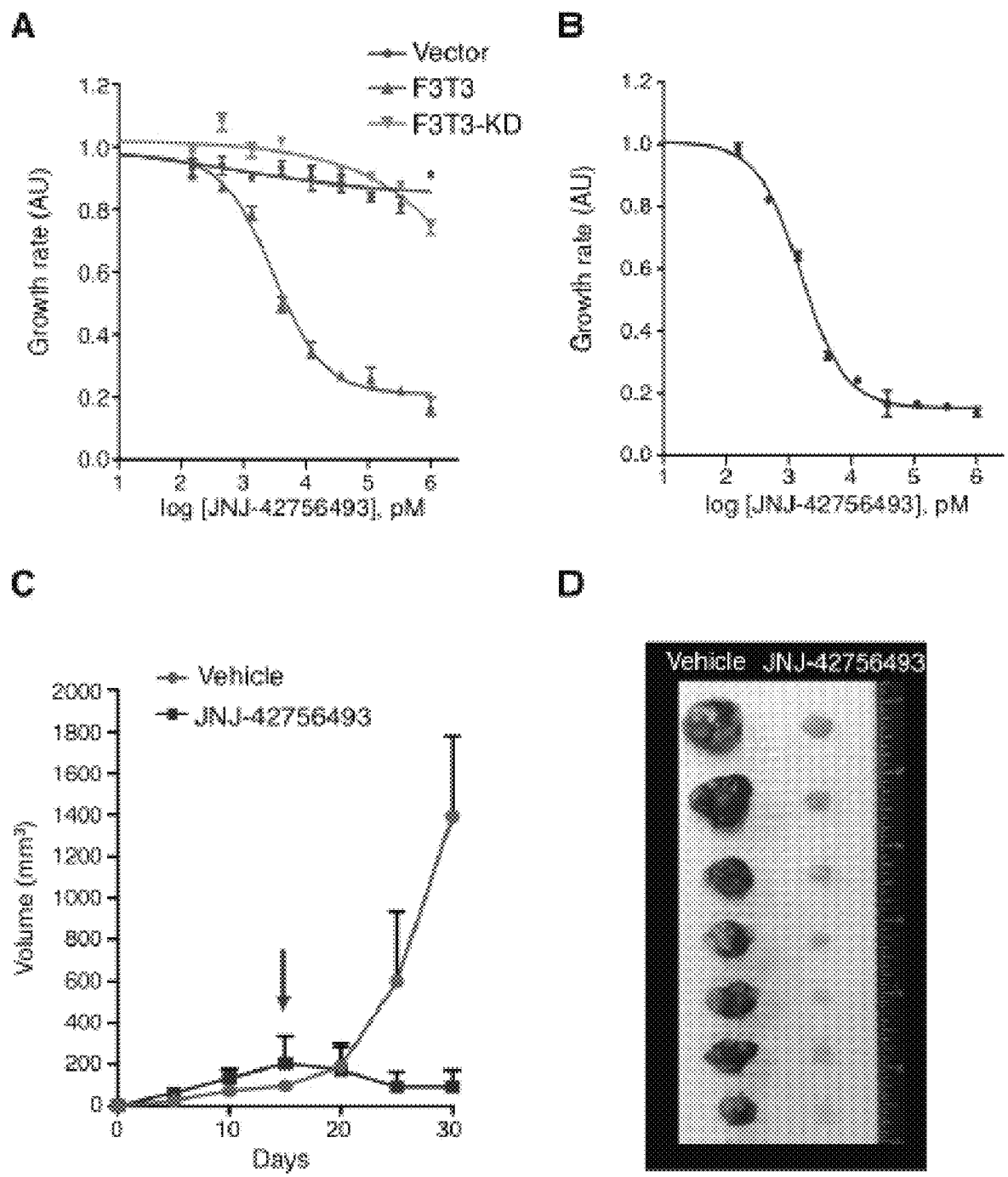
FIGS. 38A-D

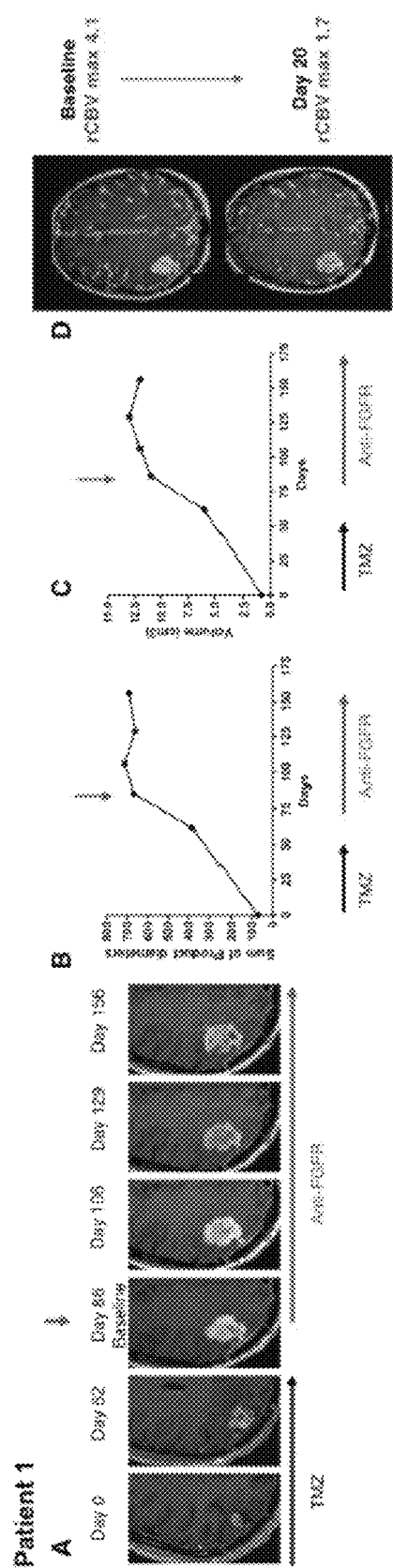
FIGS. 39A-D

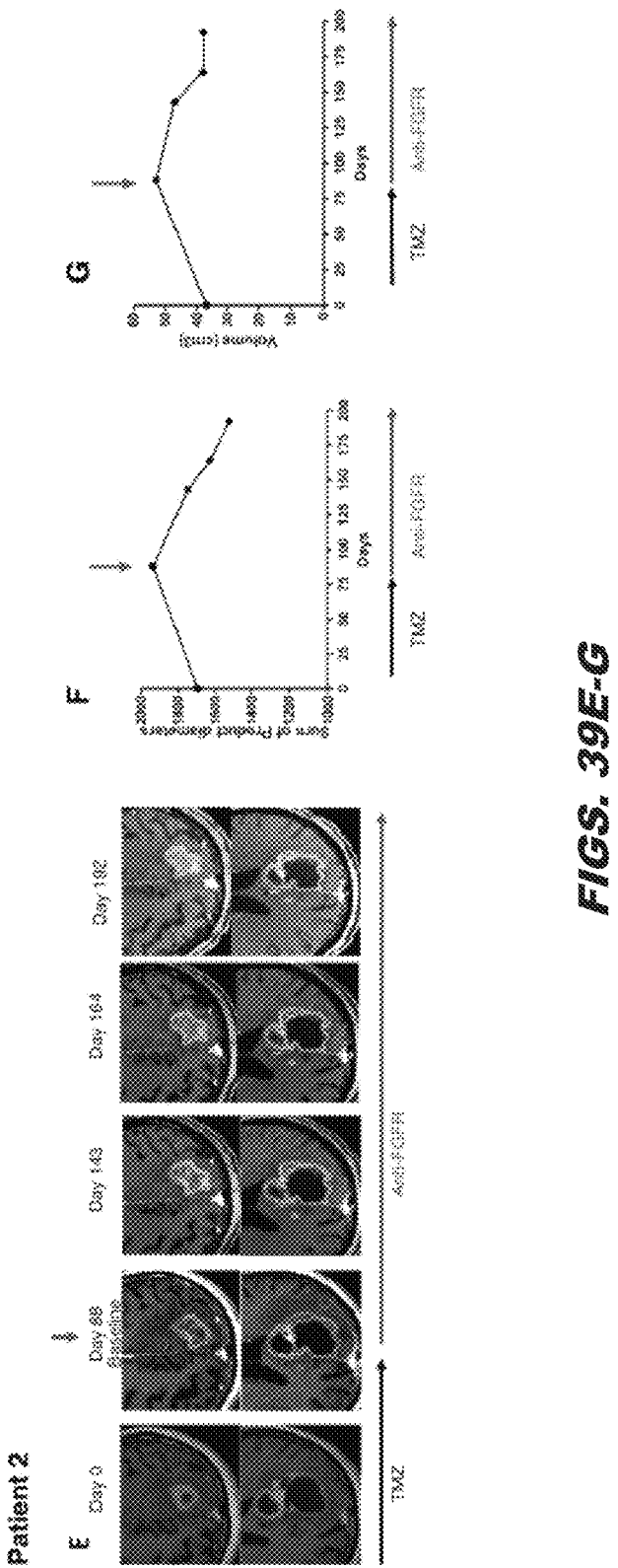
FIGS. 39E-G

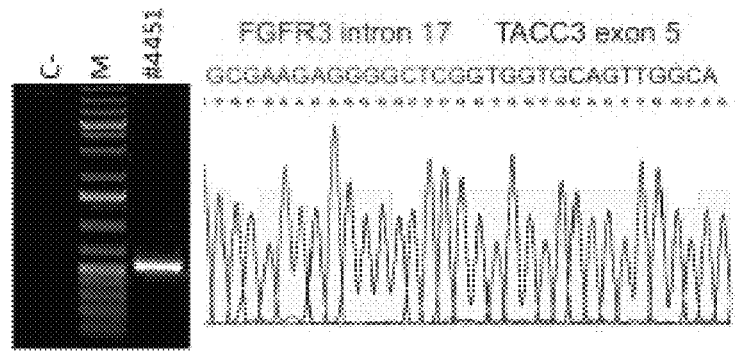
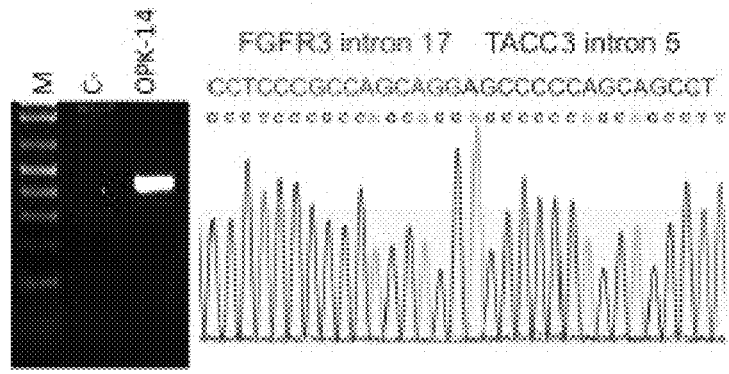
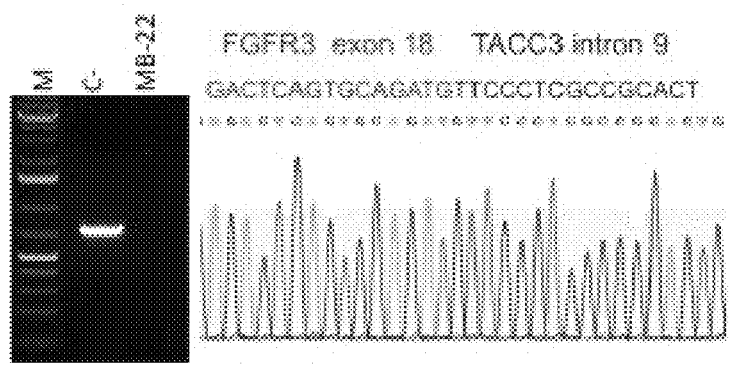
*FIG. 40*

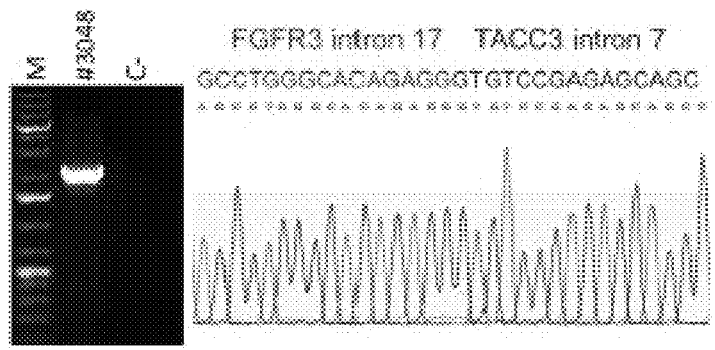
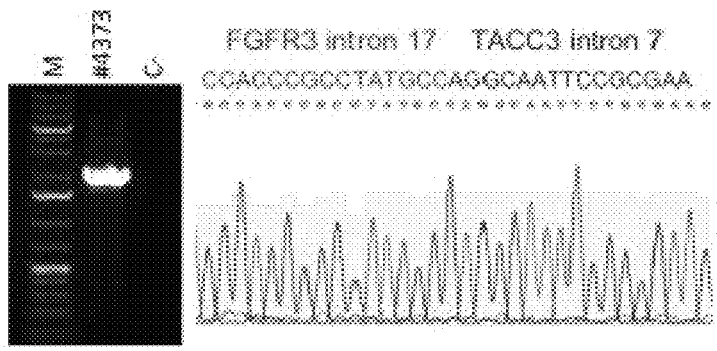
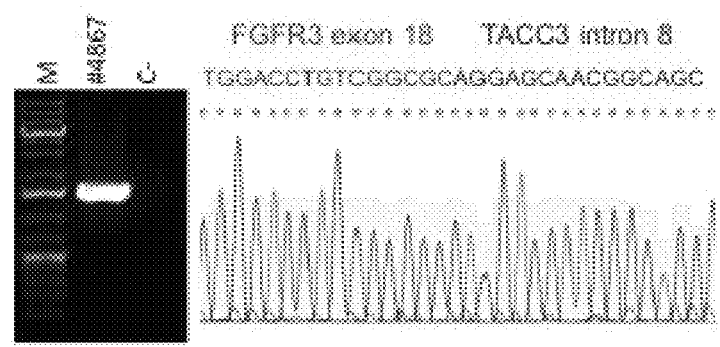
FIG. 40 cont.

Sample #3808
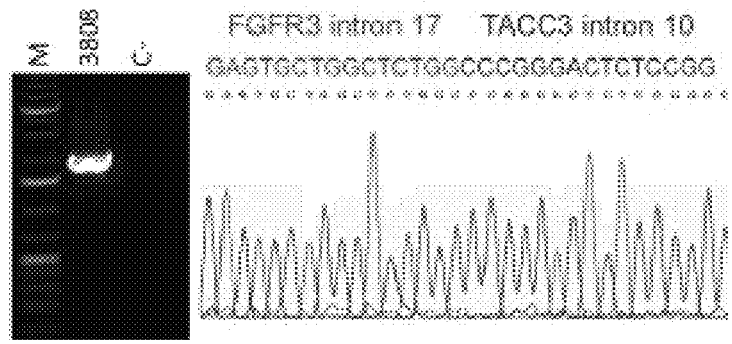
Sample #27-1835
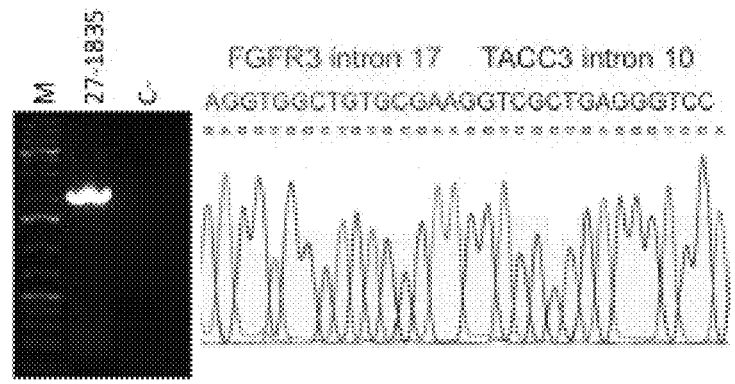
Sample #06-6390
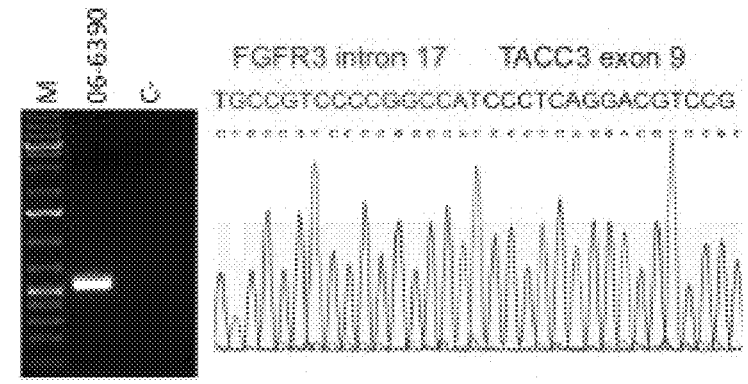
*FIG. 40 cont.*

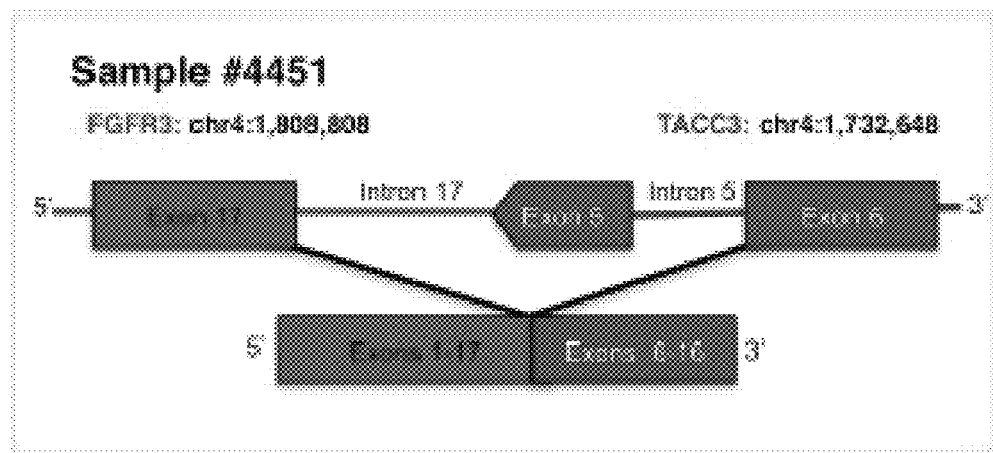
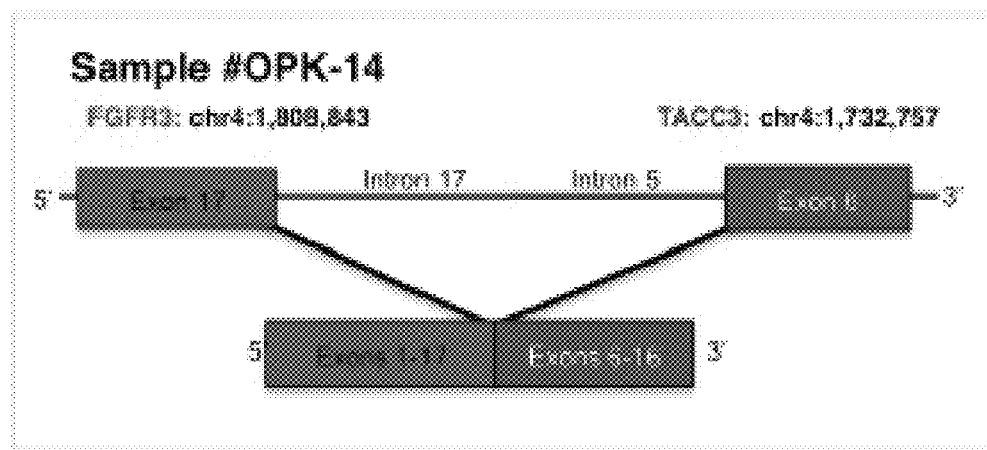
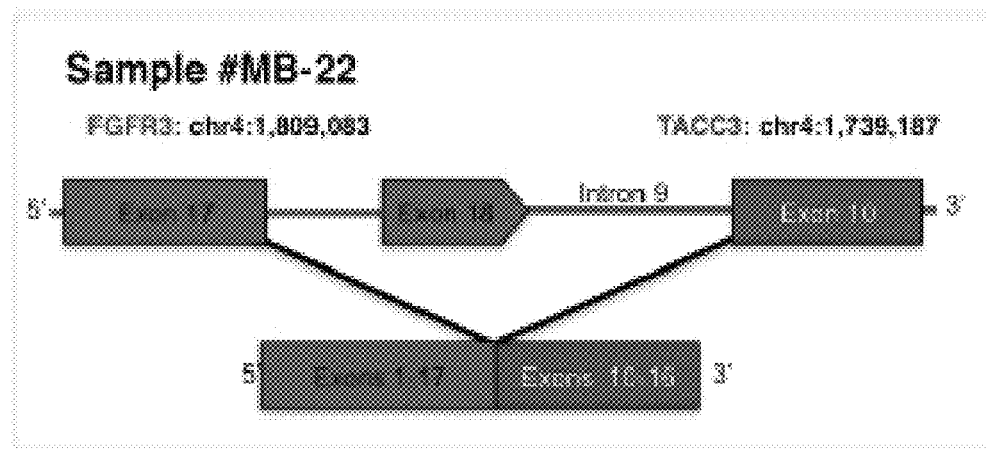
*FIG. 41*

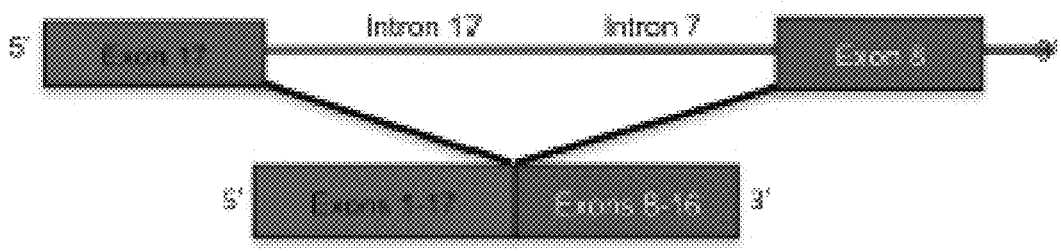
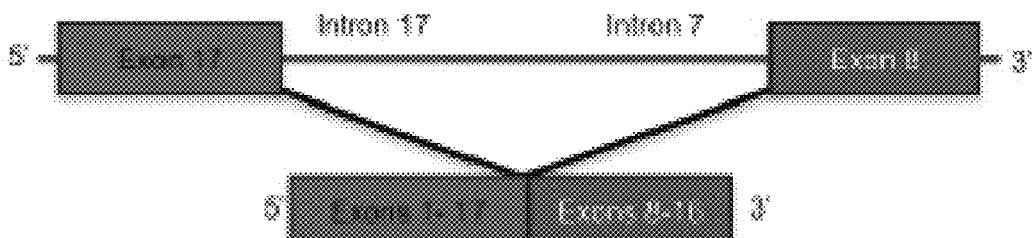
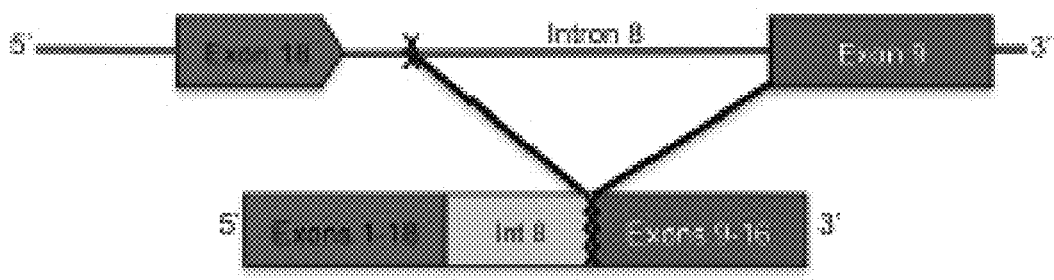
FIG. 41 cont.

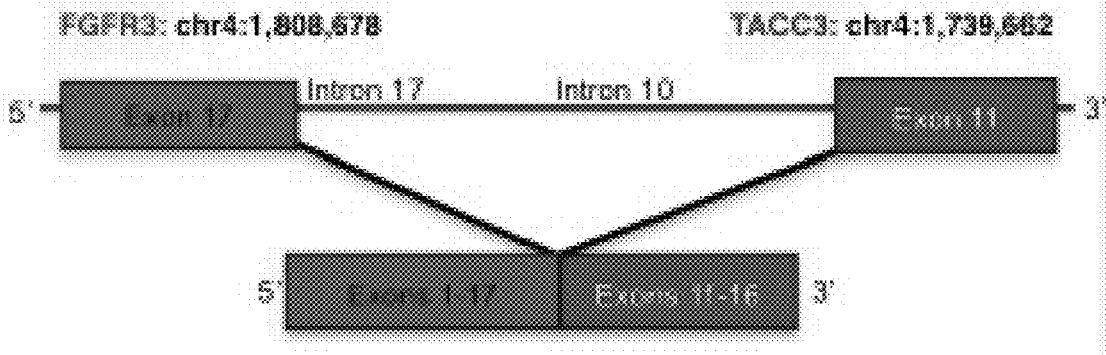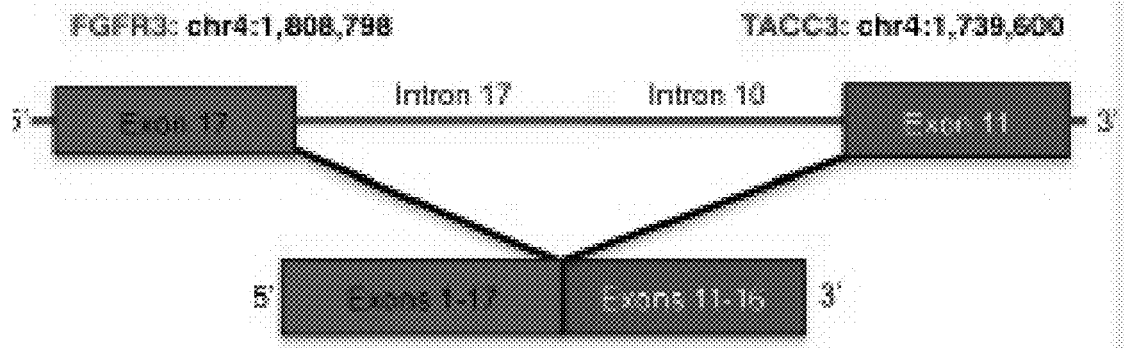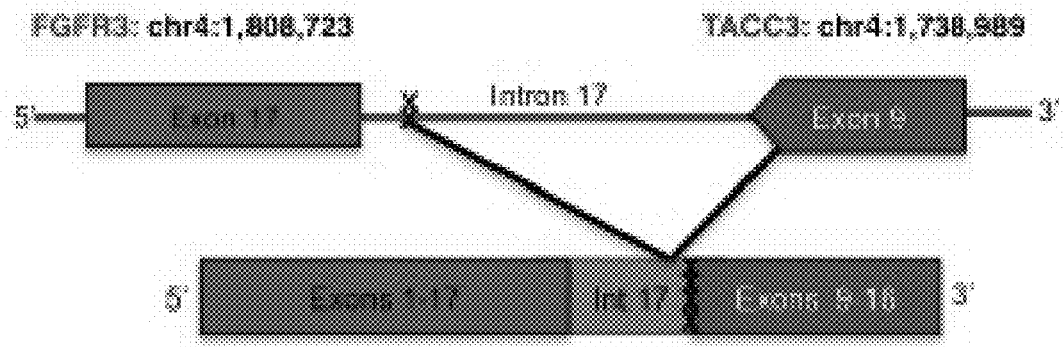
*FIG. 41 cont.*

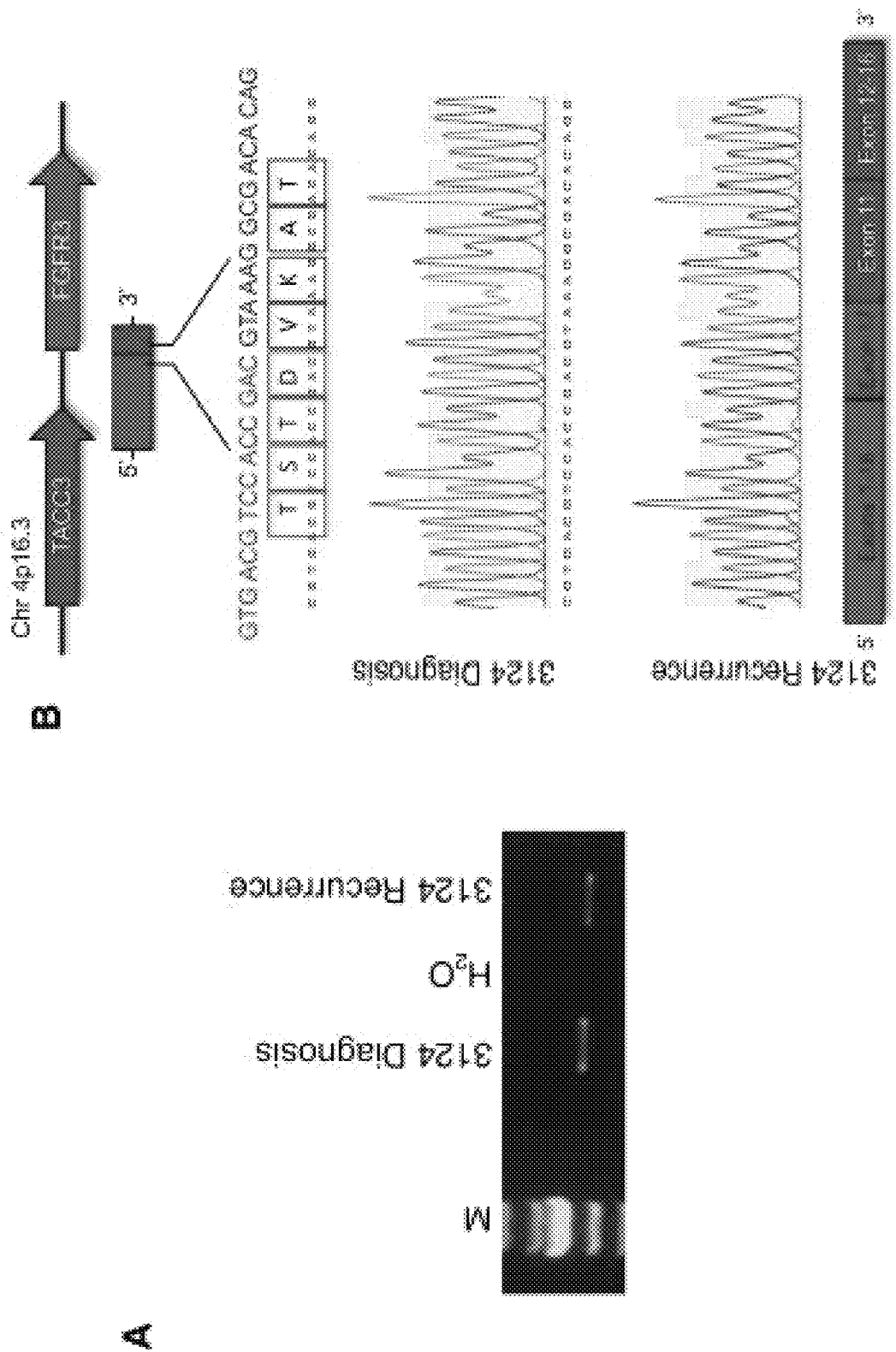
FIGS. 43A-B

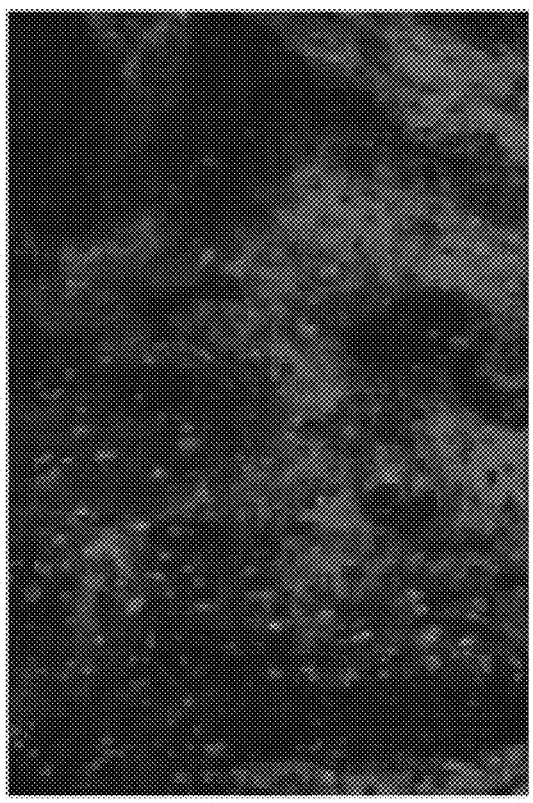
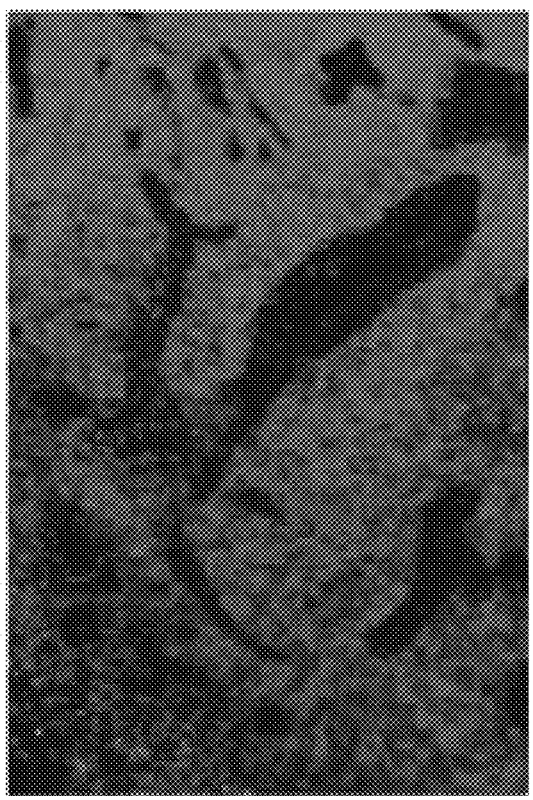
FIG. 43C

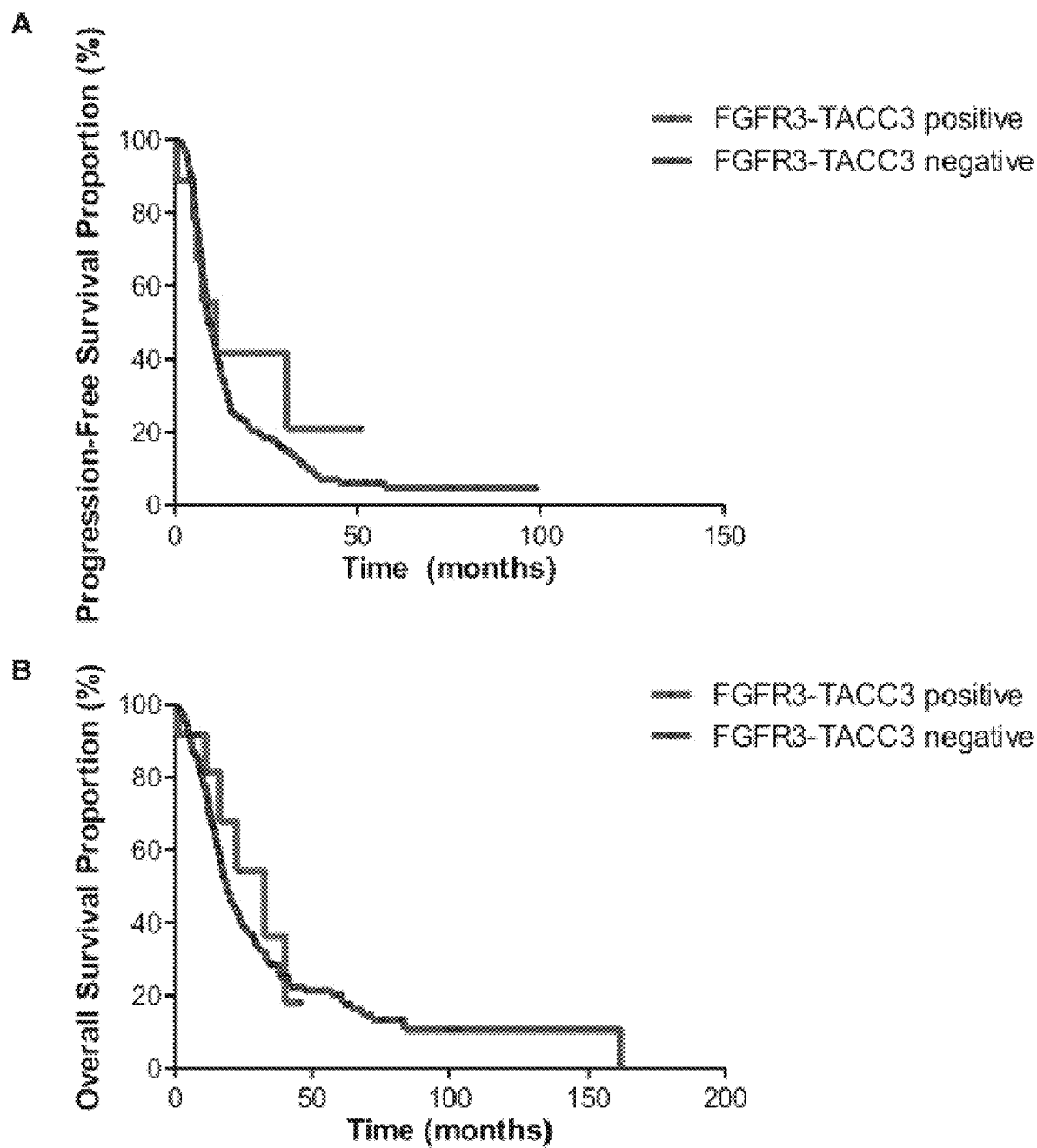
FIGS. 44A-B

US 12,006,503 B2

FUSION PROTEINS AND METHODS THEREOF

This application is a continuation of U.S. patent application Ser. No. 16/508,021, filed Jul. 10, 2019, which is a divisional of U.S. patent application Ser. No. 14/604,530, filed Jan. 23, 2015, which is a continuation-in-part of International Application No. PCT/US2013/051888, filed on Jul. 24, 2013, which claims priority to U.S. Provisional Patent Application No. 61/675,006, filed on Jul. 24, 2012, the content of each of which is hereby incorporated by reference in their entireties. U.S. patent application Ser. No. 14/604,530, filed Jan. 23, 2015 also claims priority to U.S. Provisional Patent Application No. 62/096,311, filed on Dec. 23, 2014, the content of which is hereby incorporated by reference in its entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

The instant application contains a Sequence Listing which has been submitted electronically in ASCII format and is hereby incorporated by reference in its entirety. Said ASCII copy, created on Apr. 24, 2020, is named 0019240_00984US7_SL.txt and is 470,246 bytes in size.

GOVERNMENT SUPPORT

This invention was made with government support under grant numbers CA101644, CA131126, CA178546, and NS061776 awarded by the National Institutes of Health. The government has certain rights in the invention.

BACKGROUND OF THE INVENTION

Glioblastoma multiforme (GBM) is the most common form of brain cancer and among the most incurable and lethal of all human cancers. The current standard of care includes surgery, chemotherapy, and radiation therapy. However, the prognosis of GBM remains uniformly poor. There are few available targeted therapies and none that specifically target GBM.

The target population of GBM patients who may carry FGFR-TACC gene fusions and would benefit from targeted inhibition of FGFR kinase activity is estimated to correspond to 6,000 patients per year world-wide.

SUMMARY OF THE INVENTION

The invention is based, at least in part, on the discovery of a highly expressed class of gene fusions in GBM, which join the tyrosine kinase domain of FGFR genes to the TACC domain of TACC1 or TACC3. The invention is based, at least in part, on the finding that FGFR-TACC fusions identify a subset of GBM patients who will benefit from targeted inhibition of the tyrosine kinase activity of FGFR. Identification of fusions of FGFR and TACC genes in glioblastoma patients and other subjects afflicted with a gene-fusion associated cancer (such as an epithelial cancer) are useful therapeutic targets.

The invention is also based, at least in part, on the discovery of gene fusions joining the tyrosine kinase domain of FGFR genes to the TACC domain of TACC1 or TACC3 in grade II and III glioma, The invention is based, at least in part, on the finding that FGFR-TACC fusions identify a subset of grade II and III glioma patients who will benefit from targeted inhibition of the tyrosine kinase activity of FGFR. Identification of fusions of FGFR and TACC genes in glioma patients are useful therapeutic targets.

An aspect of the invention provides for a purified fusion protein comprising a tyrosine kinase domain of an FGFR protein fused to a polypeptide that constitutively activates the tyrosine kinase domain of the FGFR protein. In one embodiment, the FGFR protein is FGFR1, FGFR2, FGFR3, or FGR4. In another embodiment, the purified fusion protein is essentially free of other human proteins.

An aspect of the invention provides for a purified fusion protein comprising a transforming acidic coiled-coil (TACC) domain fused to a polypeptide with a tyrosine kinase domain, wherein the TACC domain constitutively activates the tyrosine kinase domain. In one embodiment, the TACC protein is TACC1, TACC2, or TACC3. In another embodiment, the purified fusion protein is essentially free of other human proteins.

An aspect of the invention provides for a purified fusion protein comprising the tyrosine kinase domain of an FGFR protein fused 5' to the TACC domain of a transforming acidic coiled-coil-containing (TACC) protein. In one embodiment, the FGFR protein is FGFR1, FGFR2, FGFR3, or FGR4. In another embodiment, the TACC protein is TACC1, TACC2, or TACC3. In another embodiment, the purified fusion protein is essentially free of other human proteins.

An aspect of the invention provides for a purified fusion protein encoded by an FGFR1-TACC1 nucleic acid, wherein FGFR1-TACC1 comprises a combination of exons 1-17 of FGFR1 located on human chromosome 8p11 spliced 5' to a combination of exons 7-13 of TACC1 located on human chromosome 8p11, wherein a genomic breakpoint occurs in any one of exons 1-17 of FGFR1 and any one of exons 7-13 of TACC1. In another embodiment, the purified fusion protein is essentially free of other human proteins.

An aspect of the invention provides for a purified fusion protein encoded by an FGFR2-TACC2 nucleic acid, wherein FGFR2-TACC2 comprises a combination of any exons 1-18 of FGFR2 located on human chromosome 10q26 spliced 5' to a combination of any exons 1-23 of TACC2 located on human chromosome 10q26. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-16 of FGFR3 located on human chromosome 4p16 spliced 5' to a combination of exons 8-16 of TACC3 located on human chromosome 4p16, wherein a genomic breakpoint occurs in any one of exons 1-16 of FGFR3 and any one of exons 8-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-18 of FGFR3 located on human chromosome 4p16 spliced 5' to a combination of exons 4-16 of TACC3 located on human chromosome 4p16, wherein a genomic breakpoint occurs in any one of exons 1-18 of FGFR3 and any one of exons 4-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-16 of FGFR3 located on human chromosome 4p16 spliced 5' to a combination of exons 8-16 of TACC3 located on human chromosome 4p16, wherein a genomic breakpoint occurs in any one of introns 1-16 of FGFR3 and any one of exons 8-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-18 of FGFR3 located on human chromosome 4p16 spliced 5' to a combination of exons 4-16 of TACC3 located on human chromosome 4p16, wherein a genomic breakpoint occurs in any one of introns 1-18 of FGFR3 and any one of exons 4-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-16 of FGFR3 located on human chromosome 4p16 spliced 5' to a combination of exons 8-16 of TACC3 located on human chromosome 4p16, wherein a genomic breakpoint occurs in any one of exons 1-16 of FGFR3 and any one of introns 7-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-18 of FGFR3 located on human chromosome 4p16 spliced 5' to a combination of exons 4-16 of TACC3 located on human chromosome 4p16, wherein a genomic breakpoint occurs in any one of exons 1-18 of FGFR3 and any one of introns 3-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-16 of FGFR3 located on human chromosome 4p16 spliced 5' to a combination of exons 8-16 of TACC3 located on human chromosome 4p16, wherein a genomic breakpoint occurs in any one of introns 1-16 of FGFR3 and any one of introns 7-16 of TACC3. In another embodiment, the purified fusion protein is essentially free of other human proteins.

An aspect of the invention provides for a purified fusion protein encoded by an FGFR3-TACC3 nucleic acid, wherein FGFR3-TACC3 comprises a combination of exons 1-18 of FGFR3 located on human chromosome 4p16 spliced 5' to a combination of exons 4-16 of TACC3 located on human chromosome 4p16, wherein a genomic breakpoint occurs in any one of introns 1-18 of FGFR3 and any one of introns 3-16 of TACC3. In another embodiment, the purified fusion protein is essentially free of other human proteins.

An aspect of the invention provides for a synthetic nucleic acid encoding the fusion proteins described above.

An aspect of the invention provides for a purified FGFR3-TACC3 fusion protein comprising SEQ ID NO: 79, 158, 159, 160, 161, 539, 540, 541, 542, 543, 544, 545, 546, 547. In another embodiment, the purified fusion protein is essentially free of other human proteins.

An aspect of the invention provides for a purified FGFR3-TACC3 fusion protein having a genomic breakpoint comprising at least 3 consecutive amino acids from amino acids 730-758 of SEQ ID NO: 90 and comprising at least 3 consecutive amino acids from amino acids 549-838 of SEQ ID NO: 92. In another embodiment, the purified fusion protein is essentially free of other human proteins.

An aspect of the invention provides for a purified FGFR3-TACC3 fusion protein having a genomic breakpoint comprising at least 3 consecutive amino acids from amino acids 730-781 of SEQ ID NO: 90 and comprising at least 3 consecutive amino acids from amino acids 432-838 of SEQ ID NO: 92. In another embodiment, the purified fusion protein is essentially free of other human proteins.

An aspect of the invention provides for a purified FGFR3-TACC3 fusion protein having a genomic breakpoint comprising SEQ ID NO: 78. In another embodiment, the purified fusion protein is essentially free of other human proteins.

An aspect of the invention provides for a purified FGFR3-TACC3 fusion protein having a genomic breakpoint comprising any one of SEQ ID NOS: 85, 86, 87, 89, 516 or 518. In another embodiment, the purified fusion protein is essentially free of other human proteins.

An aspect of the invention provides for a purified FGFR1-TACC1 fusion protein comprising SEQ ID NO: 150. In another embodiment, the purified fusion protein is essentially free of other human proteins.

An aspect of the invention provides for a purified FGFR1-TACC1 fusion protein having a genomic breakpoint comprising at least 3 consecutive amino acids from amino acids 746-762 of SEQ ID NO: 146 and comprising at least 3 consecutive amino acids from amino acids 572-590 of SEQ ID NO: 148. In another embodiment, the purified fusion protein is essentially free of other human proteins.

An aspect of the invention provides for a purified FGFR1-TACC1 fusion protein having a genomic breakpoint comprising at least 3 consecutive amino acids from amino acids 746-762 of SEQ ID NO: 146 and comprising at least 3 consecutive amino acids from amino acids 571-590 of SEQ ID NO: 148. In another embodiment, the purified fusion protein is essentially free of other human proteins.

An aspect of the invention provides for a purified FGFR I-TACC1 fusion protein having a genomic breakpoint comprising SEQ ID NO: 88. In another embodiment, the purified fusion protein is essentially free of other human proteins.

An aspect of the invention provides for a purified DNA encoding an FGFR3-TACC3 fusion protein comprising SEQ ID NO: 94, 530, 531, 532, 533, 534, 535, 536, 537, or 538. In another embodiment, the purified fusion protein is essentially free of other human proteins. An aspect of the invention provides for a purified cDNA encoding an FGFR3-TACC3 fusion protein comprising SEQ ID NO: 94, 530, 531, 532, 533, 534, 535, 536, 537, or 538.

An aspect of the invention provides for a synthetic nucleic acid encoding an FGFR3-TACC3 fusion protein having a genomic breakpoint comprising at least 9 consecutive in-frame nucleotides from nucleotides 2443-2530 of SEQ ID NO: 91 and comprising at least 9 consecutive in-frame nucleotides from nucleotides 1800-2847 of SEQ ID NO: 93.

An aspect of the invention provides for a synthetic nucleic acid encoding an FGFR3-TACC3 fusion protein having a genomic breakpoint comprising any one of SEQ ID NOS: 1-77, or 519-527.

An aspect of the invention provides for a synthetic nucleic acid encoding an FGFR1-TACC1 fusion protein comprising SEQ ID NO: 151.

An aspect of the invention provides for a synthetic nucleic acid encoding an FGFR1-TACC1 fusion protein having a genomic breakpoint comprising at least 9 consecutive in-frame nucleotides from nucleotides 3178-3228 of SEQ ID NO: 147 and comprising at least 9 consecutive in-frame nucleotides from nucleotides 2092-2794 of SEQ ID NO: 149.

An aspect of the invention provides for a synthetic nucleic acid encoding an FGFR1-TACC1 fusion protein having a genomic breakpoint comprising SEQ ID NO: 83.

An aspect of the invention provides for an antibody or antigen-binding fragment thereof, that specifically binds to a purified fusion protein comprising a tyrosine kinase domain of an FGFR protein fused to a polypeptide that constitutively activates the tyrosine kinase domain of the FGFR protein. In one embodiment, the FGFR protein is FGFR1, FGFR2, FGFR3, or FGFR4. In another embodiment, the fusion protein is an FGFR-TACC fusion protein. In a further embodiment, the FGFR-TACC fusion protein is FGFR1-TACC1, FGFR2-TACC2, or FGFR3-TACC3. In some embodiments, the FGFR1-TACC1 fusion protein comprises the amino acid sequence of SEQ ID NO: 150. In other embodiments, the FGFR3-TACC3 fusion protein comprises the amino acid sequence of SEQ ID NO: 79, 158, 159, 160, 161, 539, 540, 541, 542, 543, 544, 545, 546, or 547.

An aspect of the invention provides for a composition for decreasing in a subject the expression level or activity of a fusion protein comprising the tyrosine kinase domain of an FGFR protein fused to a polypeptide that constitutively activates the tyrosine kinase domain of the FGFR protein, the composition in an admixture of a pharmaceutically acceptable carrier comprising an inhibitor of the fusion protein. In one embodiment, the fusion protein is an FGFR-TACC fusion protein. In another embodiment, the inhibitor comprises an antibody that specifically binds to a FGFR-TACC fusion protein or a fragment thereof; a small molecule that specifically binds to a FGFR protein; a small molecule that specifically binds to a TACC protein; an antisense RNA or antisense DNA that decreases expression of a FGFR-TACC fusion polypeptide; a siRNA that specifically targets a FGFR-TACC fusion gene; or a combination of the listed inhibitors. In a further embodiment, the FGFR protein is FGFR1, FGFR2, FGFR3, or FGFR4. In some embodiments, the FGFR-TACC fusion protein is FGFR1-TACC1, FGFR2-TACC2, or FGFR3-TACC3. In other embodiments, the small molecule that specifically binds to a FGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination of the listed small molecules. In other embodiments, the small molecule that specifically binds to a FGFR protein comprises an oral pan-FGFR tyrosine kinase inhibitor. In other embodiments, the small molecule that specifically binds to a FGFR protein comprises JNJ-42756493.

An aspect of the invention provides for a method for decreasing in a subject in need thereof the expression level or activity of a fusion protein comprising the tyrosine kinase domain of an FGFR protein fused to a polypeptide that constitutively activates the tyrosine kinase domain of the FGFR protein. In one embodiment, the method comprises administering to the subject a therapeutic amount of a composition for decreasing the expression level or activity in a subject of a fusion protein comprising the tyrosine kinase domain of an FGFR protein fused to a polypeptide that constitutively activates the tyrosine kinase domain of the FGFR protein. In one embodiment, the method comprises obtaining a sample from the subject to determine the level of expression of an FGFR fusion molecule in the subject. In some embodiments, the sample is incubated with an agent that binds to an FGFR fusion molecule, such as an antibody, a probe, a nucleic acid primer, and the like. In one embodiment, the detection or determining comprises nucleic acid sequencing, selective hybridization, selective amplification, gene expression analysis, or a combination thereof. In another embodiment, the detection or determination comprises protein expression analysis, for example by western blot analysis, ELISA, immunostaining, or other antibody detection methods. In a further embodiment, the method comprises determining whether the fusion protein expression level or activity is decreased compared to fusion protein expression level or activity prior to administration of the composition, thereby decreasing the expression level or activity of the fusion protein. In one embodiment, the fusion protein is an FGFR-TACC fusion protein. In a further embodiment, the FGFR protein is FGFR1, FGFR2, FGFR3, or FGFR4. In some embodiments, the FGFR-TACC fusion protein is FGFR1-TACC1, FGFR2-TACC2, or FGFR3-TACC3. In one embodiment, the composition for decreasing the expression level or activity of a fusion protein comprises an antibody that specifically binds to a FGFR-TACC fusion protein or a fragment thereof; a small molecule that specifically binds to a FGFR protein; a small molecule that specifically binds to a TACC protein; an antisense RNA or antisense DNA that decreases expression of a FGFR-TACC fusion polypeptide; a siRNA that specifically targets a FGFR-TACC fusion gene; or a combination of the listed inhibitors. In a further embodiment, the FGFR protein is FGFR1, FGFR2, FGFR3, or FGFR4. In some embodiments, the FGFR-TACC fusion protein is FGFR1-TACC1, FGFR2-TACC2, or FGFR3-TACC3. In other embodiments, the small molecule that specifically binds to a FGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination of the small molecules listed. In other embodiments, the small molecule that specifically binds to a FGFR protein comprises an oral pan-FGFR tyrosine kinase inhibitor. In other embodiments, the small molecule that specifically binds to a FGFR protein comprises JNJ-42756493.

An aspect of the invention provides for a method for treating a gene-fusion associated cancer in a subject in need thereof, the method comprising administering to the subject an effective amount of a FGFR fusion molecule inhibitor. In one embodiment, the gene-fusion associated cancer comprises an epithelial cancer. In one embodiment, the gene-fusion associated cancer comprises glioblastoma multiforme, breast cancer, lung cancer, prostate cancer, or colorectal carcinoma. In one embodiment, the gene-fusion associated cancer comprises bladder carcinoma, squamous lung carcinoma and head and neck carcinoma. In one embodiment, the gene-fusion associated cancer comprises glioma. In one embodiment, the gene-fusion associated cancer comprises grade II or III glioma. In one embodiment, the gene-fusion associated cancer comprises IDH wild-type grade II or III glioma. In one embodiment, the method comprises obtaining a sample from the subject to determine the level of expression of an FGFR fusion molecule in the subject. In some embodiments the sample from the subject is a tissue sample. In some embodiments, the sample is a paraffin embedded tissue section. In some embodiments, the tissue sample from the subject is a tumor sample. In some embodiments, the sample is incubated with an agent that binds to an FGFR fusion molecule, such as an antibody, a probe, a nucleic acid primer, and the like. In one embodiment, the detection or determining comprises nucleic acid sequencing, selective hybridization, selective amplification, gene expression analysis, or a combination thereof. In another embodiment, the detection or determination comprises protein expression analysis, for example by western blot analysis, ELISA, immunostaining, or other antibody detection methods. In another embodiment, the FGFR fusion protein comprises an FGFR protein fused to a polypeptide that constitutively activates the tyrosine kinase domain of the FGFR protein. In one embodiment, the fusion protein is an FGFR-TACC fusion protein. In another embodiment, the inhibitor comprises an antibody that specifically binds to a FGFR-TACC fusion protein or a fragment thereof; a small molecule that specifically binds to a FGFR protein; a small molecule that specifically binds to a TACC protein; an antisense RNA or antisense DNA that decreases expression of a FGFR-TACC fusion polypeptide; a siRNA that specifically targets a FGFR-TACC fusion gene; or a combination of the listed inhibitors. In a further embodiment, the FGFR protein is FGFR1, FGFR2, FGFR3, or FGFR4. In some embodiments, the FGFR-TACC fusion protein is FGFR1-TACC1, FGFR2-TACC2, or FGFR3-TACC3. In other embodiments, the small molecule that specifically binds to a FGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination of the small molecules listed. In other embodiments, the small molecule that specifically binds to a FGFR protein comprises an oral pan-FGFR tyrosine kinase inhibitor. In other embodiments, the small molecule that specifically binds to a FGFR protein comprises JNJ-42756493.

An aspect of the invention provides for a method of decreasing growth of a solid tumor in a subject in need thereof, the method comprising administering to the subject an effective amount of a FGFR fusion molecule inhibitor, wherein the inhibitor decreases the size of the solid tumor. In one embodiment, the solid tumor comprises glioblastoma multiforme, breast cancer, lung cancer, prostate cancer, or colorectal carcinoma. In one embodiment, the solid tumor comprises bladder carcinoma, squamous lung carcinoma and head and neck carcinoma. In one embodiment, the solid tumor comprises glioma. In one embodiment, the solid tumor comprises grade II or III glioma. In one embodiment, the solid tumor comprises IDH wild-type grade II or III glioma. In one embodiment, the method comprises obtaining a sample from the subject to determine the level of expression of an FGFR fusion molecule in the subject. In some embodiments the sample from the subject is a tissue sample. In some embodiments, the sample is a paraffin embedded tissue section. In some embodiments, the tissue sample from the subject is a tumor sample. In some embodiments, the sample is incubated with an agent that binds to an FGFR fusion molecule, such as an antibody, a probe, a nucleic acid primer, and the like. In one embodiment, the detection or determining comprises nucleic acid sequencing, selective hybridization, selective amplification, gene expression analysis, or a combination thereof. In another embodiment, the detection or determination comprises protein expression analysis, for example by western blot analysis, ELISA, immunostaining, or other antibody detection methods. In another embodiment, the FGFR fusion protein comprises an FGFR protein fused to a polypeptide that constitutively activates the tyrosine kinase domain of the FGFR protein. In one embodiment, the fusion protein is an FGFR-TACC fusion protein. In another embodiment, the inhibitor comprises an antibody that specifically binds to a FGFR-TACC fusion protein or a fragment thereof; a small molecule that specifically binds to a FGFR protein; a small molecule that specifically binds to a TACC protein; an antisense RNA or antisense DNA that decreases expression of a FGFR-TACC fusion polypeptide; a siRNA that specifically targets a FGFR-TACC fusion gene; or a combination of the listed inhibitors. In a further embodiment, the FGFR protein is FGFR1, FGFR2, FGFR3, or FGFR4. In some embodiments, the FGFR-TACC fusion protein is FGFR1-TACC1, FGFR2-TACC2, or FGFR3-TACC3. In other embodiments, the small molecule that specifically binds to a FGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination of the small molecules listed. In other embodiments, the small molecule that specifically binds to a FGFR protein comprises an oral pan-FGFR tyrosine kinase inhibitor. In other embodiments, the small molecule that specifically binds to a FGFR protein comprises JNJ-42756493.

An aspect of the invention provides for a diagnostic kit for determining whether a sample from a subject exhibits a presence of a FGFR fusion, the kit comprising at least one oligonucleotide that specifically hybridizes to a FGFR fusion, or a portion thereof. In one embodiment, the oligonucleotides comprise a set of nucleic acid primers or in situ hybridization probes. In another embodiment, the oligonucleotide comprises SEQ ID NO: 162, 163, 164, 165, 166, 167, 168, 169, 495, 496, 497, 498, 499, 500, 501, 502, 503, 504, 505, 506, 507, 508, 509, 510 or a combination of the listed oligonucleotides. In one embodiment, the primers prime a polymerase reaction only when a FGFR fusion is present. In another embodiment, the determining comprises gene sequencing, selective hybridization, selective amplification, gene expression analysis, or a combination thereof. In a further embodiment, the FGFR-fusion is an FGFR-TACC fusion. In some embodiments, the FGFR is FGFR1, FGFR2, FGFR3, or FGFR4. In other embodiments, the FGFR-TACC fusion is FGFR1-TACC1, FGFR2-TACC2, or FGFR3-TACC3.

An aspect of the invention provides for a diagnostic kit for determining whether a sample from a subject exhibits a presence of a FGFR fusion protein, the kit comprising an antibody that specifically binds to a FGFR fusion protein comprising SEQ ID NO: 79, 85, 86, 87, 88, 89, 150, 158, 159, 160, 161, 516, 518, 539, 540, 541, 542, 543, 544, 545, 546, or 547 wherein the antibody will recognize the protein only when a FGFR fusion protein is present. In one embodiment, the antibody directed to and FGFR fusion comprising SEQ ID NO: 79, 85, 86, 87, 88, 89, 150, 158, 159, 160, 161, 516, 518 539, 540, 541, 542, 543, 544, 545, 546, or 547. In a further embodiment, the FGFR-fusion is an FGFR-TACC fusion. In some embodiments, the FGFR is FGFR1, FGFR2, FGFR3, or FGFR4. In other embodiments, the FGFR-TACC fusion is FGFR1-TACC1, FGFR2-TACC2, or FGFR3-TACC3. In some embodiments the sample from the subject is a tissue sample. In some embodiments, the sample is a paraffin embedded tissue section. In some embodiments, the tissue sample from the subject is a tumor sample.

An aspect of the invention provides for a method for detecting the presence of a FGFR fusion in a human subject. In one embodiment, the method comprises obtaining a biological sample from the human subject. In some embodiments the sample from the subject is a tissue sample. In some embodiments, the sample is a paraffin embedded tissue section. In some embodiments, the tissue sample from the subject is a tumor sample. In some embodiments, the sample is incubated with an agent that binds to an FGFR fusion molecule, such as an antibody. In another embodiment, the detection or determination comprises protein expression analysis, for example by western blot analysis, ELISA, immunostaining or other antibody detection methods. In some embodiments, the method further comprises assessing whether to administer a FGFR fusion molecule inhibitor based on the expression pattern of the subject. In further embodiments, the method comprises administering a FGFR fusion molecule inhibitor to the subject. In other embodiments, the FGFR fusion molecule inhibitor comprises an oral pan-FGFR tyrosine kinase inhibitor. In other embodiments, the FGFR fusion molecule inhibitor comprises JNJ-42756493. In another embodiment, the method comprises detecting whether or not there is a FGFR fusion present in the subject. In one embodiment, the detecting comprises measuring FGFR fusion protein levels by ELISA using an antibody directed to SEQ ID NO: 79, 85, 86, 87, 88, 89, 150, 158, 159, 160, 161, 516, 518 539, 540, 541, 542, 543, 544, 545, 546, or 547; western blot using an antibody directed to SEQ ID NO: 79, 85, 86, 87, 88, 89, 150, 158, 159, 160, 161, 516, 518 539, 540, 541, 542, 543, 544, 545, 546, or 547; immunostaining using an antibody directed to SEQ ID NO: 79, 85, 86, 87, 88, 89, 150, 158, 159, 160, 161, 516, 518, 539, 540, 541, 542, 543, 544, 545, 546, or 547; mass spectroscopy, isoelectric focusing, or a combination of the listed methods. In some embodiments, the FGFR-fusion is an FGFR-TACC fusion. In other embodiments, the FGFR is FGFR1, FGFR2, FGFR3, or FGFR4. In other embodiments, the FGFR-TACC fusion is FGFR1-TACC1, FGFR2-TACC2, or FGFR3-TACC3.

An aspect of the invention provides for a method for detecting the presence of a FGFR fusion in a human subject. In one embodiment, the method comprises obtaining a biological sample from a human subject. In some embodiments, the sample is incubated with an agent that binds to an FGFR fusion molecule, such as a probe, a nucleic acid primer, and the like. In other embodiments, the detection or determination comprises nucleic acid sequencing, selective hybridization, selective amplification, gene expression analysis, or a combination thereof. In some embodiments, the method further comprises assessing whether to administer a FGFR fusion molecule inhibitor based on the expression pattern of the subject. In further embodiments, the method comprises administering a FGFR fusion molecule inhibitor to the subject. In another embodiment, the method comprises detecting whether or not there is a nucleic acid sequence encoding a FGFR fusion protein in the subject. In one embodiment, the nucleic acid sequence comprises any one of SEQ ID NOS: 1-77, 80-84, 95-145, 515, 517, 519-527, or 530-538. In another embodiment, the detecting comprises using hybridization, amplification, or sequencing techniques to detect a FGFR fusion. In a further embodiment, the amplification uses primers comprising SEQ ID NO: 162, 163, 164,165, 166, 167, 168, 169, 495, 496, 497, 498, 499, 500, 501, 502, 503, 504, 505, 506, 507, 508, 509 or 510. In some embodiments, the FGFR-fusion is an FGFR-TACC fusion. In other embodiments, the FGFR is FGFR1, FGFR2, FGFR3, or FGFR4. In other embodiments, the FGFR-TACC fusion is FGFR1-TACC1, FGFR2-TACC2, or FGFR3-TACC3.

An aspect of the invention provides for a method of initiating oncogenic transformation in vitro. The method comprises (a) transducing cells cultured in vitro with FGFR-TACC fusion DNA; and (b) determining whether the cells acquire the ability to grow in anchorage-independent conditions, form multi-layered foci, or a combination thereof.

An aspect of the invention provides for a method of initiating oncogenic transformation in vivo. The method comprises (a) transducing cells cultured in vitro with FGFR-TACC fusion DNA; (b) injecting a mouse with the transduced cells; and (c) determining whether a tumor grows in the mouse. In one embodiment, the injecting is a subcutaneous or intracranial injection.

An aspect of the invention provides a method of identifying a compound that decreases the oncogenic activity of a FGFR-TACC fusion. The method comprises (a) transducing a cell cultured in vitro with FGFR-TACC DNA; (b) contacting a cell with a ligand source for an effective period of time; and (c) determining whether the cells acquire the ability to grow in anchorage-independent conditions, form multi-layered foci, or a combination thereof, compared to cells cultured in the absence of the test compound.

In one embodiment, the method can comprise contacting a sample from the subject with an antibody specific for a FGFR fusion molecule, and determining the presence of an immune complex. In another embodiment, the method can comprise contacting a sample from the subject with an antibody specific for a FGFR molecule, or a TACC molecule, and determining the presence of an immune complex. In another embodiment, the antibody can recognize the FGFR3 C-terminal region, or the TACC3 N-terminal region, or a combination thereof. In another embodiment, the antibody can recognize the FGFR3 C-terminal region, or the TACC3 N-terminal region, or a combination thereof. In another embodiment, the method can comprise contacting a sample from the subject with an antibody specific for a FGFR molecule, or a TACC molecule, or a FGFR fusion molecule, and determining the amount of an immune complex formed compared to the amount of immune complex formed in non-tumor cells or tissue, wherein an increased amount of an immune complex indicates the presence of an FGFR fusion.

In one embodiment, the method can comprise contacting a sample from the subject with primers specific for a FGFR fusion molecule, and determining the presence of an PCR product. In another embodiment, the method can comprise contacting a sample from the subject with primer specific for a FGFR molecule, or a TACC molecule, and determining the presence of a PCR product. In another embodiment, the primers can recognize the nucleic acids encoding a FGFR3 C-terminal region, or nucleic acids encoding a TACC3 N-terminal region, or a combination thereof. In another embodiment, the method can comprise contacting a sample from the subject with primers specific for a FGFR molecule, or a TACC molecule, or a FGFR fusion molecule, and determining the amount of PCR product formed compared to the amount of PCR product formed in non-tumor cells or tissue, wherein an increased amount of PCR product indicates the presence of an FGFR fusion.

An aspect of the invention provides for a purified fusion protein comprising the tyrosine kinase domain of an FGFR protein fused to the TACC domain of a transforming acidic coiled-coil-containing (TACC) protein. In one embodiment, the FGFR protein is FGFR1, FGFR2, FGFR3, or FGFR4. In one embodiment, the TACC protein is TACC1, TACC2, or TACC3. In one embodiment, the fusion protein is FGFR1-TACC1, FGFR2-TACC2, or FGFR3-TACC3. In one embodiment, the fusion protein comprises SEQ ID NO: 79, SEQ ID NO: 158, SEQ ID NO: 159, SEQ ID NO: 160, SEQ ID NO: 161, SEQ ID NO: 539, SEQ ID NO: 540, SEQ ID NO: 541, SEQ ID NO: 542, SEQ ID NO: 543, SEQ ID NO: 545, SEQ ID NO: 546, or SEQ ID NO: 547. In one embodiment, the fusion protein has a breakpoint comprising at least 3 consecutive amino acids from amino acids 730-758 of SEQ ID NO: 90 and comprising at least 3 consecutive amino acids from amino acids 549-838 of SEQ ID NO: 92. In one embodiment, the fusion protein has a breakpoint comprising SEQ ID NO: 78, SEQ ID NO: 85, SEQ ID NO:

86, SEQ ID NO: 87, SEQ ID NO:89, SEQ ID NO: 516, or SEQ ID NO:518. In one embodiment, the fusion protein comprises SEQ ID NO: 150. In one embodiment, the fusion protein has a breakpoint comprising at least 3 consecutive amino acids from amino acids 746-762 of SEQ ID NO: 146 and comprising at least 3 consecutive amino acids from amino acids 572-590 of SEQ ID NO: 148. In one embodiment, the fusion protein has a breakpoint comprising SEQ ID NO: 88.

An aspect of the invention provides for a cDNA encoding a fusion protein comprising the tyrosine kinase domain of FGFR fused to the TACC domain of TACC. In one embodiment the FGFR is FGFR1, FGFR2, FGFR3, or FGFR4. In one embodiment, the TACC is TACC1, TACC2, or TACC3. In one embodiment, the fusion protein is FGFR1-TACC1, FGFR2-TACC2, or FGFR3-TACC3. In one embodiment, the cDNA comprises SEQ ID NO: 94, SEQ ID NO: 530, SEQ ID NO: 531, SEQ ID NO: 532, SEQ ID NO: 533, SEQ ID NO: 534, SEQ ID NO: 535, SEQ ID NO: 536, SEQ ID NO: 537 or SEQ ID NO: 538. In one embodiment, the cDNA has a breakpoint comprising at least 9 consecutive in-frame nucleotides from nucleotides 2443-2530 of SEQ ID NO: 91 and comprising at least 9 consecutive in-frame nucleotides from nucleotides 1800-2847 of SEQ ID NO: 93. In one embodiment, the cDNA has a breakpoint comprising any one of SEQ ID NOs: 1-77, or SEQ ID NOs: 519-527. In one embodiment, the cDNA comprises SEQ ID NO: 151. In one embodiment, the cDNA has a breakpoint comprising at least 9 consecutive in-frame nucleotides from nucleotides 3178-3228 of SEQ ID NO: 147 and comprising at least 9 consecutive in-frame nucleotides from nucleotides 2092-2794 of SEQ ID NO: 149. In one embodiment, the cDNA has a breakpoint comprising SEQ ID NO: 83. In one embodiment, the cDNA comprises a combination of exons 1-16 of FGFR3 spliced 5' to a combination of exons 8-16 of TACC3, wherein a breakpoint occurs in: a) any one of exons 1-16 of FGFR3 and any one of exons 8-16 of TACC3; b) any one of introns 1-16 of FGFR3 and any one of exons 8-16 of TACC3; c) any one of exons 1-16 of FGFR3 and any one of introns 7-16 of TACC3; or d) any one of introns 1-16 of FGFR3 and any one of introns 7-16 of TACC3. In one embodiment, the cDNA comprises a combination of exons 1-17 of FGFR1 spliced 5' to a combination of exons 7-13 of TACC1, wherein a breakpoint occurs in any one of exons 1-17 of FGFR3 and any one of exons 7-13 of TACC3. In one embodiment, the cDNA comprises a combination of exons 1-18 of FGFR2 spliced 5' to a combination of exons 1-23 of TACC2.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIGS. 1B-1, 1B-2, 1B-3 and 1B-4 show an FGFR3-TACC3 gene fusion identified by whole transcriptome sequencing of GSCs. 76 split-reads (SEQ ID NOS: 2-77, respectively) are shown aligning on the breakpoint. The predicted reading frame at the breakpoint is shown at the top (FGFR3 nucleotide sequence (left) and TACC3 nucleotide sequence (right); SEQ ID NO: 1) with FGFR3 sequences below the predicted reading frame (left) and TACC3 (right). The putative amino acid sequence (SEQ ID NO: 78) corresponding to SEQ ID NO: 1 is shown above the predicted reading frame.

FIG. 1D shows an FGFR3-TACC3 gene fusion identified by whole transcriptome sequencing of GSCs. Amino acid sequence of the FGFR3-TACC3 protein is shown (SEQ ID NO: 79). Residues corresponding to FGFR3 or to TACC3 (underlined) are shown. The fusion protein joins the tyrosine kinase domain of FGFR3 to the TACC domain of TACC3.

FIG. 2A shows recurrent gene fusions between FGFR and TACC genes in GBM. Specifically, FGFR3-TACC3 gene fusions are shown that were identified by exome sequencing analysis. Split-reads are shown aligning the genomic breakpoints of FGFR3 and TACC3 genes in the four TCGA GBM samples. For TCGA-27-1835, SEQ ID NO: 95 shows the reading frame at the breakpoint (bold), while SEQ ID NOS: 96-107, respectively, show alignments of the genomic breakpoints. For TCGA-19-5958, SEQ ID NO: 108 shows the reading frame at the breakpoint (bold), while SEQ ID NOS: 109-111, respectively, show alignments of the genomic breakpoints. For TCGA-06-6390, SEQ ID NO: 112 shows the reading frame at the breakpoint (bold), while SEQ ID NOS: 113-131, respectively, show alignments of the genomic breakpoints. For TCGA-12-0826, SEQ ID NO: 132 shows the reading frame at the breakpoint (bold), while SEQ ID NOS: 133-145, respectively, show alignments of the genomic breakpoints.

FIG. 4F shows quantitative analysis of segregation defects in Rat1A expressing FGFR1-TACC1 and FGFR3-TACC3. F3-T3: FGFR3-TACC3; F3-T3-K508M: FGFR3-TACC3-K508M.

FIG. 5D shows quantitative analysis of chromosome number in 100 metaphase cells for each condition to determine the ploidy and the diversity of chromosome counts within the cell population. (n=3 independent experiments).

FIG. 6B shows inhibition of FGFR-TK activity corrects the aneuploidy initiated by FGFR3-TACC3. Correction of premature sister chromatid separation (PMSCS) by PD173470 in cells expressing FGFR3-TACC3. Panels show representative metaphase spreads. DNA was stained by DAPI. FIG. 6C shows quantitative analysis of metaphases with loss of sister chromatid cohesion (n=3; p=0.001, FGFR3-TACC3 treated with DMSO vs. FGFR3-TACC3 treated with PD173470).

Figure 9E-6:
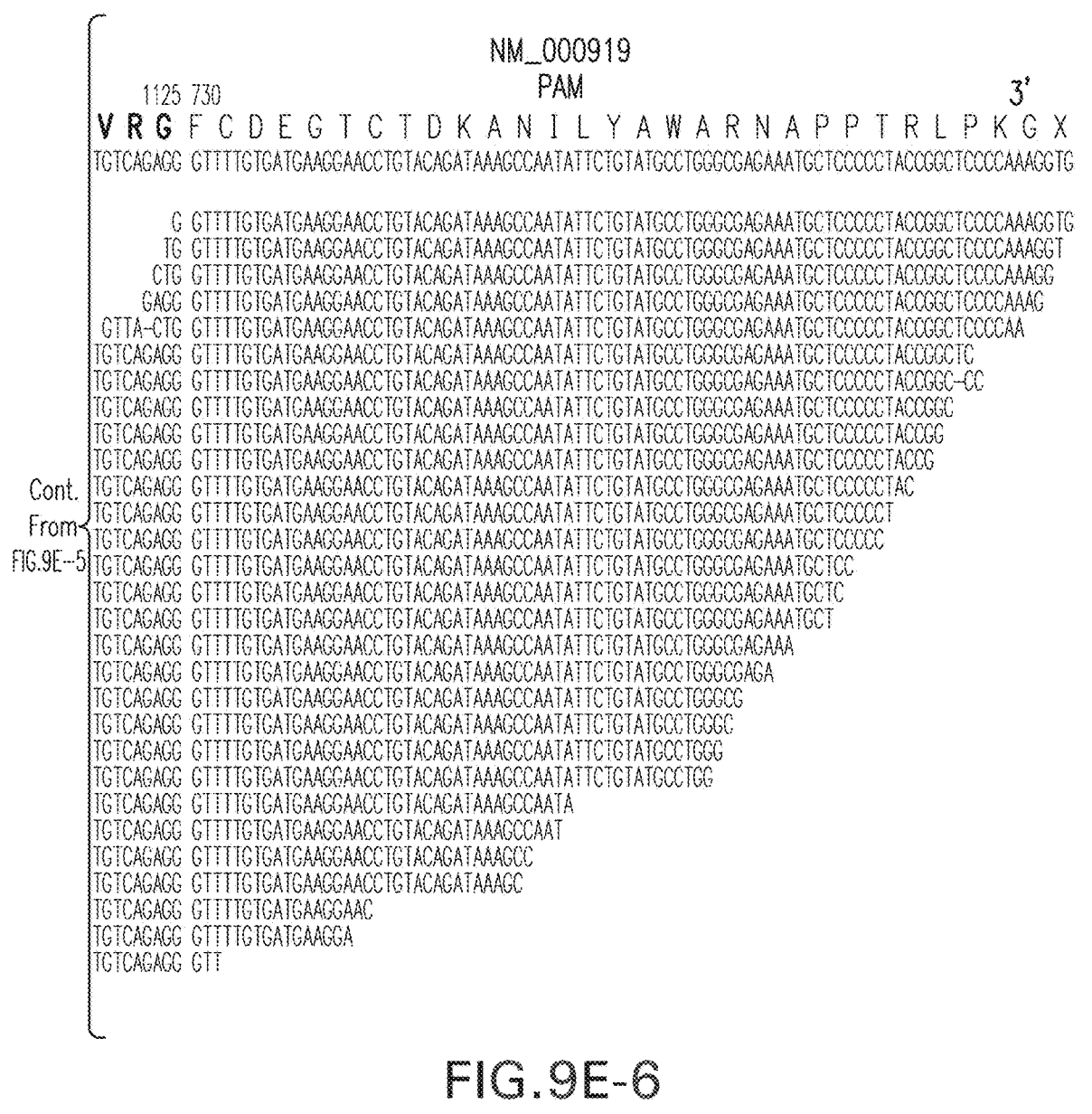

FIGS. 9E-1, 9E-2, 9E-3, 9E-4, 9E-5, 9E-6, 9E-7, and 9E-8 show the fusion transcripts identified by whole transcriptome sequencing of nine GSCs. 54 split-reads (SEQ ID NOS 329-382, respectively, in order of appearance) are shown aligning on the breakpoint of the POLR2A-WRAP53 fusion (SEQ ID NO: 327). The predicted reading frame at the breakpoint is shown at the top with POLR2A sequences in red (left) and WRAP53 in blue (right). Protein sequence disclosed as SEQ ID NO: 328. On the continued page, 48 split-reads (SEQ ID NOS 385-432, respectively, in order of appearance) are shown aligning on the breakpoint of the CAPZB-UBR4 fusion (SEQ ID NO: 383). The predicted reading frame at the breakpoint is shown at the top with CAPZB sequences in red (left) and UBR4 in blue (right). Protein sequence disclosed as SEQ ID NO: 384. On the continued page after, 29 split-reads (SEQ ID NOS 435-463, respectively, in order of appearance) are shown aligning on the breakpoint of the ST8SIA4-PAM fusion (SEQ ID NO: 433). The predicted reading frame at the breakpoint is shown at the top with ST8SIA4 sequences in red (left) and PAM in blue (right). Protein sequence disclosed as SEQ ID NO: 434. On the subsequent continued page, 17 split-reads (SEQ ID NOS 466-482, respectively, in order of appearance) are shown (top) aligning on the breakpoint of the PIGU-NCOA6 fusion (SEQ ID NO: 464). The predicted reading frame at the breakpoint is shown at the top with PIGU sequences in red (left) and NCOA6 in blue (right). Protein sequence disclosed as SEQ ID NO: 465. Also (below), 6 split-reads (SEQ ID NOS 485-490, respectively, in order of appearance) are shown aligning on the breakpoint of the IFNAR2-IL10RB fusion (SEQ ID NO: 483). The predicted reading frame at the breakpoint is shown at the top with IFNAR2 sequences in red (left) and IL10RB in blue (right). Protein sequence disclosed as SEQ ID NO: 484.

FIG. 10B shows the analysis and validation of the expression of fused transcripts in GSCs and GBM sample. Top panel, qRT-PCR showing the very high expression of FGFR3 and TACC3 mRNA sequences included in the FGFR3-TACC3 fusion transcript in GSC-1123. Bottom panel, for comparison the expression of sequences of WRAP53 mRNA included in the POLR2A-WRAP53 fusion in GSC-0114 is also shown.

FIGS. 10E-1, 10E-2, 10E-3, 10E-4, 10E-5, and 10E-6 shows MS/MS analysis of the ~150 kD fusion protein immunoprecipitated by the monoclonal anti-FGFR3 antibody from GSC-1123, identifying three unique peptides mapping to the FGFR3 (FGFR3 Peptide 1 (SEQ ID NO: 492), 2 (SEQ ID NO: 493), and 3 (SEQ ID NO: 494)) and three peptides mapping to the C-terminal region of TACC3 (TACC Peptide 1 (SEQ ID NO: 156), 2 (SEQ ID NO: 157), and 3 (SEQ ID NO: 491)).

FIGS. 11A-C shows Rat1A cells transduced with control lentivirus or lentivurus expressing FGFR3, TACC3, FGFR3-TACC3 (FIG. 11A) that were analyzed by Western blot with an antibody recognizing the N-terminus of FGFR3 (included in the FGFR3-TACC3 fusion protein) or the N-terminus of TACC3 (not included in the FGFR3-TACC3 fusion protein). FIG. 11B shows quantitative Western blot analysis of endogenous FGFR3-TACC3 in GSC-1123 compared with lentivirally expressed FGFR3-TACC3 in Rat1A. FIG. 11C shows Western blot analysis of FGFR3-TACC3 and FGFR3-TACC3-K508M in Rat1A. α-tubulin is shown as a control for loading.

FIGS. 11D-F shows expression analyses of FGFR3-TACC3 fusion construct (FIG. 11D) FGFR3 immunostaining of GBM-1123 (left, upper panel), BTSC1123 (right, upper panel), mouse GBM induced by FGFR3-TACC3 expressing lentivirus (left, lower panel), and sub-cutaneous xenograft of mouse astrocytes transformed by FGFR3-TACC3 fusion (right, lower panel); FGFR3-TACC3, red ("light grey" in black and white image); DNA (DAPI), blue ("grey" in black and white image). FIG. 11E shows quantification of FGFR3-TACC3 positive cells in the tumors and cultures of cells shown in FIG. 11D. FIG. 11F shows a quantitative Western blot analysis of ectopic FGFR3-TACC3 fusion protein in mouse astrocytes and FGFR3-TACC3 induced mouse GBM (mGBM-15 and mGBM-17) compared with the endogenous expression in GBM1123. β-actin is shown as a control for loading. F3-T3: FGFR3-TACC3. α-tubulin or β-actin is shown as a control for loading.

FIGS. 12D-F shows mitotic localization of FGFR3-TACC3 fusion protein. FIG. 12D shows maximum intensity projection confocal image of a representative FGFR3-TACC3 expressing Ink4A; Arf−/− mouse astrocyte at metaphase immunostained using the FGFR3 antibody (red; "dark grey" in black and white image). FGFR3-TACC3 displays asymmetric localization on top of one spindle pole. FIG. 12E shows maximum intensity projection confocal image of a representative TACC3 expressing Ink4A; Arf−/− mouse astrocyte at metaphase immunostained with the TACC3 antibody (red; ("dark grey" in black and white image). TACC3 staining coincides with the spindle microtubules. FIG. 12F shows maximum intensity projection confocal image of a representative FGFR3 expressing Ink4A; Arf−/− mouse astrocyte at metaphase immunostained with the FGFR3 antibody (red; ("dark grey" in black and white image). FGFR3 does not show a specific staining pattern in mitosis. Cells were co-immunostained using a-tubulin (green; ("light grey" in black and white image) to visualize the mitotic spindle. DNA was counterstained with DAPI (blue; ("grey" in black and white image). Images were acquired at 0.250 μm intervals. Endogenous levels of FGFR3 or TACC3 were undetectable under the applied experimental conditions. F3-T3: FGFR3-TACC3.

FIGS. 13B-D shows representative images of premature sister chromatid separation (PMSCS) in Ink4A; Arf−/− astrocytes (FIG. 13B) and Rat1A cells (FIG. 13C) expressing FGFR3-TACC3. Left, panels show representative metaphase spreads. Right, quantitative analysis of metaphases with loss of sister chromatid cohesion. The number of mitosis with PMSCS in Ink4A; Arf−/− astrocytes was scored in at least 100 methaphases for each condition in three independent experiments. The number of mitosis with PMSCS was scored in triplicate samples of Rat1A cells. FIG. 13D is a graph showing nocodazole was added for the indicated durations to Rat1A-H2B-GFP cells transduced with the specified lentiviruses. The mitotic index at each time point was determined by quantitating the H2B-GFP-positive cells in mitosis at each time point. Data are presented as average and standard deviation (n=3). F3-T3: FGFR3-TACC3.

FIGS. 14A-B shows growth curves of human primary astrocytes transduced with lentivirus expressing FGFR3-TACC3 fusion or the empty vector. An analysis was conducted of FGFR3-TACC3 fusion mediated growth alteration and specific effect of RTK inhibitors on cells carrying FGFR-TACC fusions. FIG. 14A is a graph that shows cell proliferation of human primary astrocytes transduced with lentivirus expressing FGFR3-TACC3 fusion or the empty vector was determined by the MTT assay 7 days after infection (passage 1). Values are the means±standard deviation (n=4). p-value: 0.0033. FIG. 14B is a graph that shows cell proliferation of human primary astrocytes transduced with lentivirus expressing FGFR3-TACC3 fusion or the empty vector was determined by the MTT assay six weeks after the infection (passage 10). Values are the means±standard deviation (n=4). p-value: 0.0018.

FIGS. 14C-D shows specific growth inhibitory effect by FGFR inhibitors on FGFR-TACC fusion expressing cells. Cell growth was determined by MTT assay. Rat1A cells transduced with the indicated lentivirus were treated for three days with BGJ398 (FIG. 14C) or AZD4547 (FIG. 14D) at the indicated concentration. Values are the means±standard error (n=4).

FIG. 25 shows the position of the peptides from FIGS. 10E1-10E6 in the amino acid sequence of the FGFR3-TACC3 fusion protein (SEQ ID NO: 79), which are highlighted in pink (FGFR3; underlined) and blue (TACC3; dotted lines).

FIGS. 27A-B are pictures that shows tumor xenografts that were induced following sub-cutaneous injection of Ink4A; Arf−/− mouse astrocytes transduced with lentivirus expressing FGFR3-TACC3 (upper panel A, right flank) or FGFR1-TACC1 (lower panel B, right flank) fusion, but not with the empty vector (upper panel, left flank) or FGFR3-TACC3 carrying a K508M mutation in the kinase domain (FGFR3-TACC3-K508M; lower panel, left flank).

FIG. 30 shows examples of SKY karyotype analysis painting two different cells from the same culture of GSC-1123, illustrating the ongoing CIN and aneuploidy. Details of the karyotype analysis of 20 cells are reported in Table 6.

FIGS. 31-1, 31-2, and 31-3 are a graphical representation of segmented CNVs data visualized using the Integrated Genomic Viewers software. Three bladder Urothelial Carcinoma harbor FGFR3-TACC3 gene fusions (black box). Red indicates amplification (A), blue indicates deletion (D).

FIGS. 32-1, 32-2, and 32-3 are a graphical representation of segmented CNVs data visualized using the Integrated Genomic Viewers software. One Breast Carcinoma harbors FGFR3-TACC3 gene fusions (black box). Red indicates amplification (A), blue indicates deletion (D).

FIGS. 33-1, 33-2, and 33-3 are a graphical representation of segmented CNVs data visualized using the Integrated Genomic Viewers software. One Colorectal Carcinoma harbors FGFR3-TACC3 gene fusions (black box). Red indicates amplification (A), blue indicates deletion (D).

FIGS. 34-1, 34-2, and 34-3 are a graphical representation of segmented CNVs data visualized using the Integrated Genomic Viewers software. One Lung Squamous Cell Carcinoma harbors FGFR3-TACC3 gene fusions (black box). Red indicates amplification (A), blue indicates deletion (D).

FIGS. 35-1, 35-2, and 35-3 are a graphical representation of segmented CNVs data visualized using the Integrated Genomic Viewers software. One Head abd Neck Squamous Cell Carcinoma harbors FGFR3-TACC3 gene fusions (black box). Red indicates amplification (A), blue indicates deletion (D).

FIGS. 37A-H show the identification and immunostaining of FGFR3-TACC3-positive tumors. Results from RT-PCR screening in representative samples from the Pitie-Salpetriere Hospital (A, C) and the Besta (B, D) datasets. M, DNA ladder. Schematic representation of the FGFR3-TACC3 fusion transcripts identified in samples GBM-4620 (C) and GBM-021 (D). The junction sequences on the mRNA (GBM-4620 (C) SEQ ID NO: 515; GBM-021 (D) SEQ ID NO: 517) and the reading frame and translation (GBM-4620 (C) SEQ ID NO: 516; GBM-021 (D) SEQ ID NO: 518) at the breakpoint are reported. Representative microphotographs of H&E and FGFR3 immunostaining in the FGFR3-TACC3 positive samples GBM-4620 (E) and GBM-021 (F) and two FGFR3-TACC3 negative samples (panels G and H); a, H&E, 10× magnification; b, H&E, 40× magnification; c, FGFR3, 10× magnification; d, FGFR3, 40× magnification. FIGS. 37C and 37D disclose chromatogram readings as SEQ ID NOs: 550 and 551, respectively.

FIGS. 38A-D show pre-clinical evaluation of FGFR3-TACC3 inhibition by JNJ-42756493. (A) Mouse astrocytes expressing FGFR3-TACC3 (F3T3), FGFR3-TACC3-KD (F3T3-KD) or the empty vector (Vector) were treated with the indicated concentration of JNJ-42756493. Cell viability was determined by the MTT assay. Error bars show mean±SEM (n=6). (B) Survival analysis of GIC28 1123 treated with JNJ-42756493. (C) The FGFR-TK inhibitor JNJ-42756493 suppresses tumor growth of subcutaneous tumors generated by GIC-1123. After tumor establishment (arrow) mice were treated with vehicle or JNJ-42756493 (12 mg/kg) for 14 days. Values are mean tumor volumes±SD, (n=9 mice per group). P-value of the slope calculated from the treatment starting point (arrow) is 0.04. (D) Photograph showing the tumors dissected from vehicle or JNJ-42756493 treated mice after two weeks of treatment.

FIGS. 39A-G show baseline and post-treatment Magnetic Resonance Imaging (MRI) of patients treated with JNJ-42756493. Patient 1 (Panels A-D). (A) Post-gadolinium T1 weighted images show the target lesion on the right parietal lobe. The interval (days) from the beginning of follow-up is indicated above each MRI. (B) Analysis of sum of product diameters (SPD) before and during the anti-FGFR treatment (RANO criteria). (C) Analysis of tumor volume (cm3) before and during the anti-FGFR treatment. During anti-FGFR treatment a stabilization of the tumor was observed according to RANO criteria and volumetry. (D) Perfusion images at baseline and after 20 days of anti-FGFR treatment. rCBV (relative cerebral blood volume). Post-gadolinium T1 weighted images with color overlay of rCBV are shown. Patient 2 (Panels E-G). (E) Two different MRI slice levels of superior and middle part of the lesion are presented. (F) Analysis of sum of product diameters (SPD) before and during the anti-FGFR treatment. During the anti-FGFR treatment a reduction of 22% of tumor size was observed. (G) Volumetric evaluation showed a 28% tumor reduction. Vertical red arrow indicates the start of anti-FGFR treatment (baseline).

FIG. 40 shows the genomic PCR images and Sanger sequences of FGFR3-TACC3 genomic breakpoints. Fusion specific PCR products and Sanger sequencing chromatograms showing the FGFR3-TACC3 genomic breakpoints (Sample #4451 SEQ ID NO:519; Sample #OPK-14 SEQ ID NO: 520; Sample #MB-22 SEQ ID NO: 521; Sample #3048 SEQ ID NO: 522; Sample #4373 SEQ ID NO: 523; Sample #4867 SEQ ID NO: 524; Sample #3808 SEQ ID NO: 525; Sample #27-1835 SEQ ID NO: 526; Sample #06-6390 SEQ ID NO: 527). The genomic sequences corresponding to FGFR3 and TACC3 are indicated in red or blue, respectively. M, DNA ladder; C, Negative Control. FIG. 40 discloses chromatogram readings as SEQ ID NOS: 552-560, respectively, in order of appearance.

FIG. 41 shows schematics of FGFR3-TACC3 genomic breakpoints. Schematic representation of the genomic fusions between FGFR3 and TACC3 compared to the corresponding mRNA. In red and blue are reported the regions belonging to FGFR3 and TACC3, respectively. The genomic breakpoint coordinates, according to the genome build GRCh37/hg19, are indicated above each fusion gene.

FIGS. 43A-C show the FGFR3-TACC3 fusion gene and protein are retained in recurrent GBM. (A) FGFR3-TACC3 fusion specific RT-PCR product from untreated and recurrent GBM from patient #3124. (B) Sanger sequencing chromatogram showing the identical reading frame at the breakpoint (SEQ ID NO: 517) and the putative translation of the fusion protein (SEQ ID NO: 86) in the untreated and recurrent tumor from the same patient. The fused exons at mRNA level are shown. Regions corresponding to FGFR3 and TACC3 are indicated in red and blue, respectively. T, threonine; S, serine; D, aspartic acid; V, valine; K, lysine; A, alanine. (C) Representative microphotographs of FGFR3 immunofluorescence (IF) staining in both untreated and recurrent GBM. Blue staining, DAPI; Red staining, FGFR3. 10× Magnification. FIG. 43B discloses chromatogram readings as SEQ ID NOs: 551 and 551, respectively, in order of appearance.

FIGS. 44A-B show PFS and OS of FGFR3-TACC3-positive glioma patients. (A) Kaplan-Meier curves in IDH wild-type glioma patients don't show significant differences in Progression Free Survival (PFS) between FGFR3-TACC3 positive (N=12, median PFS=11.20 months) and FGFR3-TACC3 negative (N=274, Median PFS=12.27 months) (P=0.85). (B) Kaplan-Meier curves in IDH wild-type glioma patients don't show significant differences in Overall Survival (OS) between FGFR3-TACC3 positive (N=12, Median OS=32.80 months) and FGFR3-TACC3 negative (N=326, Median OS=18.60 months) (P=0.6). In red FGFR3-TACC3 positive patients, in green FGFR3-TACC3 negative patients. Open circles represent censored patients.

DETAILED DESCRIPTION OF THE INVENTION

Figure 1A:
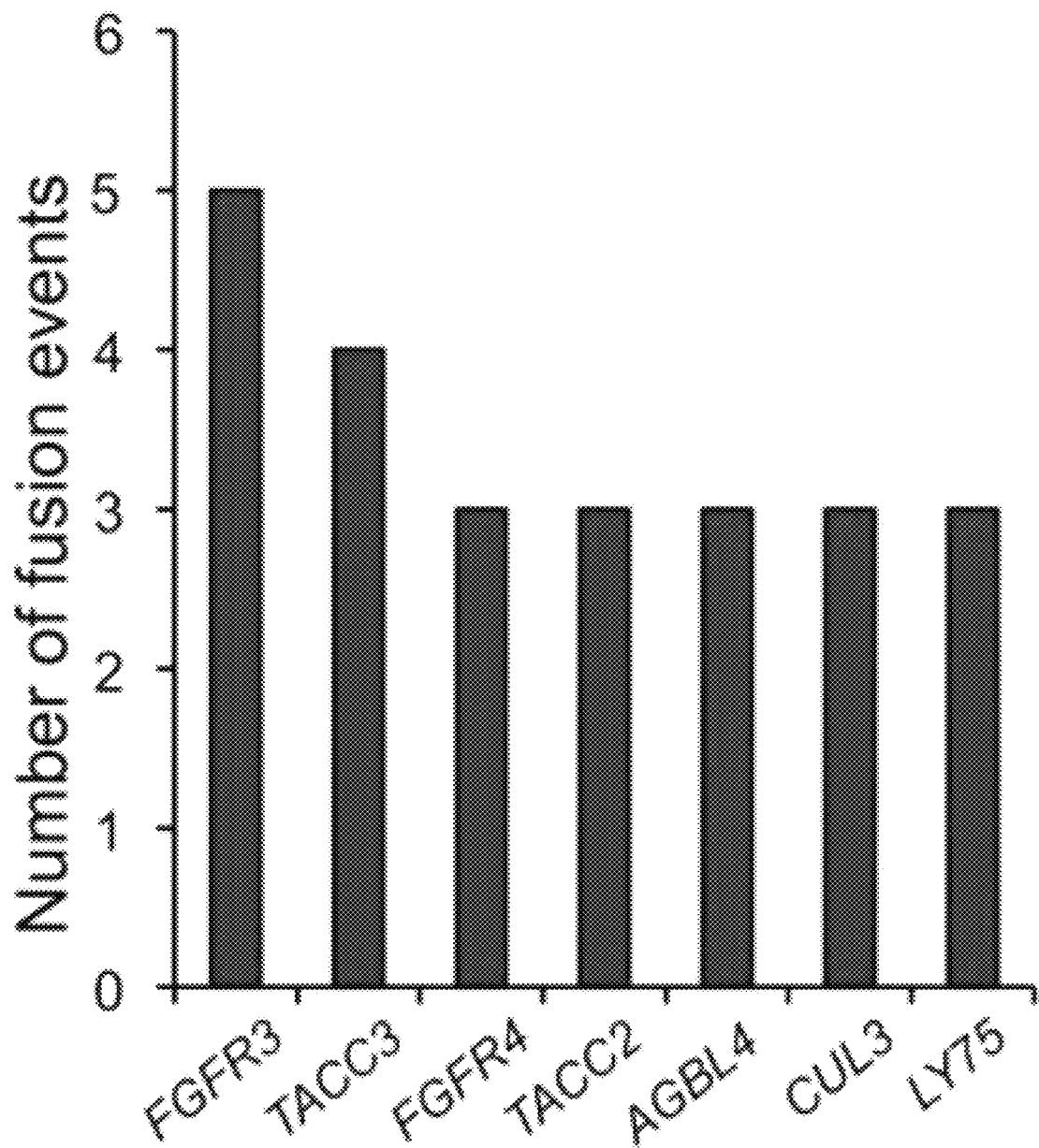
FIG. 1A is a graph that shows genes recurrently involved in gene fusions in TCGA. Only genes involved in at least three gene fusions across different samples are displayed.

Glioblastoma multiformes (GBMs) are the most common form of brain tumors in adults accounting for 12-15% of intracranial tumors and 50-60% of primary brain tumors. GBM is among the most lethal forms of human cancer. The history of successful targeted therapy of cancer largely coincides with the inactivation of recurrent and oncogenic gene fusions in hematological malignancies and recently in some types of epithelial cancer. GBM is among the most lethal and incurable forms of human cancer. Targeted therapies against common genetic alterations in GBM have not changed the dismal clinical outcome of the disease, most likely because they have systematically failed to eradicate the truly addicting oncoprotein activities of GBM. Recurrent chromosomal rearrangements resulting in the creation of oncogenic gene fusions have not been found in GBM.

GBM is among the most difficult forms of cancer to treat in humans (1). So far, the therapeutic approaches that have been tested against potentially important oncogenic targets in GBM have met limited success (2-4). Recurrent chromosomal translocations leading to production of oncogenic fusion proteins are viewed as initiating and addicting events in the pathogenesis of human cancer, thus providing the most desirable molecular targets for cancer therapy (5, 6). Recurrent and oncogenic gene fusions have not been found in GBM. Chromosomal rearrangements are hallmarks of hematological malignancies but recently they have also been uncovered in subsets of solid tumors (breast, prostate, lung and colorectal carcinoma) (7, 8). Important and successful targeted therapeutic interventions for patients whose tumors carry these rearrangements have stemmed from the discovery of functional gene fusions, especially when the translocations involve kinase-coding genes (BCR-ABL, EML4-ALK) (9, 10).

A hallmark of GBM is rampant chromosomal instability (CIN), which leads to aneuploidy (11). CIN and aneuploidy are early events in the pathogenesis of cancer (12). It has been suggested that genetic alterations targeting mitotic fidelity might be responsible for missegregation of chromosomes during mitosis, resulting in aneuploidy (13, 14).

Fibroblast growth factor receptors (FGFR) are transmembrane receptors that bind to members of the fibroblast growth factor family of proteins. The structure of the FGFRs consist of an extracellular ligand binding domain comprised of three Ig-like domains, a single transmembrane helix domain, and an intracellular domain with tyrosine kinase activity (Johnson, D. E., Williams, E. T. Structural and functional diversity in the FGF receptor multigene family. (1993) Adv. Cancer Res, 60:1-41).

Transforming acidic coiled-coiled protein (TACC) stabilize microtubules during mitosis by recruiting minispindles (Msps)/XMAP215 proteins to centrosomes. TACCs have been implicated in cancer.

From a medical perspective, the FGFR-TACC fusions provide the first "bona-fide" oncogenically addictive gene fusions in GBM whose identification has long been overdue in this disease.

Beside GBM, which features the highest grade of malignancy among glioma (grade IV), lower grade glioma which include grade II and grade III are a heterogeneous group of tumors in which specific molecular features are associated with divergent clinical outcome. The majority of grade II-III glioma (but only a small subgroup of GBM) harbor mutations in IDH genes (IDH1 or IDH2), which confer a more favorable clinical outcome. Conversely, the absence of IDH mutations is associated with the worst prognosis (5).

Described herein is the identification of FGFR-TACC gene fusions (mostly FGFR3-TACC3, and rarely FGFR1-TACC1) as the first example of highly oncogenic and recurrent gene fusions in GBM. The FGFR-TACC fusions that have been identified so far include the Tyrosine Kinase (TK) domain of FGFR and the coiled-coil domain of TACC proteins, both necessary for the oncogenic function of FGFR-TACC fusions. FGFR3-TACC3 fusions have been identified in pediatric and adult glioma, bladder carcinoma, squamous lung carcinoma and head and neck carcinoma, thus establishing FGFR-TACC fusions as one of the chromosomal translocation most frequently found across multiple types of human cancers (6-15).

Here a screening method for FGFR-TACC fusions is reported that includes a RT-PCR assay designed to identify the known and novel FGFR3-TACC3 fusion transcripts, followed by confirmation of the inframe breakpoint by Sanger sequencing. Using this assay, a dataset of 584 GBM and 211 grade II and grade III gliomas has been analyzed. It was determined that brain tumors harboring FGFR-TACC fusions manifest strong and homogeneous intra-tumor expression of the FGFR3 and TACC3 component invariably included in the fusion protein, when analyzed by immunostaining. A significant clinical benefit following treatment with a specific inhibitor of FGFR-TK is reported in two GBM patients who harbored FGFR3-TACC3 rearrangement.

DNA and Amino Acid Manipulation Methods and Purification Thereof

The practice of aspects of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., *Molecular Cloning A Laboratory Manual*, $3^{rd}$ Ed., ed. by Sambrook (2001), Fritsch and Maniatis (Cold Spring Harbor Laboratory Press: 1989); *DNA Cloning, Volumes I and II* (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription and Translation* (B. D. Hames & S. J. Higgins eds. 1984); *Culture Of Animal Cells* (R. I. Freshney, Alan R. Liss, Inc., 1987); *Immobilized Cells and Enzymes* (IRL Press, 1986); B. Perbal, *A Practical Guide To Molecular Cloning* (1984); the series, *Methods In Enzymology* (Academic Press, Inc., N.Y.), specifically, *Methods In Enzymology*, Vols. 154 and 155 (Wu et al. eds.); *Gene Transfer Vectors For Mammalian Cells* (J. H. Miller and M. P. Calos eds., 1987, Cold Spring Harbor Laboratory); *Immunochemical Methods In Cell And Molecular Biology* (Caner and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986). All patents, patent applications and references cited herein are incorporated by reference in their entireties.

One skilled in the art can obtain a protein in several ways, which include, but are not limited to, isolating the protein via biochemical means or expressing a nucleotide sequence encoding the protein of interest by genetic engineering methods.

A protein is encoded by a nucleic acid (including, for example, genomic DNA, complementary DNA (cDNA), synthetic DNA, as well as any form of corresponding RNA). For example, it can be encoded by a recombinant nucleic acid of a gene. The proteins of the invention can be obtained from various sources and can be produced according to various techniques known in the art. For example, a nucleic acid that encodes a protein can be obtained by screening DNA libraries, or by amplification from a natural source. A protein can be a fragment or portion thereof. The nucleic acids encoding a protein can be produced via recombinant DNA technology and such recombinant nucleic acids can be prepared by conventional techniques, including chemical synthesis, genetic engineering, enzymatic techniques, or a combination thereof. For example, a fusion protein of the invention comprises a tyrosine kinase domain of an FGFR protein fused to a polypeptide that constitutively activates the tyrosine kinase domain of the FGFR protein. For example, a fusion protein of the invention comprises a transforming acidic coiled-coil (TACC) domain fused to a polypeptide with a tyrosine kinase domain, wherein the TACC domain constitutively activates the tyrosine kinase domain. An example of a FGFR1-TACC1 polypeptide has the amino acid sequence shown in SEQ ID NO: 150. An example of a FGFR3-TACC3 protein is the polypeptide encoded by the nucleic acid having the nucleotide sequence shown in SEQ ID NOs: 94, 530, 531, 532, 533, 534, 535, 536, 537, or 538. Examples of a FGFR3-TACC3 polypeptide has the amino acid sequence shown in SEQ ID NO: 79, 158, 159, 160, 161, 539, 540, 541, 542, 543, 544, 545, 546, or 547.

The Genbank ID for the FGFR3 gene is 2261. Three isoforms are listed for FGFGR3, e.g., having Genebank Accession Nos. NP_000133 (corresponding nucleotide sequence NM_000142); NP_001156685 (corresponding nucleotide sequence NM_001163213); NP_075254 (corresponding nucleotide sequence NM_022965).

SEQ ID NO: 90 is the FGFR3 Amino Acid Sequence, Transcript Variant 1 (NP_000133; 806 aa). The location of exons are marked by alternating underlining. Amino acids encoded by nucleotides spanning exons are bold italicized.

```
  1 MGAPACALAL CVAVAIVAGA SSESLGTEQR VVGRAAEVPG PEPGQQEQLV FGSGDAVELS
 61 CPPPGGGPMG PTVWVKDGTG LVPSERVLVG PQRLQVLNAS HEDSGAYSCR QRLTQRVLCH
121 FSVRVTDAPS SGDDEDGEDE AEDTGVDTGA PYWTRPERMD KKLLAVPAAN TVRFRCPAAG
181 NPTPSISWLK NGREFRGEHR IGGIKLRHQQ WSLVMESVVP SDRGNYTCVV ENKFGSIRQT
241 YTLDVLERSP HRPILQAGLP ANQTAVLGSD VEFHCKVYSD AQPHIQWLKH VEVNGSKVGP
301 DGTPYVTVLK TAGANTTDKE LEVLSLHNVT FEDAGEYTCL AGNSIGFSHH SAWLVVLPAE
361 EELVEADEAG SVYAGILSYG VGFFLFILVV AAVTLCRLRS PPKKGLGSPT VHKISRFPLK
421 RQVSLESNAS MSSNTPLVRI ARLSSGEGPT LANVSELELP ADPKWELSRA RLTLGKPLGE
481 GCFGQVVMAE AIGIDKDRAA KPVTVAVKML KDDATDKDLS DLVSEMEMMK MIGKHKNIIN
541 LLGACTQGGP LYVLVEYAAK GNLREFLRAR RPPGLDYSFD TCKPPEEQLT FKDLVSCAYQ
601 VARGMEYLAS QKCIHRDLAA RNVLVTEDNV MKIADFGLAR DVHNLDYYKK TTNGRLPVKW
661 MAPEALFDRV YTHQSDVWSF GVLLWEIFTL GGSPYPGIPV EELFKLLKEG HRMDKPANCT
721 HDLYMIMREC WHAAPSQRPT FKQLVEDLDR VLTVTSTDEY LDLSAPFEQY SPGGQDTPSS
781 SSSGDDSVFA HDLLPPAPPS SGGSRT
```

SEQ ID NO: 91 is the FGFR3 Nucleotide Sequence, Transcript Variant 1 (NM_000142; 4304 bp).

```
  1 gtcgcgggca gctggcgccg cgcggtcctg ctctgccggt cgcacggacg caccggcggg
 61 ccgccggccg gagggacggg gcgggagctg ggcccgcgga cagcgagccg gagcgggagc
121 cgcgcgtagc gagccgggct ccggcgctcg ccagtctccc gagcggcgcc cgcctcccgc
181 cggtgcccgc gccgggccgt gggggggcagc atgcccgcgc gcgctgcctg aggacgccgc
241 ggccccgcc cccgccatgg gcgcccctgc ctgcgccctc gcgctctgcg tggccgtggc
301 catcgtggcc ggcgcctcct cggagtcctt ggggacggag cagcgcgtcg tggggcgagc
361 ggcagaagtc ccgggcccag agcccggcca gcaggagcag ttggtcttcg gcagcgggga
421 tgctgtggag ctgagctgtc ccccgccgg gggtggtccc atggggccca ctgtctgggt
481 caaggatggc acagggctgg tgccctcgga gcgtgtcctg gtgggccccc agcggctgca
541 ggtgctgaat gcctcccacg aggactccgg ggcctacagc tgccggcagc ggctcacgca
601 gcgcgtactg tgccacttca gtgtgcgggt gacagacgct ccatcctcgg agatgacga
661 agacgggag gacgaggctg aggacacagg tgtggacaca ggggcccctt actggacacg
721 gccgagcgg atggacaaga agctgctggc cgtgccggcc gccaacaccg tccgcttccg
781 ctgcccagcc gctggcaacc ccactccctc catctcctgg ctgaagaacg gcagggagtt
```

-continued

```
 841 ccgcggcgag caccgcattg gaggcatcaa gctgcggcat cagcagtgga gcctggtcat
 901 ggaaagcgtg gtgccctcgg accgcggcaa ctacacctgc gtcgtggaga caagtttgg
 961 cagcatccgg cagacgtaca cgctggacgt gctggagcgc tccccgcacc ggcccatcct
1021 gcaggcgggg ctgccggcca accagacggc ggtgctgggc agcgacgtgg agttccactg
1081 caaggtgtac agtgacgcac agccccacat ccagtggctc aagcacgtgg aggtgaatgg
1141 cagcaaggtg ggcccggacg gcacacccta cgttaccgtg ctcaagacgc gggcgctaa
1201 caccaccgac aaggagctag aggttctctc cttgcacaac gtcacctttg aggacgccgg
1261 ggagtacacc tgcctggcgg gcaattctat tgggttttct catcactctg cgtggctggt
1321 ggtgctgcca gccgaggagg agctggtgga ggctgacgag gcgggcagtg tgtatgcagg
1381 catcctcagc tacggggtgg gcttcttcct gttcatcctg gtggtggcgg ctgtgacgct
1441 ctgccgcctg cgcagccccc ccaagaaagg cctgggctcc ccaccgtgc acaagatctc
1501 ccgcttcccg ctcaagcgac aggtgtccct ggagtccaac gcgtccatga gctccaacac
1561 accactggtg cgcatcgcaa ggctgtcctc aggggagggc cccacgctgg ccaatgtctc
1621 cgagctcgag ctgcctgccg accccaaatg ggagctgtct cgggcccggc tgaccctggg
1681 caagcccctt ggggagggct gcttcggcca ggtggtcatg gcggaggcca tcggcattga
1741 caaggaccgg gccgccaagc ctgtcaccgt agccgtgaag atgctgaaag acgatgccac
1801 tgacaaggac ctgtcggacc tggtgtctga gatggagatg atgaagatga tcgggaaaca
1861 caaaaacatc atcaacctgc tgggcgcctg cacgcagggc gggcccctgt acgtgctggt
1921 ggagtacgcg gccaagggta acctgcggga gtttctgcgg gcgcggcggc ccccgggcct
1981 ggactactcc ttcgacacct gcaagccgcc cgaggagcag ctcaccttca aggacctggt
2041 gtcctgtgcc taccaggtgg cccggggcat ggagtacttg gcctcccaga gtgcatcca
2101 cagggacctg gctgcccgca atgtgctggt gaccgaggac aacgtgatga agatcgcaga
2161 cttcggcctg gcccgggacg tgcacaacct cgactactac aagaagacaa ccaacggccg
2221 gctgccgtg aagtggatgg cgcctgaggc cttgtttgac cgagtctaca ctcaccagag
2281 tgacgtctgg tcctttgggg tcctgctctg ggagatcttc acgctggggg gctccccgta
2341 ccccggcatc cctgtggagg agctcttcaa gctgctgaag gagggccacc gcatggacaa
2401 gcccgccaac tgcacacacg acctgtacat gatcatgcgg gagtgctggc atgccgcgcc
2461 ctcccagagg cccaccttca agcagctggt ggaggacctg accgtgtcc ttaccgtgac
2521 gtccaccgac gagtacctgg acctgtcggc gcctttcgag cagtactccc cgggtggcca
2581 ggacaccccc agctccagct cctcagggga cgactccgtg tttgcccacg acctgctgcc
2641 cccggcccca cccagcagtg ggggctcgcg gacgtgaagg gccactggtc cccaacaatg
2701 tgaggggtcc ctagcagccc acctgctgc tggtgcacag ccactccccg gcatgagact
2761 cagtgcagat ggagagacag ctacacagag ctttggtctg tgtgtgtgt tgtgcgtgt
2821 tgtgtgtgtg tgtgcacatc cgcgtgtgcc tgtgtgcgtg cgcatcttgc ctccaggtgc
2881 agaggtaccc тggggтgтccc cgctgctgtg caacggtctc ctgactggtc ctgcagcacc
2941 gagggggccтт tgttctgggg ggacccagtg cagaatgtaa gtgggcccac ccggtgggac
3001 ccccgtgggg cagggagctg ggcccgacat ggctccggcc tctgcctttt caccacggga
3061 cactcacaggg tgggcctcgg cccctcccac acccaaagct gagcctgcag ggaagcccca
3121 cаттgтccagc accttgtgcc tggggtgtta gtggcaccgc ctccccacct ccaggctttc
3181 ccacttccca ccctgcccct cagagactga aattacgggt acctgaagat gggagccttt
```

-continued

```
3241 accttttatg caaaaggttt attccggaaa ctagtgtaca tttctataaa tagatgctgt 3301 gtatatggta tatatacata tatatatata acatatatgg aagaggaaaa ggctggtaca 3361 acggaggcct gcgaccctgg gggcacagga ggcaggcatg gccctgggcg gggcgtgggg 3421 gggcgtggag ggaggcccca ggggtctca cccatgcaag cagaggacca gggcctttc 3481 tggcaccgca gttttgtttt aaaactggac ctgtatattt gtaaagctat ttatgggccc 3541 ctggcactct tgttcccaca ccccaacact tccagcattt agctggccac atggcggaga 3601 gttttaattt ttaacttatt gacaaccgag aaggtttatc ccgccgatag agggacggcc 3661 aagaatgtac gtccagcctg ccccggagct ggaggatccc ctccaagcct aaaaggttgt 3721 taatagttgg aggtgattcc agtgaagata ttttatttcc tttgtcctt ttcaggagaa 3781 ttagatttct ataggatttt tctttaggag atttatttt tggacttcaa agcaagctgg 3841 tattttcata caaattcttc taattgctgt gtgtcccagg cagggagacg gtttccaggg 3901 aggggccggc cctgtgtgca ggttccgatg ttattagatg ttacaagttt atatatatct 3961 atatatataa tttattgagt ttttacaaga tgtatttgtt gtagacttaa cacttcttac 4021 gcaatgcttc tagagtttta tagcctggac tgctacctt caaagcttgg agggaagccg 4081 tgaattcagt tggttcgttc tgtactgtta ctgggccctg agtctgggca gctgtccctt 4141 gcttgcctgc agggccatgg ctcagggtgg tctcttcttg gggcccagtg catggtggcc 4201 agaggtgtca cccaaaccgg caggtgcgat tttgttaacc cagcgacgaa ctttccgaaa 4261 aataaagaca cctggttgct aacctggaaa aaaaaaaaa aaaa
```

SEQ ID NO: 528 is the FGFR3 wt cDNA Nucleotide Sequence corresponding to the coding sequence of FGFR3 (2421 bp) (NM_000142.4 NP_000133.1). The location of exons are marked by alternating underlining.

ATGGGCGCCCCTGCCTGCGCCCTCGCGCTCTGCGTGGCCGTGGCCATCGT

GGCCGGCGCCTCCTCGGAGTCCTTGGGGACGGAGCAGCGCGTCGTGGGGC

GAGCGGCAGAAGTCCCGGGCCCAGAGCCCGGCCAGCAGGAGCAGTTGGTC

TTCGGCAGCGGGGATGCTGTGTGGAGCTGAGCTGTCCCCCGCCGGGGGTGG

TCCCATGGGGCCCACTGTCTGGGTCAAGGATGGCACAGGGCTGGTGCCCT

CGGAGCGTGTCCTGGTGGGGCCCCAGCGGCTGCAGGTGCTGAATGCCTCC

CACGAGGACTCCGGGGCCTACAGCTGCCGGCAGCGGCTCACGCAGCGCGT

ACTGTGCCACTTCAGTGTGCGGGTGACAGACGCTCCATCCTCGGGAGATG

ACGAAGACGGGGAGGACGAGGCTGAGGACACAGGTGTGGACACAGGGGCC

CCTTACTGGACACGGCCCGAGCGGATGGACAAGAAGCTGCTGGCCGTGCC

GGCCGCCAACACCGTCCGCTTCCGCTGCCCAGCCGCTGGCAACCCCACTC

CCTCCATCTCCTGGCTGAAGAACGGCAGGGAGTTCCGCGGCGAGCACCGC

ATTGGAGGCATCAAGCTGCGGCATCAGCAGTGGAGCCTGGTCATGGAAAG

CGTGGTGCCCTCGGACCGCGGCAACTACACCTGCGTCGTGGAGAACAAGT

TTGGCAGCATCCGGCAGACGTACACGCTGGACGTGCTGGAGCGCTCCCCG

CACCGGCCCATCCTGCAGGCGGGGCTGCCGGCCAACCAGACGGCGGTGCT

GGGCAGCGACGTGGAGTTCCACTGCAAGGTGTACAGTGACGCACAGCCCC

ACATCCAGTGGCTCAAGCACGTGGAGGTGAATGGCAGCAAGGTGGGCCCG

GACGGCACACCCTACGTTACCGTGCTCAAGACGGCGGGCGCTAACACCAC

CGACAAGGAGCTAGAGGTTCTCTCCTTGCACAACGTCACCTTTGAGGACG

CCGGGGAGTACACCTGCCTGGCGGGCAATTCTATTGGGTTTTCTCATCAC

TCTGCGTGGCTGGTGGTGCTGCCAGCCGAGGAGGAGCTGGTGGAGGCTGA

CGAGGCGGGCAGTGTGTATGCAGGCATCCTCAGCTACGGGGTGGGCTTCT

TCCTGTTCATCCTGGTGGTGGCGGCTGTGACGCTCTGCCGCCTGCGCAGC

CCCCCCAAGAAAGGCCTGGGCTCCCCCACCGTGCACAAGATCTCCCGCTT

CCCGCTCAAGCGACAGGTGTCCCTGGAGTCCAACGCGTCCATGAGCTCCA

ACACACCACTGGTGCGCATCGCAAGGCTGTCCTCAGGGGAGGGCCCCACG

CTGGCCAATGTCTCCGAGCTCGAGCTGCCTGCCGACCCCAAATGGGAGCT

GTCTCGGGCCCGGCTGACCCTGGGCAAGCCCCTTGGGGAGGGCTGCTTCG

GCCAGGTGGTCATGGCGGAGGCCATCGGCATTGACAAGGACCGGGCCGCC

AAGCCTGTCACCGTAGCCGTGAAGATGCTGAAAGACGATGCCACTGACAA

GGACCTGTCGGACCTGGTGTCTGAGATGGAGATGATGAAGATGATCGGGA

AACACAAAAACATCATCAACCTGCTGGGCGCCTGCACGCAGGGCGGGCCC

CTGTACGTGCTGGTGGAGTACGCGGCCAAGGGTAACCTGCGGGAGTTTCT

GCGGGCGCGGCGGCCCCCGGGCCTGGACTACTCCTTCGACACCTGCAAGC

CGCCCGAGGAGCAGCTCACCTTCAAGGACCTGGTGTCCTGTGCCTACCAG

GTGGCCCGGGGCATGGAGTACTTGGCCTCCCAGAAGTGCATCCACAGGGA

CCTGGCTGCCCGCAATGTGCTGGTGACCGAGGACAACGTGATGAAGATCG

CAGACTTCGGGCTGGCCCGGGACGTGCACAACCTCGACTACTACAAGAAG

```
ACGACCAACGGCCGGCTGCCCGTGAAGTGGATGGCGCCTGAGGCCTTGTT

TGACCGAGTCTACACTCACCAGAGTGACGTCTGGTCCTTTGGGGTCCTGC

TCTGGGAGATCTTCACGCTGGGGGGCTCCCCGTACCCCGGCATCCCTGTG

GAGGAGCTCTTCAAGCTGCTGAAGGAGGGCCACCGCATGGACAAGCCCGC

CAACTGCACACGACCTGTACATGATCATGCGGGAGTGCTGGCATGCCG

CGCCCTCCCAGAGGCCCACCTTCAAGCAGCTGGTGGAGGACCTGGACCGT

GTCCTTACCGTGACGTCCACCGACGAGTACCTGGACCTGTCGGCGCCTTT
```

```
CGAGCAGTACTCCCCGGGTGGCCAGGACACCCCCAGCTCCAGCTCCTCAG

GGGACGACTCCGTGTTTGCCCACGACCTGCTGCCCCCGGCCCCACCCAGC

AGTGGGGGCTCGCGGACGTGA
```

The Genbank ID for the TACC3 gene is 10460. SEQ ID NO: 92 is the TACC3 Amino Acid Sequence (NP_006333) (838 aa). The location of exons are marked by alternating underlining. Amino acids encoded by nucleotides spanning exons are shaded in gray. Double underlining indicates the amino acid encoded by bold italicized the nucleotides in SEQ ID NO: 529.

```
  1 MSLQVLNDKN VSNEKNTENC DFLFSPPEVT GRSSVLRVSQ KENVPPKNLA KAMKVTFQTP
 61 LRDPQTHRIL SPSMASKLEA PFTQDDTLGL ENSHPVWTQK EMQQLIKEVD AKTTHGILQK
121 PVEADTDLLG DASPAFGSGS SSESGPGALA DLDCSSSSQS PGSSENQMVS PGKVSGSPEQ
181 AVEENLSSYS LDRRVTPASE TLEDPCRTES QHKAETPHGA EEECKAETPH GAEEEECRHGG
241 VCAPAAVATS PPGAIPKEAC GGAPLQGLPG EALGCPAGVG TPVPADGTQT LTCAHTSAPE
301 STAPTNHLVA GRAMTLSPQE EVAAGQMASS SRSGPVKLEF DVSDGATSKR APPPRRLGER
361 SGLKPPLRKA AVRQQKAPQE VEEDDGRSGA GEDPPMPASR GSYHLDWDKM DDPNFIPFGG
421 DTKSGCSEAQ PPESPETRLG QPAAEQLHAG PATEEPGPCL SQQLHSASAE DTPVVQLAAE
481 TPTAESKERA LNSASTSLPT SCPGSEPVPT HQQGQPALEL KEESFRDPAE VLGTGAEVDY
541 LEQFGTSSFK ESALRKQSLY LKFDPLLRDS PGRPVPVATE TSSMHGANET PSGRPREAKL
601 VEFDFLGALD IPVPGPPPGV PAPGGPPLST GPIVDLLQYS QKDLDAVVKA TQEENRELRS
661 RCEELHGKNL ELGKIMDRFE EVVYQAMEEV QKQKELSKAE IQKVLKEKDQ LTTDLNSMEK
721 SFSDLFKRFE KQKEVIEGYR KNEESLKKCV EDYLARITQE GQRYQALKAH AEEKLQLANE
781 EIAQVRSKAQ AEALALQASL RKEQMRIQSL EKTVEQKTKE NEELTRICDD LISKMEKI
```

SEQ ID NO: 93 is the TACC3 Nucleotide Sequence (NM_006342) (2847 bp):

```
  1 gcgtttgaaa ctccggcgcg ccggcggcca tcaagggcta gaagcgcgac ggcggtagca
 61 gctaggcttg gcccccggcg tggagcagac gcggacccct ccttcctggc ggcggcggcg
121 cgggctcaga gccggcaac gggcgggcgg gcagaatgag tctgcaggtc ttaaacgaca
181 aaaatgtcag caatgaaaaa aatacagaaa attgcgactt cctgttttcg ccaccagaag
241 ttaccggaag atcgtctgtt cttcgtgtgt cacagaaaga aaatgtgcca cccaagaacc
301 tggccaaagc tatgaaggtg acttttcaga cacctctgcg ggatccacag acgcacagga
361 ttctaagtcc tagcatggcc agcaaacttg aggctccttt cactcaggat gacacccttg
421 gactggaaaa ctcacacccg gtctggacac agaaagagaa ccaacagctc atcaaggaag
481 tggatgccaa aactactcat ggaattctac agaaaccagt ggaggctgac accgacctcc
541 tgggggatgc aagcccagcc tttgggagtg gcagctccag cgagtctggc ccaggtgccc
601 tggctgacct ggactgctca agctcttccc agagcccagg aagttctgag aaccaaatgg
661 tgtctccagg aaaagtgtct ggcagccctg agcaagccgt ggaggaaaac cttagttcct
721 attccttaga cagaagagtg acacccgcct ctgagaccct agaagaccct tgcaggacag
781 agtcccagca caaagcggag actccgcacg gagccgagga agaatgcaaa gcggagactc
841 cgcacggagc cgaggaggaa tgccggcacg gtggggtctg tgctcccgca gcagtggcca
```

```
 901 cttcgcctcc tggtgcaatc cctaaggaag cctgcggagg agcacccctg cagggtctgc
 961 ctggcgaagc cctgggctgc cctgcgggtg tgggcacccc cgtgccagca gatggcactc
1021 agacccttac ctgtgcacac acctctgctc ctgagagcac agcccaacc aaccacctgg
1081 tggctggcag ggccatgacc ctgagtcctc aggaagaagt ggctgcaggc caaatggcca
1141 gctcctcgag gagcggacct gtaaaactag aatttgatgt atctgatggc gccaccagca
1201 aaagggcacc cccaccaagg agactgggag agaggtccgg cctcaagcct cccttgagga
1261 aagcagcagt gaggcagcaa aaggcccgc aggaggtgga ggaggacgac ggtaggagcg
1321 gagcaggaga ggaccccccc atgccagctt ctcgggctc ttaccacctc gactgggaca
1381 aaatggatga cccaaacttc atcccgttcg gaggtgacac caagtctggt tgcagtgagg
1441 cccagccccc agaaagccct gagaccaggc tgggccagcc agcggctgaa cagttgcatg
1501 ctgggcctgc cacggaggag ccaggtccct gtctgagcca gcagctgcat tcagcctcag
1561 cggaggacac gcctgtggtg cagttggcag ccgagacccc aacagcagag agcaaggaga
1621 gagccttgaa ctctgccagc acctcgcttc ccacaagctg tccaggcagt gagccagtgc
1681 ccacccatca gcaggggcag cctgccttgg agctgaaaga ggagagcttc agagaccccg
1741 ctgaggttct aggcacgggc gcggaggtgg attacctgga gcagtttgga acttcctcgt
1801 ttaaggagtc ggccttgagg aagcagtcct tatacctcaa gttcgacccc ctcctgaggg
1861 acagtcctgg tagaccagtg cccgtggcca ccgagaccag cagcatgcac ggtgcaaatg
1921 agactccctc aggacgtccg cgggaagcca agcttgtgga gttcgatttc ttgggagcac
1981 tggacattcc tgtgccaggc ccacccccag gtgttcccgc gcctgggggc ccacccctgt
2041 ccaccggacc tatagtggac ctgctccagt acagccagaa ggacctggat gcagtggtaa
2101 aggcgacaca ggaggagaac cgggagctga ggagcaggtg tgaggagctc cacgggaaga
2161 acctggaact ggggaagatc atggacaggt tcgaagaggt tgtgtaccag gccatggagg
2221 aagttcagaa gcagaaggaa cttttccaaag ctgaaatcca gaaagttcta aaagaaaaag
2281 accaacttac cacagatctg aactccatgg agaagtcctt ctccgacctc ttcaagcgtt
2341 ttgagaaaca gaaagaggtg atcgagggct accgcaagaa cgaagagtca ctgaagaagt
2401 gcgtggagga ttacctggca aggatcaccc aggagggcca gaggtaccaa gccctgaagg
2461 cccacgcgga ggagaagctg cagctggcaa acgaggagat cgcccaggtc cggagcaagg
2521 cccaggcgga agcgttggcc ctccaggcca gcctgaggaa ggagcagatg cgcatccagt
2581 cgctggagaa gacagtggag cagaagacta aagagaacga ggagctgacc aggatctgcg
2641 acgacctcat ctccaagatg gagaagatct gacctccacg gagccgctgt ccccgccccc
2701 ctgctcccgt ctgtctgtcc tgtctgattc tcttaggtgt catgttcttt tttctgtctt
2761 gtcttcaact tttttaaaaa ctagattgct ttgaaaacat gactcaataa aagtttcctt
2821 tcaatttaaa cactgaaaaa aaaaaaa
```

SEQ ID NO: 529 is the TACC3 wt cDNA Nucleotide Sequence corresponding to the coding sequence of TACC3 (2517 bp) (NM_006342.2, NP_006333.1). The location of exons are marked by alternating underlining.

ATGAGTCTGCAGGTCTTAAACGACAAAAATGTCAGCAATGAAAAAAATACAGAAAATTGCGACTTCCTGT

TTTCGCCACCAGAAGTTACCGGAAGATCGTCTGTTCTTCGTGTGTCACAGAAAGAAAATGTGCCACCCAA

GAACCTGGCCAAAGCTATGAA<u>GGTGACTTTTCAGACACCTCTGCGGGATCCACAGACGCACAGGATTCTA</u>

<u>AGTCCTAGCATGGCCAGCAAACTTGAGGCTCCTTTCACTCAGGATGACACCCTTGGACTGGAAAACTCAC</u>

<u>ACCCGGTCTGGACACAGAAAGAGAAC</u>CAACAGCTCATCAAGGAAGTGGATGCCAAACTACTCATGGAAT

-continued

```
TCTACAGAAACCAGTGGAGGCTGACACCGACCTCCTGGGGGATGCAAGCCCAGCCTTTGGGAGTGGCAGC
TCCAGCGAGTCTGGCCCAGGTGCCCTGGCTGACCTGGACTGCTCAAGCTCTTCCCAGAGCCCAGGAAGTT
CTGAGAACCAAATGGTGTCTCCAGGAAAAGTGTCTGGCAGCCCTGAGCAAGCCGTGGAGGAAAACCTTAG
TTCCTATTCCTTAGACAGAAGAGTGACACCCGCCTCTGAGACCCTAGAAGACCCTTGCAGGACAGAGTCC
CAGCACAAAGCGGAGACTCCGCACGGAGCCGAGGAAGAATGCAAAGCGGAGACTCCGCACGGAGCCGAGG
AGGAATGCCGGCACGGTGGGGTCTGTGCTCCCGCAGCAGTGGCCACTTCGCCTCCTGGTGCAATCCCTAA
GGAAGCCTGCGGAGGAGCACCCCTGCAGGGTCTGCCTGGCGAAGCCCTGGGCTGCCCTGCGGGTGTGGGC
ACCCCCGTGCCAGCAGATGGCACTCAGACCCTTACCTGTGCACACACCTCTGCTCCTGAGAGCACAGCCC
CAACCAACCACCTGGTGGCTGGCAGGGCCATGACCCTGAGTCCTCAGGAAGAAGTGGCTGCAGGCCAAAT
GGCCAGCTCCTCGAGGAGCGGACCTGTAAAACTAGAATTTGATGTATCTGATGGCGCCACCAGCAAAAGG
GCACCCCCACCAAGGAGACTGGGAGAGAGGTCCGGCCTCAAGCCTCCCTTGAGGAAAGCAGCAGTGAGGC
AGCAAAAGGCCCCGCAGGAGGTGGAGGAGGACGACGGTAGGAGCGGAGCAGGAGAGGACCCCCCCATGCC
AGCTTCTCGGGGCTCTTACCACCTCGACTGGGACAAAATGGATGACCCAAACTTCATCCCGTTCGGAGGT
GACACCAAGTCTGGTTGCAGTGAGGCCCAGCCCCCAGAAAGCCCTGAGACCAGGCTGGGCCAGCCAGCGG
CTGAACAGTTGCATGCTGGGCCTGCCACGGAGGAGCCAGGTCCCTGTCTGAGCCAGCAGCTGCATTCAGC
CTCAGCGGAGGACACGCCTGTGGTGCAGTTGGCAGCCGAGACCCCAACAGCAGAGAGCAAGGAGAGAGCC
TTGAACTCTGCCAGCACCTCGCTTCCCACAAGCTGTCCAGGCAGTGAGCCAGTGCCCACCCATCAGCAGG
GGCAGCCTGCCTTGGAGCTGAAAGAGGAGAGCTTCAGAGACCCCGCTGAGGTTCTAGGCACGGGCGCGGA
GGTGGATTACCTGGAGCAGTTTGGAACTTCCTCGTTTAAGGAGTCGGCCTTGAGGAAGCAGTCCTTATAC
CTCAAGTTCGACCCCCTCCTGAGGGACAGTCCTGGTAGACCAGTGCCCGTGGCCACCGAGACCAGCAGCA
TGCACGGTGCAAATGAGACTCCCTCAGGACGTCCGCGGGAAGCCAAGCTTGTGGAGTTCGATTTCTTGGG
AGCACTGGACATTCCTGTGCCAGGCCCACCCCCAGGTGTTCCCGCGCCTGGGGGCCCACCCCTGTCCACC
GGACCTATAGTGGACCTGCTCCAGTACAGCCAGAAGGACCTGGATGCAGTGGTAAAGGCGACACAGGAGG
AGAACCGGGAGCTGAGGAGCAGGTGTGAGGAGCTCCACGGGAAGAACCTGGAACTGGGGAAGATCATGGA
CAGGTTCGAAGAGGTTGTGTACCAGGCCATGGAGGAAGTTCAGAAGCAGAAGGAACTTTCCAAAGCTGAA
ATCCAGAAAGTTCTAAAAGAAAAAGACCAACTTACCACAGATCTGAACTCCATGGAGAAGTCCTTCTCCG
ACCTCTTCAAGCGTTTTGAGAAACAGAAAGAGGTGATCGAGGGCTACCGCAAGAACGAAGAGTCACTGAA
GAAGTGCGTGGAGGATTACCTGGCAAGGATCACCCAGGAGGGCCAGAGGTACCAAGCCCTGAAGGCCCAC
GCGGAGGAGAAGCTGCAGCTGGCAAACGAGGAGATCGCCCAGGTCCGGAGCAAGGCCCAGGCGGAAGCGT
TGGCCCTCCAGGCCAGCCTGAGGAAGGAGCAGATGCGCATCCAGTCGCTGGAGAAGACAGTGGAGCAGAA
GACTAAAGAGAACGAGGAGCTGACCAGGATCTGCGACGACCTCATCTCCAAGATGGAGAAGATCTGA
```

SEQ ID NO: 94 is the nucleotide sequence of FGFR3-TACC3.

```
  1 gtcgcgggca gctggcgccg cgcggtcctg ctctgccggt cgcacggacg caccggcggg
 61 ccgccggccg gagggacggg gcgggagctg ggcccgcgga cagcgagccg gagcgggagc
121 cgcgcgtagc gagccgggct ccggcgctcg ccagtctccc gagcggcgcc cgcctcccgc
181 cggtgcccgc gccgggccgt ggggggcagc atgcccgcgc gcgctgcctg aggacgccgc
241 ggccccgcc ccgccatgg gcgccctgc ctgcgccctc gcgctctgcg tggccgtggc
301 catcgtggcc ggcgcctcct cggagtcctt ggggacggag cagcgcgtcg tggggcgagc
```

-continued

```
 361 ggcagaagtc ccgggcccag agcccggcca gcaggacag ttggtcttcg gcagcgggga
 421 tgctgtggag ctgagctgtc ccccgcccgg gggtggtccc atggggccca ctgtctgggt
 481 caaggatggc acagggctgg tgccctcgga gcgtgtcctg gtgggcccc agcggctgca
 541 ggtgctgaat gcctcccacg aggactccgg ggcctacagc tgccggcagc ggctcacgca
 601 gcgcgtactg tgccacttca gtgtgcgggt gacagacgct ccatcctcgg gagatgacga
 661 agacggggag gacgaggctg aggacacagg tgtggacaca ggggccccct actggacacg
 721 gcccgagcgg atggacaaga agctgctggc cgtgccggcc gccaacaccg tccgcttccg
 781 ctgcccagcc gctggcaacc ccactccctc catctcctgg ctgaagaacg cagggagtt
 841 ccgcggcgag caccgcattg aggcatcaa gctgcggcat cagcagtgga gcctggtcat
 901 ggaaagcgtg gtgccctcgg accgcggcaa ctacacctgc gtcgtggaga caagtttgg
 961 cagcatccgg cagacgtaca cgctggacgt gctggagcgc tccccgcacc ggcccatcct
1021 gcaggcgggg ctgccggcca accagacggc ggtgctgggc agcgacgtgg agttccactg
1081 caaggtgtac agtgacgcac agccccacat ccagtggctc aagcacgtgg aggtgaatgg
1141 cagcaaggtg ggcccggacg gcacacccta cgttaccgtg ctcaagacgg cgggcgctaa
1201 caccaccgac aaggagctag aggttctctc cttgcacaac gtcacctttg aggacgccgg
1261 ggagtacacc tgcctggcgg gcaattctat tgggttttct catcactctg cgtggctggt
1321 ggtgctgcca gccgaggagg agctggtgga ggctgacgag gcgggcagtg tgtatgcagg
1381 catcctcagc tacggggtgg gcttcttcct gttcatcctg gtggtggcgg ctgtgacgct
1441 ctgccgcctg cgcagccccc ccaagaaagg cctgggctcc ccaccgtgc acaagatctc
1501 ccgcttcccg ctcaagcgac aggtgtccct ggagtccaac gcgtccatga gctccaacac
1561 accactggtg cgcatcgcaa ggctgtcctc aggggagggc cccacgctgg ccaatgtctc
1621 cgagctcgag ctgcctgccg accccaaatg ggagctgtct cgggcccggc tgaccctggg
1681 caagccccttt ggggagggct gcttcggcca gtggtcatg cgcgaggcca tcggcattga
1741 caaggaccgg gccgccaagc ctgtcaccgt agccgtgaag atgctgaaag acgatgccac
1801 tgacaaggac ctgtcggacc tggtgtctga gatggagatg atgaagatga tcgggaaaca
1861 caaaaacatc atcaacctgc tgggcgcctg cacgcagggc gggcccctgt acgtgctggt
1921 ggagtacgcg gccaagggta acctgcggga gtttctgcgg gcgcggcggc ccccgggcct
1981 ggactactcc ttcgacacct gcaagccgcc cgaggagcag ctcaccttca aggacctggt
2041 gtcctgtgcc taccaggtgg cccggggcat ggagtacttg gcctcccaga gtgcatcca
2101 cagggacctg gctgcccgca atgtgctggt gaccgaggac aacgtgatga agatcgcaga
2161 cttcgggctg gccgggacg tgcacaacct cgactactac aagaagacaa ccaacgcccg
2221 gctgccgtg aagtggatgg cgcctgaggc cttgtttgac cgagtctaca ctcaccagag
2281 tgacgtctgg tcctttgggg tcctgctctg ggagatcttc acgctggggg gctcccgta
2341 ccccggcatc cctgtggagg agctcttcaa gctgctgaag gagggccacc gcatggacaa
2401 gcccgccaac tgcacacacg acctgtacat gatcatgcgg gagtgctggc atgccgcgcc
2461 ctcccagagg cccaccttca gcagctggt ggaggacctg gaccgtgtcc ttaccgtgac
2521 gtccaccgac tttaaggagt cggccttgag gaagcagtcc ttatacctca agttcgaccc
2581 cctcctgagg gacagtcctg gtagaccagt gcccgtggcc accgagacca gcagcatgca
2641 cggtgcaaat gagactccct caggacgtcc gcgggaagcc aagcttgtgg agttcgattt
2701 cttgggagca ctggacattc ctgtgccagg cccaccccca ggtgttcccg cgcctggggg
2761 cccaccccctg tccaccggac ctatagtgga cctgctccag tacagccaga aggacctgga
```

-continued

```
2821 tgcagtggta aaggcgacac aggaggagaa ccgggagctg aggagcaggt gtgaggagct 2881 ccacgggaag aacctggaac tggggaagat catggacagg ttcgaagagg ttgtgtacca 2941 ggccatggag gaagttcaga agcagaagga actttccaaa gctgaaatcc agaaagttct 3001 aaaagaaaaa gaccaactta ccacagatct gaactccatg gagaagtcct tctccgacct 3061 cttcaagcgt tttgagaaac agaaagaggt gatcgagggc taccgcaaga acgaagagtc 3121 actgaagaag tgcgtggagg attacctggc aaggatcacc caggagggcc agaggtacca 3181 agccctgaag gcccacgcgg aggagaagct gcagctggca aacgaggaga tcgcccaggt 3241 ccggagcaag gcccaggcgg aagcgttggc cctccaggcc agcctgagga aggagcagat 3301 gcgcatccag tcgctggaga agacagtgga gcagaagact aaagagaacg aggagctgac 3361 caggatctgc gacgacctca tctccaagat ggagaagatc tgacctccac ggagccgctg 3421 tccccgcccc cctgctcccg tctgtctgtc ctgtctgatt ctcttaggtg tcatgttctt 3481 ttttctgtct tgtcttcaac tttttaaaa actagattgc tttgaaaaca tgactcaata 3541 aaagtttcct ttcaatttaa acactgaaaa aaaaaaaa
```

SEQ ID NO: 530 is the nucleotide sequence (cDNA) of FGFR3ex17-TACC3ex11. The sequence corresponding to FGFR3 is underlined. The sequence corresponding to TACC3 is italics:

ATGGGCGCCCCTGCCTGCGCCCTCGCGCTCTGCGTGGCCGTGGCCATCGTGGCCGGCGCCTCCTCGGAGTCCTTGGG
GACGGAGCAGCGCGTCGTGGGGCGAGCGGCAGAAGTCCCGGGCCCAGAGCCCGGCCAGCAGGAGCAGTTGGTCTTCG
GCAGCGGGGATGCTGTGGAGCTGAGCTGTCCCCCGCCCGGGGGTGGTCCCATGGGGCCCACTGTCTGGGTCAAGGAT
GGCACAGGGCTGGTGCCCTCGGAGCGTGTCCTGGTGGGGCCCCAGCGGCTGCAGGTGCTGAATGCCTCCCACGAGGA
CTCCGGGGCCTACAGCTGCCGGCAGCGGCTCACGCAGCGCGTACTGTGCCACTTCAGTGTGCGGGTGACAGACGCTC
CATCCTCGGGAGATGACGAAGACGGGGAGGACGAGGCTGAGGACACAGGTGTGGACACAGGGGCCCCTTACTGGACA
CGGCCCGAGCGGATGGACAAGAAGCTGCTGGCCGTGCCGGCCGCCAACACCGTCCGCTTCCGCTGCCCAGCCGCTGG
CAACCCCACTCCCTCCATCTCCTGGCTGAAGAACGGCAGGGAGTTCCGCGGCGAGCACCGCATTGGAGGCATCAAGC
TGCGGCATCAGCAGTGGAGCCTGGTCATGGAAAGCGTGGTGCCCTCGGACCGCGGCAACTACACCTGCGTCGTGGAG
AACAAGTTTGGCAGCATCCGGCAGACGTACACGCTGGACGTGCTGGAGCGCTCCCCGCACCGGCCCATCCTGCAGGC
GGGGCTGCCGGCCAACCAGACGGCGGTGCTGGGCAGCGACGTGGAGTTCCACTGCAAGGTGTACAGTGACGCACAGC
CCCACATCCAGTGGCTCAAGCACGTGGAGGTGAATGGCAGCAAGGTGGGCCCGGACGGCACACCCTACGTTACCGTG
CTCAAGACGGCGGGCGCTAACACCACCGACAAGGAGCTAGAGGTTCTCTCCTTGCACAACGTCACCTTTGAGGACGC
CGGGGAGTACACCTGCCTGGCGGGCAATTCTATTGGGTTTTCTCATCACTCTGCGTGGCTGGTGGTGCTGCCAGCCG
AGGAGGAGCTGGTGGAGGCTGACGAGGCGGGCAGTGTGTATGCAGGCATCCTCAGCTACGGGGTGGGCTTCTTCCTG
TTCATCCTGGTGGTGGCGGCTGTGACGCTCTGCCGCCTGCGCAGCCCCCCCAAGAAAGGCCTGGGCTCCCCCACCGT
GCACAAGATCTCCCGCTTCCCGCTCAAGCGACAGGTGTCCCTGGAGTCCAACGCGTCCATGAGCTCCAACACACCAC
TGGTGCGCATCGCAAGGCTGTCCTCAGGGGAGGGCCCCACGCTGGCCAATGTCTCCGAGCTCGAGCTGCCTGCCGAC
CCCAAATGGGAGCTGTCTCGGGCCCGGCTGACCCTGGGCAAGCCCCTTGGGGAGGGCTGCTTCGGCCAGGTGGTCAT
GGCGGAGGCCATCGGCATTGACAAGGACCGGGCCGCCAAGCCTGTCACCGTAGCCGTGAAGATGCTGAAAGACGATG
CCACTGACAAGGACCTGTCGGACCTGGTGTCTGAGATGGAGATGATGAAGATGATCGGGAAACACAAAAACATCATC
AACCTGCTGGGCGCCTGCACGCAGGGCGGGCCCCTGTACGTGCTGGTGGAGTACGCGGCCAAGGGTAACCTGCGGGA
GTTTCTGCGGGCGCGGCGGCCCCCGGGGCCTGGACTACTCCTTCGACACCTGCAAGCCGCCCGAGGAGCAGCTCACCT

-continued

```
TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGACGTAAAGGCGACACAGGAGGAGAACCGGGAGCTGAGG

AGCAGGTGTGAGGAGCTCCACGGGAAGAACCTGGAACTGGGGAAGATCATGGACAGGTTCGAAGAGGTTGTGTACCA

GGCCATGGAGGAAGTTCAGAAGCAGAAGGAACTTTCCAAAGCTGAAATCCAGAAAGTTCTAAAAGAAAAAGACCAAC

TTACCACAGATCTGAACTCCATGGAGAAGTCCTTCTCCGACCTCTTCAAGCGTTTTGAGAAACAGAAAGAGGTGATC

GAGGGCTACCGCAAGAACGAAGAGTCACTGAAGAAGTGCGTGGAGGATTACCTGGCAAGGATCACCCAGGAGGGCCA

GAGGTACCAAGCCCTGAAGGCCCACGCGGAGGAGAAGCTGCAGCTGGCAAACGAGGAGATCGCCCAGGTCCGGAGCA

AGGCCCAGGCGGAAGCGTTGGCCCTCCAGGCCAGCCTGAGGAAGGAGCAGATGCGCATCCAGTCGCTGGAGAAGACA

GTGGAGCAGAAGACTAAAGAGAACGAGGAGCTGACCAGGATCTGCGACGACCTCATCTCCAAGATGGAGAAGATCTG

A
```

SEQ ID NO: 531 is the nucleotide sequence (cDNA) of FGFR3ex17-TACC3ex8. The sequence corresponding to FGFR3 is underlined. The sequence corresponding to TACC3 is italicized:

```
ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGGTGGTCCCATGGGGCCCACTGTCTGGGTCAAGGAT

GGCACAGGGCTGGTGCCCTCGGAGCGTGTCCTGGTGGGGCCCCAGCGGCTGCAGGTGCTGAATGCCTCCCACGAGGA

CTCCGGGGCCTACAGCTGCCGGCAGCGGCTCACGCAGCGCGTACTGTGCCACTTCAGTGTGCGGGTGACAGACGCTC

CATCCTCGGGAGATGACGAAGACGGGGAGGACGAGGCTGAGGACACAGGTGTGGACACAGGGGCCCCTTACTGGACA

CGGCCCGAGCGGATGGACAAGAAGCTGCTGGCCGTGCCGGCCGCCAACACCGTCCGCTTCCGCTGCCCAGCCGCTGG

CAACCCCACTCCCTCCATCTCCTGGCTGAAGAACGGCAGGGAGTTCCGCGGCGAGCACCGCATTGGAGGCATCAAGC

TGCGGCATCAGCAGTGGAGCCTGGTCATGGAAAGCGTGGTGCCCTCGGACCGCGGCAACTACACCTGCGTCGTGGAG

AACAAGTTTGGCAGCATCCGGCAGACGTACACGCTGGACGTGCTGGAGCGCTCCCCGCACCGGCCCATCCTGCAGGC

GGGGCTGCCGGCCAACCAGACGGCGGTGCTGGGCAGCGACGTGGAGTTCCACTGCAAGGTGTACAGTGACGCACAGC

CCCACATCCAGTGGCTCAAGCACGTGGAGGTGAATGGCAGCAAGGTGGGCCCGGACGGCACACCCTACGTTACCGTG

CTCAAGACGGCGGGCGCTAACACCACCGACAAGGAGCTAGAGGTTCTCTCCTTGCACAACGTCACCTTTGAGGACGC

CGGGGAGTACACCTGCCTGGCGGGCAATTCTATTGGGTTTTCTCATCACTCTGCGTGGCTGGTGGTGCTGCCAGCCG

AGGAGGAGCTGGTGGAGGCTGACGAGGCGGGCAGTGTGTATGCAGGCATCCTCAGCTACGGGGTGGGCTTCTTCCTG

TTCATCCTGGTGGTGGCGGCTGTGACGCTCTGCCGCCTGCGCAGCCCCCCCAAGAAAGGCCTGGGCTCCCCCACCGT

GCACAAGATCTCCCGCTTCCCGCTCAAGCGACAGGTGTCCCTGGAGTCCAACGCGTCCATGAGCTCCAACACACCAC

TGGTGCGCATCGCAAGGCTGTCCTCAGGGGAGGGCCCCACGCTGGCCAATGTCTCCGAGCTCGAGCTGCCTGCCGAC

CCCAAATGGGAGCTGTCTCGGGCCCGGCTGACCCTGGGCAAGCCCCTTGGGGAGGGCTGCTTCGGCCAGGTGGTCAT

GGCGGAGGCCATCGGCATTGACAAGGACCGGGCCGCCAAGCCTGTCACCGTAGCCGTGAAGATGCTGAAAGACGATG

CCACTGACAAGGACCTGTCGGACCTGGTGTCTGAGATGGAGATGATGAAGATGATCGGGAAACACAAAAACATCATC

AACCTGCTGGGCGCCTGCACGCAGGGCGGGCCCCTGTACGTGCTGGTGGAGTACGCGGCCAAGGGTAACCTGCGGGA
```

-continued

GTTTCTGCGGGCGCGGCGGCCCCCGGGCCTGGACTACTCCTTCGACACCTGCAAGCCGCCCGAGGAGCAGCTCACCT

TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGA*CTTTAAGGAGTCGGCCTTGAGGAAGCAGTCCTTATAC*

*CTCAAGTTCGACCCCCTCCTGAGGGACAGTCCTGGTAGACCAGTGCCCGTGGCCACCGAGACCAGCAGCATGCACGG*

*TGCAAATGAGACTCCCTCAGGACGTCCGCGGGAAGCAAGCTTGTGGAGTTCGATTTCTTGGGAGCACTGGACATTC*

*CTGTGCCAGGCCCACCCCCAGGTGTTCCCGCGCCTGGGGGCCCACCCCTGTCCACCGGACCTATAGTGGACCTGCTC*

*CAGTACAGCCAGAAGGACCTGGATGCAGTGGTAAAGGCGACACAGGAGGAGAACCGGGAGCTGAGGAGCAGGTGTGA*

*GGAGCTCCACGGGAAGAACCTGGAACTGGGGAAGATCATGGACAGGTTCGAAGAGGTTGTGTACCAGGCCATGGAGG*

*AAGTTCAGAAGCAGAAGGAACTTTCCAAAGCTGAAATCCAGAAAGTTCTAAAAGAAAAAGACCAACTTACCACAGAT*

*CTGAACTCCATGGAGAAGTCCTTCTCCGACCTCTTCAAGCGTTTTGAGAAACAGAAAGAGGTGATCGAGGGCTACCG*

*CAAGAACGAAGAGTCACTGAAGAAGTGCGTGGAGGATTACCTGGCAAGGATCACCCAGGAGGGCCAGAGGTACCAAG*

*CCCTGAAGGCCCACGCGGAGGAGAAGCTGCAGCTGGCAAACGAGGAGATCGCCCAGGTCCGGAGCAAGGCCCAGGCG*

*GAAGCGTTGGCCCTCCAGGCCAGCCTGAGGAAGGAGCAGATGCGCATCCAGTCGCTGGAGAAGACAGTGGAGCAGAA*

*GACTAAAGAGAACGAGGAGCTGACCAGGATCTGCGACGACCTCATCTCCAAGATGGAGAAGATCTGA*

SEQ ID NO: 532 is the nucleotide sequence (cDNA) of FGFR3ex17-TACC3ex10. The sequence corresponding to FGFR3 is underlined. The sequence corresponding to TACC3 is italicized:

ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGGTGGTCCCATGGGGCCCACTGTCTGGGTCAAGGAT

GGCACAGGGCTGGTGCCCTCGGAGCGTGTCCTGGTGGGGCCCCAGCGGCTGCAGGTGCTGAATGCCTCCCACGAGGA

CTCCGGGGCCTACAGCTGCCGGCAGCGGCTCACGCAGCGCGTACTGTGCCACTTCAGTGTGCGGGTGACAGACGCTC

CATCCTCGGGAGATGACGAAGACGGGGAGGACGAGGCTGAGGACACAGGTGTGGACACAGGGGCCCCTTACTGGACA

CGGCCCGAGCGGATGGACAAGAAGCTGCTGGCCGTGCCGGCCGCCAACACCGTCCGCTTCCGCTGCCCAGCCGCTGG

CAACCCCACTCCCTCCATCTCCTGGCTGAAGAACGGCAGGGAGTTCCGCGGCGAGCACCGCATTGGAGGCATCAAGC

TGCGGCATCAGCAGTGGAGCCTGGTCATGGAAAGCGTGGTGCCCTCGGACCGCGGCAACTACACCTGCGTCGTGGAG

AACAAGTTTGGCAGCATCCGGCAGACGTACACGCTGGACGTGCTGGAGCGCTCCCCGCACCGGCCCATCCTGCAGGC

GGGGCTGCCGGCCAACCAGACGGCGGTGCTGGGCAGCGACGTGGAGTTCCACTGCAAGGTGTACAGTGACGCACAGC

CCCACATCCAGTGGCTCAAGCACGTGGAGGTGAATGGCAGCAAGGTGGGCCCGGACGGCACACCCTACGTTACCGTG

CTCAAGACGGCGGGCGCTAACACCACCGACAAGGAGCTAGAGGTTCTCTCCTTGCACAACGTCACCTTTGAGGACGC

CGGGGAGTACACCTGCCTGGCGGGCAATTCTATTGGGTTTTCTCATCACTCTGCGTGGCTGGTGGTGCTGCCAGCCG

AGGAGGAGCTGGTGGAGGCTGACGAGGCGGGCAGTGTGTATGCAGGCATCCTCAGCTACGGGGTGGGCTTCTTCCTG

TTCATCCTGGTGGTGGCGGCTGTGACGCTCTGCCGCCTGCGCAGCCCCCCCAAGAAAGGCCTGGGCTCCCCCACCGT

GCACAAGATCTCCCGCTTCCCGCTCAAGCGACAGGTGTCCCTGGAGTCCAACGCGTCCATGAGCTCCAACACACCAC

```
TGGTGCGCATCGCAAGGCTGTCCTCAGGGGAGGGCCCCACGCTGGCCAATGTCTCCGAGCTCGAGCTGCCTGCCGAC

CCCAAATGGGAGCTGTCTCGGGCCCGGCTGACCCTGGGCAAGCCCCTTGGGGAGGGCTGCTTCGGCCAGGTGGTCAT

GGCGGAGGCCATCGGCATTGACAAGGACCGGGCCGCCAAGCCTGTCACCGTAGCCGTGAAGATGCTGAAAGACGATG

CCACTGACAAGGACCTGTCGGACCTGGTGTCTGAGATGGAGATGATGAAGATGATCGGGAAACACAAAAACATCATC

AACCTGCTGGGCGCCTGCACGCAGGGCGGGCCCCTGTACGTGCTGGTGGAGTACGCGGCCAAGGGTAACCTGCGGGA

GTTTCTGCGGGCGCGGCGGCCCCCGGGCCTGGACTACTCCTTCGACACCTGCAAGCCGCCCGAGGAGCAGCTCACCT

TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGACGTGCCAGGCCCACCCCCAGGTGTTCCCGCGCCTGGG

GGCCCACCCCTGTCCACCGGACCTATAGTGGACCTGCTCCAGTACAGCCAGAAGGACCTGGATGCAGTGGTAAAGGC

GACACAGGAGGAGAACCGGGAGCTGAGGAGCAGGTGTGAGGAGCTCCACGGGAAGAACCTGGAACTGGGGAAGATCA

TGGACAGGTTCGAAGAGGTTGTGTACCAGGCCATGGAGGAAGTTCAGAAGCAGAAGGAACTTTCCAAAGCTGAAATC

CAGAAAGTTCTAAAAGAAAAAGACCAACTTACCACAGATCTGAACTCCATGGAGAAGTCCTTCTCCGACCTCTTCAA

GCGTTTTGAGAAACAGAAAGAGGTGATCGAGGGCTACCGCAAGAACGAAGAGTCACTGAAGAAGTGCGTGGAGGATT

ACCTGGCAAGGATCACCCAGGAGGGCAGAGGTACCAAGCCCTGAAGGCCCACGCGGAGGAGAAGCTGCAGCTGGCA

AACGAGGAGATCGCCCAGGTCCGGAGCAAGGCCCAGGCGGAAGCGTTGGCCCTCCAGGCCAGCCTGAGGAAGGAGCA

GATGCGCATCCAGTCGCTGGAGAAGACAGTGGAGCAGAAGACTAAAGAGAACGAGGAGCTGACCAGGATCTGCGACG

ACCTCATCTCCAAGATGGAGAAGATCTGA
```

SEQ ID NO: 533 is the nucleotide sequence (cDNA) of FGFR3ex17-TACC3ex6. The sequence corresponding to FGFR3 is underlined. The sequence corresponding to TACC3 is italicized:

```
ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGGTGGTCCCATGGGGCCCACTGTCTGGGTCAAGGAT

GGCACAGGGCTGGTGCCCTCGGAGCGTGTCCTGGTGGGGCCCCAGCGGCTGCAGGTGCTGAATGCCTCCCACGAGGA

CTCCGGGGCCTACAGCTGCCGGCAGCGGCTCACGCAGCGCGTACTGTGCCACTTCAGTGTGCGGGTGACAGACGCTC

CATCCTCGGGAGATGACGAAGACGGGGAGGACGAGGCTGAGGACACAGGTGTGGACACAGGGGCCCCTTACTGGACA

CGGCCCGAGCGGATGGACAAGAAGCTGCTGGCCGTGCCGGCCGCCAACACCGTCCGCTTCCGCTGCCCAGCCGCTGG

CAACCCCACTCCCTCCATCTCCTGGCTGAAGAACGGCAGGGAGTTCCGCGGCGAGCACCGCATTGGAGGCATCAAGC

TGCGGCATCAGCAGTGGAGCCTGGTCATGGAAAGCGTGGTGCCCTCGGACCGCGGCAACTACACCTGCGTCGTGGAG

AACAAGTTTGGCAGCATCCGGCAGACGTACACGCTGGACGTGCTGGAGCGCTCCCCGCACCGGCCCATCCTGCAGGC

GGGGCTGCCGGCCAACCAGACGGCGGTGCTGGGCAGCGACGTGGAGTTCCACTGCAAGGTGTACAGTGACGCACAGC

CCCACATCCAGTGGCTCAAGCACGTGGAGGTGAATGGCAGCAAGGTGGGCCCGGACGGCACACCCTACGTTACCGTG

CTCAAGACGGCGGGCGCTAACACCACCGACAAGGAGCTAGAGGTTCTCTCCTTGCACAACGTCACCTTTGAGGACGC

CGGGGAGTACACCTGCCTGGCGGGCAATTCTATTGGGTTTTCTCATCACTCTGCGTGGCTGGTGGTGCTGCCAGCCG

AGGAGGAGCTGGTGGAGGCTGACGAGGCGGGCAGTGTGTATGCAGGCATCCTCAGCTACGGGGTGGGCTTCTTCCTG
```

TTCATCCTGGTGGTGGCGGCTGTGACGCTCTGCCGCCTGCGCAGCCCCCCAAGAAAGGCCTGGGCTCCCCCACCGT

GCACAAGATCTCCCGCTTCCCGCTCAAGCGACAGGTGTCCCTGGAGTCCAACGCGTCCATGAGCTCCAACACACCAC

TGGTGCGCATCGCAAGGCTGTCCTCAGGGGAGGGCCCCACGCTGGCCAATGTCTCCGAGCTCGAGCTGCCTGCCGAC

CCCAAATGGGAGCTGTCTCGGGCCCGGCTGACCCTGGGCAAGCCCCTTGGGGAGGGCTGCTTCGGCCAGGTGGTCAT

GGCGGAGGCCATCGGCATTGACAAGGACCGGGCCGCCAAGCCTGTCACCGTAGCCGTGAAGATGCTGAAAGACGATG

CCACTGACAAGGACCTGTCGGACCTGGTGTCTGAGATGGAGATGATGAAGATGATCGGGAAACACAAAAACATCATC

AACCTGCTGGGCGCCTGCACGCAGGGCGGGCCCCTGTACGTGCTGGTGGAGTACGCGGCCAAGGGTAACCTGCGGGA

GTTTCTGCGGGCGCGGCGGCCCCCGGGCCTGGACTACTCCTTCGACACCTGCAAGCCGCCCGAGGAGCAGCTCACCT

TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGAC*GAGAGAGCCTTGAACTCTGCCAGCACCTCGCTTCCC*

*ACAAGCTGTCCAGGCAGTGAGCCAGTGCCCACCCATCAGCAGGGGCAGCCTGCCTTGGAGCTGAAAGAGGAGAGCTT*

*CAGAGACCCCGCTGAGGTTCTAGGCACGGGCGCGGAGGTGGATTACCTGGAGCAGTTTGGAACTTCCTCGTTTAAGG*

*AGTCGGCCTTGAGGAAGCAGTCCTTATACCTCAAGTTCGACCCCCTCCTGAGGGACAGTCCTGGTAGACCAGTGCCC*

*GTGGCCACCGAGACCAGCAGCATGCACGGTGCAAATGAGACTCCCTCAGGACGTCCGCGGGAAGCCAAGCTTGTGGA*

*GTTCGATTTCTTGGGAGCACTGGACATTCCTGTGCCAGGCCCACCCCCAGGTGTTCCCGCGCCTGGGGGCCCACCCC*

*TGTCCACCGGACCTATAGTGGACCTGCTCCAGTACAGCCAGAAGGACCTGGATGCAGTGGTAAAGGCGACACAGGAG*

*GAGAACCGGGAGCTGAGGAGCAGGTGTGAGGAGCTCCACGGGAAGAACCTGGAACTGGGGAAGATCATGGACAGGTT*

*CGAAGAGGTTGTGTACCAGGCCATGGAGGAAGTTCAGAAGCAGAAGGAACTTTCCAAAGCTGAAATCCAGAAAGTTC*

*TAAAAGAAAAAGACCAACTTACCACAGATCTGAACTCCATGGAGAAGTCCTTCTCCGACCTCTTCAAGCGTTTTGAG*

*AAACAGAAAGAGGTGATCGAGGGCTACCGCAAGAACGAAGAGTCACTGAAGAAGTGCGTGGAGGATTACCTGGCAAG*

*GATCACCCAGGAGGGCCAGAGGTACCAAGCCCTGAAGGCCCACGCGGAGGAGAAGCTGCAGCTGGCAAACGAGGAGA*

*TCGCCCAGGTCCGGAGCAAGGCCCAGGCGGAAGCGTTGGCCCTCCAGGCCAGCCTGAGGAAGGAGCAGATGCGCATC*

*CAGTCGCTGGAGAAGACAGTGGAGCAGAAGACTAAAGAGAACGAGGAGCTGACCAGGATCTGCGACGACCTCATCTC*

*CAAGATGGAGAAGATCTGA*

SEQ ID NO: 534 is the nucleotide sequence (cDNA) of FGFR3ex18-TACC3ex13. The sequence corresponding to FGFR3 is underlined. The sequence corresponding to TACC3 is italicized:

ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGGTGGTCCCATGGGGCCCACTGTCTGGGTCAAGGAT

GGCACAGGGCTGGTGCCCTCGGAGCGTGTCCTGGTGGGGCCCCAGCGGCTGCAGGTGCTGAATGCCTCCCACGAGGA

CTCCGGGGCCTACAGCTGCCGGCAGCGGCTCACGCAGCGCGTACTGTGCCACTTCAGTGTGCGGGTGACAGACGCTC

CATCCTCGGAGATGACGAAGACGGGGAGGACGAGGCTGAGGACACAGGTGTGGACACAGGGGCCCCTTACTGGACA

CGGCCCGAGCGGATGGACAAGAAGCTGCTGGCCGTGCCGGCCGCCAACACCGTCCGCTTCCGCTGCCCAGCCGCTGG

-continued

CAACCCCACTCCCTCCATCTCCTGGCTGAAGAACGGCAGGGAGTTCCGCGGCGAGCACCGCATTGGAGGCATCAAGC

TGCGGCATCAGCAGTGGAGCCTGGTCATGGAAAGCGTGGTGCCCTCGGACCGCGGCAACTACACCTGCGTCGTGGAG

AACAAGTTTGGCAGCATCCGGCAGACGTACACGCTGGACGTGCTGGAGCGCTCCCCGCACCGGCCCATCCTGCAGGC

GGGGCTGCCGGCCAACCAGACGGCGGTGCTGGGCAGCGACGTGGAGTTCCACTGCAAGGTGTACAGTGACGCACAGC

CCCACATCCAGTGGCTCAAGCACGTGGAGGTGAATGGCAGCAAGGTGGGCCCGGACGGCACACCCTACGTTACCGTG

CTCAAGACGGCGGGCGCTAACACCACCGACAAGGAGCTAGAGGTTCTCTCCTTGCACAACGTCACCTTTGAGGACGC

CGGGGAGTACACCTGCCTGGCGGGCAATTCTATTGGGTTTTCTCATCACTCTGCGTGGCTGGTGGTGCTGCCAGCCG

AGGAGGAGCTGGTGGAGGCTGACGAGGCGGGCAGTGTGTATGCAGGCATCCTCAGCTACGGGGTGGGCTTCTTCCTG

TTCATCCTGGTGGTGGCGGCTGTGACGCTCTGCCGCCTGCGCAGCCCCCCCAAGAAAGGCCTGGGCTCCCCCACCGT

GCACAAGATCTCCCGCTTCCCGCTCAAGCGACAGGTGTCCCTGGAGTCCAACGCGTCCATGAGCTCCAACACACCAC

TGGTGCGCATCGCAAGGCTGTCCTCAGGGGAGGGCCCCACGCTGGCCAATGTCTCCGAGCTCGAGCTGCCTGCCGAC

CCCAAATGGGAGCTGTCTCGGGCCCGGCTGACCCTGGGCAAGCCCCTTGGGGAGGGCTGCTTCGGCCAGGTGGTCAT

GGCGGAGGCCATCGGCATTGACAAGGACCGGGCCGCCAAGCCTGTCACCGTAGCCGTGAAGATGCTGAAAGACGATG

CCACTGACAAGGACCTGTCGGACCTGGTGTCTGAGATGGAGATGATGAAGATGATCGGGAAACACAAAAACATCATC

AACCTGCTGGGCGCCTGCACGCAGGGCGGGCCCCTGTACGTGCTGGTGGAGTACGCGGCCAAGGGTAACCTGCGGGA

GTTTCTGCGGGCGCGGCGGCCCCCGGGCCTGGACTACTCCTTCGACACCTGCAAGCCGCCCGAGGAGCAGCTCACCT

TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGACGAGTACCTGGACCTGTCGGCGCCTTTCGAGCAGTAC

TCCCCGGGTGGCCAGGACACCCCCAGA*AGCAGAAGGAACTTTCCAAAGCTGAAATCCAGAAAGTTCTAAAAGAAAAA*

*GACCAACTTACCACAGATCTGAACTCCATGGAGAAGTCCTTCTCCGACCTCTTCAAGCGTTTTGAGAAACAGAAAGA*

*GGTGATCGAGGGCTACCGCAAGAACGAAGAGTCACTGAAGAAGTGCGTGGAGGATTACCTGGCAAGGATCACCCAGG*

*AGGGCCAGAGGTACCAAGCCCTGAAGGCCCACGCGGAGGAGAAGCTGCAGCTGGCAAACGAGGAGATCGCCCAGGTC*

*CGGAGCAAGGCCCAGGCGGAAGCGTTGGCCCTCCAGGCCAGCCTGAGGAAGGAGCAGATGCGCATCCAGTCGCTGGA*

*GAAGACAGTGGAGCAGAAGACTAAAGAGAACGAGGAGCTGACCAGGATCTGCGACGACCTCATCTCCAAGATGGAGA*

*AGATCTGA*

SEQ ID NO: 535 is the nucleotide sequence (cDNA) of FGFR3ex18-TACC3ex9_INS66BP. The sequence corresponding to FGFR3 is underlined. The sequence corresponding to TACC3 is italicized. The sequence corresponding the 66 bp intronic insert is double underlined:

ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGTGGTCCCATGGGGCCCACTGTCTGGGTCAAGGAT

GGCACAGGGCTGGTGCCCTCGGAGCGTGTCCTGGTGGGGCCCCAGCGGCTGCAGGTGCTGAATGCCTCCCACGAGGA

CTCCGGGGCCTACAGCTGCCGGCAGCGGCTCACGCAGCGCGTACTGTGCCACTTCAGTGTGCGGGTGACAGACGCTC

CATCCTCGGGAGATGACGAAGACGGGGAGGACGAGGCTGAGGACACAGGTGTGGACACAGGGGCCCCTTACTGGACA

CGGCCCGAGCGGATGGACAAGAAGCTGCTGGCCGTGCCGGCCGCCAACACCGTCCGCTTCCGCTGCCCAGCCGCTGG

-continued

CAACCCCACTCCCTCCATCTCCTGGCTGAAGAACGGCAGGGAGTTCCGCGGCGAGCACCGCATTGGAGGCATCAAGC

TGCGGCATCAGCAGTGGAGCCTGGTCATGGAAAGCGTGGTGCCCTCGGACCGCGGCAACTACACCTGCGTCGTGGAG

AACAAGTTTGGCAGCATCCGGCAGACGTACACGCTGGACGTGCTGGAGCGCTCCCCGCACCGGCCCATCCTGCAGGC

GGGGCTGCCGGCCAACCAGACGGCGGTGCTGGGCAGCGACGTGGAGTTCCACTGCAAGGTGTACAGTGACGCACAGC

CCCACATCCAGTGGCTCAAGCACGTGGAGGTGAATGGCAGCAAGGTGGGCCCGGACGGCACACCCTACGTTACCGTG

CTCAAGACGGCGGGCGCTAACACCACCGACAAGGAGCTAGAGGTTCTCTCCTTGCACAACGTCACCTTTGAGGACGC

CGGGGAGTACACCTGCCTGGCGGGCAATTCTATTGGGTTTTCTCATCACTCTGCGTGGCTGGTGGTGCTGCCAGCCG

AGGAGGAGCTGGTGGAGGCTGACGAGGCGGGCAGTGTGTATGCAGGCATCCTCAGCTACGGGGTGGGCTTCTTCCTG

TTCATCCTGGTGGTGGCGGCTGTGACGCTCTGCCGCCTGCGCAGCCCCCCCAAGAAAGGCCTGGGCTCCCCCACCGT

GCACAAGATCTCCCGCTTCCCGCTCAAGCGACAGGTGTCCCTGGAGTCCAACGCGTCCATGAGCTCCAACACACCAC

TGGTGCGCATCGCAAGGCTGTCCTCAGGGGAGGGCCCCACGCTGGCCAATGTCTCCGAGCTCGAGCTGCCTGCCGAC

CCCAAATGGGAGCTGTCTCGGGCCCGGCTGACCCTGGGCAAGCCCCTTGGGGAGGGCTGCTTCGGCCAGGTGGTCAT

GGCGGAGGCCATCGGCATTGACAAGGACCGGGCCGCCAAGCCTGTCACCGTAGCCGTGAAGATGCTGAAAGACGATG

CCACTGACAAGGACCTGTCGGACCTGGTGTCTGAGATGGAGATGATGAAGATGATCGGGAAACACAAAAACATCATC

AACCTGCTGGGCGCCTGCACGCAGGGCGGGCCCCTGTACGTGCTGGTGGAGTACGCGGCCAAGGGTAACCTGCGGGA

GTTTCTGCGGGCGCGGCGGCCCCCGGGCCTGGACTACTCCTTCGACACCTGCAAGCCGCCCGAGGAGCAGCTCACCT

TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGACGAGTACCTGGACCTGTCGGCGCAGGAGCAACGGCAG

CCTACCCTCCAGCCACAGGGCTGCTGCCTTGCTGGTTACAGCCACCGTTTCT*CTAGCATGCACGGTGCAAATGAGAC*

*TCCCTCAGGACGTCCGCGGGAAGCCAAGCTTGTGGAGTTCGATTTCTTGGGAGCACTGGACATTCCTGTGCCAGGCC*

*CACCCCAGGTGTTCCCGCGCCTGGGGGCCCACCCCTGTCCACCGGACCTATAGTGGACCTGCTCCAGTACAGCCAG*

*AAGGACCTGGATGCAGTGGTAAAGGCGACACAGGAGGAGAACCGGGAGCTGAGGAGCAGGTGTGAGGAGCTCCACGG*

*GAAGAACCTGGAACTGGGGAAGATCATGGACAGGTTCGAAGAGGTTGTGTACCAGGCCATGGAGGAAGTTCAGAAGC*

*AGAAGGAACTTTCCAAAGCTGAAATCCAGAAAGTTCTAAAAGAAAAAGACCAACTTACCACAGATCTGAACTCCATG*

*GAGAAGTCCTTCTCCGACCTCTTCAAGCGTTTTGAGAAACAGAAAGAGGTGATCGAGGGCTACCGCAAGAACGAAGA*

*GTCACTGAAGAAGTGCGTGGAGGATTACCTGGCAAGGATCACCCAGGAGGGCCAGAGGTACCAAGCCCTGAAGGCCC*

*ACGCGGAGGAGAAGCTGCAGCTGGCAAACGAGGAGATCGCCCAGGTCCGGAGCAAGGCCCAGGCGGAAGCGTTGGCC*

*CTCCAGGCCAGCCTGAGGAAGGAGCAGATGCGCATCCAGTCGCTGGAGAAGACAGTGGAGCAGAAGACTAAAGAGAA*

*CGAGGAGCTGACCAGGATCTGCGACGACCTCATCTCCAAGATGGAGAAGATCTGA*

SEQ ID NO: 536 is the nucleotide sequence (cDNA) of FGFR3ex18-TACC3ex5. The sequence corresponding to FGFR3 is underlined. The sequence corresponding to TACC3 is italicized:

ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGGTGGTCCCATGGGGCCCACTGTCTGGGTCAAGGAT

-continued

```
GGCACAGGGCTGGTGCCCTCGGAGCGTGTCCTGGTGGGGCCCCAGCGGCTGCAGGTGCTGAATGCCTCCCACGAGGA
CTCCGGGGCCTACAGCTGCCGGCAGCGGCTCACGCAGCGCGTACTGTGCCACTTCAGTGTGCGGGTGACAGACGCTC
CATCCTCGGGAGATGACGAAGACGGGGAGGACGAGGCTGAGGACACAGGTGTGGACACAGGGGCCCCTTACTGGACA
CGGCCCGAGCGGATGGACAAGAAGCTGCTGGCCGTGCCGGCCGCCAACACCGTCCGCTTCCGCTGCCCAGCCGCTGG
CAACCCCACTCCCTCCATCTCCTGGCTGAAGAACGGCAGGGAGTTCCGCGGCGAGCACCGCATTGGAGGCATCAAGC
TGCGGCATCAGCAGTGGAGCCTGGTCATGGAAAGCGTGGTGCCCTCGGACCGCGGCAACTACACCTGCTCGTGGAG
AACAAGTTTGGCAGCATCCGGCAGACGTACACGCTGGACGTGCTGGAGCGCTCCCCGCACCGGCCCATCCTGCAGGC
GGGGCTGCCGGCCAACCAGACGGCGGTGCTGGGCAGCGACGTGGAGTTCCACTGCAAGGTGTACAGTGACGCACAGC
CCCACATCCAGTGGCTCAAGCACGTGGAGGTGAATGGCAGCAAGGTGGGCCCGGACGGCACACCCTACGTTACCGTG
CTCAAGACGGCGGGCGCTAACACCACCGACAAGGAGCTAGAGGTTCTCTCCTTGCACAACGTCACCTTTGAGGACGC
CGGGGAGTACACCTGCCTGGCGGGCAATTCTATTGGGTTTTCTCATCACTCTGCGTGGCTGGTGGTGCTGCCAGCCG
AGGAGGAGCTGGTGGAGGCTGACGAGGCGGGCAGTGTGTATGCAGGCATCCTCAGCTACGGGGTGGGCTTCTTCCTG
TTCATCCTGGTGGTGGCGGCTGTGACGCTCTGCCGCCTGCGCAGCCCCCCAAGAAAGGCCTGGGCTCCCCCACCGT
GCACAAGATCTCCCGCTTCCCGCTCAAGCGACAGGTGTCCCTGGAGTCCAACGCGTCCATGAGCTCCAACACACCAC
TGGTGCGCATCGCAAGGCTGTCCTCAGGGGAGGGCCCCACGCTGGCCAATGTCTCCGAGCTCGAGCTGCCTGCCGAC
CCCAAATGGGAGCTGTCTCGGGCCCGCTGACCCTGGGCAAGCCCCTTGGGGAGGGCTGCTTCGGCCAGGTGGTCAT
GGCGGAGGCCATCGGCATTGACAAGGACCGGGCCGCCAAGCCTGTCACCGTAGCCGTGAAGATGCTGAAAGACGATG
CCACTGACAAGGACCTGTCGGACCTGGTGTCTGAGATGGAGATGATGAAGATGATCGGGAAACACAAAAACATCATC
AACCTGCTGGGCGCCTGCACGCAGGGCGGGCCCCTGTACGTGCTGGTGGAGTACGCGGCCAAGGGTAACCTGCGGGA
GTTTCTGCGGGCGCGGCGGCCCCCGGGCCTGGACTACTCCTTCGACACCTGCAAGCCGCCCGAGGAGCAGCTCACCT
TCAAGGACCTGGTGTCCTGTGCCTACCAGGTGGCCCGGGGCATGGAGTACTTGGCCTCCCAGAAGTGCATCCACAGG
GACCTGGCTGCCCGCAATGTGCTGGTGACCGAGGACAACGTGATGAAGATCGCAGACTTCGGGCTGGCCCGGGACGT
GCACAACCTCGACTACTACAAGAAGACGACCAACGGCCGGCTGCCCGTGAAGTGGATGGCGCCTGAGGCCTTGTTTG
ACCGAGTCTACACTCACCAGAGTGACGTCTGGTCCTTTGGGGTCCTGCTCTGGGAGATCTTCACGCTGGGGGGCTCC
CCGTACCCCGGCATCCCTGTGGAGGAGCTCTTCAAGCTGCTGAAGGAGGGCCACCGCATGGACAAGCCCGCCAACTG
CACACACGACCTGTACATGATCATGCGGGAGTGCTGGCATGCCGCGCCCTCCCAGAGGCCCACCTTCAAGCAGCTGG
TGGAGGACCTGGACCGTGTCCTTACCGTGACGTCCACCGACGAGTACCTGGACCTGTCGGCG
CCTGTGGTGCAGTTG
GCAGCCGAGACCCCAACAGCAGAGAGCAAGGAGAGAGCCTTGAACTCTGCCAGCACCTCGCTTCCCACAAGCTGTCC
AGGCAGTGAGCCAGTGCCCACCCATCAGCAGGGGCAGCCTGCCTTGGAGCTGAAAGAGGAGAGCTTCAGAGACCCCG
CTGAGGTTCTAGGCACGGGCGCGGAGGTGGATTACCTGGAGCAGTTTGGAACTTCCTCGTTTAAGGAGTCGGCCTTG
AGGAAGCAGTCCTTATACCTCAAGTTCGACCCCCTCCTGAGGGACAGTCCTGGTAGACCAGTGCCCGTGGCCACCGA
GACCAGCAGCATGCACGGTGCAAATGAGACTCCCTCAGGACGTCCGCGGGAAGCCAAGCTTGTGGAGTTCGATTTCT
TGGGAGCACTGGACATTCCTGTGCCAGGCCCACCCCCAGGTGTTCCCGCGCCTGGGGCCCACCCCTGTCCACCGGA
CCTATAGTGGACCTGCTCCAGTACAGCCAGAAGGACCTGGATGCAGTGGTAAAGGCGACACAGGAGGAGAACCGGGA
GCTGAGGAGCAGGTGTGAGGAGCTCCACGGGAAGAACCTGGAACTGGGGAAGATCATGGACAGGTTCGAAGAGGTTG
TGTACCAGGCCATGGAGGAAGTTCAGAAGCAGAAGGAACTTTCCAAAGCTGAAATCCAGAAAGTTCTAAAAGAAAAA
GACCAACTTACCACAGATCTGAACTCCATGGAGAAGTCCTTCTCCGACCTCTTCAAGCGTTTTGAGAAACAGAAAGA
GGTGATCGAGGGCTACCGCAAGAACGAAGAGTCACTGAAGAAGTGCGTGGAGGATTACCTGGCAAGGATCACCCAGG
AGGGCCAGAGGTACCAAGCCCTGAAGGCCCACGCGGAGGAGAAGCTGCAGCTGGCAAACGAGGAGATCGCCCAGGTC
CGGAGCAAGGCCCAGGCGGAAGCGTTGGCCCTCCAGGCCAGCCTGAGGAAGGAGCAGATGCGCATCCAGTCGCTGGA
```

```
GAAGACAGTGGAGCAGAAGACTAAAGAGAACGAGGAGCTGACCAGGATCTGCGACGACCTCATCTCCAAGATGGAGA

AGATCTGA
```

SEQ ID NO: 537 is the nucleotide sequence (cDNA) of FGFR3ex18-TACC3ex5_INS33 bp. The sequence corresponding to FGFR3 is underlined. The sequence corresponding to TACC3 is italicized. The sequence corresponding the 33 bp intronic insert is double underlined:

```
ATGGGCGCCCCTGCCTGCGCCCTCGCGCTCTGCGTGGCCGTGGCCATCGTGGCCGGCGCCTCCTCGGAGTCCTTGGG

GACGGAGCAGCGCGTCGTGGGGCGAGCGGCAGAAGTCCCGGGCCCAGAGCCCGGCCAGCAGGAGCAGTTGGTCTTCG

GCAGCGGGGATGCTGTGGAGCTGAGCTGTCCCCCGCCCGGGGGTGGTCCCATGGGGCCCACTGTCTGGGTCAAGGAT

GGCACAGGGCTGGTGCCCTCGGAGCGTGTCCTGGTGGGGCCCCAGCGGCTGCAGGTGCTGAATGCCTCCCACGAGGA

CTCCGGGGCCTACAGCTGCCGGCAGCGGCTCACGCAGCGCGTACTGTGCCACTTCAGTGTGCGGGTGACAGACGCTC

CATCCTCGGGAGATGACGAAGACGGGGAGGACGAGGCTGAGGACACAGGTGTGGACACAGGGGCCCCTTACTGGACA

CGGCCCGAGCGGATGGACAAGAAGCTGCTGGCCGTGCCGGCCGCCAACACCGTCCGCTTCCGCTGCCCAGCCGCTGG

CAACCCCACTCCCTCCATCTCCTGGCTGAAGAACGGCAGGGAGTTCCGCGGCGAGCACCGCATTGGAGGCATCAAGC

TGCGGCATCAGCAGTGGAGCCTGGTCATGGAAAGCGTGGTGCCCTCGGACCGCGGCAACTACACCTGCGTCGTGGAG

AACAAGTTTGGCAGCATCCGGCAGACGTACACGCTGGACGTGCTGGAGCGCTCCCCGCACCGGCCCATCCTGCAGGC

GGGGCTGCCGGCCAACCAGACGGCGGTGCTGGGCAGCGACGTGGAGTTCCACTGCAAGGTGTACAGTGACGCACAGC

CCCACATCCAGTGGCTCAAGCACGTGGAGGTGAATGGCAGCAAGGTGGGCCCGGACGGCACACCCTACGTTACCGTG

CTCAAGACGGCGGGCGCTAACACCACCGACAAGGAGCTAGAGGTTCTCTCCTTGCACAACGTCACCTTTGAGGACGC

CGGGGAGTACACCTGCCTGGCGGGCAATTCTATTGGGTTTTCTCATCACTCTGCGTGGCTGGTGGTGCTGCCAGCCG

AGGAGGAGCTGGTGGAGGCTGACGAGGCGGGCAGTGTGTATGCAGGCATCCTCAGCTACGGGGTGGGCTTCTTCCTG

TTCATCCTGGTGGTGGCGGCTGTGACGCTCTGCCGCCTGCGCAGCCCCCCCAAGAAAGGCCTGGGCTCCCCCACCGT

GCACAAGATCTCCCGCTTCCCGCTCAAGCGACAGGTGTCCCTGGAGTCCAACGCGTCCATGAGCTCCAACACACCAC

TGGTGCGCATCGCAAGGCTGTCCTCAGGGGAGGGCCCCACGCTGGCCAATGTCTCCGAGCTCGAGCTGCCTGCCGAC

CCCAAATGGGAGCTGTCTCGGGCCCGGCTGACCCTGGGCAAGCCCCTTGGGGAGGGCTGCTTCGGCCAGGTGGTCAT

GGCGGAGGCCATCGGCATTGACAAGGACCGGGCCGCCAAGCCTGTCACCGTAGCCGTGAAGATGCTGAAAGACGATG

CCACTGACAAGGACCTGTCGGACCTGGTGTCTGAGATGGAGATGATGAAGATGATCGGGAAACACAAAAACATCATC

AACCTGCTGGGCGCCTGCACGCAGGGCGGGCCCCTGTACGTGCTGGTGGAGTACGCGGCCAAGGGTAACCTGCGGGA

GTTTCTGCGGGCGCGGCGCCCCGGGCCTGGACTACTCCTTCGACACCTGCAAGCCGCCCGAGGAGCAGCTCACCT

TCAAGGACCTGGTGTCCTGTGCCTACCAGGTGGCCCGGGGCATGGAGTACTTGGCCTCCCAGAAGTGCATCCACAGG

GACCTGGCTGCCCGCAATGTGCTGGTGACCGAGGACAACGTGATGAAGATCGCAGACTTCGGGCTGGCCCGGGACGT

GCACAACCTCGACTACTACAAGAAGACGACCAACGGCCGGCTGCCCGTGAAGTGGATGGCGCCTGAGGCCTTGTTTG

ACCGAGTCTACACTCACCAGAGTGACGTCTGGTCCTTTGGGGTCCTGCTCTGGGAGATCTTCACGCTGGGGGGCTCC

CCGTACCCCGGCATCCCTGTGGAGGAGCTCTTCAAGCTGCTGAAGGAGGGCCACCGCATGGACAAGCCCGCCAACTG

CACACACGACCTGTACATGATCATGCGGGAGTGCTGGCATGCCGCGCCCTCCCAGAGGCCCACCTTCAAGCAGCTGG

TGGAGGACCTGGACCGTGTCCTTACCGTGACGTCCACCGACGAGTACCTGGACCTGTCGGCGCCTTTCGAGCAGTAC

TCCCCGGGTGGCCAGGACACCCCCAGCTCCAGCTCCTCAGGGGAC```G```TGCGTGAGCCACCGCACCCGGCGTTTCCTAG

```G```TCAGCGGAGGACACGCCTGTGGTGCAGTTGGCAGCCGAGACCCCAACAGCAGAGAGCAAGGAGAGAGCCTTGAACT

CTGCCAGCACCTCGCTTCCCACAAGCTGTCCAGGCAGTGAGCCAGTGCCCACCCATCAGCAGGGCAGCCTGCCTTG

GAGCTGAAAGAGGAGAGCTTCAGAGACCCCGCTGAGGTTCTAGGCACGGGCGCGGAGGTGGATTACCTGGAGCAGTT

TGGAACTTCCTCGTTTAAGGAGTCGGCCTTGAGGAAGCAGTCCTTATACCTCAAGTTCGACCCCCTCCTGAGGGACA
```

-continued

*GTCCTGGTAGACCAGTGCCCGTGGCCACCGAGACCAGCAGCATGCACGGTGCAAATGAGACTCCCTCAGGACGTCCG*

*CGGGAAGCCAAGCTTGTGGAGTTCGATTTCTTGGGAGCACTGGACATTCCTGTGCCAGGCCCACCCCCAGGTGTTCC*

*CGCGCCTGGGGGCCCACCCCTGTCCACCGGACCTATAGTGGACCTGCTCCAGTACAGCCAGAAGGACCTGGATGCAG*

*TGGTAAAGGCGACACAGGAGGAGAACCGGGAGCTGAGGAGCAGGTGTGAGGAGCTCCACGGGAAGAACCTGGAACTG*

*GGGAAGATCATGGACAGGTTCGAAGAGGTTGTGTACCAGGCCATGGAGGAAGTTCAGAAGCAGAAGGAACTTTCCAA*

*AGCTGAAATCCAGAAAGTTCTAAAAGAAAAAGACCAACTTACCACAGATCTGAACTCCATGGAGAAGTCCTTCTCCG*

*ACCTCTTCAAGCGTTTTGAGAAACAGAAAGAGGTGATCGAGGGCTACCGCAAGAACGAAGAGTCACTGAAGAAGTGC*

*GTGGAGGATTACCTGGCAAGGATCACCCAGGAGGGCCAGAGGTACCAAGCCCTGAAGGCCCACGCGGAGGAGAAGCT*

*GCAGCTGGCAAACGAGGAGATCGCCCAGGTCCGGAGCAAGGCCCAGGCGGAAGCGTTGGCCCTCCAGGCCAGCCTGA*

*GGAAGGAGCAGATGCGCATCCAGTCGCTGGAGAAGACAGTGGAGCAGAAGACTAAAGAGAACGAGGAGCTGACCAGG*

*ATCTGCGACGACCTCATCTCCAAGATGGAGAAGATCTGA*

SEQ ID NO: 538 is the nucleotide sequence (cDNA) of FGFR3ex18-TACC3ex4. The sequence corresponding to FGFR3 is underlined. The sequence corresponding to TACC3 is italicized.

<u>ATGGGCGCCCCTGCCTGCGCCCTCGCGCTCTGCGTGGCCGTGGCCATCGTGGCCGGCGCCTCCTCGGAGTCCTTGGG</u>

<u>GACGGAGCAGCGCGTCGTGGGGCGAGCGGCAGAAGTCCCGGGCCCAGAGCCCGGCCAGCAGGAGCAGTTGGTCTTCG</u>

<u>GCAGCGGGGATGCTGTGGAGCTGAGCTGTCCCCCGCCCGGGGGTGGTCCCATGGGGCCCACTGTCTGGGTCAAGGAT</u>

<u>GGCACAGGGCTGGTGCCCTCGGAGCGTGTCCTGGTGGGGCCCCAGCGGCTGCAGGTGCTGAATGCCTCCCACGAGGA</u>

<u>CTCCGGGGCCTACAGCTGCCGGCAGCGGCTCACGCAGCGCGTACTGTGCCACTTCAGTGTGCGGGTGACAGACGCTC</u>

<u>CATCCTCGGGAGATGACGAAGACGGGGAGGACGAGGCTGAGGACACAGGTGTGGACACAGGGGCCCCTTACTGGACA</u>

<u>CGGCCCGAGCGGATGGACAAGAAGCTGCTGGCCGTGCCGGCCGCCAACACCGTCCGCTTCCGCTGCCCAGCCGCTGG</u>

<u>CAACCCCACTCCCTCCATCTCCTGGCTGAAGAACGGCAGGGAGTTCCGCGGCGAGCACCGCATTGGAGGCATCAAGC</u>

<u>TGCGGCATCAGCAGTGGAGCCTGGTCATGGAAAGCGTGGTGCCCTCGGACCGCGGCAACTACACCTGCGTCGTGGAG</u>

<u>AACAAGTTTGGCAGCATCCGGCAGACGTACACGCTGGACGTGCTGGAGCGCTCCCCGCACCGGCCCATCCTGCAGGC</u>

<u>GGGGCTGCCGGCCAACCAGACGGCGGTGCTGGGCAGCGACGTGGAGTTCCACTGCAAGGTGTACAGTGACGCACAGC</u>

<u>CCCACATCCAGTGGCTCAAGCACGTGGAGGTGAATGGCAGCAAGGTGGGCCCGGACGGCACACCCTACGTTACCGTG</u>

<u>CTCAAGACGGCGGGCGCTAACACCACCGACAAGGAGCTAGAGGTTCTCTCCTTGCACAACGTCACCTTTGAGGACGC</u>

<u>CGGGGAGTACACCTGCCTGGCGGGCAATTCTATTGGGTTTTCTCATCACTCTGCGTGGCTGGTGGTGCTGCCAGCCG</u>

<u>AGGAGGAGCTGGTGGAGGCTGACGAGGCGGGCAGTGTGTATGCAGGCATCCTCAGCTACGGGGTGGGCTTCTTCCTG</u>

<u>TTCATCCTGGTGGTGGCGGCTGTGACGCTCTGCCGCCTGCGCAGCCCCCCCAAGAAAGGCCTGGGCTCCCCCACCGT</u>

<u>GCACAAGATCTCCCGCTTCCCGCTCAAGCGACAGGTGTCCCTGGAGTCCAACGCGTCCATGAGCTCCAACACACCAC</u>

<u>TGGTGCGCATCGCAAGGCTGTCCTCAGGGGAGGGCCCCACGCTGGCCAATGTCTCCGAGCTCGAGCTGCCTGCCGAC</u>

<u>CCCAAATGGGAGCTGTCTCGGGCCCGGCTGACCCTGGGCAAGCCCCTTGGGGAGGGCTGCTTCGGCCAGGTGGTCAT</u>

<u>GGCGGAGGCCATCGGCATTGACAAGGACCGGGCCGCCAAGCCTGTCACCGTAGCCGTGAAGATGCTGAAAGACGATG</u>

<u>CCACTGACAAGGACCTGTCGGACCTGGTGTCTGAGATGGAGATGATGAAGATGATCGGGAAACACAAAAACATCATC</u>

<u>AACCTGCTGGGCGCCTGCACGCAGGGCGGGCCCCTGTACGTGCTGGTGGAGTACGCGGCCAAGGGTAACCTGCGGGA</u>

<u>GTTTCTGCGGGCGCGGCGGCCCCCGGGCCTGGACTACTCCTTCGACACCTGCAAGCCGCCCGAGGAGCAGCTCACCT</u>

<u>TCAAGGACCTGGTGTCCTGTGCCTACCAGGTGGCCCGGGGCATGGAGTACTTGGCCTCCCAGAAGTGCATCCACAGG</u>

<u>GACCTGGCTGCCCGCAATGTGCTGGTGACCGAGGACAACGTGATGAAGATCGCAGACTTCGGGCTGGCCCGGGACGT</u>

<u>GCACAACCTCGACTACTACAAGAAGACGACCAACGGCCGGCTGCCCGTGAAGTGGATGGCGCCTGAGGCCTTGTTTG</u>

-continued

ACCGAGTCTACACTCACCAGAGTGACGTCTGGTCCTTTGGGGTCCTGCTCTGGGAGATCTTCACGCTGGGGGGCTCC
CCGTACCCCGGCATCCCTGTGGAGGAGCTCTTCAAGCTGCTGAAGGAGGGCCACCGCATGGACAAGCCCGCCAACTG
CACACACGACCTGTACATGATCATGCGGGAGTGCTGGCATGCCGCGCCCTCCCAGAGGCCCACCTTCAAGCAGCTGG
TGGAGGACCTGGACCGTGTCCTTACCGTGACGTCCACCGACGAGTACCTGGACCTGTCGGCGCCTTTCGAGCAGTAC
TCCCCGGGTGGCCAGGACACCCCAGAAAGCCCTGAGACCAGGCTGGGCCAGCCAGCGGCTGAACAGTTGCATGCTGG
GCCTGCCACGGAGGAGCCAGGTCCCTGTCTGAGCCAGCAGCTGCATTCAGCCTCAGCGGAGGACACGCCTGTGGTGC
AGTTGGCAGCCGAGACCCCAACAGCAGAGAGCAAGGAGAGAGCCTTGAACTCTGCCAGCACCTCGCTTCCCACAAGC
TGTCCAGGCAGTGAGCCAGTGCCCACCCATCAGCAGGGGCAGCCTGCCTTGGAGCTGAAAGAGGAGAGCTTCAGAGA
CCCCGCTGAGGTTCTAGGCACGGGCGCGGAGGTGGATTACCTGGAGCAGTTTGGAACTTCCTCGTTTAAGGAGTCGG
CCTTGAGGAAGCAGTCCTTATACCTCAAGTTCGACCCCCTCCTGAGGGACAGTCCTGGTAGACCAGTGCCCGTGGCC
ACCGAGACCAGCAGCATGCACGGTGCAAATGAGACTCCCTCAGGACGTCCGCGGGAAGCCAAGCTTGTGGAGTTCGA
TTTCTTGGGAGCACTGGACATTCCTGTGCCAGGCCCACCCCCAGGTGTTCCCGCGCCTGGGGCCCACCCCTGTCCA
CCGGACCTATAGTGGACCTGCTCCAGTACAGCCAGAAGGACCTGGATGCAGTGGTAAAGGCGACACAGGAGGAGAAC
CGGGAGCTGAGGAGCAGGTGTGAGGAGCTCCACGGGAAGAACCTGGAACTGGGGAAGATCATGGACAGGTTCGAAGA
GGTTGTGTACCAGGCCATGGAGGAAGTTCAGAAGCAGAAGGAACTTTCCAAAGCTGAAATCCAGAAAGTTCTAAAAG
AAAAAGACCAACTTACCACAGATCTGAACTCCATGGAGAAGTCCTTCTCCGACCTCTTCAAGCGTTTTGAGAAACAG
AAAGAGGTGATCGAGGGCTACCGCAAGAACGAAGAGTCACTGAAGAAGTGCGTGGAGGATTACCTGGCAAGGATCAC
CCAGGAGGGCCAGAGGTACCAAGCCCTGAAGGCCCACGCGGAGGAGAAGCTGCAGCTGGCAAACGAGGAGATCGCCC
AGGTCCGGAGCAAGGCCCAGGCGGAAGCGTTGGCCCTCCAGGCCAGCCTGAGGAAGGAGCAGATGCGCATCCAGTCG
CTGGAGAAGACAGTGGAGCAGAAGACTAAAGAGAACGAGGAGCTGACCAGGATCTGCGACGACCTCATCTCCAAGAT
GGAGAAGATCTGA

The Genbank ID for the FGFR1 gene is 2260. Eight isoforms are listed for FGFR1, e.g., having Genebank Accession Nos. NP_001167534 (corresponding nucleotide sequence NM_001174063); NP_001167535 (corresponding nucleotide sequence NM_001174064); NP_001167536 (corresponding nucleotide sequence NM_001174065); NP_001167537 (corresponding nucleotide sequence NM_001174066); NP_001167538 (corresponding nucleotide sequence NM_001174067); NP_056934 (corresponding nucleotide sequence NM_015850); NP_075593 (corresponding nucleotide sequence NM_023105); NP_075594 (corresponding nucleotide sequence NM_023106); NP_075598 (corresponding nucleotide sequence NM_023110).

SEQ ID NO: 146 is the FGFR1 Amino Acid Sequence for isoform 10, having Genebank Accession No. NP_001167534 (820 aa):

```
  1 MWSWKCLLFW AVLVTATLCT ARPSPTLPEQ AQPWGAPVEV ESFLVHPGDL LQLRCRLRDD
 61 VQSINWLRDG VQLAESNRTR ITGEEVEVQD SVPADSGLYA CVTSSPSGSD TTYFSVNVSD
121 ALPSSEDDDD DDDSSSEEKE TDNTKPNRMP VAPYWTSPEK MEKKLHAVPA AKTVKFKCPS
181 SGTPNPTLRW LKNGKEFKPD HRIGGYKVRY ATWSIIMDSV VPSDKGNYTC IVENEYGSIN
241 HTYQLDVVER SPHRPILQAG LPANKTVALG SNVEFMCKVY SDPQPHIQWL KHIEVNGSKI
301 GPDNLPYVQI LKTAGVNTTD KEMEVLHLRN VSFEDAGEYT CLAGNSIGLS HHSAWLTVLE
361 ALEERPAVMT SPLYLEIIIY CTGAFLISCM VGSVIVYKMK SGTKKSDFHS QMAVHKLAKS
421 IPLRRQVSAD SSASMNSGVL LVRPSRLSSS GTPMLAGVSE YELPEDPRWE LPRDRLVLGK
481 PLGEGCFGQV VLAEAIGLDK DKPNRVTKVA VKMLKSDATE KDLSDLISEM EMMKMIGKHK
541 NIINLLGACT QDGPLYVIVE YASKGNLREY LQARRPPGLE YCYNPSHNPE EQLSSKDLVS
601 CAYQVARGME YLASKKCIHR DLAARNVLVT EDNVMKIADF GLARDIHHID YYKKTTNGRL
661 PVKWMAPEAL FDRIYTHQSD VWSFGVLLWE IFTLGGSPYP GVPVEELFKL LKEGHRMDKP
```

```
721 SNCTNELYMM MRDCWHAVPS QRPTFKQLVE DLDRIVALTS NQEYLDLSMP LDQYSPSFPD

781 TRSSTCSSGE DSVFSHEPLP EEPCLPRHPA QLANGGLKRR
```

SEQ ID NO: 147 is the FGFR1 Nucleotide Sequence for isoform 10, having Genebank Accession No. NM_001174063 (5895 bp):

```
   1 agatgcaggg gcgcaaacgc caaaggagac caggctgtag aagagaagg gcagagcgcc 61 ggacagctcg gcccgctccc cgtcctttgg ggccgcggct ggggaactac aaggcccagc 121 aggcagctgc aggggcgga ggcggaggag ggaccagcgc gggtgggagt gagagagcga 181 gccctcgcgc cccgccggcg catagcgctc ggagcgctct tgcggccaca ggcgcggcgt 241 cctcggcggc gggcggcagc tagcgggagc cgggacgccg gtgcagccgc agcgcgcgga 301 ggaacccggg tgtgccggga gctgggcggc cacgtccgga cgggaccgag accccctcgta 361 gcgcattgcg gcgacctcgc cttccccggc cgcgagcgcg ccgctgcttg aaaagccgcg 421 gaacccaagg acttttctcc ggtccgagct cggggcgccc cgcagggcgc acggtacccg 481 tgctgcagtc gggcacgccg cggcgccggg gcctccgcag ggcgatggag cccggtctgc 541 aaggaaagtg aggcgccgcc gctgcgttct ggaggagggg ggcacaaggt ctggagaccc 601 cgggtggcgg acgggagccc tccccccgcc ccgcctccgg gcaccagct ccggctccat 661 tgttcccgcc cgggctggag gcgccgagca ccgagcgccg ccgggagtcg agcgccggcc 721 gcggagctct tgcgaccccg ccaggacccg aacagagccc gggggcggcg ggccggagcc 781 ggggacgcgg gcacacgccc gctcgcacaa gccacggcgg actctcccga ggcggaacct 841 ccacgccgag cgagggtcag tttgaaaagg aggatcgagc tcactgtgga gtatccatgg 901 agatgtggag ccttgtcacc aacctctaac tgcagaactg ggatgtggag ctggaagtgc 961 ctcctcttct gggctgtgct ggtcacagcc acactctgca ccgctaggcc gtccccgacc 1021 ttgcctgaac aagcccagcc ctggggagcc cctgtggaag tggagtcctt cctggtccac 1081 cccggtgacc tgctgcagct tcgctgtcgg ctgcgggacg atgtgcagag catcaactgg 1141 ctgcgggacg gggtgcagct ggcggaaagc aaccgcaccc gcatcacagg ggaggaggtg 1201 gaggtgcagg actccgtgcc cgcagactcc ggcctctatg cttgcgtaac cagcagcccc 1261 tcgggcagtg acaccaccta cttctccgtc aatgtttcag atgctctccc ctcctcggag 1321 gatgatgatg atgatgatga ctcctcttca gaggagaaag aaacagataa caccaaacca 1381 aaccgtatgc ccgtagctcc atattggaca tccccagaaa agatggaaaa gaaattgcat 1441 gcagtgccgg ctgccaagac agtgaagttc aaatgccctt ccagtgggac cccaaacccc 1501 acactgcgct ggttgaaaaa tggcaaagaa ttcaaacctg accacagaat tggaggctac 1561 aaggtccgtt atgccacctg gagcatcata atggactctg tggtgccctc tgacaagggc 1621 aactacacct gcattgtgga gaatgagtac ggcagcatca ccacacata ccagctggat 1681 gtcgtggagc ggtcccctca ccggcccatc ctgcaagcag ggttgccgc caacaaaaca 1741 gtggccctgg gtagcaacgt ggagttcatg tgtaaggtgt acagtgaccc gcagccgcac 1801 atccagtggc taaagcacat cgaggtgaat gggagcaaga ttgggccaga caacctgcct 1861 tatgtccaga tcttgaagac tgctggagtt aataccaccg acaaagagat ggaggtgctt 1921 cacttaagaa atgtctcctt tgaggacgca ggggagtata cgtgcttggc gggtaactct 1981 atcggactct cccatcactc tgcatggttg accgttctgg aagccctgga agagaggccg 2041 gcagtgatga cctcgcccct gtacctggag atcatcatct attgcacagg ggccttcctc
```

```
-continued
2101 atctcctgca tggtggggtc ggtcatcgtc tacaagatga agagtggtac caagaagagt
2161 gacttccaca gccagatggc tgtgcacaag ctggccaaga gcatccctct gcgcagacag
2221 gtgtctgctg actccagtgc atccatgaac tctggggttc ttctggttcg gccatcacgg
2281 ctctcctcca gtgggactcc catgctagca ggggtctctg agtatgagct tcccgaagac
2341 cctcgctggg agctgcctcg ggacagactg gtcttaggca aacccctggg agagggctgc
2401 tttgggcagg tggtgttggc agaggctatc gggctggaca aggacaaacc caaccgtgtg
2461 accaaagtgg ctgtgaagat gttgaagtcg gacgcaacag agaaagactt gtcagacctg
2521 atctcagaaa tggagatgat gaagatgatc gggaagcata agaatatcat caacctgctg
2581 ggggcctgca cgcaggatgg tcccttgtat gtcatcgtgg agtatgcctc caagggcaac
2641 ctgcgggagt acctgcaggc ccggaggccc ccagggctgg aatactgcta caaccccagc
2701 cacaacccag aggagcagct ctcctccaag gacctggtgt cctgcgccta ccaggtggcc
2761 cgaggcatgg agtatctggc ctccaagaag tgcatacacc gagacctggc agccaggaat
2821 gtcctggtga cagaggacaa tgtgatgaag atagcagact ttggcctcgc acgggacatt
2881 caccacatcg actactataa aaagacaacc aacggccgac tgcctgtgaa gtggatggca
2941 cccgaggcat tatttgaccg gatctacacc caccagagtg atgtgtggtc tttcggggtg
3001 ctcctgtggg agatcttcac tctgggcggc tccccatacc ccggtgtgcc tgtggaggaa
3061 cttttcaagc tgctgaagga gggtcaccgc atggacaagc ccagtaactg caccaacgag
3121 ctgtacatga tgatgcggga ctgctggcat gcagtgccct cacagagacc caccttcaag
3181 cagctggtgg aagacctgga ccgcatcgtg gccttgacct ccaaccagga gtacctggac
3241 ctgtccatgc cctggacca gtactccccc agctttcccg acacccggag ctctacgtgc
3301 tcctcagggg aggattccgt cttctctcat gagccgctgc ccgaggagcc ctgcctgccc
3361 cgacacccag cccagcttgc caatggcgga ctcaaacgcc gctgactgcc acccacacgc
3421 cctccccaga ctccaccgtc agctgtaacc ctcacccaca gccctgctg ggcccaccac
3481 ctgtccgtcc ctgtcccctt tcctgctggc aggagccggc tgcctaccag gggccttcct
3541 gtgtggcctg ccttcacccc actcagctca cctctccctc cacctcctct ccacctgctg
3601 gtgagaggtg caaagaggca gatctttgct gccagccact tcatcccctc ccagatgttg
3661 gaccaacacc cctccctgcc accaggcact gcctggaggg cagggagtgg gagccaatga
3721 acaggcatgc aagtgagagc ttcctgagct ttctcctgtc ggtttggtct gttttgcctt
3781 cacccataag cccctcgcac tctggtggca ggtgccttgt cctcagggct acagcagtag
3841 ggaggtcagt gcttcgtgcc tcgattgaag gtgacctctg ccccagatag gtggtgccag
3901 tggcttatta attccgatac tagtttgctt tgctgaccaa atgcctggta ccagaggatg
3961 gtgaggcgaa ggccaggttg ggggcagtgt tgtggccctg ggcccagcc ccaaactggg
4021 ggctctgtat atagctatga agaaaacaca aagtgtataa atctgagtat atatttacat
4081 gtcttttttaa aagggtcgtt accagagatt tacccatcgg gtaagatgct cctggtggct
4141 gggaggcatc agttgctata tattaaaaac aaaaaagaaa aaaaaggaaa atgttttttaa
4201 aaaggtcata tattttttgc tacttttgct gttttatttt tttaaattat gttctaaacc
4261 tattttcagt ttaggtccct caataaaaat tgctgctgct tcatttatct atgggctgta
4321 tgaaaagggt gggaatgtcc actggaaaga agggacaccc acgggccctg ggctaggtc
4381 tgtcccgagg gcaccgcatg ctcccggcgc aggttccttg taacctcttc ttcctaggtc
4441 ctgcacccag acctcacgac gcacctcctg cctctccgct gcttttggaa agtcagaaaa
4501 agaagatgtc tgcttcgagg gcaggaaccc catccatgca gtagaggcgc tgggcagaga
```

-continued

```
4561 gtcaaggccc agcagccatc gaccatggat ggtttcctcc aaggaaaccg gtggggttgg
4621 gctggggagg gggcacctac ctaggaatag ccacggggta gagctacagt gattaagagg
4681 aaagcaaggg cgcggttgct cacgcctgta atcccagcac tttgggacac cgaggtgggc
4741 agatcacttc aggtcaggag tttgagacca gcctggccaa cttagtgaaa ccccatctct
4801 actaaaaatg caaaaattat ccaggcatgg tggcacacgc ctgtaatccc agctccacag
4861 gaggctgagg cagaatccct tgaagctggg aggcggaggt tgcagtgagc cgagattgcg
4921 ccattgcact ccagcctggg caacagagaa acaaaaagg aaaacaaatg atgaaggtct
4981 gcagaaactg aaacccagac atgtgtctgc cccctctatg tgggcatggt tttgccagtg
5041 cttctaagtg caggagaaca tgtcacctga ggctagtttt gcattcaggt ccctggcttc
5101 gtttcttgtt ggtatgcctc cccagatcgt ccttcctgta tccatgtgac cagactgtat
5161 ttgttgggac tgtcgcagat cttggcttct tacagttctt cctgtccaaa ctccatcctg
5221 tccctcagga acgggggaa aattctccga atgttttttgg ttttttggct gcttggaatt
5281 tacttctgcc acctgctggt catcactgtc ctcactaagt ggattctggc tcccccgtac
5341 ctcatggctc aaactaccac tcctcagtcg ctatattaaa gcttatattt tgctggatta
5401 ctgctaaata caaaagaaag ttcaatatgt tttcatttct gtagggaaaa tgggattgct
5461 gctttaaatt tctgagctag ggattttttg gcagctgcag tgttggcgac tattgtaaaa
5521 ttctctttgt ttctctctgt aaatagcacc tgctaacatt acaatttgta tttatgttta
5581 aagaaggcat catttggtga acagaactag gaaatgaatt tttagctctt aaaagcattt
5641 gctttgagac cgcacaggag tgtctttcct tgtaaaacag tgatgataat ttctgccttg
5701 gccctacctt gaagcaatgt tgtgtgaagg gatgaagaat ctaaaagtct tcataagtcc
5761 ttgggagagg tgctagaaaa atataaggca ctatcataat tacagtgatg tccttgctgt
5821 tactactcaa atcacccaca aatttcccca aagactgcgc tagctgtcaa ataaaagaca
5881 gtgaaattga cctga
```

SEQ ID NO: 185 is the FGFR1 Amino Acid Sequence for isoform 1, having Genebank Accession No. NP_075598 (822 aa):

SEQ ID NO: 186 is the FGFR1 Nucleotide Sequence for isoform 1, having Genebank Accession No. NM_023110 (5917 bp):

```
  1 MWSWKCLLFW AVLVTATLCT ARPSPTLPEQ AQPWGAPVEV ESFLVHPGDL LQLRCRLRDD
 61 VQSINWLRDG VQLAESNRTR ITGEEVEVQD SVPADSGLYA CVTSSPSGSD TTYFSVNVSD
121 ALPSSEDDDD DDDSSSEEKE TDNTKPNRMP VAPYWTSPEK MEKKLHAVPA AKTVKFKCPS
181 SGTPNPTLRW LKNGKEFKPD HRIGGYKVRY ATWSIIMDSV VPSDKGNYTC IVENEYGSIN
241 HTYQLDVVER SPHRPILQAG LPANKTVALG SNVEFMCKVY SDPQPHIQWL KHIEVNGSKI
301 GPDNLPYVQI LKTAGVNTTD KEMEVLHLRN VSFEDAGEYT CLAGNSIGLS HHSAWLTVLE
361 ALEERPAVMT SPLYLEIIIY CTGAFLISCM VGSVIVYKMK SGTKKSDFHS QMAVHKLAKS
421 IPLRRQVTVS ADSSASMNSG VLLVRPSRLS SSGTPMLAGV SEYELPEDPR WELPRDRLVL
481 GKPLGEGCFG QVVLAEAIGL DKDKPNRVTK VAVKMLKSDA TEKDLSDLIS EMEMMKMIGK
541 HKNIINLLGA CTQDGPLYVI VEYASKGNLR EYLQARRPPG LEYCYNPSHN PEEQLSSKDL
601 VSCAYQVARG MEYLASKKCI HRDLAARNVL VTEDNVMKIA DFGLARDIHH IDYYKKTTNG
661 RLPVKWMAPE ALFDRIYTHQ SDVWSFGVLL WEIFTLGGSP YPGVPVEELF KLLKEGHRMD
721 KPSNCTNELY MMMRDCWHAV PSQRPTFKQL VEDLDRIVAL TSNQEYLDLS MPLDQYSPSF
781 PDTRSSTCSS GEDSVFSHEP LPEEPCLPRH PAQLANGGLK RR
```

```
   1  agatgcaggg gcgcaaacgc caaaggagac caggctgtag gaagagaagg gcagagcgcc
  61  ggacagctcg gcccgctccc cgtcctttgg ggccgcggct ggggaactac aaggcccagc
 121  aggcagctgc aggggcgga ggcggaggag ggaccagcgc gggtgggagt gagagagcga
 181  gccctcgcgc cccgccggcg catagcgctc ggagcgctct tgcggccaca ggcgcggcgt
 241  cctcggcggc gggcggcagc tagcgggagc cgggacgccg gtgcagccgc agcgcgcgga
 301  ggaacccggg tgtgccggga gctgggcggc cacgtccgga cgggaccgag accccctcgta
 361  gcgcattgcg gcgacctcgc cttccccggc cgcgagcgcg ccgctgcttg aaaagccgcg
 421  gaacccaagg acttttctcc ggtccgagct cggggcgccc cgcagggcgc acggtacccg
 481  tgctgcagtc gggcacgccg cggcgccggg gcctccgcag ggcgatggag cccggtctgc
 541  aaggaaagtg aggcgccgcc gctgcgttct ggaggagggg ggcacaaggt ctggagaccc
 601  cgggtggcgg acgggagccc tcccccgcc ccgcctccgg ggcaccagct ccggctccat
 661  tgttcccgcc cgggctggag gcgccgagca ccgagcgccg ccgggagtcg agcgccggcc
 721  gcggagctct tgcgaccccc ccaggacccg aacagagccc ggggcggcg ggccggagcc
 781  ggggacgcgg gcacacgccc gctcgcacaa gccacggcgg actctcccga ggcggaacct
 841  ccacgccgag cgagggtcag tttgaaaagg aggatcgagc tcactgtgga gtatccatgg
 901  agatgtggag ccttgtcacc aacctctaac tgcagaactg ggatgtggag ctggaagtgc
 961  ctcctcttct gggctgtgct ggtcacagcc acactctgca ccgctaggcc gtccccgacc
1021  ttgcctgaac aagcccagcc ctggggagcc cctgtggaag tggagtcctt cctggtccac
1081  cccggtgacc tgctgcagct tcgctgtcgg ctgcgggacg atgtgcagag catcaactgg
1141  ctgcgggacg gggtgcagct ggcggaaagc aaccgcaccc gcatcacagg ggaggaggtg
1201  gaggtgcagg actccgtgcc cgcagactcc ggcctctatg cttgcgtaac cagcagcccc
1261  tcgggcagtg acaccaccta cttctccgtc aatgtttcag atgctctccc ctcctcggag
1321  gatgatgatg atgatgatga ctcctcttca gaggagaaag aaacagataa caccaaacca
1381  aaccgtatgc ccgtagctcc atattggaca tccccagaaa agatggaaaa gaaattgcat
1441  gcagtgccgg ctgccaagac agtgaagttc aaatgccctt ccagtgggac cccaaacccc
1501  acactgcgct ggttgaaaaa tggcaaagaa ttcaaacctg accacagaat tggaggctac
1561  aaggtccgtt atgccacctg gagcatcata atggactctg tggtgccctc tgacaagggc
1621  aactacacct gcattgtgga gaatgagtac ggcagcatca accacacata ccagctggat
1681  gtcgtggagc ggtcccctca ccggcccatc ctgcaagcag ggttgcccgc caacaaaaca
1741  gtggccctgg gtagcaacgt ggagttcatg tgtaaggtgt acagtgaccc gcagccgcac
1801  atccagtggc taaagcacat cgaggtgaat gggagcaaga ttgcccagat caacctgcct
1861  tatgtccaga tcttgaagac tgctggagtt aataccaccg acaaagagat ggaggtgctt
1921  cacttaagaa atgtctcctt tgaggacgca ggggagtata cgtgcttggc gggtaactct
1981  atcggactct cccatcactc tgcatggttg accgttctgg aagccctgga agagaggccg
2041  gcagtgatga cctcgcccct gtacctggag atcatcatct attgcacagg ggccttcctc
2101  atctcctgca tggtggggtc ggtcatcgtc tacaagatga agagtggtac caagaagagt
2161  gacttccaca gccagatggc tgtgcacaag ctggccaaga gcatccctct cgcagacag
2221  gtaacagtgt ctgctgactc cagtgcatcc atgaactctg ggttcttct ggttcggca
2281  tcacggctct cctccagtgg gactcccatg ctagcagggg tctctgagta tgagcttccc
2341  gaagaccctc gctgggagc gcctcgggac agactggtct taggcaaacc cctgggagag
2401  ggctgctttg ggcaggtggt gttggcagag gctatcgggc tggacaagga caaacccaac
```

-continued

```
2461  cgtgtgacca aagtggctgt gaagatgttg aagtcggacg caacagagaa agacttgtca
2521  gacctgatct cagaaatgga gatgatgaag atgatcggga agcataagaa tatcatcaac
2581  ctgctggggg cctgcacgca ggatggtccc ttgtatgtca tcgtggagta tgcctccaag
2641  ggcaacctgc gggagtacct gcaggcccgg aggccccag ggctggaata ctgctacaac
2701  cccagccaca acccagagga gcagctctcc tccaaggacc tggtgtcctg cgcctaccag
2761  gtggcccgag gcatggagta tctggcctcc aagaagtgca tacaccgaga cctggcagcc
2821  aggaatgtcc tggtgacaga ggacaatgtg atgaagatag cagactttgg cctcgcacgg
2881  gacattcacc acatcgacta ctataaaaag acaaccaacg gccgactgcc tgtgaagtgg
2941  atggcacccg aggcattatt tgaccggatc tacacccacc agagtgatgt gtggtctttc
3001  ggggtgctcc tgtgggagat cttcactctg gcggctccc catacccgg tgtgcctgtg
3061  gaggaacttt tcaagctgct gaaggagggt caccgcatgg acaagcccag taactgcacc
3121  aacgagctgt acatgatgat gcgggactgc tggcatgcag tgccctcaca gagacccacc
3181  ttcaagcagc tggtggaaga cctggaccgc atcgtggcct tgacctccaa ccaggagtac
3241  ctggacctgt ccatgccccct ggaccagtac tcccccagct ttcccgacac ccggagctct
3301  acgtgctcct caggggagga ttccgtcttc tctcatgagc cgctgcccga ggagccctgc
3361  ctgccccgac acccagccca gcttgccaat ggcggactca aacgccgctg actgccaccc
3421  acacgccctc cccagactcc accgtcagct gtaaccctca cccacagccc ctgctgggcc
3481  caccacctgt ccgtccctgt cccctttcct gctggcagga gccggctgcc taccaggggc
3541  cttcctgtgt ggcctgcctt caccccactc agctcacctc tccctccacc tcctctccac
3601  ctgctggtga gaggtgcaaa gaggcagatc tttgctgcca gccacttcat cccctcccag
3661  atgttggacc aacacccctc cctgccacca ggcactgcct ggagggcagg gagtgggagc
3721  caatgaacag gcatgcaagt gagagcttcc tgagcttct cctgtcggtt tggtctgttt
3781  tgccttcacc cataagcccc tcgcactctg gtggcaggtg ccttgtcctc agggctacag
3841  cagtagggag gtcagtgctt cgtgcctcga ttgaaggtga cctctgcccc agataggtgg
3901  tgccagtggc ttattaattc cgatactagt ttgctttgct gaccaaatgc ctggtaccag
3961  aggatggtga ggcgaaggcc aggttggggg cagtgttgtg gccctgggc ccagccccaa
4021  actgggggct ctgtatatag ctatgaagaa acacaaagt gtataaatct gagtatatat
4081  ttacatgtct ttttaaaagg gtcgttacca gagatttacc catcgggtaa gatgctcctg
4141  gtggctggga ggcatcagtt gctatatatt aaaaacaaaa aagaaaaaaa aggaaaatgt
4201  ttttaaaaag gtcatatatt ttttgctact tttgctgttt tatttttta aattatgttc
4261  taaacctatt ttcagtttag gtccctcaat aaaaattgct gctgcttcat ttatctatgg
4321  gctgtatgaa aagggtggga atgtccactg gaaagaaggg acacccacgg gccctggggc
4381  taggtctgtc ccgagggcac cgcatgctcc cggcgcaggt tccttgtaac ctcttcttcc
4441  taggtcctgc acccagacct cacgacgcac ctcctgcctc tccgctgctt ttggaaagtc
4501  agaaaaagaa gatgtctgct tcgagggcag gaaccccatc catgcagtag aggcgctggg
4561  cagagagtca aggcccagca gccatcgacc atggatggtt tcctccaagg aaaccggtgg
4621  ggttgggctg ggaggggggc acctacctag gaatagccac ggggtagagc tacagtgatt
4681  aagaggaaag caagggcgcg gttgctcacg cctgtaatcc cagcactttg ggacaccgag
4741  gtgggcagat cacttcaggt caggagtttg agaccagcct ggccaactta gtgaaacccc
4801  atctctacta aaaatgcaaa aattatccag gcatggtggc acacgcctgt aatcccagct
```

-continued

```
4861  ccacaggagg ctgaggcaga atcccttgaa gctgggaggc ggaggttgca gtgagccgag 4921  attgcgccat tgcactccag cctgggcaac agagaaaaca aaaaggaaaa caaatgatga 4981  aggtctgcag aaactgaaac ccagacatgt gtctgccccc tctatgtggg catggttttg 5041  ccagtgcttc taagtgcagg agaacatgtc acctgaggct agttttgcat tcaggtccct 5101  ggcttcgttt cttgttggta tgcctcccca gatcgtcctt cctgtatcca tgtgaccaga 5161  ctgtatttgt tgggactgtc gcagatcttg gcttcttaca gttcttcctg tccaaactcc 5221  atcctgtccc tcaggaacgg ggggaaaatt ctccgaatgt ttttggtttt ttggctgctt 5281  ggaatttact tctgccacct gctggtcatc actgtcctca ctaagtggat tctggctccc 5341  ccgtacctca tggctcaaac taccactcct cagtcgctat attaaagctt atattttgct 5401  ggattactgc taaatacaaa agaaagttca atatgttttc atttctgtag ggaaaatggg 5461  attgctgctt taaatttctg agctagggat tttttggcag ctgcagtgtt ggcgactatt 5521  gtaaaattct ctttgtttct ctctgtaaat agcacctgct aacattacaa tttgtattta 5581  tgtttaaaga aggcatcatt tggtgaacag aactaggaaa tgaatttta gctcttaaaa 5641  gcatttgctt tgagaccgca caggagtgtc tttccttgta aaacagtgat gataatttct 5701  gccttggccc taccttgaag caatgttgtg tgaagggatg aagaatctaa aagtcttcat 5761  aagtccttgg gagaggtgct agaaaaatat aaggcactat cataattaca gtgatgtcct 5821  tgctgttact actcaaatca cccacaaatt tccccaaaga ctgcgctagc tgtcaaataa 5881  aagacagtga aattgacctg aaaaaaaaaa aaaaaaa
```

The Genbank ID for the TACC1 gene is 6867. Three isoforms are listed for TACC1, e.g., having Genebank Accession Nos. NP_006274 (corresponding nucleotide sequence NM_001174063); NP_001167535 (corresponding nucleotide sequence NM_001174064); NP_001167536 (corresponding nucleotide sequence NM_001174065).

SEQ ID NO: 148 is the TACC1 Amino Acid Sequence for isoform 1, having Genebank Accession No. NP_006274 (805 aa):

```
  1  MAFSPWQILS PVQWAKWTWS AVRGGAAGED EAGGPEGDPE EEDSQAETKS LSFSSDSEGN

61  FETPEAETPI RSPFKESCDP SLGLAGPGAK SQESQEADEQ LVAEVVEKCS SKTCSKPSEN

121  EVPQQAIDSH SVKNFREEPE HDFSKISIVR PFSIETKDST DISAVLGTKA AHGCVTAVSG

181  KALPSSPPDA LQDEAMTEGS MGVTLEASAE ADLKAGNSCP ELVPSRRSKL RKPKPVPLRK

241  KAIGGEFSDT NAAVEGTPLP KASYHFSPEE LDENTSPLLG DARFQKSPPD LKETPGTLSS

301  DTNDSGVELG EESRSSPLKL EFDFTEDTGN IEARKALPRK LGRKLGSTLT PKIQKDGISK

361  SAGLEQPTDP VARDGPLSQT SSKPDPSQWE SPSFNPFGSH SVLQNSPPLS SEGSYHFDPD

421  NFDESMDPFK PTTTLTSSDF CSPTGNHVNE ILESPKKAKS RLITSGCKVK KHETQSLALD

481  ACSRDEGAVI SQISDISNRD GHATDEEKLA STSCGQKSAG AEVKGEPEED LEYFECSNVP

541  VSTINHAFSS SEAGIEKETC QKMEEDGSTV LGLLESSAEK APVSVSCGGE SPLDGICLSE

601  SDKTAVLTLI REEIITKEIE ANEWKKKYEE TRQEVLEMRK IVAEYEKTIA QMIEDEQRTS

661  MTSQKSFQQL TMEKEQALAD LNSVERSLSD LFRRYENLKG VLEGFKKNEE ALKKCAQDYL

721  ARVKQEEQRY QALKIHAEEK LDKANEEIAQ VRTKAKAESA ALHAGLRKEQ MKVESLERAL

781  QQKNQEIEEL TKICDELIAK LGKTD
```

SEQ ID NO: 149 is the TACC1 Nucleotide Sequence for isoform 1, having Genebank Accession No. NM_006283 (7802 bp):

```
   1 agctgatgcg cgccccgccg gccgggaggc gggagtccgc gagccgggag cgggagcagc
  61 agaggtctag cagccgggcg ccgcgggccg ggggcctgag gaggccacag gacgggcgtc
 121 ttcccggcta gtggagcccg gcgcgggcc cgctgcggcc gcaccgtgag gggaggaggc
 181 cgaggaggac gcagcgccgg ctgccggcgg gaggaagcgc tccaccaggg cccccgacgg
 241 cactcgttta accacatccg cgcctctgct ggaaacgctt gctggcgcct gtcaccggtt
 301 ccctccattt tgaaagggaa aaaggctctc cccacccatt cccctgcccc taggagctgg
 361 agccggagga gccgcgctca tggcgttcag cccgtggcag atcctgtccc ccgtgcagtg
 421 ggcgaaatgg acgtggtctg cggtacgcgg cggggccgcc ggcgaggacg aggctggcgg
 481 gcccgagggc gaccccgagg aggaggattc gcaagccgag accaaatcct tgagtttcag
 541 ctcggattct gaaggtaatt ttgagactcc tgaagctgaa accccgatcc gatcaccttt
 601 caaggagtcc tgtgatccat cactcggatt ggcaggacct ggggccaaaa gccaagaatc
 661 acaagaagct gatgaacagc ttgtagcaga agtggttgaa aaatgttcat ctaagacttg
 721 ttctaaacct tcagaaaatg aagtgccaca gcaggccatt gactctcact cagtcaagaa
 781 tttcagagaa gaacctgaac atgattttag caaaatttcc atcgtgaggc cattttcaat
 841 agaaacgaag gattccacgg atatctcggc agtcctcgga acaaaagcag ctcatggctg
 901 tgtaactgca gtctcaggca aggctctgcc ttccagcccg ccagacgccc tccaggacga
 961 ggcgatgaca gaaggcagca tgggggtcac cctcgaggcc tccgcagaag ctgatctaaa
1021 agctggcaac tcctgtccag agcttgtgcc cagcagaaga agcaagctga gaaagcccaa
1081 gcctgtcccc ctgaggaaga aagcaattgg aggagagttc tcagacacca acgctgctgt
1141 ggagggcaca cctctcccca aggcatccta tcacttcagt cctgaagagt tggatgagaa
1201 cacaagtcct ttgctaggag atgccaggtt ccagaagtct cccccctgacc ttaaagaaac
1261 tcccggcact ctcagtagtg acaccaacga ctcaggggtt gagctgggg aggagtcgag
1321 gagctcacct ctcaagcttg agtttgattt cacagaagat acaggaaaca tagaggccag
1381 gaaagcccct ccaaggaagc ttggcaggaa actgggtagc acactgactc ccaagataca
1441 aaaagatggc atcagtaagt cagcaggttt agaacagcct acagacccag tggcacgaga
1501 cgggcctctc tcccaaacat cttccaagcc agatcctagt cagtgggaaa gccccagctt
1561 caaccccttt gggagccact ctgttctgca gaactcccca cccctctctt ctgagggctc
1621 ctaccacttt gacccagata actttgacga atccatggat ccctttaaac caactacgac
1681 cttaacaagc agtgactttt gttctcccac tggtaatcac gttaatgaaa tcttagaatc
1741 acccaagaag gcaaagtcgc gtttaataac gagtggctgt aaggtgaaga agcatgaaac
1801 tcagtctctc gccctggatg catgttctcg ggatgaaggg gcagtgatct cccagatttc
1861 agacatttct aatagggatg gccatgctac tgatgaggag aaactggcat ccacgtcatg
1921 tggtcagaaa tcagctggtg ccgaggtgaa aggtgagcca gaggaagacc tggagtactt
1981 tgaatgttcc aatgttcctg tgtctaccat aaatcatgcg ttttcatcct cagaagcagg
2041 catagagaag gagacgtgcc agaagatgga agaagacggg tccactgtgc ttgggctgct
2101 ggagtcctct gcagagaagg cccctgtgtc ggtgtcctgt ggaggtgaga gccccctgga
2161 tgggatctgc ctcagcgaat cagacaagac agccgtgctc accttaataa gagaagagat
2221 aattactaaa gagattgaag caaatgaatg gaagaagaaa tacgaagaga cccggcaaga
```

```
2281 agttttggag atgaggaaaa ttgtagctga atatgaaaag actattgctc aaatgattga
2341 agatgaacaa aggacaagta tgacctctca gaagagcttc cagcaactga ccatggagaa
2401 ggaacaggcc ctggctgacc ttaactctgt ggaaaggtcc ctttctgatc tcttcaggag
2461 atatgagaac ctgaaaggtg ttctggaagg gttcaagaag aatgaagaag ccttgaagaa
2521 atgtgctcag gattacttag ccagagttaa acaagaggag cagcgatacc aggccctgaa
2581 aatccacgca gaagagaaac tggacaaagc caatgaagag attgctcagg ttcgaacaaa
2641 agcaaaggct gagagtgcag ctctccatgc tggactccgc aaagagcaga tgaaggtgga
2701 gtccctggaa agggccctgc agcagaagaa ccaagaaatt gaagaactga caaaaatctg
2761 tgatgagctg attgcaaagc tgggaaagac tgactgagac actcccctg ttagctcaac
2821 agatctgcat ttggctgctt ctcttgtgac cacaattatc ttgccttatc caggaataat
2881 tgcccctttg cagagaaaaa aaaaaactta aaaaaagcac atgcctactg ctgcctgtcc
2941 cgctttgctg ccaatgcaac agccctggaa gaaaccctag agggttgcat agtctagaaa
3001 ggagtgtgac ctgacagtgc tggagcctcc tagtttcccc ctatgaaggt tcccttaggc
3061 tgctgagttt gggtttgtga tttatcttta gtttgttta aagtcatctt tactttccca
3121 aatgtgttaa atttgtaact cctctttggg gtcttctcca ccacctgtct gatttttttg
3181 tgatctgttt aatcttttaa ttttttagta tcagtggttt tatttaagga dacagtttgg
3241 cctattgtta cttccaattt ataatcaaga aggggctctg gatcccecttt taaattacac
3301 acactctcac acacatacat gtatgtttat agatgctgct gctcttttcc ctgaagcata
3361 gtcaagtaag aactgctcta cagaaggaca tatttccttg gatgtgagac cctattttga
3421 aatagagtcc tgactcagaa caccaactta agaatttggg ggattaaaga tgtgaagacc
3481 acagtcttgg gttttcatat ctggagaaga ctatttgcca tgacgtttg ttgccctggt
3541 atttggacac tcctcagctt taatgggtgt ggcccctta gggttagtcc tcagactaat
3601 gatagtgtct gctttctgca tgaacggcaa tatgggactc cctccaagct agggtttggc
3661 aagtctgccc tagagtcatt tactctcctc tgcctccatt tgttaataca gaatcaacat
3721 ttagtcttca ttatctttt tttttttttt gagacagagt ttcgatctat tttaagtatg
3781 tgaagaaaat ctacttgtaa aaggctcaga tcttaattaa aaggtaattg tagcacatta
3841 ccaattataa ggtgaagaaa tgttttttttc ccaagtgtga tgcattgttc ttcagatgtt
3901 gaaagaaag caaaaaatac cttctaactt aagacagaat ttttaacaaa atgagcagta
3961 aaagtcacat gaaccactcc aaaaatcagt gcattttgca tatttttaaa caaagacagc
4021 ttgttgaata ctgagaagag gagtgcaagg agaaggtctg tactaacaaa gccaaattcc
4081 tcaagctctt actggactca gttcagagtg gtgggccatt aaccccaaca tggaattttt
4141 ccatataaat ctcaatgaat tcccttcat ttgaataggc aaacccaaat ccatgcaagt
4201 gttttaaagc actgtcctgt cttaatctta catgctgaaa gtcttcatgg tgatatgcac
4261 tatattcagt atacgtatgt tttcctactt ctcttgtaaa actgttgcat gatccaactt
4321 cagcaatgaa ttgtgcctag tggagaacct ctatagatct taaaaaatga attattcttt
4381 agcagtgtat tactccacatg ggtgcaatct ttagccccag ggaggtcaat aatgtctttt
4441 aaagccagaa gtcacatttt accaatatgc atttatcata attggtgctt aggctgtata
4501 ttcaagcctt ttgtcttaac atttttgtata aaaagaaca acagaaatta tctgtcattt
4561 gagaagtggc ttgacaatca tttgagcttt gaaagcagtc actgtggtgt aatatgaatg
4621 ctgtcctagt ggtcatagta ccaagggcac gtgtctcccc ttggtataac tgatttcctt
4681 tttagtcctc tactgctaaa taagttaatt ttgcattttg cagaaagaaa cattgattgc
```

-continued

```
4741 taaatctttt tgctgctgtg ttttggtgtt ttcatgttta cttgttttat attgatctgt
4801 tttaagtatg agaggcttat agtgccctcc attgtaaatc catagtcatc tttttaagct
4861 tattgtgttt aagaaagtag ctatgtgtta acagaggtg atggcagccc ttccctagca
4921 cactggtgga agagacccct taagaacctg accccagtga atgaagctga tgcacaggga
4981 gcaccaaagg accttcgtta agtgataatt gtcctggcct ctcagccatg accgttatga
5041 ggaaatatcc cccattcgaa cttaacagat gcctcctctc caaagagaat taaaatcgta
5101 gcttgtacag atcaagagaa tatactgggc agaatgaagt atgtttgttt attttctttt
5161 aaaaataaag gattttggaa ctctggagag taagaatata gtatagagtt tgcctcaaca
5221 catgtgaggg ccaaataacc tgctagctag gcagtaataa actctgttac agaagagaaa
5281 aagggccggg cacagtggct tattcctgta atcccaacac tgtggaaggc cgaggcagga
5341 ggatcacttg agtccaggag tttgaaacct acctaggcaa catggtgaaa ccttgtctct
5401 accaaaataa aaattagctg gcatggtgg cacgtgcctg tggtcccagc tacttgggag
5461 gctgaggtgg gagcctggga ggtcaaggct gcagtgagcc atgatcatgc cactgcactc
5521 catcctgggt gacagcaaga tcttgtctca aaaaaaaaa aaaaaaaaaa aaaaccagga
5581 gtgaaaaagg aaagtagaag gcagctgctg gcctagatgt tggtttggga atattaggtg
5641 atcctgttga gattctggat ccagagcaat ttctttagct tttgactttg ccaaagtgta
5701 gatagccttt atccagcagt attttaagtg gggaatgcaa cgtgaggcca actgaacaat
5761 tcccccgtg gctgcccaga tagtcacagt caaggttgga gagtctcctt ccagccagtg
5821 acctacccaa accttttgtt ctgtaaaact gctctggaaa taccgggaag cccagttttc
5881 tcacgtggtt tctagcttct tcagactcag cccaaattag gaagtgcaga agcacatgat
5941 ggtgaaaaac ctaggatttg gcagccttcc agaatggtat ggaatctgag ggaagattta
6001 tgtttcgttt tggaggatag ctcaagttga attttctttc cagccagtta ccctttcaac
6061 ctacccatac tttgtacaac tcttacacaa atacttagat atttattaga tagccctgaa
6121 ttcactctaa ttataaacag ggagtgtaaa ctgcccccag atgttcctgg gctgggtaaa
6181 agcagctgga gtgaagcact catttttccat aaaggtaaca aagggcagct cagtggttac
6241 tcaagctcaa aagggttttt ttaagagcaa gcattggtta agtctgtgta tactgagttg
6301 gaagtgattt cagcacattc ttttttagtg gagtgaaagt tctgaagccc cttttaact
6361 tcctcttggt ttttcattat aattggtagc catctcatga actgtctctg actgttgtct
6421 ctttgtggtc atgtgattgt gagcttgctt tctgacttgc atttctgact ttatcctgtt
6481 gttaggaaga tagaaactag gttttgaaag attacatgat tcaagcgagg gattttaaag
6541 taaagatgta tttattctga agaatctaaa agataacaga ttatttgctt atgaaagaac
6601 aatatagtct gggaatccca gaatgtcaag ccaaaggtct aagaagtcat ctccttcaaa
6661 tactttaata aagaagtatt tcgaggagat atctgtccaa aaaggtttga ctggcctcca
6721 gattccagtt attttttaaaa agcaacttac cactaaatcc ttgagtctcc atagagtaac
6781 agtaaagaaa ctgatgtaac agactctcct ctcaaaggat ctcctctgga agagactatc
6841 agcggcagca ttctccaggg aagacccatc ccctagtgcc agagcttgca tcctggagac
6901 taaagattgc acttttttgt agttttttgt ccaaatgcaa tcccatttct gtgcctctta
6961 gcatgcagtt agatttggac aaacaagatt cctaaggaat gactttatta actataatat
7021 ggttacagct attatataaa tatatattct ggttatagtt ctaatatgga gatgttgtgt
7081 gcaatgctgg cctgtggtgg tctgtgtaat gctttaactt gtatggagga ggccaggctc
```

```
7141 agagctgaga tgtggcctga accttccctg tatcgatcct ttaatttaga actgtcaaga 7201 tgtcactttc tcccctctg ccttttagtg gtatctgaca tatactcaaa acagtaattt 7261 cctggtcaca tcattaactg ctaattctgt atttataaag aattttcaga tggacatgta 7321 caaatttgaa ctcaaaccat ccccagtcca gatacagggc agcgtgtagg tgaccacacc 7381 agagcctcag cctcggtcct tctcagccgt cgggatagga tccaggcatt tcttttaaat 7441 ctcagaggta gcagtaaact tttcagtatt gctgttagca agtgtgtgtt tgccaataga 7501 tacccattat actaatgtgc caagtaaatg ttcattgcac atctgcttcc actgtgttcc 7561 cacgggtgcc atgaagtgtg tgaggagccc ctcatctgga gggatgagtg ctgcgttgac 7621 tactgctatc aggattgtgt tgtgtggaat attcatctac ataaatttta tatgcacagt 7681 aatttcccctt tttatatgtc aagtaactat ttgtaaaagt tatactcaca aattattata 7741 atgattacta atatattttt tccatgtttc attgcctgaa taaaaactgt ttaccactgt 7801 ta
```

SEQ ID NO: 150 is the amino acid sequence of the FGFR1-TACC1 fusion protein.

MWSWKCLLFWAVLVTATLCTARPSPTLPEQDALPSSEDDDDDDDSSSEEKE
TDNTKPNPVAPYWTSPEKMEKKLHAVPAAKTVKFKCPSSGTPNPTLRWLKN
GKEFKPDHRIGGYKVRYATWSIIMDSVVPSDKGNYTCIVENEYGSINHTYQ
LDVVERSPHRPILQAGLPANKTVALGSNVEFMCKVYSDPQPHIQWLKHIEV
NGSKIGPDNLPYVQILKTAGVNTTDKEMEVLHLRNVSFEDAGEYTCLAGNS
IGLSHHSAWLTVLEALEERPAVMTSPLYLEIIIYCTGAFLISCMVGSVIVY
KMKSGTKKSDFHSQMAVHKLAKSIPLRRQVTVSADSSASMNSGVLLVRPSR
LSSSGTPMLAGVSEYELPEDPRWELPRDRLVLGKPLGEGCFGQVVLAEAIG
LDKDKPNRVTKVAVKMLKSDATEKDLSDLISEMEMMKMIGKHKNIINLLGA
CTQDGPLYVIVEYASKGNLREYLQARRPPGLEYCYNPSHNPEEQLSSKDLV
SCAYQVARGMEYLASKKCIHRDLAARNVLVTEDNVMKIADFGLARDIHHID
YYKKTTNGRLPVKWMAPEALFDRIYTHQSDVWSFGVLLWEIFTLGGSPYPG
VPVEELFKLLKEGHRMDKPSNCTNELYMMMRDCWHAVPSQRPTFKQLVEDL
DRIVALTSNQGLLESSAEKAPVSVSCGGESPLDGICLSESDKTAVLTLIRE
EIITKEIEANEWKKKYEETRQEVLEMRKIVAEYEKTIAQMIEDEQRTSMTS
QKSFQQLTMEKEQALADLNSVERSLSDLFRRYENLKGVLEGFKKNEEALKK
CAQDYLARVKQEEQRYQALKIHAEEKLDKANEEIAQVRTKAKAESAALHAG
LRKEQMKVESLERALQQKNQEIEELTKICDELIAKLGKTD

SEQ ID NO: 151 is the nucleotide sequence that encodes the FGFR1-TACC1 fusion protein.

```
atgtggagctggaagtgcctcctcttctgggctgtgctggtcacagccaca
ctctgcaccgctaggccgtccccgaccttgcctgaacaagcccagccctgg
ggagcccctgtggaagtggagtccttcctggtccaccccggtgacctgctg
cagcttcgctgtcggctgcgggacgatgtgcagagcatcaactggctgcgg
gacggggtgcagctggcggaaagcaaccgcacccgcatcacaggggaggag
gtggaggtgcaggactccgtgcccgcagactccggcctctatgcttgcgta
accagcagcccctcgggcagtgacaccacctacttctccgtcaatgtttca
gatgctctcccctcctcggaggatgatgatgatgatgatgactcctcttca
gaggagaaagaaacagataacaccaaaccaaaccgtatgcccgtagctcca
tattggacatccccagaaaagatggaaaagaaattgcatgcagtgccggct
gccaagacagtgaagttcaaatgccctcccagtgggaccccaaacccaca
ctgcgctggttgaaaaatggcaaagaattcaaacctgaccacagaattgga
ggctacaaggtccgttatgccacctggagcatcataatggactctgtggtg
ccctctgacaagggcaactacacctgcattgtggagaatgagtacggcagc
atcaaccacatacccgctggatgtcgtggagcggtcccctcaccggccc
atcctgcaagcagggttgcccgccaacaaaacagtggccctgggtagcaac
gtggagttcatgtgtaaggtgtacagtgacccgcagccgcacatccagtgg
ctaaagcacatcgaggtgaatgggagcaagattggcccagacaacctgcct
tatgtccgatcttgaagactgctggagttaataccaccgacaaagagatg
gaggtgcttcacttaagaaatgtctcctttgaggacgcaggggagtatacg
tgcttggcgggtaactctatcggactctcccatcactctgcatggttgacc
gttctggaagccctggaagagaggccggcagtgatgacctcgcccctgtac
ctggagatcatcatctattgcacaggggccttcctcatctcctgcatggtg
gggtcggtcatcgtctacaagatgaagagtggtaccaagaagagtgacttc
cacagccagatggctgtgcacaagctggccaagagcatccctctgcgcaga
caggtgtctgctgactccagtgcatccatgaactctgggtgtcttctggtt
cggccatcacggctctcctccagtgggactcccatgctagcaggggtctct
gagtatgagcttcccgaagaccctcgctgggagctgcctcgggacagactg
gtcttaggcaaaccctgggagagggctgctttgggcaggtggtgttggca
gaggctatcgggctggacaaggacaaacccaaccgtgtgaccaaagtggct
gtgaagatgttgaagtcggacgcaacagagaaagacttgtcagacctgatc
tcagaaatggagatgatgaagatgatcgggaagcataagaatatcatcaac
```

```
ctgctgggggcctgcacgcaggatggtcccttgtatgtcatcgtggagtat gcctccaagggcaacctgcgggagtacctgcaggcccggaggcccccaggg ctggaatactgctacaaccccagccacaacccagaggagcagctctcctcc aaggacctggtgtcctgcgcctaccaggtggcccgaggcatggagtatctg gcctccaagaagtgcatacaccgagacctggcagccaggaatgtcctggtg acagaggacaatgtgatgaagatagcagactttggcctcgcacgggacatt caccacatcgactactataaaaagacaaccaacggccgactgcctgtgaag tggatggcacccgaggcattatttgaccggatctacacccaccagagtgat gtgtggtctttcggggtgctcctgtgggagatcttcactctgggcggctcc ccataccccggtgtgcctgtggaggaacttttcaagctgctgaaggagggt caccgcatggacaagcccagtaactgcaccaacgagctgtacatgatgatg cgggactgctggcatgcagtgccctcacagagacccaccttcaagcagctg gtggaagacctggaccgcatcgtgccttgacctccaaccagtgggctgct ggagtcctctgcagagaaggccctgtgtcggtgtcctgtggaggtgagag cccctggatgggatctgcctcagcgaatcagacaagacagccgtgctcac cttaataagagaagagataattactaaagagattgaagcaaatgaatggaa gaagaaatacgaagagaccggcaagaagttttggagatgaggaaaattgt agctgaatatgaaaagactattgctcaaatgattgaagatgaacaaggac aagtatgacctctcagaagagcttccagcaactgaccatggagaaggaaca
```

```
ggccctggctgacctaactctgtggaaaggtcctttctgatctcttcag gagatatgagaacctgaaaggtgttctggaagggttcaagaagaatgaaga agccttgaagaaatgtgctcaggattacttagccagagttaaacaagagga gcagcgataccaggccctgaaaatccacgcagaagagaaactggacaaagc caatgaagagattgctcaggttcgaacaaaagcaaggctgagagtgcagc tctccatgctggactccgcaaagagcagatgaaggtggagtccctggaaag ggccctgcagcagaagaaccaagaaattgaagaactgacaaaaatctgtga tgagctgattgcaaagctgggaaagactgac
```

The Genbank ID for the FGFR2 gene is 2263. Eight isoforms are listed for FGFR2, e.g., having Genebank Accession Nos. NP_000132 (corresponding nucleotide sequence NM_000141); NP_001138385 (corresponding nucleotide sequence NM_001144913); NP_001138386 (corresponding nucleotide sequence NM_001144914); NP_001138387 (corresponding nucleotide sequence NM_001144915); NP_001138388 (corresponding nucleotide sequence NM_001144916); NP_001138389 (corresponding nucleotide sequence NM_001144917); NP_001138390 (corresponding nucleotide sequence NM_001144918); NP_001138391 (corresponding nucleotide sequence NM_001144919); NP_075259 (corresponding nucleotide sequence NM_022970).

SEQ ID NO: 152 is the FGFR2 Amino Acid Sequence for isoform 1, having Genebank Accession No. NP_000132 (821 aa):

```
  1 MVSWGRFICL VVVTMATLSL ARPSFSLVED TTLEPEEPPT KYQISQPEVY VAAPGESLEV
 61 RCLLKDAAVI SWTKDGVHLG PNNRTVLIGE YLQIKGATPR DSGLYACTAS RTVDSETWYF
121 MVNVTDAISS GDDEDDTDGA EDFVSENSNN KRAPYWTNTE KMEKRLHAVP AANTVKFRCP
181 AGGNPMPTMR WLKNGKEFKQ EHRIGGYKVR NQHWSLIMES VVPSDKGNYT CVVENEYGSI
241 NHTYHLDVVE RSPHRPILQA GLPANASTVV GGDVEFVCKV YSDAQPHIQW IKHVEKNGSK
301 YGPDGLPYLK VLKAAGVNTT DKEIEVLYIR NVTFEDAGEY TCLAGNSIGI SFHSAWLTVL
361 PAPGREKEIT ASPDYLEIAI YCIGVFLIAC MVVTVILCRM KNTTKKPDFS SQPAVHKLTK
421 RIPLRRQVTV SAESSSSMNS NTPLVRITTR LSSTADTPML AGVSEYELPE DPKWEFPRDK
481 LTLGKPLGEG CFGQVVMAEA VGIDKDKPKE AVTVAVKMLK DDATEKDLSD LVSEMEMMKM
541 IGKHKNIINL LGACTQDGPL YVIVEYASKG NLREYLRARR PPGMEYSYDI NRVPEEQMTF
601 KDLVSCTYQL ARGMEYLASQ KCIHRDLAAR NVLVTENNVM KIADFGLARD INNIDYYKKT
661 TNGRLPVKWM APEALFDRVY THQSDVWSFG VLMWEIFTLG GSPYPGIPVE ELFKLLKEGH
721 RMDKPANCTN ELYMMMRDCW HAVPSQRPTF KQLVEDLDRI LTLTTNEEYL DLSQPLEQYS
781 PSYPDTRSSC SSGDDSVFSP DPMPYEPCLP QYPHINGSVK T
```

SEQ ID NO: 153 is the FGFR2 Nucleotide Sequence for isoform 1, having Genebank Accession No. NM_000141 (4654 bp):

```
  1 ggcggcggct ggaggagagc gcggtggaga gccgagcggg cggcggcgg gtgcggagcg
 61 ggcgagggag cgcgcgcggc cgccacaaag ctcgggcgcc gcggggctgc atgcggcgta
121 cctggcccgg cgcggcgact gctctccggg ctggcggggg ccggccgcga gccccggggg
```

-continued

```
 181 ccccgaggcc gcagcttgcc tgcgcgctct gagccttcgc aactcgcgag caaagtttgg
 241 tggaggcaac gccaagcctg agtcctttct tcctctcgtt ccccaaatcc gagggcagcc
 301 cgcgggcgtc atgcccgcgc tcctccgcag cctggggtac gcgtgaagcc cgggaggctt
 361 ggcgccggcg aagacccaag gaccactctt ctgcgtttgg agttgctccc cgcaaccccg
 421 ggctcgtcgc tttctccatc ccgacccacg cggggcgcgg ggacaacaca ggtcgcggag
 481 gagcgttgcc attcaagtga ctgcagcagc agcggcagcg cctcggttcc tgagcccacc
 541 gcaggctgaa ggcattgcgc gtagtccatg cccgtagagg aagtgtgcag atgggattaa
 601 cgtccacatg gagatatgga agaggaccgg ggattggtac cgtaaccatg gtcagctggg
 661 gtcgtttcat ctgcctggtc gtggtcacca tggcaacctt gtccctggcc cggccctcct
 721 tcagtttagt tgaggatacc acattagagc cagaagagcc accaaccaaa taccaaatct
 781 ctcaaccaga agtgtacgtg gctgcgccag gggagtcgct agaggtgcgc tgcctgttga
 841 aagatgccgc cgtgatcagt tggactaagg atggggtgca cttggggccc aacaatagga
 901 cagtgcttat tggggagtac ttgcagataa agggcgccac gcctagagac tccggcctct
 961 atgcttgtac tgccagtagg actgtagaca gtgaaacttg gtacttcatg gtgaatgtca
1021 cagatgccat ctcatccgga gatgatgagg atgacaccga tggtgcggaa gattttgtca
1081 gtgagaacag taacaacaag agagcaccat actggaccaa cacagaaaag atggaaaagc
1141 ggctccatgc tgtgcctgcg gccaacactg tcaagtttcg ctgcccagcc ggggggaacc
1201 caatgccaac catgcggtgg ctgaaaaacg ggaaggagtt taagcaggag catcgcattg
1261 gaggctacaa ggtacgaaac cagcactgga gcctcattat ggaaagtgtg gtcccatctg
1321 acaagggaaa ttatacctgt gtagtggaga atgaatacgg gtccatcaat cacacgtacc
1381 acctggatgt tgtggagcga tcgcctcacc ggcccatcct caagccggga ctgccggcaa
1441 atgcctccac agtggtcgga ggagacgtag agtttgtctg caaggtttac agtgatgccc
1501 agccccacat ccagtggatc aagcacgtgg aaaagaacgg cagtaaatac gggcccgacg
1561 ggctgcccta cctcaaggtt ctcaaggccg ccggtgttaa caccacggac aaagagattg
1621 aggttctcta tattcggaat gtaacttttg aggacgctgg ggaatatacg tgcttggcgg
1681 gtaattctat tgggatatcc tttcactctg catggttgac agttctgcca gcgcctggaa
1741 gagaaaagga gattacagct tccccagact acctggagat agccatttac tgcatagggg
1801 tcttcttaat cgcctgtatg gtggtaacag tcatcctgtg ccgaatgaag aacacgacca
1861 agaagccaga cttcagcagc cagccggctg tgcacaagct gaccaaacgt atcccccctg
1921 ggagacaggt aacagtttcg gctgagtcca gctcctccat gaactccaac accccgctgg
1981 tgaggataac aacacgcctc tcttcaacgg cagacacccc catgctggca gggtctccg
2041 agtatgaact tccagaggac ccaaaatggg agtttccaag agataagctg acactgggca
2101 agccccctgg gagaaggttgc tttgggcaag tggtcatggc ggaagcagtg ggaattgaca
2161 aagacaagcc caaggaggcg gtcaccgtgg ccgtgaagat gttgaaagat gatgccacag
2221 agaaagacct ttctgatctg gtgtcagaga tggagatgat gaagatgatt gggaaacaca
2281 agaatatcat aaatcttctt ggagcctgca cacaggatgg gcctctctat gtcatagttg
2341 agtatgcctc taaaggcaac ctccgagaat acctccgagc ccggaggcca cccgggatgg
2401 agtactccta tgacattaac cgtgttcctg aggagcagat gaccttcaag gacttggtgt
2461 catgcaccta ccagctggcc agaggcatgg agtacttggc ttcccaaaaa tgtattcatc
2521 gagatttagc agccagaaat gttttggtaa cagaaaacaa tgtgatgaaa atagcagact
2581 ttggactcgc cagagatatc aacaatatag actattacaa aaagaccacc aatgggcggc
```

```
2641 ttccagtcaa gtggatggct ccagaagccc tgtttgatag agtatacact catcagagtg 2701 atgtctggtc cttcggggtg ttaatgtggg agatcttcac tttaggggc tcgccctacc 2761 cagggattcc cgtggaggaa cttttaagc tgctgaagga aggacacaga atggataagc 2821 cagccaactg caccaacgaa ctgtacatga tgatgaggga ctgttggcat gcagtgccct 2881 cccagagacc aacgttcaag cagttggtag aagacttgga tcgaattctc actctcacaa 2941 ccaatgagga atacttggac ctcagccaac ctctcgaaca gtattcacct agttaccctg 3001 acacaagaag ttcttgttct tcaggagatg attctgtttt ttctccagac cccatgcctt 3061 acgaaccatg ccttcctcag tatccacaca taaacggcag tgttaaaaca tgaatgactg 3121 tgtctgcctg tccccaaaca ggacagcact gggaacctag ctacactgag cagggagacc 3181 atgcctccca gagcttgttg tctccacttg tatatatgga tcagaggagt aaataattgg 3241 aaaagtaatc agcatatgtg taaagattta tacagttgaa aacttgtaat cttccccagg 3301 aggagaagaa ggtttctgga gcagtggact gccacaagcc accatgtaac ccctctcacc 3361 tgccgtgcgt actggctgtg gaccagtagg actcaaggtg gacgtgcgtt ctgccttcct 3421 tgttaatttt gtaataattg gagaagattt atgtcagcac acacttacag agcacaaatg 3481 cagtatatag gtgctggatg tatgtaaata tattcaaatt atgtataaat atatattata 3541 tatttacaag gagttattt ttgtattgat tttaaatgga tgtcccaatg cacctagaaa 3601 attggtctct cttttttaa tagctatttg ctaaatgctg ttcttacaca taatttctta 3661 attttcaccg agcagaggtg gaaaaatact tttgctttca gggaaaatgg tataacgtta 3721 atttattaat aaattggtaa tatacaaaac aattaatcat ttatagtttt ttttgtaatt 3781 taagtggcat ttctatgcag gcagcacagc agactagtta atctattgct tggacttaac 3841 tagttatcag atcctttgaa aagagaatat ttacaatata tgactaattt ggggaaaatg 3901 aagtttgat ttatttgtgt ttaaatgctg ctgtcagacg attgttctta gacctcctaa 3961 atgccccata ttaaaagaac tcattcatag gaaggtgttt cattttggtg tgcaaccctg 4021 tcattacgtc aacgcaacgt ctaactggac ttcccaagat aaatggtacc agcgtcctct 4081 taaaagatgc cttaatccat tccttgagga cagaccttag ttgaaatgat agcagaatgt 4141 gcttctctct ggcagctggc cttctgcttc tgagttgcac attaatcaga ttagcctgta 4201 ttctcttcag tgaattttga taatggcttc cagactcttt ggcgttggag acgcctgtta 4261 ggatcttcaa gtcccatcat agaaaattga acacagagt tgttctgctg atagttttgg 4321 ggatacgtcc atctttttaa gggattgctt tcatctaatt ctggcaggac ctcaccaaaa 4381 gatccagcct cataccctaca tcagacaaaa tatcgccgtt gttccttctg tactaaagta 4441 ttgtgttttg ctttggaaac acccactcac tttgcaatag ccgtgcaaga tgaatgcaga 4501 ttacactgat cttatgtgtt acaaaattgg agaaagtatt taataaaacc tgttaatttt 4561 tatactgaca ataaaaatgt ttctacagat attaatgtta acaagacaaa ataaatgtca 4621 cgcaacttat ttttttaata aaaaaaaaa aaaa
```

The Genbank ID for the TACC2 gene is 10579. Four isoforms are listed for TACC2, e.g., having Genebank Accession Nos. NP_996744 (corresponding nucleotide sequence NM_206862); NP_996743 (corresponding nucleotide sequence NM_206861); NP_996742 (corresponding nucleotide sequence NM_206860); NP_008928 (corresponding nucleotide sequence NM_006997).

SEQ ID NO: 154 is the TACC2 Amino Acid Sequence for isoform a, having Genebank Accession No. NP_996744 (2948 aa):

```
  1 MGNENSTSDN QRTLSAQTPR SAQPPGNSQN IKRKQQDTPG SPDHRDASSI GSVGLGGFCT

61 ASESSASLDP CLVSPEVTEP RKDPQGARGP EGSLLPSPPP SQEREHPSSS MPFAECPPEG
```

```
121  CLASPAAAPE DGPQTQSPRR EPAPNAPGDI AAAFPAERDS STPYQEIAAV PSAGRERQPK
181  EEGQKSSFSF SSGIDQSPGM SPVPLREPMK APLCGEGDQP GGFESQEKEA AGGFPPAESR
241  QGVASVQVTP EAPAAAQQGT ESSAVLEKSP LKPMAPIPQD PAPRASDRER GQGEAPPQYL
301  TDDLEFLRAC HLPRSNSGAA PEAEVNAASQ ESCQQPVGAY LPHAELPWGL PSPALVPEAG
361  GSGKEALDTI DVQGHPQTGM RGTKPNQVVC VAAGGQPEGG LPVSPEPSLL TPTEEAHPAS
421  SLASFPAAQI PIAVEEPGSS SRESVSKAGM PVSADAAKEV VDAGLVGLER QVSDLGSKGE
481  HPEGDPGEVP APSPQERGEH LNTEQSHEVQ PGVPPPPLPK EQSHEVQPGA PPPPLPKAPS
541  ESARGPPGPT DGAKVHEDST SPAVAKEGSR SPGDSPGGKE EAPEPPDGGD PGNLQGEDSQ
601  AFSSKRDPEV GKDELSKPSS DAESRDHPSS HSAQPPRKGG AGHTDGPHSQ TAEADASGLP
661  HKLGEEDPVL PPVPDGAGEP TVPEGAIWEG SGLQPKCPDT LQSREGLGRM ESFLTLESEK
721  SDFPPTPVAE VAPKAQEGES TLEIRKMGSC DGEGLLTSPD QPRGPACDAS RQEFHAGVPH
781  PPQGENLAAD LGLTALILDQ DQQGIPSCPG EGWIRGAASE WPLLSSEKHL QPSQAQPETS
841  IFDVLKEQAQ PPENGKETSP SHPGFKDQGA DSSQIHVPVE PQEDNNLPTH GGQEQALGSE
901  LQSQLPKGTL SDTPTSSPTD MVWESSLTEE SELSAPTRQK LPALGEKRPE GACGDGQSSR
961  VSPPAADVLK DFSLAGNFSR KETCCTGQGP NKSQQALADA LEEGSQHEEA CQRHPGASEA
1021 ADGCSPLWGL SKREMASGNT GEAPPCQPDS VALLDAVPCL PALAPASPGV TPTQDAPETE
1081 ACDETQEGRQ QPVPAPQQKM ECWATSDAES PKLLASFPSA GEQGGEAGAA ETGGSAGAGD
1141 PGKQQAPEKP GEATLSCGLL QTEHCLTSGE EASTSALRES CQAEHPMASC QDALLPAREL
1201 GGIPRSTMDF STHQAVPDPK ELLLSGPPEV AAPDTPYLHV DSAAQRGAED SGVKAVSSAD
1261 PRAPGESPCP VGEPPLALEN AASLKLFAGS LAPLLQPGAA GGEIPAVQAS SGSPKARTTE
1321 GPVDSMPCLD RMPLLAKGKQ ATGEEKAATA PGAGAKASGE GMAGDAAGET EGSMERMGEP
1381 SQDPKQGTSG GVDTSSEQIA TLTGFPDFRE HIAKIFEKPV LGALATPGEK AGAGRSAVGK
1441 DLTRPLGPEK LLDGPPGVDV TLLPAPPARL QVEKKQQLAG EAEISHLALQ DPASDKLLGP
1501 AGLTWERNLP GAGVGKEMAG VPPTLREDER PEGPGAAWPG LEGQAYSQLE RSRQELASGL
1561 PSPAATQELP VERAAAFQVA PHSHGEEAVA QDRIPSGKQH QETSACDSPH GEDGPGDFAH
1621 TGVPGHVPRS TCAPSPQREV LTVPEANSEP WTLDTLGGER RPGVTAGILE MRNALGNQST
1681 PAPPTGEVAD TPLEPGKVAG AAGEAEGDIT LSTAETQACA SGDLPEAGTT RTFSVVAGDL
1741 VLPGSCQDPA CSDKAPGMEG TAALHGDSPA RPQQAKEQPG PERPIPAGDG KVCVSSPPEP
1801 DETHDPKLQH LAPEELHTDR ESPRPGPSML PSVPKKDAPR VMDKVTSDET RGAEGTESSP
1861 VADDIIQPAA PADLESPTLA ASSYHGDVVG QVSTDLIAQS ISPAAAHAGL PPSAAEHIVS
1921 PSAPAGDRVE ASTPSCPDPA KDLSRSSDSE EAFETPESTT PVKAPPAPPP PPPEVIPEPE
1981 VSTQPPPEEP GCGSETVPVP DGPRSDSVEG SPFRPPSHSF SAVFDEDKPI ASSGTYNLDF
2041 DNIELVDTFQ TLEPRASDAK NQEGKVNTRR KSTDSVPISK STLSRSLSLQ ASDFDGASSS
2101 GNPEAVALAP DAYSTGSSSA SSTLKRTKKP RPPSLKKKQT TKKPTETPPV KETQQEPDEE
2161 SLVPSGENLA SETKTESAKT EGPSPALLEE TPLEPAVGPK AACPLDSESA EGVVPPASGG
2221 GRVQNSPPVG RKTLPLTTAP EAGEVTPSDS GGQEDSPAKG LSVRLEFDYS EDKSSWDNQQ
2281 ENPPPTKKIG KKPVAKMPLR RPKMKKTPEK LDNTPASPPR SPAEPNDIPI AKGTYTFDID
2341 KWDDPNFNPF SSTSKMQESP KLPQQSYNFD PDTCDESVDP FKTSSKTPSS PSKSPASFEI
2401 PASAMEANGV DGDGLNKPAK KKKTPLKTDT FRVKKSPKRS PLSDPPSQDP TPAATPETPP
2461 VISAVVHATD EEKLAVTNQK WTCMTVDLEA DKQDYPQPSD LSTFVNETKF SSPTEELDYR
```

-continued

```
2521 NSYEIEYMEK IGSSLPQDDD APKKQALYLM FDTSQESPVK SSPVRMSESP TPCSGSSFEE

2581 TEALVNTAAK NQHPVPRGLA PNQESHLQVP EKSSQKELEA MGLGTPSEAI EITAPEGSFA

2641 SADALLSRLA HPVSLCGALD YLEPDLAEKN PPLFAQKLQE ELEFAIMRIE ALKLARQIAL

2701 ASRSHQDAKR EAAHPTDVSI SKTALYSRIG TAEVEKPAGL LFQQPDLDSA LQIARAEIIT

2761 KEREVSEWKD KYEESRREVM EMRKIVAEYE KTIAQMIEDE QREKSVSHQT VQQLVLEKEQ

2821 ALADLNSVEK SLADLFRRYE KMKEVLEGFR KNEEVLKRCA QEYLSRVKKE EQRYQALKVH

2881 AEEKLDRANA EIAQVRGKAQ QEQAAHQASL RKEQLRVDAL ERTLEQKNKE IEELTKICDE

2941 LIAKMGKS
```

SEQ ID NO: 155 is the TACC2 Nucleotide Sequence for isoform a, having Genebank Accession No. NM_206862 (9706 bp)

```
   1 gcctgctcca agggaaggat caggagagaa gaaacgcaaa tcccagaacc gtgccaacat 61 ataaaacccc acattaaggg ttgtacagtg cactgggatt tctcaagtca cccgcttggt 121 cctcttccaa gtatacttta cttcctttca ttcctctcta aactttttt aaaaactttc 181 actcctgctc taaaagttat cttggtttct tactctacct tatgccccct gggcgaattt 241 tttcctctga ggagggaaga atagagttgc tgctgcagac acatcagatt ccctactggt 301 aacagctgga gtgcgtcacc tctgacaaaa ttctggggac gctgggaaca ctgaatcaac 361 atgggcaatg agaacagcac ctcggacaac cagaggactt atcagctca gactccaagg 421 tccgcgcagc cacccgggaa cagtcagaat ataaaaagga agcagcagga cacgcccgga 481 agccctgacc acagagacgc gtccagcatt ggcagcgttg ggcttggagg cttctgcacc 541 gcttctgaga gttctgccag cctggatcca tgccttgtgt ccccagaggt gactgagcca 601 aggaaggacc cacagggagc caggggggcca gaaggttctt tgctgcccag cccaccaccg 661 tcccaggagc gagagcaccc ctcgtcctcc atgccctttg ccgagtgtcc cccggaaggt 721 tgcttggcaa gtccagcagc ggcacctgaa gatggtcctc agactcagtc tcccaggagg 781 gaacctgccc caaatgcccc aggagacatc gcggcggcat ttcccgctga gagggacagc 841 tctactccat accaagagat tgctgccgtc cccagtgctg gaagagagag acagccgaag 901 gaagaaggac agaagtcctc cttctccttc tccagtggca tcgaccagtc acctggaatg 961 tcgccagtac ccctcagaga gccaatgaag gcaccgctgt gtggagaggg ggaccagcct 1021 ggtggttttg agtcccaaga gaaagaggct gcaggtggct ttccccctgc agagtccagg 1081 caggggggtgg cttctgtgca agtgacccct gaggcccctg ctgcagccca gcagggcaca 1141 gaaagctcag cggtcttgga gaagtccccc ctaaaaccca tggccccgat cccacaagat 1201 ccagccccaa gagcctcaga cagagaaaga ggccaagggg aggcgccgcc tcagtattta 1261 acagatgact tggaattcct cagggcctgc catctcccta ggagcaattc aggggctgcc 1321 ccagaagcag aagtgaatgc cgcttcccag gagagctgcc agcagccagt gggagcatat 1381 ctgccgcacg cagagctgcc ctggggcttg ccaagtcctg ccctggtgcc agaggctggg 1441 ggctctggga aggaggctct ggacaccatt gatgttcagg gtcacccaca gacagggatg 1501 cgaggaacca agcccaatca agttgtctgt gtggcagcag gcggccagcc cgaaggggt 1561 ttgcctgtga gccctgaacc ttccctgctc actccgactg aggaagcaca tccagcttca 1621 agcctcgctt cattcccagc tgctcagatt cctattgctg tagaagaacc tggatcatca 1681 tccagggaat cagtttccaa ggctgggatg ccagtttctg cagatgcagc caaagaggtg
```

-continued

```
1741 gtggatgcag ggttggtggg actggagagg caggtgtcag atcttggaag caagggagag 1801 catccagaag gggaccctgg agaggttcct gccccatcac cccaggagag gggagagcac 1861 ttgaacacgg agcaaagcca tgaggtccaa ccaggagtac caccccctcc tcttcccaag 1921 gagcaaagcc atgaggtcca accaggagca ccaccccctc ctcttcccaa ggcaccaagt 1981 gaaagtgcca gagggccacc ggggccaacg gatggagcca aggtccatga agattccaca 2041 agcccagccg tggctaaaga aggaagcaga tcacctggtg acagccctgg aggaaaggag 2101 gaagcccag agccacctga tggtggagac cagggaacc tgcaaggaga ggactctcag 2161 gctttcagca gcaagcgtga tccagaagta ggcaaagatg agctttcaaa gccaagcagt 2221 gatgcagaga gcagagacca tcccagctca cactcagcac agccacccag aaagggggt 2281 gctgggcaca cggacgggcc ccactctcag acagcagagg ctgatgcatc tggcctacca 2341 cacaagctgg gtgaggagga cccgtcctg cccctgtgc cagatggagc tggtgagccc 2401 actgttcccg aaggagccat ctgggagggg tcaggattgc agcccaaatg tcctgacacc 2461 cttcagagca gggaaggatt gggaagaatg gagtctttcc tgactttaga atcagagaaa 2521 tcagattttc caccaactcc tgttgcagag gttgcaccca agcccagga aggtgagagc 2581 acattggaaa taaggaagat gggcagctgt gatgggagg gcttgctgac gtccccagat 2641 caaccccgcg ggccggcgtg tgatgcgtcg agacaggaat tcatgctggg ggtgccacat 2701 ccccccccagg gggagaactt ggcagcagac ctgggctca cggcactcat cctggaccaa 2761 gatcagcagg gaatcccatc ctgcccaggg gaaggctgga taagaggagc tgcatccgag 2821 tggcccctac tatcttctga gaagcatctc cagccatccc aggcacaacc agagacatcc 2881 atctttgacg tgctcaagga gcaggcccag ccacctgaaa atgggaaaga gacttctcca 2941 agccatccag gttttaagga ccaggagca gattcttccc aaatccatgt acctgtggaa 3001 cctcaggaag ataacaactt gcccactcat ggaggacagg agcaggcttt gggatcagaa 3061 cttcaaagtc agctccccaa aggcaccctg tctgatactc caacttcatc tcccactgac 3121 atggtttggg agagttctct gacagaagag tcagaattgt cagcaccaac gagacagaag 3181 ttgcctgcac tagggagaa gcggccagag ggagcatgcg gtgatggtca gtcctcgagg 3241 gtctcgcctc cagcagcaga tgtcttaaaa gactttctc ttgcagggaa cttcagcaga 3301 aaggaaactt gctgcactgg gcaggggcca acaagtctc acaggcatt ggctgatgcc 3361 ttggaagaag gcagccagca tgaagaagca tgtcaaaggc atccaggagc ttctgaagca 3421 gctgatggtt gttccccact ctggggcttg agtaagaggg agatggcaag tggaaacaca 3481 ggggaggccc caccttgtca gcctgactca gtagctctcc tggatgcagt tccctgcctg 3541 ccagccctgg cgcccgccag ccccggagtc acacccaccc aggatgcccc agagacagag 3601 gcatgtgatg aaacccagga aggcaggcag caaccagtgc cggccccgca gcagaaaatg 3661 gagtgctggg ccacttcgga tgcagagtcc ccaaagcttc ttgcaagttt cccatcagct 3721 ggggagcaag gtggtgaagc cggggctgct gagactggtg gcagcgctgg tgcaggagac 3781 ccaggaaagc agcaggctcc ggagaaacct ggagaagcta ctttgagttg tggcctcctt 3841 cagactgagc actgccttac ctccggggag gaagcttcta cctctgccct acgtgagtcc 3901 tgccaagctg agcaccccat ggccagctgc caggatgcct tgctgccagc cagagagctg 3961 ggtgggattc ccaggagcac catggatttt tctacacacc aggctgtccc agacccaaag 4021 gagctcctgc tgtctgggcc accagaagtg gctgctcctg acaccccctta cctgcatgtc 4081 gacagtgctg cccagagagg agcagaagac agtggagtga agctgtttc ctctgcagac 4141 cccagagctc ctggcgaaag cccctgtcct gtagggagc ccccacttgc cttggaaaat
```

```
4201 gctgcctcct tgaagctgtt tgctggctcc ctcgccccc tgttgcaacc aggagctgca
4261 ggtgggaaa tccctgcagt gcaagccagc agtggtagtc ccaaagccag aaccactgag
4321 ggaccagtgg actccatgcc atgcctggac cggatgccac ttctggccaa gggcaagcag
4381 gcaacagggg aagagaaagc agcaacagct ccaggtgcag gtgccaaggc cagtggggag
4441 ggcatggcag gtgatgcagc aggagagaca gagggcagca tggagaggat gggagagcct
4501 tcccaggacc caaagcaggg cacatcaggt ggtgtggaca caagctctga gcaaatcgcc
4561 accctcactg gcttcccaga cttcagggag cacatcgcca agatcttcga gaagcctgtg
4621 ctcggagccc tggccacacc tggagaaaag gcaggagctg ggaggagtgc agtgggtaaa
4681 gacctcacca ggccattggg cccagagaag cttctagatg gcctccagg agtggatgtc
4741 acccttctcc ctgcacctcc tgctcgactc caggtggaga agaagcaaca gttggctgga
4801 gaggctgaga tttcccatct ggctctgcaa gatccagctt cagacaagct tctgggtcca
4861 gcagggctga cctgggagcg gaacttgcca ggtgccggtg tggggaagga gatggcaggt
4921 gtcccaccca cactgaggga agacgagagg ccagaggggc ctggggcagc ctggccaggc
4981 ctggaaggcc aggcttactc acagctggag aggagcaggc aggaattagc ttcaggtctt
5041 ccttcaccag cagctactca ggagctccct gtggagagag ctgctgcctt ccaggtggct
5101 ccccatagcc atggagaaga ggccgtggcc caagacagaa ttccttctgg aaagcagcac
5161 caggaaacat ctgcctgcga cagtccacat ggagaagatg gtcccgggga ctttgctcac
5221 acagggttc caggacatgt gccaaggtcc acgtgtgccc cttctcctca gaggaggtt
5281 ttgactgtgc ctgaggccaa cagtgagccc tggacccttg acacgcttgg gggtgaaagg
5341 agacccggag tcactgctgg catcttggaa atgcgaaatg ccctgggcaa ccagagcacc
5401 cctgcaccac caactggaga agtggcagac actccctgg agcctggcaa ggtggcaggc
5461 gctgctgggg aagcagaggg tgacatcacc ctgagcacag ctgagacaca ggcatgtgcg
5521 tccggtgatc tgcctgaagc aggtactacg aggacattct ccgttgtggc aggtgacttg
5581 gtgctgccag aagctgtca ggacccagct tgctctgaca aggctccggg gatggagggt
5641 acagctgccc ttcatgggga cagcccagcc aggcccagc aggctaagga gcagccaggg
5701 cctgagcgcc ccattccagc tggggatggg aaggtgtgcg tctcctcacc tccagagcct
5761 gacgaaactc acgacccgaa gctgcaacat ttggctccag aagagctcca cactgacaga
5821 gagagcccca ggcctggccc atccatgtta ccttcggttc ctaagaagga tgctccaaga
5881 gtcatggata aagtcacttc agatgagacc agaggtgcgg aaggaacaga aagttcacct
5941 gtggcagatg atatcatcca gcccgctgcc cccgcagacc tggaaagccc aaccttagct
6001 gcctcttcct accacggtga tgttgttggc caggtctcta cggatctgat agcccagagc
6061 atctccccag ctgctgccca tgcgggtctt cctccctcgg ctgcagaaca catagtttcg
6121 ccatctgccc cagctggtga cagagtagaa gcttccactc cctcctgccc agatccggcc
6181 aaggacctca gcaggagttc cgattctgaa gaggcatttg agaccccgga gtcaacgacc
6241 cctgtcaaag ctccgccagc tccaccccca ccacccccg aagtcatccc agaacccgag
6301 gtcagcacac agccaccccc ggaagaacca ggatgtggtt ctgagacagt ccctgtccct
6361 gatggcccac ggagcgactc ggtggaagga agtcccttcc gtccccgtc acactccttc
6421 tctgccgtct tcgatgaaga caagccgata gccagcagtg ggacttacaa cttggacttt
6481 gacaacattg agcttgtgga tacctttcag accttggagc ctcgtgcctc agacgctaag
6541 aatcaggagg gcaaagtgaa cacacggagg aagtccacgg attccgtccc catctctaag
```

-continued

```
6601 tctacactgt cccggtcgct cagcctgcaa gccagtgact tgatggtgc ttcttcctca
6661 ggcaatcccg aggccgtggc ccttgcccca gatgcatata gcacgggttc cagcagtgct
6721 tctagtaccc ttaagcgaac taaaaaaccg aggccgcctt ccttaaaaaa gaaacagacc
6781 accaagaaac ccacagagac cccccccagtg aaggagacgc aacaggagcc agatgaagag
6841 agccttgtcc ccagtgggga gaatctagca tctgagacga aaacggaatc tgccaagacg
6901 gaaggtccta gcccagcctt attggaggag acgccccttg agcccgctgt ggggcccaaa
6961 gctgcctgcc ctctggactc agagagtgca gaaggggttg tcccccccggc ttctggaggt
7021 ggcagagtgc agaactcacc ccctgtcggg aggaaaacgc tgcctcttac cacggccccg
7081 gaggcagggg aggtaacccc atcggatagc gggggggcaag aggactctcc agccaaaggg
7141 ctctccgtaa ggctggagtt tgactattct gaggacaaga gtagttggga caaccagcag
7201 gaaaaccccc ctcctaccaa aaagataggc aaaaagccag ttgccaaaat gcccctgagg
7261 aggccaaaga tgaaaaagac acccgagaaa cttgacaaca ctcctgcctc acctcccaga
7321 tccccctgctg aacccaatga catccccatt gctaaaggta cttacacctt tgatattgac
7381 aagtgggatg accccaattt taacccttt tcttccacct caaaaatgca ggagtctccc
7441 aaactgcccc aacaatcata caactttgac ccagacacct gtgatgagtc cgttgaccccc
7501 tttaagacat cctctaagac ccccagctca ccttctaaat ccccagcctc ctttgagatc
7561 ccagccagtg ctatggaagc caatggagtg gacggggatg ggctaaacaa gcccgccaag
7621 aagaagaaga cgcccctaaa gactgacaca tttagggtga aaaagtcgcc aaaacggtct
7681 cctctctctg atccaccttc caggaccccc accccagctg ctacaccaga acaccacca
7741 gtgatctctg cggtggtcca cgccacagat gaggaaaagc tggcggtcac caaccagaag
7801 tggacgtgca tgacagtgga cctagaggct gacaaacagg actacccgca gccctcggac
7861 ctgtccacct ttgtaaacga gaccaaattc agttcaccca ctgaggagtt ggattacaga
7921 aactcctatg aaattgaata tatggagaaa attggctcct ccttacctca ggacgacgat
7981 gccccgaaga agcaggcctt gtaccttatg tttgacactt ctcaggagag ccctgtcaag
8041 tcatctcccg tccgcatgtc agagtccccg acgccgtgtt cagggtcaag ttttgaagag
8101 actgaagccc ttgtgaacac tgctgcgaaa aaccagcatc ctgtcccacg aggactggcc
8161 cctaaccaag agtcacactt gcaggtgcca gagaaatcct cccagaagga gctgaggcc
8221 atgggcttgg gcaccccttc agaagcgatt gaaattacag ctcccgaggg ctcctttgcc
8281 tctgctgacg ccctcctcag caggctagct caccccgtct ctctctgtgg tgcacttgac
8341 tatctggagc ccgacttagc agaaaagaac ccccactat tcgctcagaa actccaggag
8401 gagttagagt ttgccatcat gcggatagaa gccctgaagc tggccaggca gattgctttg
8461 gcttcccgca gccaccagga tgccaagaga gaggctgctc acccaacaga cgtctccatc
8521 tccaaaacag ccttgtactc ccgcatcggg accgctgagg tggagaaacc tgcaggcctt
8581 ctgttccagc agcccgacct ggactctgcc ctccagatcg ccagagcaga gatcataacc
8641 aaggagagag aggtctcaga atggaaagat aaatatgaag aaagcaggcg ggaagtgatg
8701 gaaatgagga aaatagtggc cgagtatgag aagaccatcg ctcagatgat agaggacgaa
8761 cagagagaga agtcagtctc ccaccagacg gtgcagcagc tggttctgga aaggagcaa
8821 gccctggccg acctgaactc cgtggagaag tctctggccg acctcttcag aagatatgag
8881 aagatgaagg aggtcctaga aggcttccgc aagaatgaag aggtgttgaa gagatgtgcg
8941 caggagtacc tgtcccgggt gaagaaggag gagcagaggt accaggccct gaaggtgcac
9001 gcggaggaga aactggacag ggccaatgct gagattgctc aggttcgagg caaggcccag
```

```
9061 caggagcaag ccgcccacca ggccagcctg cggaaggagc agctgcgagt ggacgccctg 9121 gaaaggacgc tggagcagaa gaataaagaa atagaagaac tcaccaagat tgtgacgaa 9181 ctgattgcca aaatggggaa aagctaactc tgaaccgaat gttttggact taactgttgc 9241 gtgcaatatg accgtcggca cactgctgtt cctccagttc catggacagg ttctgttttc 9301 acttttcgt atgcactact gtatttcctt tctaaataaa attgatttga ttgtatgcag 9361 tactaaggag actatcagaa tttcttgcta ttggtttgca ttttcctagt ataattcata 9421 gcaagttgac ctcagagttc ctgtatcagg gagattgtct gattctctaa taaaagacac 9481 attgctgacc ttggccttgc cctttgtaca caagttccca gggtgagcag cttttggatt 9541 taatatgaac atgtacagcg tgcataggga ctcttgcctt aaggagtgta aacttgatct 9601 gcatttgctg atttgttttt aaaaaaacaa gaaatgcatg tttcaaataa aattctctat 9661 tgtaaataaa attttttctt tggatcttgg caaaaaaaaa aaaaaa
```

SEQ ID NO: 158 is the amino acid sequence of the FGFR3-TACC3-1 fusion protein. The bolded text corresponds to the FGFR3 protein:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGESHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMENMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDFKESALR
KQSLYLKFDPLLRDSPGRPVPVATETSSMHGANETPSGRPREAKLVEFDFL
GALDIPVPGPPPGVPAPGGPPLSTGPIVDLLQYSQKDLDAVVKATQEENRE
LRSRCEELHGKNLELGKIMDRFEEVVYQAMEEVQKQKELSKAEIQKVLKEK
DQLTTDLNSMEKSFSDLFKRFEKQKEVIEGYRKNEESLKKCVEDYLARITQ
EGQRYQALKAHAEEKLQLANEEIAQVRSKAQAEALALQASLRKEQMRIQSL
EKTVEQKTKENEELTRICDDLISKMEKI

SEQ ID NO: 159 is the amino acid sequence of the FGFR3-TACC3-2 fusion protein. The bolded text corresponds to the FGFR3 protein:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGESHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMENMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDVSAGSGL
VPPAYAPPPAVPGHPSGRPREAKLVEFDFLGALDIPVPGPPPGVPAPGGPP
LSTGPIVDLLQYSQKDLDAVVKATQEENRELRSRCEELHGKNLELGKIMDR
FEEVVYQAMEEVQKQKELSKAEIQKVLKEKDQLTTDLNSMEKSFSDLFKRF
EKQKEVIEGYRKNEESLKKCVEDYLARITQEGQRYQALKAHAEEKLQLANE
EIAQVRSKAQAEALALQASLRKEQMRIQSLEKTVEQKTKENEELTRICDDL
ISKMEKI

SEQ ID NO: 160 is the amino acid sequence of the FGFR3-TACC3-3 fusion protein. The bolded text corresponds to the FGFR3 protein:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV

TVLKTAGANTTDKELEVLSLHNVTFEDAGEYTCLAGNSIGESHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMENMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDVPGPPPG
VPAPGGPPLSTGPIVDLLQYSQKDLDAVVKATQEENRELRSRCEELHGKNL
ELGKIMDRFEEVVYQAMEEVQKQKELSKAEIQKVLKEKDQLTTDLNSMEKS
FSDLFKRFEKQKEVIEGYRKNEESLKKCVEDYLARITQEGQRYQALKAHAE
EKLQLANEEIAQVRSKAQAEALALQASLRKEQMRIQSLEKTVEQKTKENEE
LTRICDDLISKMEKI

SEQ ID NO: 161 is the amino acid sequence of the FGFR3-TACC3-4 fusion protein. The bolded text corresponds to the FGFR3 protein:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGESHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDVKATQEE
NRELRSRCEELHGKNLELGKIMDRFEEVVYQAMEEVQKQKELSKAEIQKVL
KEKDQLTTDLNSMEKSFSDLFKRFEKQKEVIEGYRKNEESLKKCVEDYLAR
ITQEGQRYQALKAHAEEKLQLANEEIAQVRSKAQAEALALQASLRKEQMRI
VQSLEKTEQKTKENEELTRICDDLISKMEKI

SEQ ID NO: 539 is the amino acid sequence of FGFR3ex17-TACC3ex11. The sequence corresponding to FGFR3 is underlined. The sequence corresponding to TACC3 is italicized:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGFSHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTD*VKATQEE
NRELRSRCEELHGKNLELGKIMDRFEEVVYQAMEEVQKQKELSKAEIQKVL
KEKDQLTTDLNSMEKSFSDLFKRFEKQKEVIEGYRKNEESLKKCVEDYLAR
ITQEGQRYQALKAHAEEKLQLANEEIAQVRSKAQAEALALQASLRKEQMRI
QSLEKTVEQKTKENEELTRICDDLISKMEKI*

SEQ ID NO: 540 is the amino acid sequence of FGFR3ex17-TACC3ex8. The sequence corresponding to FGFR3 is underlined. The sequence corresponding to TACC3 is italicized:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGFSHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTD*FKESALR
KQSLYLKFDPLLRDSPGRPVPVATETSSMHGANETPSGRPREAKLVEFDFL
GALDIPVPGPPPGVPAPGGPPLSTGPIVDLLQYSQKDLDAVVKATQEENRE
LRSRCEELHGKNLELGKIMDRFEEVVYQAMEEVQKQKELSKAEIQKVLKEK
DQLTTDLNSMEKSFSDLFKRFEKQKEVIEGYRKNEESLKKCVEDYLARITQ*

-continued

*EGQRYQALKAHAEEKLQLANEEIAQVRSKAQAEALALQASLRKEQMRIQSL*

*EKTVEQKTKENEELTRICDDLISKMEKI*

SEQ ID NO: 541 is the amino acid sequence of FGFR3ex17-TACC3ex10. The sequence corresponding to FGFR3 is underlined. The sequence corresponding to TACC3 is italicized:

MGAPACALALCVAVAIVAGASSESLGTEQRVVGRAAEVPGPEPGQQEQLVF

GSGDAVELSCPPPGGGPMGPTVWVKDGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTCVVENKFGSIRQTYTLDVLERSPHRPIL

QAGLPANQTAVLGSDVEFHCKVYSDAQPHIQWLKHVEVNGSKVGPDGTPYV

TVLKTAGANTTDKELEVLSLHNVTFEDAGEYTCLAGNSIGFSHHSAWLVVL

PAEEELVEADEAGSVYAGILSYGVGFFLFILVVAAVTLCRLRSPPKKGLGS

PTVHKISRFPLKRQVSLESNASMSSNTPLVRIARLSSGEGPTLANVSELEL

PADPKWELSRARLTLGKPLGEGCFGQVVMAEAIGIDKDRAAKPVTVAVKML

KDDATDKDLSDLVSEMEMMKMIGKHKNIINLLGACTQGGPLYVLVEYAAKG

NLREFLRARRPPGLDYSFDTCKPPEEQLTFKDLVSCAYQVARGMEYLASQK

CIHRDLAARNVLVTEDNVMKIADFGLARDVHNLDYYKKTTNGRLPVKWMAP

EALFDRVYTHQSDVWSFGVLLWEIFTLGGSPYPGIPVEELFKLLKEGHRMD

KPANCTHDLYMIMRECWHAAPSQRPTFKQLVEDLDRVLTVTSTD*VPGPPPG*

*VPAPGGPPLSTGPIVDLLQYSQKDLDAVVKATQEENRELRSRCEELHGKNL*

*ELGKIMDRFEEVVYQAMEEVQKQKELSKAEIQKVLKEKDQLTTDLNSMEKS*

*FSDLFKRFEKQKEVIEGYRKNEESLKKCVEDYLARITQEGQRYQALKAHAE*

*EKLQLANEETAQVRSKAQAEALALQASLRKEQMRIQSLEKTVEQKTKENE*

*ELTRICDDLISKMEKI*

SEQ ID NO: 542 is the amino acid sequence of FGFR3ex17-TACC3ex6. The sequence corresponding to FGFR3 is underlined. The sequence corresponding to TACC3 is italicized:

MGAPACALALCVAVAIVAGASSESLGTEQRVVGRAAEVPGPEPGQQEQLVF

GSGDAVELSCPPPGGGPMGPTVWVKDGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTCVVENKFGSIRQTYTLDVLERSPHRPIL

QAGLPANQTAVLGSDVEFHCKVYSDAQPHIQWLKHVEVNGSKVGPDGTPYV

TVLKTAGANTTDKELEVLSLHNVTFEDAGEYTCLAGNSIGFSHHSAWLVVL

PAEEELVEADEAGSVYAGILSYGVGFFLFILVVAAVTLCRLRSPPKKGLGS

PTVHKISRFPLKRQVSLESNASMSSNTPLVRIARLSSGEGPTLANVSELEL

PADPKWELSRARLTLGKPLGEGCFGQVVMAEAIGIDKDRAAKPVTVAVKML

KDDATDKDLSDLVSEMEMMKMIGKHKNIINLLGACTQGGPLYVLVEYAAKG

NLREFLRARRPPGLDYSFDTCKPPEEQLTFKDLVSCAYQVARGMEYLASQK

CIHRDLAARNVLVTEDNVMKIADFGLARDVHNLDYYKKTTNGRLPVKWMAP

EALFDRVYTHQSDVWSFGVLLWEIFTLGGSPYPGIPVEELFKLLKEGHRMD

KPANCTHDLYMIMRECWHAAPSQRPTFKQLVEDLDRVLTVTSTD*ERALNSA*

*STSLPTSCPGSEPVPTHQQGQPALELKEESERDPAEVLGTGAEVDYLEQFG*

*TSSEKESALRKQSLYLKFDPLLRDSPGRPVPVATETSSMHGANETPSGRPR*

*EAKLVEFDFLGALDIPVPGPPPGVPAPGGPPLSTGPIVDLLQYSQKDLDAV*

*VKATQEENRELRSRCEELHGKNLELGKIMDRFEEVVYQAMEEVQKQKELSK*

*AEIQKVLKEKDQLTTDLNSMEKSFSDLEKRFEKQKEVIEGYRKNEESLKKC*

*VEDYLARITQEGQRYQALKAHAEEKLQLA*

SEQ ID NO: 543 is the amino acid sequence of FGFR3ex18-TACC3ex13. The sequence corresponding to FGFR3 is underlined. The sequence corresponding to TACC3 is italicized:

MGAPACALALCVAVAIVAGASSESLGTEQRVVGRAAEVPGPEPGQQEQLVF

GSGDAVELSCPPPGGGPMGPTVWVKDGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTCVVENKFGSIRQTYTLDVLERSPHRPIL

QAGLPANQTAVLGSDVEFHCKVYSDAQPHIQWLKHVEVNGSKVGPDGTPYV

TVLKTAGANTTDKELEVLSLHNVTFEDAGEYTCLAGNSIGFSHHSAWLVVL

PAEEELVEADEAGSVYAGILSYGVGFFLFILVVAAVTLCRLRSPPKKGLGS

PTVHKISRFPLKRQVSLESNASMSSNTPLVRIARLSSGEGPTLANVSELEL

PADPKWELSRARLTLGKPLGEGCFGQVVMAEAIGIDKDRAAKPVTVAVKML

KDDATDKDLSDLVSEMEMMKMIGKHKNIINLLGACTQGGPLYVLVEYAAKG

NLREFLRARRPPGLDYSFDTCKPPEEQLTFKDLVSCAYQVARGMEYLASQK

CIHRDLAARNVLVTEDNVMKIADFGLARDVHNLDYYKKTTNGRLPVKWMAP

EALFDRVYTHQSDVWSFGVLLWEIFTLGGSPYPGIPVEELFKLLKEGHRMD

KPANCTHDLYMIMRECWHAAPSQRPTFKQLVEDLDRVLTVTSTDEYLDLSA

PFEQYSPGGQDTPSKQKELSKAEIQKVLKEKDQLTTDLNSMEKSFSDLFKR

*FEKQKEVIEGYRKNEESLKKCVEDYLARITQEGQRYQALKAHAEEKLQLAN*

*EEIAQVRSKAQAEALALQASLRKEQMRIQSLEKTVEQKTKENEELTRICDD*

*LISKMEKI*

SEQ ID NO: 544 is the amino acid sequence of FGFR3ex18-TACC3ex9_INS66BP. The sequence corresponding to FGFR3 is underlined. The sequence corresponding to TACC3 is italicized. The sequence corresponding the 66 bp intronic insert is double underlined:

MGAPACALALCVAVAIVAGASSESLGTEQRVVGRAAEVPGPEPGQQEQLVF

DGSGDAVELSCPPPGGGPMGPTVWVKGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGFSHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDEYLDLSA
QEEQRQPTLQPQGCCLAGYSHRS*SMHGANETPSGRPREAKLVEFDFLGALDI*
*PVPGPPPGVPAPGGPPLSTGPIVDLLQYSQKDLDAVVKATQEENRELRSRC*
*EELHGKNLELGKIMDRFEEVVYQAMEEVQKQKELSKAEIQKVLKEKDQLTT*
*DLNSMEKSFSDLFKRFEKQKEVIEGYRKNEESLKKCVEDYLARITQEGQRY*
*QALKAHAEEKLQLANEEIAQVRSKAQAEALALQASLRKEQMRIQSLEKTVE*
*QKTKENEELTRICDDLISKMEKI*

SEQ ID NO: 545 is the amino acid sequence of FGFR3ex18-TACC3ex5. The sequence corresponding to FGFR3 is underlined. The sequence corresponding to TACC3 is italicized:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGFSHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECHWAAPSQRPTFKQLVEDLDRVLTVTSTDEYLDLSA
*PVVQLAAETPTAESKERALNSASTSLPTSCPGSEPVPTHQQGQPALELKEE*
*SFRDPAEVLGTGAEVDYLEQFGTSSFKESALRKQSLYLKFDPLLRDSPGRP*
*VPVATETSSMHGANETPSGRPREAKLVEFDFLGALDIPVPGPPPGVPAPGG*
*PPLSTGPIVDLLQYSQKDLDAVVKATQEENRELRSRCEELHGKNLELGKIM*
*DRFEEVVYQAMEEVQKQKELSKAEIQKVLKEKDQLTTDLNSMEKSFSDLFK*
*RFEKQKEVIEGYRKNEESLKKCVEDYLARITQEGQRYQALKAHAEEKLQLA*
*NEEIAQVRSKAQAEALALQASLRKEQMRIQSLEKTVEQKTKENEELTRICD*
*DLISKMEKI*

SEQ ID NO: 546 is the amino acid sequence of FGFR3ex18-TACC3ex5_INS33 bp. The sequence corresponding to FGFR3 is underlined. The sequence corresponding to TACC3 is italicized. The sequence corresponding the 33 bp intronic insert is double underlined:

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV
TVLKTAGANTTDKELEVLSLHNVTFEDAGEYTCLAGNSIGFSHHSAWLVVL
PAEEELVEADEAGSVYAGILSYGVGFFLFILVVAAVTLCRLRSPPKKGLGS
PTVHKISRFPLKRQVSLESNASMSSNTPLVRIARLSSGEGPTLANVSELEL
PADPKWELSRARLTLGKPLGEGCFGQVVMAEAIGIDKDRAAKPVTVAVKML
KDDATDKDLSDLVSEMEMMKMIGKHKNIINLLGACTQGGPLYVLVEYAAKG
NLREFLRARRPPGLDYSFDTCKPPEEQLTFKDLVSCAYQVARGMEYLASQK
CIHRDLAARNVLVTEDNVMKIADFGLARDVHNLDYYKKTTNGRLPVKWMAP
EALFDRVYTHQSDVWSFGVLLWEIFTLGGSPYPGIPVEELFKLLKEGHRMD
KPANCTHDLYMIMRECWHAAPSQRPTFKQLVEDLDRVLTVTSTDEYLDLSA
PFEQYSPGGQDTPSSSSSG<u>VREPPHPAFPX</u>*SAEDTPVVQLAAETPTAESKE*
*RALNSASTSLPTSCPGSEPVPTHQQGQPALELKEESFRDPAEVLGTGAEVD*
*YLEQFGTSSFKESALRKQSLYLKFDPLLRDSPGRPVPVATETSSMHGANET*
*PSGRPREAKLVEFDFLGALDIPVPGPPPGVPAPGGPPLSTGPIVDLLQYSQ*
*KDLDAVVKATQEENRELRSRCEELHGKNLELGKIMDRFEEVVYQAMEEVQK*
*QKELSKAEIQKVLKEKDQLTTDLNSMEKSFSDLFKRFEKQKEVIEGYRKNE*
*ESLKKCVEDYLARITQEGQRYQALKAHAEEKLQLANEEIAQVRSKAQAEAL*
*ALQASLRKEQMRIQSLEKTVEQKTKENEELTRICDDLISKMEKI*

SEQ ID NO: 547 is the amino acid sequence of FGFR3ex18-TACC3ex4. The sequence corresponding to FGFR3 is underlined. The sequence corresponding to TACC3 is italicized.

MGAPACALALCVAVAIVAGASSESLGTEQRVVGRAAEVPGPEPGQQEQLVF
GSGDAVELSCPPPGGGPMGPTVWVKDGTGLVPSERVLVGPQRLQVLNASHE
DSGAYSCRQRLTQRVLCHFSVRVTDAPSSGDDEDGEDEAEDTGVDTGAPYW
TRPERMDKKLLAVPAANTVRFRCPAAGNPTPSISWLKNGREFRGEHRIGGI
KLRHQQWSLVMESVVPSDRGNYTCVVENKFGSIRQTYTLDVLERSPHRPIL
QAGLPANQTAVLGSDVEFHCKVYSDAQPHIQWLKHVEVNGSKVGPDGTPYV

-continued

TVLKTAGANTTDKELEVLSLHNVTFEDAGEYTCLAGNSIGFSHHSAWLVVL

PAEEELVEADEAGSVYAGILSYGVGFFLFILVVAAVTLCRLRSPPKKGLGS

PTVHKISRFPLKRQVSLESNASMSSNTPLVRIARLSSGEGPTLANVSELEL

PADPKWELSRARLTLGKPLGEGCFGQVVMAEAIGIDKDRAAKPVTVAVKML

KDDATDKDLSDLVSEMEMMKMIGKHKNIINLLGACTQGGPLYVLVEYAAKG

NLREFLRARRPPGLDYSFDTCKPPEEQLTFKDLVSCAYQVARGMEYLASQK

CIHRDLAARNVLVTEDNVMKIADFGLARDVHNLDYYKKTTNGRLPVKWMAP

EALFDRVYTHQSDVWSFGVLLWEIFTLGGSPYPGIPVEELFKLLKEGHRMD

KPANCTHDLYMIMRECWHAAPSQRPTFKQLVEDLDRVLTVTSTDEYLDLSA

PFEQYSPGGQDT*PESPETRLGQPAAEQLHAGPATEEPGPCLSQQLHSASAE*

*DTPVVQLAAETPTAESKERALNSASTSLPTSCPGSEPVPTHQQGQPALELK*

*EESFRDPAEVLGTGAEVDYLEQFGTSSFKESALRKQSLYLKFDPLLRDSPG*

*RPVPVATETSSMHGANETPSGRPREAKLVEFDFLGALDIPVPGPPPGVPAP*

*GGPPLSTGPIVDLLQYSQKDLDAVVKATQEENRELRSRCEELHGKNLELGK*

*IMDRFEEVVYQAMEEVQKQKELSKAEIQKVLKEKDQLTTDLNSMEKSFSDL*

*FKRFEKQKEVIEGYRKNEESLKKCVEDYLARITQEGQRYQALKAHAEEKLQ*

*LANEEIAQVRSKAQAEALALQASLRKEQMRIQSLEKTVEQKTKENEELTRI*

*CDDLISKMEKI*

The Genbank ID for the FGFR4 gene is 2264. Three isoforms are listed for FGFR4, e.g., having Genebank Accession Nos. NP_002002 (corresponding nucleotide sequence NM_002011); NP_075252 (corresponding nucleotide sequence NM_022963); NP_998812 (corresponding nucleotide sequence NM_213647).

As used herein, a "FGFR fusion molecule" can be a nucleic acid (e.g., synthetic, purified, and/or recombinant) which encodes a polypeptide corresponding to a fusion protein comprising a tyrosine kinase domain of an FGFR protein fused to a polypeptide that constitutively activates the tyrosine kinase domain of the FGFR protein, or a nucleic acid encoding a fusion protein comprising a transforming acidic coiled-coil (TACC) domain fused to a polypeptide with a tyrosine kinase domain, wherein the TACC domain constitutively activates the tyrosine kinase domain. It can also be a fusion protein comprising a tyrosine kinase domain of an FGFR protein fused to a polypeptide that constitutively activates the tyrosine kinase domain of the FGFR protein, or a fusion protein comprising a transforming acidic coiled-coil (TACC) domain fused to a polypeptide with a tyrosine kinase domain, wherein the TACC domain constitutively activates the tyrosine kinase domain. For example, a FGFR fusion molecule can include a FGFR1-TACC1 (e.g., comprising the amino acid sequence shown in SEQ ID NO: 150, or comprising the nucleic acid sequence shown in SEQ ID NO: 88), FGFR2-TACC2, FGFR3-TACC3 (e.g., comprising the amino acid sequence shown in SEQ ID NOS: 79, 158-161, or 539-547 or comprising the nucleic acid sequence shown in SEQ ID NOS: 80-82, 84, 94-145, 515, 517, 519-527, or 530-538), or other FGFR-TACC fusion proteins (e.g., an N-terminal fragment of FGFR4 containing its tyrosine kinase domain fused to a fragment of TACC1, TACC2, or TACC3). For example, a FGFR fusion molecule can include a FGFR1-containing fusion comprising the amino acid sequence corresponding to Genebank Accession no. NP_001167534, NP_001167535, NP_001167536, NP_001167537, NP_001167538, NP_056934, NP_075593, NP_075594, or NP_075598; or a FGFR1-containing fusion comprising the nucleotide sequence corresponding to Genebank Accession no. NM_001174063, NM_001174064, NM_001174065, NM_001174066, NM_001174067, NM_015850, NM_023105, NM_023106, or NM_023110. For example, a FGFR fusion molecule can include a FGFR2-containing fusion comprising the amino acid sequence corresponding to Genebank Accession no. NP_000132, NP_001138385, NP_001138386, NP_001138387, NP_001138388, NP_001138389, NP_001138390, NP_001138391, or NP_075259; or a FGFR2-containing fusion comprising the nucleotide sequence corresponding to Genebank Accession no. NM_000141, NM_001144913, NM_001144914, NM_001144915, NM_001144916, NM_001144917, NM_001144918, NM_001144919, or NM_022970. For example, a FGFR fusion molecule can include a FGFR3-containing fusion comprising the amino acid sequence corresponding to Genebank Accession no. NP_000133, NP_001156685, or NP_075254; or a FGFR3-containing fusion comprising the nucleotide sequence corresponding to Genebank Accession no. NM_000142, NM_001163213, or NM_022965. For example, a FGFR fusion molecule can include a FGFR4-containing fusion comprising the amino acid sequence corresponding to Genebank Accession no. NP_002002, NP_075252, or NP_998812; or a FGFR4-containing fusion comprising the nucleotide sequence corresponding to Genebank Accession no. NM_002011, NM_022963, or NM_213647. A FGFR fusion molecule can also include a tyrosine kinase domain of an FGFR protein fused to a protein encoded by any one of the genes listed in Table 1A. A FGFR fusion molecule can include a variant of the above described examples, such as a fragment thereof.

TABLE 1A

Fusion Partners

| gene | gene | gene | gene |
| --- | --- | --- | --- |
| ABCA13 | C21orf29 | CAMKK1 | DNAJC6 |
| ABCC1 | CACNA1C | CAMSAP1 | DYRK3 |
| ABCC12 | CACNA1G | CAMTA1 | EIF2C2 |
| ABCC6 | CNTNAP4 | CAP2 | FAM184B |
| ABL1 | CUL3 | CCDC147 | FREM2 |
| ADAM12 | DMD | CCDC158 | GDPD2 |
| ADCY10 | DUSP27 | CELF2 | GLI3 |
| ADCY2 | ECE1 | CILP | IL1RN |
| ADCY8 | EYS | CMYA5 | ISX |
| AGBL4 | FAM172A | COL14A1 | KIDINS220 |
| AHNAK | FAM184B | CORO7 | LRBA |
| ANXA7 | FGFR4 | CSMD2 | LY75 |
| AP4S1 | ITGAV | CUL3 | MDH2 |
| AQP2 | LRP1 | DDI2 | MMP12 |
| ARMC6 | LY75 | DEPDC5 | N4BP2L2 |
| ATP5B | MAPKAP1 | DEPDC7 | NCF2 |
| ATP6AP1L | MYT1 | DI10L | NCOR1 |
| ATP6V0D2 | NCF2 | DMD | NCRNA00157 |
| ATXN1 | NCOR1 | EDA | NRXN3 |
| BAHD1 | NHSL2 | EFHC1 | PARP16 |
| BBX | NKAIN2 | EFS | PLA2G2F |
| BCA10 | NR3C1 | EIF2C2 | PLEK2 |
| C15orf23 | NUP188 | ENTPD2 | PRKCH |
| C15orf33 | OSBPL10 | EYS | PTPRS |
| C21orf29 | PACSIN1 | FAM160A1 | ROBO1 |
| C2CD3 | PARP16 | MUSK | SASH3 |
| C6orf170 | PDZRN4 | NEUROG1 | SH3BP5 |
| C7orf44 | POLM | NHSL2 | SLC44A2 |
| CACNA1C | PPP1R3A | NR3C1 | SLC5A4 |
| CACNA1G | PSEN1 | ODZ1 | SNX5 |
| FAM168A | PTPRD | PCDH12 | SORCS2 |
| FAM172A | PTPRS | PLCL1 | SRRM1 |

TABLE 1A-continued

Fusion Partners

| gene | gene | gene | gene |
|---|---|---|---|
| FAM192A | RALYL | PLEKHM3 | SSX3 |
| FAM19A2 | RERE | PLOD3 | STAG2 |
| FBXL4 | RIMBP2 | PRKCH | STK24 |
| FH | RNF216 | PSEN1 | SURF6 |
| FREM2 | SDAD1 | SEPT5 | SYNPO2 |
| GAPVD1 | SEC14L3 | SLC44A2 | TAF1 |
| GLI3 | SH3RF3 | SNTA1 | TMEM80 |
| GPR182 | SLC9A1 | USP48 | TNFRSF10B |
| GSTA3 | SMOC2 | VSNL1 | TTYH1 |
| IGFBP3 | SNX5 | WDFY1 | UNC93B1 |
| ITGA9 | TACC2 | WISP2 | VSNL1 |
| ITGB2 | SRGAP1 | XRRA1 | XRCC4 |
| JOSD2 | SSX3 | LRRC4B | ZNF410 |
| KIDINS220 | SUMF1 | LRRK2 | TRIOBP |
| LAMA2 | SYNPO2 | MAPKAP1 | TTYH1 |
| LCLAT1 | TNFRSF10B | MST1R | LRBA |
| LIN9 | | | |

For example, a FGFR fusion molecule can include a FGFR3-containing fusion comprising the amino acid sequence corresponding to residues 1-760 of FGFR3 (e.g. SEQ ID NO: 90) fused to the amino acid sequence corresponding residues 648-838 of TACC3 (e.g. SEQ ID NO: 92). A FGFR fusion molecule can also include a FGFR3-containing fusion comprising the amino acid sequence corresponding to residues 1-760 of FGFR3 (e.g. SEQ ID NO: 90) fused to the amino acid sequence corresponding residues 549-838 of TACC3 (e.g. SEQ ID NO: 92). A FGFR fusion molecule can include a FGFR3-containing fusion comprising the amino acid sequence corresponding to residues 1-760 of FGFR3 (e.g. SEQ ID NO: 90) fused to the amino acid sequence corresponding residues 613-838 of TACC3 (e.g. SEQ ID NO: 92). A FGFR fusion molecule can include a FGFR3-containing fusion comprising the amino acid sequence corresponding to residues 1-760 of FGFR3 (e.g. SEQ ID NO: 90) fused to the amino acid sequence corresponding residues 488-838 of TACC3 (e.g. SEQ ID NO: 92). A FGFR fusion molecule can include a FGFR3-containing fusion comprising the amino acid sequence corresponding to residues 1-781 of FGFR3 (e.g. SEQ ID NO: 90) fused to the amino acid sequence corresponding residues 689-838 of TACC3 (e.g. SEQ ID NO: 92). A FGFR fusion molecule can include a FGFR3-containing fusion comprising the amino acid sequence corresponding to residues 1-765 of FGFR3 (e.g. SEQ ID NO: 90) fused to the amino acid sequence corresponding residues 583-838 of TACC3 (e.g. SEQ ID NO: 92). A FGFR fusion molecule can include a FGFR3-containing fusion comprising the amino acid sequence corresponding to residues 1-767 of FGFR3 (e.g. SEQ ID NO: 90) fused to the amino acid sequence corresponding residues 462-838 of TACC3 (e.g. SEQ ID NO: 92). A FGFR fusion molecule can include a FGFR3-containing fusion comprising the amino acid sequence corresponding to residues 1-767 of FGFR3 (e.g. SEQ ID NO: 90) fused to the amino acid sequence corresponding residues 472-838 of TACC3 (e.g. SEQ ID NO: 92). A FGFR fusion molecule can include a FGFR3-containing fusion comprising the amino acid sequence corresponding to residues 1-780 of FGFR3 (e.g. SEQ ID NO: 90) fused to the amino acid sequence corresponding residues 432-838 of TACC3 (e.g. SEQ ID NO: 92). A FGFR fusion molecule can include a FGFR1-containing fusion comprising the amino acid sequence corresponding to residues 1-762 of FGFR1 (e.g. SEQ ID NOS: 146, 185) fused to the amino acid sequence corresponding residues 571-805 of TACC1 (e.g. SEQ ID NO: 148). For example, a FGFR fusion molecule can include SEQ ID NOs: 539-543, 545, and 547.

The alteration in a chromosome region occupied by a FGFR fusion molecule, e.g., a FGFR1-TACC1, FGFR2-TACC2, FGFR3-TACC3 or other FGFR-TACC nucleic acid, can result in amino acid substitutions, RNA splicing or processing, product instability, the creation of stop codons, production of oncogenic fusion proteins, frame-shift mutations, and/or truncated polypeptide production. A FGFR fusion molecule can include FGFR and TACC exons joined in the fused mRNA or cDNA. A FGFR fusion molecule can also include FGFR and TACC exons joined in the fused mRNA or cDNA along with the presence of FGFR or TACC introns that are spliced in the fusion cDNA. FGFR or TACC introns can encode amino acids of the FGFR fusion molecule. For example, a FGFR fusion molecule can include a FGFR3-containing fusion comprising the amino acid sequence corresponding to residues 1-765 of FGFR3 (e.g. SEQ ID NO: 90) fused to a 22 amino acid sequence encoded by a TACC3 intron fused to the amino acid sequence corresponding to residues 583-838 of TACC3 (e.g. SEQ ID NO: 92). For example, a FGFR fusion molecule can include a FGFR3-containing fusion comprising the amino acid sequence corresponding to residues 1-767 of FGFR3 (e.g. SEQ ID NO: 90) fused to a 11 amino acid sequence encoded by a TACC3 intron fused to the amino acid sequence corresponding to residues 472-838 of TACC3 (e.g. SEQ ID NO: 92). For example, a FGFR fusion molecule can include SEQ ID NOs: 544 and 546.

A FGFR fusion protein can also include a fusion protein encoded by an FGFR3-TACC3 nucleic acid, wherein FGFR3-TACC3 comprises a combination of introns and exons 1-18 of FGFR3 located on human chromosome 4p16 spliced 5' to a combination of introns and exons 4-16 of TACC3 located on human chromosome 4p16, wherein a genomic breakpoint occurs in any one of introns or exons 1-18 of FGFR3 and any one of introns or exons 3-16 of TACC3. For example, a FGFR fusion protein can also include a fusion protein encoded by an FGFR3-TACC3 nucleic acid, wherein the nucleic acid comprises exons 1-17 of FGFR3 located on human chromosome 4p16 spliced 5' to exons 11-16 of TACC3 located on human chromosome 4p16. In one embodiment, a genomic breakpoint occurs in intron 17 of FGFR3 and in intron 10 of TACC3. For example, a FGFR fusion protein can also include a fusion protein encoded by an FGFR3-TACC3 nucleic acid, wherein the nucleic acid comprises exons 1-17 of FGFR3 located on human chromosome 4p16 spliced 5' to exons 8-16 of TACC3 located on human chromosome 4p16. In one embodiment, a genomic breakpoint occurs in intron 17 of FGFR3 and in intron 7 of TACC3. For example, a FGFR fusion protein can also include a fusion protein encoded by an FGFR3-TACC3 nucleic acid, wherein the nucleic acid comprises exons 1-17 of FGFR3 located on human chromosome 4p16 spliced 5' to exons 10-16 of TACC3 located on human chromosome 4p16. In one embodiment, a genomic breakpoint occurs in exon 18 of FGFR3 and in intron 9 of TACC3. For example, a FGFR fusion protein can also include a fusion protein encoded by an FGFR3-TACC3 nucleic acid, wherein the nucleic acid comprises exons 1-17 of FGFR3 located on human chromosome 4p16 spliced 5' to exons 6-16 of TACC3 located on human chromosome 4p16. In one embodiment, a genomic breakpoint occurs in intron 17 of FGFR3 and in intron 5 of TACC3. In one embodiment, a genomic breakpoint occurs in intron 17 of FGFR3 and in exon 5 of TACC3. For example, a FGFR fusion protein can also include a fusion protein encoded by an FGFR3-TACC3 nucleic acid, wherein the nucleic acid comprises exons 1-18 of FGFR3 located on human chromosome 4p16 spliced 5' to exons 13-16 of TACC3 located on human chromosome 4p16. In one embodiment, a genomic breakpoint occurs in exon 18 of FGFR3 and in intron 12 or exon 13 of TACC3. For example, a FGFR fusion protein can also include a fusion protein encoded by an FGFR3-TACC3 nucleic acid, wherein the nucleic acid comprises exons 1-18 of FGFR3 located on human chromosome 4p16 spliced 5' to a portion of intron 8 of TACC3 and exons 9-16 of TACC3 located on human chromosome 4p16. In one embodiment, a genomic breakpoint occurs in exon 18 of FGFR3 and in intron 8 of TACC3. For example, a FGFR fusion protein can also include a fusion protein encoded by an FGFR3-TACC3 nucleic acid, wherein the nucleic acid comprises exons 1-18 of FGFR3 located on human chromosome 4p16 spliced 5' to exons 5-16 of TACC3 located on human chromosome 4p16. In one embodiment, a genomic breakpoint occurs in exon 18 of FGFR3 and in intron 4 or exon 5 of TACC3. For example, a FGFR fusion protein can also include a fusion protein encoded by an FGFR3-TACC3 nucleic acid, wherein the nucleic acid comprises exons 1-18 of FGFR3 located on human chromosome 4p16 spliced 5' to a portion of intron 4 of TACC 3 and exons 5-16 of TACC3 located on human chromosome 4p16. In one embodiment, a genomic breakpoint occurs in exon 18 of FGFR3 and in intron 4 or exon 5 of TACC3. For example, a FGFR fusion protein can also include a fusion protein encoded by an FGFR3-TACC3 nucleic acid, wherein the nucleic acid comprises exons 1-18 of FGFR3 located on human chromosome 4p16 spliced 5' to exons 4-16 of TACC3 located on human chromosome 4p16. In one embodiment, a genomic breakpoint occurs in exon 18 of FGFR3 and in intron 3 or exon 4 of TACC3. For example, a FGFR fusion protein can also include a fusion protein encoded by an FGFR3-TACC3 nucleic acid, wherein the nucleic acid comprises exons 1-17 of FGFR3 and a portion of intron 17 of FGFR3 located on human chromosome 4p16 spliced 5' to exons 9-16 of TACC3 located on human chromosome 4p16. In one embodiment, a genomic breakpoint occurs in intron 17 of FGFR3 and in exon 9 of TACC3. For example, a FGFR fusion protein can also include a fusion protein encoded by an FGFR1-TACC1 nucleic acid, wherein the nucleic acid comprises exons 1-17 of FGFR1 located on human chromosome 8p11 spliced 5' to exons 7-13 of TACC1 located on human chromosome 8p11. In one embodiment, a genomic breakpoint occurs in intron 17 or exon 17 of FGFR1 and in intron 6 or exon 7 of TACC1.

In one embodiment, the coordinates comprising FGFR3 translocations comprise chr4:1,795,039-1,810,599. In a further embodiment, the genomic breakpoint coordinate according to the genome build GRCh37/hg19 for FGFR3 is chr4:1,808,808, chr4:1,808,843, chr4:1,809,083, chr4:1,808,785, chr4:1,808,700, chr4:1,808,864, chr4:1,808,678, chr4:1, 808,798, or chr4:1,808,723. In a further embodiment, the coordinates comprising TACC3 translocations comprise chr4:1,723,217-1,746,905. In a further embodiment, the genomic breakpoint coordinate according to the genome build GRCh37/hg19 for TACC3 is chr4:1,732,648, chr4:1,732,757, chr4:1,739,187, chr4:1,737,091, chr4:1, 737,062, chr4:1,737741, chr4:1,739,662, chr4:1,739,600, or chr4:1,738,989.

The nucleic acid can be any type of nucleic acid, including genomic DNA, complementary DNA (cDNA), recombinant DNA, synthetic or semi-synthetic DNA, as well as any form of corresponding RNA. A cDNA is a form of DNA artificially synthesized from a messenger RNA template and is used to produce gene clones. A synthetic DNA is free of modifications that can be found in cellular nucleic acids, including, but not limited to, histones and methylation. For example, a nucleic acid encoding a FGFR fusion molecule can comprise a recombinant nucleic acid encoding such a protein. The nucleic acid can be a non-naturally occurring nucleic acid created artificially (such as by assembling, cutting, ligating or amplifying sequences). It can be double-stranded or single-stranded.

The invention further provides for nucleic acids that are complementary to a FGFR fusion molecule. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

In one embodiment, a FGFR fusion molecule comprises a protein or polypeptide encoded by a nucleic acid sequence encoding a FGFR fusion molecule, such as the sequences shown in SEQ ID NOS: 80-82, 84, 94-145, 515, 517, 519-527, or 530-538. In some embodiments, the nucleic acid sequence encoding a FGFR fusion molecule is about 70%, about 75%, about 80%, about 85%, about 90%, about 93%, about 95%, about 97%, about 98%, or about 99% identical to SEQ ID NOS: 80-82, 84, 94-145, 515, 517, 519-527, or 530-538. In another embodiment, the polypeptide can be modified, such as by glycosylations and/or acetylations and/or chemical reaction or coupling, and can contain one or several non-natural or synthetic amino acids. An example of a FGFR fusion molecule is the polypeptide having the amino acid sequence shown in SEQ ID NOS: 79, 88, 150, 158-161, or 539-547. In some embodiments, the FGFR fusion molecule that is a polypeptide is about 70%, about 75%, about 80%, about 85%, about 90%, about 93%, about 95%, about 97%, about 98%, or about 99% identical to SEQ ID NOS: 79, 88, 150, 158-161, or 539-547. In another embodiment, a FGFR fusion molecule can be a fragment of a FGFR fusion protein. For example, the FGFR fusion molecule can encompass any portion of at least about 8 consecutive amino acids of SEQ ID NOS: 79, 88, 150, 158-161, or 539-547. The fragment can comprise at least about 10 amino acids, a least about 20 amino acids, at least about 30 amino acids, at least about 40 amino acids, a least about 50 amino acids, at least about 60 amino acids, or at least about 75 amino acids of SEQ ID NOS: 79, 88, 150, 158-161, or 539-547. Fragments include all possible amino acid lengths between about 8 and 100 about amino acids, for example, lengths between about 10 and 100 amino acids, between about 15 and 100 amino acids, between about 20 and 100 amino acids, between about 35 and 100 amino acids, between about 40 and 100 amino acids, between about 50 and 100 amino acids, between about 70 and 100 amino acids, between about 75 and 100 amino acids, or between about 80 and 100 amino acids. Fragments include all possible amino acid lengths between about 100 and 800 amino acids, for example, lengths between about 125 and 800 amino acids, between about 150 and 800 amino acids, between about 175 and 800 amino acids, between about 200 and 800 amino acids, between about 225 and 800 amino acids, between about 250 and 800 amino acids, between about 275 and 800 amino acids, between about 300 and 800 amino acids, between about 325 and 800 amino acids, between about 350 and 800 amino acids, between about 375 and 800 amino acids, between about 400 and 800 amino acids, between about 425 and 800 amino acids, between about 450 and 800 amino acids, between about 475 and 800 amino acids, between about 500 and 800 amino acids, between about 525 and 800 amino acids, between about 550 and 800 amino acids, between about 575 and 800 amino acids, between about 600 and 800 amino acids, between about 625 and 800 amino acids, between about 650 and 800 amino acids, between about 675 and 800 amino acids, between about 700 and 800 amino acids, between about 725 and 800 amino acids, between about 750 and 800 amino acids, or between about 775 and 800 amino acids.

Chemical Synthesis. Nucleic acid sequences encoding a FGFR fusion molecule can be synthesized, in whole or in part, using chemical methods known in the art. Alternatively, a polypeptide can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer).

Optionally, polypeptides fragments can be separately synthesized and combined using chemical methods to produce a full-length molecule. For example, these methods can be utilized to synthesize a fusion protein of the invention. In one embodiment, the fusion protein comprises a tyrosine kinase domain of an FGFR protein fused to a polypeptide that constitutively activates the tyrosine kinase domain of the FGFR protein. In another embodiment, a fusion protein comprises a transforming acidic coiled-coil (TACC) domain fused to a polypeptide with a tyrosine kinase domain, wherein the TACC domain constitutively activates the tyrosine kinase domain. An example of a fusion protein is the FGFR1-TACC1 polypeptide, which comprises the amino acid sequence shown in SEQ ID NO: 150. An example of a fusion protein is the FGFR3-TACC3 polypeptide, which has the amino acid sequence comprising SEQ ID NO: 79, 158, 159, 160, 161,539, 540, 541, 542, 543, 544, 545, 546, or 547.

Obtaining, Purifying and Detecting FGFR fusion molecules. A polypeptide encoded by a nucleic acid, such as a nucleic acid encoding a FGFR fusion molecule, or a variant thereof, can be obtained by purification from human cells expressing a protein or polypeptide encoded by such a nucleic acid. Non-limiting purification methods include size exclusion chromatography, ammonium sulfate fractionation, ion exchange chromatography, affinity chromatography, and preparative gel electrophoresis.

A synthetic polypeptide can be substantially purified via high performance liquid chromatography (HPLC), such as ion exchange chromatography (IEX-HPLC). The composition of a synthetic polypeptide, such as a FGFR fusion molecule, can be confirmed by amino acid analysis or sequencing.

Other constructions can also be used to join a nucleic acid sequence encoding a polypeptide/protein of the claimed invention to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Including cleavable linker sequences (i.e., those specific for Factor Xa or enterokinase (Invitrogen, San Diego, Calif.)) between the purification domain and a polypeptide encoded by a nucleic acid of the invention also can be used to facilitate purification. For example, the skilled artisan can use an expression vector encoding 6 histidine residues that precede a thioredoxin or an enterokinase cleavage site in conjunction with a nucleic acid of interest. The histidine residues facilitate purification by immobilized metal ion affinity chromatography, while the enterokinase cleavage site provides a means for purifying the polypeptide encoded by, for example, an FGFR1-TACC1, FGFR2-TACC2, FGFR3-TACC3, other FGFR-TACC, FGFR-containing, or TACC containing nucleic acid.

Host cells which contain a nucleic acid encoding a FGFR fusion molecule, and which subsequently express the same, can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding a FGFR fusion molecule can be detected by DNA-DNA or DNA-RNA hybridization or amplification using probes or fragments of nucleic acids encoding the same. In one embodiment, a nucleic acid fragment of a FGFR fusion molecule can encompass any portion of at least about 8 consecutive nucleotides of SEQ ID NOS: 80-82, 84, 94-145, 515, 517, 519-527, or 530-538. In another embodiment, the fragment can comprise at least about 10 consecutive nucleotides, at least about 15 consecutive nucleotides, at least about 20 consecutive nucleotides, or at least about 30 consecutive nucleotides of SEQ ID NOS: 80-82, 84, 94-145, 515, 517, 519-527, 530-538. Fragments can include all possible nucleotide lengths between about 8 and about 100 nucleotides, for example, lengths between about 15 and about 100 nucleotides, or between about 20 and about 100 nucleotides. Nucleic acid amplification-based assays involve the use of oligonucleotides selected from sequences encoding a FGFR fusion molecule nucleic acid, or FGFR fusion molecule nucleic acid to detect transformants which contain a nucleic acid encoding a protein or polypeptide of the same.

Protocols are known in the art for detecting and measuring the expression of a polypeptide encoded by a nucleic acid, such as a nucleic acid encoding a FGFR fusion molecule, using either polyclonal or monoclonal antibodies specific for the polypeptide. Non-limiting examples include enzyme-linked immunosorbent assay (ELISA), radioimmunoassay (RIA), immunostaining, and fluorescence activated cell sorting (FACS). A two-site, monoclonal-based immunoassay using monoclonal antibodies reactive to two non-interfering epitopes on a polypeptide encoded by a nucleic acid, such as a nucleic acid encoding a FGFR fusion molecule, can be used, or a competitive binding assay can be employed.

Labeling and conjugation techniques are known by those skilled in the art and can be used in various nucleic acid and amino acid assays. Methods for producing labeled hybridization or PCR probes for detecting sequences related to nucleic acid sequences encoding a protein, such as FGFR fusion molecule, include, but are not limited to, oligolabeling, nick translation, end-labeling, or PCR amplification using a labeled nucleotide. Alternatively, nucleic acid sequences, such as nucleic acids encoding a FGFR fusion molecule, can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

A fragment can be a fragment of a protein, such as a FGFR fusion protein. For example, a fragment of a FGFR fusion molecule can encompass any portion of at least about 8 consecutive amino acids of SEQ ID NOS: 79, 88, 150, 158-161, or 539-547. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 75 consecutive amino acids, at least about 80 consecutive amino acids, at least about 85 consecutive amino acids, at least about 90 consecutive amino acids, at least about 95 consecutive amino acids, at least about 100 consecutive amino acids, at least about 200 consecutive amino acids, at least about 300 consecutive amino acids, at least about 400 consecutive amino acids, at least about 500 consecutive amino acids, at least about 600 consecutive amino acids, at least about 700 consecutive amino acids, or at least about 800 consecutive amino acids of SEQ ID NOS: 79, 88, 150, 158-161, or 539-547. Fragments include all possible amino acid lengths between about 8 and 100 about amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids.

Cell Transfection

Host cells transformed with a nucleic acid sequence of interest can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence, such as a nucleic acid encoding a FGFR fusion molecule, can be designed to contain signal sequences which direct secretion of soluble polypeptide molecules encoded by the nucleic acid. Cell transfection and culturing methods are described in more detail below.

A eukaryotic expression vector can be used to transfect cells in order to produce proteins encoded by nucleotide sequences of the vector, e.g. those encoding a FGFR fusion molecule. Mammalian cells can contain an expression vector (for example, one that contains a nucleic acid encoding a fusion protein comprising a tyrosine kinase domain of an FGFR protein fused to a polypeptide that constitutively activates the tyrosine kinase domain of the FGFR protein, or a nucleic acid encoding a fusion protein comprises a transforming acidic coiled-coil (TACC) domain fused to a polypeptide with a tyrosine kinase domain, wherein the TACC domain constitutively activates the tyrosine kinase domain) via introducing the expression vector into an appropriate host cell via methods known in the art.

A host cell strain can be chosen for its ability to modulate the expression of the inserted sequences or to process the expressed polypeptide encoded by a nucleic acid, in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

An exogenous nucleic acid can be introduced into a cell via a variety of techniques known in the art, such as lipofection, microinjection, calcium phosphate or calcium chloride precipitation, DEAE-dextran-mediated transfection, or electroporation. Electroporation is carried out at approximate voltage and capacitance to result in entry of the DNA construct(s) into cells of interest (such as glioma cells (cell line SF188), neuroblastoma cells (cell lines IMR-32, SK-N-SH, SH-F and SH-N), astrocytes and the like). Other transfection methods also include modified calcium phosphate precipitation, polybrene precipitation, liposome fusion, and receptor-mediated gene delivery.

Cells that will be genetically engineered can be primary and secondary cells obtained from various tissues, and include cell types which can be maintained and propagated in culture. Non-limiting examples of primary and secondary cells include epithelial cells, neural cells, endothelial cells, glial cells, fibroblasts, muscle cells (such as myoblasts) keratinocytes, formed elements of the blood (e.g., lymphocytes, bone marrow cells), and precursors of these somatic cell types.

Vertebrate tissue can be obtained by methods known to one skilled in the art, such a punch biopsy or other surgical methods of obtaining a tissue source of the primary cell type of interest. In one embodiment, a punch biopsy or removal (e.g., by aspiration) can be used to obtain a source of cancer cells (for example, glioma cells, neuroblastoma cells, and the like). A mixture of primary cells can be obtained from the tissue, using methods readily practiced in the art, such as explanting or enzymatic digestion (for examples using enzymes such as pronase, trypsin, collagenase, elastase dispase, and chymotrypsin). Biopsy methods have also been described in U.S. Pat. No. 7,419,661 and PCT application publication WO 2001/32840, and each are hereby incorporated by reference.

Primary cells can be acquired from the individual to whom the genetically engineered primary or secondary cells are administered. However, primary cells can also be obtained from a donor, other than the recipient, of the same species. The cells can also be obtained from another species (for example, rabbit, cat, mouse, rat, sheep, goat, dog, horse, cow, bird, or pig). Primary cells can also include cells from a purified vertebrate tissue source grown attached to a tissue culture substrate (for example, flask or dish) or grown in a suspension; cells present in an explant derived from tissue; both of the aforementioned cell types plated for the first time; and cell culture suspensions derived from these plated cells. Secondary cells can be plated primary cells that are removed from the culture substrate and replated, or passaged, in addition to cells from the subsequent passages. Secondary cells can be passaged one or more times. These primary or secondary cells can contain expression vectors having a gene that encodes a FGFR fusion molecule.

Cell Culturing

Various culturing parameters can be used with respect to the host cell being cultured. Appropriate culture conditions for mammalian cells are well known in the art (Cleveland W L, et al., *J Immunol Methods,* 1983, 56(2): 221-234) or can be determined by the skilled artisan (see, for example, *Animal Cell Culture: A Practical Approach* 2nd Ed., Rickwood, D. and Hames, B. D., eds. (Oxford University Press: New York, 1992)). Cell culturing conditions can vary according to the type of host cell selected. Commercially available medium can be utilized. Non-limiting examples of medium include, for example, Minimal Essential Medium (MEM, Sigma, St. Louis, Mo.); Dulbecco's Modified Eagles Medium (DMEM, Sigma); Ham's F10 Medium (Sigma); HyClone cell culture medium (HyClone, Logan, Utah); RPMI-1640 Medium (Sigma); and chemically-defined (CD) media, which are formulated for various cell types, e.g., CD-CHO Medium (Invitrogen, Carlsbad, Calif.).

The cell culture media can be supplemented as necessary with supplementary components or ingredients, including optional components, in appropriate concentrations or amounts, as necessary or desired. Cell culture medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that can be required at very low concentrations, usually in the micromolar range.

The medium also can be supplemented electively with one or more components from any of the following categories: (1) salts, for example, magnesium, calcium, and phosphate; (2) hormones and other growth factors such as, serum, insulin, transferrin, and epidermal growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example pluronic polyol; and (8) galactose. In one embodiment, soluble factors can be added to the culturing medium.

The mammalian cell culture that can be used with the present invention is prepared in a medium suitable for the type of cell being cultured. In one embodiment, the cell culture medium can be any one of those previously discussed (for example, MEM) that is supplemented with serum from a mammalian source (for example, fetal bovine serum (FBS)). In another embodiment, the medium can be a conditioned medium to sustain the growth of host cells.

Three-dimensional cultures can be formed from agar (such as Gey's Agar), hydrogels (such as matrigel, agarose, and the like; Lee et al., (2004) *Biomaterials* 25: 2461-2466) or polymers that are cross-linked. These polymers can comprise natural polymers and their derivatives, synthetic polymers and their derivatives, or a combination thereof. Natural polymers can be anionic polymers, cationic polymers, amphipathic polymers, or neutral polymers. Non-limiting examples of anionic polymers can include hyaluronic acid, alginic acid (alginate), carageenan, chondroitin sulfate, dextran sulfate, and pectin. Some examples of cationic polymers, include but are not limited to, chitosan or polylysine. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73). Examples of amphipathic polymers can include, but are not limited to collagen, gelatin, fibrin, and carboxymethyl chitin. Non-limiting examples of neutral polymers can include dextran, agarose, or pullulan. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73).

Cells to be cultured can harbor introduced expression vectors, such as plasmids. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 2001, *Molecular Cloning, A Laboratory Manual,* Cold Spring Harbor Press, Plainview, N.Y. and in F. M. Ausubel et al., 1989, *Current Protocols in Molecular Biology,* John Wiley & Sons, New York, N.Y.

FGFR Fusion Molecule Inhibitors

The invention provides methods for use of compounds that decrease the expression level or activity of a FGFR fusion molecule in a subject. In addition, the invention provides methods for using compounds for the treatment of a gene-fusion associated cancer. In one embodiment, the gene-fusion associated cancer is an epithelial cancer. In one embodiment, the gene-fusion associated cancer comprises glioblastoma multiforme, breast cancer, lung cancer, prostate cancer, or colorectal carcinoma.

As used herein, a "FGFR fusion molecule inhibitor" refers to a compound that interacts with a FGFR fusion molecule of the invention and modulates its activity and/or its expression. For example, the compound can decrease the activity or expression of a FGFR fusion molecule. The compound can be an antagonist of a FGFR fusion molecule (e.g., a FGFR fusion molecule inhibitor). Some non-limiting examples of FGFR fusion molecule inhibitors include peptides (such as peptide fragments comprising a FGFR fusion molecule, or antibodies or fragments thereof), small molecules, and nucleic acids (such as siRNA or antisense RNA specific for a nucleic acid comprising a FGFR fusion molecule). Antagonists of a FGFR fusion molecule decrease the amount or the duration of the activity of an FGFR fusion protein. In one embodiment, the fusion protein comprises a tyrosine kinase domain of an FGFR protein fused to a polypeptide that constitutively activates the tyrosine kinase domain of the FGFR protein (e.g., FGFR1-TACC1, FGFR2-TACC2, FGFR3-TACC3 or other FGFR-TACC), or a fusion protein comprises a transforming acidic coiled-coil (TACC) domain fused to a polypeptide with a tyrosine kinase domain, wherein the TACC domain constitutively activates the tyrosine kinase domain. Antagonists include proteins, nucleic acids, antibodies, small molecules, or any other molecule which decrease the activity of a FGFR fusion molecule.

The term "modulate," as it appears herein, refers to a change in the activity or expression of a FGFR fusion molecule. For example, modulation can cause a decrease in protein activity, binding characteristics, or any other biological, functional, or immunological properties of a FGFR fusion molecule, such as an FGFR fusion protein.

In one embodiment, a FGFR fusion molecule inhibitor can be a peptide fragment of a FGFR fusion protein that binds to the protein itself.

For example, the FGFR fusion polypeptide can encompass any portion of at least about 8 consecutive amino acids of SEQ ID NOS: 79, 88, 150, 158-161, or 539-547. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 75 consecutive amino acids, at least about 80 consecutive amino acids, at least about 85 consecutive amino acids, at least about 90 consecutive amino acids, at least about 95 consecutive amino acids, at least about 100 consecutive amino acids, at least about 200 consecutive amino acids, at least about 300 consecutive amino acids, at least about 400 consecutive amino acids, at least about 500 consecutive amino acids, at least about 600 consecutive amino acids, at least about 700 consecutive amino acids, or at least about 800 consecutive amino acids of SEQ ID NOS: 79, 88, 150, 158-161, or 539-547. Fragments include all possible amino acid lengths between about 8 and 100 about amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) Solid Phase Peptide Synthesis: a Practical Approach. IRL Press, Oxford, England). The FGFR fusion peptide fragments can be isolated from a natural source, genetically engineered, or chemically prepared. These methods are well known in the art.

A FGFR fusion molecule inhibitor can be a protein, such as an antibody (monoclonal, polyclonal, humanized, chimeric, or fully human), or a binding fragment thereof, directed against a FGFR fusion molecule of the invention. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) Ann. Rev. Biomed. Eng. 2:339-76; Hudson (1998) Curr. Opin. Biotechnol. 9:395-402). Antibodies can be obtained commercially, custom generated, or synthesized against an antigen of interest according to methods established in the art (see U.S. Pat. Nos. 6,914,128, 5,780,597, 5,811,523; Roland E. Kontermann and Stefan Diibel (editors), Antibody Engineering, Vol. I & II, (2010) 2n d ed., Springer; Antony S. Dimitrov (editor), Therapeutic Antibodies: Methods and Protocols (Methods in Molecular Biology), (2009), Humana Press; Benny Lo (editor) Antibody Engineering: Methods and Protocols (Methods in Molecular Biology), (2004) Humana Press, each of which are hereby incorporated by reference in their entireties). For example, antibodies directed to a FGFR fusion molecule can be obtained commercially from Abeam, Santa Cruz Biotechnology, Abgent, R&D Systems, Novus Biologicals, etc. Human antibodies directed to a FGFR fusion molecule (such as monoclonal, humanized, fully human, or chimeric antibodies) can be useful antibody therapeutics for use in humans. In one embodiment, an antibody or binding fragment thereof is directed against SEQ ID NOS: 79, 88, 150, 158-161, or 539-547.

Inhibition of RNA encoding a FGFR fusion molecule can effectively modulate the expression of a FGFR fusion molecule. Inhibitors are selected from the group comprising: siRNA; interfering RNA or RNAi; dsRNA; RNA Polymerase III transcribed DNAs; ribozymes; and antisense nucleic acids, which can be RNA, DNA, or an artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a FGFR fusion molecule can be synthesized, e.g., by conventional phosphodiester techniques (Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59). Antisense nucleotide sequences include, but are not limited to: morpholinos, 2'-O-methyl polynucleotides, DNA, RNA and the like.

siRNA comprises a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. See also, McMnaus and Sharp (2002) Nat Rev Genetics, 3:737-47, and Sen and Blau (2006) FASEB J., 20:1293-99, the entire disclosures of which are herein incorporated by reference.

The siRNA can be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. One or both strands of the siRNA can also comprise a 3' overhang. As used herein, a 3' overhang refers to at least one unpaired nucleotide extending from the 3'-end of a duplexed RNA strand. For example, the siRNA can comprise at least one 3' overhang of from 1 to about 6 nucleotides (which includes ribonucleotides or deoxyribonucleotides) in length, or from 1 to about 5 nucleotides in length, or from 1 to about 4 nucleotides in length, or from about 2 to about 4 nucleotides in length. For example, each strand of the siRNA can comprise 3' overhangs of dithymidylic acid ("TT") or diuridylic acid ("uu").

siRNA can be produced chemically or biologically, or can be expressed from a recombinant plasmid or viral vector (for example, see U.S. Pat. Nos. 7,294,504 and 7,422,896, the entire disclosures of which are herein incorporated by reference). Exemplary methods for producing and testing dsRNA or siRNA molecules are described in U.S. Patent Application Publication No. 2002/0173478 to Gewirtz, U.S. Pat. No. 8,071,559 to Hannon et al., and in U.S. Pat. No. 7,148,342 to Tolentino et al., the entire disclosures of which are herein incorporated by reference.

In one embodiment, an siRNA directed to a human nucleic acid sequence comprising a FGFR fusion molecule can be generated against any one of SEQ ID NOS: 80-82, 84, 94-145, 515, 517, 519-527 or 530-538. In another embodiment, an siRNA directed to a human nucleic acid sequence comprising a breakpoint of an FGFR fusion molecule can be generated against any one of SEQ ID NOS: 1-77, 80-82, 84-145, 515, 517, 519-527 or 530-538. In one embodiment, the hairpin sequences targeting the FGFR3 gene comprise SEQ ID NOS: 182, 183, or 184.

RNA polymerase III transcribed DNAs contain promoters, such as the U6 promoter. These DNAs can be transcribed to produce small hairpin RNAs in the cell that can function as siRNA or linear RNAs, which can function as antisense RNA. The FGFR fusion molecule inhibitor can comprise ribonucleotides, deoxyribonucleotides, synthetic nucleotides, or any suitable combination such that the target RNA and/or gene is inhibited. In addition, these forms of nucleic acid can be single, double, triple, or quadruple stranded. (see for example Bass (2001) Nature, 411:428-429; Elbashir et al., (2001) Nature, 411:494 498; U.S. Pat. No. 6,509,154; U.S. Patent Application Publication No. 2003/0027783; and PCT Publication Nos. WO 00/044895, WO 99/032619, WO 00/01846, WO 01/029058, WO 00/044914).

FGFR fusion molecule inhibitor can be a small molecule that binds to a FGFR fusion protein described herein and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that inhibit a FGFR fusion protein can be identified via in silico screening or high-through-put (HTP) screening of combinatorial libraries according to methods established in the art (e.g., see Potyrailo et al., (2011) ACS Comb Sci. 13(6):579-633; Mensch et al., (2009) J Pharm Sci. 98(12):4429-68; Schnur (2008) Curr Opin Drug Discov Devel. 11(3):375-80; and Jhoti (2007) Ernst Schering Found Symp Proc. (3):169-85, each of which are hereby incorporated by reference in their entireties.) Most conventional pharmaceuticals, such as aspirin, penicillin, and many chemotherapeutics, are small molecules, can be obtained commercially, can be chemically synthesized, or can be obtained from random or combinatorial libraries as described below (see, e.g., Werner et al., (2006) Brief Funct. Genomic Proteomic 5(1):32-6).

Non-limiting examples of FGFR fusion molecule inhibitors include the FGFR inhibitors AZD4547 (see Gavine et al., (2012) Cancer Res, 72(8); 2045-56; see also PCT Application Publication No. WO 2008/075068, each of which are hereby incorporated by reference in their entireties); NVP-BGJ398 (see Guagnano et al., (2011) J. Med. Chem., 54:7066-7083; see also U.S. Patent Application Publication No. 2008-0312248 A1, each of which are hereby incorporated by reference in their entireties); PD173074 (see Guagnano et al., (2011) J. Med. Chem., 54:7066-7083; see also Mohammadi et al., (1998) EMBO J., 17:5896-5904, each of which are hereby incorporated by reference in their entireties); NF449 (EMD Millipore (Billerica, MA) Cat. No. 480420; see also Krejci, (2010) the Journal of Biological Chemistry, 285(27):20644-20653, which is hereby incorporated by reference in its entirety); LY2874455 (Active Biochem; see Zhao et al. (2011) Mol Cancer Ther. (11): 2200-10; see also PCT Application Publication No. WO 2010129509, each of which are hereby incorporated by reference in their entireties); TK1258 (Dovitinib); BIBF-1120 (Intedanib-Vargatef); BMS-582664 (Brivanib alaninate); AZD-2171 (Cediranib); TSU-68 (Orantinib); AB-1010 (Masitinib); AP-24534 (Ponatinib); and E-7080 (by Eisai). A non-limiting example of an FGFR fusion molecule inhibitor includes the TACC inhibitor KHS101 (Wurdak et al., (2010) PNAS, 107(38): 16542-47, which is hereby incorporated by reference in its entirety).

Structures of FGFR fusion molecule inhibitors useful for the invention include, but are not limited to: the FGFR inhibitor AZD4547,

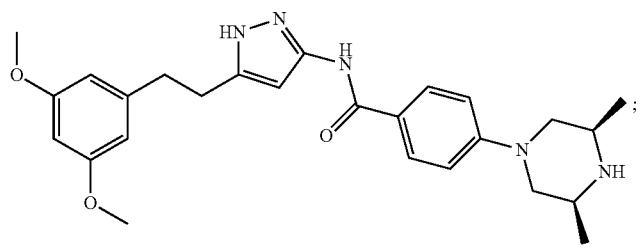

the FGFR inhibitor NVP-BGJ398

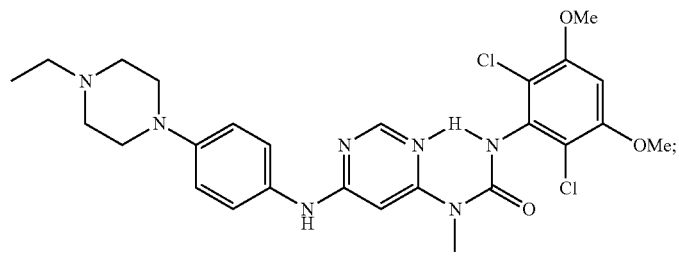
the FGFR inhibitor PD173074
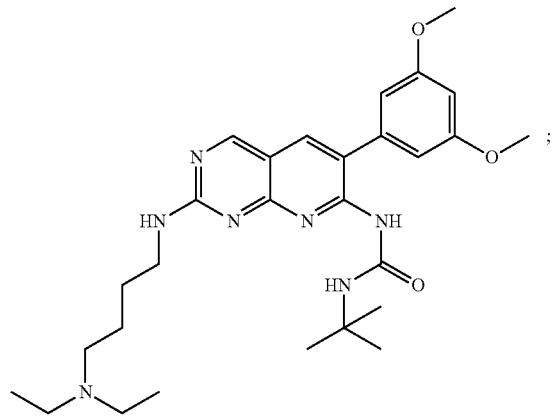
the FGFR inhibitor LY2874455
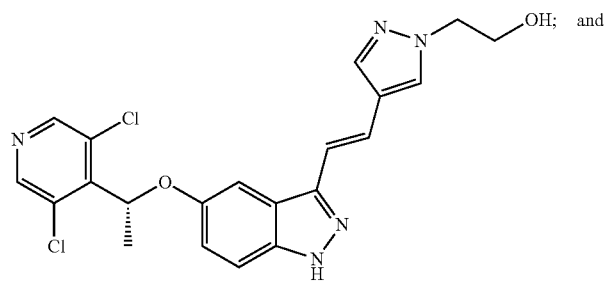
the FGFR inhibitor NF449 (EMD Millipore (Billerica, MA) Cat. No. 480420)
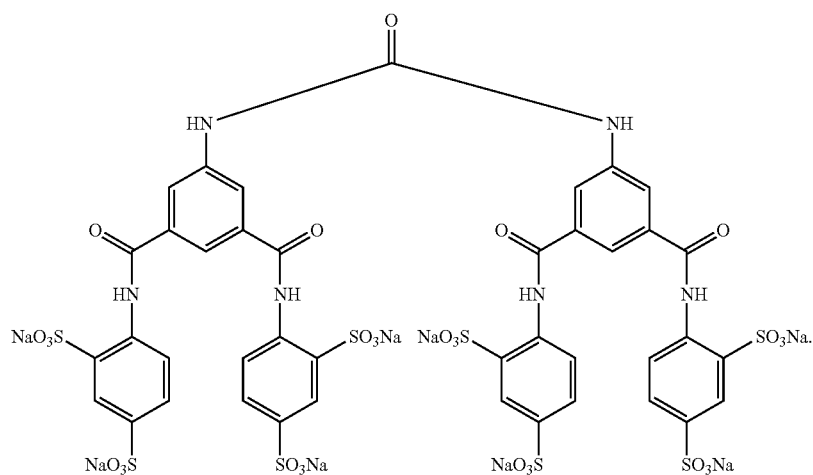

Other FGFR inhibitors include, but are not limited to:

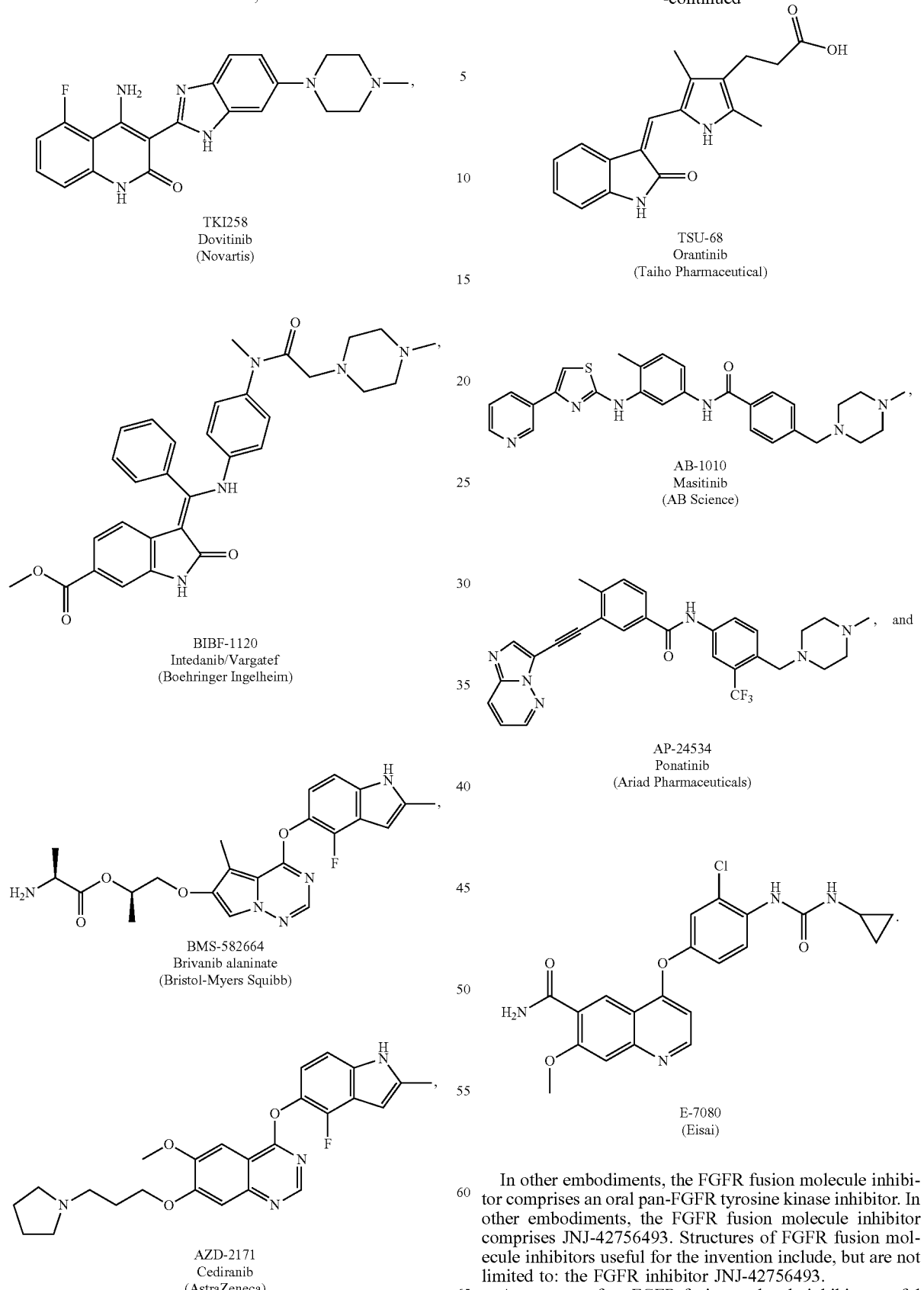

TKI258
Dovitinib
(Novartis)

BIBF-1120
Intedanib/Vargatef
(Boehringer Ingelheim)

BMS-582664
Brivanib alaninate
(Bristol-Myers Squibb)

AZD-2171
Cediranib
(AstraZeneca)

TSU-68
Orantinib
(Taiho Pharmaceutical)

AB-1010
Masitinib
(AB Science)

AP-24534
Ponatinib
(Ariad Pharmaceuticals)

E-7080
(Eisai)

In other embodiments, the FGFR fusion molecule inhibitor comprises an oral pan-FGFR tyrosine kinase inhibitor. In other embodiments, the FGFR fusion molecule inhibitor comprises JNJ-42756493. Structures of FGFR fusion molecule inhibitors useful for the invention include, but are not limited to: the FGFR inhibitor JNJ-42756493.

A structure of an FGFR fusion molecule inhibitor useful for the invention include, but is not limited to the TACC inhibitor KHS101,

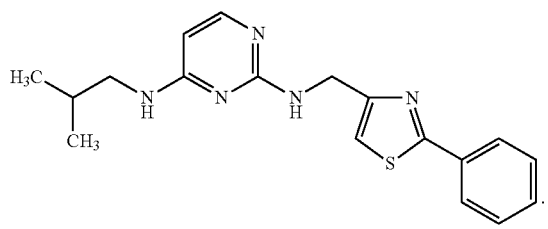 [SMILES: CC(C)CNc1ccnc(NCc2csc(-c3ccccc3)n2)n1]

Assessment and Therapeutic Treatment

The invention provides a method of decreasing the growth of a solid tumor in a subject. The tumor is associated with, but not limited to, glioblastoma multiforme, breast cancer, lung cancer, prostate cancer, or colorectal carcinoma. In another embodiment, the tumor is associated with, but not limited to, bladder carcinoma, squamous lung carcinoma and head and neck carcinoma. In one embodiment, the tumor is associated with, but not limited to, glioma. In one embodiment, the tumor is associated with, but not limited to, grade II or III glioma. In one embodiment, the tumor is associated with, but not limited to, IDH wild-type grade II or III glioma. In one embodiment, the method comprises detecting the presence of a FGFR fusion molecule in a sample obtained from a subject. In some embodiments, the sample is incubated with an agent that binds to an FGFR fusion molecule, such as an antibody, a probe, a nucleic acid primer, and the like. In further embodiments, the method comprises administering to the subject an effective amount of a FGFR fusion molecule inhibitor, wherein the inhibitor decreases the size of the solid tumor. In further embodiments, the method comprises further detecting the presence of IDH1 mutations, EGFR amplification, CDK4 amplification, or MDM2 amplification. In further embodiments, a FGFR fusion molecule inhibitor can be administered in combination with CDK4 inhibitors, MDM2 inhibitors, or a combination thereof.

The invention also provides a method for treating or preventing a gene-fusion associated cancer in a subject. In one embodiment, the gene-fusion associated cancer comprises an epithelial cancer. In one embodiment, the gene-fusion associated cancer comprises glioblastoma multiforme, breast cancer, lung cancer, prostate cancer, or colorectal carcinoma. In some embodiments, the epithelial cancer comprises bladder urothelial carcinoma, breast carcinoma, colorectal cancer, prostate carcinoma, lung squamous cell carcinoma, head and neck squamous cell carcinoma, or a combination of the epithelial cancers described. In one embodiment, the gene-fusion associated cancer comprises glioma. In one embodiment, the gene-fusion associated cancer comprises grade II or III glioma. In one embodiment, the gene-fusion associated cancer comprises IDH wild-type grade II or III glioma. In one embodiment, the method comprises detecting the presence of a FGFR fusion molecule in a sample obtained from a subject, the presence of the fusion being indicative of a gene-fusion associated cancer, and, administering to the subject in need a therapeutic treatment against a gene-fusion associated cancer. In some embodiments, the sample is incubated with an agent that binds to an FGFR fusion molecule, such as an antibody, a probe, a nucleic acid primer, and the like. In further embodiments, the method comprises further detecting the presence of IDH1 mutations, EGFR amplification, CDK4 amplification, or MDM2 amplification. In further embodiments, an agent that binds to an FGFR fusion molecule can be administered in combination with CDK4 inhibitors, MDM2 inhibitors, or a combination thereof.

The invention also provides a method for decreasing in a subject in need thereof the expression level or activity of a fusion protein comprising the tyrosine kinase domain of an FGFR protein fused to a polypeptide that constitutively activates the tyrosine kinase domain of the FGFR protein. In some embodiments, the method comprises obtaining a biological sample from the subject. In some embodiments, the sample is incubated with an agent that binds to an FGFR fusion molecule, such as an antibody, a probe, a nucleic acid primer, and the like. In some embodiments, the method comprises administering to the subject a therapeutic amount of a composition comprising an admixture of a pharmaceutically acceptable carrier an inhibitor of the fusion protein of the invention. In one embodiment, the inhibitor is JNJ-42756493. In another embodiment, the method further comprises determining the fusion protein expression level or activity. In another embodiment, the method further comprises detecting whether the fusion protein expression level or activity is decreased as compared to the fusion protein expression level or activity prior to administration of the composition, thereby decreasing the expression level or activity of the fusion protein. In some embodiments, the fusion protein is an FGFR-TACC fusion protein. In further embodiments, the method comprises further detecting the presence of IDH1 mutations, EGFR amplification, CDK4 amplification, or MDM2 amplification.

The administering step in each of the claimed methods can comprise a drug administration, such as FGFR fusion molecule inhibitor (for example, a pharmaceutical composition comprising an antibody that specifically binds to a FGFR fusion molecule or a fragment thereof; a small molecule that specifically binds to a FGFR protein; a small molecule that specifically binds to a TACC protein; an antisense RNA or antisense DNA that decreases expression of a FGFR fusion molecule; a siRNA that specifically targets a gene encoding a FGFR fusion molecule; a small molecule such as JNJ-42756493; or a combination thereof). In one embodiment, the therapeutic molecule to be administered comprises a polypeptide of a FGFR fusion molecule, comprising at least about 75%, at least about 80%, at least about 85%, at least about 90%, at least about 93%, at least about 95%, at least about 97%, at least about 98%, at least about 99%, or 100% of the amino acid sequence of SEQ ID NOS: 79, 88, 150, 158-161, or 539-547 and exhibits the function of decreasing expression of such a protein, thus treating a gene fusion-associated cancer. In another embodiment, administration of the therapeutic molecule decreases the size of the solid tumor associated with glioblastoma multiforme, breast cancer, lung cancer, prostate cancer, colorectal carcinoma, bladder carcinoma, squamous lung carcinoma and head and neck carcinoma, glioma, grade II or III glioma, or IDH wild-type grade II or III glioma. In further embodiments, the therapeutic molecule can be administered in combination with CDK4 inhibitors, MDM2 inhibitors, or a combination thereof.

In another embodiment, the therapeutic molecule to be administered comprises an siRNA directed to a human nucleic acid sequence comprising a FGFR fusion molecule. In one embodiment, the siRNA is directed to any one of SEQ ID NOS: 80-82, 84, 94-145, 515, 517, 519-527, or 530-538. In another embodiment, the siRNA is directed to any one of SEQ ID NOS: 1-77, 80-82, 84-145, 515, 517, 519-527, or 530-538. In a further embodiment, the therapeutic molecule to be administered comprises an antibody or binding fragment thereof, which is directed against SEQ ID NOS: 79, 88, 150, 158-161, or 539-547. In some embodiments, the therapeutic molecule to be administered comprises a small molecule that specifically binds to a FGFR protein, such as AZD4547, NVP-BGJ398, PD173074, NF449, TK1258, BIBF-1120, BMS-582664, AZD-2171, TSU68, AB1010, AP24534, E-7080, or LY2874455. In some embodiments, the therapeutic molecule to be administered is JNJ-42756493. In other embodiments, the therapeutic molecule to be administered comprises a small molecule that specifically binds to a TACC protein, such as KHS101.

In one embodiment, the invention provides for the detection of a chromosomal rearrangement at given chromosomal coordinates. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, immunostaining, ELISA, or other antibody detection methods.

In one embodiment, the biological sample comprises neuronal cells, serum, bone marrow, blood, peripheral blood, lymph nodes, cerebro-spinal fluid, urine, a saliva sample, a buccal swab, a serum sample, a sputum sample, a lacrimal secretion sample, a semen sample, a vaginal secretion sample, a fetal tissue sample, or a combination thereof. In some embodiments the sample is a tissue sample. In some embodiments, the sample is a paraffin embedded tissue section. In some embodiments, the tissue sample is a tumor sample.

A FGFR fusion molecule, for example, a fusion between FGFR1, FGFR2, FGFR3, or any other FGFR, and TACC1, TACC2, TACC3 or any other TACC, can be determined at the level of the DNA, RNA, or polypeptide. Optionally, detection can be determined by performing an oligonucleotide ligation assay, a confirmation based assay, a hybridization assay, a sequencing assay, an allele-specific amplification assay, a microsequencing assay, a melting curve analysis, a denaturing high performance liquid chromatography (DHPLC) assay (for example, see Jones et al, (2000) Hum Genet., 106(6):663-8), or a combination thereof. In one embodiment, the detection is performed by sequencing all or part of a FGFR fusion molecule (e.g., a FGFR1-TACC1, FGFR2-TACC2, FGFR3-TACC3 or other FGFR-TACC nucleic acid, or a FGFR1, TACC1, FGFR2, TACC2, FGFR3, TACC3 or other FGFR or TACC nucleic acid), or by selective hybridization or amplification of all or part of a FGFR fusion molecule (e.g., a FGFR1-TACC1, FGFR2-TACC2, FGFR3-TACC3 or other FGFR-TACC nucleic acid, or a FGFR1, TACC1, FGFR2, TACC2, FGFR3, TACC3 or other FGFR or TACC nucleic acid). A FGFR fusion molecule specific amplification (e.g., a FGFR1-TACC1, FGFR2-TACC2, FGFR3-TACC3 or other FGFR-TACC nucleic acid specific amplification) can be carried out before the fusion identification step.

The invention provides for a method of detecting a chromosomal alteration in a subject afflicted with a gene-fusion associated cancer. In one embodiment, the chromosomal alteration is an in-frame fused transcript described herein, for example an FGFR fusion molecule. In some embodiments, the chromosomal alteration is a chromosomal translocation, for example an FGFR fusion molecule. An alteration in a chromosome region occupied by a FGFR fusion molecule, such as a FGFR1-TACC1, FGFR2-TACC2, FGFR3-TACC3 or other FGFR-TACC nucleic acid, can be any form of mutation(s), deletion(s), rearrangement(s) and/or insertions in the coding and/or non-coding region of the locus, alone or in various combination(s). Mutations can include point mutations. Insertions can encompass the addition of one or several residues in a coding or non-coding portion of the gene locus. Insertions can comprise an addition of between 1 and 50 base pairs in the gene locus. Deletions can encompass any region of one, two or more residues in a coding or non-coding portion of the gene locus, such as from two residues up to the entire gene or locus. Deletions can affect smaller regions, such as domains (introns) or repeated sequences or fragments of less than about 50 consecutive base pairs, although larger deletions can occur as well. Rearrangement includes inversion of sequences. The alteration in a chromosome region occupied by a FGFR fusion molecule, e.g., a FGFR1-TACC1, FGFR2-TACC2, FGFR3-TACC3 or other FGFR-TACC nucleic acid, can result in amino acid substitutions, RNA splicing or processing, product instability, the creation of stop codons, production of oncogenic fusion proteins, frame-shift mutations, and/or truncated polypeptide production. The alteration can result in the production of a FGFR fusion molecule, for example, one encoded by a FGFR1-TACC1, FGFR2-TACC2, FGFR3-TACC3 or other FGFR-TACC nucleic acid, with altered function, stability, targeting or structure. The alteration can also cause a reduction, or even an increase in protein expression. In one embodiment, the alteration in the chromosome region occupied by a FGFR fusion molecule can comprise a chromosomal rearrangement resulting in the production of a FGFR fusion molecule, such as a FGFR1-TACC1, FGFR2-TACC2, FGFR3-TACC3 or other FGFR-TACC fusion. This alteration can be determined at the level of the DNA, RNA, or polypeptide. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, ELISA, immunostaining or other antibody detection methods. In one embodiment, the coordinates comprising FGFR1 translocations comprise chr8:38,268,656-38,325,363. In another embodiment, the coordinates comprising FGFR2 translocations comprise chr10:123,237,844-123,357,972. In a further embodiment, the coordinates comprising FGFR3 translocations comprise chr4:1,795,039-1,810,599. In yet another embodiment, the coordinates comprising FGFR4 translocations comprise chr5:176,513,921-176,525,126. In one embodiment, the coordinates comprising TACC1 translocations comprise chr8:38,644,722-38,710,546. In another embodiment, the coordinates comprising TACC2 translocations comprise chr10:123,748,689-124,014,057. In a further embodiment, the coordinates comprising TACC3 translocations comprise chr4:1,723,217-1,746,905.

The present invention provides a method for treating a gene-fusion associated cancer in a subject in need thereof. In one embodiment, the method comprises obtaining a sample from the subject to determine the level of expression of an FGFR fusion molecule in the subject. In some embodiments, the sample is incubated with an agent that binds to an FGFR fusion molecule, such as an antibody, a probe, a nucleic acid primer, and the like. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, immunostaining, ELISA, or other antibody detection methods. In some embodiments, the method further comprises assessing whether to administer a FGFR fusion molecule inhibitor based on the expression pattern of the subject. In further embodiments, the method comprises administering a FGFR fusion molecule inhibitor to the subject. In one embodiment, the FGFR fusion molecule inhibitor is JNJ-42756493. In one embodiment, the gene-fusion associated cancer comprises an epithelial cancer. In one embodiment, the gene-fusion associated cancer comprises glioblastoma multiforme, breast cancer, lung cancer, prostate cancer, or colorectal carcinoma. In some embodiments, the epithelial cancer comprises bladder urothelial carcinoma, breast carcinoma, colorectal cancer, prostate carcinoma, lung squamous cell carcinoma, head and neck squamous cell carcinoma, or a combination of the epithelial cancers described. In one embodiment, the gene-fusion associated cancer comprises glioma, grade II or III glioma, or IDH wild-type grade II or III glioma. In further embodiments, the method comprises further detecting the presence of IDH1 mutations, EGFR amplification, CDK4 amplification, or MDM2 amplification. In further embodiments, a FGFR fusion molecule inhibitor can be administered in combination with CDK4 inhibitors, MDM2 inhibitors, or a combination thereof.

In one embodiment, the invention provides for a method of detecting the presence of altered RNA expression of an FGFR fusion molecule in a subject, for example one afflicted with a gene-fusion associated cancer. In another embodiment, the invention provides for a method of detecting the presence of an FGFR fusion molecule in a subject. In some embodiments, the method comprises obtaining a sample from the subject to determine whether the subject expresses an FGFR fusion molecule. In some embodiments, the sample is incubated with an agent that binds to an FGFR fusion molecule, such as an antibody, a probe, a nucleic acid primer, and the like. In other embodiments, the detection or determination comprises nucleic acid sequencing, selective hybridization, selective amplification, gene expression analysis, or a combination thereof. In another embodiment, the detection or determination comprises protein expression analysis, for example by western blot analysis, ELISA, or other antibody detection methods. In some embodiments, the method further comprises assessing whether to administer a FGFR fusion molecule inhibitor based on the expression pattern of the subject. In further embodiments, the method comprises administering a FGFR fusion molecule inhibitor to the subject. In one embodiment, the FGFR fusion molecule inhibitor is NJ-42756493. Altered RNA expression includes the presence of an altered RNA sequence, the presence of an altered RNA splicing or processing, or the presence of an altered quantity of RNA. These can be detected by various techniques known in the art, including sequencing all or part of the RNA or by selective hybridization or selective amplification of all or part of the RNA. In a further embodiment, the method can comprise detecting the presence or expression of a FGFR fusion molecule, such as one encoded by a FGFR1-TACC1, FGFR2-TACC2, FGFR3-TACC3 or other FGFR-TACC nucleic acid. Altered polypeptide expression includes the presence of an altered polypeptide sequence, the presence of an altered quantity of polypeptide, or the presence of an altered tissue distribution. These can be detected by various techniques known in the art, including by sequencing and/or binding to specific ligands (such as antibodies). In one embodiment, the detecting comprises using a northern blot; real time PCR and primers directed to SEQ ID NOS: 80-82, 84, 94-145, 515, 517, 519-527, or 530-538; a ribonuclease protection assay; a hybridization, amplification, or sequencing technique to detect an FGFR fusion molecule, such as one comprising SEQ ID NOS: 80-82, 84, 94-145, 515, 517, 519-527, or 530-538; or a combination thereof. In another embodiment, the PCR primers comprise SEQ ID NOS: 162, 163, 164, 165 166, 167, 168, 169, 495, 496, 497, 498, 507, 508, 509, 510, 511, 512, 513, or 514. In a further embodiment, primers used for the screening of FGFR fusion molecules, such as FGFR-TACC fusions, comprise SEQ ID NOS: 166, 167, 168, 169, 495, 496, 497, 498, 507, 508, 509, or 510. In some embodiments, primers used for genomic detection of an FGFR3-TACC3 fusion comprise SEQ ID NOS: 170 171, 499, 500, 501, 502, 503, 504, 505, or 506.

In some aspects of the invention, the method comprises further detecting the presence of IDH1 mutations, EGFR amplification, CDK4 amplification, or MDM2 amplification. MDM2 encodes a nuclear-localized E3 ubiquitin ligase. Alternative splicing results in a multitude of transcript variants, many of which may be expressed only in tumor cells. EGFR (epidermal growth factor receptor) is a transmembrane glycoprotein that is a member of the protein kinase superfamily. This protein is a receptor for members of the epidermal growth factor family. EGFR is a cell surface protein that binds to epidermal growth factor. Multiple alternatively spliced transcript variants that encode different protein isoforms have been found for this gene. CDK4 (cyclin dependent kinase 4) is a member of the Ser/Thr protein kinase family. It is a catalytic subunit of the protein kinase complex that is important for cell cycle G1 phase progression. The activity of this kinase is restricted to the G1-S phase, which is controlled by the regulatory subunits D-type cyclins and CDK inhibitor p16(INK4a). Multiple polyadenylation sites of this gene have been reported. IDH1 (isocitrate dehydrogenase 1 (NADP+), soluble) catalyzes the oxidative decarboxylation of isocitrate to 2-oxoglutarate. Alternatively spliced transcript variants encoding the same protein have been found for this gene. IDH1 mutations, EGFR amplification, CDK4 amplification, or MDM2 amplification can be detected using various techniques know in the art, including, but not limited to sequencing and qPCR.

Various techniques known in the art can be used to detect or quantify altered gene or RNA expression or nucleic acid sequences, which include, but are not limited to, hybridization, sequencing, amplification, and/or binding to specific ligands (such as antibodies). Other suitable methods include allele-specific oligonucleotide (ASO), oligonucleotide ligation, allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, denaturing HLPC, melting curve analysis, heteroduplex analysis, RNase protection, chemical or enzymatic mismatch cleavage, ELISA, radio-immunoassays (RIA) and immuno-enzymatic assays (IEMA).

Some of these approaches (such as SSCA and constant gradient gel electrophoresis (CGGE)) are based on a change in electrophoretic mobility of the nucleic acids, as a result of the presence of an altered sequence. According to these techniques, the altered sequence is visualized by a shift in mobility on gels. The fragments can then be sequenced to confirm the alteration. Some other approaches are based on specific hybridization between nucleic acids from the subject and a probe specific for wild type or altered gene or RNA. The probe can be in suspension or immobilized on a substrate. The probe can be labeled to facilitate detection of hybrids. Some of these approaches are suited for assessing a polypeptide sequence or expression level, such as Northern blot, ELISA and RIA. These latter require the use of a ligand specific for the polypeptide, for example, the use of a specific antibody.

Hybridization. Hybridization detection methods are based on the formation of specific hybrids between complementary nucleic acid sequences that serve to detect nucleic acid sequence alteration(s). A detection technique involves the use of a nucleic acid probe specific for a wild type or altered gene or RNA, followed by the detection of the presence of a hybrid. The probe can be in suspension or immobilized on a substrate or support (for example, as in nucleic acid array or chips technologies). The probe can be labeled to facilitate detection of hybrids. In one embodiment, the probe according to the invention can comprise a nucleic acid directed to SEQ ID NOS: 80-82, 84, 94-145, 515, 517, 519-527, or 530-538. For example, a sample from the subject can be contacted with a nucleic acid probe specific for a gene encoding a FGFR fusion molecule, and the formation of a hybrid can be subsequently assessed. In one embodiment, the method comprises contacting simultaneously the sample with a set of probes that are specific for an FGFR fusion molecule. Also, various samples from various subjects can be investigated in parallel.

According to the invention, a probe can be a polynucleotide sequence which is complementary to and specifically hybridizes with a, or a target portion of a, gene or RNA corresponding to a FGFR fusion molecule. Useful probes are those that are complementary to the gene, RNA, or target portion thereof. Probes can comprise single-stranded nucleic acids of between 8 to 1000 nucleotides in length, for instance between 10 and 800, between 15 and 700, or between 20 and 500. Longer probes can be used as well. A useful probe of the invention is a single stranded nucleic acid molecule of between 8 to 500 nucleotides in length, which can specifically hybridize to a region of a gene or RNA that corresponds to a FGFR fusion molecule.

The sequence of the probes can be derived from the sequences of the FGFR fusion genes provided herein. Nucleotide substitutions can be performed, as well as chemical modifications of the probe. Such chemical modifications can be accomplished to increase the stability of hybrids (e.g., intercalating groups) or to label the probe. Some examples of labels include, without limitation, radioactivity, fluorescence, luminescence, and enzymatic labeling.

A guide to the hybridization of nucleic acids is found in e.g., Sambrook, ed., *Molecular Cloning: A Laboratory Manual* (3$^{rd}$ Ed.), Vols. 1-3, Cold Spring Harbor Laboratory, 1989; *Current Protocols In Molecular Biology*, Ausubel, ed. John Wiley & Sons, Inc., New York, 2001; *Laboratory Techniques In Biochemistry And Molecular Biology: Hybridization With Nucleic Acid Probes, Part I. Theory and Nucleic Acid Preparation*, Tijssen, ed. Elsevier, N.Y., 1993.

Sequencing. Sequencing can be carried out using techniques well known in the art, using automatic sequencers. The sequencing can be performed on the complete FGFR fusion molecule or on specific domains thereof.

Amplification. Amplification is based on the formation of specific hybrids between complementary nucleic acid sequences that serve to initiate nucleic acid reproduction. Amplification can be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Useful techniques in the art encompass real-time PCR, allele-specific PCR, or PCR based single-strand conformational polymorphism (SSCP). Amplification usually requires the use of specific nucleic acid primers, to initiate the reaction. For example, nucleic acid primers useful for amplifying sequences corresponding to a FGFR fusion molecule are able to specifically hybridize with a portion of the gene locus that flanks a target region of the locus. In one embodiment, amplification comprises using forward and reverse PCR primers directed to SEQ ID NOS: 80-82, 84, 94-145, 515, 517, 519-527, or 530-538. Nucleic acid primers useful for amplifying sequences from a FGFR fusion molecule (e.g., a FGFR1-TACC1, FGFR2-TACC2, FGFR3-TACC3 or other FGFR-TACC nucleic acid); the primers specifically hybridize with a portion of an FGFR fusion molecule. In certain subjects, the presence of an FGFR fusion molecule corresponds to a subject with a gene fusion-associated cancer. In one embodiment, amplification can comprise using forward and reverse PCR primers comprising nucleotide sequences of SEQ ID NOS: 80-82, 84, 94-145, 515, 517, 519-527, or 530-538. In one embodiment, amplification can comprise using forward and reverse PCR primers comprising nucleotide sequences of SEQ ID NOS: 162-169, or 495-514.

Non-limiting amplification methods include, e.g., polymerase chain reaction, PCR (*PCR Protocols, A Guide To Methods And Applications*, ed. Innis, Academic Press, N.Y., 1990 and *PCR Strategies*, 1995, ed. Innis, Academic Press, Inc., N.Y.); ligase chain reaction (LCR) (Wu (1989) *Genomics* 4:560; Landegren (1988) *Science* 241:1077; Barringer (1990) *Gene* 89:117); transcription amplification (Kwoh (1989) *PNAS* 86:1173); and, self-sustained sequence replication (Guatelli (1990) *PNAS* 87:1874); Q Beta replicase amplification (Smith (1997) *J. Clin. Microbiol.* 35:1477-1491), automated Q-beta replicase amplification assay (Burg (1996) *Mol. Cell. Probes* 10:257-271) and other RNA polymerase mediated techniques (e.g., NASBA, Cangene, Mississauga, Ontario; see also Berger (1987) *Methods Enzymol.* 152:307-316; U.S. Pat. Nos. 4,683,195 and 4,683,202; and Sooknanan (1995) *Biotechnology* 13:563-564). All the references stated above are incorporated by reference in their entireties.

The invention provides for a nucleic acid primer, wherein the primer can be complementary to and hybridize specifically to a portion of a FGFR fusion molecule, such as a FGFR1-TACC1, FGFR2-TACC2, FGFR3-TACC3 or other FGFR-TACC nucleic acid (e.g., DNA or RNA) in certain subjects having a gene fusion-associated cancer. In one embodiment, the gene-fusion associated cancer comprises glioblastoma multiforme, breast cancer, lung cancer, prostate cancer, or colorectal carcinoma. Primers of the invention can be specific for fusion sequences in a FGFR1-TACC1, FGFR2-TACC2, FGFR3-TACC3 or other FGFR-TACC nucleic acid (DNA or RNA). By using such primers, the detection of an amplification product indicates the presence of a fusion of a FGFR1 and TACC1, FGFR2 and TACC2, FGFR3 and TACC3 or other FGFR and TACC nucleic acid. Examples of primers of this invention can be single-stranded nucleic acid molecules of about 5 to 60 nucleotides in length, or about 8 to about 25 nucleotides in length. The sequence can be derived directly from the sequence of a FGFR fusion molecule, e.g. FGFR1-TACC1, FGFR2-TACC2, FGFR3-TACC3 or other FGFR-TACC nucleic acid. Perfect complementarity is useful to ensure high specificity; however, certain mismatch can be tolerated. For example, a nucleic acid primer or a pair of nucleic acid primers as described above can be used in a method for detecting the presence of a gene fusion-associated cancer in a subject. In one embodiment, primers can be used to detect an FGFR fusion molecule, such as a primer comprising SEQ ID NOS: 80-82, 84, 94-145, 515, 517, 519-527, or 530-538; or a combination thereof. In another embodiment, the PCR primers comprise SEQ ID NOS: 162, 163, 164, 165, 166, 167, 168, 169, 495, 496, 497, 498, 507, 508, 509, 510, 511, 512, 513, or 514. Ina further embodiment, primers used for the screening of FGFR fusion molecules, such as FGFR-TACC fusions, comprise SEQ ID NOS: 166, 167, 168, 169, 495, 496, 497, 498, 507, 508, 509, or 510. In some embodiments, primers used for genomic detection of an FGFR3-TACC3 fusion comprise SEQ ID NOS: 170, 171, 499, 500, 501, 502, 503, 504, 505, or 506. In one embodiment, the method can comprise contacting a sample from the subject with primers specific for a FGFR fusion molecule, and determining the presence of an PCR product. In another embodiment, the method can comprise contacting a sample from the subject with primer specific for a FGFR molecule, or a TACC molecule, and determining the presence of a PCR product. In another embodiment, the primers can recognize the nucleic acids encoding a FGFR3 C-terminal region, or nucleic acids encoding a TACC3 N-terminal region, or a combination thereof. In another embodiment, the method can comprise contacting a sample from the subject with primers specific for a FGFR molecule, or a TACC molecule, or a FGFR fusion molecule, and determining the amount of PCR product formed compared to the amount of PCR product formed in non-tumor cells or tissue, wherein an increased amount of PCR product indicates the presence of an FGFR fusion. In one embodiment, primers and/or the PCR product are labeled to enable detection of the PCR product. For example, nucleic acid primers useful for amplifying sequences corresponding to a FGFR fusion molecules can be labeled with fluorescent molecules, radioactive molecules, chemiluminescent molecules, or affinity molecules (e.g. biotin) which can then be detected by methods known in the art (e.g. fluorescently labeled streptavidin). PCR products can also be detected by using dyes that can be incorporated into newly formed PCR products, such as, but not limited to, SYBR Green.

Specific Ligand Binding. As discussed herein, a nucleic acid encoding a FGFR fusion molecule or expression of a FGFR fusion molecule, can also be detected by screening for alteration(s) in a sequence or expression level of a polypeptide encoded by the same. Different types of ligands can be used, such as specific antibodies. In one embodiment, the sample is contacted with an antibody specific for a polypeptide encoded by a FGFR fusion molecule and the formation of an immune complex is subsequently determined. Various methods for detecting an immune complex can be used, such as ELISA, immunostaining, radioimmunoassays (RIA) and immuno-enzymatic assays (IEMA).

For example, an antibody can be a polyclonal antibody, a monoclonal antibody, as well as fragments or derivatives thereof having substantially the same antigen specificity. Fragments include Fab, Fab'2, or CDR regions. Derivatives include single-chain antibodies, humanized antibodies, or poly-functional antibodies. An antibody specific for a polypeptide encoded by a FGFR fusion molecule can be an antibody that selectively binds such a polypeptide. In one embodiment, the antibody is raised against a polypeptide encoded by a FGFR fusion molecule (such as FGFR1-TACC1, FGFR2-TACC2, FGFR3-TACC3 or other FGFR-TACC fusion) or an epitope-containing fragment thereof. Although non-specific binding towards other antigens can occur, binding to the target polypeptide occurs with a higher affinity and can be reliably discriminated from non-specific binding. In one embodiment, the method can comprise contacting a sample from the subject with an antibody specific for a FGFR fusion molecule, and determining the presence of an immune complex. Optionally, the sample can be contacted to a support coated with antibody specific for a FGFR fusion molecule. In one embodiment, the sample can be contacted simultaneously, or in parallel, or sequentially, with various antibodies specific for different forms of a FGFR fusion molecule, e.g., FGFR1-TACC1, FGFR2-TACC2, FGFR3-TACC3 or other FGFR-TACC fusion.

In one embodiment, the method can comprise contacting a sample from the subject with an antibody specific for a FGFR fusion molecule, and determining the presence of an immune complex. In another embodiment, the method can comprise contacting a sample from the subject with an antibody specific for a FGFR molecule, or a TACC molecule, and determining the presence of an immune complex. In another embodiment, the antibody can recognize the FGFR3 C-terminal region, or the TACC3 N-terminal region, or a combination thereof. In another embodiment, the antibody can recognize the FGFR3 C-terminal region, or the TACC3 N-terminal region, or a combination thereof. In another embodiment, the method can comprise contacting a sample from the subject with an antibody specific for a FGFR molecule, or a TACC molecule, or a FGFR fusion molecule, and determining the amount of an immune complex formed compared to the amount of immune complex formed in non-tumor cells or tissue, wherein an increased amount of an immune complex indicates the presence of an FGFR fusion.

Detection the formation of a complex between an antibody and a protein can be performed by a variety of method known in the art. For example, an antibody-protein complex can be detected by using antibodies or secondary antibodies labeled with fluorescent molecules, chromogenic molecules, chemiluminescent molecules, radioactive isotopes, or affinity molecules (e.g. biotin) which can then be detected by methods known in the art (e.g. fluorescently labeled streptavidin).

The invention also provides for a diagnostic kit comprising products and reagents for detecting in a sample from a subject the presence of a FGFR fusion molecule. The kit can be useful for determining whether a sample from a subject exhibits increased or reduced expression of a FGFR fusion molecule. For example, the diagnostic kit according to the present invention comprises any primer, any pair of primers, any nucleic acid probe and/or any ligand, or any antibody directed specifically to a FGFR fusion molecule. The diagnostic kit according to the present invention can further comprise reagents and/or protocols for performing a hybridization, amplification, or antigen-antibody immune reaction. In one embodiment, the kit can comprise nucleic acid primers that specifically hybridize to and can prime a polymerase reaction from a FGFR fusion molecule comprising SEQ ID NOS: 80-82, 84, 94-145, 515, 517, 519-527, or 530-538, or a combination thereof. In one embodiment, primers can be used to detect a FGFR fusion molecule, such as a primer directed to SEQ ID NOS: 80-82, 84, 94-145, 515, 517, 519-527, or 530-538; or a combination thereof. In another embodiment, the PCR primer comprises SEQ ID NOS: 162, 163, 164, 165, 166, 167, 168, 169, 495, 496, 497, 498, 507, 508, 509, 510, 511, 512, 513, or 514. Ina further embodiment, primers used for the screening of FGFR fusion molecules, such as FGFR-TACC fusions, comprise SEQ ID NOS: 166, 167, 168, 169, 495, 496, 497, 498, 507, 508, 509, or 510. In some embodiments, primers used for genomic detection of an FGFR3-TACC3 fusion comprise SEQ ID NOS: 170, 171, 499, 500, 501, 502, 503, 504, 505, or 506. In some embodiments, the kit comprises an antibody that specifically binds to a FGFR fusion molecule comprising SEQ ID NOS: 79, 85-89, 150, 158-161, or 539-547, wherein the antibody will recognize the protein only when a FGFR fusion molecule is present. The diagnosis methods can be performed in vitro, ex vivo, or in vivo. These methods utilize a sample from the subject in order to assess the status of a FGFR fusion molecule. The sample can be any biological sample derived from a subject, which contains nucleic acids or polypeptides. Examples of such samples include, but are not limited to, fluids, tissues, cell samples, organs, and tissue biopsies. Non-limiting examples of samples include blood, liver, plasma, serum, saliva, urine, or seminal fluid. In some embodiments the sample is a tissue sample. In some embodiments, the sample is a paraffin embedded tissue section. In some embodiments, the tissue sample is a tumor sample. The sample can be collected according to conventional techniques and used directly for diagnosis or stored. The sample can be treated prior to performing the method, in order to render or improve availability of nucleic acids or polypeptides for testing. Treatments include, for instance, lysis (e.g., mechanical, physical, or chemical), centrifugation. The nucleic acids and/or polypeptides can be pre-purified or enriched by conventional techniques, and/or reduced in complexity. Nucleic acids and polypeptides can also be treated with enzymes or other chemical or physical treatments to produce fragments thereof. In one embodiment, the sample is contacted with reagents, such as probes, primers, or ligands, in order to assess the presence of a FGFR fusion molecule. Contacting can be performed in any suitable device, such as a plate, tube, well, or glass. In some embodiments, the contacting is performed on a substrate coated with the reagent, such as a nucleic acid array or a specific ligand array. The substrate can be a solid or semi-solid substrate such as any support comprising glass, plastic, nylon, paper, metal, or polymers. The substrate can be of various forms and sizes, such as a slide, a membrane, a bead, a column, or a gel. The contacting can be made under any condition suitable for a complex to be formed between the reagent and the nucleic acids or polypeptides of the sample.

Nucleic Acid Delivery Methods

Delivery of nucleic acids into viable cells can be effected ex vivo, in situ, or in vivo by use of vectors, such as viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (See, for example, Anderson, *Nature,* 1998) supplement to 392 (6679):250. Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., (1992) *J Gen Virol.* 73(Pt 6):1533-6), adenovirus (Berkner (1992) *Curr Top Microbiol Immunol.* 158: 39-66; Berkner (1988) *Biotechniques,* 6(7):616-29; Gorziglia and Kapikian (1992) *J Virol.* 66(7):4407-12; Quantin et al., (1992) *Proc Natl Acad Sci USA.* 89(7):2581-4; Rosenfeld et al., (1992) *Cell.* 68(1):143-55; Wilkinson et al., (1992) *Nucleic Acids Res.* 20(9):2233-9; Stratford-Perricaudet et al., (1990) *Hum Gene Ther.* 1(3):241-56), vaccinia virus (Moss (1992) *Curr Opin Biotechnol.* 3(5):518-22), adeno-associated virus (Muzyczka, (1992) *Curr Top Microbiol Immunol.* 158:97-129; Ohi et al., (1990) *Gene.* 89(2): 279-82), herpesviruses including HSV and EBV (Margolskee (1992) *Curr Top Microbiol Immunol.* 158:67-95; Johnson et al., (1992) *Brain Res Mol Brain Res.* 12(1-3): 95-102; Fink et al., (1992) *Hum Gene Ther.* 3(1):11-9; Breakefield and Geller (1987) *Mol Neurobiol.* 1(4):339-71; Freese et al., (1990) *Biochem Pharmacol.* 40(10):2189-99), and retroviruses of avian (Bandyopadhyay and Temin (1984) *Mol Cell Biol.* 4(4):749-54; Petropoulos et al., (1992) *J Virol.* 66(6):3391-7), murine (Miller et al. (1992) *Mol Cell Biol.* 12(7):3262-72; Miller et al., (1985) *J Virol.* 55(3):521-6; Sorge et al., (1984) *Mol Cell Biol.* 4(9):1730-7; Mann and Baltimore (1985) *J Virol.* 54(2):401-7; Miller et al., (1988) *J Virol.* 62(11):4337-45), and human origin (Shimada et al., (1991) *J Clin Invest.* 88(3):1043-7; Helseth et al., (1990) *J Virol.* 64(12):6314-8; Page et al., (1990) *J Virol.* 64(11): 5270-6; Buchschacher and Panganiban (1992) *J Virol.* 66(5): 2731-9).

Non-limiting examples of in vivo gene transfer techniques include transfection with viral (e.g., retroviral) vectors (see U.S. Pat. No. 5,252,479, which is incorporated by reference in its entirety) and viral coat protein-liposome mediated transfection (Dzau et al., (1993) *Trends in Biotechnology* 11:205-210), incorporated entirely by reference). For example, naked DNA vaccines are generally known in the art; see Brower, (1998) *Nature Biotechnology,* 16:1304-1305, which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of nucleic acid delivery protocols and methods see Anderson et al. (1992) *Science* 256:808-813; U.S. Pat. Nos. 5,252,479, 5,747,469, 6,017,524, 6,143,290, 6,410,010 6,511,847; and U.S. Application Publication No. 2002/0077313, which are all hereby incorporated by reference in their entireties. For additional reviews, see Friedmann (1989) *Science,* 244:1275-1281; Verma, *Scientific American:* 68-84 (1990); Miller (1992) *Nature,* 357: 455-460; Kikuchi et al. (2008) *J Dermatol Sci.* 50(2):87-98; Isaka et al. (2007) *Expert Opin Drug Deliv.* 4(5):561-71; Jager et al. (2007) *Curr Gene Ther.* 7(4):272-83; Waehler et al. (2007) *Nat Rev Genet.* 8(8):573-87; Jensen et al. (2007) *Ann Med.* 39(2):108-15; Herweijer et al. (2007) *Gene Ther.* 14(2):99-107; Eliyahu et al. (2005) *Molecules* 10(1):34-64; and Altaras et al. (2005) *Adv Biochem Eng Biotechnol.* 99:193-260, all of which are hereby incorporated by reference in their entireties.

A FGFR fusion nucleic acid can also be delivered in a controlled release system. For example, the FGFR fusion molecule can be administered using intravenous infusion, an implantable osmotic pump, a transdermal patch, liposomes, or other modes of administration. In one embodiment, a pump can be used (see Sefton (1987) *Biomed. Eng.* 14:201; Buchwald et al. (1980) *Surgery* 88:507; Saudek et al. (1989) *N. Engl. J. Med.* 321:574). In another embodiment, polymeric materials can be used (see *Medical Applications of*

*Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target thus requiring only a fraction of the systemic dose (see, e.g., Goodson, in *Medical Applications of Controlled Release*, supra, vol. 2, pp. 115-138 (1984)). Other controlled release systems are discussed in the review by Langer (*Science* (1990) 249:1527-1533).

Pharmaceutical Compositions and Administration for Therapy

An inhibitor of the invention can be incorporated into pharmaceutical compositions suitable for administration, for example the inhibitor and a pharmaceutically acceptable carrier A FGFR fusion molecule or inhibitor of the invention (e.g. JNJ-42756493) can be administered to the subject once (e.g., as a single injection or deposition). Alternatively, a FGFR fusion molecule or inhibitor can be administered once or twice daily to a subject in need thereof for a period of from about two to about twenty-eight days, or from about seven to about ten days. A FGFR fusion molecule or inhibitor can also be administered once or twice daily to a subject for a period of 1, 2, 3, 4, 5, 6, 7, 8, 9, 10, 11, 12 times per year, or a combination thereof. A FGFR fusion molecule or inhibitor can also be administered in seven to ten day repeating cycles (i.e. administration of a FGFR fusion molecule or inhibitor for seven to ten days, followed by no administration of a FGFR fusion molecule or inhibitor for seven to ten days). Furthermore, a FGFR fusion molecule or inhibitor of the invention can be co-administrated with another therapeutic. Where a dosage regimen comprises multiple administrations, the effective amount of the FGFR fusion molecule or inhibitor administered to the subject can comprise the total amount of gene product administered over the entire dosage regimen.

A FGFR fusion molecule or inhibitor can be administered to a subject by any means suitable for delivering the FGFR fusion molecule or inhibitor to cells of the subject, such as cancer cells, e.g., glioblastoma multiforme, breast cancer, lung cancer, prostate cancer, colorectal carcinoma, bladder carcinoma, squamous lung carcinoma, head and neck carcinoma, glioma, grade II or III glioma, or IDH wild-type grade II or III glioma. For example, a FGFR fusion molecule or inhibitor can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery; bioballistic or particle acceleration; calcium phosphate precipitation, and transfection mediated by viral vectors.

The compositions of this invention can be formulated and administered to reduce the symptoms associated with a gene fusion-associated cancer, e.g., glioblastoma multiforme, breast cancer, lung cancer, prostate cancer, colorectal carcinoma, bladder carcinoma, squamous lung carcinoma, head and neck carcinoma, glioma, grade II or III glioma, or IDH wild-type grade II or III glioma, by any means that produces contact of the active ingredient with the agent's site of action in the body of a subject, such as a human or animal (e.g., a dog, cat, or horse). They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

A therapeutically effective dose of FGFR fusion molecule or inhibitor (e.g. JNJ-42756493) can depend upon a number of factors known to those or ordinary skill in the art. The dose(s) of the FGFR fusion molecule inhibitor can vary, for example, depending upon the identity, size, and condition of the subject or sample being treated, further depending upon the route by which the composition is to be administered, if applicable, and the effect which the practitioner desires the a FGFR fusion molecule inhibitor to have upon the nucleic acid or polypeptide of the invention. For example, 12 mg of JNJ-42756493 can be orally administered daily. JNJ-42756493 can be administered in seven to ten day repeating cycles (i.e. administration of JNJ-42756493 for seven to ten days, followed by no administration of JNJ-42756493 for seven to ten days). These amounts can be readily determined by a skilled artisan. Any of the therapeutic applications described herein can be applied to any subject in need of such therapy, including, for example, a mammal such as a dog, a cat, a cow, a horse, a rabbit, a monkey, a pig, a sheep, a goat, or a human.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A pharmaceutical composition containing FGFR fusion molecule inhibitor can be administered in conjunction with a pharmaceutically acceptable carrier, for any of the therapeutic effects discussed herein. Such pharmaceutical compositions can comprise, for example antibodies directed to a FGFR fusion molecule, or a variant thereof, or antagonists of a FGFR fusion molecule, or JNJ-42756493. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

Sterile injectable solutions can be prepared by incorporating the FGFR fusion molecule inhibitor (e.g., a polypeptide or antibody) in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

In some embodiments, the FGFR fusion molecule inhibitor can be applied via transdermal delivery systems, which slowly releases the active compound for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

"Subcutaneous" administration can refer to administration just beneath the skin (i.e., beneath the dermis). Generally, the subcutaneous tissue is a layer of fat and connective tissue that houses larger blood vessels and nerves. The size of this layer varies throughout the body and from person to person. The interface between the subcutaneous and muscle layers can be encompassed by subcutaneous administration. This mode of administration can be feasible where the subcutaneous layer is sufficiently thin so that the factors present in the compositions can migrate or diffuse from the locus of administration. Thus, where intradermal administration is utilized, the bolus of composition administered is localized proximate to the subcutaneous layer.

Administration of the cell aggregates (such as DP or DS aggregates) is not restricted to a single route, but can encompass administration by multiple routes. For instance, exemplary administrations by multiple routes include, among others, a combination of intradermal and intramuscular administration, or intradermal and subcutaneous administration. Multiple administrations can be sequential or concurrent. Other modes of application by multiple routes will be apparent to the skilled artisan.

In other embodiments, this implantation method will be a one-time treatment for some subjects. In further embodiments of the invention, multiple cell therapy implantations will be required. In some embodiments, the cells used for implantation will generally be subject-specific genetically engineered cells. In another embodiment, cells obtained from a different species or another individual of the same species can be used. Thus, using such cells can require administering an immunosuppressant to prevent rejection of the implanted cells. Such methods have also been described in U.S. Pat. No. 7,419,661 and PCT application publication WO 2001/32840, and are hereby incorporated by reference.

A pharmaceutical composition of the invention is formulated to be compatible with its intended route of administration. Examples of routes of administration include parenteral, e.g., intravenous, intradermal, subcutaneous, oral (e.g., inhalation or ingestion), transdermal (topical), transmucosal, and rectal administration. For example, JNJ-42756493 can be orally administered. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the inhibitor (e.g., a polypeptide or antibody or small molecule) of the invention in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions (e.g. of JNJ-42756493) generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier and subsequently swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the effective amount of the administered FGFR fusion molecule inhibitor (e.g. JNJ-42756493) is at least about 0.0001 µg/kg body weight, at least about 0.00025 µg/kg body weight, at least about 0.0005 µg/kg body weight, at least about 0.00075 µg/kg body weight, at least about 0.001 µg/kg body weight, at least about 0.0025 µg/kg body weight, at least about 0.005 µg/kg body weight, at least about 0.0075 µg/kg body weight, at least about 0.01 µg/kg body weight, at least about 0.025 µg/kg body weight, at least about 0.05 µg/kg body weight, at least about 0.075 µg/kg body weight, at least about 0.1 pig/kg body weight, at least about 0.25 µg/kg body weight, at least about 0.5 µg/kg body weight, at least about 0.75 µg/kg body weight, at least about 1 µg/kg body weight, at least about 5 µg/kg body weight, at least about 10 µg/kg body weight, at least about 25 µg/kg body weight, at least about 50 µg/kg body weight, at least about 75 µg/kg body weight, at least about 100 µg/kg body weight, at least about 150 µg/kg body weight, at least about 200 µg/kg body weight, at least about 250 µg/kg body weight, at least about 300 µg/kg body weight, at least about 350 µg/kg body weight, at least about 400 µg/kg body weight, at least about 450 µg/kg body weight, at least about 500 µg/kg body weight, at least about 550 µg/kg body weight, at least about 600 µg/kg body weight, at least about 650 µg/kg body weight, at least about 700 µg/kg body weight, at least about 750 µg/kg body weight, at least about 800 µg/kg body weight, at least about 850 µg/kg body weight, at least about 900 µg/kg body weight, at least about 950 µg/kg body weight, at least about 1,000 µg/kg body weight, at least about 2,000 µg/kg body weight, at least about 3,000 µg/kg body weight, at least about 4,000 µg/kg body weight, at least about 5,000 µg/kg body weight, at least about 6,000 µg/kg body weight, at least about 7,000 µg/kg body weight, at least about 8,000 µg/kg body weight, at least about 9,500 µg/kg body weight, or at least about 10,000 µg/kg body weight.

In some embodiments, the effective amount of the administered FGFR fusion molecule inhibitor (e.g. JNJ-42756493) is at least about 1 mg, 2 mg, 3 mg, 4 mg, 5 mg, 6 mg, 7 mg, 8 mg, 9 mg, 10 mg, 11 mg, 12 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

The invention is further illustrated in Singh et al., Science (2012), 337(6099):1231-5 (including the accompanying Supplementary Information). The entire contents of Singh et al., Science (2012), 337(6099):1231-5, including the accompanying "Supplementary Information," is expressly incorporated by reference. The invention is also further illustrated in Di Stefano et al., "Detection, characterization and inhibition of FGFR-TACC fusions in IDH wild type glioma" Clin. Cancer Res. (2015), the entire contents of which are expressly incorporated by reference.

Example 1: Transforming and Recurrent Fusions of FGFR and TACC Gene in Glioblastoma The history of successful targeted therapy of cancer largely coincides with the inactivation of recurrent, oncogenic and addicting gene fusions in hematological malignancies and recently in some types of epithelial cancer. Glioblastoma multiforme (GBM) is among the most lethal forms of human cancer. Here, an integrated gene fusion discovery pipeline was developed for the detection of in-frame fused transcripts from RNA-seq and genomic fusions from whole exome sequences. The application of the pipeline to human GBM unraveled recurrent chromosomal translocations, which fuse in-frame the tyrosine kinase domain of FGFR genes (FGFR1 or FGFR3) to the TACC domain of TACC1 or TACC3, respectively. The frequency of FGFR-TACC fusions is 3 of 97 GBM (3.1%). The FGFR-TACC fusion protein displays strong oncogenic activity when introduced into astrocytes or transduced by lentivirus-mediated stereotactic delivery to the adult mouse brain. The FGFR-TACC fusion protein mis-localizes over the mitotic spindle pole, has constitutive tyrosine kinase activity and dysregulates the mitotic cycle with delayed mitotic progression. The impaired mitotic fidelity triggers chromatid cohesion defects, defective spindle checkpoint activation, chromosomal mis-segregation, and rampant aneuploidy. Inhibition of FGFR kinase corrects the aneuploidy and oral administration of a specific FGFR tyrosine kinase inhibitor under clinical investigation arrests tumor growth and prolongs survival of mice harboring intracranial FGFR3-TACC3-initiated glioma. FGFR-TACC fusions identify a subset of GBM patients who may benefit from targeted inhibition of the tyrosine kinase activity of FGFR.

Glioblastoma multiforme (GBM) is among the most difficult forms of cancer to treat in humans (Ohgaki and Kleihues, 2005). So far, the targeted therapeutic approaches that have been tested against potentially important oncogenic drivers in GBM have met limited success (Lo, 2010; Reardon et al., 2010; van den Bent et al., 2009). Recurrent chromosomal translocations leading to production of oncogenic fusion proteins are viewed as initiating and addicting events in the pathogenesis of human cancer, thus providing the most desirable molecular targets for cancer therapy (Ablain et al., 2011; Mitelman et al., 2007). Chromosomal rearrangements resulting in recurrent and oncogenic gene fusions are hallmarks of hematological malignancies and recently they have also been uncovered in subsets of solid tumors (breast, prostate, lung and colorectal carcinoma), but they have not been found in GBM (Bass et al., 2011; Prensner and Chinnaiyan, 2009). Important and successful targeted therapeutic interventions for patients whose tumors carry these rearrangements have stemmed from the discovery of functional gene fusions, especially when the translocations involve kinase-coding genes (BCR-ABL, EML4-ALK) (Druker, 2009; Gerber and Minna, 2010).

A hallmark of GBM is rampant chromosomal instability (CIN), which leads to aneuploidy (Furnari et al., 2007). CIN and aneuploidy are early events in the pathogenesis of cancer (Cahill et al., 1999). It has been suggested that genetic alterations targeting mitotic fidelity might be responsible for mis-segregation of chromosomes during mitosis, resulting in aneuploidy (Gordon et al., 2012; Solomon et al., 2011). Here, the first cases of recurrent and oncogenic gene fusions in human GBM are described. The resulting fusion protein localizes to mitotic cells, disrupts the normal control of chromosome segregation and induces aneuploidy. A therapeutic strategy with FGFR tyrosine kinase inhibitors is also reported for the targeted therapy of GBM patients harboring these chromosomal rearrangements.

Figure 8:
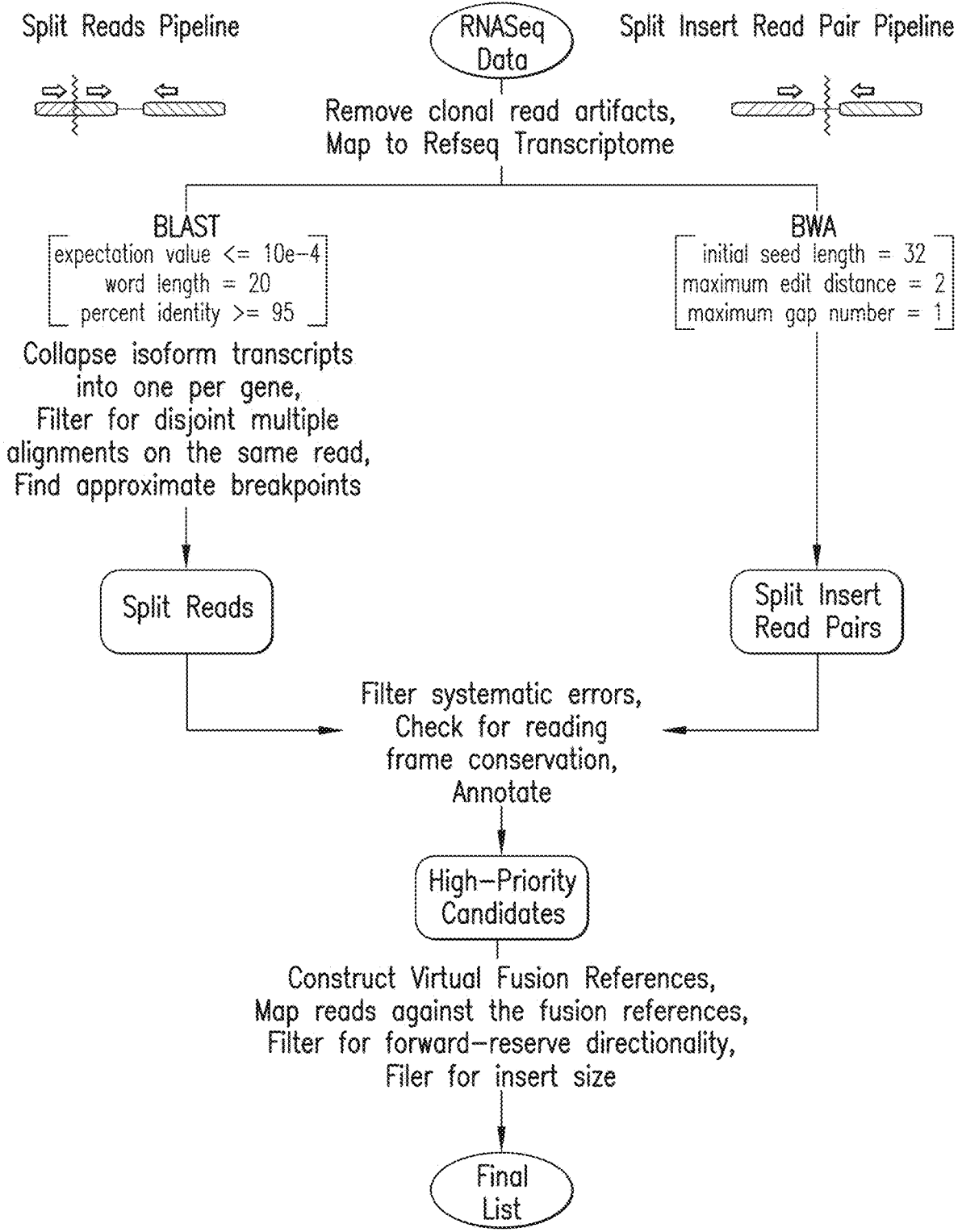
FIG. 8 shows a schematic of the TX-Fuse pipeline for the identification of fusion transcripts from RNA-Seq data generated from nine GSC cultures. The continued figure shows a schematic of the Exome-Fuse pipeline for the identification of gene fusion rearrangements from DNA exome sequences of 84 GBM TCGA tumor samples.
Figure 9A:
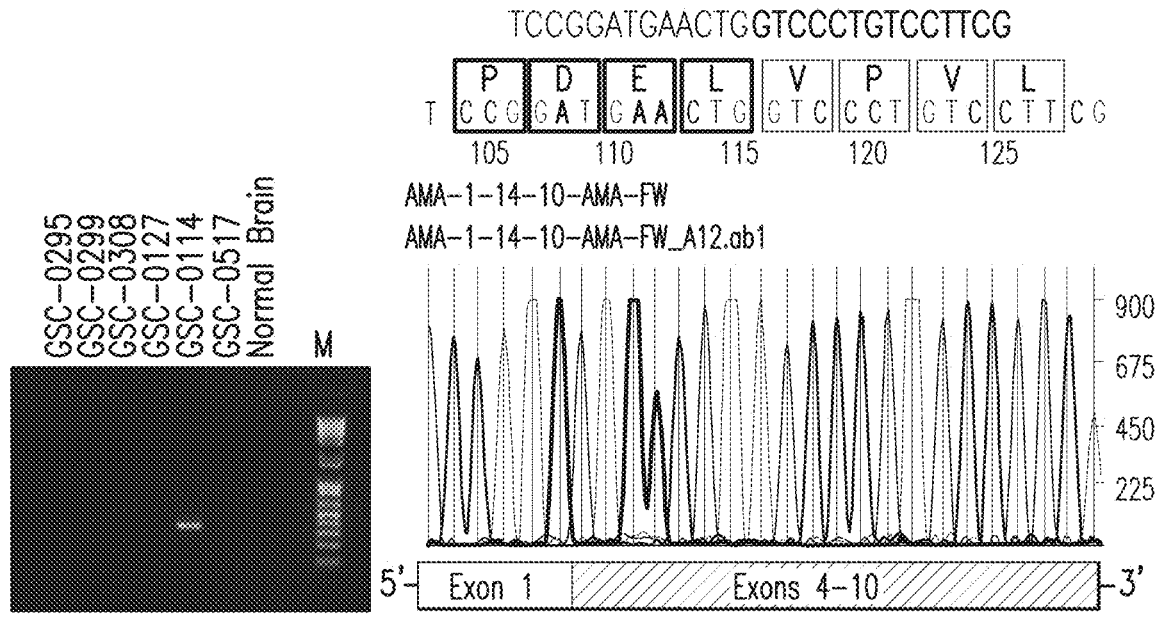
FIGS. 9A-D shows the validation of fusion transcripts identified by RNA-seq of nine GSCs. Sanger sequencing chromatograms show the reading frames at the breakpoint and putative translation of the fusion proteins in the positive samples (right side). The left side shows gels of RT-PCR conducted. (A) POLR2A-WRAP53. DNA sequence disclosed as SEQ ID NO: 319 and protein sequence disclosed as SEQ ID NO: 320. (B) CAPZB-UBR4. DNA sequence disclosed as SEQ ID NO: 321 and protein sequence disclosed as SEQ ID NO: 322. (C) ST8SIA4-PAM. DNA sequence disclosed as SEQ ID NO: 323 and protein sequence disclosed as SEQ ID NO: 324. (D) PIGU-NCOA6. DNA sequence disclosed as SEQ ID NO: 325 and protein sequence disclosed as SEQ ID NO: 326.
Figure 9B:
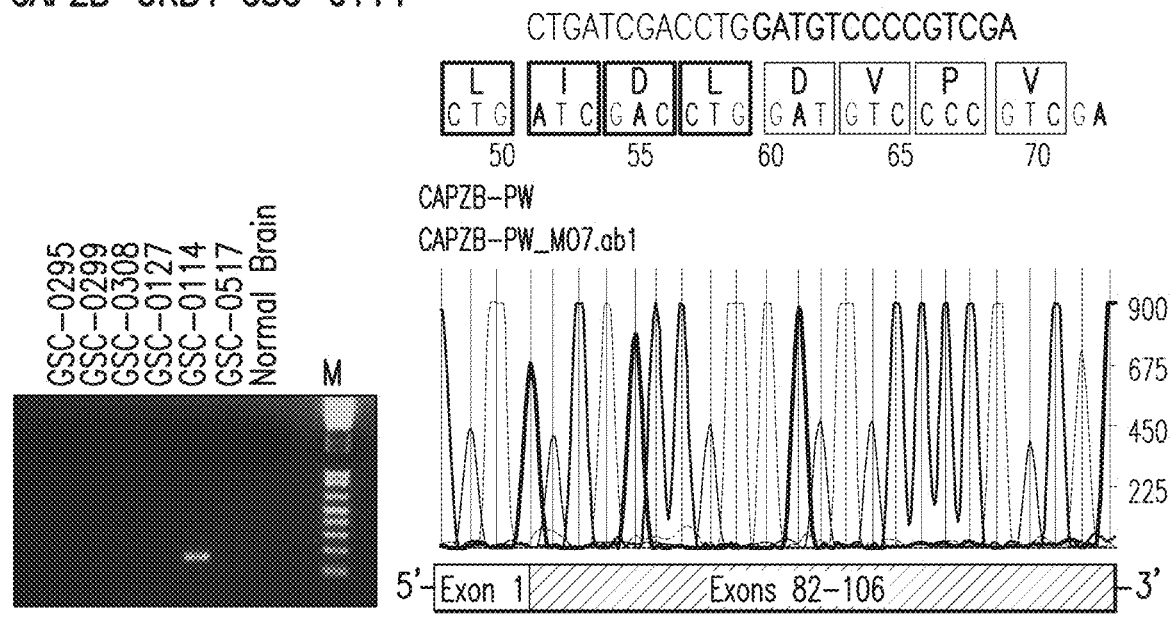
Figure 9C:
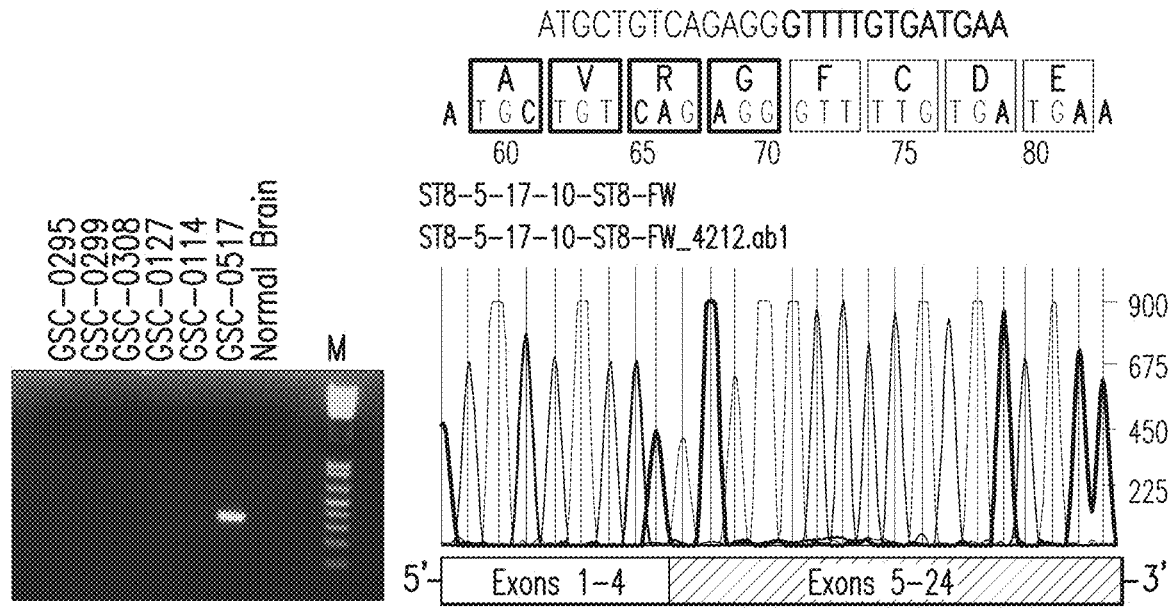
Figure 9D:
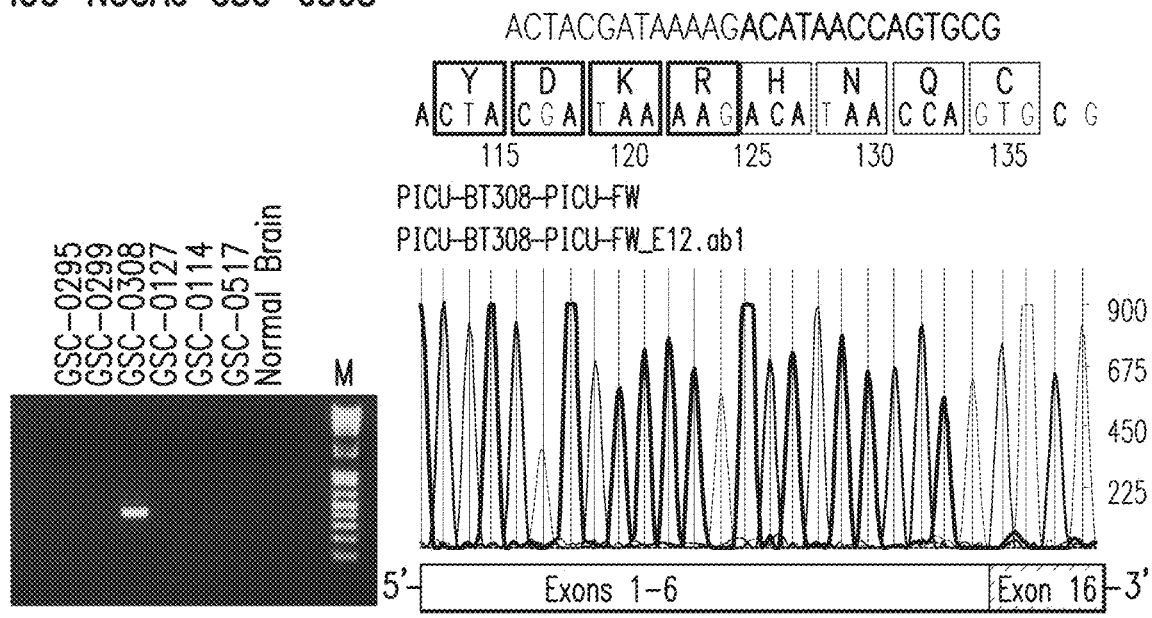

Identification of recurrent fusions of FGFR and TACC genes. To identify genomic rearrangements in GBM that generate functional fusion proteins and are recurrent, gene pairs discovered as in-frame fused transcripts from the analysis of massively parallel, paired-end sequencing of expressed transcripts (RNA-seq) would also emerge as fused gene pairs from the genomic analysis of human GBM. Towards this aim, two complementary gene fusion discovery methods were devised and were applied to two GBM cohorts. The first, TX-Fuse, is an algorithm for the discovery of candidate fusion transcripts from RNA-seq (FIG. 8). The second, Exome-Fuse, detects fusion genes from whole exome DNA sequences (FIG. 8). As first step for the detection of fused transcripts, RNA-seq data was generated from short-term cultures of glioma stem-like cells (GSCs) freshly isolated from nine patients carrying primary GBM. The culture of primary GBM tumors under serum-free conditions selects cells that retain phenotypes and genotypes closely mirroring primary tumor profiles as compared to serum-cultured glioma cell lines that have largely lost their developmental identities (Lee et al., 2006). Therefore, without being bound by theory, if glioma cells carry gene fusions causally responsible for the most aggressive hallmarks of GBM, they should be selected in GSCs. RNA-seq generated an average of 60.3 million paired reads for each GSC culture, of which over 80% were mapped to the reference transcriptome and genome. TX-Fuse detects two main sources of evidence: split reads and split inserts (see Experimental Procedures). The application of TX-Fuse to the RNA-seq dataset from nine GSCs led to the discovery of five candidate rearrangements (all of which were intrachromosomal) that give rise to in-frame fusion transcripts (Table 1B).

TABLE 1B

Predicted in-frame fusion proteins from RNA-Seq of nine GSCs

| # Split Inserts | # Split Reads | Sample | Gene 1 | Gene 2 | Ref Seq 1 | Ref Seq 2 | Tx Pos 1 | Tx Pos 2 |
|---|---|---|---|---|---|---|---|---|
| 294 | 76 | GSC-1123 | FGFR3 | TACC3 | NM_000142 | NM_006342 | 2530 | 1751 |
| 37 | 54 | GSC-0114 | POLR2A | WRAP53 | NM_000937 | NM_001143990 | 479 | 798 |
| 7 | 48 | GSC-0114 | CAPZB | UBR4 | NM_001206540 | NM_020765 | 228 | 12111 |
| 8 | 29 | GSC-0517 | ST8SIA4 | PAM | NM_005668 | NM_000919 | 1125 | 730 |
| 6 | 17 | GSC-0308 | PIGU | NCOA6 | NM_080476 | NM_014071 | 729 | 6471 |
| 1 | 6 | GSC-0127 | IFNAR2 | IL10RB | NM_000874 | NM_000628 | 1083 | 149 |

| # Split Inserts | # Split Reads | Sample | Chr 1 | Strand 1 | hg19_GenPos 1 | Chr 2 | Strand 2 | hg19_GenPos 2 |
|---|---|---|---|---|---|---|---|---|
| 294 | 76 | GSC-1123 | 4 | + | 1808842 | 4 | + | 1737004 |
| 37 | 54 | GSC-0114 | 17 | + | 7399259 | 17 | + | 7604059 |
| 7 | 48 | GSC-0114 | 1 | − | 19712098 | 1 | − | 19433440 |
| 8 | 29 | GSC-0517 | 5 | − | 100147809 | 5 | + | 102260661 |
| 6 | 17 | GSC-0308 | 20 | − | 33203914 | 20 | − | 33303130 |
| 1 | 6 | GSC-0127 | 21 | + | 34632901 | 21 | + | 34640699 |

Next, genomic rearrangements leading to gene fusions were identified in GBM by applying Exome-Fuse to a dataset of paired-end exome DNA sequences from 84 GBM samples from TCGA (Table 2).

This analysis detected 147 paired gene fusions, thus producing an average of 1.75 gene fusion events per tumor (Table 3).

The FGFR and TACC families of genes were markedly enriched among those recurrently involved in genomic fusions, with eight tumors harboring FGFR rearrangements and seven tumors harboring fusions that implicate TACC genes (FIG. 1A). The comparative analysis of the TX-Fuse and Exon-Fuse outputs revealed that FGFR3-TACC3 was the only fusion pair identified as either an in-frame transcript by TX-Fuse and genomic fusions by Exome-Fuse (Tables 1B, 2 and 3).

Table 2 shows fusion breakpoint information of recurrent gene fusions identified by Exome-fuse analysis of 84 GBM from TCGA. As multiple junctions may exist in each fusion candidate, information for all breakpoints is displayed. Column definitions include: sample=TCGA sample ID, virtForSplitReads/virtRevSplitReads/virtTotSplitReads=#forward/reverse/total split reads, splitInserts=#split inserts, dirA/dirB=forward (1) or reverse (0) direction of split read portion mapping to gene A/B, dirAB matepair=direction of mate pair of split read, cosmicA+B=#recorded mutations of gene A+B in COSMIC.

TABLE 2

Fusion breakpoint information of recurrent gene fusions identified by Exome-fuse analysis of 84 GBM from TCGA.

| Sample | virtForSplitReads | virRevSplitReads | virtTortSplitReads | splitinsorts | geneA | chrA | senseA |
|---|---|---|---|---|---|---|---|
| TGCA-06-6390 | 10 | 9 | 19 | 8 | FGFR3 | chr4 | + |
| TCGA-12-0826 | 5 | 6 | 11 | 5 | FGFR3 | chr4 | + |
| TCGA-19-5958 | 3 | 0 | 3 | 2 | FGFR3 | chr4 | + |
| TCGA-27-1835 | 11 | 1 | 12 | 4 | FGFR3 | chr4 | + |
| TCGA-12-0820 | 7 | 2 | 9 | 4 | FGFR3 | chr4 | + |
| TCGA-12-1088 | 3 | 1 | 4 | 4 | ABL1 | chr9 | + |
| TCGA-06-1802 | 7 | 1 | 3 | 8 | ADAM12 | chr10 | − |
| TCGA-06-1801 | 7 | 0 | 7 | 5 | HIP1 | chr7 | − |
| TCGA-12-1088 | 3 | 0 | 3 | 3 | KIDINS220 | chr2 | − |
| TCGA-12-1088 | 37 | 1 | 38 | 10 | KIDINS220 | chr2 | − |
| TCGA-32-2491 | 2 | 17 | 19 | 6 | ODZ1 | chrX | − |
| TCGA-32-2491 | 11 | 1 | 12 | 10 | ODZ1 | chrX | − |
| TCGA-12-0829 | 24 | 0 | 24 | 13 | LRRK2 | chr12 | + |
| TCGA-12-0329 | 25 | 1 | 26 | 13 | LRRK2 | chr12 | + |
| TCGA-12-0829 | 87 | 16 | 103 | 58 | LRRK2 | chr12 | + |
| TCGA-19-0957 | 3 | 2 | 5 | 6 | NUDT19 | chr19 | + |
| TCGA-12-1088 | 12 | 1 | 13 | 5 | GLI3 | chr7 | − |
| TCGA-12-1088 | 5 | 0 | 5 | 1 | GLI3 | chr7 | − |
| TCGA-12-1089 | 10 | 0 | 10 | 5 | AHNAK | chr11 | − |
| TCGA-06-1801 | 27 | 1 | 28 | 12 | CROCC | chr1 | + |
| TCGA-12-1089 | 12 | 1 | 13 | 6 | CLK3 | chr15 | + |
| TCGA-12-1089 | 14 | 2 | 16 | 8 | CLK3 | chr15 | + |
| TCGA-12-1089 | 42 | 5 | 47 | 24 | LAMA2 | chr6 | + |
| TCGA-06-1802 | 48 | 9 | 57 | 27 | LAMA2 | chr6 | + |
| TCGA-19-0957 | 4 | 16 | 20 | 6 | CSMD2 | chr1 | − |
| TCGA-06-1801 | 21 | 1 | 22 | 4 | FAM192A | chr16 | − |
| TCGA-12-1089 | 27 | 0 | 27 | 2 | FGFR4 | chr5 | + |
| TCGA-19-0957 | 0 | 1 | 1 | 4 | EML1 | chr14 | + |
| TCGA-06-1801 | 19 | 133 | 152 | 51 | NHSL2 | chrX | + |
| TCGA-06-1801 | 51 | 3 | 54 | 8 | NHSL2 | chrX | + |
| TCGA-12-1089 | 9 | 0 | 9 | 4 | CACNA1C | chr12 | + |
| TCGA-19-0957 | 8 | 1 | 9 | 0 | CDH11 | chr16 | − |
| TCGA-12-0829 | 12 | 3 | 15 | 4 | ENTPD2 | chr9 | − |
| TCGA-12-0829 | 2 | 3 | 5 | 1 | EFS | chr14 | − |
| TCGA-12-0829 | 56 | 6 | 62 | 14 | DIS3 | chr15 | + |
| TCGA-12-0829 | 8 | 2 | 10 | 3 | EFS | chr14 | − |
| TCGA-12-0829 | 9 | 65 | 74 | 37 | DIS3L | chr15 | + |
| TCGA-27-1835 | 14 | 0 | 14 | 4 | FAM19A2 | chr12 | − |
| TCGA-06-1801 | 20 | 0 | 20 | 2 | FREM2 | chr13 | + |
| TCGA-12-0827 | 2 | 0 | 2 | 2 | ABCC12 | chr16 | − |
| TCGA-12-0829 | 35 | 0 | 35 | 7 | ANXA7 | chr10 | − |
| TCGA-06-2559 | 60 | 37 | 97 | 1 | PLEXHM3 | chr2 | − |
| TCGA-12-1088 | 2 | 0 | 2 | 2 | PLCL1 | chr2 | + |
| TCGA-05-1601 | 10 | 0 | 10 | 4 | FGFR4 | chr5 | + |
| TCGA-06-1802 | 15 | 0 | 15 | 2 | PDHA2 | chr4 | + |
| TCGA-06-1802 | 4 | 0 | 4 | 2 | PDHA2 | chr4 | + |
| TCGA-06-6390 | 53 | 0 | 53 | 18 | GPR182 | chr12 | + |
| TCGA-12-0829 | 1121 | 252 | 1373 | 602 | ADCY8 | chr8 | + |
| TCGA-12-0829 | 14 | 8 | 22 | 3 | ADCY8 | chr8 | − |
| TCGA-12-0829 | 9 | 42 | 51 | 18 | ADAM12 | chr10 | − |
| TCGA-12-2633 | 22 | 0 | 22 | 10 | JOSD2 | chr19 | − |
| TCGA-12-0829 | 100 | 0 | 100 | 20 | COL14A1 | chr8 | + |
| TCGA-12-0829 | 152 | 0 | 152 | 24 | COL14A1 | chr8 | + |
| TCGA-06-1802 | 11 | 47 | 58 | 19 | MUSK | chr9 | + |
| TCGA-06-1805 | 6 | 4 | 10 | 6 | COL14A1 | chr8 | + |
| TCGA-12-0822 | 37 | 0 | 37 | 3 | C7orf44 | chr7 | − |
| TCGA-12-0829 | 0 | 2 | 2 | 365 | GSTA3 | chr6 | − |
| TCGA-12-0829 | 124 | 16 | 140 | 51 | GSTA3 | chr6 | − |
| TCGA-12-0829 | 21 | 7 | 28 | 10 | HIP1 | chr7 | − |
| TCGA-12-0829 | 268 | 123 | 391 | 242 | HIP1 | chr7 | − |

TABLE 2-continued

Fusion breakpoint information of recurrent gene fusions identified by Exome-fuse analysis of 84 GBM from TCGA.

| | | | | | | | |
|---|---|---|---|---|---|---|---|
| TCGA-12-0829 | 36 | 641 | 677 | 365 | GSTA3 | chr6 | − |
| TCGA-12-1088 | 10 | 1 | 11 | 3 | CAMTA1 | chr1 | + |
| TCGA-12-1088 | 65 | 0 | 65 | 6 | ADCY10 | chr1 | + |
| TCGA-12-1088 | 8 | 1 | 9 | 4 | CAMTA1 | chr1 | + |
| TCGA-27-1835 | 83 | 1 | 84 | 22 | CNTYA5 | chr5 | + |
| TCGA-06-1801 | 0 | 43 | 43 | 31 | CAMTA1 | chr1 | + |
| TCGA-06-1801 | 13 | 41 | 54 | 31 | CAMTA1 | chr1 | + |
| TCGA-06-1801 | 24 | 66 | 90 | 61 | CAMTA1 | chr1 | + |
| TCGA-12-0829 | 2 | 0 | 2 | 3 | CCDC147 | chr10 | + |
| TCGA-12-1088 | 7 | 1 | 8 | 5 | CMYA5 | chr5 | + |
| TCGA-06-1801 | 7 | 1 | 13 | 4 | DEPDC5 | chr22 | + |
| TCGA-12-0820 | 110 | 20 | 130 | 23 | ABCA13 | chr7 | + |
| TCGA-12-0820 | 29 | 4 | 33 | 3 | ABCA13 | chr7 | + |
| TCGA-12-0829 | 46 | 2 | 48 | 4 | LIN9 | chr1 | − |
| TCGA-12-3644 | 3 | 0 | 3 | 1 | EFHC1 | chr6 | + |
| TCGA-12-3644 | 3 | 10 | 13 | 3 | EFHC1 | chr6 | + |
| TCGA-19-5958 | 6 | 6 | 12 | 7 | DEPDC5 | chr22 | + |
| TCGA-06-1801 | 4 | 4 | 8 | 5 | KCND3 | chr1 | − |
| TCGA-12-0820 | 26 | 1 | 27 | 2 | BBX | chr3 | + |
| TCGA-12-0828 | 8 | 67 | 75 | 31 | ADCY2 | chr5 | + |
| TCGA-12-0829 | 13 | 21 | 34 | 16 | AGBL4 | chr1 | − |
| TCGA-12-0829 | 64 | 308 | 372 | 197 | EYS | chr6 | − |
| TCGA-12-0829 | 7 | 25 | 32 | 11 | ABL4 | chr1 | − |
| TCGA-12-0829 | 9 | 0 | 9 | 1 | LRBA | chr4 | − |
| TCGA-12-1093 | 65 | 4 | 69 | 21 | OSBPL10 | chr3 | − |
| TCGA-12-1600 | 9 | 0 | 9 | 5 | 5-Sep | chr22 | + |
| TCGA-19-0957 | 18 | 1 | 19 | 7 | ADCY10 | chr1 | − |
| TCGA-19-0957 | 34 | 2 | 36 | 11 | ADCY10 | chr1 | − |
| TCGA-12-0822 | 0 | 1 | 1 | 16 | ITGB2 | chr21 | − |
| TCGA-12-0822 | 6 | 2 | 8 | 1 | ITGB2 | chr21 | − |
| TCGA-12-0827 | 25 | 3 | 28 | 8 | CUL3 | chr22 | − |
| TCGA-12-0828 | 7 | 2 | 9 | 4 | FH | chr1 | − |
| TCGA-12-0829 | 24 | 0 | 24 | 9 | ITGA9 | chr3 | + |
| TCGA-12-1089 | 17 | 2 | 19 | 5 | ABCC1 | chr16 | + |
| TCGA-12-1089 | 6 | 0 | 6 | 8 | CAMSAP1 | chr9 | − |
| TCGA-19-0957 | 16 | 0 | 16 | 4 | CCDC147 | chr10 | + |
| TCGA-06-1801 | 5 | 33 | 38 | 18 | AP4S1 | chr14 | + |
| TCGA-06-1805 | 3 | 14 | 17 | 9 | UL3 | chr2 | − |
| TCGA-12-0829 | 14 | 27 | 41 | 23 | ADCY2 | chr5 | + |
| TCGA-12-0829 | 59 | 7 | 66 | 18 | NR3C1 | chr5 | − |
| TCGA-12-0829 | 9 | 40 | 49 | 28 | ADCY2 | chr5 | + |
| TCGA-12-1093 | 20 | 0 | 20 | 4 | GAPVD1 | chr9 | + |
| TCGA-12-1600 | 7 | 0 | 7 | 4 | CILP | chr15 | − |
| TCGA-19-0957 | 13 | 3 | 15 | 6 | AQP2 | chr12 | + |
| TCGA-19-0967 | 6 | 0 | 6 | 1 | AQP2 | chr12 | + |
| TCGA-06-0166 | 2 | 0 | 2 | 3 | CCDC158 | chr4 | − |
| TCGA-06-1802 | 30 | 0 | 30 | 9 | RANBP2 | chr2 | + |
| TCGA-06-1805 | 4 | 0 | 4 | 3 | C2CD3 | chr11 | − |
| TCGA-06-1805 | 6 | 1 | 7 | 5 | NEUROG1 | chr5 | − |
| TCGA-12-0820 | 27 | 0 | 27 | 2 | RANBP2 | chr2 | + |
| TCGA-12-0820 | 58 | 7 | 65 | 15 | RANBP2 | chr2 | + |
| TCGA-12-0829 | 6 | 128 | 134 | 35 | C2CD3 | chr11 | − |
| TCGA-12-0829 | 84 | 443 | 527 | 227 | C2CD3 | chr11 | − |
| TCGA-12-1088 | 10 | 0 | 10 | 2 | PACSIN1 | chr6 | + |
| TCGA-12-1088 | 12 | 0 | 12 | 2 | PACSIN1 | chr6 | + |
| TCGA-19-0957 | 34 | 19 | 53 | 17 | PRKCH | chr14 | + |
| TCGA-19-0957 | 7 | 1 | 8 | 7 | MAPKAP1 | chr9 | − |
| TCGA-19-0957 | 8 | 39 | 47 | 21 | PRKCH | chr14 | − |
| TCGA-06-1801 | 5 | 11 | 16 | 4 | MAOA | chrX | + |
| TCGA-06-1802 | 10 | 12 | 22 | 12 | DNM1L | chr12 | + |
| TCGA-06-1802 | 18 | 42 | 60 | 24 | MUC4 | chr3 | − |
| TCGA-12-0829 | 6 | 0 | 6 | 6 | ATXN1 | chr6 | − |
| TCGA-12-0829 | 7 | 0 | 7 | 3 | ATP6V0D2 | chr8 | + |
| TCGA-12-1088 | 11 | 1 | 12 | 6 | BCAS3 | chr17 | + |
| TCGA-12-1098 | 15 | 2 | 17 | 5 | ABCC1 | chr16 | + |
| TCGA-12-1089 | 17 | 3 | 20 | 4 | MST1R | chr3 | − |
| TCGA-12-1088 | 4 | 0 | 4 | 2 | FBXL4 | chr6 | − |
| TCGA-12-1092 | 39 | 4 | 43 | 12 | CNTN2 | chr1 | + |
| TCGA-12-1598 | 4 | 0 | 4 | 5 | MPP1 | chrX | − |
| TCGA-19-1786 | 5 | 19 | 24 | 7 | ATP5B | chr12 | − |
| TCGA-19-2621 | 21 | 0 | 21 | 3 | BCAS3 | chr17 | + |
| TCGA-06-1801 | 15 | 0 | 15 | 9 | C15orf23 | chr15 | + |
| TCGA-06-1805 | 6 | 3 | 9 | 5 | FAM19A2 | chr12 | − |
| TCGA-12-0829 | 13 | 94 | 97 | 44 | ATP5B | chr12 | − |
| TCGA-12-0829 | 158 | 207 | 365 | 44 | ATP5B | chr12 | − |
| TCGA-12-0829 | 2 | 1 | 3 | 2 | DDI2 | chr1 | + |
| TCGA-12-0829 | 25 | 6 | 31 | 44 | ATP5B | chr12 | − |
| TCGA-12-0529 | 34 | 21 | 55 | 44 | ATP5B | chr12 | − |

TABLE 2-continued

Fusion breakpoint information of recurrent gene fusions identified by Exome-fuse analysis of 84 GBM from TCGA.

| | | | | | | | |
|---|---|---|---|---|---|---|---|
| TCGA-12-0829 | 44 | 6 | 50 | 4 | ABCC6 | chr16 | − |
| TCGA-12-0829 | 53 | 28 | 81 | 35 | DDI2 | chr1 | + |
| TCGA-12-0829 | 9 | 0 | 9 | 5 | DMD | chrX | − |
| TCGA-12-1052 | 9 | 0 | 5 | 4 | LRRC4B | chr19 | − |
| TCGA-19-2521 | 3 | 22 | 25 | 11 | PCDH12 | chr5 | − |
| TCGA-06-1801 | 6 | 4 | 12 | 5 | BAHD1 | chr15 | + |
| TCGA-12-0828 | 11 | 0 | 11 | 1 | PLOD3 | chr7 | + |
| TCGA-12-0828 | 40 | 9 | 49 | 20 | PLOD3 | chr7 | − |
| TCGA-12-0829 | 16 | 2 | 16 | 9 | c21orf29 | chr21 | − |
| TCGA-12-0829 | 196 | 0 | 196 | 37 | IGFBP3 | chr7 | − |
| TCGA-12-0829 | 5 | 1 | 6 | 1 | FAM1684 | chr21 | − |
| TCGA-12-0829 | 5 | 18 | 23 | 9 | FAM168A | chr11 | − |
| TCGA-12-1089 | 20 | 0 | 20 | 2 | SLC44A2 | chr19 | + |
| TCGA-19-0957 | 17 | 1 | 18 | 4 | PAX3 | chr2 | − |
| TCGA-06-1801 | 5 | 0 | 5 | 1 | CAP2 | chr6 | + |
| TCGA-06-1801 | 6 | 32 | 38 | 15 | CAP2 | chr6 | + |
| TCGA-06-1805 | 3 | 0 | 3 | 8 | PLCL1 | ch2 | + |
| TCGA-06-1805 | 7 | 2 | 9 | 4 | PLCLI | chr2 | + |
| TCGA-12-0822 | 17 | 4 | 21 | 4 | TAAR6 | chr6 | + |
| TCGA-12-0828 | 17 | 0 | 17 | 8 | AQP2 | chr12 | + |
| TCGA-12-0828 | 7 | 0 | 7 | 1 | AQP2 | chr12 | + |
| TCGA-12-0829 | 12 | 0 | 12 | 7 | CACNA1G | chr17 | + |
| TCGA-19-0957 | 4 | 0 | 4 | 3 | PCDH12 | chr5 | − |
| TCGA-15-0957 | 8 | 2 | 10 | 2 | PCDH12 | chr5 | − |
| TCGA-06-1801 | 13 | 1 | 14 | 1 | ABCC6 | chr15 | − |
| TCGA-06-1801 | 33 | 7 | 40 | 4 | ABCC6 | chr16 | − |
| TCGA-06-1805 | 10 | 3 | 13 | 6 | ABCC6 | chr1 | − |
| TCGA-12-0829 | 11 | 0 | 11 | 4 | FAM160A1 | chr4 | + |
| TCGA-12-0829 | 17 | 1 | 18 | 5 | FAM160A1 | chr1 | + |
| TCGA-12-0829 | 487 | 83 | 570 | 249 | CORO7 | chr16 | − |
| TCGA-12-1088 | 2 | 12 | 14 | 4 | FAM172A | chr5 | − |
| TCGA-06-1801 | 30 | 7 | 37 | 18 | DEPDC7 | chr11 | + |
| TCGA-06-1801 | 40 | 28 | 68 | 33 | MAP7 | chr6 | − |
| TCGA-12-1093 | 6 | 15 | 21 | 8 | CORO7 | chr16 | − |
| TCGA-12-3644 | 33 | 0 | 33 | 4 | EDA | chrX | + |
| TCGA-12-3644 | 37 | 15 | 52 | 17 | C15orf33 | chr15 | − |
| TCGA-09-1791 | 14 | 3 | 17 | 8 | PSEN1 | chr14 | + |
| TCGA-06-1802 | 35 | 2 | 37 | 17 | CELF2 | chr10 | + |
| TCGA-06-1802 | 63 | 26 | 39 | 25 | CELF2 | chr10 | + |
| TCGA-06-1802 | 8 | 2 | 10 | 3 | LCLAT1 | chr2 | + |
| TCGA-06-2562 | 6 | 0 | 6 | 4 | SNTA1 | chr20 | − |
| TCGA-12-0829 | 16 | 1 | 17 | 4 | LASS6 | chr2 | + |
| TCGA-12-0829 | 7 | 0 | 7 | 2 | LASS6 | chr2 | + |
| TCGA-14-0813 | 339 | 39 | 378 | 5 | SNTA1 | chr20 | − |
| TCGA-12-0820 | 49 | 3 | 52 | 11 | CAMKK1 | chr17 | − |
| TCGA-12-0826 | 8 | 18 | 26 | 13 | C'ELF2 | chr10 | + |
| TCGA-12-1089 | 17 | 4 | 21 | 10 | C6orf170 | chr6 | − |
| TCGA-12-1600 | 19 | 0 | 19 | 3 | ATP6AP1L | chr5 | + |
| TCGA-12-1600 | 5 | 35 | 40 | 6 | ATP6AP1L | chr5 | + |
| TCGA-19-1790 | 4 | 0 | 4 | 4 | ARMC6 | chr19 | + |
| TCGA-06-1802 | 12 | 0 | 12 | 8 | EIF2C2 | chr8 | − |
| TCGA-14-0781 | 22 | 2 | 24 | 8 | FAM160A1 | chr4 | + |

| Sample | posA | gene B | chr B | senseB | posB | dirA | dirB | dirAB_matepair | cosmicA + B |
|---|---|---|---|---|---|---|---|---|---|
| TGCA-06-6390 | 1773521 | TACC3 | chr4 | + | 1708787 | 1 | 1 | 0 | 2803 |
| TCGA-12-0826 | 1778502 | TACC3 | chr4 | + | 1707185 | 0 | 0 | 1 | 2803 |
| TCGA-19-5958 | 1778539 | TACC3 | chr4 | + | 1707203 | 0 | 1 | 1 | 2803 |
| TCGA-27-1835 | 1773595 | TACC3 | chr4 | + | 1709397 | 0 | 0 | 2 | 2803 |
| TCGA-12-0820 | 1779184 | PRK62 | chr4 | + | 82338347 | 1 | 1 | 0 | 2805 |
| TCGA-12-1088 | 132597569 | TNFRSF10B | chr8 | − | 22936252 | 0 | 0 | 1 | 892 |
| TCGA-06-1802 | 127698245 | PTPRD | chr9 | − | 8596127 | 0 | 1 | 1 | 54 |
| TCGA-06-1801 | 75010010 | PTPRD | chr9 | − | 9387093 | 1 | 0 | 0 | 52 |
| TCGA-12-1088 | 8886300 | PPP1R3A | chr7 | − | 113305567 | 0 | 0 | 1 | 45 |
| TCGA-12-1088 | 8887075 | PPP1R3A | chr7 | − | 113305191 | 1 | 1 | 0 | 45 |
| TCGA-32-2491 | 123342503 | STAG2 | chrX | + | 123019118 | 0 | 1 | 0 | 36 |
| TCGA-32-2491 | 123526882 | SASH3 | chrX | + | 128749198 | 2 | 0 | 0 | 34 |
| TCGA-12-0829 | 39032542 | VSNL1 | chr2 | + | 17630556 | 2 | 1 | 0 | 32 |
| TCGA-12-0329 | 38975444 | VSNL1 | chr2 | + | 17639377 | 1 | 0 | 0 | 32 |
| TCGA-12-0829 | 38975652 | VSNL1 | chr2 | + | 17639552 | 0 | 1 | 1 | 32 |
| TCGA-19-0957 | 37891921 | ODZ1 | chrX | − | 123925223 | 1 | 0 | 0 | 32 |
| TCGA-12-1088 | 42031380 | RIMBP2 | chr12 | − | 129517282 | 1 | 0 | 0 | 31 |
| TCGA-12-1088 | 42031574 | RIMPP2 | chr12 | − | 129517455 | 0 | 1 | 1 | 31 |
| TCGA-12-1089 | 62056459 | C21orf29 | chr21 | − | 44923276 | 0 | 1 | 1 | 30 |
| TCGA-06-1801 | 17171362 | CSMD2 | chr1 | − | 34381139 | 1 | 0 | 0 | 29 |
| TCGA-12-1089 | 72705401 | LRP1 | chr12 | + | 55880002 | 0 | 1 | 1 | 28 |
| TCGA-12-1089 | 72705248 | LRP1 | chr12 | + | 55879646 | 2 | 0 | 0 | 28 |
| TCGA-12-1089 | 129836071 | PDE10A | chr6 | − | 165358426 | 1 | 0 | 0 | 28 |

TABLE 2-continued

Fusion breakpoint information of recurrent gene fusions identified by Exome-fuse analysis of 84 GBM from TCGA.

| | | | | | | | | | |
|---|---|---|---|---|---|---|---|---|---|
| TCGA-06-1802 | 129483265 | SEC14L3 | chr22 | − | 29193005 | 1 | 1 | 0 | 27 |
| TCGA-19-0957 | 34115076 | MDH2 | chr7 | + | 75525221 | 0 | 0 | 1 | 27 |
| TCGA-06-1801 | 55757701 | LRP1 | chr12 | + | 55858598 | 0 | 0 | 1 | 26 |
| TCGA-12-1089 | 176447670 | LILRB1 | chr19 | + | 59840807 | 1 | 0 | 0 | 25 |
| TCGA-19-0957 | 99349006 | NRXN3 | chr14 | + | 79233969 | 1 | 0 | 0 | 24 |
| TCGA-06-1801 | 71082676 | TAF1 | chrX | + | 70520522 | 1 | 0 | 0 | 22 |
| TCGA-06-1801 | 71083319 | TAF1 | chrX | + | 70521607 | 1 | 0 | 1 | 22 |
| TCGA-12-1089 | 2325330 | ITGAV | chr2 | + | 187195411 | 0 | 0 | 2 | 22 |
| TCGA-19-0957 | 63579650 | RERE | chr1 | − | 8538774 | 0 | 0 | 1 | 22 |
| TCGA-12-0829 | 139062591 | FREM2 | chr13 | + | 38318644 | 1 | 1 | 0 | 21 |
| TCGA-12-0829 | 22896776 | NRXN3 | chr14 | + | 78678529 | 1 | 0 | 1 | 21 |
| TCGA-12-0829 | 64377566 | GLI3 | chr7 | − | 42032535 | 1 | 0 | | |
| TCGA-12-0829 | 22896431 | NRXN3 | chr14 | + | 78678139 | 1 | 0 | | |
| TCGA-12-0829 | 64377398 | GLI3 | chr7 | − | 42032341 | 1 | 0 | | |
| TCGA-27-1835 | 60707200 | GLI1 | chr12 | + | 56146523 | 0 | 0 | | |
| TCGA-06-1801 | 38163882 | RALYL | chr8 | + | 8578,5432 | 1 | 1 | | |
| TCGA-12-0827 | 46722685 | FGFR4 | chr5 | + | 176457194 | 1 | 1 | | |
| TCGA-12-0829 | 74808655 | CACNA1C | chr12 | + | 2438351 | 1 | 1 | | |
| TCGA-06-2559 | 208426920 | PTPRS | chr19 | − | 5222592 | 0 | 0 | | |
| TCGA-12-1088 | 198630224 | TACC2 | chr10 | + | 123987513 | 1 | 1 | | |
| TCGA-05-1601 | 176450528 | WISP2 | chr20 | + | 42782576 | 0 | 1 | | |
| TCGA-06-1802 | 96980717 | PDZRN4 | chr12 | + | 39959553 | 0 | 1 | | |
| TCGA-06-1802 | 96980509 | PDZRN4 | chr12 | + | 39959384 | 1 | 0 | | |
| TCGA-06-6390 | 55675639 | PDZRN4 | chr12 | + | 39957003 | 1 | 0 | | |
| TCGA-12-0829 | 131886108 | SSX3 | chrX | − | 48091929 | 0 | 0 | | |
| TCGA-12-0829 | 131886506 | SSX3 | chrX | − | 48091719 | 1 | 1 | | |
| TCGA-12-0829 | 127733231 | DAPK1 | chr9 | + | 89454764 | 0 | 1 | | |
| TCGA-12-2633 | 55705579 | PTPRS | chr19 | − | 5245999 | 0 | 1 | | |
| TCGA-12-0829 | 121370990 | MMP12 | chr11 | − | 102242881 | 1 | 0 | | |
| TCGA-12-0829 | 121371195 | MMP12 | chr11 | − | 102242953 | 0 | 1 | | |
| TCGA-06-1802 | 112509906 | SYNPO2 | chr4 | + | 120172123 | 0 | 0 | | |
| TCGA-06-1805 | 121332080 | NCRNA0015 | chr21 | − | 18174873 | 1 | 1 | | |
| TCGA-12-0822 | 43683128 | TACC2 | chr10 | + | 123835337 | 1 | 0 | | |
| TCGA-12-0829 | 52878492 | TACC2 | chr10 | + | 123884543 | 0 | 1 | | |
| TCGA-12-0829 | 52878680 | TACC2 | chr10 | + | 123884705 | 0 | 1 | | |
| TCGA-12-0829 | 75022909 | MASP1 | chr3 | − | 188452372 | 0 | 0 | | |
| TCGA-12-0829 | 75022741 | MASP1 | chr3 | − | 188452581 | 1 | 1 | | |
| TCGA-12-0829 | 52878496 | TACC2 | chr10 | + | 123884531 | 0 | 1 | | |
| TCGA-12-1088 | 7710762 | TMPRSS3 | chr21 | − | 42665918 | 0 | 1 | | |
| TCGA-12-1088 | 166139873 | DUSP27 | chr1 | + | 165521555 | 0 | 0 | | |
| TCGA-12-1088 | 7714539 | TMPRSS33 | chr21 | − | 42665044 | 1 | 0 | | |
| TCGA-27-1835 | 79120729 | SRRM1 | chr1 | + | 24870899 | 0 | 0 | | |
| TCGA-06-1801 | 7264935 | GDPD2 | chrX | + | 69563759 | 0 | 1 | | |
| TCGA-06-1801 | 7265429 | GDPD2 | chrX | | 69563431 | 1 | 0 | | |
| TCGA-06-1801 | 7265556 | GDPD2 | chrX | + | 69563762 | 0 | 1 | | |
| TCGA-12-0829 | 106165013 | ISX | chr22 | + | 33795708 | 0 | 1 | | |
| TCGA-12-1088 | 79045621 | STK24 | chr13 | − | 97969547 | 1 | 0 | | |
| TCGA-06-1801 | 30619774 | ROBO1 | chr13 | − | 79802538 | 0 | 1 | | |
| TCGA-12-0820 | 48597322 | NHSL2 | chrK | + | 71077547 | 1 | 0 | | |
| TCGA-12-0820 | 48597477 | NHSL2 | chrX | + | 71077690 | 0 | 1 | | |
| TCGA-12-0829 | 224536835 | NCOR1 | chr17 | − | 15883585 | 0 | 0 | | |
| TCGA-12-3644 | 52432073 | LRBA | chr4 | − | 151418615 | 1 | 0 | | |
| TCGA-12-3644 | 52431890 | LRBA | chr4 | − | 151418438 | 1 | 0 | | |
| TCGA-19-5958 | 30504095 | SLC5A4 | chr22 | − | 30974671 | 0 | 1 | | |
| TCGA-06-1801 | 112227957 | LY75 | chr2 | − | 160443238 | 1 | 1 | | |
| TCGA-12-0820 | 108997451 | CUL3 | chr2 | − | 225108623 | 0 | 0 | | |
| TCGA-12-0828 | 7558840 | SDAD1 | chr4 | − | 77096208 | 1 | 1 | | |
| TCGA-12-0829 | 48902776 | NUP188 | chr9 | + | 130808425 | 0 | 0 | | |
| TCGA-12-0829 | 64513356 | IL1RN | chr2 | + | 113603712 | 0 | 1 | | |
| TCGA-12-0829 | 48902600 | NUP188 | chr9 | + | 130808628 | 1 | 1 | | |
| TCGA-12-0829 | 151790893 | PSEN1 | chr14 | + | 72707609 | 1 | 0 | | |
| TCGA-12-1093 | 31887272 | TRAPPC9 | chr8 | − | 140828099 | 1 | 1 | | |
| TCGA-12-1600 | 18088018 | NCOR1 | chr17 | − | 15915170 | 0 | 1 | | |
| TCGA-19-0957 | 166060045 | AKT3 | chr1 | − | 241743142 | 0 | 1 | | |
| TCGA-19-0957 | 166060502 | AKT3 | chr1 | − | 241742588 | 1 | 0 | | |
| TCGA-12-0822 | 45147805 | SH3RF3 | chr2 | + | 109430489 | 0 | 1 | | |
| TCGA-12-0822 | 45147994 | SH3RF3 | chr2 | + | 109430069 | 0 | 1 | | |
| TCGA-12-0827 | 225126210 | LY75 | chr2 | − | 160455052 | 1 | 0 | | |
| TCGA-12-0828 | 239743589 | SRGAP1 | chr12 | − | 62723692 | 0 | 1 | | |
| TCGA-12-0829 | 37712050 | SNX5 | chr20 | − | 17885523 | 0 | 1 | | |
| TCGA-12-1089 | 16077635 | RNF216 | chr7 | − | 5692038 | 1 | 1 | | |
| TCGA-12-1089 | 137867066 | NCF2 | chr1 | − | 181799321 | 1 | 0 | | |
| TCGA-19-0957 | 106114657 | STK4 | chr20 | + | 43161359 | 0 | 0 | | |
| TCGA-06-1801 | 30611930 | EYS | chr6 | − | 64770011 | 1 | 0 | | |
| TCGA-06-1805 | 225064315 | SLC44A2 | chr19 | + | 10608393 | 1 | 0 | | |
| TCGA-12-0829 | 7798041 | C14orf174 | chr14 | + | 76914809 | 1 | 0 | | |
| TCGA-12-0829 | 142760085 | SORCS2 | chr4 | + | 7354165 | 0 | 0 | | |
| TCGA-12-0829 | 7798641 | C14orf174 | chr14 | + | 76915034 | 0 | 1 | | |

TABLE 2-continued

Fusion breakpoint information of recurrent gene fusions identified by Exome-fuse analysis of 84 GBM from TCGA.

| TCGA-12-1093 | 127104266 | MAPKAP1 | chr9 | − | 127490362 | 1 | 0 | 1 | 10 |
|---|---|---|---|---|---|---|---|---|---|
| TCGA-12-1600 | 63283865 | PARP16 | chr15 | − | 63350048 | 0 | 1 | 1 | 10 |
| TCGA-19-0957 | 48635567 | CDH4 | chr20 | + | 59413648 | 0 | 1 | 1 | 10 |
| TCGA-19-0967 | 48635406 | CDH4 | chr20 | + | 59413498 | 1 | 0 | 0 | 10 |
| TCGA-06-0166 | 77541796 | SNX5 | chr20 | − | 17885346 | 0 | 1 | 1 | 9 |
| TCGA-06-1802 | 109759804 | SATB2 | chr2 | − | 199995572 | 0 | 1 | 1 | 9 |
| TCGA-06-1805 | 73430819 | XRRA1 | chr11 | − | 74309669 | 1 | 1 | 0 | 9 |
| TCGA-06-1805 | 134898853 | PRKCH | chr14 | + | 61027580 | 1 | 1 | 0 | 9 |
| TCGA-12-0820 | 109749908 | TTC27 | chr2 | + | 32939367 | 0 | 1 | 1 | 9 |
| TCGA-12-0820 | 199749412 | TTC27 | chr2 | + | 32837790 | 1 | 0 | 0 | 9 |
| TCGA-12-0829 | 73529639 | CAPZB | chr1 | − | 19556435 | 0 | 0 | 1 | 9 |
| TCGA-12-0829 | 73529293 | CAPZB | chr1 | − | 19556627 | 1 | 1 | 0 | 9 |
| TCGA-12-1088 | 34589431 | TNC | chr9 | − | 116884742 | 0 | 1 | 0 | 9 |
| TCGA-12-1088 | 34589619 | TNC | chr9 | − | 116884958 | 1 | 0 | 1 | 9 |
| TCGA-19-0957 | 61032978 | ZFAND3 | chr6 | + | 36228111 | 0 | 0 | 1 | 9 |
| TCGA-19-0957 | 127348507 | SLC9A1 | chr1 | − | 27302334 | 0 | 1 | 0 | 9 |
| TCGA-19-0957 | 61032774 | ZFAND3 | chr6 | + | 38227949 | 1 | 0 | 0 | 9 |
| TCGA-06-1801 | 43486192 | SH3RF3 | chr2 | + | 109237058 | 1 | 0 | 1 | 8 |
| TCGA-06-1802 | 32736794 | 3SYNPO2 | chr4 | + | 120172271 | 0 | 1 | 1 | 8 |
| TCGA-06-1802 | 196992875 | SMOC2 | chr6 | + | 168676813 | 1 | 0 | 1 | 8 |
| TCGA-12-0829 | 16669201 | CACNA1G | chr17 | + | 46004995 | 0 | 0 | 1 | 8 |
| TCGA-12-0829 | 87186716 | RERE | chr1 | − | 8336574 | 1 | 1 | 0 | 8 |
| TCGA-12-1088 | 56321892 | CACNA1G | chr17 | + | 46010698 | 1 | 1 | 0 | 8 |
| TCGA-12-1098 | 16135771 | AGBL4 | chr1 | − | 49315120 | 1 | 0 | 0 | 8 |
| TCGA-12-1089 | 49910627 | WDFY1 | chr2 | − | 224512774 | 1 | 0 | 0 | 8 |
| TCGA-12-1088 | 99431443 | SY4PO2 | chr4 | + | 120172560 | 0 | 0 | 1 | 8 |
| TCGA-12-1092 | 203302926 | DNAJC6 | chr1 | + | 65591195 | 0 | 0 | 1 | 8 |
| TCGA-12-1598 | 153673715 | SRGAP1 | chr12 | − | 62777947 | 0 | 0 | 1 | 8 |
| TCGA-19-1786 | 55320148 | USP48 | chr1 | − | 21920103 | 1 | 0 | 1 | 8 |
| TCGA-19-2621 | 56731673 | TTYH1 | chr19 | + | 59638801 | 1 | 1 | 0 | 8 |
| TCGA-06-1801 | 38469150 | DMD | chrX | − | 32092185 | 0 | 1 | 1 | 7 |
| TCGA-06-1805 | 60547321 | POLM | chr7 | − | 44082653 | 0 | 1 | 0 | 7 |
| TCGA-12-0829 | 55319484 | PRC1 | chr15 | − | 89330475 | 1 | 0 | 1 | 7 |
| TCGA-12-0829 | 55320850 | PRC1 | chr15 | − | 89334458 | 1 | 1 | 0 | 7 |
| TCGA-12-0829 | 15825507 | KIDINS220 | chr2 | − | 8805399 | 0 | 1 | 0 | 7 |
| TCGA-12-0829 | 55321832 | PRC1 | chr15 | − | 89335627 | 1 | 0 | 1 | 7 |
| TCGA-12-0529 | 551321200 | PRC1 | chr3 | − | 89335044 | 0 | 1 | 0 | 7 |
| TCGA-12-0829 | 16204784 | SUMF1 | chr3 | − | 4470138 | 1 | 0 | 0 | 7 |
| TCGA-12-0829 | 15825941 | KIDINS220 | chr2 | − | 8805580 | 1 | 0 | 1 | 7 |
| TCGA-12-0829 | 32013100 | N4BP2L2 | chr13 | − | 32008512 | 0 | 0 | 1 | 7 |
| TCGA-12-1052 | 55754780 | NR3C1 | chr5 | − | 142660156 | 0 | 1 | 0 | 7 |
| TCGA-19-2521 | 141309153 | SLC36A2 | chr5 | − | 150679274 | 1 | 1 | 0 | 7 |
| TCGA-06-1801 | 38539023 | OSBPL10 | chr3 | − | 31729622 | 0 | 1 | 1 | 6 |
| TCGA-12-0828 | 100646340 | VSNL1 | chr2 | + | 17638618 | 1 | 1 | 0 | 6 |
| TCGA-12-0828 | 100646511 | VSNL1 | chr2 | + | 17637955 | 0 | 0 | 1 | 5 |
| TCGA-12-0829 | 44922864 | MYT1 | chr20 | + | 62300829 | 0 | 0 | 1 | 6 |
| TCGA-12-0829 | 45922866 | SMOC2 | chr6 | + | 168722450 | 0 | 0 | 1 | 6 |
| TCGA-12-0829 | 72835771 | NCF2 | chr1 | + | 181826115 | 1 | 0 | 1 | 6 |
| TCGA-12-0829 | 72839534 | NCF2 | chr1 | − | 181825930 | 1 | 0 | 0 | 6 |
| TCGA-12-1089 | 10602997 | XRCC4 | chr5 | + | 82430803 | 1 | 0 | 0 | 6 |
| TCGA-19-0957 | 222778052 | WDFY1 | chr2 | − | 224453159 | 1 | 0 | 1 | 6 |
| TCGA-06-1801 | 17571234 | DN4JC6 | chr1 | + | 65602700 | 1 | 0 | 0 | 5 |
| TCGA-06-1801 | 17571666 | DNAJC6 | chr1 | + | 65603089 | 0 | 1 | 1 | 5 |
| TCGA-06-1805 | 198578552 | SURF6 | chr9 | − | 135188818 | 0 | 1 | 0 | 5 |
| TCGA-06-1805 | 198578671 | SURF6 | chr9 | − | 135189294 | 1 | 0 | 1 | 5 |
| TCGA-12-0822 | 132533266 | TTYH1 | chr19 | + | 59629451 | 0 | 1 | 1 | 5 |
| TCGA-12-0828 | 48634800 | ECE1 | chr1 | − | 21515240 | 0 | 1 | 1 | 5 |
| TCGA-12-0828 | 48534610 | ECE1 | chr1 | − | 21515033 | 1 | 0 | 0 | 5 |
| TCGA-12-0829 | 46039372 | CNTNAP4 | chr16 | + | 74873868 | 0 | 1 | 1 | 5 |
| TCGA-19-0957 | 141316624 | SH3BP5 | chr3 | − | 15315567 | 0 | 0 | 1 | 5 |
| TCGA-15-0957 | 141316405 | SH3BP5 | chr3 | − | 15315731 | 1 | 1 | 0 | 5 |
| TCGA-06-1801 | 16205051 | CMTM7 | chr3 | + | 32443880 | 0 | 1 | 1 | 4 |
| TCGA-06-1801 | 16204860 | CMTM7 | chr3 | + | 32443722 | 1 | 0 | 0 | 4 |
| TCGA-06-1805 | 49449813 | NOX4 | chr11 | − | 853714996 | 0 | 0 | 1 | 4 |
| TCGA-12-0829 | 152595916 | LY75 | chr2 | − | 160440194 | 0 | 1 | 0 | 4 |
| TCGA-12-0829 | 152596097 | LY75 | chr2 | − | 160440376 | 1 | 0 | 1 | 4 |
| TCGA-12-0829 | 4375428 | DYRK3 | chr1 | + | 204876154 | 0 | 0 | 1 | 4 |
| TCGA-12-1088 | 93052315 | TRIOBP | chr22 | + | 36427382 | 0 | 1 | 1 | 4 |
| TCGA-06-1801 | 33003811 | EIF2C2 | chr8 | − | 141618836 | 1 | 0 | 0 | 3 |
| TCGA-06-1801 | 136728609 | SH3RF3 | chr2 | + | 109392677 | 0 | 0 | | |
| TCGA-12-1093 | 4398302 | PLEK2 | chr14 | − | 66934201 | 0 | 1 | | |
| TCGA-12-3644 | 69073054 | SSX3 | chrX | − | 48094443 | 1 | 1 | | |
| TCGA-12-3644 | 47424122 | PARP16 | chr15 | − | 63350289 | 0 | 0 | | |
| TCGA-09-1791 | 72748293 | ZNE410 | chr14 | + | 73431112 | 0 | 0 | | |
| TCGA-06-1802 | 11352537 | PLA2G2F | chr1 | + | 20348173 | 1 | 1 | | |
| TCGA-06-1802 | 11352765 | PLA263F | chr1 | + | 20347997 | 0 | 0 | | |
| TCGA-06-1802 | 30535977 | PACSIN1 | chr6 | + | 34576195 | 1 | 0 | | |
| TCGA-06-2562 | 31473415 | IMEM80 | chr11 | + | 689744 | 0 | 0 | | |

TABLE 2-continued

Fusion breakpoint information of recurrent gene fusions identified by Exome-fuse analysis of 84 GBM from TCGA.

| TCGA-12-0829 | 169045211 | NKAIN2 | chr6 | + | 125021252 | 0 | 0 |
| TCGA-12-0829 | 169045333 | NKAIN2 | chr6 | + | 125021072 | 1 | 1 |
| TCGA-14-0813 | 31481069 | TMEM80 | chr11 | + | 686739 | 0 | 0 |
| TCGA-12-0820 | 3712344 | FAM184B | chr4 | − | 17271273 | 0 | 1 |
| TCGA-12-0826 | 11406463 | NME4 | chr16 | + | 389427 | 1 | 1 |
| TCGA-12-1089 | 121478035 | NKAIN2 | chr6 | + | 125083380 | 1 | 0 |
| TCGA-12-1600 | 81649744 | FAM172A | chr5 | − | 93336459 | 1 | 0 |
| TCGA-12-1600 | 81649902 | FAM172A | chr5 | − | 93336676 | 1 | 0 |
| TCGA-19-1790 | 19026932 | FAM184B | chr4 | − | 17391210 | 1 | 0 |
| TCGA-06-1802 | 141648334 | TNFRSF10B | chr8 | − | 22940680 | 0 | 0 |
| TCGA-14-0781 | 152584637 | UNC93B1 | chr11 | − | 67523253 | 1 | 0 |

TABLE 3

Recurrent gene fusion pairs from Exome-fuse analysis of 84 GBM from TCGA.

| Sample | gene A | gene B | Sample | gene A | gene B |
| --- | --- | --- | --- | --- | --- |
| TCGA-12-0820 | ABCA13 | NH5L2 | TCGA-12-0820 | CAMKK1 | FAM184B |
| TCGA-12-1089 | ABCC1 | RNF216 | TCGA-12-1089 | CAMSAP1 | NCF2 |
| TCGA-12-1088 | ABCC1 | AGBL4 | TCGA-12-1088 | CAMTA1 | TMPRS53 |
| TCGA-12-0827 | ABCC12 | FGFR4 | TCGA-06-1801 | CAMTA1 | GDPD2 |
| TCGA-12-0829 | ABCC6 | SUMF1 | TCGA-06-1801 | CAP2 | DNAJC6 |
| TCGA-06-1801 | ABCC6 | CMTM7 | TCGA-19-0957 | CCDC147 | STK4 |
| TCGA-12-1088 | ABL1 | TNFRSF10B | TCGA-12-0829 | CCDC147 | ISX |
| TCGA-06-1802 | ADAM12 | PTPRD | TCGA-06-0166 | CCDC158 | SNX5 |
| TCGA-12-0829 | ADAM12 | DAPK1 | TCGA-19-0957 | CDH11 | RERE |
| TCGA-12-1088 | ADCY10 | DUSP27 | TCGA-06-1802 | CELF2 | PLA2G2F |
| TCGA-19-0957 | ADCY10 | AKT3 | TCGA-12-0826 | CELF2 | NME4 |
| TCGA-12-0828 | ADCY2 | SDAD1 | TCGA-12-1600 | CILP | PARP16 |
| TCGA-12-0829 | ADCY2 | C14orf174 | TCGA-12-1089 | CLK3 | LRP1 |
| TCGA-12-0829 | ADCY8 | SSX3 | TCGA-12-1088 | CMYA5 | STK24 |
| TCGA-12-0829 | AGBL4 | NUP188 | TCGA-27-1835 | CMYA5 | SRRM1 |
| TCGA-06-1805 | AGBL4 | NOX4 | TCGA-12-1092 | CNTN2 | DNAJC6 |
| TCGA-12-1089 | AHNAK | C21orf29 | TCGA-06-1805 | COL14A1 | NCRNA00157 |
| TCGA-12-0829 | ANχA7 | CACNA1C | TCGA-12-0829 | COL14A1 | MMP12 |
| TCGA-06-1801 | AP4S1 | EYS | TCGA-12-1093 | CORO7 | PLEK2 |
| TCGA-12-0828 | AQP2 | ECE1 | TCGA-12-0829 | CORO7 | DYRK3 |
| TCGA-19-0957 | AQP2 | CDH4 | TCGA-06-1801 | CROCC | CSMD2 |
| TCGA-19-1790 | ARMC6 | FAM184B | TCGA-19-0957 | CSMD2 | MDH2 |
| TCGA-19-1786 | ATP58 | USP48 | TCGA-06-1805 | CUL3 | SLC44A2 |
| TCGA-12-0829 | ATP58 | PRC1 | TCGA-12-0827 | CUL3 | LY75 |
| TCGA-12-1600 | ATP6AP1L | FAM172A | TCGA-12-0829 | DDI2 | KIDINS220 |
| TCGA-12-0829 | ATP6V0D2 | RERE | TCGA-19-5958 | DEPDC5 | SLC5A4 |
| TCGA-12-0829 | ATXN1 | CACNA1G | TCGA-06-1801 | DEPDC5 | ROBO1 |
| TCGA-06-1802 | BAHD1 | OSBPL10 | TCGA-06-1801 | DEPDC7 | EIF2C2 |
| TCGA-12-0820 | BBX | CUL3 | TCGA-12-0829 | DIS3L | GLI3 |
| TCGA-19-2621 | BCA53 | TTYH1 | TCGA-12-0829 | DMD | N4BP2L2 |
| TCGA-12-1088 | BCA53 | CACNA1G | TCGA-06-1802 | DNM1L | SYNPO2 |
| TCGA-06-1801 | C15orf23 | DMD | TCGA-12-3644 | EDA | SSX3 |
| TCGA-12-3644 | C15orf33 | PARP16 | TCGA-12-3644 | EFHC1 | LRBA |
| TCGA-12-0829 | C21orf29 | MYT1 | TCGA-12-0829 | EPS | NRXN3 |
| TCGA-06-1805 | C2CD3 | XRRA1 | TCGA-06-1802 | EIF2C2 | TNFRSF10B |
| TCGA-12-0829 | C2CD3 | CAPZB | TCGA-19-0957 | EML1 | NRXN3 |
| TCGA-12-1089 | C6orf170 | NKAIN2 | TCGA-12-0829 | ENTPD2 | FREM2 |
| TCGA-12-0822 | C7orf44 | TACC2 | TCGA-12-0829 | EYS | IL1RN |
| TCGA-12-1089 | CACNA1C | ITGAV | TCGA-14-0781 | FAM160A1 | UNC93B1 |
| TCGA-12-0829 | CACNA1G | CNTNAP4 | TCGA-12-0829 | FAM160A1 | LY75 |

Table 3 above shows recurrent gene fusion pairs from Exome-fuse analysis of 84 GBM from TCGA. Fusion candidates have been nominated if they have at least two split inserts and at least two split reads. To further filter the list on recurrence, any fusion candidate was kept in which one of the genes is involved in at least two fusions across different samples.

Figure 1C:
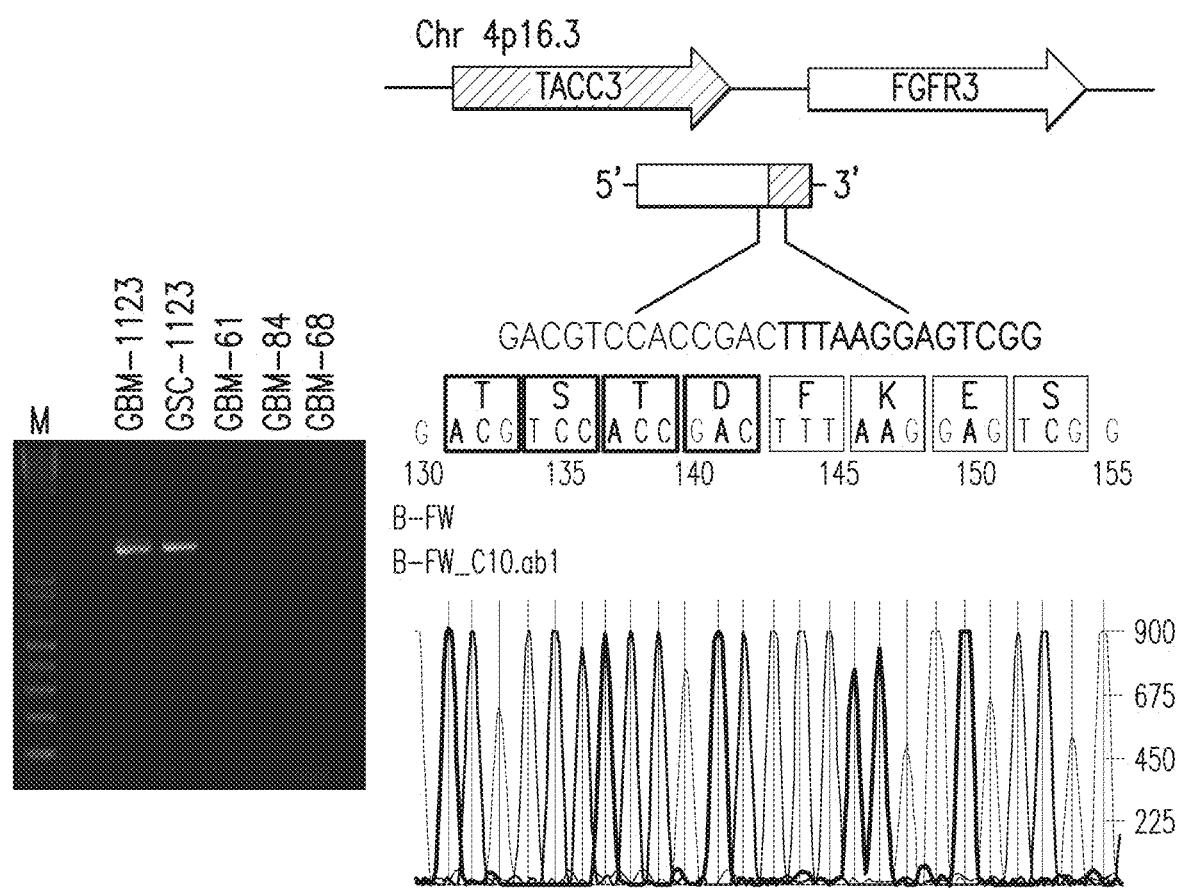
FIG. 1C shows an FGFR3-TACC3 gene fusion identified by whole transcriptome sequencing of GSCs. On the left, FGFR3-TACC3-specific PCR from cDNA derived from GSCs and GBM is shown. On the right, Sanger sequencing chromatogram shows the reading frame at the breakpoint (SEQ ID NO: 80) and putative translation of the fusion protein (SEQ ID NO: 85) in the positive samples.
Figure 10A:
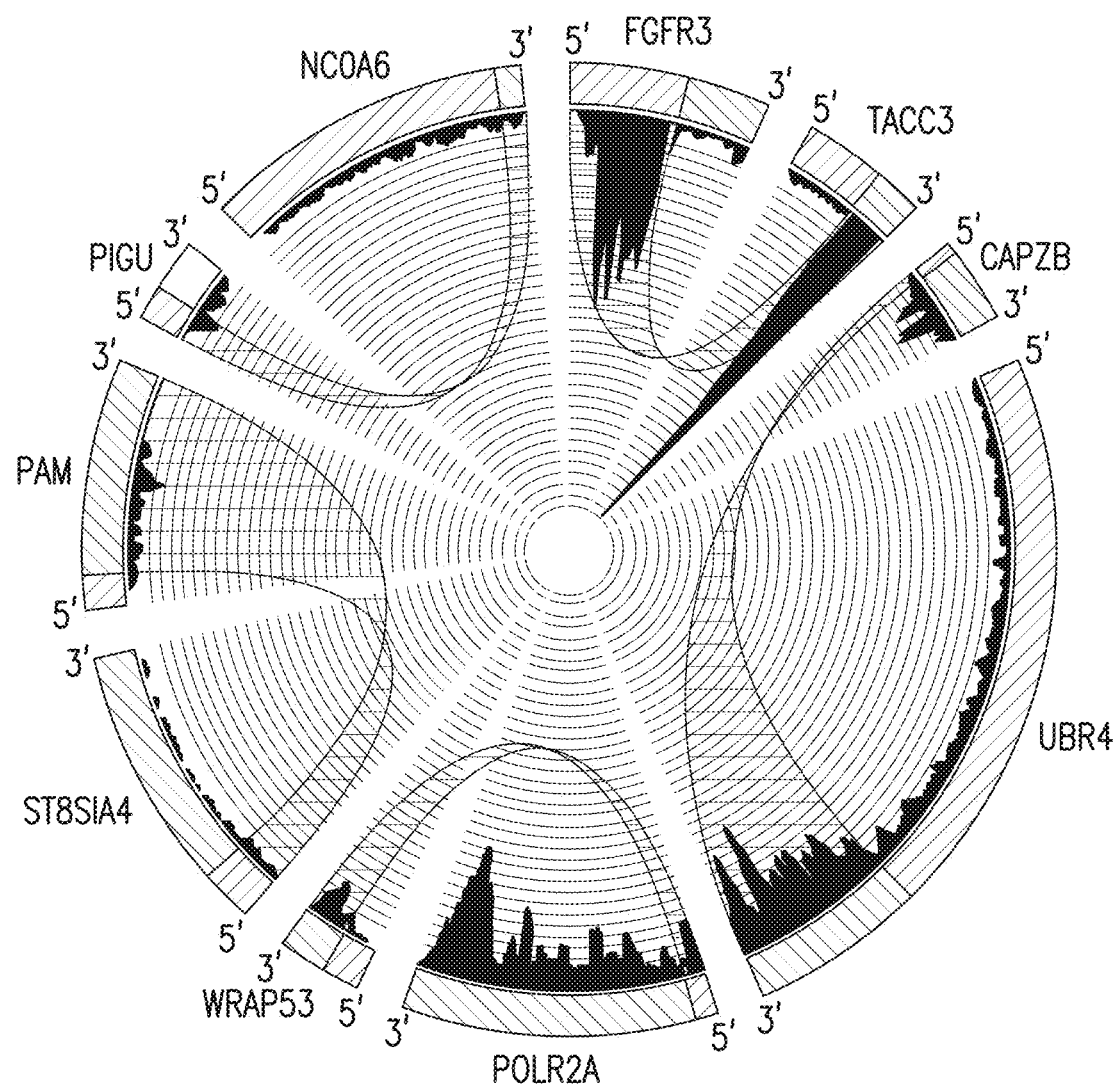
FIG. 10A shows the analysis and validation of the expression of fused transcripts in GSCs and GBM sample. Expression measured by read depth from RNA-seq data. Light grey arcs indicate predicted components of transcripts fused together. Overall read depth (blue; "grey" in black and white image) and split insert depth (red; "dark grey" in black and white image) are depicted in the graph, with a 50-read increment and a maximum range of 1800 reads. Note the very high level of expression in the regions of the genes implicated in the fusion events, particularly for FGFR3-TACC3.
Figure 10C:
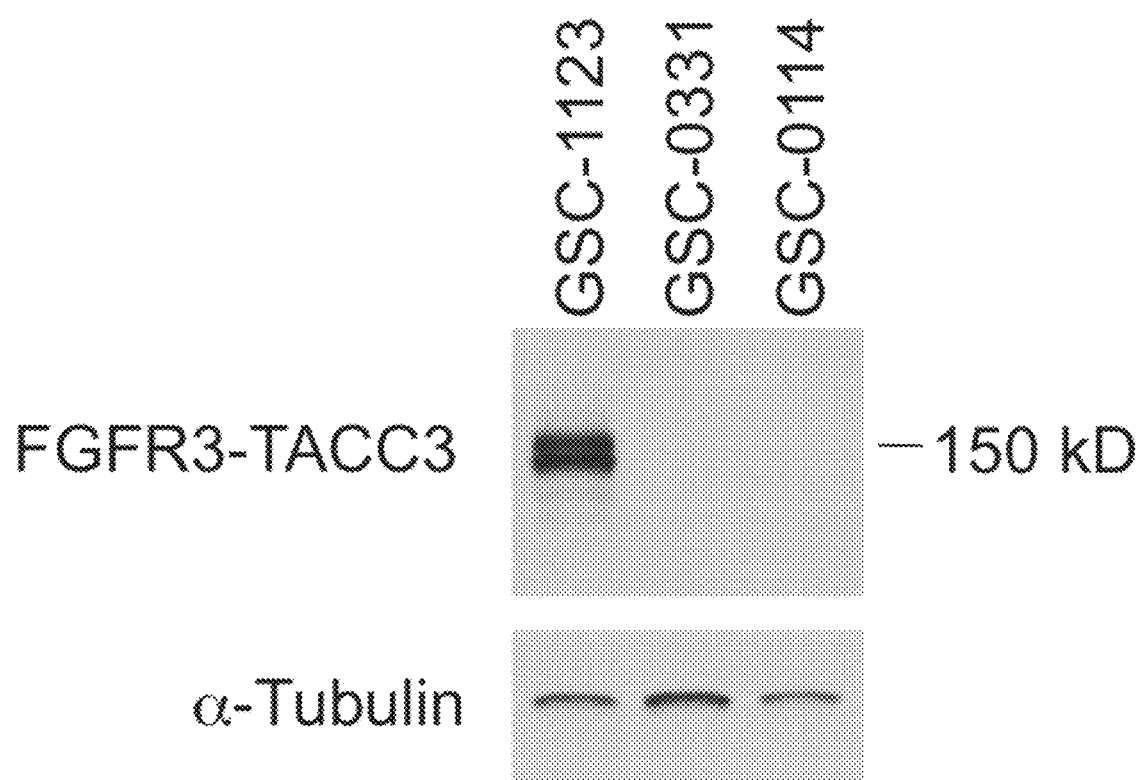
FIG. 10C shows the expression of the FGFR3-TACC3 protein in GSC-1123 and GBM-1123. Western blot analysis with a monoclonal antibody, which recognizes the N-terminal region of human FGFR3 shows expression of a ~150 kD protein in GSC-1123 but not in the GSC cultures GSC-0331 and GSC-0114, which lack the FGFR3-TACC3 rearrangement.
Figure 10D:
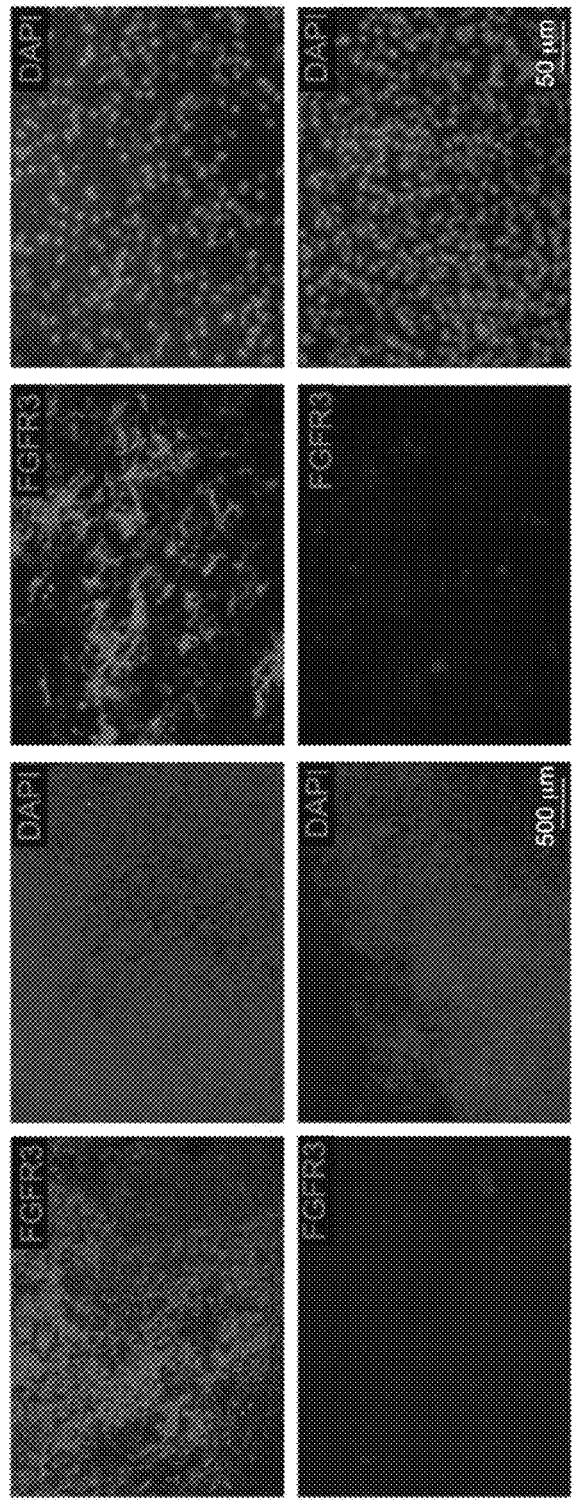
FIG. 10D shows the analysis and validation of the expression of fused transcripts in GSCs and GBM sample. Immunostaining analysis with the FGFR3 antibody of the tumor GBM-1123 (top panel) and a GBM tumor lacking the FGFR3-TACC3 rearrangement. FGFR3 (red; "light grey" in black and white image), DNA (DAPI, blue; "grey" in black and white image). The pictures were taken at low (left) and high (right) magnification.
Figures 1, 10E:
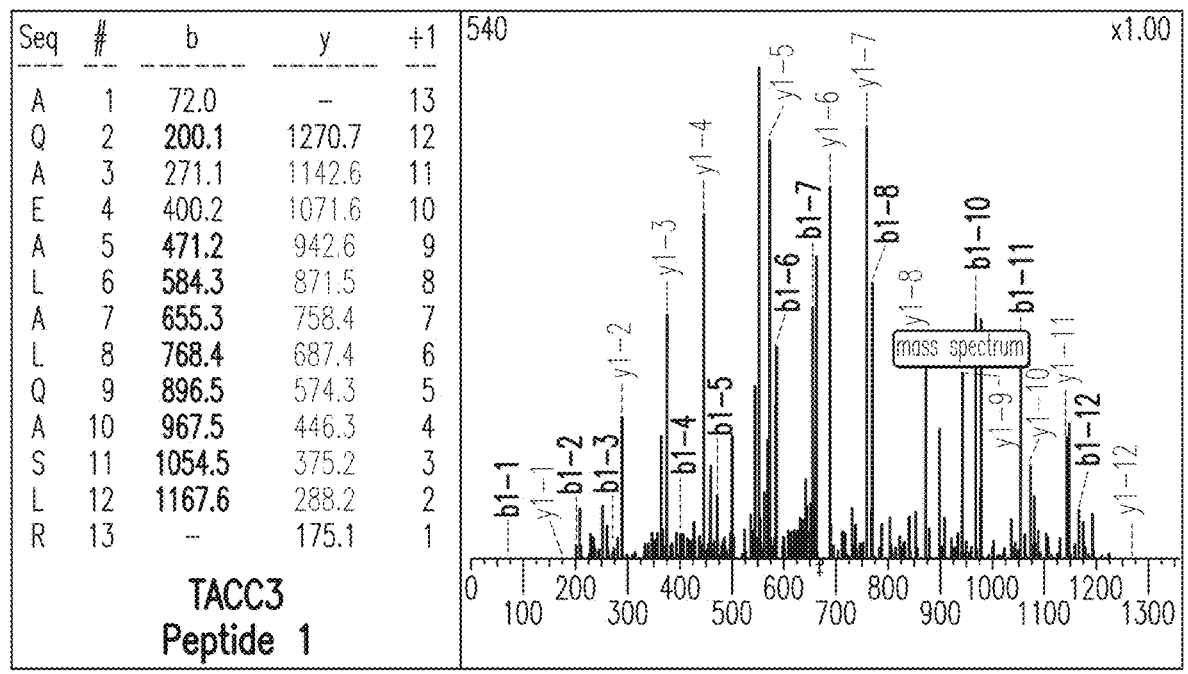
Figures 2, 10E:
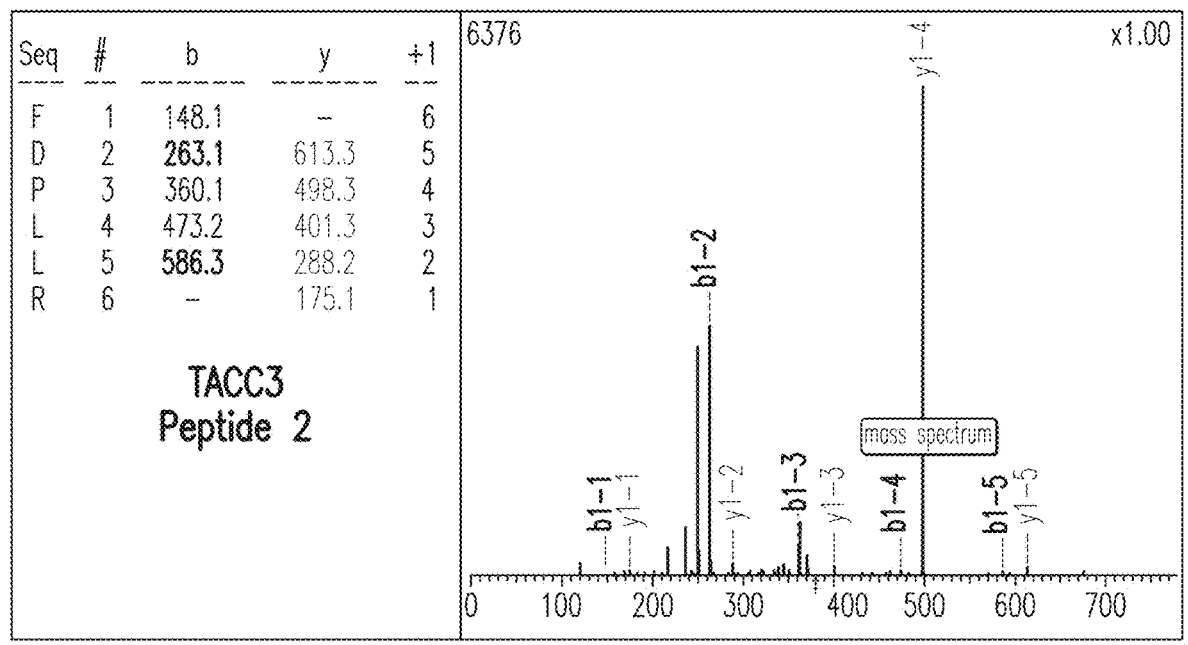
Figures 3, 10E:
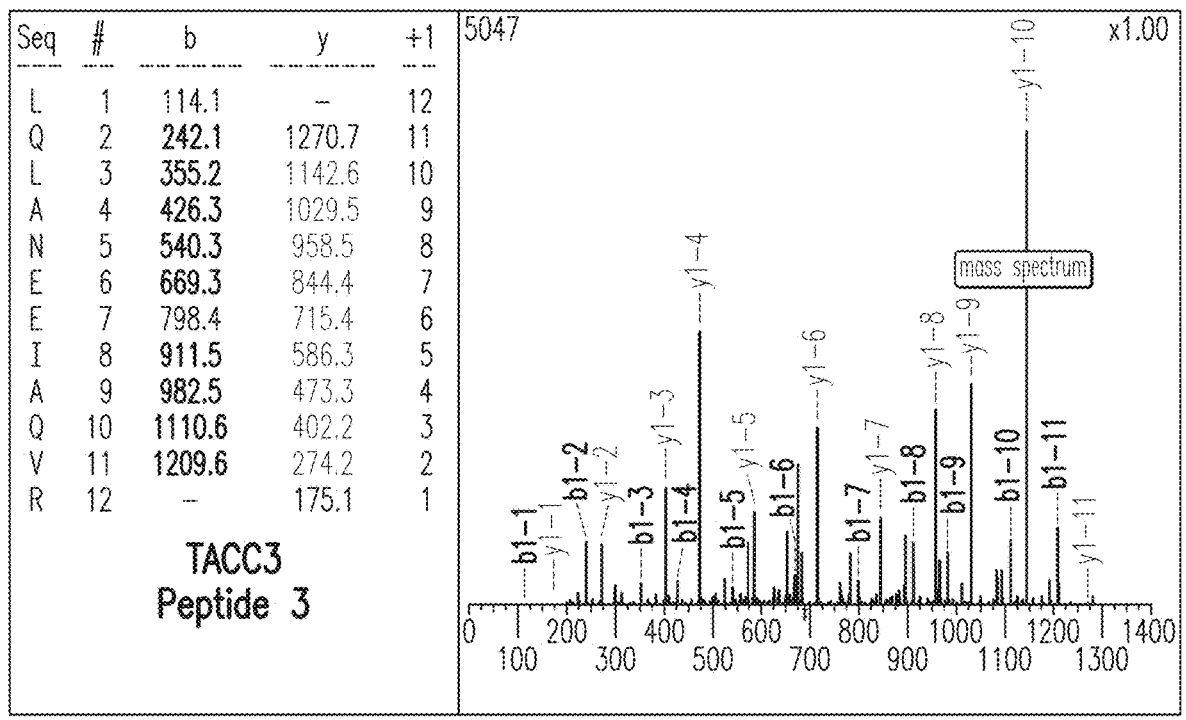
Figures 4, 10E:
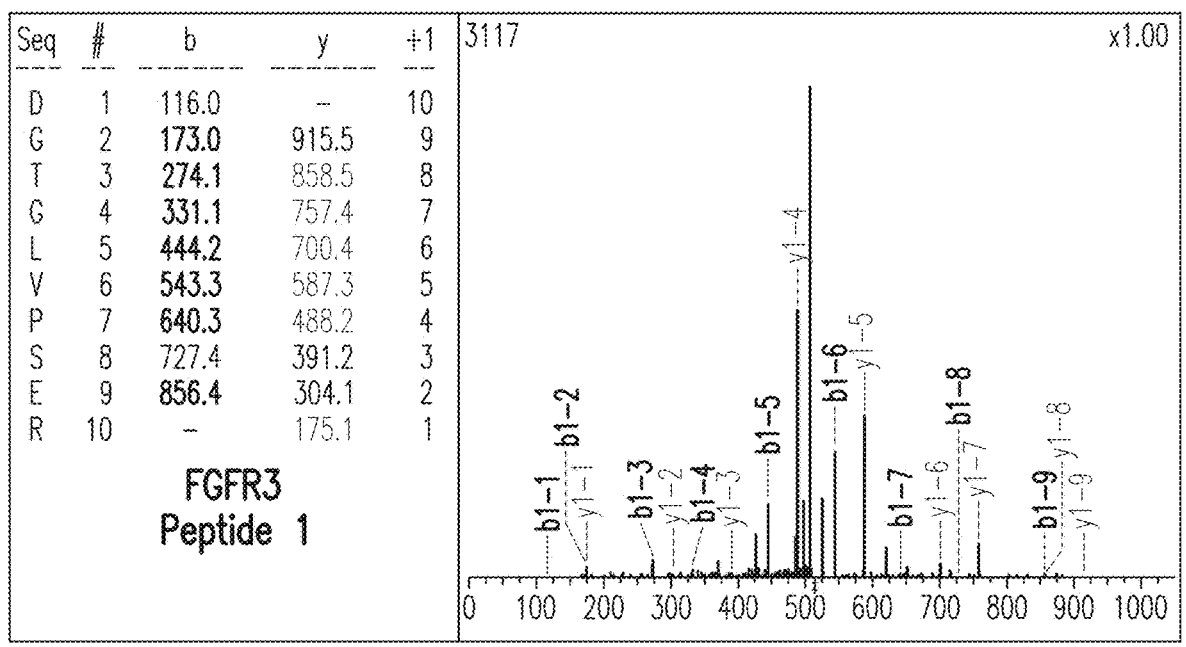
Figures 5, 10E:
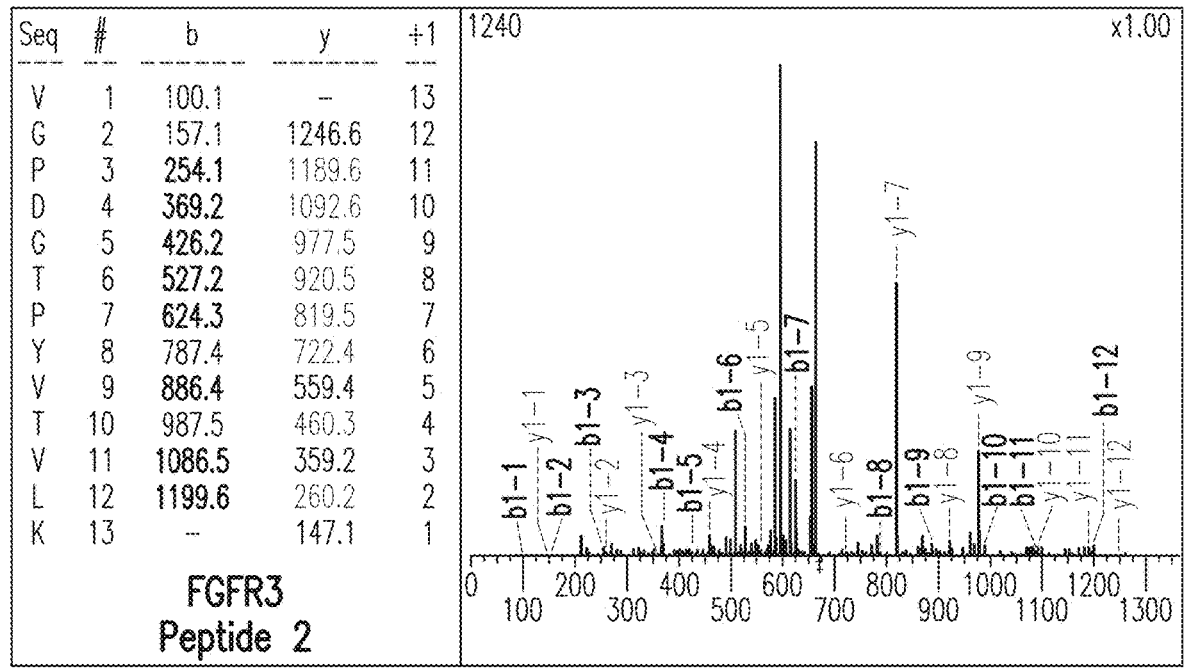
Figures 6, 10E:
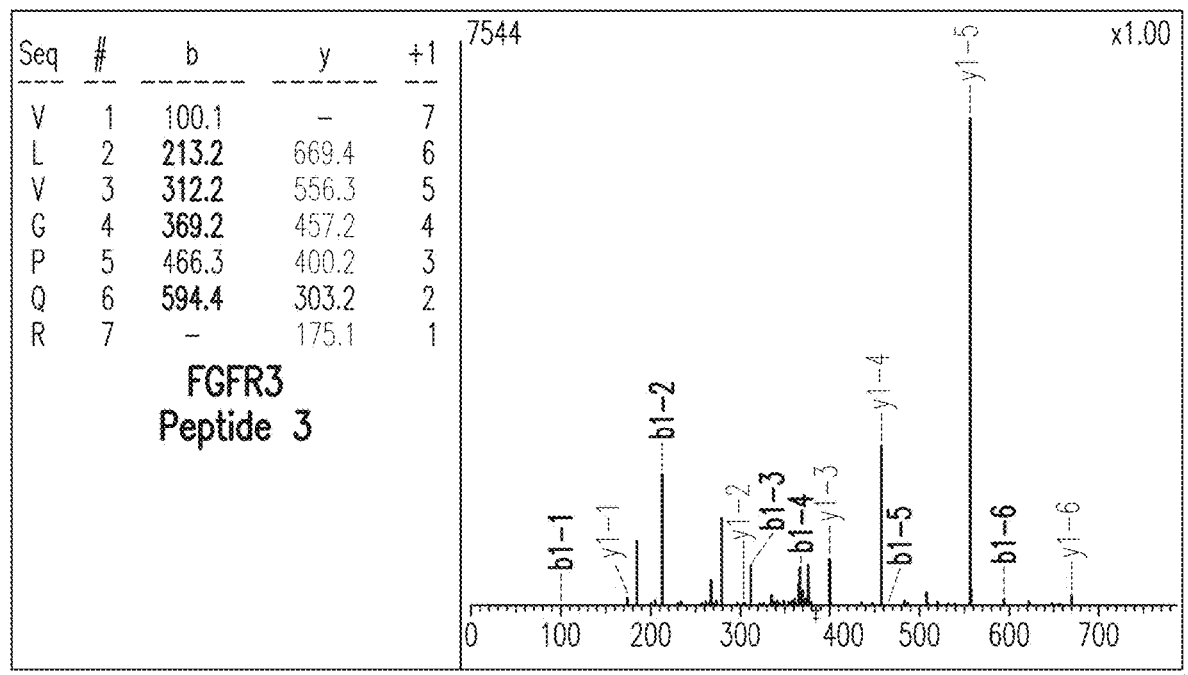

To experimentally validate the computational predictions that emerged from TX-Fuse, the PCR products spanning the fusion breakpoint were sequenced and validated each of the five in-frame fusion predictions (FIGS. 1 and 9). In FIG. 1B, the prediction is shown and in FIG. 1C, the cDNA sequence validation for the fusion with the highest read support involving FGFR3 fused in-frame with TACC3 in GSC-1123 is shown. The same FGFR3-TACC3 fusion transcript was also detected in the primary GBM-1123 tumor specimen from which the GSC-1123 culture was established (FIG. 1C). The amplified cDNA contained an open reading frame for a protein of 1,048 amino acids resulting from the fusion of a FGFR3 amino-terminal portion of residues 1-758 with a TACC3 carboxy-terminal portion of residues 549-838 (FIG. 1D). FGFR3 is a member of the FGFR receptor tyrosine kinase (TK) family that transduces intracellular signals after binding to FGF ligands (Turner and Grose, 2010). TACC3 belongs to the evolutionarily conserved TACC gene family, which also includes TACC1 and TACC2. The distinctive feature of TACC proteins is the presence of a coiled-coil domain at the C-terminus, known as the TACC domain. Through the TACC domain, TACC proteins localize to the mitotic spindle during metaphase and stabilize the microtubule spindle network (Hood and Royle, 2011; Peset and Vernos, 2008). In the predicted fusion protein the intracellular TK domain of FGFR3 is fused upstream of the TACC domain of TACC3 (FIG. 1D).

Figure 1E:
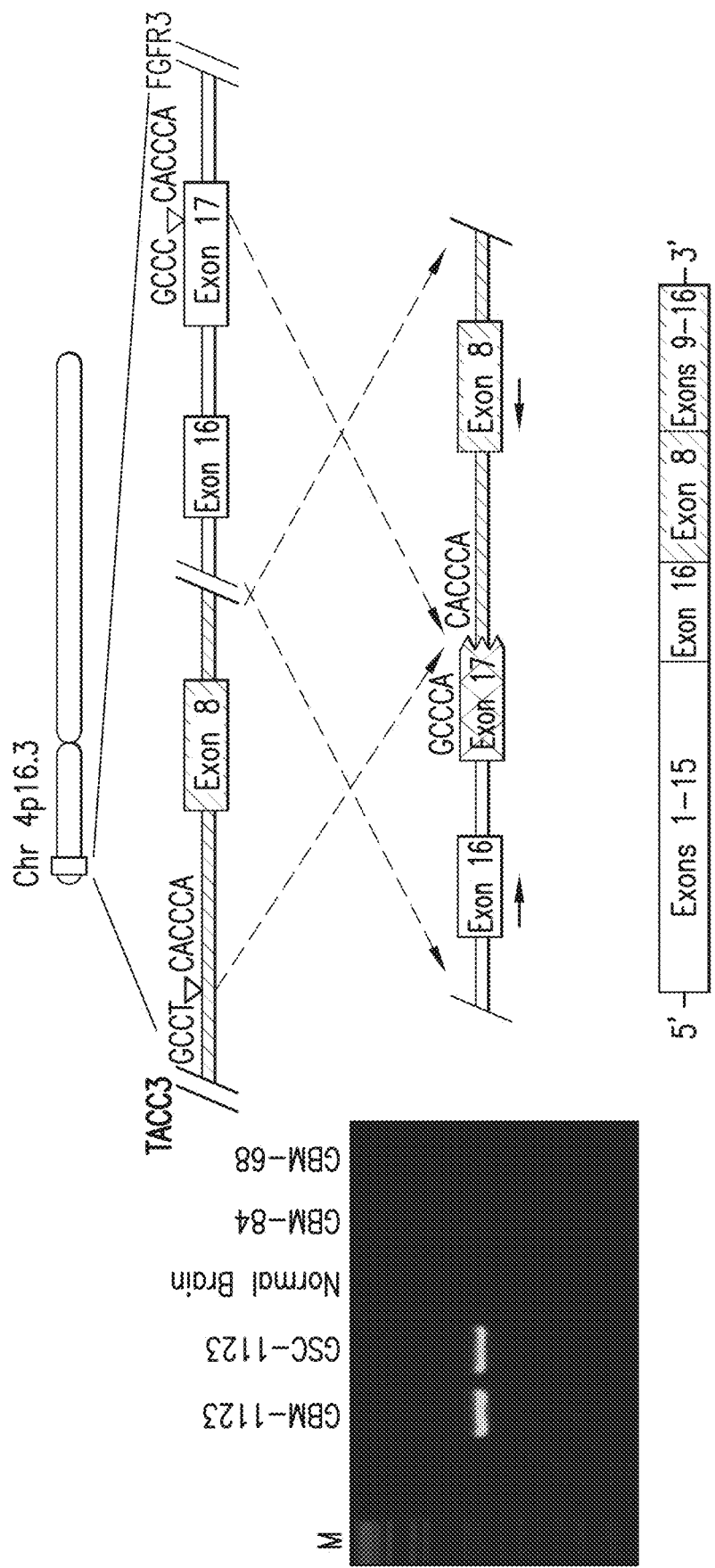
FIG. 1E shows an FGFR3-TACC3 gene fusion identified by whole transcriptome sequencing of GSCs. Genomic fusion of FGFR3 exon 17 with intron 7 of TACC3 is shown. In the fused mRNA, exon 16 of FGFR3 is spliced 5' to exon 8 of TACC3. Filled arrows indicate the position of the fusion-genome primers, which generate fusion-specific PCR products in GSC-1123 and GBM-1123.

Exon-specific gene expression analysis from the RNA-seq coverage in GSC-1123 demonstrated that the FGFR3 and TACC3 exons implicated in the fusion are highly overexpressed compared with the mRNA sequences not included in the fusion event (FIG. 10A). Quantitative RT-PCR showed that the expression of the fused FGFR3-TACC3 exons is significantly higher in GSC-1123 than other GSCs and the normal brain (80 to 130-fold, FIG. 10B). Without being bound by theory, functionally significant genetic rearrangements may result in marked overexpression (outlier) of the genes implicated in the fusion events (Tomlins et al., 2007; Tomlins et al., 2005). The FGFR3-TACC3 fusion protein was also abundantly expressed in GSC-1123 and in the primary tumor GBM-1123, as shown by Western blot and immunohistochemistry (FIGS. 10C and 10D). On a Western Blot, the FGFR3-TACC3 fusion protein migrated at a size of ~150 kD and immunoprecipitation followed by mass spectrometry revealed the presence of FGFR3 and TACC3 peptides consistent with the cDNA translation prediction (FIG. 10E). Using PCR, the genomic breakpoint coordinates were mapped to chromosome 4 (#1,808,966 for FGFR3 and #1,737,080 for TACC3, genome build GRCh37/hg19) falling within FGFR3 exon 17 and TACC3 intron 7, which gives rise to a transcript in which the 5' FGFR3 exon 16 is spliced to the 3' TACC3 exon 8. The DNA junctions of FGFR3 and TACC3 show microhomology within a 10-base region, an observation consistent with results previously reported for other chromosomal rearrangements in human cancer (Bass et al., 2011; Stephens et al., 2009) (FIG. 1E).

Figure 2A:
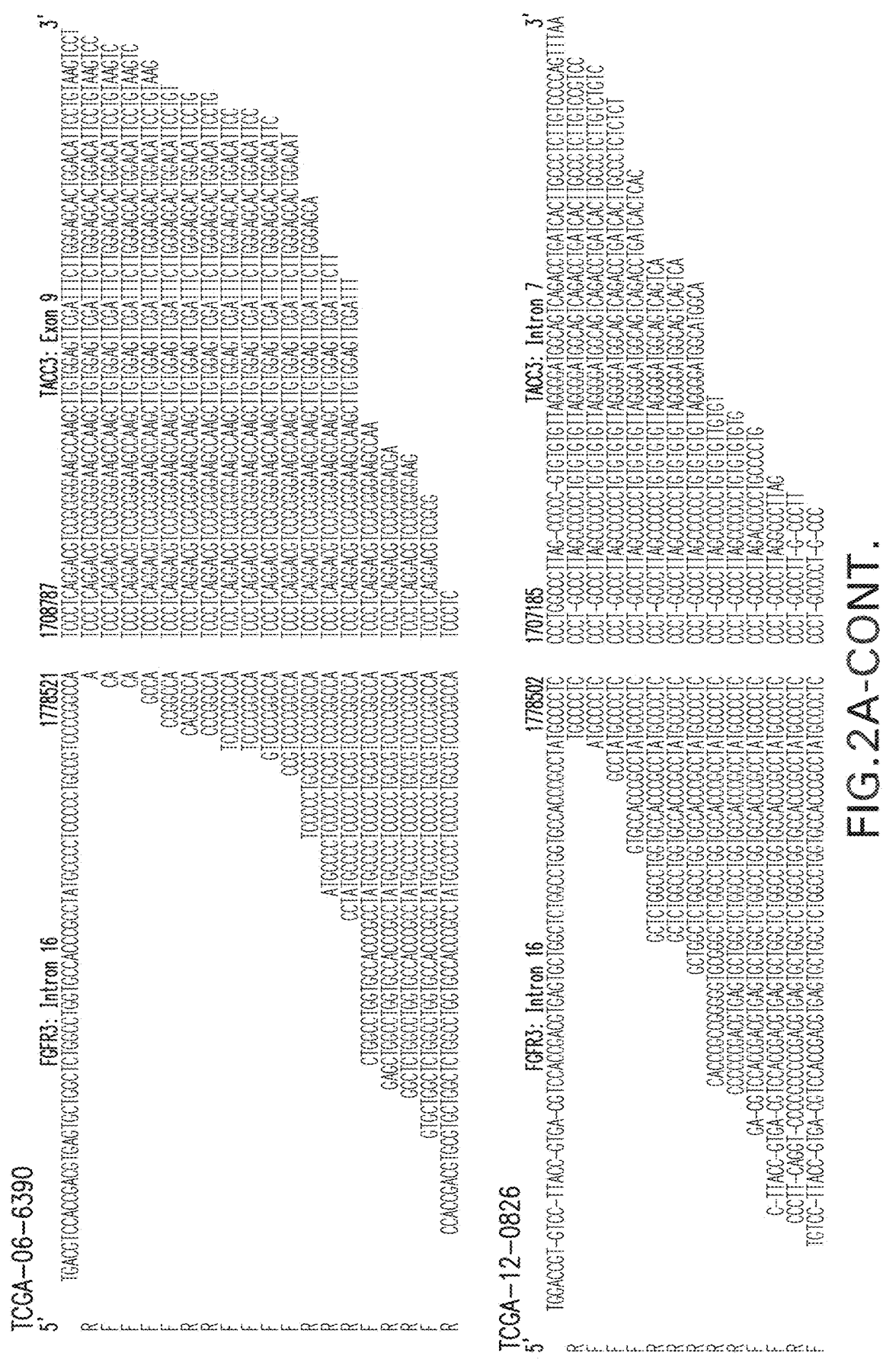
Figure 2B:
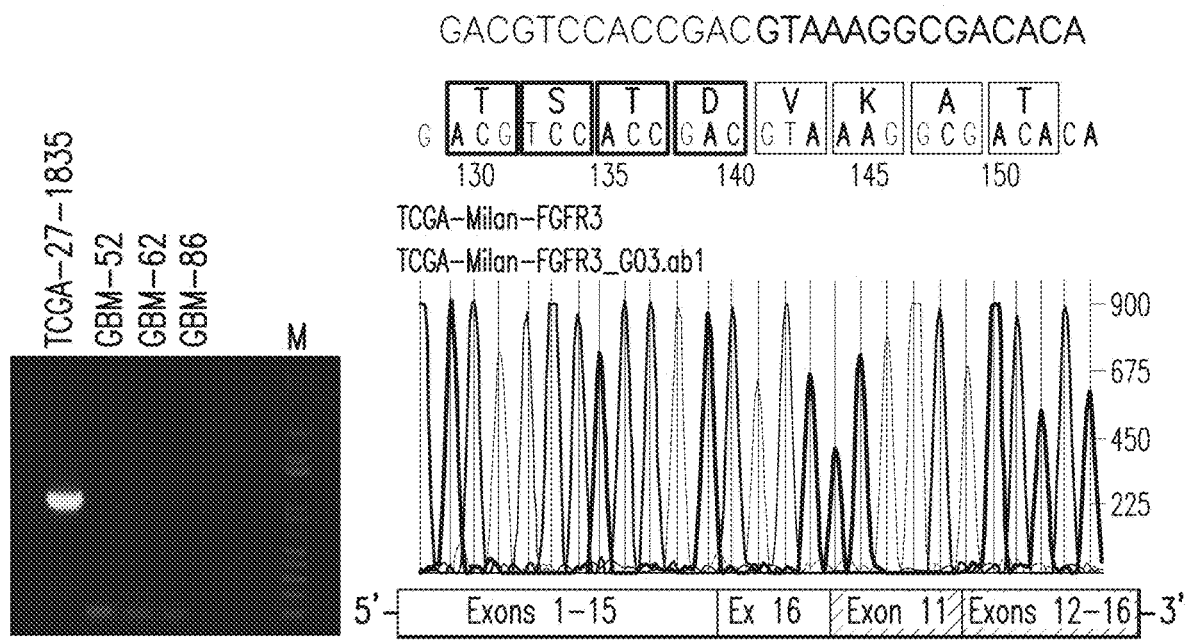
FIG. 2B shows recurrent gene fusions between FGFR and TACC genes in GBM. On the left, a gel of FGFR-TACC-specific PCR is shown for FGFR3-TACC3 from a GBM cDNA sample. On the right, Sanger sequencing chromatograms show the reading frame at the breakpoint (SEQ ID NO: 81) and putative translation of the fusion protein (SEQ ID NO: 86) in the positive samples.
Figure 2C:
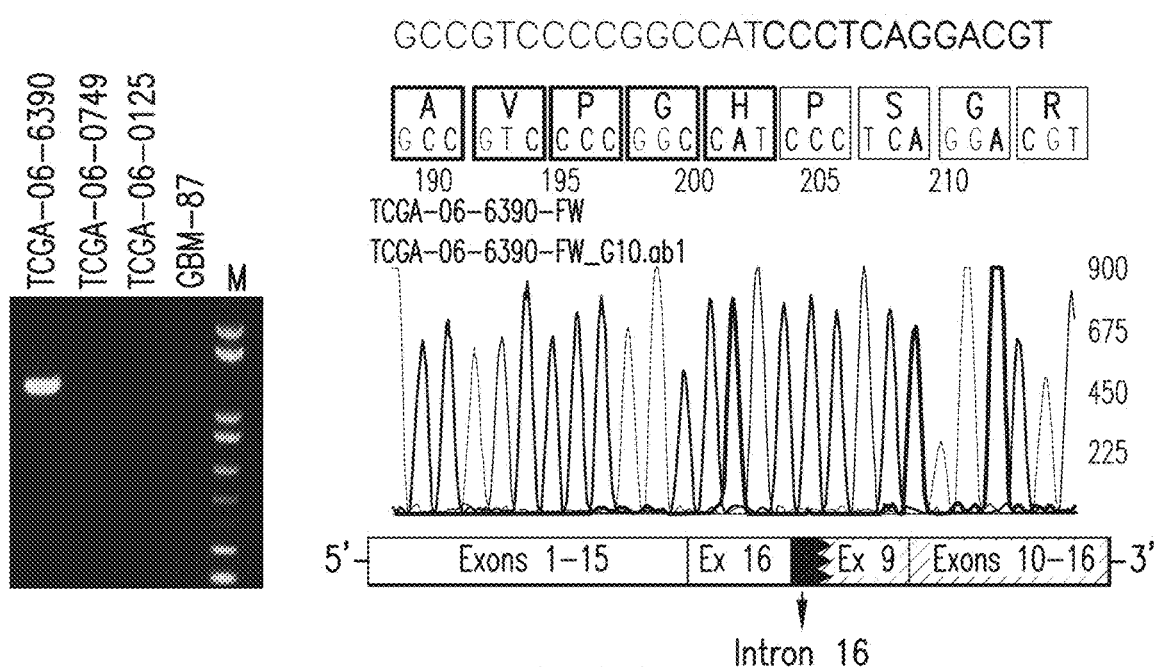
FIG. 2C shows recurrent gene fusions between FGFR and TACC genes in GBM. On the left, a gel of FGFR-TACC-specific PCR is shown for FGFR3-TACC3 from a GBM cDNA sample. On the right, Sanger sequencing chromatograms show the reading frame at the breakpoint (SEQ ID NO: 82) and putative translation of the fusion protein (SEQ ID NO: 87) in the positive samples.
Figure 2D:
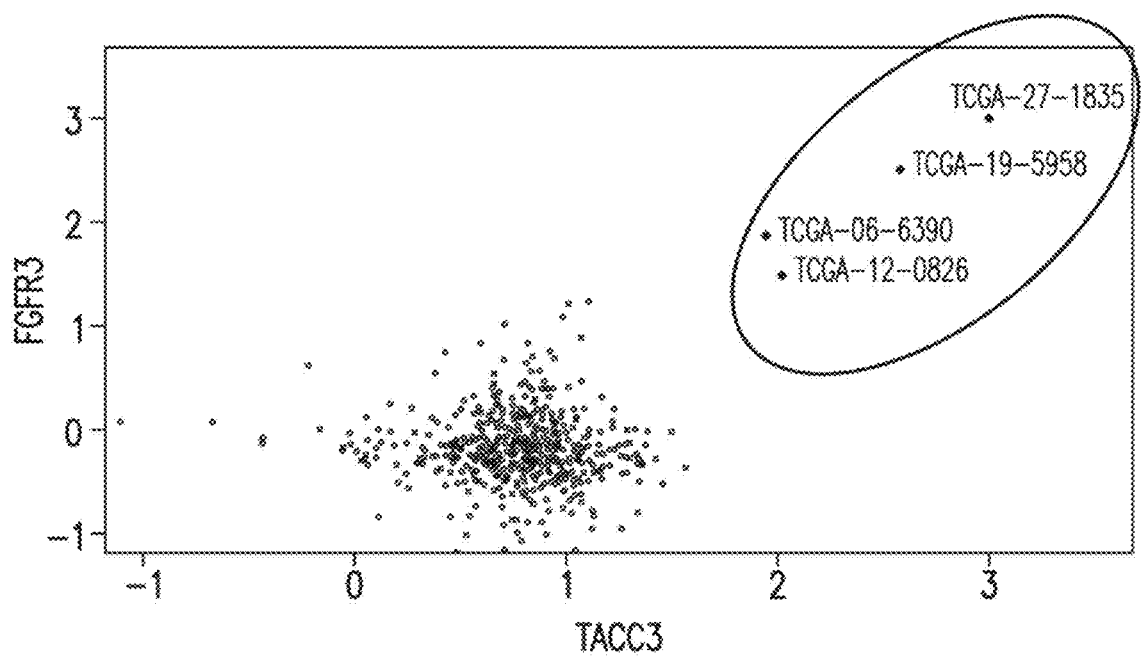
FIG. 2D shows recurrent gene fusions between FGFR and TACC genes in GBM. Co-outlier expression of FGFR3 and TACC3 in four GBM tumors from Atlas-TCGA is shown in the plot.
Figure 2E:
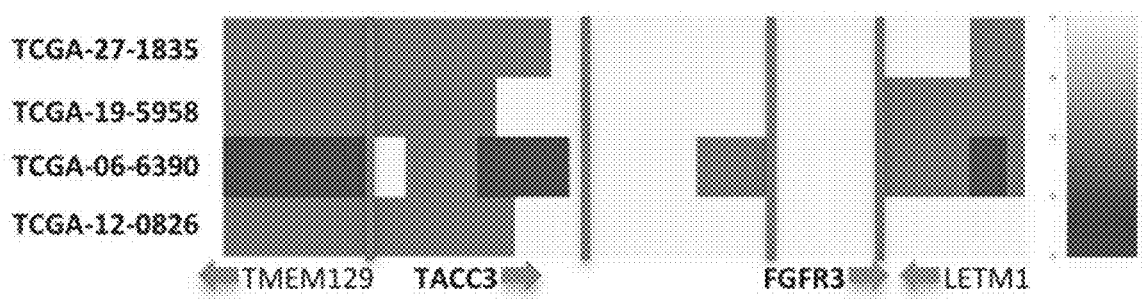
FIG. 2E shows recurrent gene fusions between FGFR and TACC genes in GBM. CNV analysis shows micro-amplifications of the rearranged portions of the FGFR3 and TACC3 genes in the same four Atlas-TCGA GBM samples.

The experimental validation of the inferred genomic fusions was focused on FGFR3-TACC3. Exome-Fuse identified FGFR3-TACC3 gene fusions in four GBM samples with breakpoints spanning invariably within intron 16 of FGFR3 (which is downstream to the coding region for the TK domain) and intron 7-10 of TACC3 (which is upstream to the TACC domain) (FIG. 2A, Tables 4 and 5). Among the four positive TCGA GBM specimens, two were available from TCGA centers for molecular analysis (TCGA-27-1835 and TCGA-06-6390) and, by Sanger sequencing, each of them were confirmed to carry an in-frame fusion transcript that is consistent with the predicted genomic breakpoints (FIGS. 2B and 2C). Thus, the frames of the FGFR3-TACC3 fusion proteins invariably result in juxtaposing the TK domain of FGFR3 upstream of the TACC domain of TACC3. Consistent with the abundant expression of FGFR3-TACC3 in GSC-1123 and GBM-1123, the mRNA expression analysis of the TCGA tumors revealed that the four FGFR3-TACC3-positive GBM display marked co-outlier expression of FGFR3 and TACC3 (FIG. 2D). Recurrent gene fusions can be associated with local copy number variations (CNV) of the breakpoint regions (Wang et al., 2009). Accordingly, the analysis of SNP arrays in the TCGA dataset revealed the presence of microamplification events of the FGFR3 and TACC3 genes in all four FGFR3-TACC3-positive GBM (FIG. 2E).

TABLE 4

List of split inserts supporting the identification of FGFR3-TACC3 fusion genes in four GBM samples from the ATLAS-TCGA exome collection (SEQ ID NOS 187-224, respectively, in order of appearance)

| TCGA sample ID | gene1 | gene 1 length | read_ID | % identity | length | mismatch | gap |
|---|---|---|---|---|---|---|---|
| TCGA-06-6390 | FGFR3 | 76 | C01PRACXX110628:1:1301:1934:116558 | 100 | 76 | 0 | 0 |
| TCGA-06-6390 | FGFR3 | 76 | C01RDACXX110628:2:2305:4872:47008 | 98.68 | 76 | 1 | 0 |
| TCGA-06-6390 | FGFR3 | 76 | D03U9ACXX11625:6:1203:16178:138219 | 100 | 76 | 0 | 0 |
| TCGA-06-6390 | TACC3 | 76 | C01PRACXX110628:2:1102:13552:120312 | 100 | 76 | 0 | 0 |
| TCGA-06-6390 | TACC3 | 76 | C01PRACXX110628:8:2308:6515:60354 | 100 | 76 | 0 | 0 |
| TCGA-06-6390 | TACC3 | 76 | C01RDACXX110628:6:1305:16843:57213 | 98.68 | 76 | 1 | 0 |
| TCGA-06-6390 | TACC3 | 75 | D03U9ACXX110625:2:1202:19578:90281 | 100 | 75 | 0 | 0 |
| TCGA-06-6390 | TACC3 | 76 | D03U9ACXX110625:4:2306:2694:174970 | 100 | 76 | 0 | 0 |
| TCGA-12-0826 | FGFR3 | 72 | 61C59AAXX:4:21:17613:20886 | 98.61 | 72 | 0 | 1 |
| TCGA-12-0826 | TACC3 | 75 | 42MINAAXX090813:5:30:1412:1280#0 | 100 | 75 | 0 | 0 |
| TCGA-12-0826 | TACC3 | 76 | 61C59AAXX100217:4:2:4279:6949 | 100 | 76 | 0 | 0 |
| TCGA-12-0826 | TACC3 | 76 | 42MJNAAXX090813:5:37:435:1250#0 | 100 | 76 | 0 | 0 |
| TCGA-12-0826 | TACC3 | 51 | 61C59AAXX100217:5:89:7727:2557 | 98.04 | 51 | 1 | 0 |
| TCGA-19-5958 | TACC3 | 62 | D03U9ACXX110625:4:2206:9451:114168 | 90.32 | 62 | 6 | 0 |
| TCGA-19-5958 | TACC3 | 74 | D03U9ACXX110625:1:2204:20064:21192 | 95.95 | 74 | 3 | 0 |
| TCGA-27-1835 | FGFR3 | 76 | C00HWABXX110325:7:2202:17680:110666 | 100 | 76 | 0 | 0 |
| TCGA-27-1835 | TACC3 | 76 | C00HWABXX110325:7:1104:10731:5183 | 100 | 76 | 0 | 0 |
| TCGA-27-1835 | TACC3 | 60 | B09V2ABXX110408:2:2201:5811:24541 | 100 | 60 | 0 | 0 |
| TCGA-27-1835 | TACC3 | 61 | B09UABXX110405:4:2102:15742:63594 | 91.8 | 61 | 5 | 0 |

| TCGA sample ID | read start | read end | hg18 genome start | hg18 genome end | e-value | bit score | read 1 fasta |
|---|---|---|---|---|---|---|---|
| TCGA-06-6390 | 1 | 76 | 1778372 | 1778447 | 8E-40 | 151 | GTGCTGCCATGCCGCGCCCTCCCAG AGGCCCACCTTCAGCACCTGGTGGA GGACCTGGACCGTGTCCTTACCGTG |
| TCGA-06-6390 | 1 | 76 | 1778364 | 1778439 | 2E-37 | 143 | ATGCGGGAGTGCTGGCATGACGCGC CCTCCCAGAGGCCCACCTTCAAGGA GCTGGTGGAGGACCTGGACCGTGTCC |

TABLE 4-continued

List of split inserts supporting the identification of FGFR3-TACC3
fusion genes in four GBM samples from the ATLAS-TCGA exome collection
(SEQ ID NOS 187-224, respectively, in order of appearance)

| TCGA-06-6390 | 1 | 76 | 1778413 | 1778488 | 8E-40 | 151 | ACCTGGTGGAGGACCTGGACCGTGT CCTTACCGTGACGTCCACCGACGTG AGTGCTGGCTCTGGCCTGGTGCCACC |
| TCGA-06-6390 | 1 | 76 | 1708918 | 1708843 | 8E-40 | 151 | CCCTTAAAACAACTCGTTCCCTCAG ACCACACACAAGACAGTTCAAGAGG GACTCAAGGACTTACAGGAATGTCCA |
| TCGA-06-6390 | 1 | 76 | 1708956 | 1708881 | 8E-40 | 151 | AACCAAAGGCTCAGACCCCCAGGAA TAGAAAATATAGGCCCTTAAAACAA CTCGTTCCCTCAGACCACACACAAGA |
| TCGA-06-6390 | 1 | 76 | 1708865 | 1708790 | 2E-37 | 143 | TCAAGGACTTACAGGAATGTCCAGT GCTCCCAAGAAATCGAACTCCACAA GCTTGGCTTCCCGCGCACGTCCTGAG |
| TCGA-06-6390 | 1 | 75 | 1708861 | 1708787 | 3E-39 | 149 | GGACTTACAGGAATGTCCAGTGCTC CCAAGAAATCGAACTCCACAAGCTT GGCTTCCCGCGGACGTCCTGAGGGAT |
| TCGA-06-6390 | 1 | 76 | 1708896 | 1708821 | 8E-40 | 151 | CAGACCACACACAAGACAGTTCAAG AGGGACTCAAGGACTTACAGGAATG TCCAGTGCTCCCAAGAAATCGAACTC |
| TCGA-12-0826 | 1 | 71 | 1778439 | 1778510 | 2E-34 | 133 | CTTACCGTGACGTCCACCGACGTGA GTGCTGGCTCTGGCCTGGTGCCACC CGCCTATGCCCCTCCCCTGCCCTTAG |
| TCGA-12-0826 | 2 | 76 | 1707299 | 1707225 | 3E-39 | 149 | AAACTTGAGGTATAAGGACTGCTTC CTCAAGGCCGACTCCTTAAACTGGG GACAAGAGGGCAAGTGATCAGGTCTG |
| TCGA-12-0826 | 1 | 76 | 1707299 | 1707224 | 8E-40 | 151 | AACTTGAGGTATAAGGACTGCTTCC TCAAGGCCGACTCCTTAAACTGGGG ACAAGAGGGCAAGTGATCAGGTCTGA |
| TCGA-12-0826 | 1 | 76 | 1778346 | 1778421 | 8E-40 | 151 | GCCCGCAGGTACATGATCATGCGGG AGTGCTGGCATGCCGCGCCCTCCCA GAGGCCCACCTTCAAGCAGCTGGTGG |
| TCGA-12-0826 | 1 | 51 | 1778443 | 1778493 | 4E-24 | 93.7 | ACCGTGACGTCCACCGACGTGAGTG CTGGCTCTGGCCTGGTGCGACCCGC CGATCTCTCTCCCCTGTCCTTTTCCT |
| TCGA-19-5958 | 1 | 62 | 1707141 | 1707202 | 4E-17 | 75.8 | TGGGAGGGTGCGGGGGGCGGGGGG GGAGTGTGCAGGTGAGCTCCCTGG CCCTTGGCCCCCTGCCCTCTGGGGGG |
| TCGA-19-5958 | 1 | 74 | 1707097 | 1707170 | 5E-33 | 123 | CTGGGAATGGTGGTGTCTCGGGCAG GGTTGTGGGTGACCGGGGGTGGGAG GGTGCGGGGGACCGGGGGGGGAGGG |
| TCGA-27-1835 | 1 | 76 | 1778338 | 1778413 | 8E-40 | 151 | AGCGCCCTGCCCGCAGGTACATGAT CATGCGGGAGTGCTGGCATGCCGCG CCCTCCCAGAGGCCCACCTTCAAGCA |
| TCGA-27-1835 | 1 | 76 | 1709492 | 1709417 | 8E-40 | 151 | GCCAACGCCATGCCCAGGCCGGAGA GTCCCGGGGAGGCTGCTGGTGGGCA GCTGACTGCGGGGACACTGGGTGAA |
| TCGA-27-1835 | 1 | 60 | 1709504 | 1709445 | 3E-30 | 119 | AGGCCACCAGAGGCCAACGCCATGC CCAGGCCGGAGAGTCCCGGGGAGGC TGCTGGTGGGAGGCGAACGCGGGGA |
| TCGA-27-1835 | 1 | 61 | 1709482 | 1709422 | 6E-19 | 81.8 | TGCCCAGGCCGGAGAGTCCCGGGGC GGCTGCTGGGGGGAGCTGACTGGG GGGGCACTGGGGGGAGACCCGGGCC |

| TCGA sample ID | gene2 | gene 2 length | read_ID | % identity | length | mis- match | gap |
|---|---|---|---|---|---|---|---|
| TCGA-06-6390 | TACC3 | 76 | C01PRACXX110628:1:1301:1934:116558 | 100 | 76 | 0 | 0 |
| TCGA-06-6390 | TACC3 | 76 | C01RDACXX110628:3:2305:4872:47008 | 100 | 76 | 0 | 0 |
| TCGA-06-6390 | TACC3 | 76 | D0389ACXX110625:6:1203:16178:138219 | 100 | 76 | 0 | 0 |
| TCGA-06-6390 | FGFR3 | 76 | C01PRACXX110628:2:1102:13552:120312 | 100 | 76 | 0 | 0 |
| TCGA-06-6390 | FGFR3 | 76 | C01PRACXX110628:8:2308:6515:60354 | 100 | 76 | 0 | 0 |

TABLE 4-continued

List of split inserts supporting the identification of FGFR3-TACC3
fusion genes in four GBM samples from the ATLAS-TCGA exome collection
(SEQ ID NOS 187-224, respectively, in order of appearance)

| TCGA-06-6390 | FGFR3 | 76 | C01RDACXX110628:6:1305:16843:57213 | 96.05 | 76 | 3 | 0 |
| TCGA-06-6390 | FGFR3 | 76 | D03U9ACXX110625:2:1202:19578:90281 | 100 | 76 | 0 | 0 |
| TCGA-06-6390 | FGFR3 | 76 | D03U9ACXX110625:4:2306:2694:174970 | 100 | 76 | 0 | 0 |
| TCGA-12-0826 | TACC3 | 72 | 61C59AAXX100217:4:21:17613:20886 | 95.83 | 72 | 3 | 0 |
| TCGA-12-0826 | FGFR3 | 76 | 42MHNAXX090813:5:30:1412:128#0 | 98.68 | 76 | 1 | 0 |
| TCGA-12-0826 | FGFR3 | 76 | 61C59AAXX100217:4:2:4279:6949 | 98.68 | 7 | 0 | 1 |
| TCGA-12-0826 | TACC3 | 67 | 42MJNAXX090813:5:37:435:1250#0 | 98.51 | 67 | 1 | 0 |
| TCGA-12-0826 | TACC3 | 75 | 61C59AAXX100217:5:89:7727:2557 | 97.33 | 75 | 2 | 0 |
| TCGA-19-5958 | FGFR3 | 76 | D03U9ACXX110625:4:2206:9451:114168 | 98.68 | 76 | 1 | 0 |
| TCGA-19-5958 | FGFR3 | 76 | D03U9ACXX110625:1:2204:20064:21192 | 100 | 76 | 0 | 0 |
| TCGA-27-1835 | TACC3 | 76 | C00HWABXX110325:7:2202:17680:110666 | 96.05 | 76 | 3 | 0 |
| TCGA-27-1835 | FGFR3 | 76 | C00HWABXX110325:7:1104:10731:5183 | 96.05 | 76 | 3 | 0 |
| TCGA-27-1835 | FGFR3 | 76 | B09V2ABXX110408:2:2201:5811:24541 | 100 | 76 | 0 | 0 |
| TCGA-27-1835 | FGFR3 | 76 | B097UABXX110405:4:2102:15742:6359 | 100 | 76 | 0 | 0 |

| TCGA sample ID | read start | read end | hg18 genome start | hg18 genome end | e-value | bit score | read 2 fasta |
| --- | --- | --- | --- | --- | --- | --- | --- |
| TCGA-06-6390 | 1 | 76 | 1708922 | 1708847 | 8E-40 | 151 | TAGGCCCTTAAAACAACTCGTTCCC TCAGACCACACACAAGACAGTTCAA GAGGGACTCAAGGACTTACAGGAATG |
| TCGA-06-6390 | 1 | 76 | 1708867 | 1708792 | 8E-40 | 151 | ACTCAAGGACTTACAGGAATGTCCA GTGCTCCCAAGAAATCGAACTCCAC AAGCTTGGCTTCCCGCGGACGTCCTG |
| TCGA-06-6390 | 1 | 76 | 1708921 | 1708846 | 8E-40 | 151 | AGGCCCTTAAAACAACTCGTTCCCT CAGACCACACACAAGACAGTTCAAG AGGGACTCAAGGACTTACAGGAATGT |
| TCGA-06-6390 | 1 | 76 | 1778387 | 1778462 | 8E-40 | 151 | GCCCTCCCAGAGGCCCACCTTCAAG CAGCTGGTGGAGGACCTGGACCGTG TCCTTACCGTGACGTCCACCGACGTG |
| TCGA-06-6390 | 1 | 76 | 1778382 | 1778457 | 8E-40 | 151 | GCCGCGCCCTCCCAGAGGCCCACCT TCAAGCAGCTGGTGGAGGACCTGGA CCGTGTCCTTACCGTGACGTCCACCG |
| TCGA-06-6390 | 1 | 76 | 1778417 | 1778492 | 1E-32 | 127 | GGTGGAGGACCTGGACCGTGACCTT ACCGGGACGTCCACCGACGGGAGTG CTGGCTCTGGCCTGGTGCCACCCGCC |
| TCGA-06-6390 | 1 | 76 | 1778447 | 1778522 | 8E-40 | 151 | GACGTCCACCGACGTGAGTGCTGGC TCTGGCCTGGTGCCACCCGCCTATG CCCCTCCCCCTGCCGTCCCCGGCCAT |
| TCGA-06-6390 | 1 | 76 | 1778435 | 1778510 | 8E-40 | 151 | TGTCCTTACCGTGACGTCCACCGAC GTGAGTGCTGGCTCTGGCCTGGTGC CACCCGCCTATGCCCCTCCCCTGCCC |
| TCGA-12-0826 | 1 | 72 | 1707362 | 1707291 | 3E-30 | 119 | TACCTGCTGGTCTCGGTGGCCACGG GCACTGGTCTACCAGGGCTGTCCCT CCGGAGGGGGTCAAACTTGAGGGATA |
| TCGA-12-0826 | 1 | 76 | 1778427 | 1778502 | 2E-37 | 143 | CTGGACCGTGTCCTTACCGTGACGT CCACCGACGTGAGTGCTGGCTCTGG CCTGGTGCCACCCGCCCATGCCCCTC |
| TCGA-12-0826 | 1 | 75 | 1778435 | 1778510 | 8E-37 | 141 | TGTCCTTACCGTGACGTCCACCGAC GTGAGTGCTGGCTCTGGCCTGGTGC CACCCGCCTATGCCCCTCCCCTGCCC |
| TCGA-12-0826 | 1 | 67 | 1707635 | 1707569 | 5E-32 | 125 | AAAAGATTTAAGTTTAGATCTTTAA TATACCTAGAACGGTGGCTGTAACC AGCAAGGCAGGAGCCCTTTGTGTTGG |
| TCGA-12-0826 | 2 | 76 | 1707306 | 1707232 | 5E-36 | 133 | TGGGTCAAACTTGAGGTATAAGGAC TGCTTCCTCAAGGCCGACTCCTTAT ACTGGGGACAAGAGGGCAAGTGATCA |
| TCGA-19-5958 | 1 | 76 | 1778462 | 1778537 | 2E-37 | 143 | GAGTGCTGGCTCTGGCCTGGTGCCA CCCGCCTATGCCCCTCCCCTGGCG TCCCCGGCCATCCTGCCCCCCAGAGT |

TABLE 4-continued

List of split inserts supporting the identification of FGFR3-TACC3
fusion genes in four GBM samples from the ATLAS-TCGA exome collection
(SEQ ID NOS 187-224, respectively, in order of appearance)

```
TCGA-19-5958    1    76    1778462    1778537    2E-41    151    GAGTGCTGGCTCTGGCCTGGTGCCA
                                                                CCCGCCTATGCCCCTCCCCCTGCCG
                                                                TCCCCGGCCATCCTGCCCCCCAGAGT

TCGA-27-1835    1    76    1709492    1709417    1E-32    127    GCCAACGCCATGCCCAGGCCGGAGA
                                                                GTCCCGGGGAGGCTGCTGGTGGGGA
                                                                GCTGACTTCGGGGACACTGGGGGGAA

TCGA-27-1835    1    76    1778363    1778438    1E-32    127    CATGCGGGAGTGCTGGCATGGCGCG
                                                                CCCTCCCAGCGGCCCACCTTCAAGC
                                                                AGCTGGTGGGGGACCTGGACCGTGTC

TCGA-27-1835    1    76    1778458    1778533    8E-40    151    ACGTGAGTGCTGGCTCTGGCCTGGT
                                                                GCCACCCGCCTATGCCCCTCCCCCT
                                                                GCCGTCCCCGGCCATCCTGCCCCCCA

TCGA-27-1835    1    76    1778388    1778463    8E-40    151    CCCTCCCAGAGGCCCACCTTCAAGC
                                                                AGCTGGTGGAGGACCTGGACCGTGT
                                                                CCTTACCGTGACGTCCACCGACGTGA
```

TABLE 5

List of split reads supporting the identification of FGFR3-TACC3 fusion genes in
four GBM samples from the ATLAS-TCGA exome collection (SEQ ID NOS 225-318,
respectively, in order of appearance)

| sample | Gene split 1 | readiID | Direction split | hg18 start split1 | hg18 stop split1 |
|---|---|---|---|---|---|
| TCGA-06-6390 | TACC3 | D03U9ACXX110625:2:1202:19578:90281 | R | 1778521 | 1778521 |
| TCGA-06-6390 | FGFR3 | C01PRACXX110628:3:1104:10052:66371 | F | 1778520 | 1778521 |
| TCGA-06-6390 | FGFR3 | C01PRACXX110628:5:1108:3119:22892 | F | 1778520 | 1778521 |
| TCGA-06-6390 | FGFR3 | D03U9ACXX110625:8:2304:13007:108632 | F | 1778520 | 1778521 |
| TCGA-06-6390 | FGFR3 | C01PRACXX110628:5:2108:1999:91559 | F | 1778518 | 1778521 |
| TCGA-06-6390 | FGFR3 | C01RDACXX110628:3:1308:1446:66311 | F | 1778515 | 1778521 |
| TCGA-06-6390 | TACC3 | D03U9ACXX110625:5:2205:12523:196352 | R | 1778514 | 1778521 |
| TCGA-06-6390 | TACC3 | C01PRACXX110628:5:2103:6815:17943 | R | 1778514 | 1778521 |
| TCGA-06-6390 | FGFR3 | C01PRACXX110628:3:1204:10831:2928 | F | 1778512 | 1778521 |
| TCGA-06-6390 | FGFR3 | C01PRACXX110628:5:2204:6732:191360 | F | 1778512 | 1778521 |
| TCGA-06-6390 | FGFR3 | C01PRACXX110628:8:1308:2911:26590 | F | 1778511 | 1778521 |
| TCGA-06-6390 | FGFR3 | C01PRACXX110628:8:2207:458684017 | F | 1778509 | 1778521 |
| TCGA-06-6390 | TACC3 | C01PRACXX110628:7:2205:11825:39734 | R | 1778501 | 1778521 |
| TCGA-06-6390 | TACC3 | C01PRACXX110628:6:1106:12159:179499 | R | 1778494 | 1778521 |
| TCGA-06-6390 | TACC3 | D03U9ACXX110625:4:2202:12501:40389 | R | 1778491 | 1778521 |
| TCGA-06-6390 | FGFR3 | C01PRACXX110628:3:1305:3044:13238 | F | 1778473 | 1778521 |
| TCGA-06-6390 | TACC3 | D03U9ACXX110625:5:2205:12523:196352 | R | 1778470 | 1778521 |
| TCGA-06-6390 | TACC3 | C01PRACXX110628:7:2205:11825:39734 | F | 1778469 | 1778521 |
| TCGA-06-6390 | FGFR3 | D03U9ACXX110625:7:2106:4492:173350 | F | 1778464 | 1778521 |
| TCGA-06-6390 | TACC3 | C01PRACXX110628:5:2103:6815:17943 | F | 1778452 | 1778521 |
| TCGA-12-0826 | TACC3 | 61C59AAXX100217:4:93:15133:6133 | R | 1778495 | 1778502 |
| TCGA-12-0826 | TACC3 | 61C59AAXX100217:5:107:10675:16040 | R | 1778495 | 1778502 |
| TCGA-12-0826 | FGFR3 | 61C59AAXX100217:5:108:1809:11295 | F | 1778494 | 1778502 |
| TCGA-12-0826 | FGFR3 | 61C59AAXX100217:5:82:13129:10637 | F | 1778490 | 1778502 |
| TCGA-12-0826 | FGFR3 | 42MJNAAXX090813:6:80:691:1877#0 | F | 1778481 | 1778502 |
| TCGA-12-0826 | TACC3 | 61C59AAXX100217:3:75:10586:12881 | R | 1778470 | 1778502 |
| TCGA-12-0826 | TACC3 | 61C59AAXX100217:4:114:5844:3161 | R | 1778470 | 1778502 |
| TCGA-12-0826 | TACC3 | 61C59AAXX100217:4:93:15133:6133 | R | 1778495 | 1778502 |
| TCGA-12-0826 | TACC3 | 42MJNAAXX090813:5:70:888:108#0 | R | 1778466 | 1778502 |
| TCGA-12-0826 | TACC3 | 61C59AAXX100217:3:55:4966:15975 | R | 1778451 | 1778502 |
| TCGA-12-0826 | FGFR3 | 42MJNAAXX090813:5:23:156:1150#0 | F | 1778447 | 1778502 |
| TCGA-12-0826 | FGFR3 | 61C59AAXX100217:4:21:17613:20886 | F | 1778439 | 1778502 |
| TCGA-12-0826 | FGFR3 | 61C59AAXX100217:4:2:4279:6949 | F | 1778435 | 1778502 |
| TCGA-19-5958 | TACC3 | C01RDACXX110628:6:1102:11157:101962 | R | 1778533 | 1778539 |
| TCGA-19-5958 | TACC3 | C01REACXX110629:2:2104:5009:98392 | R | 1778517 | 1778539 |
| TCGA-19-5958 | TACC3 | C01PRACXX110628:7:2103:12434:91988 | R | 1778501 | 1778539 |
| TCGA-27-1835 | TACC3 | B06UCABXX110322:6:1103:9262:46754 | R | 1778586 | 1778595 |
| TCGA-27-1835 | FGFR3 | C00HWABXX110325:4:1201:20980:90877 | F | 1778567 | 1778595 |
| TCGA-27-1835 | TACC3 | B06UCABXX110322:5:1108:14043:83287 | R | 1778564 | 1778595 |
| TCGA-27-1835 | TACC3 | B097UACXX110405:4:2204:19445:88453 | R | 1778558 | 1778595 |
| TCGA-27-1835 | TACC3 | B097UACXX110405:4:2201:20658:44401 | R | 1778557 | 1778595 |
| TCGA-27-1835 | TACC3 | B097UACXX110405:2:2104:15688:71022 | R | 1778555 | 1778595 |

TABLE 5-continued

List of split reads supporting the identification of FGFR3-TACC3 fusion genes in
four GBM samples from the ATLAS-TCGA exome collection (SEQ ID NOS 225-318,
respectively, in order of appearance)

| | | | | | | |
|---|---|---|---|---|---|---|
| TCGA-27-1835 | TACC3 | C00HWABXX110325:6:2102:20394:42427 | | R | 1778543 | 1778595 |
| TCGA-27-1835 | TACC3 | B09V2ABXX110408:6:1203:18187:141862 | | R | 1778543 | 1778595 |
| TCGA-27-1835 | TACC3 | B09V2ABXX110408:8:1205:4774:81604 | | R | 1778537 | 1778595 |
| TCGA-27-1835 | TACC3 | C00HWABXX110325:2:1107:16168:23614 | | R | 1778535 | 1778595 |
| TCGA-27-1835 | TACC3 | C00HWABXX110325:7:2107:1225:167363 | | R | 1778530 | 1778595 |
| TCGA-27-1835 | TACC3 | B097UABXX110405:2:2104:15688:71022 | | R | 1778523 | 1778595 |

| sample | length 1 | mis- match 1 | gap 1 | seqsplit |
|---|---|---|---|---|
| TCGA-06-6390 | 1 | 0 | 0 | GGACTTACAGGAATGTCCAGTGCTCCCAAGAAATCGAACTCCA CAAGCTTGGCTTCCCGCGGACGTCCTGAGGGA\*\*\*T |
| TCGA-06-6390 | 2 | 0 | 0 | CA\*\*\*TCCCTCAGGACGTCCGCGGGAAGCCAAGCTTGTGGAGT TCGATTTCTTGGGAGCACTGGACATTCCTGTAAGTC |
| TCGA-06-6390 | 2 | 0 | 0 | CA\*\*\*TCCCTCAGGACGTCCGCGGGAAGCCAAGCTTGTGGAGT TCGATTTCTTGGGAGCACTGGACATTCCTGTAAGTC |
| TCGA-06-6390 | 2 | 0 | 0 | CA\*\*\*TCCCTCAGGACGTCCGCGGGAAGCCAAGCTTGTGGAGT TCGATTTCTTGGGAGCACTGGACATTCCTGTAAGTC |
| TCGA-06-6390 | 4 | 0 | 0 | GCCA\*\*\*TCCCTCAGGACGTCCGCGGGAAGCCAAGCTTGTGGA GTTCGATTTCTTGGGAGCACTGGACATTCCTGTAAG |
| TCGA-06-6390 | 7 | 0 | 0 | CCGGCCA\*\*\*TCCCTCAGGACGTCCGCGGGAAGCCAAGCTTGT GGAGTTCGATTTCTTGGGAGCACTGGACATTCCTGT |
| TCGA-06-6390 | 8 | 1 | 0 | CAGGAATGTCCAGTGCTACCAAGAAATCGAACTCCACAAGCTT GGGTTCCCGCGGACGTCCTCCGGGA\*\*\*TGGCCGTG |
| TCGA-06-6390 | 8 | 0 | 0 | CAGGAATGTCCAGTGCTCCCAAGAAATCGAACTCCACAAGCTT GGCTTCCCGCGGACGTCCTGAGGGA\*\*\*TGGCCGGG |
| TCGA-06-6390 | 10 | 0 | 0 | TCCCCGGCCA\*\*\*TCCCTCAGGACGTCCGCGGGAAGCCAAGCT TGTGGAGTTCGATTTCTTGGGAGCACTGGACATTCC |
| TCGA-06-6390 | 10 | 0 | 0 | TCCCCGGCCA\*\*\*TCCCTCAGGANGTCCGCGGGAAGCCAAGCT TGTGGAGTTCGATTTCTTGGGAGCACTGGACATTCC |
| TCGA-06-6390 | 11 | 0 | 0 | GTCCCCGGCCA\*\*\*TCCCTCAGGACGTCCGCGGGAAGCCAAGC TTGTGGAGTTCGATTTCTTGGGAGCACTGGACATTC |
| TCGA-06-6390 | 13 | 0 | 0 | CCGTCCCCGGCCA\*\*\*TCCCTCAGGACGTCCGCGGGAAGCCAA GCTTGTGGAGTTCGATTTCTTGGGAGCACTGGACAT |
| TCGA-06-6390 | 21 | 0 | 0 | TGCTCCCAAGAAATCGAACTCCACAAGCTTGGCTTCCCGCGGA CGTCCTGAGGGA\*\*\*TGGCCGGGGACGGCAGGGGGA |
| TCGA-06-6390 | 28 | 0 | 0 | AAGAAATCGAACTCCACAAGCTTGGCTTCCCGCGGACGTCCTG AGGGA\*\*\*TGGCCGGGGACGGCAGGGGGAGGGGCAT |
| TCGA-06-6390 | 31 | 1 | 0 | AAATCGAACTCCACAAGCTTGGCTTCCCGCGGACGTCCTGAGG GA\*\*\*TGGCCGGGGCGGCAGGGGGAGGGGCATAGG |
| TCGA-06-6390 | 49 | 0 | 0 | CTGGCCTGGTGCCACCCGCCTATGCCCCTCCCCCTGCCGTCCC CGGCCA\*\*\*TCCCTCAGGACGTCCGCGGGAAGCCAA |
| TCGA-06-6390 | 52 | 4 | 0 | TCGTCCCCGCGGACTTCCTGATGGA\*\*\*TCGCCGGGGACGGCAG GGGGAGGGGCATAGGCGTGTGGCACCAGGCCAGCTC |
| TCGA-06-6390 | 53 | 1 | 0 | CTTCCCGCGGACGTCCTGAGGGA\*\*\*TGGCCGGGGACGGNAGG GGGAGGGGCATAGGCGGGTGGCACCAGGCCAGAGCC |
| TCGA-06-6390 | 58 | 0 | 0 | GTGCTGGCTCTGGCCTGGTGCCACCCGCCTATGCCCCTCCCCC TGCCGTCCCCGGCCA\*\*\*TCCCTCAGGACGTCCGCG |
| TCGA-06-6390 | 70 | 0 | 0 | GAGGGA\*\*\*TGGCCGGGGACGGCAGGGGGAGGGGCATAGGCGG GTGGCACCAGGCCAGAGCCAGCACTCACGTCGGTGG |
| TCGA-12-0826 | 8 | 0 | 0 | GGACAAGAGGGCAAGTGATCAGGTCTGACTGCCATCCCCTAAC ACACACAGGGGGGCTAAGGGCAGGG\*\*\*GAGGGGCA |
| TCGA-12-0826 | 8 | 0 | 0 | GGACAAGAGGGCAAGTGATCAGGTCTGACTGCCATCCCCTAAC ACACACAGGGGGGCTAAGGGCAGGG\*\*\*GAGGGGCA |

TABLE 5-continued

List of split reads supporting the identification of FGFR3-TACC3 fusion genes in four GBM samples from the ATLAS-TCGA exome collection (SEQ ID NOS 225-318, respectively, in order of appearance)

| | | | | |
|---|---|---|---|---|
| TCGA-12-0826 | 9 | 0 | 0 | ATGCCCCTC***CCCTGCCCTTAGCCCCCCTGTGTGTGTTAGG GGATGGCAGTCAGACCTGATCACTTGCCCTCTTGTC |
| TCGA-12-0826 | 13 | 0 | 0 | GCCTATGCCCCTC***CCCTGCCCTTAGCCCCCCTGTGTGTGT TAGGGGATGGCAGTCAGACCTGATCACTTGCCCTCT |
| TCGA-12-0826 | 22 | 0 | 0 | GTGCCACCCGCCTATGCCCCTC***CCCTGCCCTTAGCCCCCC TGTGTGTGTTAGGGGATGGCAGTCAGACCTGATCAC |
| TCGA-12-0826 | 33 | 1 | 0 | TGACTGCCATCCCCTAACACACAGGGGGGCTAAGGGCAGGG ***GAGGGGCATAGGCGGGGGGCACCAGGCCAGAGC |
| TCGA-12-0826 | 33 | 1 | 0 | TGACTGCCATCCCCTAACACACAGGGGGGCTAAGGGCAGGG ***GAGGGGCATAGGCGGGGGGCACCAGGCCAGAGC |
| TCGA-12-0826 | 37 | 3 | 0 | TGCCATCCCCTAACACACAGGGGGGCTAAGGGCAGGG***G AGGGGCATAGGCGGGGGGCACCAGGACAGAGGCAGC |
| TCGA-12-0826 | 52 | 5 | 0 | CACACAGGGGGGCTAAGGGCAGGG***GAGGGGCATAGGCGGG GGGGACCAGGCCCGAGCCAGCACTCACGTCGGGGGG |
| TCGA-12-0826 | 56 | 0 | 0 | GACGTCCACCGACGTGAGTGCTGGCTCTGGCCTGGTGCCACCC GCCTATGCCCCTC***CCCTGCCCTTAGACCCCCTG |
| TCGA-12-0826 | 64 | 0 | 0 | CTTACCGTGACGTCCACCGACGTGAGTGCTGGCTCTGGCCTGG TGCCACCCGCCTATGCCCCTC***CCCTGCCCTTAG |
| TCGA-12-0826 | 68 | 0 | 0 | TGTCCTTACCGTGACGTCCACCGACGTGAGTGCTGGCTCTGGC CTGGTGCCACCCGCCTATGCCCCTC***CCCTGCCC |
| TCGA-19-5958 | 7 | 0 | 0 | CGGGGGTGGGAGTGTGCGGGTGACCGGGGGTGGGAGTGTGCAG GTGACCTCCCTGGCCCTTAGCCCCCT***GCACTCT |
| TCGA-19-5958 | 23 | 0 | 0 | CGGGTGACCGGGGAGGGAGTGTGCAGGGGACCTCCCTGGCCC TTAGCCCCCT***GCACTCTGGGGGGCAGGATGGCC |
| TCGA-19-5958 | 39 | 0 | 0 | GGAGTGTGCAGGTGACCTCCCTGGCCCTTAGCCCCCT***GCA CTCTGGGGGGCAGGATGGCCGGGGACGGCAGGGGGA |
| TCGA-27-1835 | 10 | 1 | 0 | GGGGAGGCTGCTGGTGGGCAGCTGACTGCGGGGACACTGGGAG GAAGCCTGGACCCTCAGCGAACT***TCGCCCAGCC |
| TCGA-27-1835 | 29 | 0 | 0 | ACAGCCTGGGCACAGAGGTGGCTGTGCGA***AGGTCGCTGAG GGTCCAGGCTTCCACCCAGTGTCCCCGCAGTCAGCT |
| TCGA-27-1835 | 32 | 0 | 0 | TGACTGCGGGGACACTGGGTGGAAGCCTGGACCCTCAGCGACC T***TCGCACAGCCACCTCTGTGCCCAGGCTGTGCC |
| TCGA-27-1835 | 38 | 0 | 0 | CGGGGACACTGGGTGGAAGCCTGGACCCTCAGCGACCT***TC GCACAGCCACCTCTGTGCCCAGGCTGTGCCCCAGAA |
| TCGA-27-1835 | 39 | 2 | 0 | GGGGACACTGGGTGGAAGCCTGGACCCTCAGCGACCT***TCG CACAGCCACCTCTGTGGCCAGGCTGTGCCACAGAAG |
| TCGA-27-1835 | 41 | 0 | 0 | GGACACTGGGTGGAAGCCTGGACCCTCAGCGACCT***TCGCA CAGCCACCTCTGTGCCCAGGCTGTGCCCCAGAAGGC |
| TCGA-27-1835 | 53 | 3 | 0 | GAAGCCTGGACCCTCAGCGACCT***TCGCACAGCCACCTCTG TGCCCCGGCTGTGCCCCAGCCGGCCCGCCCCACACC |
| TCGA-27-1835 | 53 | 0 | 0 | GAAGCCTGGACCCTCAGCGACCT***TCGCACAGCCACCTCTG TGCCCAGGCTGTGCCCCAGAAGGCCCGCCCCACACC |
| TCGA-27-1835 | 59 | 0 | 0 | TGGACCCTCAGCGACCT***TCGCACAGCCACCTCTGTGCCCA GGCTGTGCCCCAGAAGGCCCGCCCCACACCTCAGCA |
| TCGA-27-1835 | 61 | 0 | 0 | GACCCTCAGCGACCT***TCGCACAGCCACCTCTGTGCCCAGG CTGTGCCCCAGAAGGCCCGCCCCACACCTCAGCACT |
| TCGA-27-1835 | 66 | 0 | 0 | TCAGCGACCT***TCGCACAGCCACCTCTGTGCCCAGGCTGTG CCCCAGAAGGCCCGCCCCACACCTCAGCACTCTGGG |
| TCGA-27-1835 | 73 | 0 | 0 | CCT***TCGCACAGCCACCTCTGTGCCCAGGCTGTGCCCCAGA AGGCCCGCCCCACACCTCAGCACTCTGGGGGGCAGG |

TABLE 5-continued

List of split reads supporting the identification of FGFR3-TACC3 fusion genes in four GBM samples from the ATLAS-TCGA exome collection (SEQ ID NOS 225-318, respectively, in order of appearance)

| sample | gene split 2 | readi_ID | direction split | hg18 start split2 | hg18 stop split2 |
|---|---|---|---|---|---|
| TCGA-06-6390 | FGFR3 | D03U9ACXX110625:2:1202:19578:90281 | R | 1708787 | 1708861 |
| TCGA-06-6390 | TACC3 | C01PRACXX110628:3:1104:10052:66371 | F | 1708787 | 1708860 |
| TCGA-06-6390 | TACC3 | C01PRACXX110628:5:1108:3319:22892 | F | 1708787 | 1708860 |
| TCGA-06-6390 | TACC3 | D03U9ACXX110625:8:2304:13007:108632 | F | 1708787 | 1708860 |
| TCGA-06-6390 | TACC3 | C01PRACXX110628:5:2108:1999:91559 | F | 1708787 | 1708858 |
| TCGA-06-6390 | TACC3 | C01PRACXX110628:3:1308:1446:66311 | F | 1708787 | 1708855 |
| TCGA-06-6390 | FGFR3 | D03U9ACXX110625:5:2205:12523:196352 | R | 1708787 | 1708854 |
| TCGA-06-6390 | FGFR3 | C01PRACXX110628:5:2103:6815:17943 | R | 1708787 | 1708854 |
| TCGA-06-6390 | TACC3 | C01PRACXX110628:3:1204:10831:2928 | F | 1708787 | 1708852 |
| TCGA-06-6390 | TACC3 | C01PRACXX110628:5:2204:6732:191360 | F | 1708787 | 1708852 |
| TCGA-06-6390 | TACC3 | C01PRACXX110628:8:1308:2911:26590 | F | 1708787 | 1708851 |
| TCGA-06-6390 | TACC3 | C01PRACXX110628:8:2207:4586:84017 | F | 1708787 | 1708849 |
| TCGA-06-6390 | FGFR3 | C01PRACXX110628:7:2205:11825:39734 | R | 1708787 | 1708841 |
| TCGA-06-6390 | FGFR3 | C01PRACXX110628:6:1106:12159:179499 | R | 1708787 | 1708834 |
| TCGA-06-6390 | FGFR3 | D03U9ACXX110625:4:2202:12501:40389 | R | 1708787 | 1708831 |
| TCGA-06-6390 | TACC3 | C01PRACXX110628:3:1305:3044:13238 | F | 1708787 | 1708813 |
| TCGA-06-6390 | FGFR3 | D03U9ACXX110625:5:2205:12523:196352 | R | 1708787 | 1708810 |
| TCGA-06-6390 | FGFR3 | C01PRACXX110628:7:2205:11825:39734 | R | 1708787 | 1708809 |
| TCGA-06-6390 | TACC3 | D03U9ACXX110625:7:2106:4492:173350 | F | 1708787 | 1708804 |
| TCGA-06-6390 | FGFR3 | C01PRACXX110628:5:2103:6815:17943 | R | 1708787 | 1708792 |
| TCGA-12-0826 | FGFR3 | 61C59AAXX100217:4:93:15133:6133 | R | 1707185 | 1707253 |
| TCGA-12-0826 | FGFR3 | 61C59AAXX100217:5:107:10675:16040 | R | 1707185 | 1707253 |
| TCGA-12-0826 | TACC3 | 61C59AAXX100217:5:108:1809:11295 | F | 1707185 | 1707252 |
| TCGA-12-0826 | TACC3 | 61C59AAXX100217:5:82:13129:10637 | F | 1707185 | 1707248 |
| TCGA-12-0826 | TACC3 | 42MJNAAXX0908136:80:691:1877#0 | F | 1707185 | 1707239 |
| TCGA-12-0826 | FGFR3 | 61C59AAXX100217:3:75:10586:12881 | R | 1707185 | 1707228 |
| TCGA-12-0826 | FGFR3 | 61C59AAXX100217:4:114:5844:3161 | R | 1707185 | 1707228 |
| TCGA-12-0826 | FGFR3 | 42MJNAAXX090813:5:70:888:108#0 | R | 1707185 | 1707224 |
| TCGA-12-0826 | FGFR3 | 61C59AAXX100217:3:55:4966:15975 | R | 1707185 | 1707209 |
| TCGA-12-0826 | TACC3 | 42MJNAAXX090813:5:23:156:1150#0 | F | 1707185 | 1707205 |
| TCGA-12-0826 | TACC3 | 61C59AAXX100217:4:21:17613:20886 | F | 1707185 | 1707197 |
| TCGA-12-0826 | TACC3 | 61C59AAXX100217:4:2:279:6949 | F | 1707185 | 1707193 |
| TCGA-19-5958 | FGFR3 | C01RDACXX110628:6:1102:11157:101962 | R | 1707202 | 1707270 |
| TCGA-19-5958 | FGFR3 | C01REACXX110629:2:2104:5009:98392 | R | 1707202 | 1707254 |
| TCGA-19-5958 | FGFR3 | C01PRACXX110628:7:2103:12434:91988 | R | 1707202 | 1707238 |
| TCGA-27-1835 | FGFR3 | B06UCABXX110322:6:1103:9262:46754 | R | 1709397 | 1709462 |
| TCGA-27-1835 | TACC3 | C00HWABXX110325:4:1201:20980:90877 | F | 1709397 | 1709443 |
| TCGA-27-1835 | FGFR3 | B06UCABXX110322:5:1108:14043:83287 | R | 1709397 | 1709440 |
| TCGA-27-1835 | FGFR3 | B097UABXX110405:4:2204:19445:88453 | R | 1709397 | 1709434 |
| TCGA-27-1835 | FGFR3 | B097UABXX110405:4:2201:20658:44401 | R | 1709397 | 1709433 |
| TCGA-27-1835 | FGFR3 | B097UABXX110405:2:2104:15688:71022 | R | 1709397 | 1709431 |
| TCGA-27-1835 | FGFR3 | C00HWABXX110325:6:2102:20394:42427 | R | 1709397 | 1709419 |
| TCGA-27-1835 | FGFR3 | B09V2ABXX110408:6:1203:18187:141862 | R | 1709397 | 1709419 |
| TCGA-27-1835 | FGFR3 | B09V2ABXX110408:8:1205:4774:81604 | R | 1709397 | 1709413 |
| TCGA-27-1835 | FGFR3 | C00HWABXX110325:2:1107:16168:23614 | R | 1709397 | 1709411 |
| TCGA-27-1835 | FGFR3 | C00HWABXX110325:7:2107:1225:167363 | R | 1709397 | 1709406 |
| TCGA-27-1835 | FGFR3 | B097UABXX110405:2:2104:15688:71022 | R | 1709397 | 1709399 |

| sample | length 2 | mismatch 2 | gap 2 | seq_mate |
|---|---|---|---|---|
| TCGA-06-6390 | 75 | 0 | 0 | GACGTCCACCGACGTGAGTGCTGGCTCTGGCCTGGTGCCACCCGCCTATGCCCCTCCCCCTGCCGTCCCCGGCCAT |
| TCGA-06-6390 | 74 | 0 | 0 | CAAGAGGGACTCAAGGACTTACAGGAATGTCCAGTGCTCCCAAGAAATCGAACTCCACAAGCTTGGCTTCCCGCGG |
| TCGA-06-6390 | 74 | 0 | 0 | CAAGAGGGACTCAAGGACTTACAGGAATGTCCAGTGCTCCCAAGAAATCGAACTCCACAAGCTTGGCTTCCCGCGG |
| TCGA-06-6390 | 74 | 0 | 0 | ATAGGCCCTTAAAACAACTCGTTCCCTCAGACCACACACAAGACAGTTCAAGAGGGACTCAAGGACTTACAGGAAT |
| TCGA-06-6390 | 72 | 0 | 0 | TCAAGAGGGACTCAAGGACTTACAGGAATGTCCAGTGCTCCCAAGAAATCGAACTCCACAAGCTTGGCTTCCCGCG |
| TCGA-06-6390 | 69 | 0 | 0 | ACCACACACAAGACAGTTCAAGAGGGACTCAAGGACTTACAGGAATGTCCAGTGCTCCCAAGAAATCGAACTCCAC |
| TCGA-06-6390 | 68 | 4 | 0 | GAGCTGGCCTGGTGCCACACGCCTATGCCCCTCCCCCTGCCGTCCCCGGCGATCCATCAGGAAGTCCGCGGGACGA |

TABLE 5-continued

List of split reads supporting the identification of FGFR3-TACC3 fusion genes in four GBM samples from the ATLAS-TCGA exome collection (SEQ ID NOS 225-318, respectively, in order of appearance)

| | | | | |
|---|---|---|---|---|
| TCGA-06-6390 | 68 | 0 | 0 | CCACCGACGTGAGTGCTGGCTCTGGCCTGGTGCCACCCGCCT ATGCCCCTCCCCCTGCCGTCCCCGGCCATCCCTC |
| TCGA-06-6390 | 66 | 0 | 0 | CAAGAGCCTCAGACAGTGCATGAGGGACCCGAGACAGTGCGG CGAGGGAACAGCACAGCGGCCCCATGCCCCCAAC |
| TCGA-06-6390 | 66 | 1 | 0 | CAAGAGCCTCAGACAGTGCATGAGGGACCCGAGACAGTGCGG CGAGGGAACAGCACAGGGGCCCCATGCCCCCAAC |
| TCGA-06-6390 | 65 | 0 | 0 | GCTTCCCTCAGACCACACACAAGACAGTTCAAGAGGGACTCA AGGACTTACAGGAATGTCCAGTGCTCCCAAGAGA |
| TCGA-06-6390 | 63 | 0 | 0 | CCAGGAATAGAAAATATAGGCCCTTAAAACAACTCGTTCCCT CAGACCACACACAAGACAGTTCAAGAGGGACTCA |
| TCGA-06-6390 | 55 | 0 | 0 | GGCTCTGGCCTGGTGCCACCCGCCTATGCCCCTCCCCCTNCC GTCCCCGGCCATCCCTCAGGACGTCCGCGGGAAG |
| TCGA-06-6390 | 48 | 0 | 0 | GCCCTGCCCGCAGGTACATGATCATGCGGGAGTGCTGGCATG CCGCGCCCTCCCAGAGGCCCACCTTCAAGCAGCT |
| TCGA-06-6390 | 45 | 0 | 0 | CTGGCATGCCGCGCCCTCCCAGAGGCCCACCTTTAAGCAGCT GGTAGAGGGCCTGGACCGTGTCCTTACCGTGACG |
| TCGA-06-6390 | 27 | 0 | 0 | TAAAACAACTCGTTCCCTCAGACCACACACAAGACAGTTCAA GAGGGACTCAAGGACTTACAGGAATGTCCAGTGC |
| TCGA-06-6390 | 24 | 4 | 0 | CACGGCCATCCCGGAGGACGTCCGCGGGAACCCAAGCTTGTG GAGTTCGATTTCTTGGTAGCACTGGACATTCCTG |
| TCGA-06-6390 | 23 | 0 | 0 | TCCCCCTGCCGTCCCCGGCCATCCCTCAGGACGTCCGCGGGA AGCCAAGCTTGTGGAGTTCGATTTCTTGGGAGCA |
| TCGA-06-6390 | 18 | 0 | 0 | AGACCACACACAAGACAGTTCAAGAGGGACTCAAGGACTTAC AGGAATGTCCAGTGCTCCCAAGAAATCGAACTCC |
| TCGA-06-6390 | 6 | 0 | 0 | CCCGGCCATCCCTCAGGACGTCCGCGGGAAGCCAAGCTTGTG GAGTTCGATTTCTTGGGAGCACTGGACATTCCTG |
| TCGA-12-0826 | 69 | 2 | 1 | GGCATGCCGCGCCCTCCCAGAGGCCCACCTTCAAGCAGCTGG TGGAGGACCTGGACCGTGTCCTTACCGTGACGTC |
| TCGA-12-0826 | 69 | 2 | 1 | GGCATGCCGCGCCCTCCCAGAGGCCCACCTTCAAGCAGCTGG TGGAGGACCTGGACCGTGTCCTTACCGTGACGTC |
| TCGA-12-0826 | 68 | 2 | 1 | CGGCGCACATACCTGCTGGTCTCGGTGGCCACGGGCACTGGT CTACCAGGACTGTCCCTCAGGAGGGGTCAAACT |
| TCGA-12-0826 | 64 | 2 | 1 | ATACCTGCTGGTCTCGGTGGCCACGGGCACTGGTCTACCAGG ACTGTCCCTCAGGAGGGGTCAAACTTGAGGTAT |
| TCGA-12-0826 | 55 | 2 | 1 | AGGTATAAGGACTGCTTCCTCAAGGCCGACTCCTTAAACTGG GGACAAGAGGGCAAGTGATCAGGTCTGACTGCCA |
| TCGA-12-0826 | 44 | 2 | 1 | GGAGGACCTGGACTGTGTCCTTACCGTGACGTCCACCGACGT GAGTGCTGGCTCTGGCCTGGTGCCACCCGCCTAT |
| TCGA-12-0826 | 44 | 2 | 1 | GGAGGACCTGGACTGTGTCCTTACCGTGACGTCCACCGACGT GAGTGCTGGCTCTGGCCTGGTGCCACCCGCCTAT |
| TCGA-12-0826 | 40 | 2 | 1 | CAAGCAGCTGGTGGAGGACCTGGACCGTGTCCTTACCGTGAC GTCCACCGACGTGAGTGCTGGCTCTGGCCTGGTG |
| TCGA-12-0826 | 25 | 2 | 1 | ACCTTCAAGCAGCTGGTGGAGGACCTGGACCGTGTCCTTACC GTGACGTCCACCGACGTGAGTGCTGGCTCTGGCC |
| TCGA-12-0826 | 21 | 2 | 1 | CAAACTTGAGGTATAAGGACTGCTTCCTCAAGGCCGACTCCT TAAACTGGGGACAAGAGGGCAAGTGATCAGGTCT |
| TCGA-12-0826 | 13 | 0 | 1 | TACCTGCTGGTCTCGGTGGCCACGGGCACTGGTCTACCAGGG CTGTCCCTCCGGAGGGGGTCAAACTTGAGGGATA |
| TCGA-12-0826 | 9 | 0 | 1 | AACTTGAGGTATAAGGACTGCTTCCTCAAGGCCGACTCCTTA AACTGGGGACAAGAGGGCAAGTGATCAGGTCTGA |

TABLE 5-continued

List of split reads supporting the identification of FGFR3-TACC3 fusion genes in four GBM samples from the ATLAS-TCGA exome collection (SEQ ID NOS 225-318, respectively, in order of appearance)

| | | | | |
|---|---|---|---|---|
| TCGA-19-5958 | 69 | 1 | 0 | AGCTGGTGGAGGACCTGGACCGTGTCCTTACCGTGACGTCCA CCGACGTGAGTGCTGGCTCTGGCCTGGTGCCACC |
| TCGA-19-5958 | 53 | 3 | 0 | GCGCCCTCCCAGAGGCCCACCTTCAAGCAGCTGGTGGAGGAC CTGGACCGTGTCCTTACCGTGACGTCCACCGACG |
| TCGA-19-5958 | 37 | 1 | 0 | GCGGGAGTGCTGGGCATGCCGCGCCCTCCCAGAGGCCCACCT CAAGCAGCTGGTGGAGGACCTGGACCGTGTCCTT |
| TCGA-27-1835 | 66 | 2 | 0 | CCTCCACTGGGTCCTCAGGGGTGGGGGTCCCTCCGGGGCTGG GCGGGGAGGGACTGGCAGGCCTGCAGGGGGGTT |
| TCGA-27-1835 | 47 | 0 | 0 | TCACGGCAGCAAGAACCACACTCACTGCTGCAAGGCCACCAG AGGCCAACGCCATGCCCAGGCCGGAGAGTCCCGG |
| TCGA-27-1835 | 44 | 0 | 0 | TACATGATCATGCGGGAGGGCTGGCATGCCGCGCCCTCCCAG AGGCCCACCTTCAAGCAGCTGGTGGAGGGCCGGG |
| TCGA-27-1835 | 38 | 0 | 0 | GGTGGGAAGCGGCGGGGCTCACTCCTGAGCGCCCTGCCCGCA GGGACATGATCATGCGGGGTGCTGGCCTTGCCC |
| TCGA-27-1835 | 37 | 0 | 0 | GCGCCCTCCCAGAGGCCCACCTTCAAGCAGCTGGTGGAGGAC CTGGACCGTGTCCTTACCGTGACGTCCAACGACG |
| TCGA-27-1835 | 35 | 0 | 0 | CCTGCCCCCAGAGTGCTGAGGTGTGGGGCGGGCCTTCTGGG GCACAGCCTGGGCACAGAGGTGGCTGTGCGAAGG |
| TCGA-27-1835 | 23 | 0 | 0 | GCAGGTACATGATCATGCGGGAGTGCCGGCATTTCGGGACCT TCCCTCGGGCCACCCTCTTCCGGTTGTTGTGGGC |
| TCGA-27-1835 | 23 | 0 | 0 | GCAGGTACATGATCATGCGGGAGTGCTGGCATGCCGCGCCCT CCCCGAGGACCACCTTCCAGCAGCCGGGGGAGGG |
| TCGA-27-1835 | 17 | 0 | 0 | CCCGAATAAGGTGGGAAGCGGCGGGGCTCACTCCTGAGCGCC CTGACCGCAGGTACATGAGCATGCGGGAGTGGCG |
| TCGA-27-1835 | 15 | 0 | 0 | CGTGTCCTTACCGTGACGTCCACCGACGTGAGTGCTGGCTCT GGCCTGGTGCCACCCGCCTATGCCCCTCCCCCTG |
| TCGA-27-1835 | 10 | 0 | 0 | ACATGATCATGCGGGAGTGCTGGCATGCCGCGCCCCCCCAG GGCCCACCTTCAAGCAGCTGGTGGAGGACCTGGA |
| TCGA-27-1835 | 3 | 0 | 0 | GCCTTCTGGGGCACAGCCTGGGCACAGAGGTGGCTGTGCGAA GGTCGCTGAGGGTCCAGGCTTCCACCCAGTGTCC |

Figure 2F:
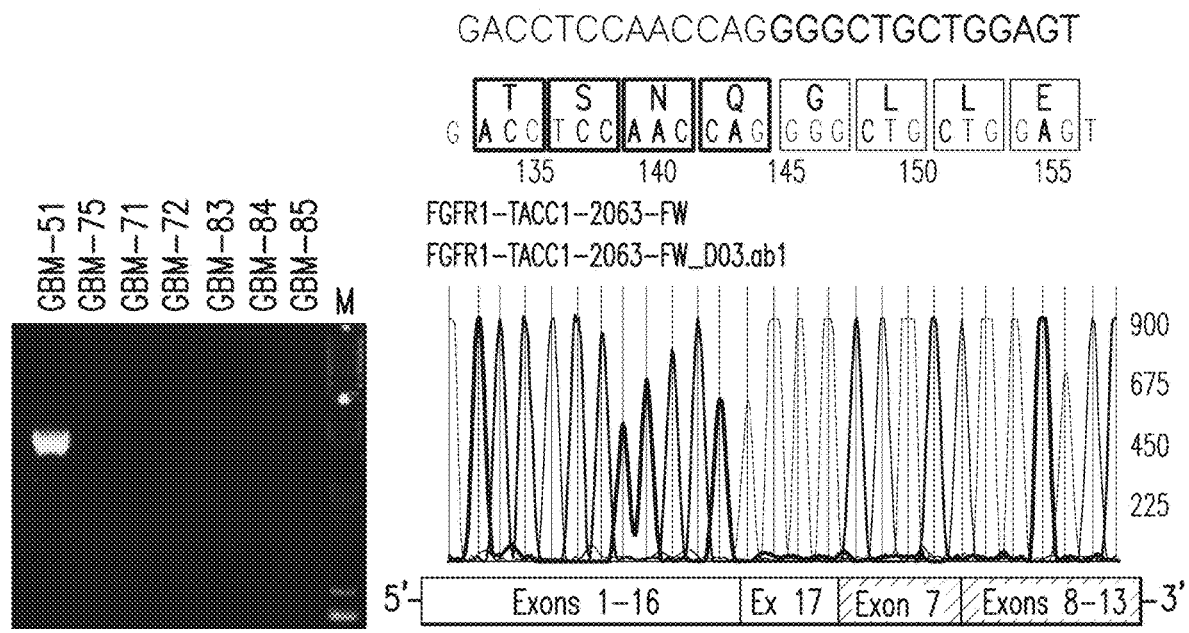
FIG. 2F shows recurrent gene fusions between FGFR and TACC genes in GBM. On the left, a gel of FGFR-TACC-specific PCR is shown for FGFR1-TACC1 from a GBM cDNA sample. On the right, Sanger sequencing chromatograms show the reading frame at the breakpoint (SEQ ID NO: 83) and putative translation of the fusion protein (SEQ ID NO: 88) in the positive samples.
Figure 2G:
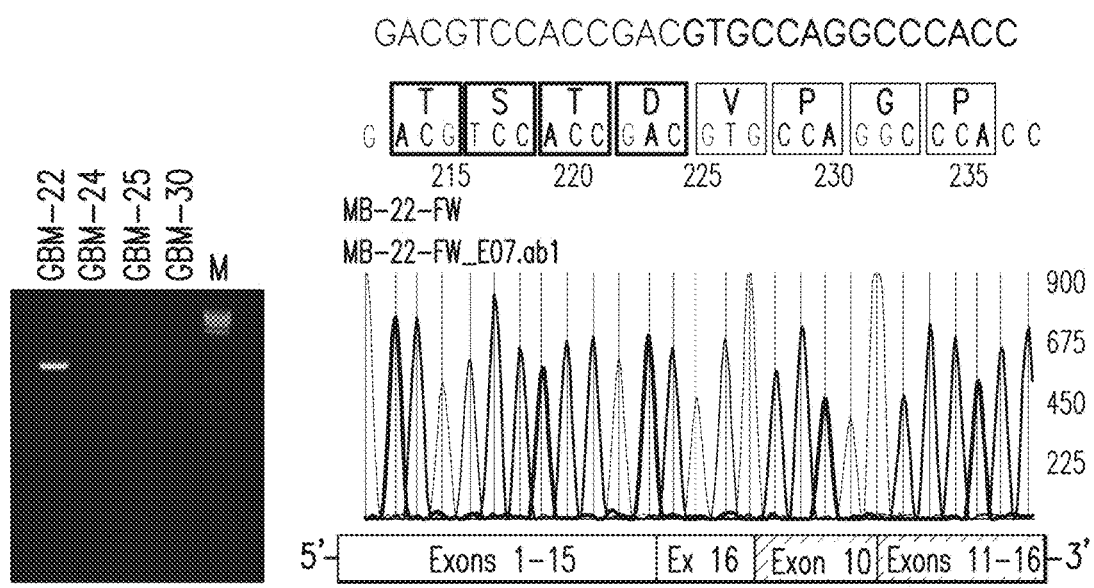
FIG. 2G shows recurrent gene fusions between FGFR and TACC genes in GBM. On the left, a gel of FGFR-TACC-specific PCR is shown for FGFR3-TACC3 from a GBM cDNA sample. On the right, Sanger sequencing chromatograms show the reading frame at the breakpoint (SEQ ID NO: 84) and putative translation of the fusion protein (SEQ ID NO: 89) in the positive samples.

The FGFR3 and TACC3 genes are located 48-Kb apart on human chromosome 4p16. The other members of the FGFR and TACC families retain the close physical association of FGFR3 and TACC3, with FGFR1 and TACC1 paired on chromosome 8p11 and FGFR2 and TACC2 paired on chromosome 10q26. Without being bound by theory, the ancestral FGFR and TACC genes were physically linked and that this tandem gene cluster was duplicated at least twice to generate the FGFR1-TACC1, FGFR2-TACC2 and FGFR3-TACC3 pairs that mark mammalian evolution (Still et al., 1999). The highly conserved TK domains among FGFR genes and TACC domains among TACC genes together with their invariable fusion in the FGFR3-TACC3 rearrangements prompted to ask whether other intra-chromosomal FGFR-TACC fusion combinations exist in human GBM.

cDNA from a panel of 88 primary GBM were screened using pairs of upstream PCR primers that bind the amino-terminal coding region of the TK domains of FGFR1, FGFR2 and FGFR3 and downstream primers that bind to the carboxy-terminal coding region of the TACC domains of TACC1, TACC2 and TACC3 genes, respectively. The screening resulted in the identification of intrachromosomal FGFR-TACC fusions in two additional cases (one harboring FGFR1-TACC1 and one FGFR3-TACC3), corresponding to three of 97 total GBM (3.1%), including the GBM-1123 case. The FGFR1-TACC1 fusion breakpoint in GBM-51 joined in-frame exon 17 of FGFR1 to exon 7 of TACC1, resulting in a novel protein in which the TK domain of FGFR1 is fused upstream of the TACC domain of TACC1 (FIG. 2F). The same structure was conserved again in GBM-22 in which exon 16 of FGFR3 is joined in-frame to exon 10 of TACC3 (FIG. 2G). None of the tumors harboring FGFR-TACC fusions had mutations in IDH1 or IDH2 genes, thus indicating that FGFR-TACC-positive GBM mark an independent subgroup of patients from those carrying IDH mutations (Table 6) (Yan et al., 2009). The constant linkage of the FGFR-TK to the TACC domain created in each of the seven GBM harboring FGFR-TACC rearrangements suggests that FGFR-TACC fusion proteins may generate important functional consequences for oncogenesis in the brain.

TABLE 6

| Samples | Type | Time | Status | Age at initial pathologic diagnosis | IDH1-2 status (Sanger) | IDH1-2 status (exome) |
|---|---|---|---|---|---|---|
| TCGA-12-0826 | FGFR3-TACC3 | 845 | DECEASED | 38 | WT | WT |
| TCGA-27-1835 | FGFR3-TACC3 | 648 | DECEASED | 53 | NA | WT |
| TCGA-19-5958 | FGFR3-TACC3 | 164 | LIVING | 56 | NA | WT |
| TCGA-06-6390 | FGFR3-TACC3 | 163 | DECEASED | 58 | WT | WT |
| GBM-22 | FGFR3-TACC3 | 390 | DECEASED | 60 | WT | NA |
| GBN-1123 | FGFR3-TACC3 | NA | DECEASED | 62 | WT | NA |
| GBM-51 | FGFR3-TACC1 | NA | NA | NA | WT | NA |

Figure 3A:
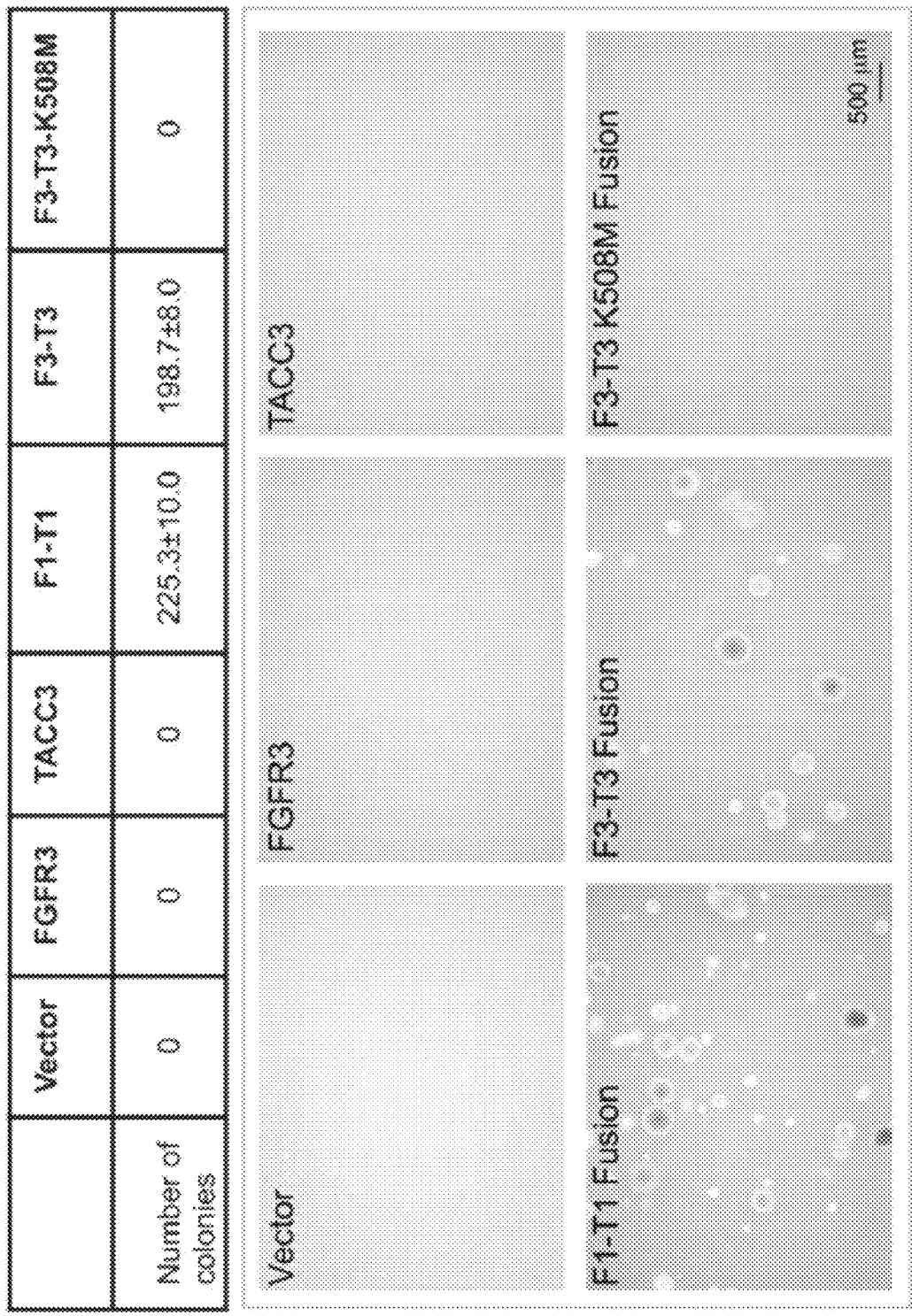
FIG. 3A shows transforming activity of FGFR-TACC fusion proteins. FGFR1-TACC1 and FGFR3-TACC3 induce anchorage-independent growth in Rat1A fibroblasts. The number of soft agar colonies was scored from triplicate samples 14 days after plating. Representative microphotographs are shown.
Figure 3B:
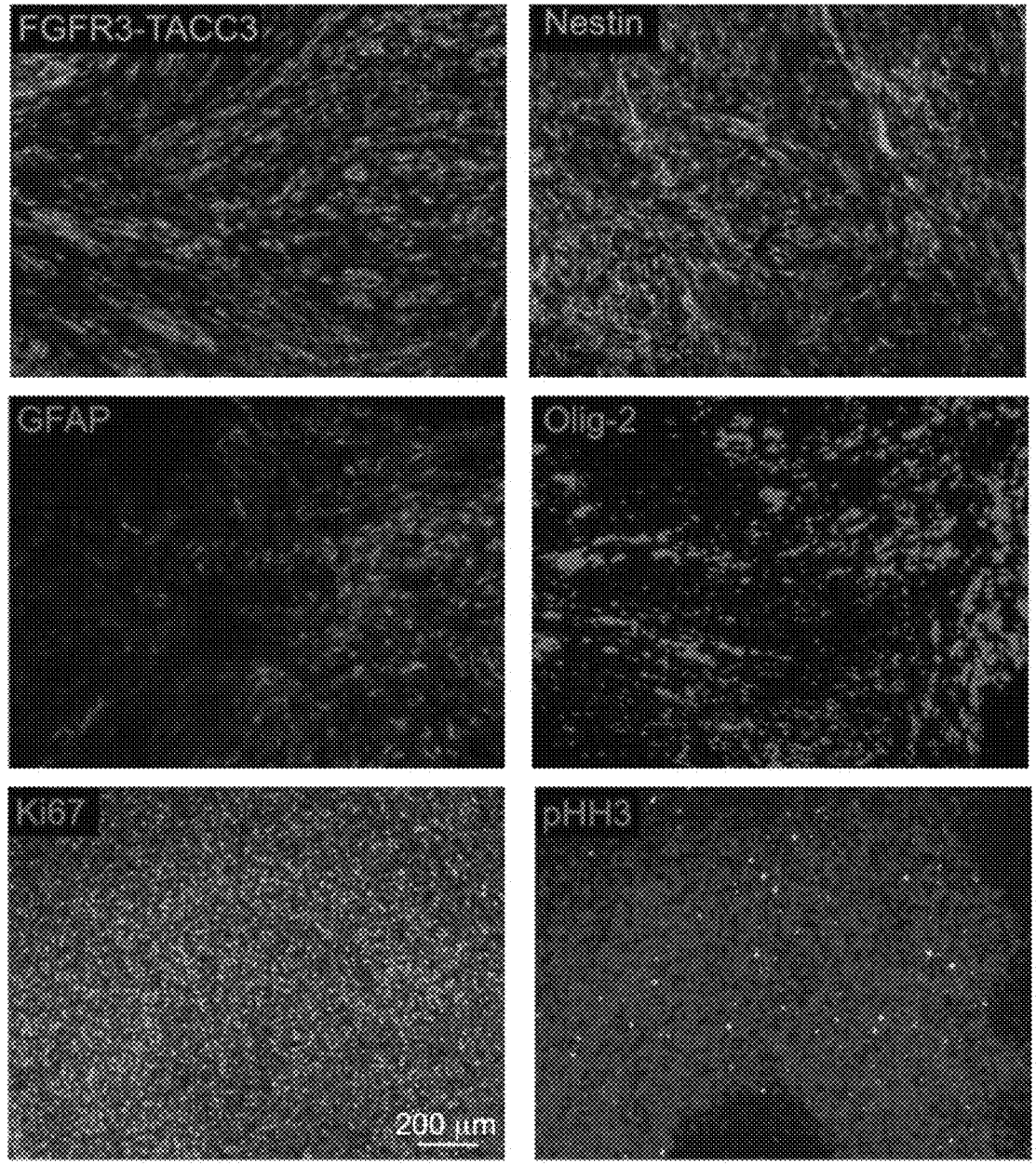
FIG. 3B are photomicrographs showing of immunofluoresence staining of tumors from mice injected with Ink4A; Arf−/− astrocytes expressing FGFR3-TACC3 showing positivity for glioma-specific (Nestin, Oig2 and GFAP) and proliferation markers (Ki67 and pHH3). Sub-cutaneous tumors were generated by Ink4A; Arf−/− astrocytes expressing FGFR-TACC fusions.

Time = Survival (days after diagnosis)
Sanger = analysis done by Sanger sequencing of genomic DNA
Exome = alnalysis done by SAVI (Statistical Algorithm for Variant Identification), an algorithm developed to detect point mutation in cancer (BRAF Mutations in Hairy-Cell Leukemia, Tiacci E et al. The New Englad Journal of Medicine 2011 Jun. 16;364(24):2305-15)
NA = Not Available
WT = Wild type sequence for R132 and R172 of IDH1 and IDH2, respectively Transforming activity of FGFR-TACC fusions. To test the functional importance of the FGFR-TACC fusions in GBM, the FGFR3-TACC3 cDNA was cloned from GSC-1123 and recombinant lentiviruses were prepared expressing FGFR3-TACC3, FGFR1-TACC1, a kinase-dead FGFR3-TACC3 protein (FGFR3-TACC3-K508M), wild type FGFR3 and wild type TACC3. Transduction of Rat1A fibroblasts and Ink4A; Arf−/− astrocytes with the FGFR3-TACC3 lentivirus resulted in the expression of the fusion protein at levels comparable to those present in GSC-1123 (FIG. 11). Having reconstituted in non-transformed cells the endogenous level of the FGFR-TACC protein that accumulates in GBM cells, it was determined whether it was sufficient to initiate oncogenic transformation in vitro and in vivo. Rat1A cells expressing FGFR3-TACC3 and FGFR1-TACC1 but not those expressing FGFR3-TACC3-K508M, FGFR3, TACC3 or the empty lentivirus acquired the ability to grow in anchorage-independent conditions in soft agar (FIG. 3A). Transduction of the same lentiviruses in primary Ink4A; Arf−/− astrocytes followed by subcutaneous injection into immunodeficient mice revealed that only astrocytes expressing FGFR3-TACC3 and FGFR1-TACC1 formed tumors. The tumors emerged in 100% of the mice injected with astrocytes expressing the fusion proteins and were glioma-like lesions with strong positivity for Ki67, phospho-histone H3, nestin, GFAP and Olig2 (FIG. 3B).

Figure 3C:
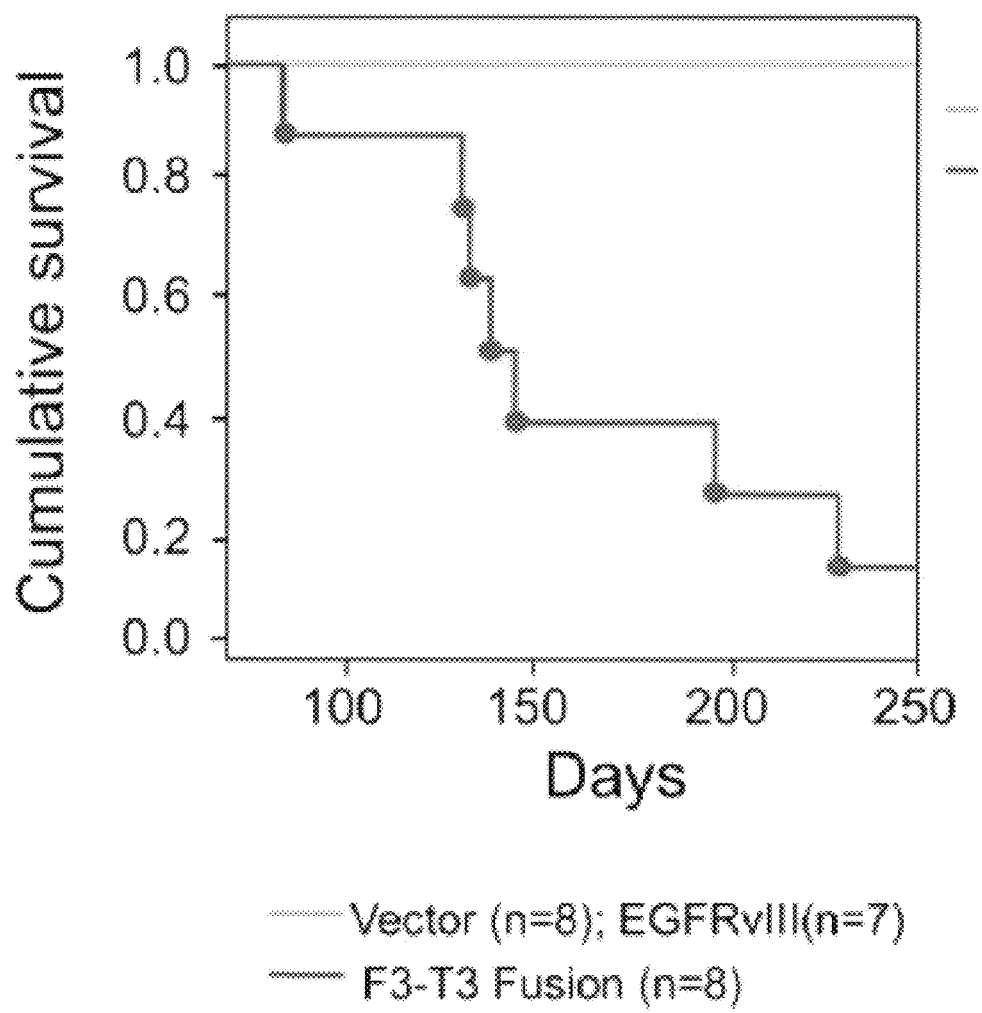
FIG. 3C shows Kaplan-Meier survival curves of mice injected intracranially with pTomo-shp53 (n=8) or pTomo-EGFRvIII-shp53 (n=7) (green line; "light grey" in black and white image) and pTomo-FGFR3-TACC3-shp53 (n=8, red line; "dark grey" in black and white image). Points on the curves indicate deaths (log-rank test, p=0.00001, pTomo-shp53 vs. pTomo-FGFR3-TACC3-shp53).
Figure 3D:
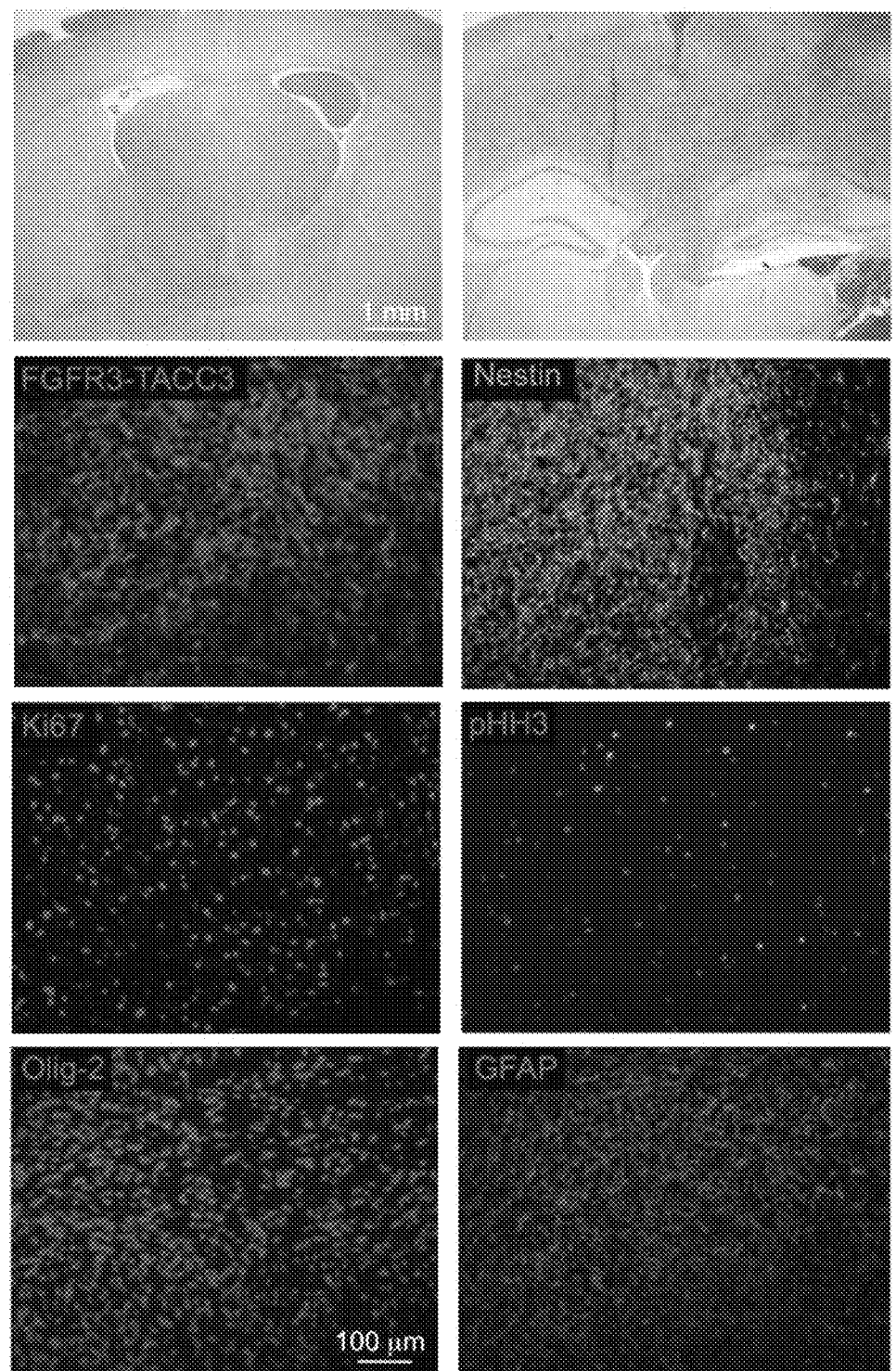
FIG. 3D shows representative photomicrographs of Hematoxylin and Eosin staining of advanced FGFR3-TACC3-shp53 generated tumors showing histological features of high-grade glioma. Of note is the high degree of infiltration of the normal brain by the tumor cells. Immunofluorescence staining shows that glioma and stem cell markers (Nestin, Olig2 and GFAP), the proliferation markers (Ki67 and pHH3) and the FGFR3-TACC3 protein are widely expressed in the FGFR3-TACC3-shp53 brain tumors. F1-T1: FGFR1-TACC1; F3-T3: FGFR3-TACC3; F3-T3-K508M: FGFR3-TACC3-K508M.

Next, it was determined whether the FGFR3-TACC3 fusion protein is oncogenic when transduced to a small number of cells directly into the brain of immunocompetent animals. A recently described mouse glioma model was used in which brain tumors are initiated by lentiviral transduction of oncogenes and inactivation of p53 in the mouse brain (Marumoto et al., 2009). To target adult NSCs, the adult mouse hippocampus was stereotactically transduced with purified lentivirus expressing the FGFR3-TACC3 protein and shRNA against p53 (pTomo-FGFR3-TACC3-shp53). Seven of eight mice (87.5%) transduced with FGFR3-TACC3 succumbed from malignant brain tumors within 240 days (FIG. 3C). None of the mice transduced with a lentivirus expressing the most frequent gain-of-function mutation in GBM (the constitutively active EGFRvIII, pTomo-EGFRvIII-shp53) or the pTomo-shp53 control lentivirus died or developed clinical signs of brain tumors (FIG. 3C). The FGFR3-TACC3 tumors were high-grade glioma with strong propensity to invade the normal brain and stained positive for the glioma stem cell markers nestin and Olig2 and the glial marker GFAP. They were also highly positive for Ki67 and phospho-histone H3, thus displaying rapid tumor growth (FIG. 3D). The expression of FGFR3-TACC3 in the xenograft and intracranial tumor models was comparable to the expression of the endogenous protein in the human GSCs and tumor (FIGS. 11D, 11E and 11F).

These data show that FGFR-TACC fusion proteins possess transforming activity in two independent cellular models and this activity is not the result of the overexpression of individual FGFR and TACC genes. They also show that direct transduction of the FGFR3-TACC3 protein to the adult mouse brain leads to efficient development of malignant glioma.

Figure 4A:
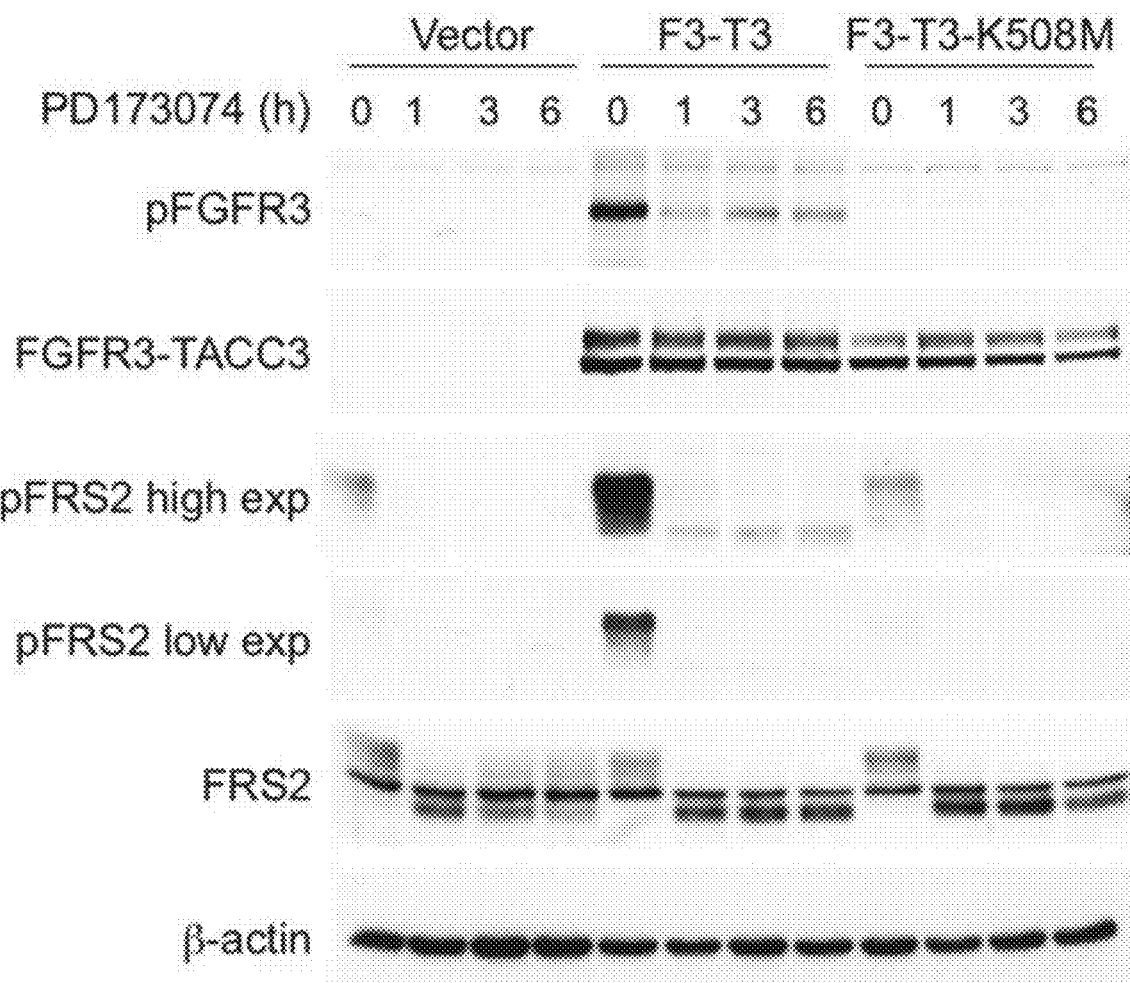
FIG. 4A shows that FGFR3-TACC3 localizes to spindle poles, delays mitotic progression and induces chromosome segregation defects and aneuploidy Constitutive auto-phosphorylation of FGFR3-TACC3 fusion. Ink4A; Arf−/− astrocytes transduced with empty lentivirus or a lentivirus expressing FGFR3-TACC3 or FGFR3-TACC3-K508M were left untreated (0) or treated with 100 nM of the FGFR inhibitor PD173074 for the indicated times. Phospho-proteins and total proteins were analyzed by Western blot using the indicated antibodies.
Figure 4B:
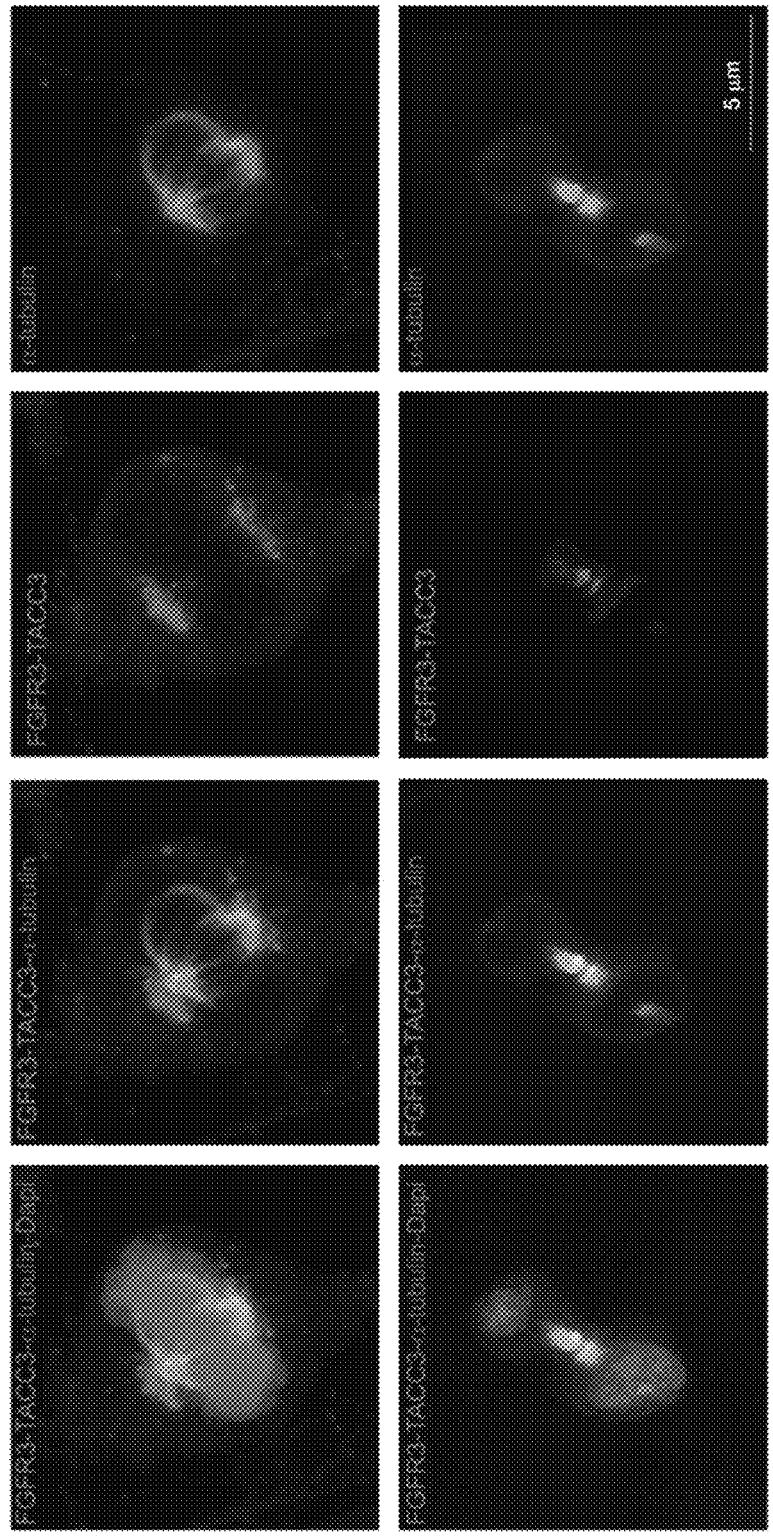
FIG. 4B shows that FGFR3-TACC3 localizes to spindle poles, delays mitotic progression and induces chromosome segregation defects. Photomicrographs are shown of confocal microscopy analysis of FGFR3-TACC3 in Ink4A; Arf−/− astrocytes. Maximum intensity projection of z-stacked images shows FGFR3-TACC3 (red; "dark grey" in black and white image) coating the spindle poles of a representative mitotic cell (upper panels). In telophase (lower panels) FGFR3-TACC3 localizes to the mid-body. α-tubulin (green; "grey" in black and white image), DNA (DAPI, blue; "light grey" in black and white image).
Figure 12A:
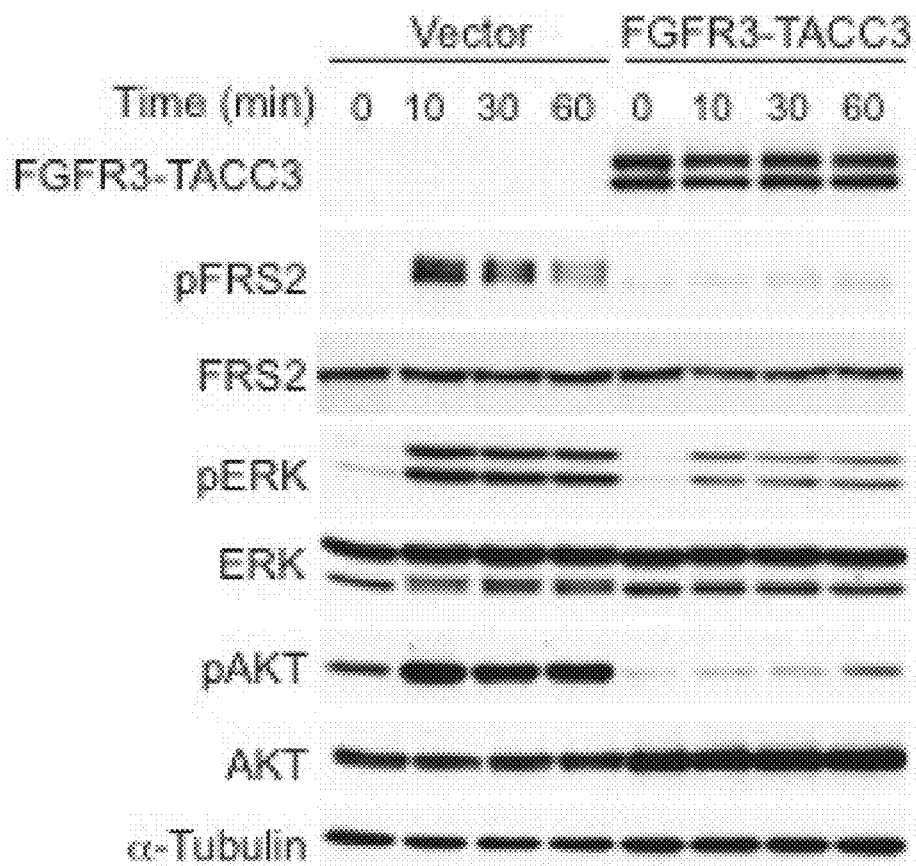
FIG. 12A shows a western blot. Ink4A; Arf−/− astrocytes transduced with empty lentivirus or a lentivirus expressing FGFR3-TACC3 were starved of mitogens and left untreated (time 0) or treated with FGF-2 at concentration of 50 ng/ml for the indicated times. Phospho-proteins and total proteins were analyzed by Western blot using the indicated antibodies. α-tubulin is shown as a control for loading.
Figure 12B:
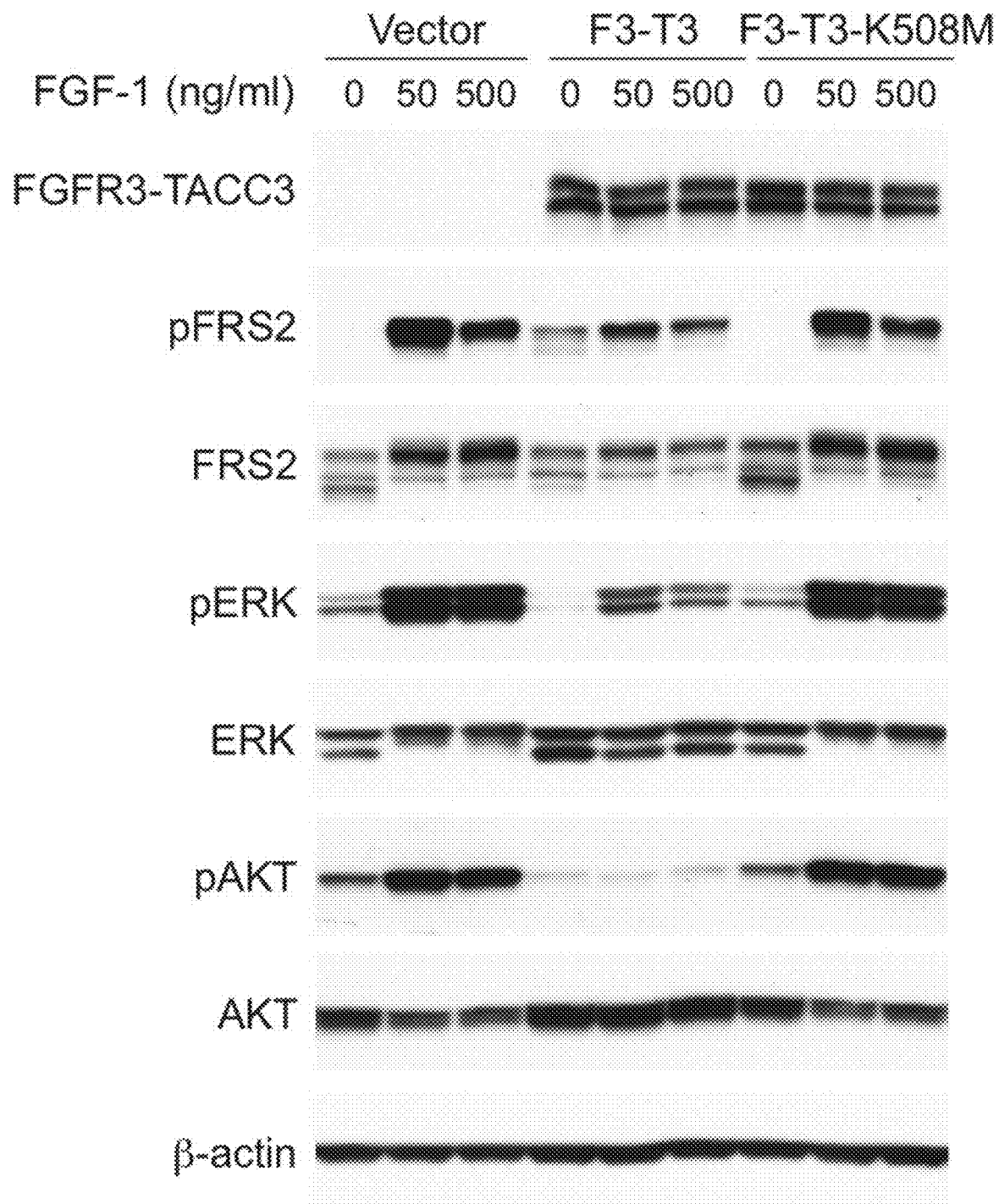
FIG. 12B show western blots. Ink4A; Arf−/− astrocytes transduced with empty lentivirus or a lentivirus expressing FGFR3-TACC3 or FGFR3-TACC3-K508M were starved of mitogens and left untreated (time 0) or treated for 10 min with FGF-1 at the indicated concentrations. Phospho-proteins and total proteins were analyzed by Western blot using the indicated antibodies. 0-actin is shown as a control for loading.
Figure 12C:
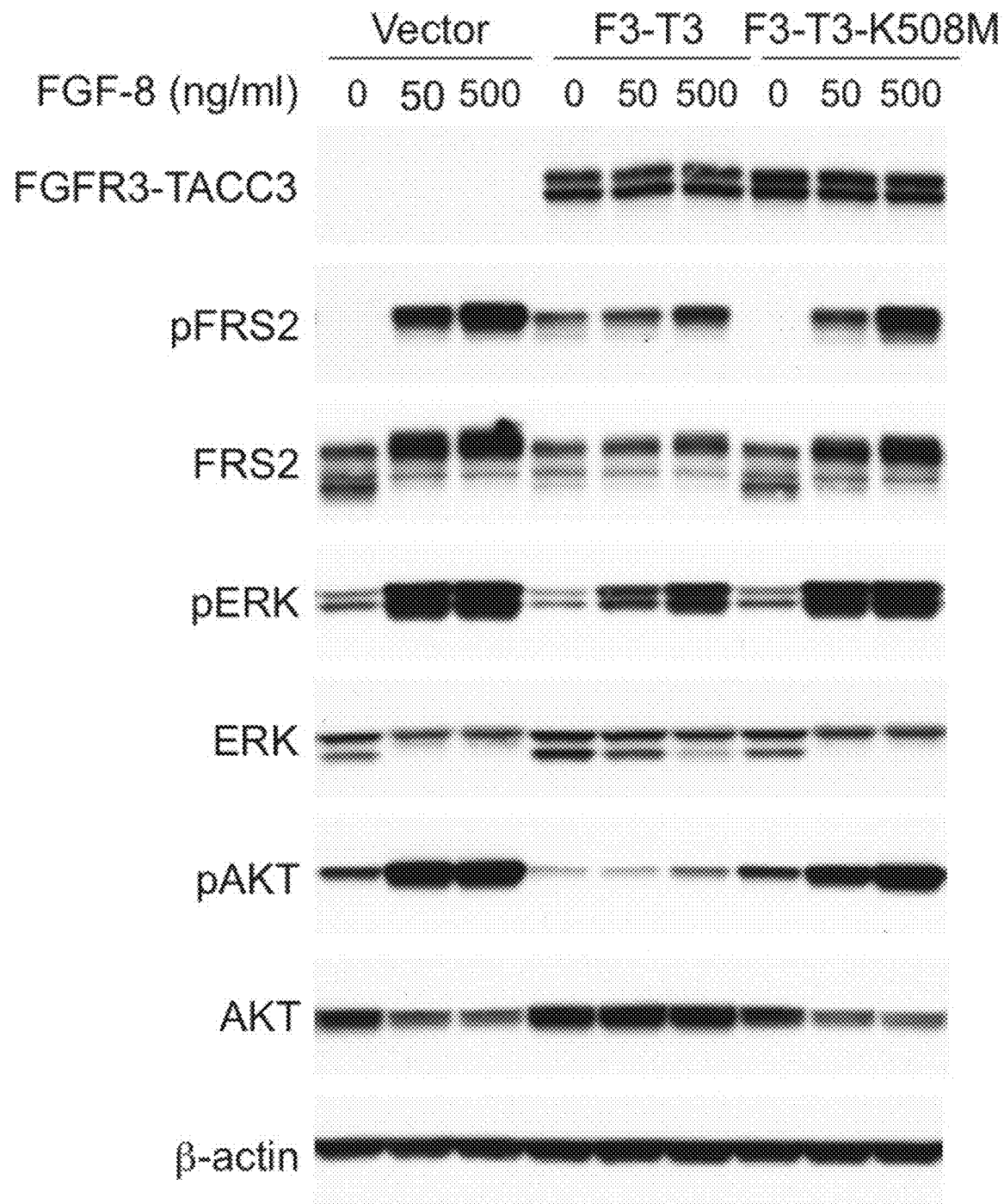
FIG. 12C show western blots. Ink4A; Arf−/− astrocytes transduced with empty lentivirus or a lentivirus expressing FGFR3-TACC3 or FGFR3-TACC3-K508M were starved of mitogens and left untreated (time 0) or treated for 10 min with FGF-8 at the indicated concentrations. Phospho-proteins and total proteins were analyzed by Western blot using the indicated antibodies. β-actin is shown as a control for loading.

The FGFR-TACC fusions interfere with mitotic progression and induce chromosome missegregation and aneuploidy. To elucidate the mechanism by which the FGFR-TACC fusion drives oncogenesis, it was explored whether it activates downstream FGFR signaling. FGFR3-TACC3 failed to hyperactivate the canonical signaling events downstream of FGFR (pERK and pAKT) in the presence or absence of the ligands FGF-1, FGF-2 or FGF-8 (Wesche et al., 2011) (FIGS. 12A, 12B and 12C). However, FGFR3-TACC3 displayed constitutive phosphorylation of its TK domain and the adaptor protein FRS2, both of which were abolished by the specific inhibitor of FGFR-associated TK activity PD173074 (Mohammadi et al., 1998) or the K508M mutation (FIG. 4A). Thus, FGFR3-TACC3 gains constitutive kinase activity that is essential for oncogenic transformation but the downstream signaling of this aberrant activity is distinct from the canonical signaling events downstream to FGFR. By driving the localization of the fusion protein, the TACC domain can create entirely novel TK-dependent functions. The TACC domain is essential for the localization of TACC proteins to the mitotic spindle (Hood and Royle, 2011; Peset and Vernos, 2008). Confocal imaging showed that FGFR3-TACC3 designed an arc-shaped structure bending over and encasing the metaphase spindle poles, frequently displaying asymmetry towards one of the two poles and relocated to the midbody as cells progressed into the late stages of mitosis (telophase and cytokinesis) (FIGS. 4B and 12D). Conversely, the localization of TACC3 was restricted to spindle microtubules and did not relocalize to the midbody (FIG. 12E). Wild type FGFR3 lacked discrete localization patterns in mitosis (FIG. 12F).

Figure 4C:
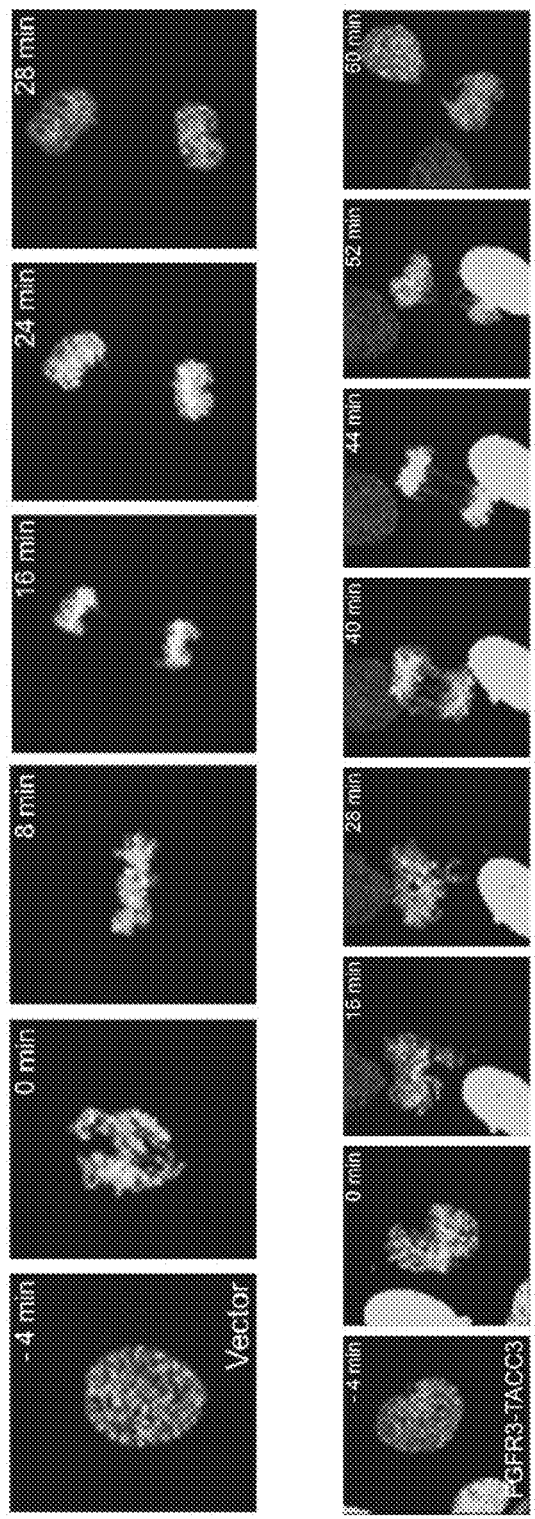
FIG. 4C shows representative fluorescence video-microscopy for cells transduced with vector or FGFR3-TACC3.
Figure 4D:
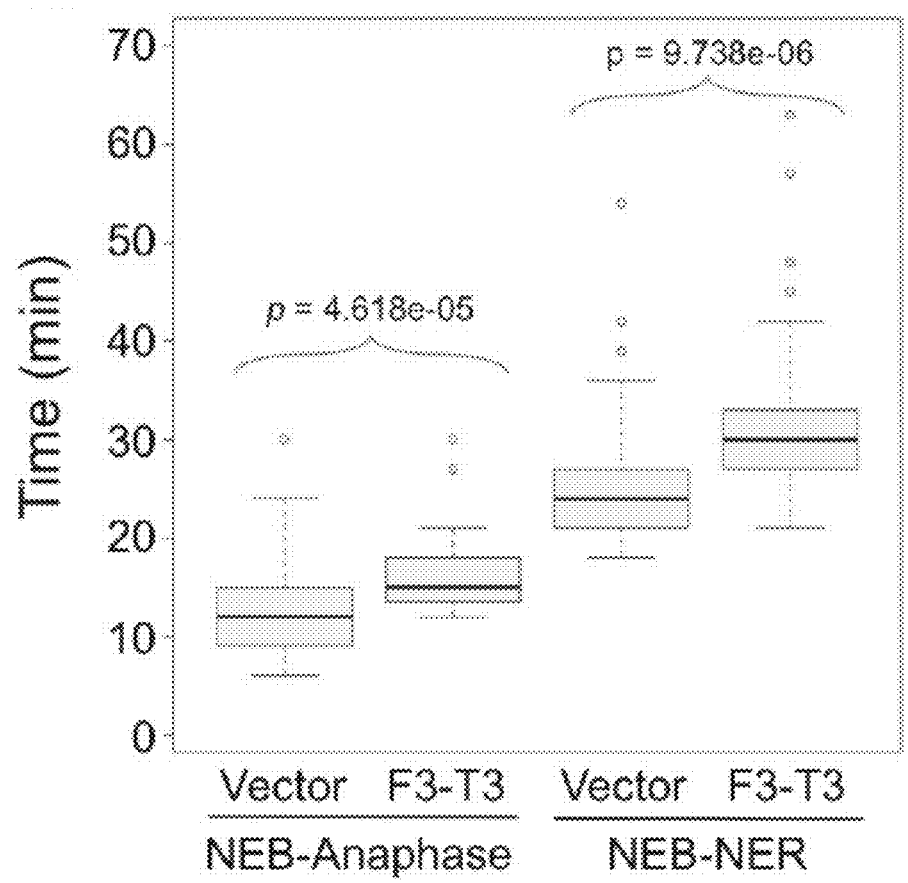
FIG. 4D shows a Box and Whisker plot representing the analysis of the time from nuclear envelope breakdown (NEB) to anaphase onset and from NEB to nuclear envelope reconstitution (NER). The duration of mitosis was measured by following 50 mitoses for each condition by time-lapse microscopy.

The mitotic localization of FGFR3-TACC3 indicates that it may impact the fidelity of mitosis and perturb the accurate delivery of the diploid chromosomal content to daughter cells, thus generating aneuploidy. Mitotic progression of individual cells was examined in vector-transduced and FGFR3-TACC3 expressing cells co-expressing histone H2B-GFP by time-lapse microscopy. The average time from nuclear envelope breakdown to anaphase onset was increased in cells expressing FGFR3-TACC3 in comparison with control cells. The mitotic delay was further exacerbated by difficulties in completing cytokinesis (FIGS. 4C and 4D).

Figure 5A:
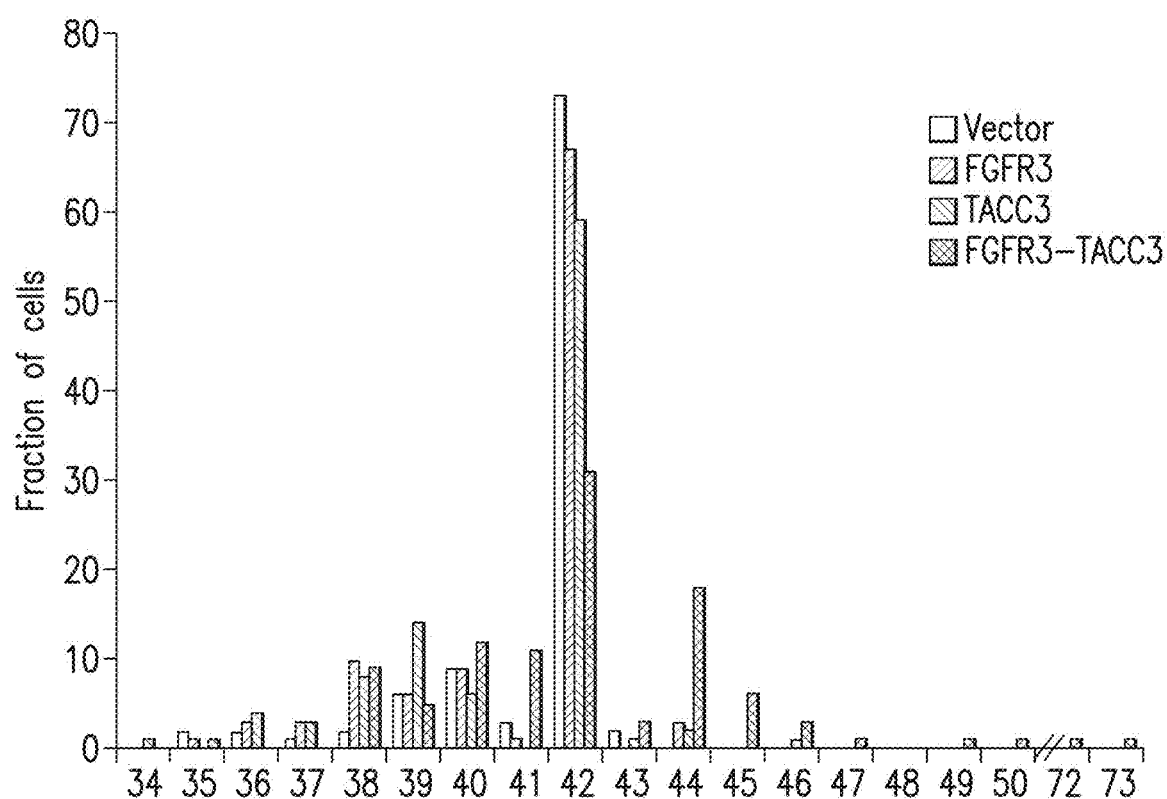
FIG. 5A shows karyotype analysis of Rat1A cells transduced with control, FGFR3, TACC3 or FGFR3-TACC3 expressing lentivirus. Distribution of chromosome counts of cells arrested in mitosis and analyzed for karyotypes using DAPI. Chromosomes were counted in 100 metaphase cells for each condition to determine the ploidy and the diversity of chromosome counts within the cell population. FGFR3-TACC3 fusion induces aneuploidy.

Next, it was determined whether the expressions of the FGFR-TACC fusion proteins induce defects of chromosomal segregation. Quantitative analyses of mitoses revealed that cells expressing FGFR3-TACC3 or FGFR1-TACC1 exhibit a three to five fold increase of chromosomal segregation errors than control cells. The most frequent mitotic aberrations triggered by the fusion proteins were misaligned chromosomes during metaphase, lagging chro- Karyotype analysis revealed that FGFR3-TACC3 increased over 2.5 fold the percent of aneuploidy and led to the accumulation of cells with broad distribution of chromosome counts in comparison with cells transduced with empty vector, FGFR3 or TACC3 (FIG. 5A). Accordingly, GSC-1123 contained aneuploid modal number of chromosomes (49) and manifested a broad distribution of chromosome counts characterized by 60% of metaphase spreads that deviate from the mode (Table 7)

TABLE 7

Chromosome analysis by SKY of 20 cells from the GSC-1123 culture

| Cell # | Chr # | +1 | +2 | +3 | t(3; 14) | +4 | (−4) | del(4) | +5 | +6 | +7 | del(7) | +8 | −9 | +9 | −10 | +10 | +11 |
|---|---|---|---|---|---|---|---|---|---|---|---|---|---|---|---|---|---|---|
| 1 | 97 | 2 | 2 | 2 | | 2 | | 1 | 2 | 2 | 4 | | 2 | | 2 | | | 2 |
| 2 | 51 | | | | | | | | | | 1 | | | | | | 1 | |
| 3 | 49 | | | | | | | | | | 1 | | | | | | 1 | |
| 4 | 50 | | | | | | | | | | 1 | | | | | | 1 | |
| 5 | 49 | | | | | | | | | | 1 | | | | | | 1 | |
| 6 | 86 | 2 | 2 | 2 | | 2 | | | 2 | | 3 | | 1 | | 1 | | | 2 |
| 7 | 95 | 2 | 2 | 2 | | 2 | | | 1 | 2 | 4 | | 2 | | 2 | | | 2 |
| 8 | 98 | 2 | 3 | 2 | 1 | 2 | | | 1 | 2 | 4 | | 3 | | 1 | | | 2 |
| 9 | 86 | 2 | 1 | 1 | 1 | 1 | | | 1 | 1 | 6 | | 2 | | 3 | | 1 | 1 |
| 10 | 44 | | | 1 | 1 | | 1 | | | | 1 | 1 | | 1 | | 1 | | |
| 11 | 49 | | | | | | | | | | 1 | 1 | | | | 1 | | |
| 12 | 49 | | | | | | | | | | 1 | | | | | 1 | | |
| 13 | 98 | 2 | 2 | 2 | 2 | | | | 2 | 2 | 4 | | 2 | | 2 | | | 2 |
| 14 | 49 | | | | | | | | | | 1 | | | | | 1 | | |
| 15 | 48 | | | | | | | | | | 1 | | | | | 1 | | |
| 16 | 51 | | | | | | | | | | 1 | | | | | 1 | | |
| 17 | 49 | | | | | | | | | | 1 | | | | | 1 | | |
| 18 | 50 | | | | | | | | | | 1 | 1 | | | | 1 | | |
| 19 | 49 | | | | | | | | | | 1 | | | | | 1 | | |
| 20 | 49 | | | | | | | | | | 1 | | | | | 1 | | |

Figure 4E:
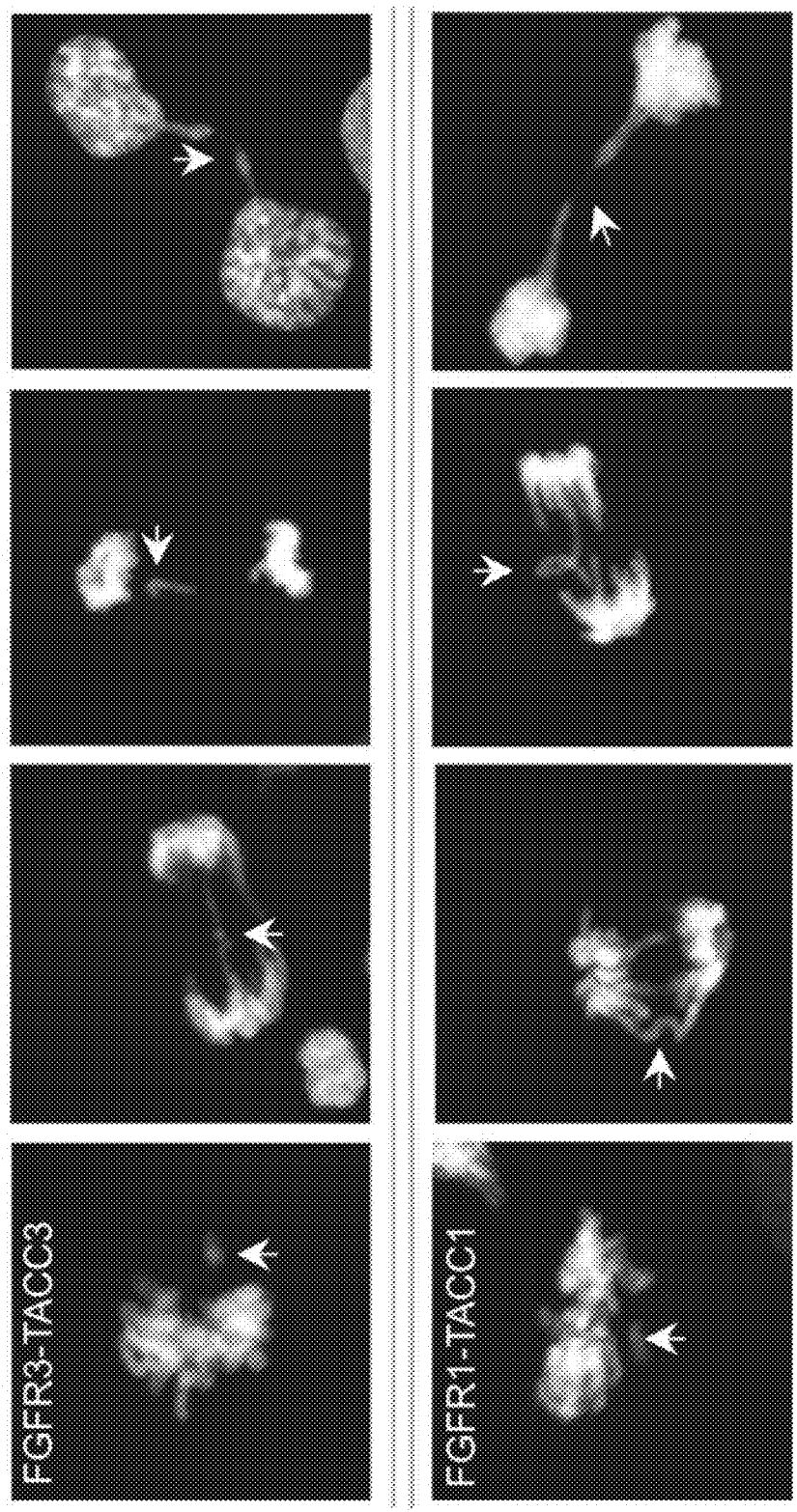
FIG. 4E shows that FGFR3-TACC3 localizes to spindle poles, delays mitotic progression and induces chromosome segregation defects. Representative images are shown of cells with chromosome missegregation. Arrows point to chromosome misalignments, lagging chromosomes, and chromosome bridges.
Figure 13A:
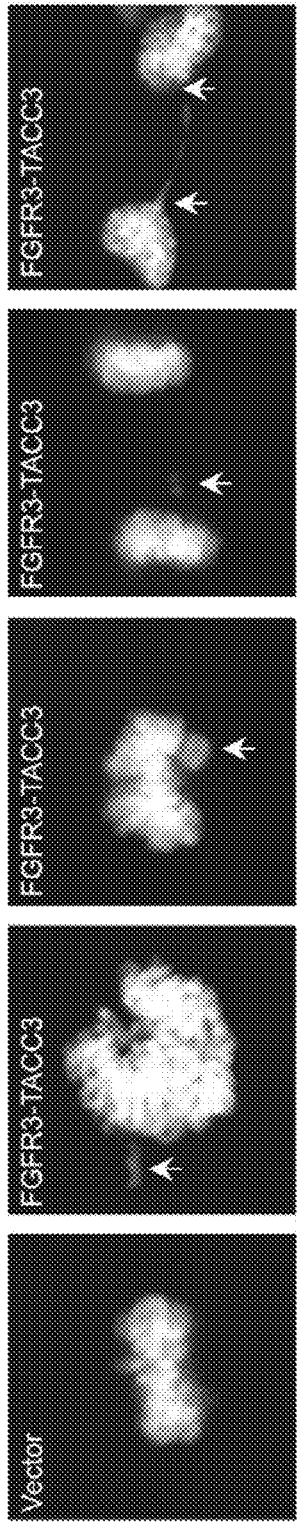
FIG. 13A shows that the FGFR3-TACC3 protein induces chromosomal mis-segregation, chromatid cohesion defects and defective spindle checkpoint. Quantitative analysis of metaphase spreads for chromosome segregation defects in Ink4A; ARF−/− astrocytes expressing vector control or FGFR3-TACC3 (upper panel). Microscope imaging analysis of chromosome segregation defects in Ink4A; Arf−/− astrocytes expressing FGFR3-TACC3 or vector control. Representative images of cells with chromosome missegregation. Arrows point to chromosome misalignments, lagging chromosomes and chromosome bridges.

| Cell # | Chr # | +12 | +13 | del(13) | −14 | +14 | +15 | −16 | +16 | +17 | +18 | +19 | +20 | −21 | +21 | −22 | +22 | +X |
|---|---|---|---|---|---|---|---|---|---|---|---|---|---|---|---|---|---|---|
| 1 | 97 | 2 | 2 | 2 | | 2 | 2 | | 2 | 2 | 3 | 4 | 4 | | 2 | | 2 | 2 |
| 2 | 51 | | 2 | 2 | | | | | | | 1 | 1 | 1 | | | | | |
| 3 | 49 | | | 1 | | | | | | | 1 | 1 | 1 | | | | | |
| 4 | 50 | | | 1 | | | | | | | 1 | 1 | 1 | | | | | |
| 5 | 49 | | | 1 | | | | | | | 1 | 1 | 1 | | | | | |
| 6 | 86 | 2 | 2 | 2 | | 2 | 2 | | | 2 | 4 | 3 | 3 | | 1 | | | 2 |
| 7 | 95 | 2 | 2 | 2 | | 2 | 2 | | 2 | 2 | 4 | 2 | 4 | | 2 | | 2 | 2 |
| 8 | 98 | 2 | 2 | 2 | | 2 | 2 | | 2 | 2 | 3 | 4 | 4 | | 3 | | 2 | 2 |
| 9 | 86 | 2 | 2 | 2 | | | | | 2 | 1 | 4 | 3 | 1 | | 2 | | 1 | 2 |
| 10 | 44 | | | | 1 | | 1 | | | | 1 | | 1 | | | 1 | | |
| 11 | 49 | | | | | | | | | | 1 | 1 | 1 | | | | | |
| 12 | 49 | | | | 1 | | | | | | 1 | 1 | 1 | | | | | |
| 13 | 98 | 2 | 2 | | | 2 | 2 | | 2 | 2 | 4 | 4 | 4 | | 2 | 2 | | 2 |
| 14 | 49 | | | | 1 | | | | | | 1 | 1 | 1 | | | | | |
| 15 | 48 | | | | | | | | | | 1 | 1 | 1 | 1 | | | | |
| 16 | 51 | | | | 1 | | 1 | | | | 1 | | | | | | 2 | 1 |
| 17 | 49 | | 1 | | | | | | | | 1 | 1 | 1 | | | | | |
| 18 | 50 | | 1 | 1 | | | | | | | 1 | 1 | 1 | | | | | |
| 19 | 49 | | | | | | | | | | 1 | 1 | 1 | | | | | |
| 20 | 49 | | | | 1 | | | | | | 1 | 1 | 1 | | | | | | mosomes at anaphase and chromosome bridges that impaired cytokinesis and generated micronuclei in the daughter cells (FIGS. 4E, 4F and 13A). Aberrations at the metaphase-anaphase transition frequently lead to the inability of mitotic cells to maintain a metaphase arrest after treatment with a spindle poison. Over 18% of cells expressing FGFR3-TACC3 displayed prematurely separated sister chromatids in contrast with less than 3% in control, FGFR3 or TACC3-expressing cells (FIGS. 13B and 13C). Accordingly, cells expressing the fusion protein were unable to efficiently arrest in metaphase after nocodazole treatment (FIG. 13D).

The above findings indicate that expression of the FGFR3-TACC3 fusion protein may spark aneuploidy.

Figure 5B:
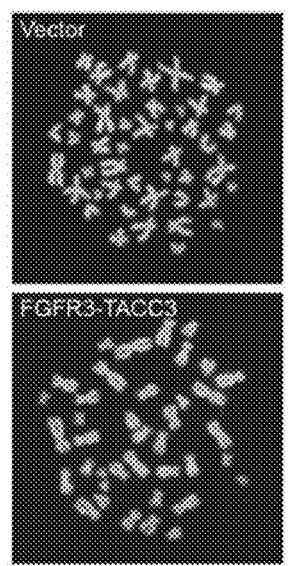
FIG. 5B shows representative karyotypes and FIG. 5C shows distribution of chromosome counts of human astrocytes transduced with control or FGFR3-TACC3 expressing lentivirus. Chromosomes were counted in 100 metaphase cells for each condition to determine the ploidy and the diversity of chromosome counts within the cell population.
Figure 5C:
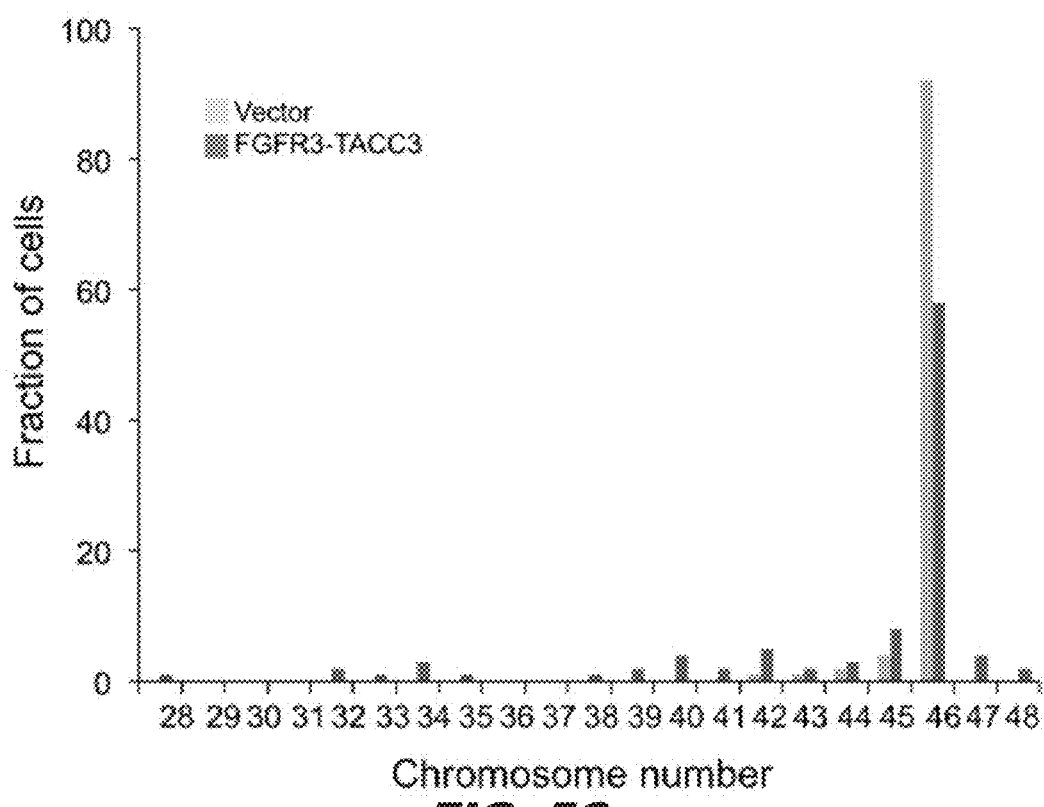

Next, it was determined whether aneuploidy is a direct consequence of FGFR3-TACC3 expression and is induced in human diploid neural cells. Primary human astrocytes analyzed six days after transduction with the FGFR3-TACC3 lentivirus exhibited a 5-fold increase of the rate of aneuploidy and a significantly wider distribution of chromosome counts (FIGS. 5B, 5C and 5D). Consistent that aneuploidy is detrimental to cellular fitness, acute expression of FGFR3-TACC3 compromised the proliferation capacity of human astrocytes. However, continuous culture of FGFR3-TACC3-expressing human astrocytes led to progressive gain of proliferative capacity that overrode that of control cells (FIG. 14A, 14B). Thus, the acute expression of FGFR3-TACC3 in primary normal human cells from the central nervous system causes CIN and aneuploidy with an acute fitness cost manifested by slower proliferation.

Figure 6A:
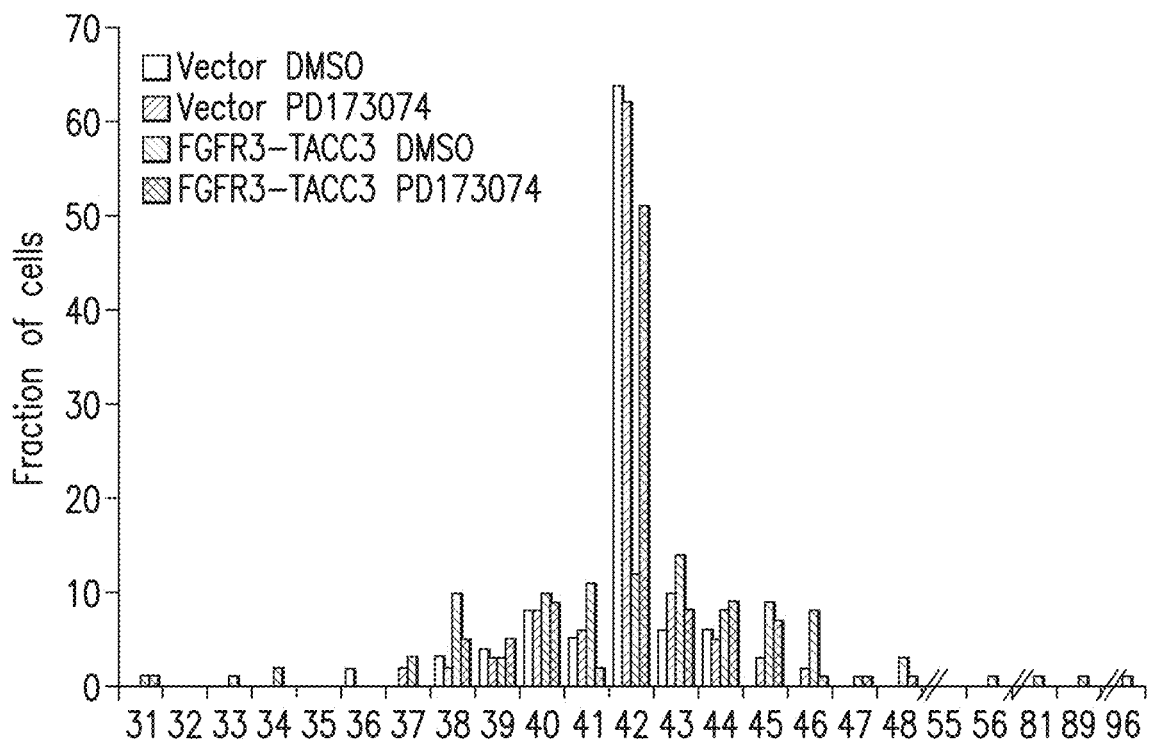
FIG. 6A shows inhibition of FGFR-TK activity corrects the aneuploidy initiated by FGFR3-TACC3. The upper panel is a karyotype analysis of Rat1A cells transduced with control or FGFR3-TACC3 lentivirus and treated with vehicle (DMSO) or PD173470 (100 nM) for five days. The lower panel shows the ploidy and the diversity of chromosome counts within the cell population were determined by quantitative analysis of chromosome number in 100 metaphase cells for each condition.

It was also determined whether the CIN and aneuploidy caused by FGFR3-TACC3 requires the TK activity of FGFR3 and can be corrected. Treatment with PD173074 rescued the aneuploidy caused by FGFR3-TACC3 by over 80%, restored the narrow distribution of chromosome counts typical of control cells and largely corrected the cohesion defect (FIGS. 6A, 6B and 6C). Together, these findings indicate that the CIN and aneuploidy caused by rearrangements of FGFR and TACC genes are reversible and suggest that specific FGFR kinase inhibition may be a valuable therapeutic strategy in tumor cells expressing FGFR-TACC fusion proteins.

Figure 7A:
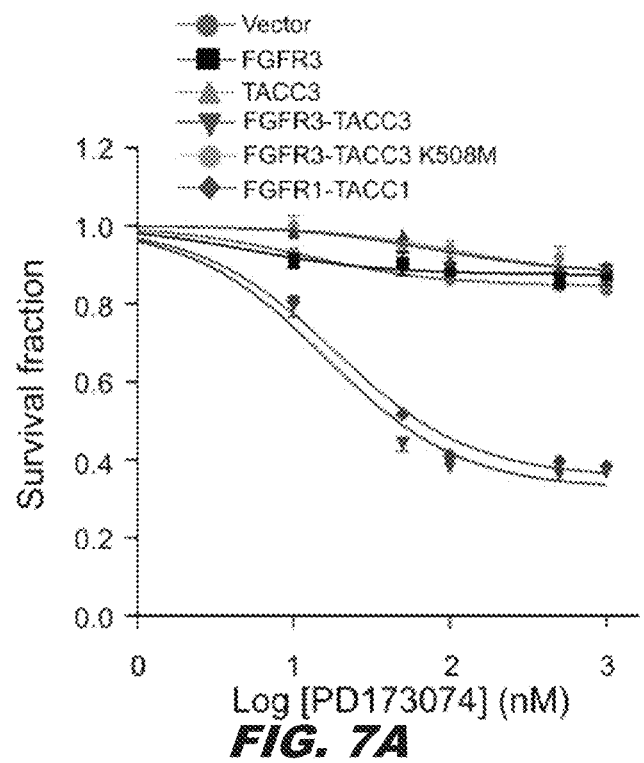
FIG. 7A shows inhibition of FGFR-TK activity suppresses tumor growth initiated by FGFR3-TACC3. Growth rate of Rat1A transduced with the indicated lentiviruses and treated for three days with increasing concentrations of PD173074. Cell growth was determined by the MTT assay. Data are presented as the means±standard error (n=4).
Figure 7B:
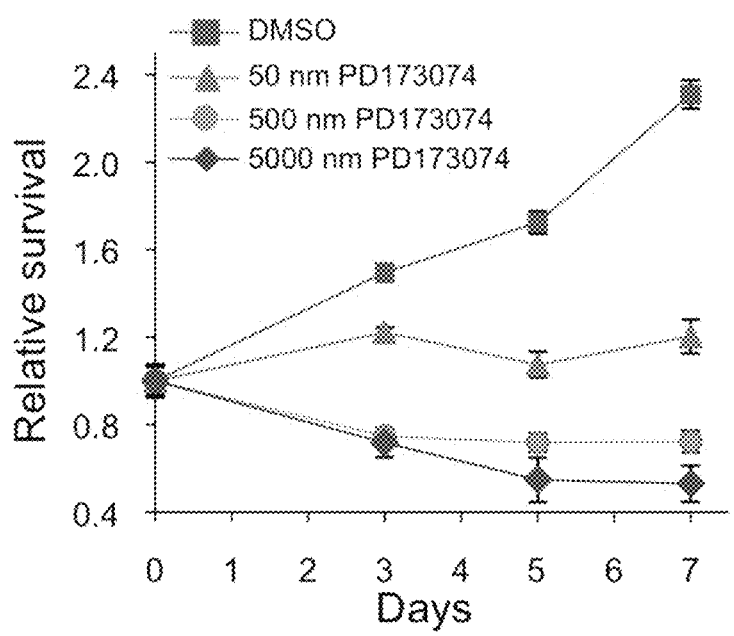
FIG. 7B shows the growth rate of GSC-1123 treated with PD173470 at the indicated concentrations for the indicated times. Cell growth was determined by the MTT assay. Data are presented as the means±standard error (n=4).
Figure 7C:
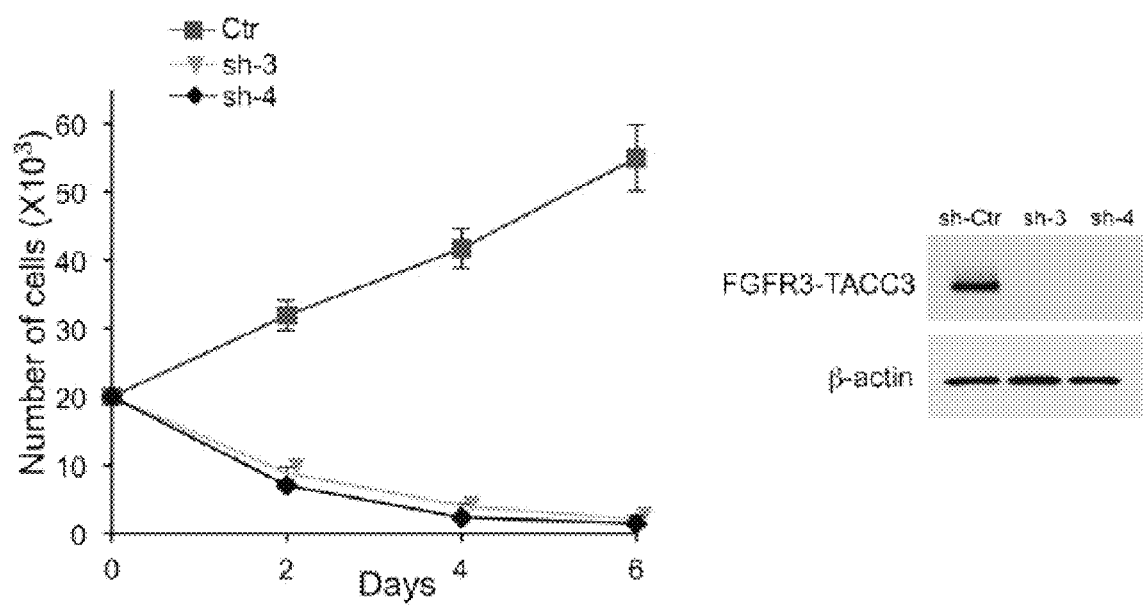
FIG. 7C shows the growth inhibitory effect of silencing FGFR3-TACC3 fusion. At the left, parallel cultures of GSC-1123 cells were transduced in triplicate. Rat1A cells expressing FGFR3-TACC3 fusion were transduced with lentivirus expressing a non-targeting shRNA (Ctr) or shRNA sequences targeting FGFR3 (sh2, sh3, sh4). Five days after infection cells were plated at density of $2\lambda 10^4$ cells/well in triplicate and the number of trypan blue excluding cells was scored at the indicated times. Infection with lentivirus expressing sh-3 and sh-4, the most efficient FGFR3 silencing sequences reverted the growth rate of FGFR3-TACC3 expressing cultures to levels comparable to those of Rat1A transduced with empty vector. Values are the means±standard deviation (n=3). At the right sided figure, GSC-1123 cells were transduced with lentivirus expressing a non-targeting shRNA (sh-Ctr) or lentivirus expressing sh-3 and sh-4 sequences targeting FGFR3. Western Blot analysis was performed on parallel cultures using the FGFR3 antibody to the detect FGFT3-TACC3 fusion protein. β-actin is shown as a control for loading.
Figure 14E:
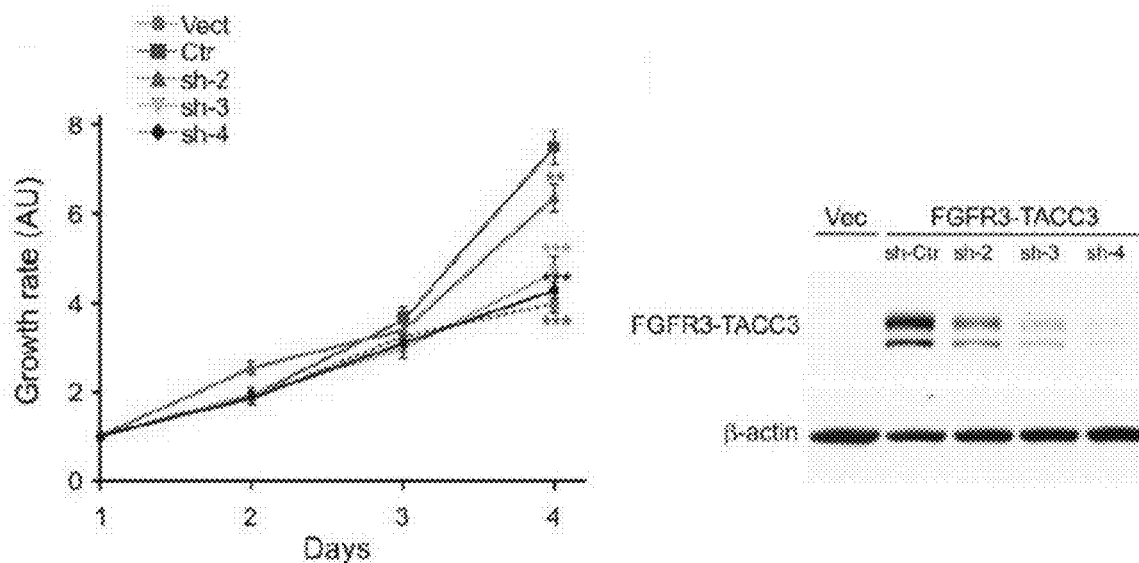
FIG. 14E shows the growth inhibitory effect of silencing FGFR3-TACC3 fusion. (left) GSC-1123 cells were transduced in triplicate with lentivirus expressing a non-targeting shRNA (Ctr) or lentivirus expressing sh-3 and sh-4 sequences targeting FGFR3. Five days after infection cells were plated at density of $2 \times 10^4$ cells/well in triplicate and the number of trypan blue excluding cells was scored at the indicated times. Values are the means±standard deviation (n=3). (right) Western Blot analysis was performed on parallel cultures collected five days after infection using the FGFR3 antibody to the detect FGFT3-TACC3 fusion protein. β-actin is shown as a control for loading. (: p-value=<0.005; *: p-value=<0.0001).
Figure 15:
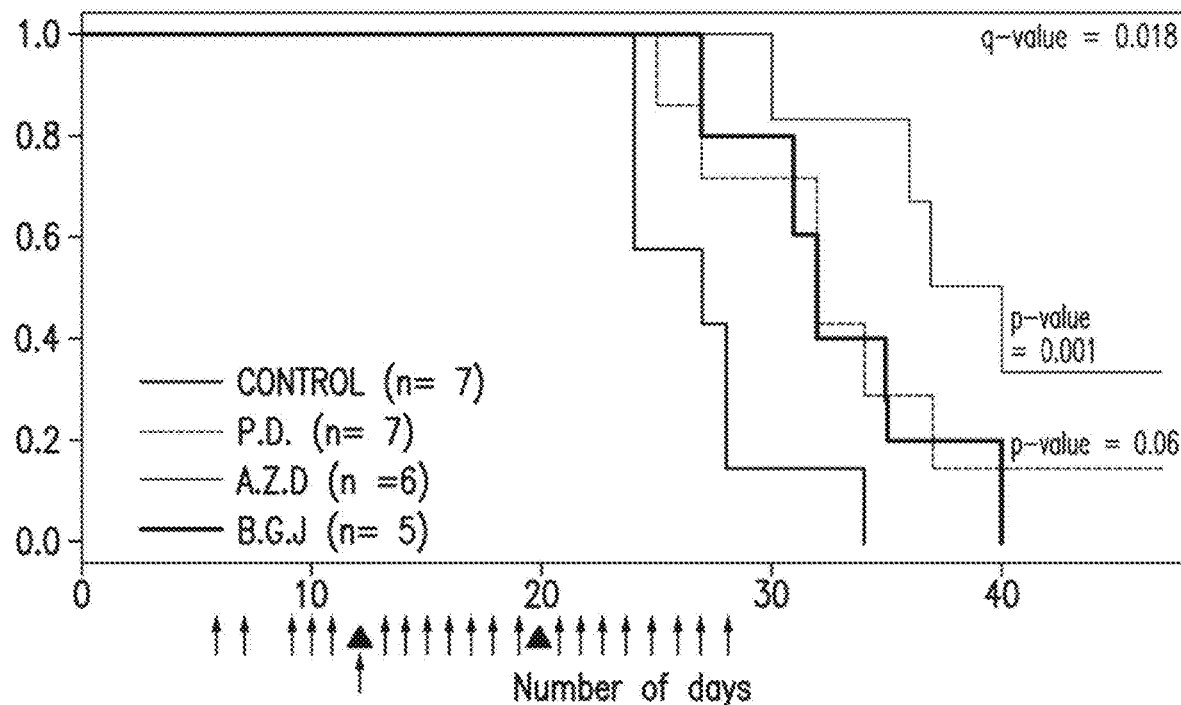
FIG. 15 shows a survival plot of cells treated with PD173074, NVP-BGJ398, or AZD4547.
Figure 16:
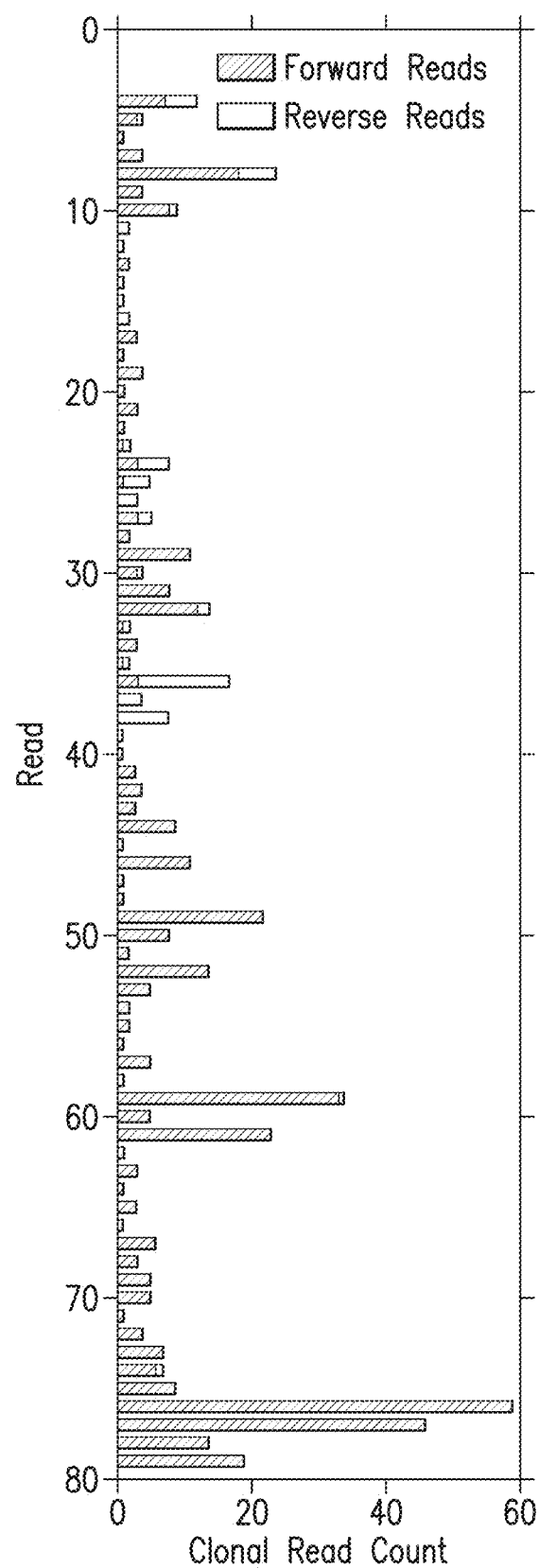
FIG. 16 shows an FGFR3-TACC3 gene fusion identified by whole transcriptome sequencing of GSCs. The histogram describes the absolute frequency of each forward and reverse sequence read spanning the breakpoint.
Figure 17:
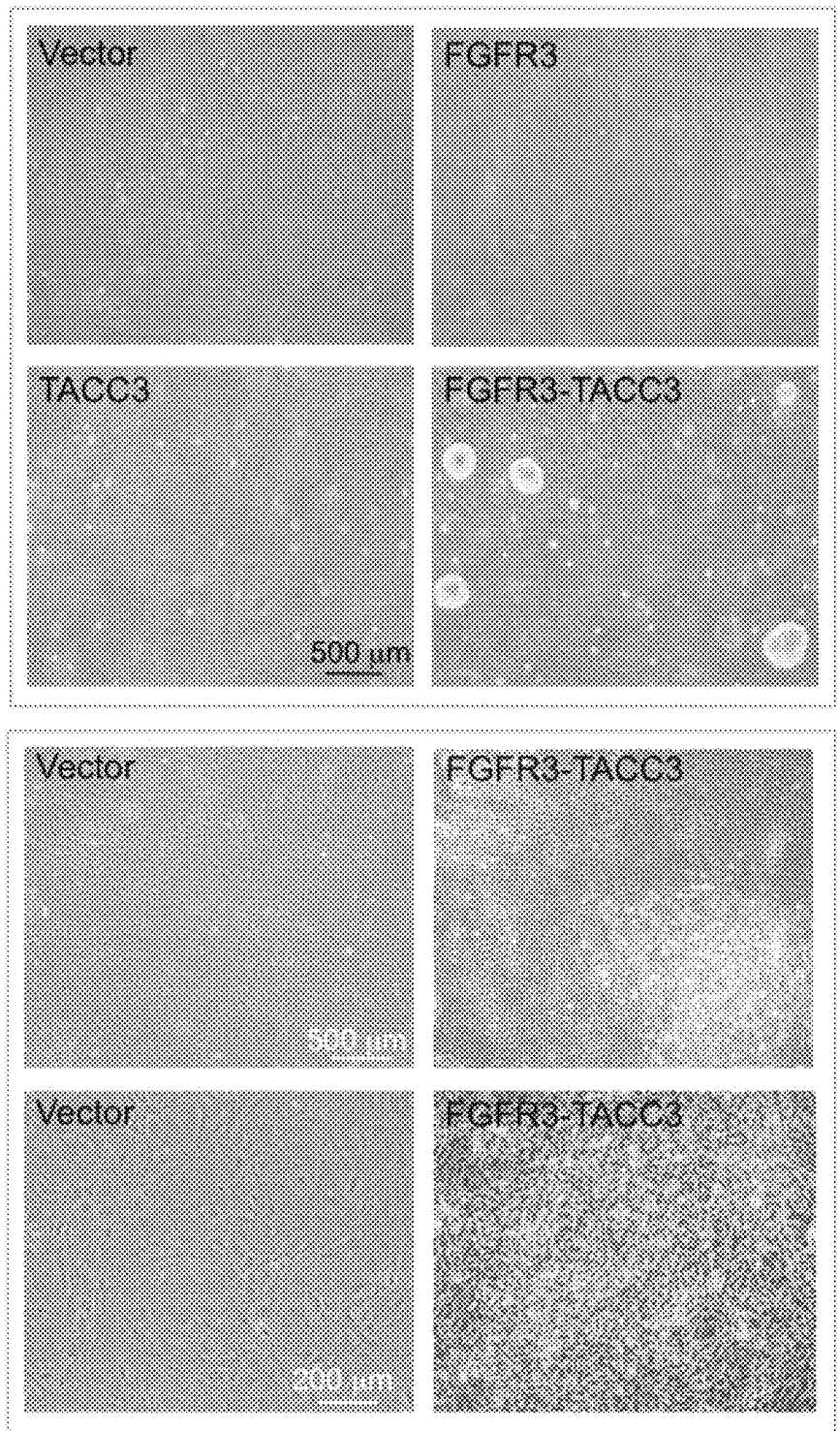
FIG. 17 shows transforming activity of FGFR3-TACC3. FGFR3-TACC3 induces anchorage-independent growth in Rat1A fibroblasts (top panels) and a transformed phenotype in Ink4A; Arf−/− primary astrocytes (bottom panels).
Figure 18:
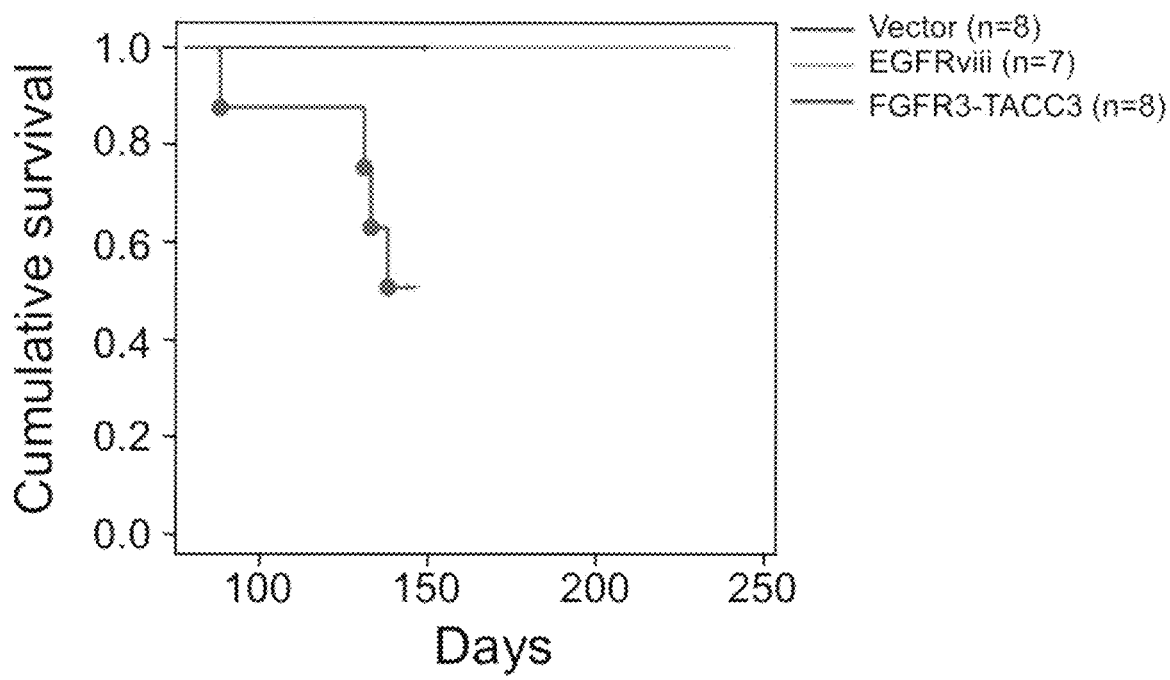
FIG. 18 shows transforming activity of FGFR3-TACC3. Kaplan-Meier survival curves of mice injected intracranially with pTomo-shp53 (n=8), pTomo-FGFR3-TACC3-shp53 (n=8) and pTomo-EGFRvIII-shp53 (n=7) are shown. Points on the curves indicate deaths (log-rank test, p=0.025, pTomo-shp53 vs. pTomo-FGFR3-TACC3-shp53).
Figure 19:
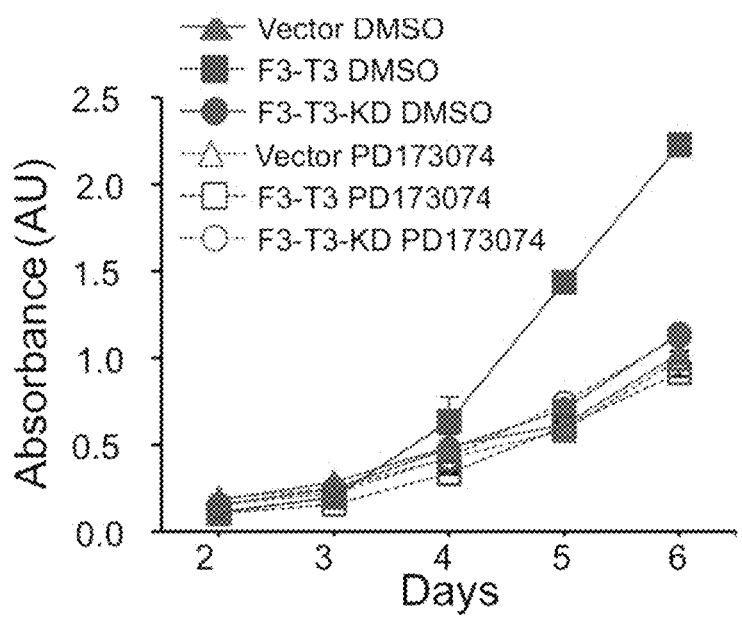
FIG. 19 shows that inhibition of FGFR-TK activity corrects the aneuploidy and suppresses tumor growth initiated by FGFR3-TACC3. Short-term growth inhibition assays are shown of Rat1A transduced with the indicated lentivirus and treated with PD173470 at the indicated concentrations. Cells were treated for three days. Cell viability was determined by the MTT assay. Error bars show means±standard error (n=4).
Figure 20:
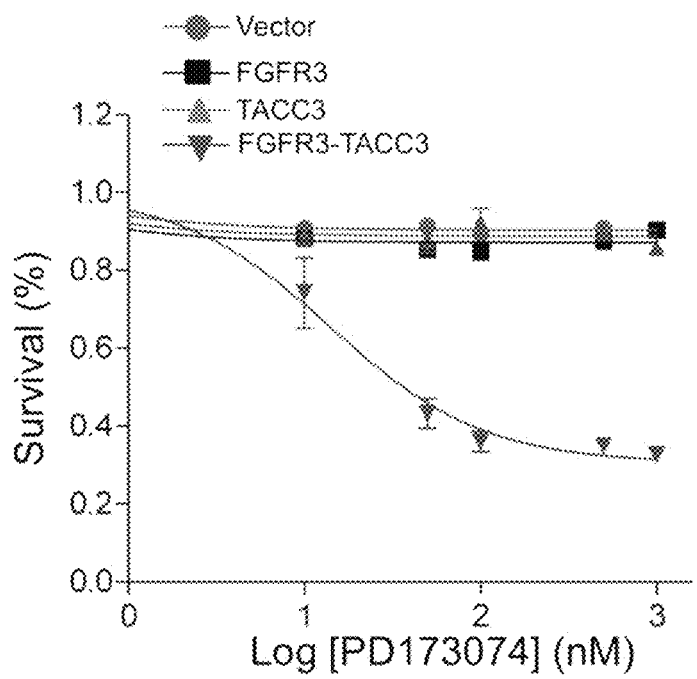
FIG. 20 is a growth inhibition assay of human astrocytes transduced with the indicated lentivirus and treated for four days with PD173470 at the indicated concentration. Cell viability was determined by the MTT assay. Error bars show means±standard error (n=4).
Figure 21:
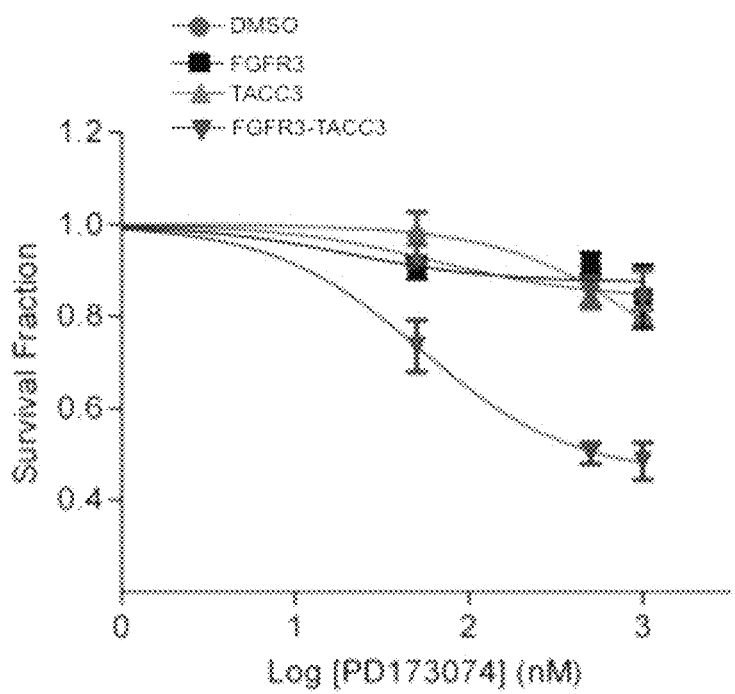
FIG. 21 is a graph showing a growth inhibition assay of human astrocytes transduced with the indicated lentivirus and treated for four days with PD173470 at the indicated concentration. Cell viability was determined by the MTT assay. Error bars show means±standard error (n=4).
Figure 22:
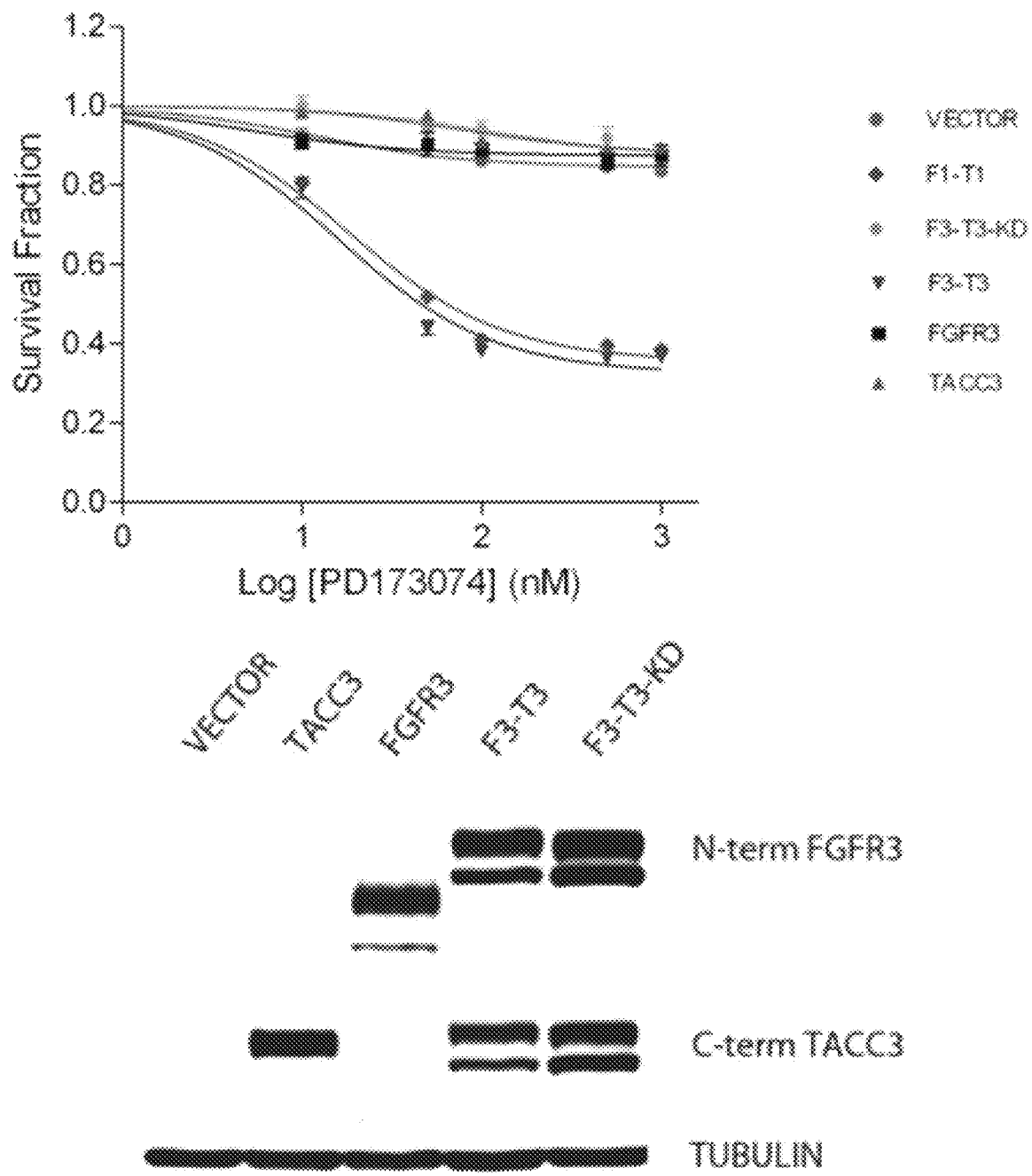
FIG. 22 shows graphs of the survival of Rat1A cells in short-term growth inhibition assays. (Top graph) Rat1A cells were transduced with the indicated ptomo constructs and treated with PD173074 at the indicated concentrations. Cells were treated for three days. Cell viability was determined by the MTT assay. Error bars show means±standard error (n=4). In the bottom panel, a western blot photograph is shown.
Figure 23:
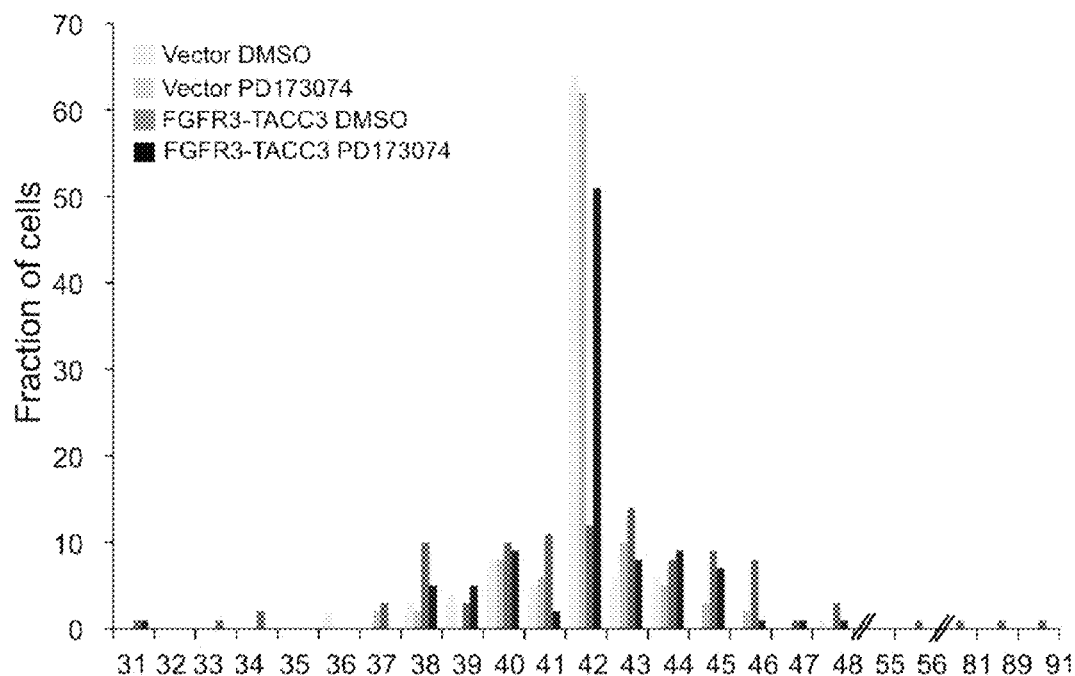
FIG. 23 shows that inhibition of FGFR-TK activity corrects the aneuploidy and suppresses tumor growth initiated by FGFR3-TACC3. A plot is shown of karyotype analysis of Rat1A cells transduced with control or FGFR3-TACC3 lentivirus and treated with vehicle (DMSO) or PD173470 (100 nM) for five days.
Figure 24:
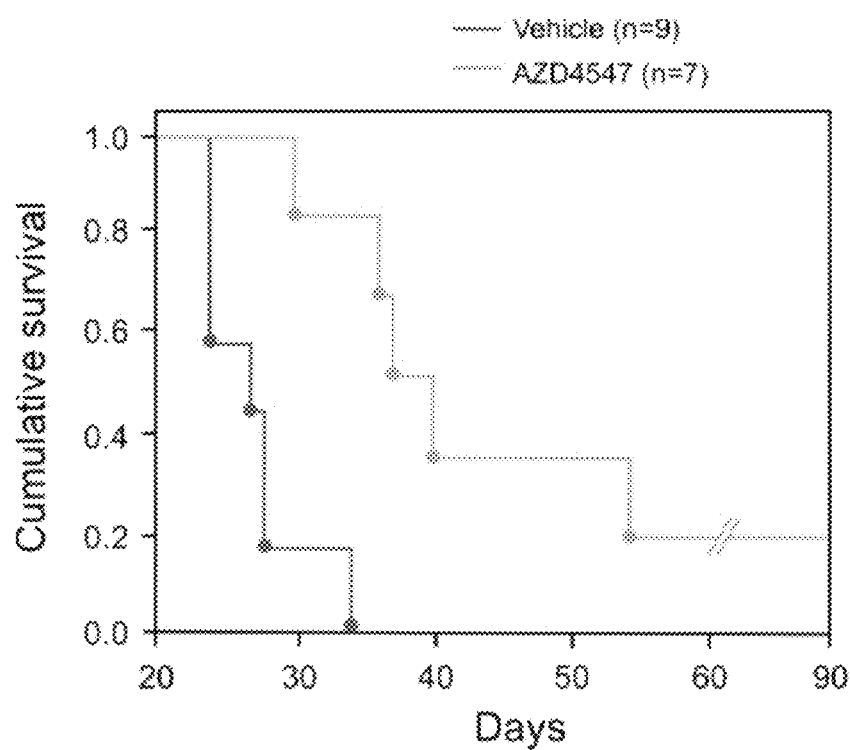
FIG. 24 shows Survival of glioma-bearing mice was tracked following intracranial implantation of Ink4A; Arf−/− astrocytes transduced with FGFR3-TACC3. After tumor engraftment mice were treated with vehicle or AZD4547 (50 mg/kg) for 20 days (vehicle, n=7; AZD4547, n=6; p=0.001).
Figure 26:
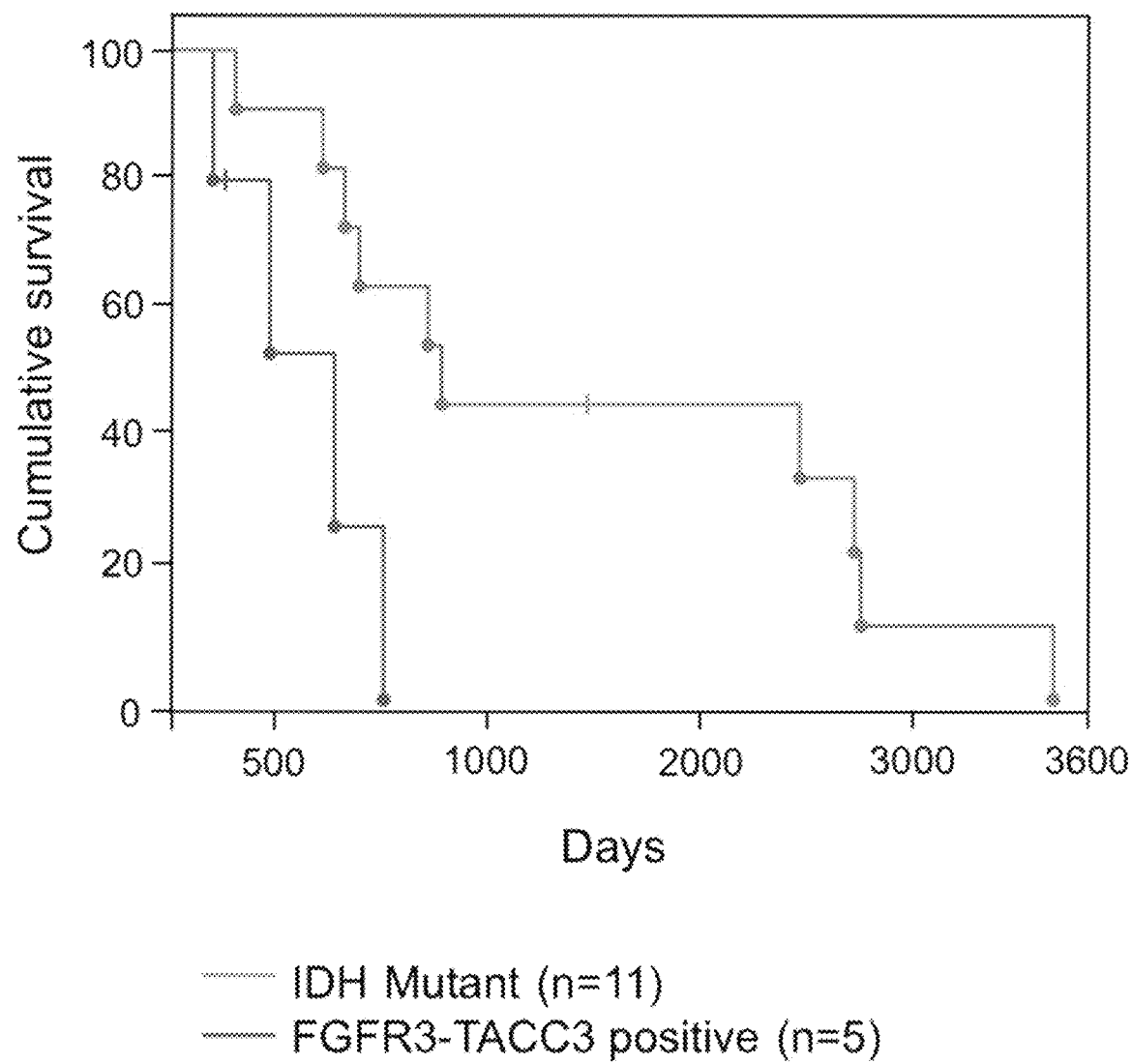
FIG. 26 shows Kaplan-Meier analysis of IDH mutant and FGFR3-TACC3 positive human GBM. Log rank test p-value: 0.0169.
Figure 28:
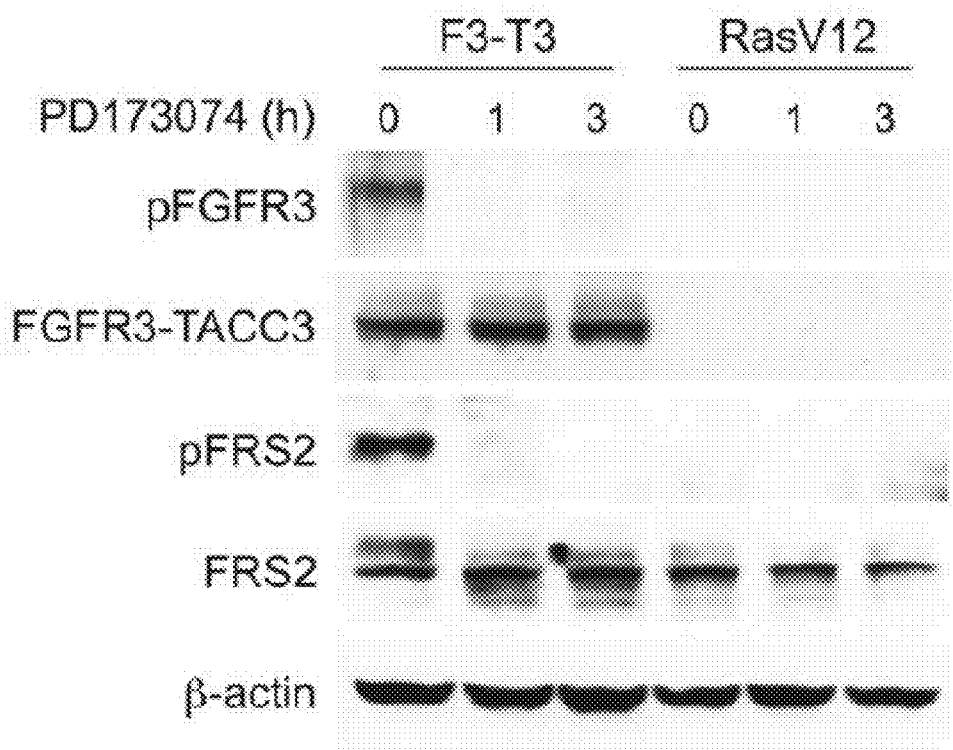
FIG. 28 shows constitutive auto-phosphorylation of FGFR3-TACC3 fusion. BTSC derived from FGFR3-TACC3 or RasV12 induced mouse GBM were left untreated or treated with 500 nM PD173074 for the indicated times. Phospho-proteins and total proteins were analyzed by Western blot using the indicated antibodies. β-actin is shown as a control for loading.
Figure 29:
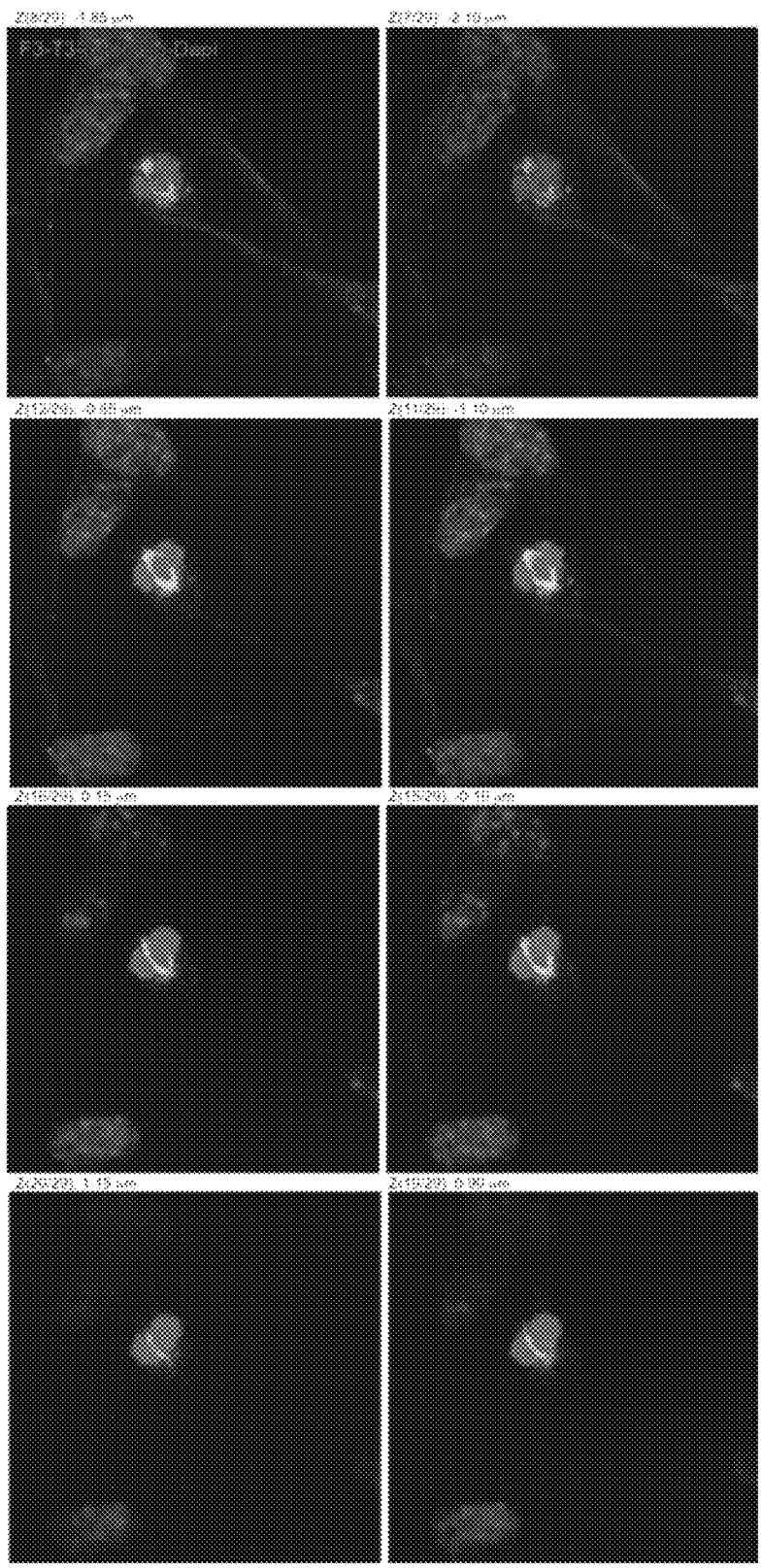
FIG. 29 shows Z-stacked confocal images of the representative FGFR3-TACC3 expressing Ink4A; Arf−/− mouse astrocyte shown as a maximum intensity projection. Cells were immunostained using FGFR3 (red; "dark grey" in black and white image) and a-tubulin (green; ("light grey" in black and white image). DNA was counterstained with DAPI (blue; ("grey" in black and white image). Images were acquired at 0.250 μm intervals. Coordinates of the image series are indicated. F3-T3: FGFR3-TACC3.

FGFR-TACC fusion proteins are new therapeutic targets in GBM. Driver genetic alterations trigger a state of oncogene addiction in the cancer cells harboring them that can be exploited therapeutically. To ask whether FGFR-TACC fusions confer addiction to FGFR-TK activity, cell growth was analyzed in the presence of PD173074, AZD4547 or BGJ398, the latter being two highly specific inhibitors of FGFR-TK under clinical investigation (Gavine et al., 2012; Guagnano et al., 2011). Each of the three drugs inhibited growth of cells expressing FGFR3-TACC3 and FGFR1-TACC1 at concentrations <10 nM whereas they were ineffective at concentrations as high as 1 µM in cells transduced with vector, FGFR3, TACC3 and the FGFR3-TACC3-K508M mutant (FIGS. 7A, 14C and 14D). These findings underscore the elevated degree of specificity for FGFR kinase inhibition towards cells carrying the fusion protein. The growth of GSC-1123 cells, which naturally harbor the FGFR3-TACC3 translocation, was also abolished by nanomolar concentrations of FGFR-TK inhibitors (FIG. 7B). Targeting of the fusion gene by FGFR3 shRNA inhibited the growth of cells ectopically expressing FGFR3-TACC3 and GSC-1123 proportionally to the silencing efficiency of FGFR3-TACC3 (FIGS. 7C and 14E).

Figure 7D:
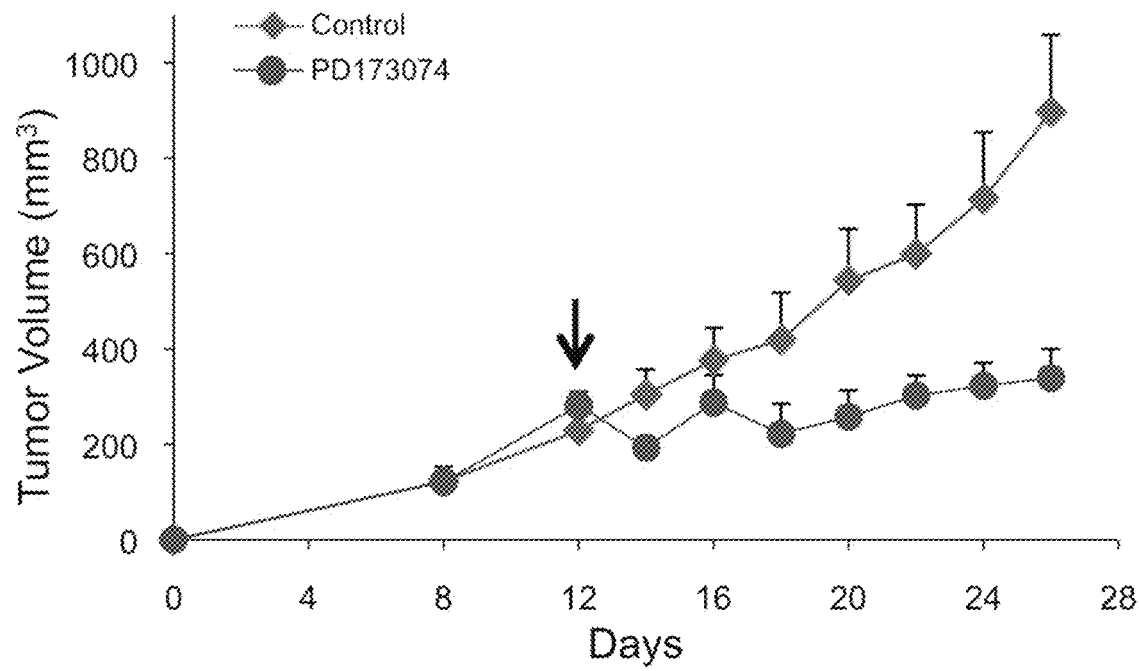
FIG. 7D shows that the FGFR inhibitor PD173074 suppresses tumor growth of glioma sub-cutaneous xenografts generated by Ink4A; Arf−/− astrocytes expressing FGFR3-TACC3. After tumor establishment (200-300 mm 3, arrow) mice were treated with vehicle or PD173074 (50 mg/kg) for 14 days. Values are mean tumor volumes±standard error (n=7 mice per group).
Figure 7E:
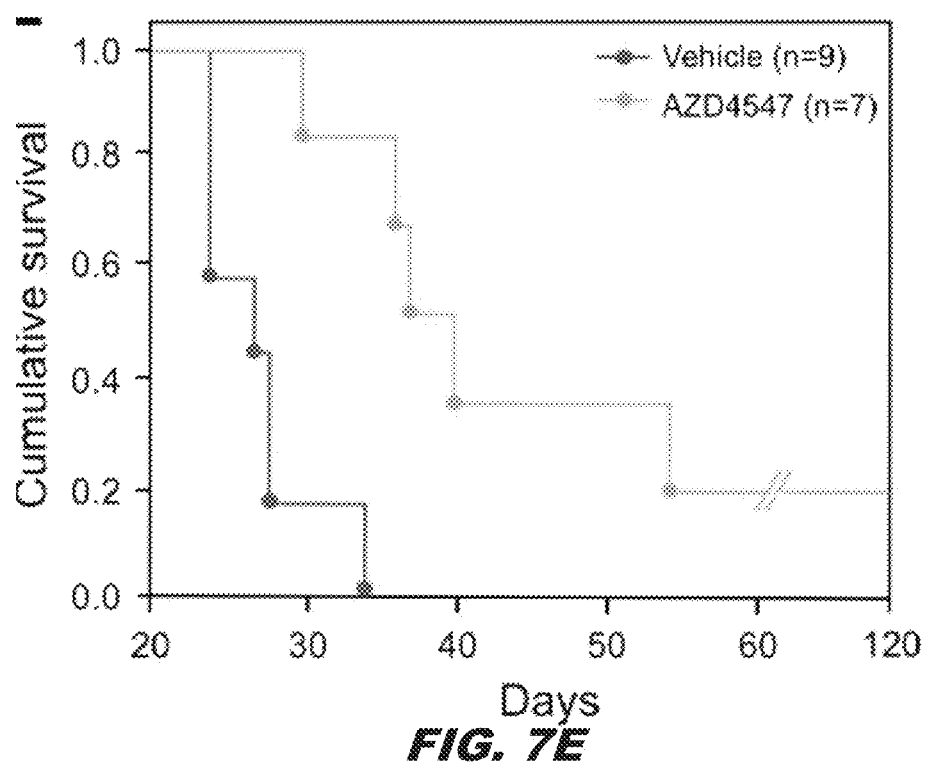
FIG. 7E is a Kaplan-Meier analysis of glioma-bearing mice following orthotopic implantation of Ink4A; Arf−/− astrocytes transduced with FGFR3-TACC3. After tumor engraftment mice were treated with vehicle (n=9) or AZD4547 (50 mg/kg) (n=7) for 20 days (p=0.001).

Finally, it was determined whether treatment with PD173074 of mice bearing glioma xenografts of FGFR3-TACC3 transformed astrocytes inhibits tumor growth. Twelve days after injection of tumor cells, subcutaneous tumors were present in all animals. The mice were randomized in two cohorts and treated with PD173074 or vehicle. PD173074 elicited a potent growth inhibition of FGFR3-TACC3 glioma (FIG. 7D). To confirm the efficacy of a clinically meaningful FGFR-TK inhibitor using a more anatomically relevant model, the AZD4547 FGFR inhibitor, a compound under clinical investigation (Gavine et al., 2012), was used against intracranial luciferase-expressing FGFR3-TACC3-driven glioma xenografts. After an engraftment period, tumor-bearing animals were treated with either AZD4547 or vehicle. Oral administration of AZD4547 markedly prolonged survival (FIG. 7E). Taken together, the data provide a strong rationale for a clinical trial based on FGFR inhibitors in GBM harboring FGFR-TACC rearrangements.

DISCUSSION

This work has established that recurrent, oncogenic and addicting gene fusions identify a subset of GBM patients. The functional characterization of FGFR-TACC fusions indicates that the constitutively active FGFR-TK and the TACC domain of the fusion protein are both essential for oncogenesis. The TACC-dependent mis-localization to mitotic cells of the FGFR kinase results in aberrant compartmentalization of a constitutively active TK to the mitotic spindle pole, thus providing a mechanistic explanation for the impaired mitotic fidelity, chromosome mis-segregation and aneuploidy instigated by the fusion protein.

Without being bound by theory, mutation of the genes that control chromosome segregation during mitosis can explain the high rate of CIN and aneuploidy, which is typical of most solid tumors including GBM (Gordon et al., 2012). A few examples of mutational inactivation of candidate genes have been reported in human cancer (Solomon et al., 2011; Thompson et al., 2010). However, gain-of-function mutations causally implicated in the control of mitotic fidelity have not been described. This clashes with the classical observation from cell fusion experiments that the underlying mechanisms that cause CIN behave as dominant traits, indicating that the CIN phenotype results from gain-of-function events rather than gene inactivation (Lengauer et al., 1997, 1998). The FGFR-TACC gene fusion is a novel mechanism for the initiation of CIN and provides a clue to the nature of dominant mutations responsible for aneuploidy in human cancer.

The rapid emergence of mitotic defects and aneuploid cell populations triggered by the fusion protein in normal human astrocytes, combined with the correction of aneuploidy after short inhibition of FGFR-TK activity indicate that aneuploidy is a key event in tumor induction by the FGFR-TACC gene fusions. Induction of aneuploidy per se is detrimental to cellular fitness (Sheltzer and Amon, 2011). Full-blown tumorigenesis requires cooperation between aneuploidy and genetic lesions that confer growth advantage and protect cells against the detrimental effects of aneuploidy (Coschi and Dick, 2012; Holland and Cleveland, 2009; Weaver and Cleveland, 2009). Therefore, the potent tumor-initiating activity of FGFR-TACC fusions shows that the novel oncoproteins have growth-promoting signaling functions that complement the loss of mitotic fidelity with ensuing karyotypic alterations (Sheltzer and Amon, 2011).

Targeted therapies against common genetic alterations in GBM have not changed the dismal clinical outcome of the disease, most likely because they have systematically failed to eradicate the truly addicting oncoprotein activities of GBM. The highly specific anti-tumor effects and the correction of aneuploidy precipitated by FGFR-TK inhibition of FGFR-TACC-driven GBM provide a strong rationale for clinical trials based on FGFR inhibitors in patients harboring FGFR-TACC rearrangements. The computational gene fusion discovery pipeline reported here detected other GBM cases in which FGFR family genes are implicated in additional gene fusions beyond the FGFR-TACC rearrangements. Therefore, the frequency of 3.1% is likely to be an underestimate of the target GBM patient population that may benefit from FGFR-TK inhibition.

Experimental Procedures

Cell culture and isolation and maintenance of GSCs. Rat1A, mouse astrocytes Ink4A; Arf−/−, and human astrocytes were cultured in DMEM supplemented with 10% FBS. Isolation and culture of GSCs was performed as described (Carro et al., 2010). For treatment in vitro with PD173074, AZD4547 or BJG398, cells infected with vector control, FGFR3, TACC3, FGFR-TACC fusions or FGFR3-TACC3-K508M were seeded in 96-well plates and treated with increasing concentrations of FGFR inhibitors. After 72-120 h, growth rate was measured using the 3-(4,5-dimethythiazol-2-yl)-2,5-diphenyl tetrazolium bromide (MTT) assay. Data were expressed as mean±SD. Proliferation rate in GSC-1123 infected with FGFR3 shRNA lentivirus was determined by plating dissociated gliomaspheres at $2\times10^4$ cells/well in twelve-well plates 5 days after infection. The number of viable cells was determined by trypan blue exclusion in triplicate cultures obtained from triplicate independent infections. Cell number was scored every other day.

DNA, RNA Preparation, Genomic and Real-Time Quantitative PCR (qRT-PCR).

The validation of fusion transcripts was performed using both genomic and RT-PCR with forward and reverse primer combinations designed within the margins of the paired-end read sequences detected by RNA-seq. DNA, RNA preparation and qRT-PCR were performed as described (Carro et al., 2010; Zhao et al., 2008). To identify novel fusion transcripts within the GBM cohort, PCR primers pairs were designed to bind upstream to the TK domain of the FGFR genes and inside or downstream the Coiled Coil domain of the TACC genes. Expressed fusion transcript variants were subjected to direct sequencing to confirm sequence and frame. Primer sequences are included below.

Subcutaneous xenografts and drug treatment. Rat1A or Ink4A; Arf–/– astrocytes ($5\times10^5$) transduced with different lentiviral constructs were suspended in 150 µl of PBS, together with 30 µl of Matrigel (BD Biosciences), and injected subcutaneously in the flank of athymic nude (Nu/Nu) mice (Charles River Laboratories, Wilmington, MA). For experiments with FGFR inhibitors, mice carrying ~200-300 mm 3 subcutaneous tumors derived from Ink4A; Arf–/– astrocytes were randomized to receive 50 mg/kg PD173074 in 0.05 M lactate buffer (pH 5) or an equal volume of lactate buffer by oral gavage. Treatment was administered for three cycles consisting of four consecutive days followed by two days of rest. Tumor diameters were measured with caliper, and tumor volumes estimated using the formula: $0.5\times \text{length}\times\text{width}^2$. Data are expressed as mean±SE. Mice were sacrificed when tumors in the control group reached the maximal size allowed.

Orthotopic transplantation and drug treatment. Ink4A; Arf–/– astrocytes carrying a luciferase expressing vector were transduced with FGFR3-TACC3 lentivitus. $1\times10^3$ cells in 2 µl of saline were injected in the caudate-putamen of 4-6 week old male athymic nude (Nu/Nu) mice using a stereotaxic frame (coordinates relative to bregma: 0.5 mm anterior; 1.1 mm lateral; 3.0 mm ventral) and a 26 gauge Hamilton syringe. Six days after injection, mice underwent bioluminescence imaging using a Xenogen CCD apparatus and were randomized to receive 50 mg/kg AZD4547 in 1% Tween 80 (treatment group) or DMSO in an equal volume of vehicle by oral gavage (control group). AZD4547 was administered daily for two cycles of 10 days with a two day interval. Mice were monitored daily and sacrificed when neurological symptoms appeared. Kaplan-Meier survival curve was generated using the DNA Statview software package (AbacusConcepts, Berkeley, CA). Log-rank analysis was performed on the Kaplan-Meier survival curve to determine statistical significance.

Intracranial injections of lentiviruses. Intracranial injection of FGFR3-TACC3-shp53, EGFRvIII-shp53 or shp53 pTomo lentiviruses was performed in 4 week-old C57/BL/6J mice in accordance with guidelines of IACUC Committee. Briefly, 1.8 µl of purified lentiviral particles in PBS ($1\times10^9$/ml) were injected into the dentate gyrus using a stereotaxic frame (coordinates relative to bregma: 1.45 mm posterior; 1.65 mm lateral; 2.4 mm ventral) and a 26 gauge Hamilton syringe. Mice were monitored daily and sacrificed when neurological symptoms appeared. Mouse brain was analyzed histopathologically and by immunofluorescence staining.

Histology and immunostaining. Tissue preparation and immunohistochemistry on brain tumors and immunofluorescence staining were performed as previously described (Carro et al., 2010; Zhao et al., 2009; Zhao et al., 2008). Antibodies used in immunostaining and immunoblotting are listed below.

Cloning and Lentiviral production. Lentivirus preparation and infections were performed as described (Carro et al., 2010) and are detailed in Extended Experimental Procedures.

Karyotype analysis. Cultured cells were colcemid (20 ng/ml) treated for 90 minutes before harvesting for karyotopic analysis as detailed in Extended Experimental procedures. At least one hundred cells in metaphase were examined for chromosome count. PMSCS was scored in cells where a majority of the sister chromosomes were no longer associated. Two-tailed unpaired t-tests with Welch's correction were performed for comparison of means analysis.

Immunofluorescence and live-cell microscopy. Immunofluorescence microscopy was performed on cells fixed with 4% PFA in PHEM (60 mM Pipes, 27 mM Hepes, 10 mM EGTA, 4 mM $MgSO_4$, pH 7.0). Cells were permeabilized using 1% Triton X-100. Mitotic spindles were visualized by anti-a-tubulin antibody (Sigma). Secondary antibodies conjugated to Alexa Fluor-488/-594 (Molecular Probes) were used. All staining with multiple antibodies were performed in a sequential manner. DNA was stained by DAPI (Sigma). Fluorescence microscopy was performed on a Nikon AIR MP microscope.

Identification of gene fusions from whole transcriptome (RNA-seq) and exome sequencing. RNA-Sequencing was performed from total RNA extracted from GSC cultures isolated from nine GBM patients using Illumina HiSeq 2000, producing roughly 60.3 million paired reads per sample. Using the global alignment software Burrows-Wheeler Aligner (BWA) (Li and Durbin, 2009) with modified Mott's trimming, an initial seed length of 32, maximum edit distance of 2 and a maximum gap number of 1, on average 43.1 million reads were mapped properly to the RefSeq transcriptome and, of the remaining, 8.6 million were mapped to the hg19 genome per sample. The remaining 14.3% of paired reads—including those that failed to map to either transcriptome or genome with proper forward-reverse (F-R) orientation, within expected insert size, and with minimal soft clipping (unmapped portions at the ends of a read)—were considered to be appropriate for gene fusion analysis.

A novel computational pipeline was constructed called TX-Fuse that identifies two sources of evidence for the presence of a gene fusion: 1. Split inserts, in which each read of a mate pair maps entirely to one side of a breakpoint, and 2. Individual split reads that span a breakpoint. Split inserts are readily detected from BWA mapping. On the other hand, split reads demand precision alignment of smaller nucleotide stretches. To that end, the pipeline employs the local alignment package BLAST with word size of 20, identity cutoff of 95%, expectation cutoff of 10', and soft filtering to map raw paired reads against the RefSeq transcriptome. From this procedure, a list of potential split reads were obtained that were filtered to ensure maintenance of coding frame in the predicted fusion transcript given the proper F-R orientation in the read pair. False positive candidates produced from paralogous gene pairs were also screened out using the Duplicated Genes Database and the EnsemblCompara GeneTrees (Vilella et al., 2009). Pseudogenes in the candidate list were annotated using the list from HUGO Gene Nomenclature Committee (HGNC) database (Seal et al., 2011) and given lower priority. For each remaining gene fusion candidate, a virtual reference was created based on the predicted fusion transcript and re-mapped all unmapped reads using BLAST with word size of 16, identity cutoff of 85%, query coverage greater than 85%, and expectation cutoff of $10^{-4}$ to obtain a final count of split reads and inserts. Moreover, sequencing depth per base of the virtual reference was calculated to corroborate that components of each gene participating in the gene fusion were highly expressed.

To establish the recurrence of the initial panel of gene fusion candidates, the gene fusion discovery pipeline was modified to produce EXome-Fuse, which probes for fusions within the available dataset of paired-read exome DNA sequencing of 84 matched GBM samples from TCGA. To increase sensitivity for gene fusion identification, reads unmapped by BWA were aligned to the gene pair participating in each fusion candidate using a BLAST word size of 24 for split inserts and 16 for split read and split insert discovery. Given that the breakpoint detected in DNA cannot directly indicate the resulting breakpoint in the transcribed RNA, no restriction was made on split insert orientation. For split reads, it was only required that the component of the split read mapped to the same gene as its mate maintained F-R directionality.

Co-outlier expression and CNV analysis from TCGA GBM samples. Tomlins et al. (Tomlins et al., 2005) reported that outlier gene expression from microarray datasets identifies candidate oncogenic gene fusions. Wang et al. (Wang et al., 2009) suggested a "breakpoint principle" for intragenic copy number aberrations in fusion partners. The two principles (outlier expression and intragenic CNV) were combined to identify candidate gene fusions in GBM samples from Atlas-TCGA. Genomic and expression data sets were downloaded from TCGA public data portal as available on Dec. 1, 2011, where a description of TCGA data types, platforms, and analyses is also available (2008). Specific data sources were (according to Data Levels and Data Types) as follows: Expression data, "Level 2" normalized signals per probe set (Affymetrix HT_HG-U133A) of 84 samples; Copy number data, "Level 1" raw signals per probe (Affymetrix Genome-Wide Human SNP Array 6.0) of the 4 FGFR3-TACC3 gene fusion positive samples (tumor and matched normal control).

The gene expression analysis was performed first using $R^3$. The median absolute deviation (MAD) was calculated and then a gene was labeled as an outlier according to the following formula: $Z_{i,j}=0.6745(x_{i,j}-\text{mean}(x_i))/\text{MAD}_i>3.5$ (Iglewicz and Hoaglin, 1993). Samples were identified as ECFS (expression candidate fusion sample) if both genes of interest (e.g. FGFR3 and TACC3) displayed outlier behavior (co-outliers). Next, ECFS were analyzed for CNV using pennCNV (Wang et al., 2007). Tumors samples were paired to their normal controls to obtain the log ratio values and the VEGA algorithm was used to obtain a more accurate segmentation (Morganella et al., 2010).

Karyotypic Analysis. The colcemid treated cells were trypsinized, centrifuged for 7 minutes at 200×g, and the cell pellet re-suspended in warmed hypotonic solution and incubated at 37° C. for 13 minutes. The swollen cells were then centrifuged and the pellet re-suspended in 8 ml of Carnoy's fixative (3:1 methanol:glacial acetic acid). The cell suspension was centrifuged and washed twice in Carnoy's fixative. After the last centrifugation, the cells were resuspended in 0.5 to 1 ml of freshly prepared fixative to produce an opalescent cell suspension. Drops of the final cell suspension were placed on clean slides and air-dried. Slides were stained with DAPI and metaphases were analyzed under a fluorescent microscope.

Cloning and Lentiviral production. Lentiviral expression vectors, pLOC-GFP (Open Biosystems) and pTomo-shp53, were used to clone FGFR3, TACC3, FGFR3-TACC3, FGFR3-TACC3-K508M, and FGFR1-TACC1. pTomo-shp53 was a gift of Inder Verma and Dinorah Friedman-Morvinski (Salk Institute, San Diego). The FGFR3-TACC3-K508M mutant was generated using the Phusion Site Direct Mutagenesis kit (NEB, USA). MISSION shRNAs clones (pLK0.1 lentiviral expression vectors) against FGFR3 were purchased from Sigma. The hairpin sequences targeting the FGFR3 gene are—

```
(#TRCN0000000372; Sh#2)
                              (SEQ ID NO: 182)
5'-TGCGTCGTGGAGAACAAGTTT-3';

(#TRCN0000430673; Sh#3)
                              (SEQ ID NO: 183)
5'-GTTCCACTGCAAGGTGTACAG-3';

(#TRCN0000000374; Sh#4)
                              (SEQ ID NO: 184)
5'-GCACAACCTCGACTACTACAA-3'.
```

Genomic and mRNA RT-PCR. Total RNA was extracted from cells by using RNeasy Mini Kit (QIAGEN), following the manufacturer instructions. 500 ng of total RNA was retro-transcribed by using the Superscript III kit (Invitrogen), following the manufacturer instructions. The cDNAs obtained after the retro-transcription was used as templates for qPCR. The reaction was performed with a Roche480 thermal cycler, by using the Absolute Blue QPCR SYBR Green Mix from Thermo Scientific. The relative amount of specific mRNA was normalized to 18S. Results are presented as the mean±SD of triplicate amplifications.

Primers used are:

```
hFGFR3-RT-FW1:
                              (SEQ ID NO: 162)
5'-GTAACCTGCGGGAGTTTCTG-3';

hFGFR3-RT-REV1:
                              (SEQ ID NO: 163)
5'-ACACCAGGTCCTTGAAGGTG-3';

hTACC3-RT-FW2:
                              (SEQ ID NO: 164)
5'-CCTGAGGGACAGTCCTGGTA-3';

hTACC3-RT-REV2:
                              (SEQ ID NO: 165)
5'-AGTGCTCCCAAGAAATCGAA-3';

hWRAP53-RT-FW1:
                              (SEQ ID NO: 180)
5'-AGAGGTGACCACCAATCAGC-3';

hWRAP53-RT-REV1:
                              (SEQ ID NO: 181)
5'-CGTGTCCCACACAGAGACAG-3'.
```

Primers used for the screening of FGFR-TACC fusions are:

```
FGFR3-FW1:
                              (SEQ ID NO: 166)
5'-CGTGAAGATGCTGAAAGACGATG-3';
```

```
TACC3-REV1:
                         (SEQ ID NO: 167)
5'-AAACGCTTGAAGAGGTCGGAG-3';

FGFR1-FW1:
                         (SEQ ID NO: 168)
5'-ATGCTAGCAGGGGTCTCTGA-3';

TACC1-REV1:
                         (SEQ ID NO: 169)
5'-CCCTTCCAGAACACCTTTCA-3'.
```

Primers used for genomic detection of FGFR3-TACC3 fusion in GBM-1123 and GSC-1123 are:

```
Genomic FGFR3-FW1:
                         (SEQ ID NO: 170)
5'-ATGATCATGCGGGAGTGC-3';

genomicTACC3-REV1:
                         (SEQ ID NO: 171)
5'-GGGGGTCGAACTTGAGGTAT-3'.
```

Primers used to validate fusions detected by RNA-seq are:

```
POLR2A-FW1:
                         (SEQ ID NO: 172)
5'-CGCAGGCTTTTTGTAGTGAG-3';

WRAP53-REV1:
                         (SEQ ID NO: 173)
5'-TGTAGGCGCGAAAGGAAG-3';

PIGU-FW1:
                         (SEQ ID NO: 174)
5'-GAACTCATCCGGACCCCTAT-3';

NCOA6-REV1:
                         (SEQ ID NO: 175)
5'-GCTTTCCCCATTGCACTTTA-3';

ST8SIA4-FW1:
                         (SEQ ID NO: 176)
5'-GAGGAGAGAAGCACGTGGAG-3';

PAM-REV1:
                         (SEQ ID NO: 177)
5'-GGCAGACGTGTGAGGTGTAA-3';

CAPZB-FW:
                         (SEQ ID NO: 178)
5'-GTGATCAGCAGCTGGACTGT-3';

UBR4-REV1:
                         (SEQ ID NO: 179)
5'-GAGCCTGGGCATGGATCT-3'.
```

Confocal microscopy imaging. For immunofluorescence of fixed cells, images were recorded with a Z-optical spacing of 0.25 μm using a Nikon AIR MP and a 60×1.3 oil objective and analyzed using ImageJ software (National Institute of Health). For live-cell analyses, Rat1A cells infected with pLNCX-H2B retrovirus and transduced with lentiviral vector or FGFR3-TACC3 fusion were seeded in glass bottom dishes in phenol red free DMEM and followed by time-lapse microscopy using the Nikon AIR MP biostation at 37° C. and 5% $CO_2$/95% air. Images with a Z-optical spacing of 1 μm were recorded every 4 min for 8 h. Images of unchallenged mitosis from early prophase until cytokinesis were processed using ImageJ software (National Institute of Health). The time-point of nuclear envelope breakdown (NEB) was defined as the first frame showing loss of smooth appearance of chromatin and anaphase was the first frame when chromosome movement towards the poles became apparent. Nuclear envelope reconstitution (NER) was defined as the first frame showing nuclei decondensation.

Box and whisker plots were calculated from image sequences from at least 50 recorded cells. Two-tailed unpaired t-tests with Welch's correction were performed for comparison of means analysis using StatView software (AbacusConcepts, Berkeley, CA).

Immunofluorescence. Antibodies and concentrations used in immunofluorescence staining are:

| Anti-Ki67 | Rabbit | 1:1000 | Vector Labs |
| Anti-pHH3 | Rabbit | 1:500 | Millipore |
| Anti-FGFR3 | Mouse | 1:1000 | Santa Cruz |
| Anti-Tacc3 | Goat | 1:1000 | USBiological |
| Anti-a-tubulin | Mouse | 1:1000 | Sigma |
| Anti-Nestin | Mouse | 1:1000 | BD Pharmingen |
| Anti-Olig2 | Rabbit | 1:200 | IBL |
| Anti-GFAP | Rabbit | 1:200 | Dako |
| Anti-ERK | Rabbit | 1:1000 | Cell Signaling |
| Anti-pERK | Rabbit | 1:1000 | Cell Signaling |
| AntiFRS | Rabbit | 1:250 | Santa Cruz |
| Anti-pFRS | Rabbit | 1:1000 | Cell Signaling |
| Anti-AKT | Rabbit | 1:1000 | Cell Signaling |
| Anti-pAKT473 | Rabbit | 1:1000 | Cell Signaling |

REFERENCES

Ablain, J., Nasr, R., Bazarbachi, A., and de The, H. (2011). The Drug-Induced Degradation of Oncoproteins: An Unexpected Achilles' Heel of Cancer Cells? Cancer Discov. 1, 117-127.

Bass, A. J., Lawrence, M. S., Brace, L. E., Ramos, A. H., Drier, Y., Cibulskis, K., Sougnez, C., Voet, D., Saksena, G., Sivachenko, A., et al. (2011). Genomic sequencing of colorectal adenocarcinomas identifies a recurrent VTI1A-TCF7L2 fusion. Nat. Genet. 43, 964-968.

Cahill, D. P., Kinzler, K. W., Vogelstein, B., and Lengauer, C. (1999). Genetic instability and darwinian selection in tumours. Trends Cell. Biol. 9, M57-60.

Carro, M. S., Lim, W. K., Alvarez, M. J., Bollo, R. J., Zhao, X., Snyder, E. Y., Sulman, E. P., Anne, S. L., Doetsch, F., Colman, H., et al. (2010). The transcriptional network for mesenchymal transformation of brain tumours. Nature 463, 318-325.

Coschi, C. H., and Dick, F. A. (2012). Chromosome instability and deregulated proliferation: an unavoidable duo. Cell. Mol. Life Sci. 69, 2009-2024

Druker, B. J. (2009). Perspectives on the development of imatinib and the future of cancer research. Nat. Med. 15, 1149-1152.

Furnari, F. B., Fenton, T., Bachoo, R. M., Mukasa, A., Stommel, J. M., Stegh, A., Hahn, W. C., Ligon, K. L., Louis, D. N., Brennan, C., et al. (2007). Malignant astrocytic glioma: genetics, biology, and paths to treatment. Genes Dev. 21, 2683-2710.

Gavine, P. R., Mooney, L., Kilgour, E., Thomas, A. P., Al-Kadhimi, K., Beck, S., Rooney, C., Coleman, T., Baker, D., Mellor, M. J., et al. (2012). AZD4547: An Orally Bioavailable, Potent, and Selective Inhibitor of the Fibroblast Growth Factor Receptor Tyrosine Kinase Family. Cancer Res. 72, 2045-2056.

Gerber, D. E., and Minna, J. D. (2010). ALK inhibition for non-small cell lung cancer: from discovery to therapy in record time. Cancer Cell 18, 548-551.

Gordon, D. J., Resio, B., and Pellman, D. (2012). Causes and consequences of aneuploidy in cancer. Nature reviews Genet. 13, 189-203.

Guagnano, V., Furet, P., Spanka, C., Bordas, V., Le Douget, M., Stamm, C., Brueggen, J., Jensen, M. R., Schnell, C., Schmid, H., et al. (2011). Discovery of 3-(2,6-dichloro-3,5-dimethoxy-phenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase. J. Med. Chem. 54, 7066-7083.

Holland, A. J., and Cleveland, D. W. (2009). Boveri revisited: chromosomal instability, aneuploidy and tumorigenesis. Nat. Rev. Mol. Cell. Biol. 10, 478-487.

Hood, F. E., and Royle, S. J. (2011). Pulling it together: The mitotic function of TACC3. Bioarchitecture 1, 105-109.

Lee, J., Kotliarova, S., Kotliarov, Y., Li, A., Su, Q., Donin, N. M., Pastorino, S., Purow, B. W., Christopher, N., Zhang, W., et al. (2006). Tumor stem cells derived from glioblastomas cultured in bFGF and EGF more closely mirror the phenotype and genotype of primary tumors than do serum-cultured cell lines. Cancer Cell 9, 391-403.

Lengauer, C., Kinzler, K. W., and Vogelstein, B. (1997). Genetic instability in colorectal cancers. Nature 386, 623-627.

Lengauer, C., Kinzler, K. W., and Vogelstein, B. (1998). Genetic instabilities in human cancers. Nature 396, 643-649.

Lo, H. W. (2010). EGFR-targeted therapy in malignant glioma: novel aspects and mechanisms of drug resistance. Curr. Mol. Pharmacol. 3, 37-52.

Marumoto, T., Tashiro, A., Friedmann-Morvinski, D., Scadeng, M., Soda, Y., Gage, F. H., and Verma, I. M. (2009). Development of a novel mouse glioma model using lentiviral vectors. Nat. Med. 15, 110-116.

Mitelman, F., Johansson, B., and Mertens, F. (2007). The impact of translocations and gene fusions on cancer causation. Nat. Rev. Cancer 7, 233-245.

Mohammadi, M., Froum, S., Hamby, J. M., Schroeder, M. C., Panek, R. L., Lu, G. H., Eliseenkova, A. V., Green, D., Schlessinger, J., and Hubbard, S. R. (1998). Crystal structure of an angiogenesis inhibitor bound to the FGF receptor tyrosine kinase domain. EMBO J. 17, 5896-5904.

Ohgaki, H., and Kleihues, P. (2005). Population-based studies on incidence, survival rates, and genetic alterations in astrocytic and oligodendroglial gliomas. J. Neuropathol. Exp. Neurol. 64, 479-489.

Peset, I., and Vernos, I. (2008). The TACC proteins: TACC-ling microtubule dynamics and centrosome function. Trends Cell. Biol. 18, 379-388.

Prensner, J. R., and Chinnaiyan, A. M. (2009). Oncogenic gene fusions in epithelial carcinomas. Curr Opin Genet. Dev. 19, 82-91.

Reardon, D. A., Desjardins, A., Vredenburgh, J. J., Gururangan, S., Friedman, A. H., Herndon, J. E., 2nd, Marcello, J., Norfleet, J. A., McLendon, R. E., Sampson, J. H., et al. (2010). Phase 2 trial of erlotinib plus sirolimus in adults with recurrent glioblastoma. J. Neurooncol. 96, 219-230.

Sheltzer, J. M., and Amon, A. (2011). The aneuploidy paradox: costs and benefits of an incorrect karyotype. Trends Genet. 27, 446-453.

Solomon, D. A., Kim, T., Diaz-Martinez, L. A., Fair, J., Elkahloun, A. G., Harris, B. T., Toretsky, J. A., Rosenberg, S. A., Shukla, N., Ladanyi, M., et al. (2011). Mutational inactivation of STAG2 causes aneuploidy in human cancer. Science 333, 1039-1043.

Stephens, P. J., McBride, D. J., Lin, M. L., Varela, I., Pleasance, E. D., Simpson, J. T., Stebbings, L. A., Leroy, C., Edkins, S., Mudie, L. J., et al. (2009). Complex landscapes of somatic rearrangement in human breast cancer genomes. Nature 462, 1005-1010.

Still, I. H., Vince, P., and Cowell, J. K. (1999). The third member of the transforming acidic coiled coil-containing gene family, TACC3, maps in 4p16, close to translocation breakpoints in multiple myeloma, and is upregulated in various cancer cell lines. Genomics 58, 165-170.

Thompson, S. L., Bakhoum, S. F., and Compton, D. A. (2010). Mechanisms of chromosomal instability. Curr. Biol. 20, R285-295.

Tomlins, S. A., Laxman, B., Dhanasekaran, S. M., Helgeson, B. E., Cao, X., Morris, D. S., Menon, A., Jing, X., Cao, Q., Han, B., et al. (2007). Distinct classes of chromosomal rearrangements create oncogenic ETS gene fusions in prostate cancer. Nature 448, 595-599.

Tomlins, S. A., Rhodes, D. R., Perner, S., Dhanasekaran, S. M., Mehra, R., Sun, X. W., Varambally, S., Cao, X., Tchinda, J., Kuefer, R., et al. (2005). Recurrent fusion of TMPRSS2 and ETS transcription factor genes in prostate cancer. Science 310, 644-648.

Turner, N., and Grose, R. (2010). Fibroblast growth factor signalling: from development to cancer. Nat. Rev. Cancer 10, 116-129.

van den Bent, M. J., Brandes, A. A., Rampling, R., Kouwenhoven, M. C., Kros, J. M., Carpentier, A. F., Clement, P. M., Frenay, M., Campone, M., Baurain, J. F., et al. (2009). Randomized phase II trial of erlotinib versus temozolomide or carmustine in recurrent glioblastoma: EORTC brain tumor group study 26034. J. Clin. Oncol. 27, 1268-1274.

Wang, X. S., Prensner, J. R., Chen, G., Cao, Q., Han, B., Dhanasekaran, S. M., Ponnala, R., Cao, X., Varambally, S., Thomas, D. G., et al. (2009). An integrative approach to reveal driver gene fusions from paired-end sequencing data in cancer. Nat. Biotechnol. 27, 1005-1011.

Weaver, B. A., and Cleveland, D. W. (2009). The role of aneuploidy in promoting and suppressing tumors. J. Cell. Biol. 185, 935-937.

Wesche, J., Haglund, K., and Haugsten, E. M. (2011). Fibroblast growth factors and their receptors in cancer. Biochem. J. 437, 199-213.

Yan, H., Parsons, D. W., Jin, G., McLendon, R., Rasheed, B. A., Yuan, W., Kos, I., Batinic-Haberle, I., Jones, S., Riggins, G. J., et al. (2009). IDH1 and IDH2 mutations in gliomas. New Engl. J. Med. 360, 765-773.

Zhao, X., D, D. A., Lim, W. K., Brahmachary, M., Carro, M. S., Ludwig, T., Cardo, C. C., Guillemot, F., Aldape, K., Califano, A., et al. (2009). The N-Myc-DLL3 cascade is suppressed by the ubiquitin ligase Huwel to inhibit proliferation and promote neurogenesis in the developing brain. Dev. Cell 17, 210-221.

Zhao, X., Heng, J. I., Guardavaccaro, D., Jiang, R., Pagano, M., Guillemot, F., Iavarone, A., and Lasorella, A. (2008). The HECT-domain ubiquitin ligase Huwe 1 controls neural differentiation and proliferation by destabilizing the N-Myc oncoprotein. Nat Cell Biol 10, 643-653.

(2008). Comprehensive genomic characterization defines human glioblastoma genes and core pathways. Nature 455, 1061-1068.

Iglewicz, B., and Hoaglin, D. C. (1993). How to detect and handle outliers (Milwaukee, Wis.: ASQC).

Li, H., and Durbin, R. (2009). Fast and accurate short read alignment with Burrows-Wheeler transform. Bioinformatics 25, 1754-1760.

Morganella, S., Cerulo, L., Viglietto, G., and Ceccarelli, M. (2010). VEGA: variational segmentation for copy number detection. Bioinformatics 26, 3020-3027.

Seal, R. L., Gordon, S. M., Lush, M. J., Wright, M. W., and Bruford, E. A. (2011). genenames.org: the HGNC resources in 2011. Nucleic Acids Res 39, D514-519.

Tomlins, S. A., Rhodes, D. R., Perner, S., Dhanasekaran, S. M., Mehra, R., Sun, X. W., Varambally, S., Cao, X., Tchinda, J., Kuefer, R., et al. (2005). Recurrent fusion of TMPRSS2 and ETS transcription factor genes in prostate cancer. Science 310, 644-648.

Vilella, A. J., Severin, J., Ureta-Vidal, A., Heng, L., Durbin, R., and Birney, E. (2009). EnsemblCompara GeneTrees: Complete, duplication-aware phylogenetic trees in vertebrates. Genome Res. 19, 327-335.

Wang, K., Li, M., Hadley, D., Liu, R., Glessner, J., Grant, S. F., Hakonarson, H., and Bucan, M. (2007). PennCNV: an integrated hidden Markov model designed for high-resolution copy number variation detection in whole-genome SNP genotyping data. Genome Res. 17, 1665-1674.

Wang, X. S., Prensner, J. R., Chen, G., Cao, Q., Han, B., Dhanasekaran, S. M., Ponnala, R., Cao, X., Varambally, S., Thomas, D. G., et al. (2009). An integrative approach to reveal driver gene fusions from paired-end sequencing data in cancer. Nat. Biotechnol. 27, 1005-1011.

Example 2—Fusions in GBM

TABLE 8

Soft agar colony assay

| Cell line | Vector | FSFR3 | TACC3 | F1-T1 Fusion | F3-T3 Fusion | F3-T3-K508M Fusion |
|---|---|---|---|---|---|---|
| Rat1 | 0 | 0 | 0 | 225.3 ± 10.0 | 199.7 ± 8.0 | 0 |
| Balb 3T3 | 0 | 0 | 0 | n.d. | 45.5 ± 8.9 | n.d. | n.d.: not done

TABLE 9

Subcutaneous tumor xenografts

| Cell line | Vector | FGFR3 | TACC3 | F1-T1 Fusion | F3-T3 Fusion | F3-T3-K508M Fusion |
|---|---|---|---|---|---|---|
| Rat1 | 0/5 | 0/5 | 0/5 | n.d | 5/5 | n.d |
| Ink4Arf-/- Astrocytes | 0/9 | 0/5 | 0/5 | 8/8 | 12/12 | 0/8 | n.d.: not done

TABLE 10

Analysis of chromosomal number in Rat1 cells

| Cell line | Number of cells counted | Percent aneuploidy | Range | Mean number | Average variation from mean number | p-value |
|---|---|---|---|---|---|---|
| Rat1A Vector | 100 | 27 | 35-43 | 41.2 | 1.2 | n.s. |
| Rat1A FGFR3 | 100 | 33 | 35-44 | 42.1 | 1.3 | n.s. |
| Rat1A TACC3 | 100 | 41 | 34-46 | 40.7 | 1.1 | <0.0001 |
| Rat1A FSFR3-TACC3 | 100 | 69 | 35-73 | 43.0 | 3.1 | |

TABLE 11

Analysis of chromosomal number in human astrocytes

| Cell line | Number of cells counted | Percent aneuploidy | Range | Mean number | Average variation from mean number | p-value |
|---|---|---|---|---|---|---|
| Human Astrocytes | 100 | 8 | 42-46 | 45.65 | 0.28 | p = <0.001 |
| Human Astrocytes FGFR3-TACC3 | 100 | 42 | 28-48 | 42.24 | 3.33 | |

Example 3—Fusions in Other Cancers

Figures 1, 31:
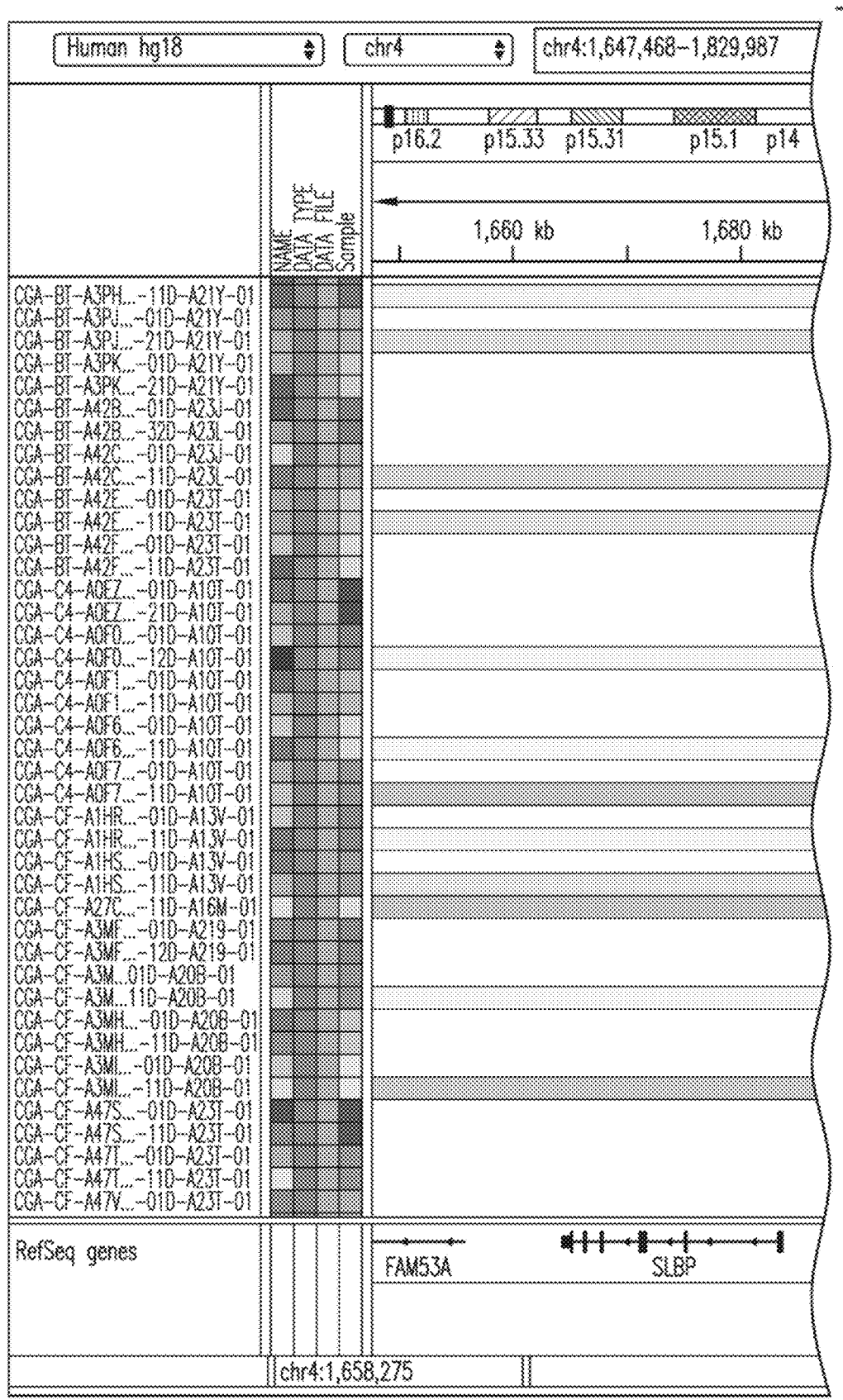
Figures 2, 31:
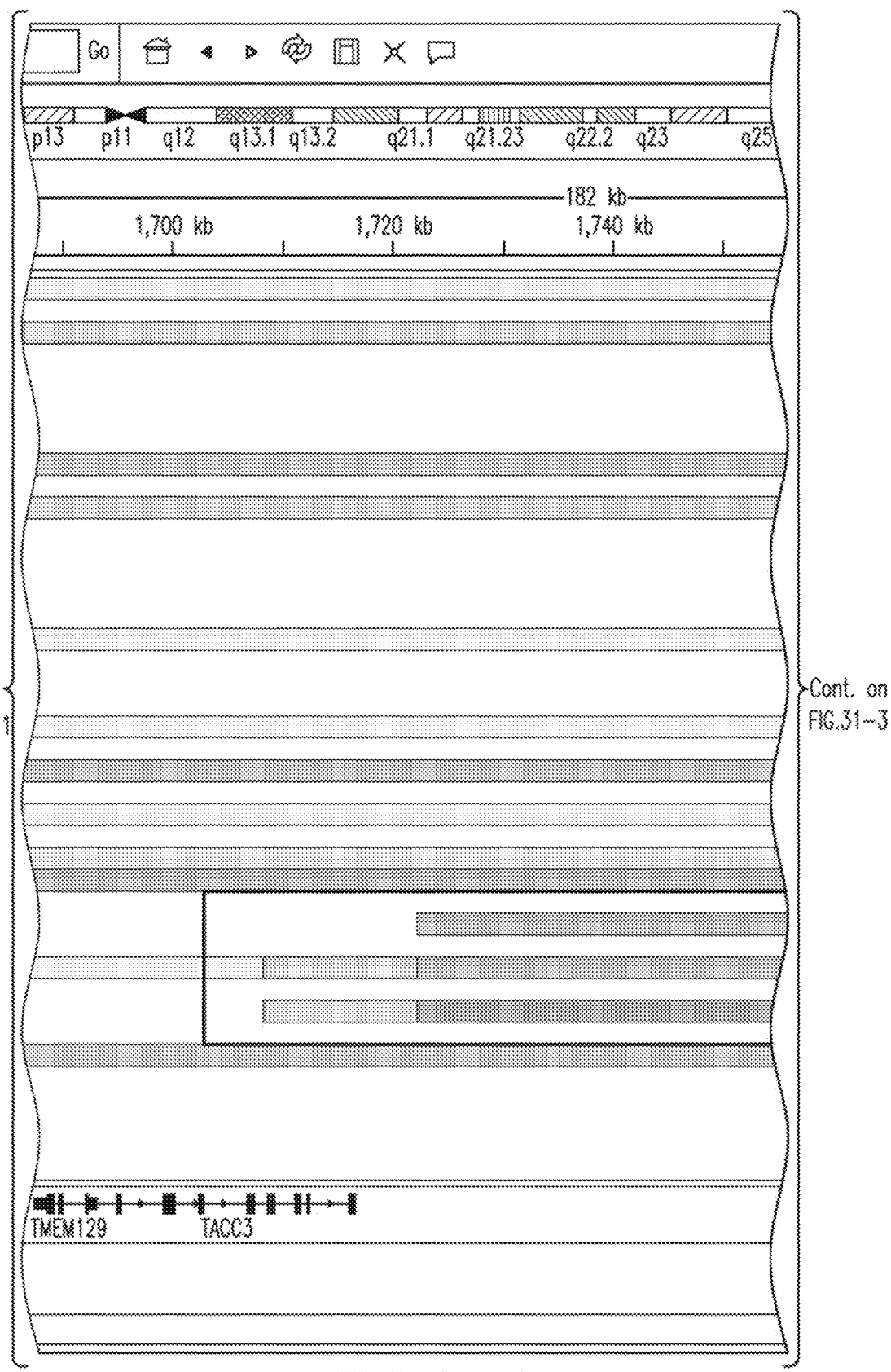
Figures 3, 31:
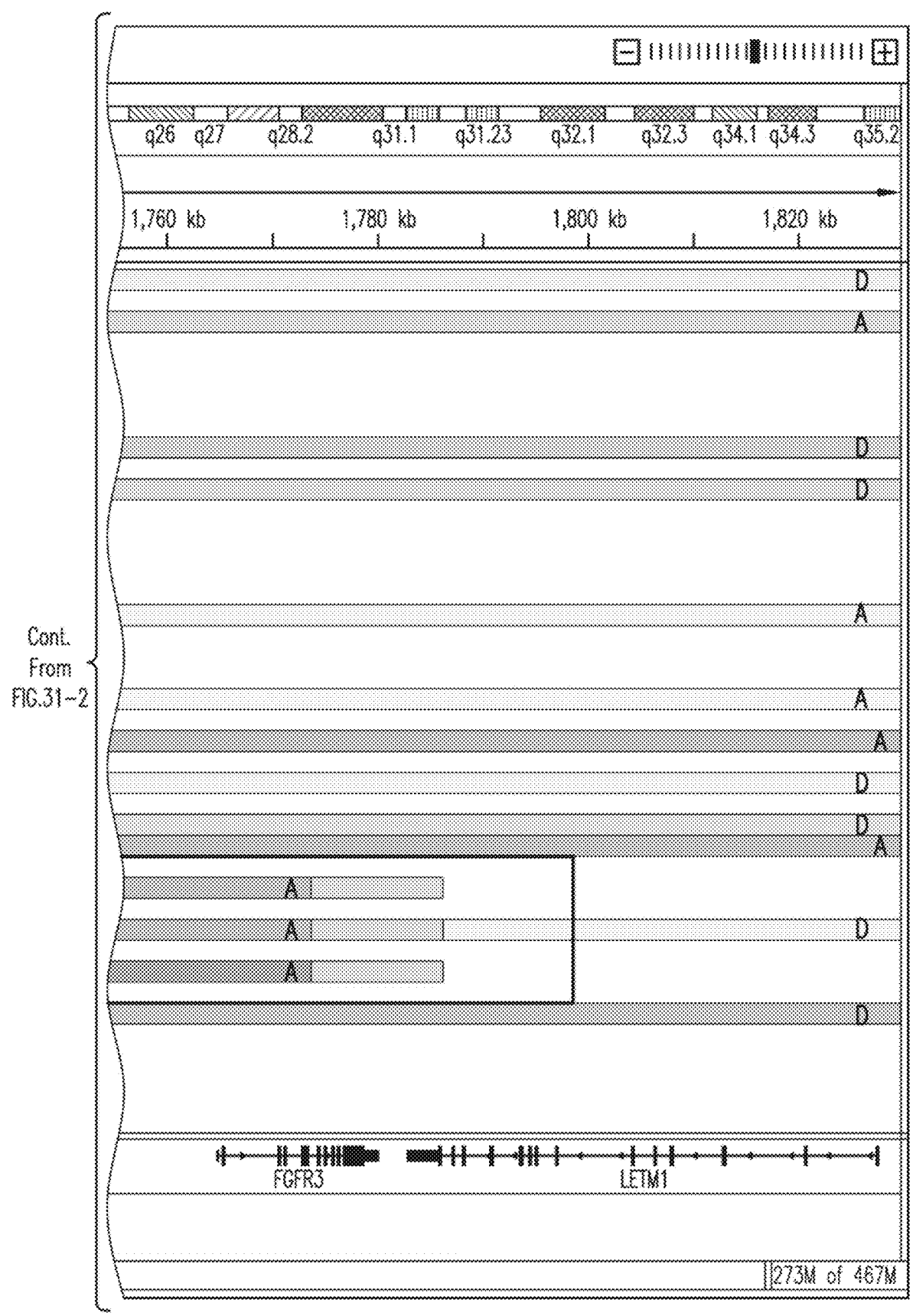
Figures 1, 32:
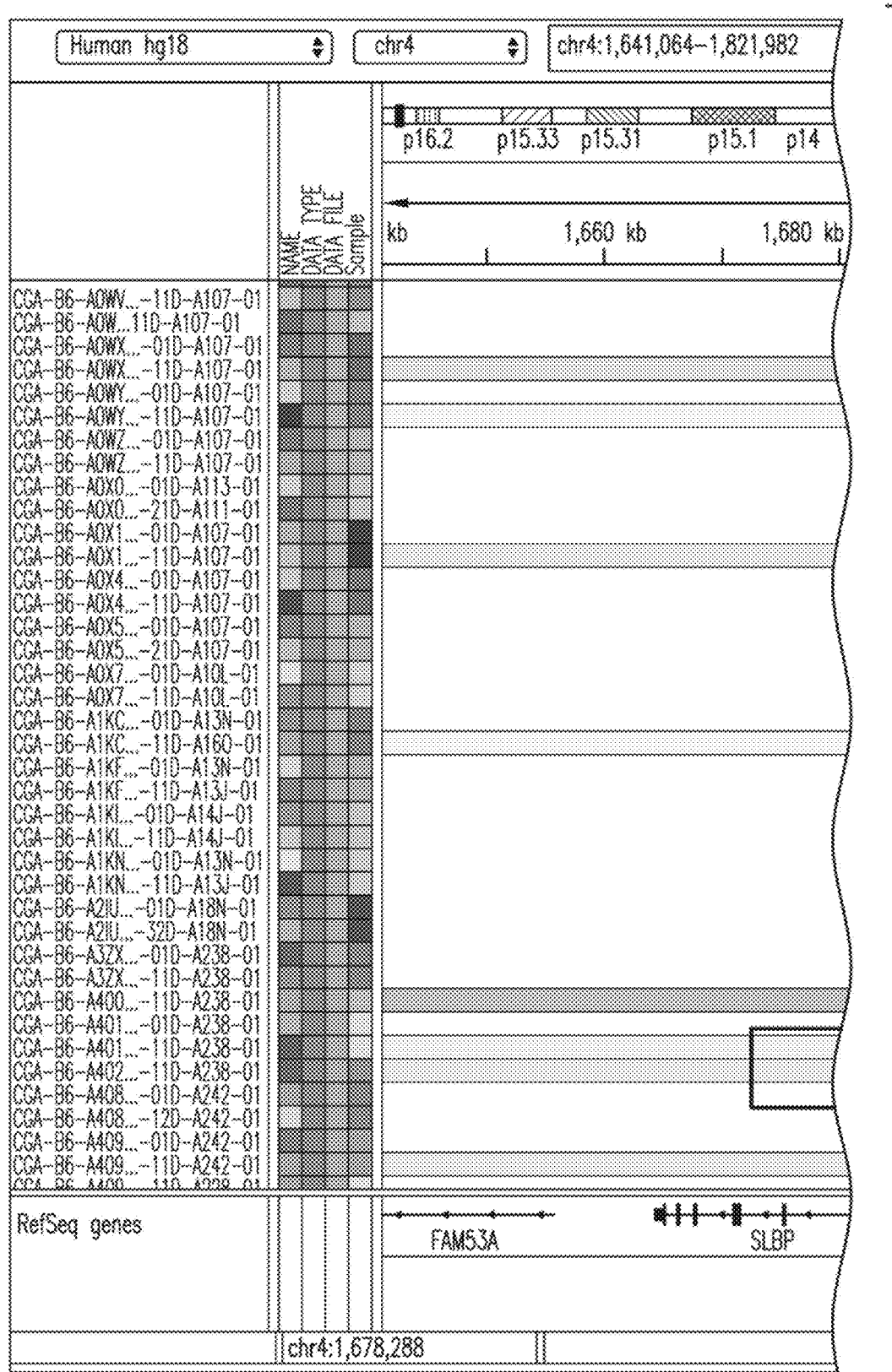
Figures 2, 32:
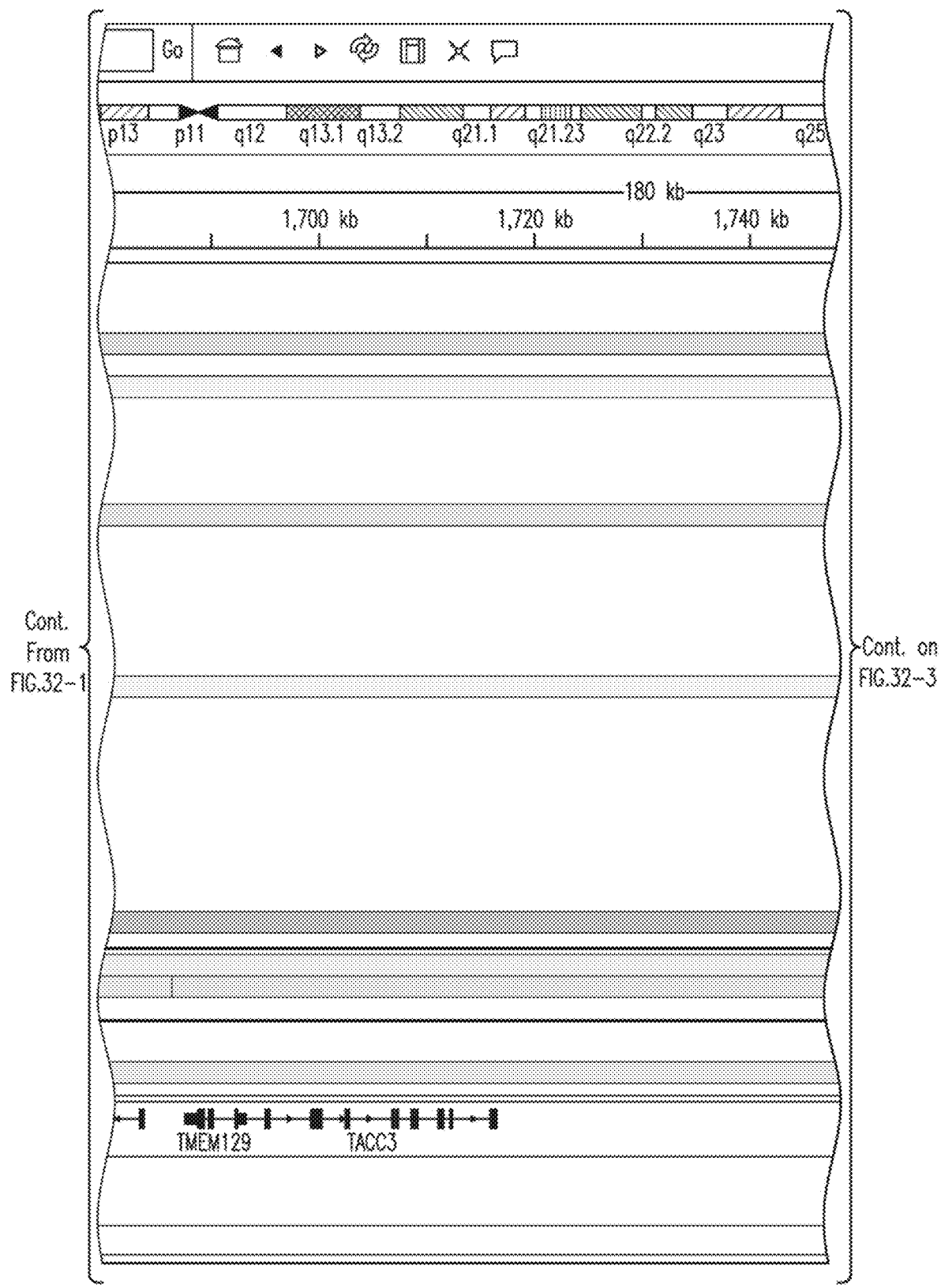
Figures 3, 32:
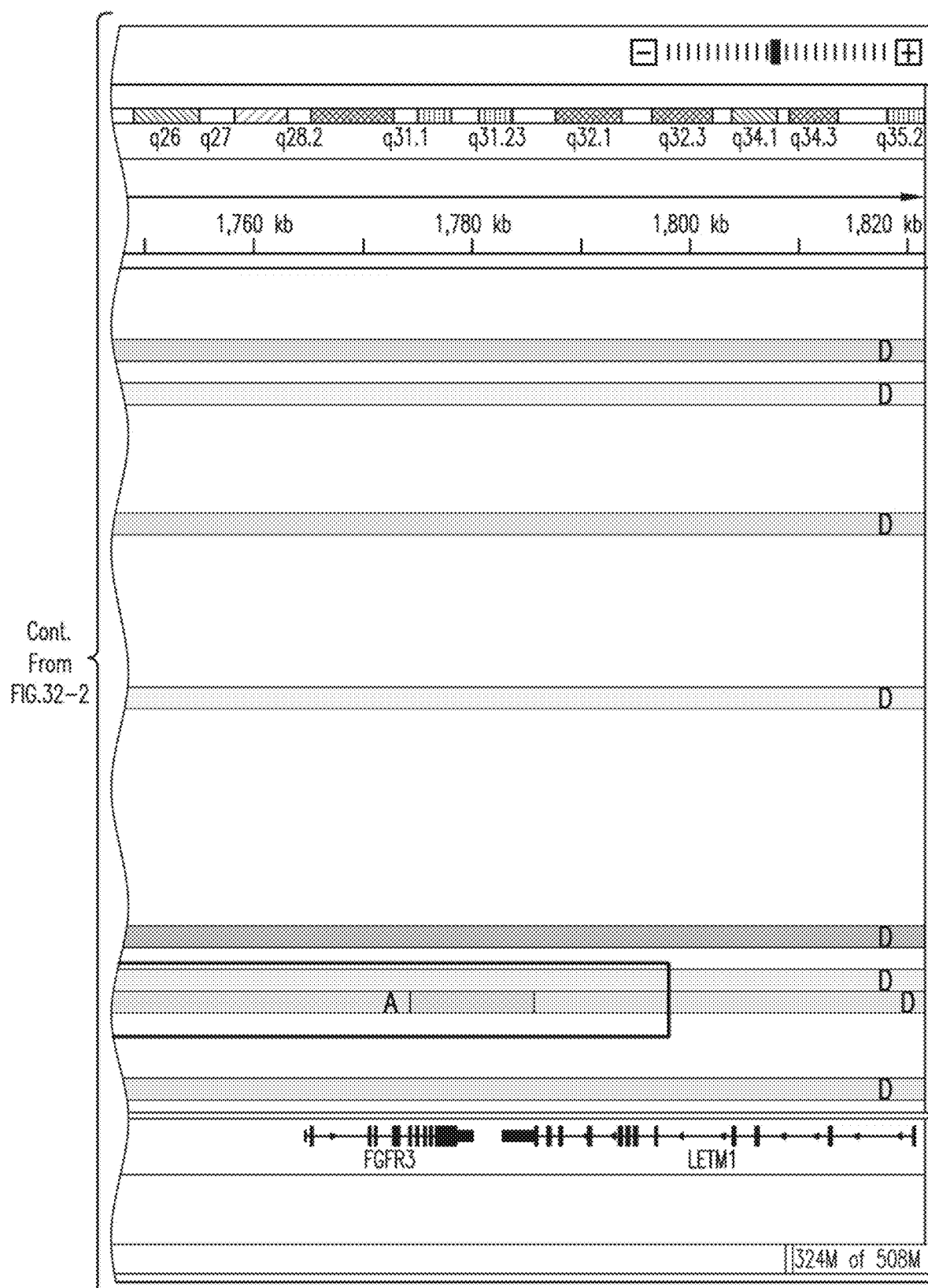
Figures 1, 33:
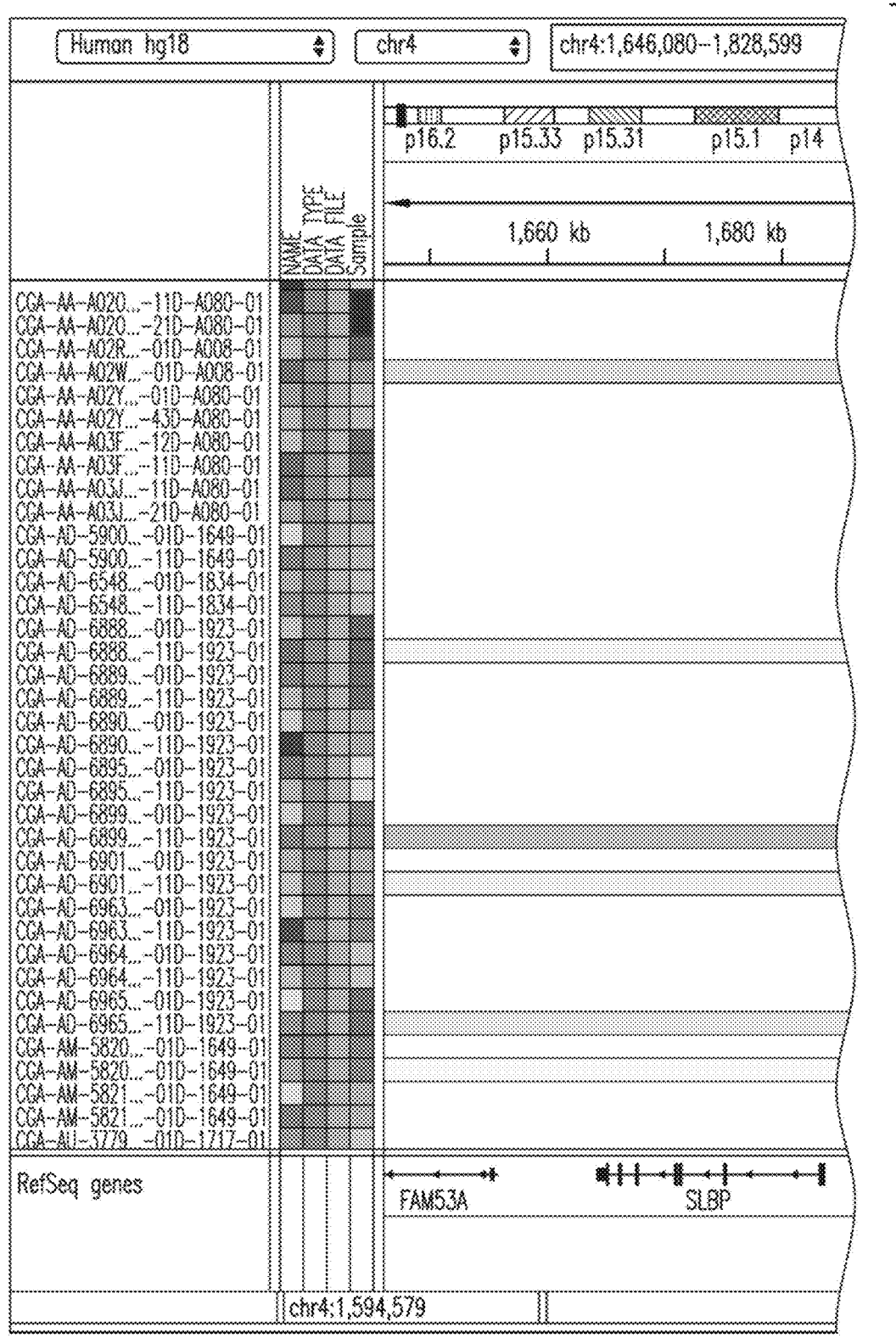
Figures 2, 33:
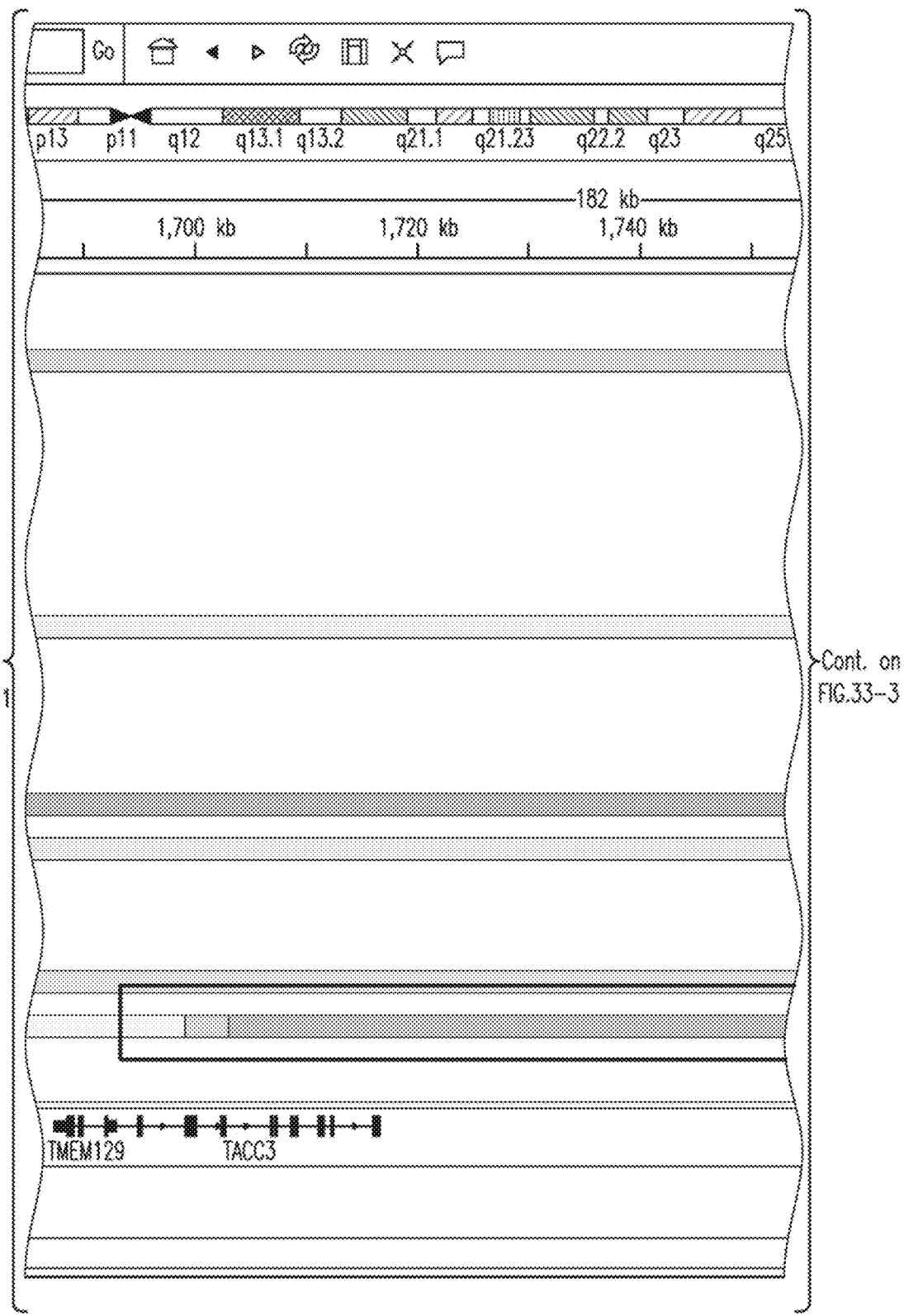
Figures 3, 33:
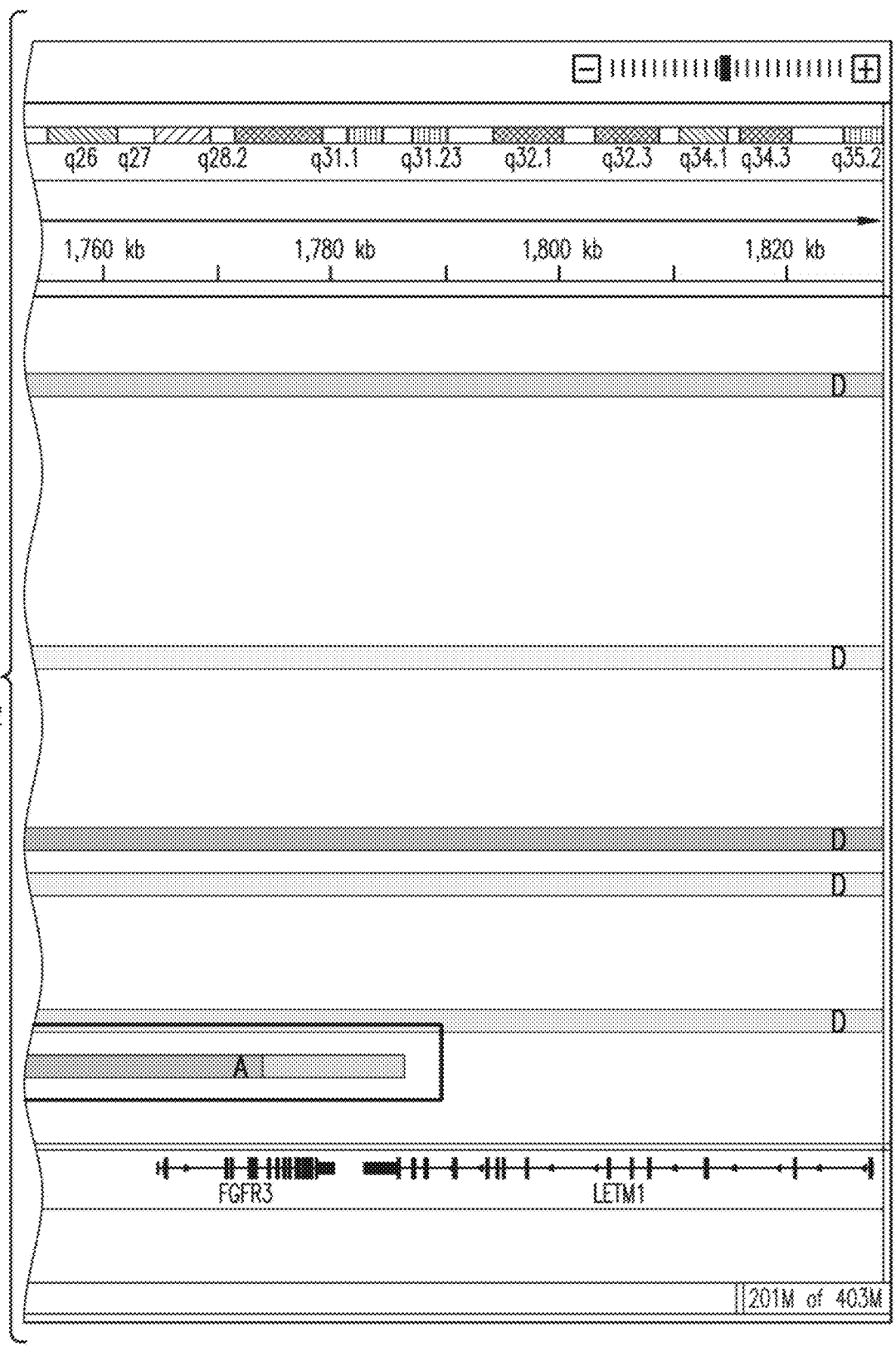
Figures 1, 34:
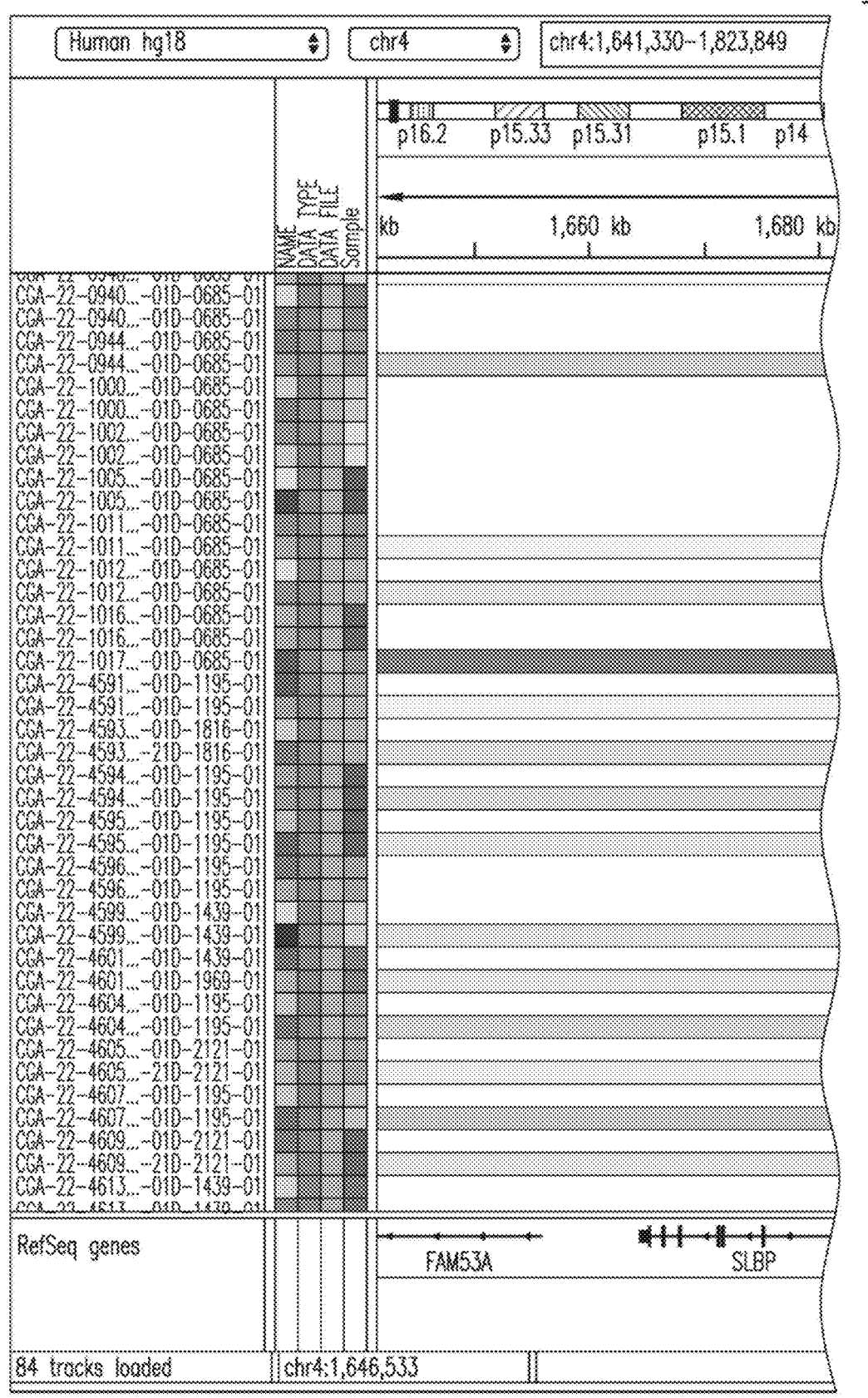
Figures 2, 34:
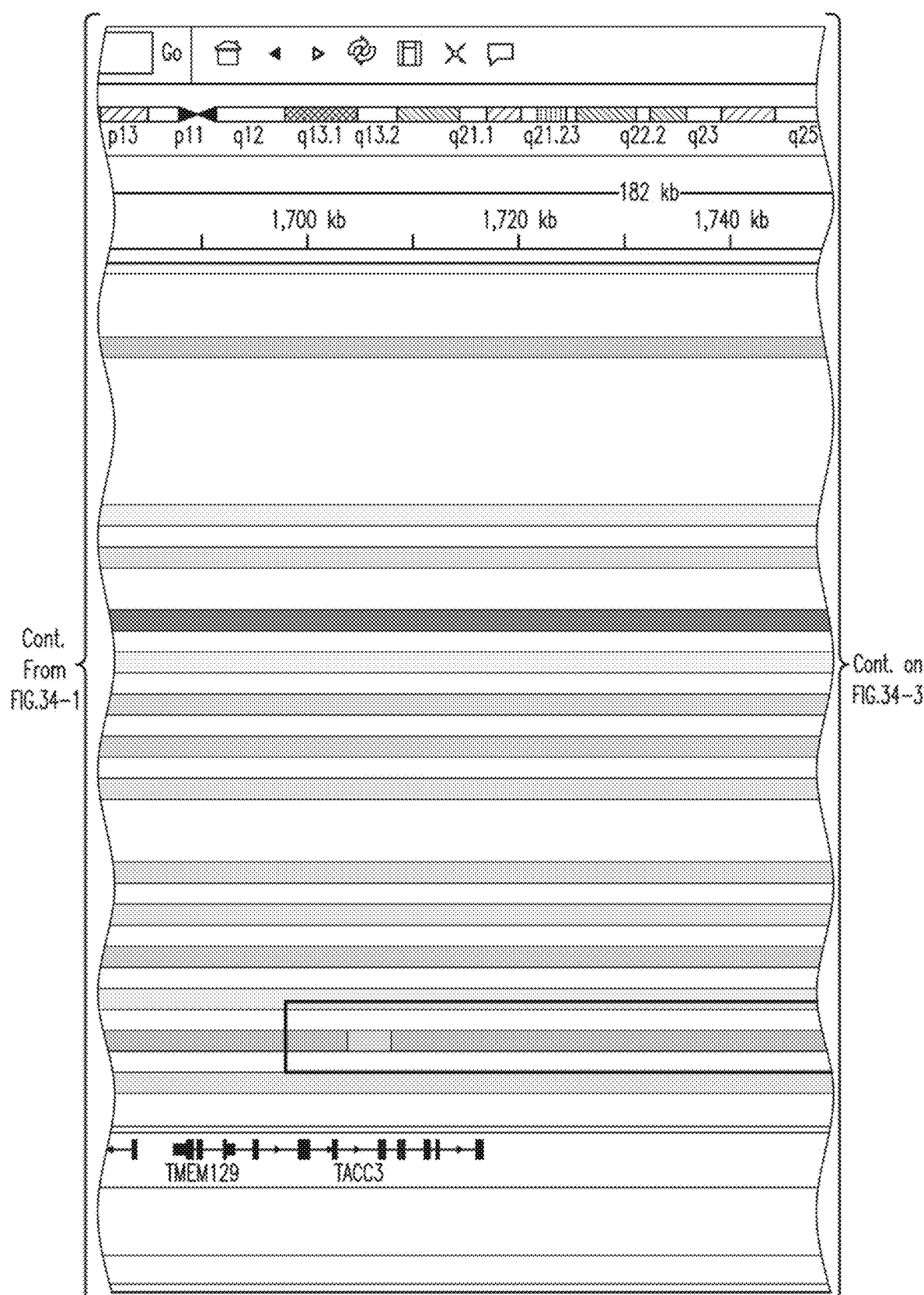
Figures 3, 34:
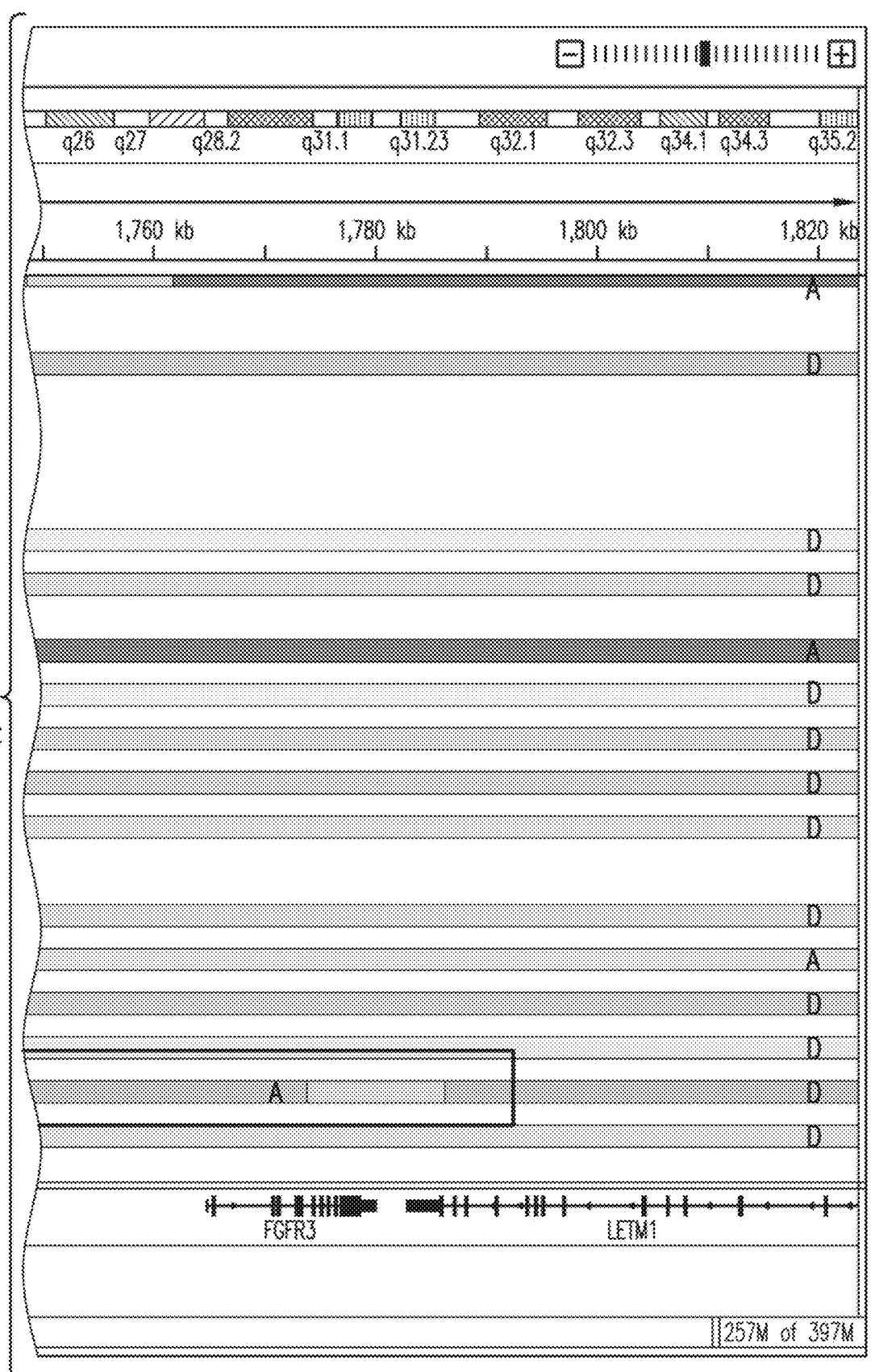
Figures 1, 35:
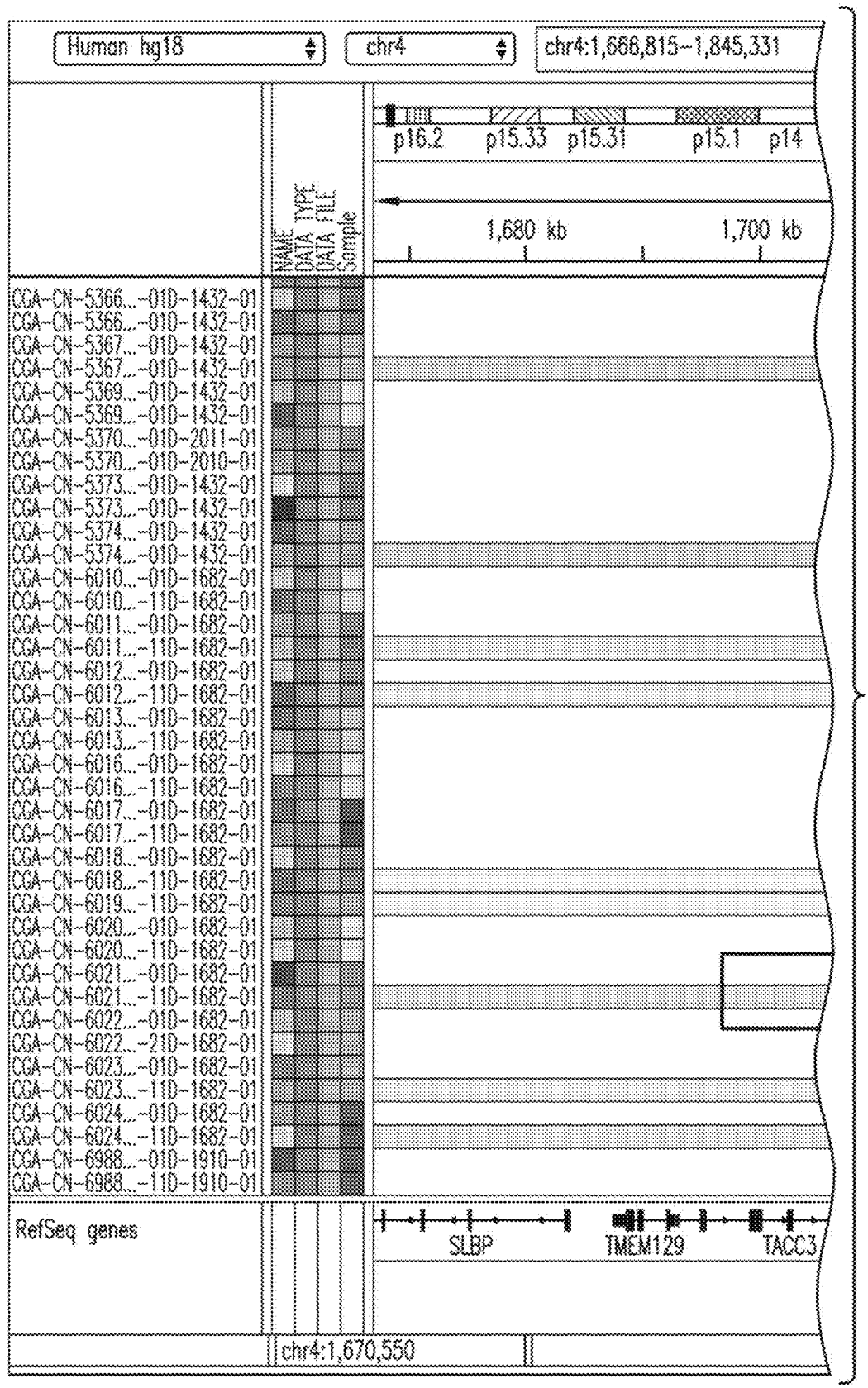
Figures 2, 35:
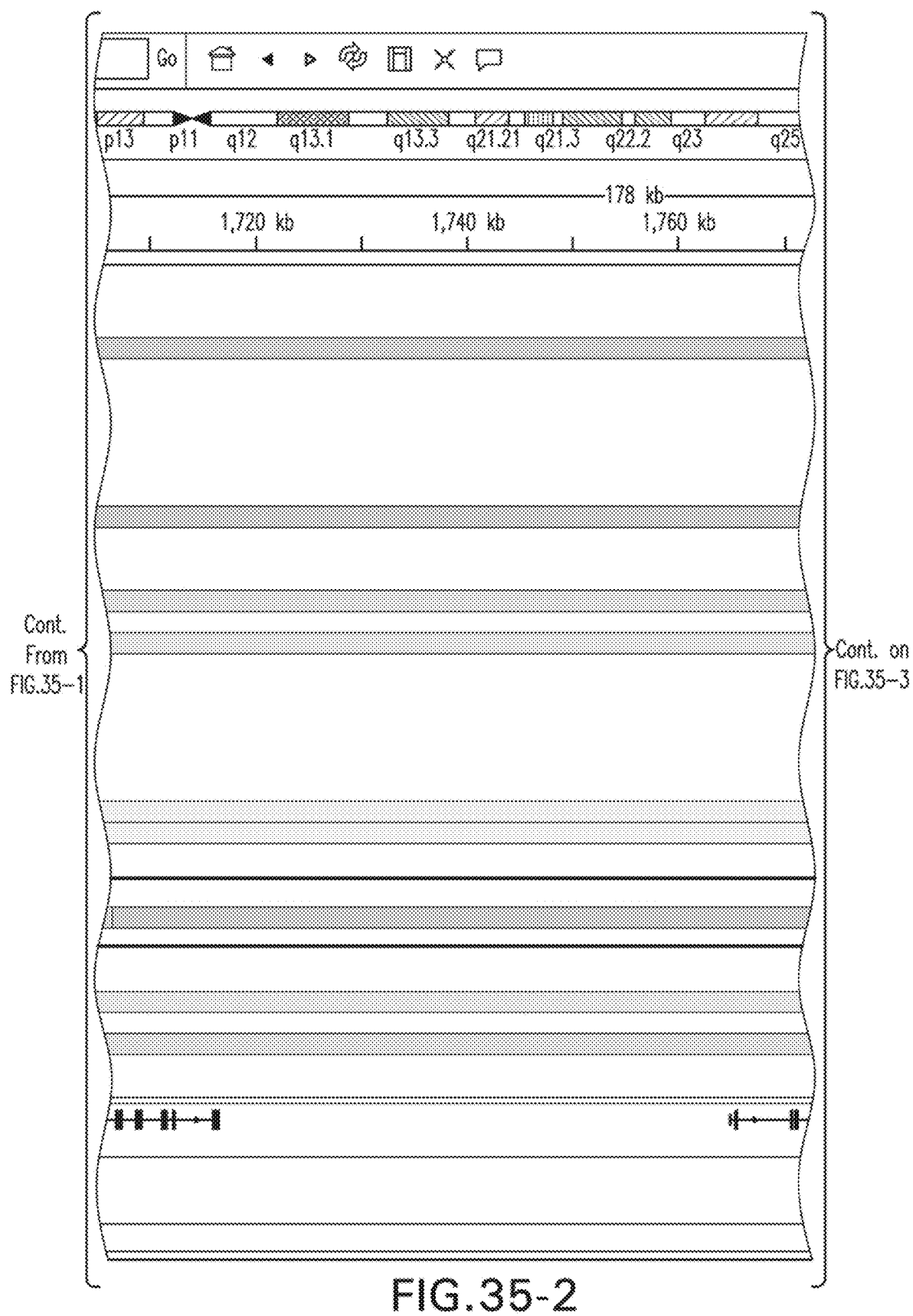
Figures 3, 35:
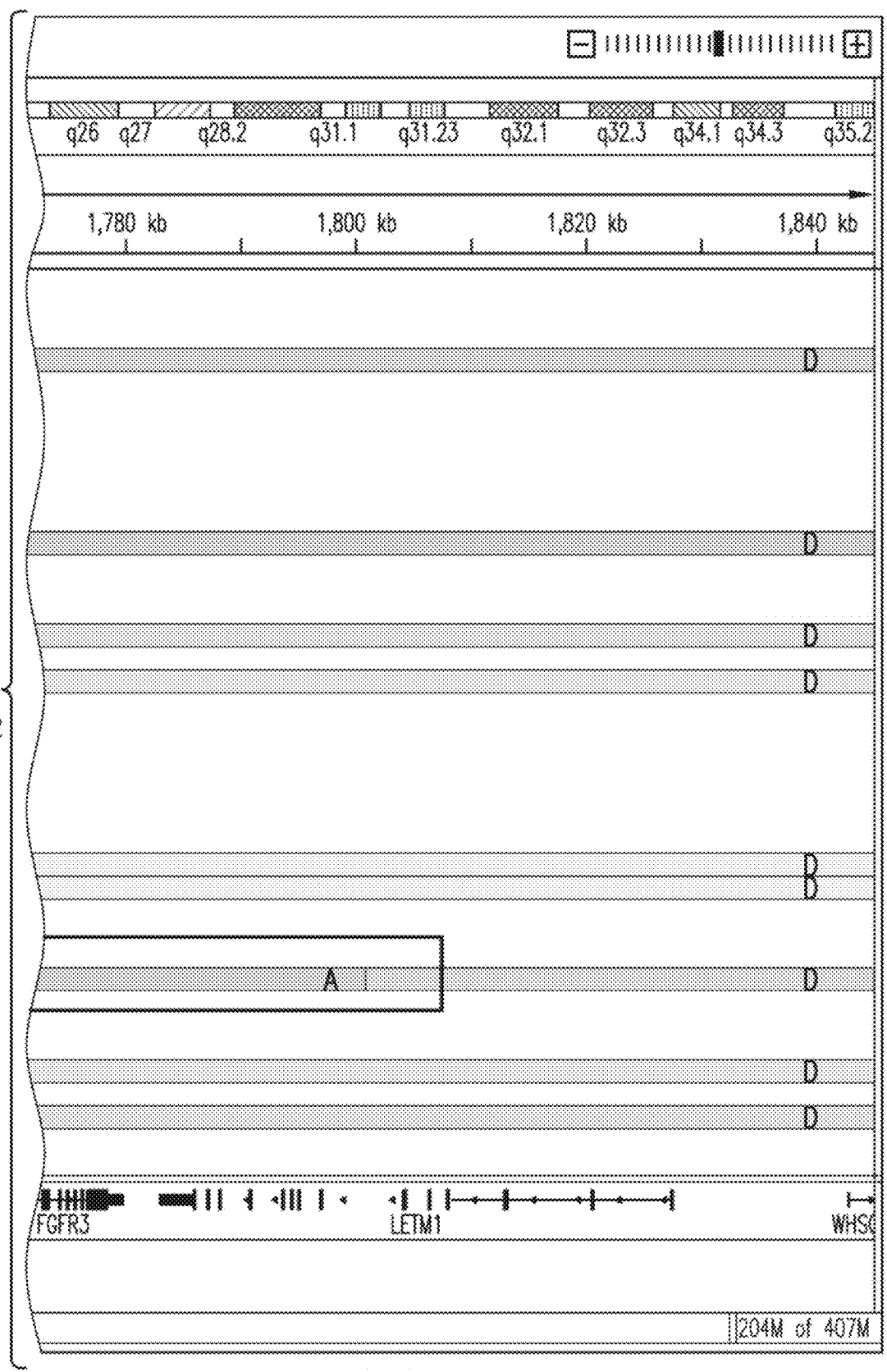

The inventors previously reported in Example 1 that 3.1% of human glioblastoma harbor FGFR3-TACC3 and FGFR1-TACC1 gene fusions. Tumors harboring FGFR3-TACC3 gene fusions are identified by the presence of highly specific focal micro-amplification events of the rearranged portions of the FGFR3 and TACC3 genes (See FIG. 2E). Therefore, these micro-amplification events can be used as distinctive marks for the presence of FGFR3-TACC3 gene fusions. It was asked whether other types of human tumors also harbor FGFR3-TACC3 gene fusions from the analysis of Copy Number Variations (CNVs) of SNP arrays generated from the Atlas-TCGA project. This analysis was performed using segmented CNVs data visualized using the Integrated Genomic Viewers software. The analysis revealed that the following tumors, shown in the FIGS. 31-35, display focal micro-amplification events of FGFR3 and TACC3 that indicate the presence of FGFR3-TACC3 gene fusions (in FIGS. 31-35, red indicates amplification (A), blue indicates deletion (D); FIG. 31: Bladder Urothelial Carcinoma; FIG. 32: Breast Carcinoma; FIG. 33: Colorectal Carcinoma; FIG. 34: Lung Squamous Cell Carcinoma; FIG. 35: Head and Neck Squamous Cell Carcinoma).

Taken together, these data indicate that the same FGFR3-TACC3 gene fusions reported for the first time in Glioblastoma also occur in several other types of human tumors. Therefore, as for Glioblastoma and other epithelial cancers (such as the human tumors discussed herein), the identification of FGFR-TACC gene fusions also provides a new diagnostic and therapeutic target for treatment with drugs that inhibit FGFR-TACC gene fusions.

Example 4—Detection, Characterization and Inhibition of FGFR-TACC Fusions in IDH Wild Type Glioma Translational Relevance Described herein is an unbiased screening assay for FGFR-TACC fusions in glioma that overcomes the great variability of variants that are generated by FGFR-TACC chromosomal translocation in human cancer. FGFR-TACC fusions occur in grade II and III glioma harboring wildtype IDH1 with frequency similar to glioblastoma (GBM), therefore providing a clue to the aggressive clinical behavior of this glioma subtype. The molecular characterization of fusion-positive glioma revealed that FGFR-TACC is mutually exclusive with EGFR amplification but co-occurs with CDK4 amplification. FGFR-TACC-positive glioma displays strikingly uniform and strong expression of the fusion protein at the single cell level. Preclinical experiments with FGFR3-TACC3-positive glioma cells treated with the FGFR inhibitor JNJ-42756493 showed strong antitumor effects and treatment of two patients with recurrent GBM harboring FGFR3-TACC3 resulted in clinical improvement and radiological tumor reduction. These findings validate the treatment with FGFR inhibitors of glioma patients harboring FGFR-TACC chromosomal translocations.

Abstract

Purpose. Oncogenic fusions consisting of FGFR and TACC are present in a subgroup of glioblastoma (GBM) and other human cancers and have been proposed as new therapeutic targets. Frequency, molecular features of FGFR-TACC fusions, and the therapeutic efficacy of inhibiting FGFR kinase in GBM and grade-II-III glioma were analyzed.

Experimental Design. Overall, 795 gliomas (584 GBM, 85 grade-II-III with wild-type and 126 with IDH1/2 mutation) were screened for FGFR-TACC breakpoints and associated molecular profile. Expression of the FGFR3 and TACC3 components of the fusions were also analyzed. The effects of the specific FGFR inhibitor JNJ-42756493 for FGFR3-TACC3-positive glioma were determined in preclinical experiments. Two patients with advanced FGFR3-TACC3-positive GBM received JNJ-42756493 and were assessed for therapeutic response.

Results. Three of 85 IDH1/2 wild type (3.5%) but none of 126 IDH1/2 mutant grade-II-III glioma harbored FGFR3-TACC3 fusions. FGFR-TACC rearrangements were present in 17 of 584 GBM (2.9%). FGFR3-TACC3 fusions were associated with strong and homogeneous FGFR3 immunostaining. They are mutually exclusive with IDH1/2 mutations and EGFR amplification whereas co-occur with CDK4 amplification. JNJ-42756493 inhibited growth of glioma cells harboring FGFR3-TACC3 in vitro and in vivo. The two patients with FGFR3-TACC3 rearrangements who received JNJ-42756493 manifested clinical improvement with stable disease and minor response, respectively.

Conclusions. RT-PCR-sequencing is a sensitive and specific method to identify FGFR-TACC-positive patients. FGFR3-TACC3 fusions are associated with uniform intratumor expression of the fusion protein. The clinical response observed in the FGFR3-TACC3-positive patients treated with a FGFR inhibitor supports clinical studies of FGFR inhibition in FGFR-TACC-positive patients.

Introduction

The history of successful targeted therapy of cancer largely coincides with the inactivation of recurrent, oncogenic and addicting gene fusions in hematological malignancies and recently in some types of epithelial cancer (1, 2). Glioblastoma multiforme (GBM) is among the most lethal forms of human cancer and targeted therapies against common genetic alterations in GBM have not changed the dismal outcome of the disease (3, 4). Underlying biological features including infiltrative growth behavior, intratumoral heterogeneity, and adaptive resistance mechanisms coupled with the unique challenges of intracranial location present significant problems in its effective management. Despite surgery and chemo-radiotherapy, most patients rapidly recur and no effective treatment options are available at that stage. Beside GBM, which features the highest grade of malignancy among glioma (grade IV), lower grade glioma which include grade II and grade III are a heterogeneous group of tumors in which specific molecular features are associated with divergent clinical outcome. The majority of grade II-III glioma (but only a small subgroup of GBM) harbor mutations in IDH genes (IDH1 or IDH2), which confer a more favorable clinical outcome. Conversely, the absence of IDH mutations is associated with the worst prognosis (5).

Described herein is the identification of FGFR-TACC gene fusions (mostly FGFR3-TACC3, and rarely FGFR1-TACC1) as the first example of highly oncogenic and recurrent gene fusions in GBM. The FGFR-TACC fusions that have been identified so far include the Tyrosine Kinase (TK) domain of FGFR and the coiled-coil domain of TACC proteins, both necessary for the oncogenic function of FGFR-TACC fusions. Tumor dependency on FGFR-TACC fusions was also tested in preclinical mouse models of FGFR-TACC glioma and observed marked anti-tumor effects by FGFR inhibition (6). FGFR3-TACC3 fusions have been identified in pediatric and adult glioma, bladder carcinoma, squamous lung carcinoma and head and neck carcinoma, thus establishing FGFR-TACC fusions as one of the chromosomal translocation most frequently found across multiple types of human cancers (6-15).

From a mechanistic standpoint, the unexpected capacity of FGFR-TACC fusions to trigger aberrant chromosome segregation during mitosis, thus initiating chromosome instability (CIN) and aneuploidy, two hallmarks of cancer, is described herein. However, the full repertoire of the structural variants of FGFR-TACC fusions occurring in GBM and lower grade glioma is not completely understood. Furthermore, it remains unknown whether FGFR-TACC fusions mark distinct grades of glioma and GBM subtypes.

To date eight variants of the FGFR3-TACC3 fusion have been reported that mostly differ for the breakpoint in the TACC3 gene (6-15). Because of the close proximity of FGFR3 and TACC3 (the two genes map at a distance of 70 Kb on chromosome 4p16.3), detection of FGFR3-TACC3 rearrangements by FISH is not a feasible option with the currently available methods. Here a screening method for FGFR-TACC fusions is reported that includes a RT-PCR assay designed to identify the known and novel FGFR3-TACC3 fusion transcripts, followed by confirmation of the inframe breakpoint by Sanger sequencing. Using this assay, a dataset of 584 GBM and 211 grade II and grade III gliomas has been analyzed.

A crucial question with fundamental clinical relevance for any novel candidate target mutation is the frequency of the alteration in the cancer cell population, thus discriminating between a clonal or sub-clonal origin of the mutation. In fact, GBM is characterized by a formidable degree of subclonal heterogeneity, whereby neighboring cells display amplification and expression of different Receptor Tyrosine Kinase (RTK)-coding genes (16-19). This notion poses major therapeutic challenges for targeting any individual RTK will result, at best, in the eradication of a limited tumor sub-clone. Described herein, it was determined that brain tumors harboring FGFR-TACC fusions manifest strong and homogeneous intra-tumor expression of the FGFR3 and TACC3 component invariably included in the fusion protein, when analyzed by immunostaining. A significant clinical benefit following treatment with a specific inhibitor of FGFR-TK is reported in two GBM patients who harbored FGFR3-TACC3 rearrangement.

Materials and Methods

Patients and tissue samples. This example includes a cohort of 746 untreated patients with histologic diagnosis of glioma from 5 institutions. Forty-nine recurrent gliomas from Pitie-Salpetriere Hospital and one recurrent glioma from the University of Calgary were also included. A summary of the patient cohort is provided in Table 12.

TABLE 12

Frequency of FGFR3-TACC3 Fusions in GBM and Grade II-III glioma. Distribution of the FGFR3-TACC3 fusions in GBM (upper panel) and lower grade glioma (lower panel) samples stratified according to the Institution of origin. The table reports number of cases analyzed, number of tumors harboring FGFR3-TACC3 fusion transcripts, and results of FGFR3 immunostaining. Lower grade glioma samples are further classified according to IDH status (IDH1 and IDH2). The respective frequency of FGFR3-TACC3 in GBM, Glioma grade II-III IDH wild type (wt), and IDH mutant (Mut) glioma is reported in parentheses.

| Tumor Sample Source | No of cases (GBM) | No of detected fusions | Immunostaining FGFR3 positive/Sample analyzed |
|---|---|---|---|
| Pitié-Salpêtrière Hospital | 380 | 9 | 9/9 |
| Besta Neurological Institute | 85 | 5 | 2/2 |
| University of Calgary | 60 + 1R[§] | 2 + 1R[§] | 1/1 + 1/1 1R[§] |
| Montreal Neurological Institute | 51 | 1 | — |
| University of British Columbia | 8 | 0 | — |
| Total | 584(100%)[£] | 17(2.9%) | |

| Tumor Sample Source | IDH Status | No of cases (Grade II-III) | No of detected fusions | Immunostaining FGFR3 positive/Sample analyzed |
|---|---|---|---|---|
| Pitié-Salpêtrière Hospital | IDH wt | 85* (100%) | 3 (3.5%) | 3/3 |
| | IDH1/IDH2 Mut | 126 (100%) | 0 (0%) | 0 |

R[§], Recurrent GBM.
[£]Recurrent GBM from the University of Calgary Dataset is not included in the total count of GBM.
*25 cases out of 85 are unknown for IDH2 status.

Tumor specimens, blood samples and clinico-pathological information were collected with informed consent and relevant ethical board approval in accordance with the tenets of the Declaration of Helsinki. For the samples from the Pitie-Salpetriere Hospital, clinical data and follow-up are available in the neuro-oncology database (Onconeurotek, GH Pitié-Salpêtrière, Paris).

Two recurrent GBM patients harboring FGFR3-TACC3 were enrolled in the dose escalation part of JNJ-42756493 trial at the Gustave Roussy Institute.

Identification of fusion transcripts and analysis of genomic breakpoints. Total RNA was extracted from frozen tissues using Trizol (Invitrogen) according to manufacturer instructions. Two to three hundred nanograms of total RNA were retro-transcribed with the Maxima First Strand cDNA Synthesis Kit (Thermo Scientific) or SuperScript II (Invitrogen). RT-PCR was performed using AccuPrime Taq DNA Polymerase (Invitrogen). Primer pairs used for the FGFR3-TACC3 fusions screening were: FGFR3ex12-FW: 5'-CGTGAAGATGCTGAAAGACGATG-3 (SEQ ID NO: 495) and TACC3ex14-RV: 5'-AAACGCTTGAAGAGGTCGGAG-3 (SEQ ID NO: 496); amplification conditions were 94° C.-3 min, (94° C.-30 sec/61° C.-30 sec/68° C.-1 min 40 sec) for 35 cycles, 68° C.-7 min. FGFR1-TACC1 fusions were amplified with FGFR1ex16-FW: 5'-TGCCTGTGGAG-GAACTTTTCA-3' (SEQ ID NO: 497) and TACC1ex13-RV: 5'-CCCAAACTCAGCAGCCTAAG-3' (SEQ ID NO: 498) primers (94° C.-30 sec/60° C.-30 sec/68° C.-1 min 40 sec for 35 cycles). PCR products were subjected to Sanger sequencing.

FGFR3-TACC3 genomic breakpoints were analyzed in 6 FGFR3-TACC3 positive samples, 5 of which from the Pitié-Salpêtrière Hospital and 1 from Montreal Neurological Institute. Three additional samples (MB-22, TCGA 27-1835 and TCGA 06-6390) available from the previous study (6) were also included in the analysis. Fifty nanograms of genomic DNA were used in the PCR reaction, performed with Accuprime Taq Polymerase (Invitrogen) and PCR products were Sanger sequenced. Primers used in genomic PCR were designed according to the breakpoint sequence in the mRNA; the list of primers used are: FGFR3ex17-FW 5'-TGGACCGTGTCCTTACCGT-3' (SEQ ID NO: 499) (PCR Samples 3048, 4373, 4867, 4451, MB-22, OPK-14, 06-6390, 27-1835 and Sequencing samples 3048, 4373, 4867, 4451, MB-22, OPK14, 06-6390, 27-1835); FGFR3ex16-FW 5'-GGTCCTTTGGGGTCCTGCT-3' (SEQ ID NO: 500) (PCR and Sequencing Sample 3808); TACC3ex6-RV 5'-CCTCTTTCAGCTCCAAGGCA-3' (SEQ ID NO: 501) (PCR and Sequencing Samples PCR 4451 and OPK-14); TACC3ex8-RV 5'-TCTACCAGGACTGTCCCTCAG-3' (SEQ ID NO: 502) (Sequencing Samples 3048 and 4373); TACC3ex9-RV 5'-GGGAGTCTCATTTGCACCGT-3' (SEQ ID NO: 503) (PCR Samples 3048,4373,4867 and Sequencing Sample 4867); TACC3ex10-RV 5'-CTGCATCCAGGTCCTTCTGG-3' (SEQ ID NO: 504) (PCR and Sequencing Samples MB-22 and 06-6390); TACC3ex11-RV 5'-CCAGTTCCAGGTTCTTCCCG-3' (SEQ ID NO: 505) (Sequencing Samples 27-1837 and 3808); TACC3ex12-RV 5'-CAACCTCTTCGAACCTGTCCA-3' (SEQ ID NO: 506) (PCR and Sequencing Samples 27-1837 and 3808). PCR conditions were 94° C.-30 sec/60° C.-30 sec/68° C.-2 min 30 sec for 40 cycles. For amplifications performed with the primer TACC3ex9-RV, the program was 94° C.-30 sec/56° C.-30 sec/68° C.-2 min 30 sec) for 40 cycles.

Quantitation of FGFR3 and TACC3 transcripts in GBM. The relative expression of FGFR3 and TACC3 regions included in or excluded from the fusion transcript was assessed by qRT-PCR. Primer pairs with comparable efficiency of amplification were identified and efficiency was assessed using serial dilutions of cDNA (20) prepared from OAW28 ovarian carcinoma cells that contain wild type FGFR3 and TACC3 (21). Primers used are: N-terminal region of FGFR3, FGFR3-N: Forward 5'-AAGACGATGCCACTGACAAG-3' (SEQ ID NO: 507), Reverse 5'-CCCAGCAGGTTGATGATGTTTTTG-3' (SEQ ID NO: 508); C-terminal region of TACC3, TACC3-C: Forward 5'-TCCTTCTCCGACCTCTTCAAGC-3' (SEQ ID NO: 509), Reverse 5'-TAATCCTCCACGCACTTCTTCAG-3' (SEQ ID NO: 510). To amplify transcripts in regions excluded from FGFR3-TACC3 fusion, primers were designed in the C-terminal region of FGFR3, FGFR3-C: Forward 5'-TACCTGGACCTGTCGGCG-3' (SEQ ID NO: 511), Reverse 5'-TGGGCAAACACGGAGTCG-3' (SEQ ID NO: 512) and N-terminal domain of TACC3, TACC3-N: Forward 5'-CCACAGACGCACAGGATTCTAAGTC-3' (SEQ ID NO: 513), Reverse 5'-TGAGTTTTCCAGTCCAAGGGTG-3' (SEQ ID NO: 514). All reactions were performed in triplicate and the data are reported as Fold Change±Standard Deviation.

Immunofluorescence and immunohistochemistry. For immunofluorescence (IF) staining of FGFR3, 5 μm FFPE sections subjected to antigen retrieval with citrate buffer for 8 min. Primary antibodies were: FGFR3-N(1:400, sc-13121, Santa Cruz Biotechnology), FGFR3-C(1:2000, sc-123, Santa Cruz Biotechnology), TACC3-N(1:600, ab134153, Abcam), and TACC3-C(1:300, NBP1-01032, Novus Biological). Secondary biotinylated antibodies were used at 1:50,000 followed by streptavidin and TSA Cy3-conjugated. Nuclei were counterstained with DAPI. For immunohistochemical analysis (IHC) of FGFR3 expression, antigen retrieval was performed for 12 min and FGFR-3 antibody (sc-13121, Santa Cruz Biotechnology) was diluted 1:500. Biotinylated anti-mouse antibody (1:30,000) and streptavidin were added before incubation with the chromogen. Nuclei were counterstaining with hematoxylin.

Molecular characterization of tumor samples. Mutational status of IDH1, IDH2, TERT promoter, as well as the methylation status of the MGMT promoter was analyzed in the Pitie-Salpetriere cohort. Expression of IDH1-R13214 mutant was analyzed by IHC in 500 cases as previously described (22). IDH1 and IDH2 gene mutations were identified by Sanger sequencing in 464 and 388 gliomas, respectively (5). IDH wild-type tumors are defined according to the absence of IDH1-R13211 immunopositivity and/or mutations in IDH1 and IDH2 genes. TERT promoter status was determined by the same technique in 277 samples (23). Hyper-methylation of the MGMT promoter was tested in 242 samples by bisulfite pyro-sequencing (24). The presence of EGFRvIII was evaluated by RT-PCR in 118 samples using EGFR-FW 5'-CTTCGGGGAGCAGCGATGCGAC-3' (SEQ ID NO: 548) and EGFR-RV 5'CTGTC-CATCCAGAGGAGGAGTA-3' (SEQ ID NO: 549) primers (25).

Copy number variations analyses have been performed on 192 tissue samples using CGH arrays using BAC arrays (N=187), Agilent 4×180 K (N=2), Nimblegen 3×720 K (N=2), Agilent 8×60K (N=1). Results were normalized using control DNA from matched blood samples as previously described (26). Additional analyses of 193 tumor specimens were performed by SNP array, using Illumina Omni (N=110), Illumina HumCore (N=32), Illumina 370K (N=27), or Illumina 610K (N=24), as previously described (27). Array processing was outsourced to Integragen. Raw copy numbers were estimated at each of the SNP and copy-number markers. Biodiscovery property SNP-FASST2 algorithm was then used to segment copy number data. Segments were mapped to hg18 genome assembly (28). Copy number alterations (CAN) magnitudes called log-R ratio (LRR) were classified using simple thresholds: deletion ($x \leq -1$), loss ($-1 < x \leq -0.2$), gain ($0.2 \leq x < 1$) or amplification ($x > 1$) according to default Nexus 7.5 software. For additional 56 gliomas, 10q loss was assessed on tumor and blood DNA by microsatellite analysis, while amplification of EGFR, MDM2 and CDK4, and deletion of CDKN2A gene, were determined by qPCR, as previously reported (29, 30).

The molecular profiles obtained in Pitie-Salpetriere dataset were combined with those available in the TCGA dataportal. TCGA GBM segmented copy number variation profile was downloaded from The UCSC Cancer Genomics Browser (31). Copy Number Variations (CNVs) were measured experimentally using the Affymetrix Genome-Wide Human SNP Array 6.0 platform at the Broad TCGA genome characterization center (32). Raw copy numbers were estimated at each of the SNP and copy-number markers. Circular binary segmentation was then used to segment the copy number data (28). Segments are mapped to hg18 genome assembly at Broad.

For CNV analysis of the regions across FGFR3 and TACC3 genes, samples for which RNAseq and CNV data were available or samples for which only CNV data were available and RT-PCR-sequencing of FGFR3-TACC3 fusion had been performed were considered. Overall, 158 GBM (all with a wild type IDH1 gene) satisfied these criteria. Among them, 5 harbored an FGFR3-TACC3 fusion whereas 153 were FGFR-TACC-negative. The CNV magnitudes, called log-R ratio (LRR), were classified using the following thresholds: deletion ($x < -1$), loss ($-1 \leq x \leq -0.2$), gain ($0.2 \leq x \leq 1$) or amplification ($x > 1$), according to the Atlas-TCGA (32). The analysis of the genomic regions encompassing EGFR, MDM2, CDK4, CDKN2A, 7p, 10q, according to hg18 genome assembly, was performed to evaluate their CNV. EGFRvIII mutation status was inferred according to Brennan et al. (32). The frequencies of the aberrations of these genes in FGFR3-TACC3 positive and negative samples were calculated and the obtained data were then combined with the Pitie-Salpetriere Hospital dataset.

Statistical Analysis. Differences in the distribution on categorical variables were analyzed using Fisher Exact test. The p-values were adjusted for multiple testing according to Benjamini and Hochberg false discovery rate (FDR). A q-value$\leq$0.05 (two-sided) was considered to be statistically significant.

Overall survival (OS) was defined as the time between the diagnosis and death or last follow-up. Patients who were still alive at the last follow-up were considered as censored events in the analysis. Progression-free survival (PFS) was defined as the time between the diagnosis and recurrence or last follow-up. Patients who were recurrence-free at the last follow-up were considered as censored events in the analysis. Survival curves were calculated by the Kaplan-Meier method and differences between curves assessed using the Log-Rank test. A Log-Rank test p-value$\leq$0.05 (two-sided) was considered to be statistically significant.

Cell culture and cell growth assay. GIC-1123 gliomaspheres were cultured in neurobasal medium (Invitrogen) supplemented with B27, N2 (Invitrogen), EGF and FGF2 (20 ng/ml, PeproTech). Mouse astrocytes Ink4A-Arf−/− were cultured in DMEM supplemented with 10% Fetal Bovine Serum. Cells were seeded at 1,000 cells/well in a 96-well plate and treated with JNJ-42756493. After 72 hours cell viability was assessed using the 3-(4,5-dimethythiazol-2-yl)-2,5-diphenyl tetrazolium bromide (MTT) assay. Data are mean±SEM of six replicates. Experiments were performed three times.

Subcutaneous xenografts and drug treatment. GIC-1123 cells ($5 \times 10^5$) were injected subcutaneously in the flank of athymic nude (Nu/Nu) mice (Charles River Laboratories). Mice carrying ~200 mm 3 subcutaneous tumors were randomized to receive 12 mg/kg JNJ-42756493 or DMSO in 1% Tween 80 by oral gavage. Tumor diameters were measured with caliper and tumor volumes estimated using the formula: 0.5×length×width 2. Data are mean±SD of nine mice in each group. Mice were sacrificed when tumors in the control group reached the maximal size allowed by the IACUC Committee at Columbia University.

MRI imaging and evaluation of clinical response to JNJ-42756493. Baseline and follow-up imaging assessments were performed on 1.5 Tesla MR imaging systems, including at least axial T1 weighted images before gadolinium injection, Axial or 3D FLAIR (Fluid-Attenuated Inversion-Recovery), dynamic susceptibility contrast MR perfusion (0.1 mmol/kg of gadobutrol), axial and 3D T1 weighted images after gadolinium injection. Tumor response was assessed according to the RANO criteria (33). Contrast-enhancing lesion volume was assessed with the help of a semi-automated volumetry tool (SegmentiX), based on shape-detection and thresholding, with control and manual correction of edges when necessary. Since exclusion of cystic or necrotic portions of the lesion may be affected by operator subjectivity, both were included for volumetric and axial measurements.

DSC (dynamic susceptibility contrast) perfusion datasets were processed with vendor's software suite (Neuroperfusion, Philips), including coregistration and rCBV (relative cerebral blood volume) parametric maps generation with 3 different algorithms (Gamma-variate fitting, Arterial Input Function based deconvolution and Model Free).

Results

Figure 36:
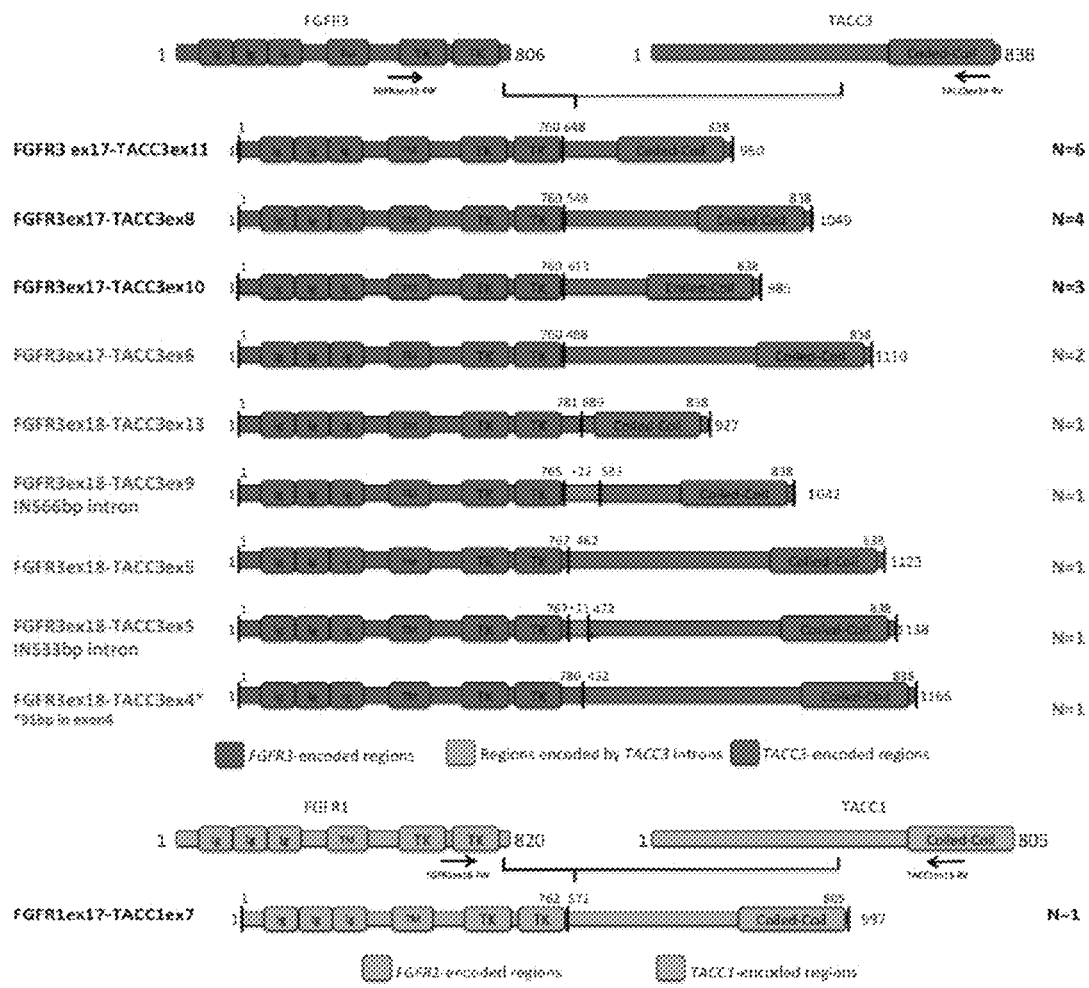
FIG. 36 shows the structure of FGFR-TACC gene fusions identified by RT-PCR-Sanger sequencing (see also SEQ ID NOs: 530-547). Predicted FGFR-TACC fusion proteins encoded by the transcripts identified by RT-PCR. Regions corresponding to FGFR3 or TACC3 are shown in red or blue, respectively. FGFR1 and TACC1 corresponding regions are shown in yellow and green. On the left are indicated the FGFR and TACC exons joined in the fused mRNA; the presence of TACC3 introns is also reported when they are spliced in the fusion cDNA. On the right, the number of patients harboring the corresponding fusion variant is indicated. The novel transcripts discovered in this study are highlighted in red. Black arrows indicate the position of the primers used for the FGFR-TACC fusions screening.

Detection of FGFR1-TACC1 and FGFR3-TACC3 fusions in GBM and grade II-III glioma. To determine the frequency and molecular features of FGFR-TACC fusions in human glioma patients, a cohort of 584 GBM and 211 grade II-III glioma treated at five Neurooncology centers (Table 12) were screened. 108 were grade III (49 IDH wild type, 52 IDH1 mutant and 7 IDH2 mutant) and 103 were grade II (36 IDH wild type, 63 IDH1 mutant and 4 IDH2 mutant). The IDH mutational status of 333 GBM was also established and it was determined that 303 harbored wild type IDH1/2 and 30 were mutated at codon 132 of IDH1. A RT-PCR assay was designed for the detection of all known and possibly new variants of FGFR1-TACC1 and FGFR3-TACC3 fusions that retain the mRNA sequences coding for the key FGFR-TK and TACC domains required for the oncogenic activity of the fusion protein (FIG. 36 and FIGS. 37A-D). Overall, 20 tumors with an FGFR3-TACC3 fusion were found, of which 17 were GBM (2.9% positives) and 3 lower grade glioma harboring wild type IDH1/2 genes (3.5% positives). The size of the FGFR3-TACC3 RT-PCR amplicons ranged from 928 bp (for FGFR3ex18-TACC3ex13) to 1706 bp (for FGFR3ex18-TACC3ex4). The FGFR1-TACC1 fusion was detected in one grade II IDH wild type glioma (FIG. 36). Conversely, an IDH1/2 mutant glioma harboring FGFR-TACC fusions (p<0.02) was not found. Sanger sequencing of the fusion amplicons revealed that each FGFR-TACC cDNA joined in-frame the sequence coding for the entire TK domain upstream of TACC-coding sequences that invariably include the coiled-coil TACC domain (FIG. 36). However, a notable variability among FGFR3-TACC3 fusion isoforms was detected, whereby 5 of the identified variants occurred only in individual cases (FIG. 36). Furthermore, 6 fusion transcripts emerged as new variants that have not been reported before in human cancer (marked in red in FIG. 36).

Next, suitable PCR primers were designed to map the genomic breakpoint coordinates for 9 FGFR3-TACC3-positive samples for which genomic DNA was available (FIGS. 40 and 41). The genomic breakpoints were successfully reconstructed by Sanger sequencing and found that they differ for each of the 9 positive cases. Interestingly, even cases harboring the same FGFR3-TACC3 transcript splice variants (#4451 and #OPK-14 joining exon 17 of FGFR3 to exon 6 of TACC3; #3048 and #4373 joining exon 17 of FGFR3 to exon 8 of TACC3; #3808 and #27-1835 joining exon 17 of FGFR3 to exon 11 of TACC3) had different genomic breakpoints (FIG. 41). Taken together, the above findings indicate that the noticeable variability among FGFR3-TACC3 fusion transcripts and genomic breakpoints is efficiently resolved by the RT-PCR screening assay.

Figure 42A:
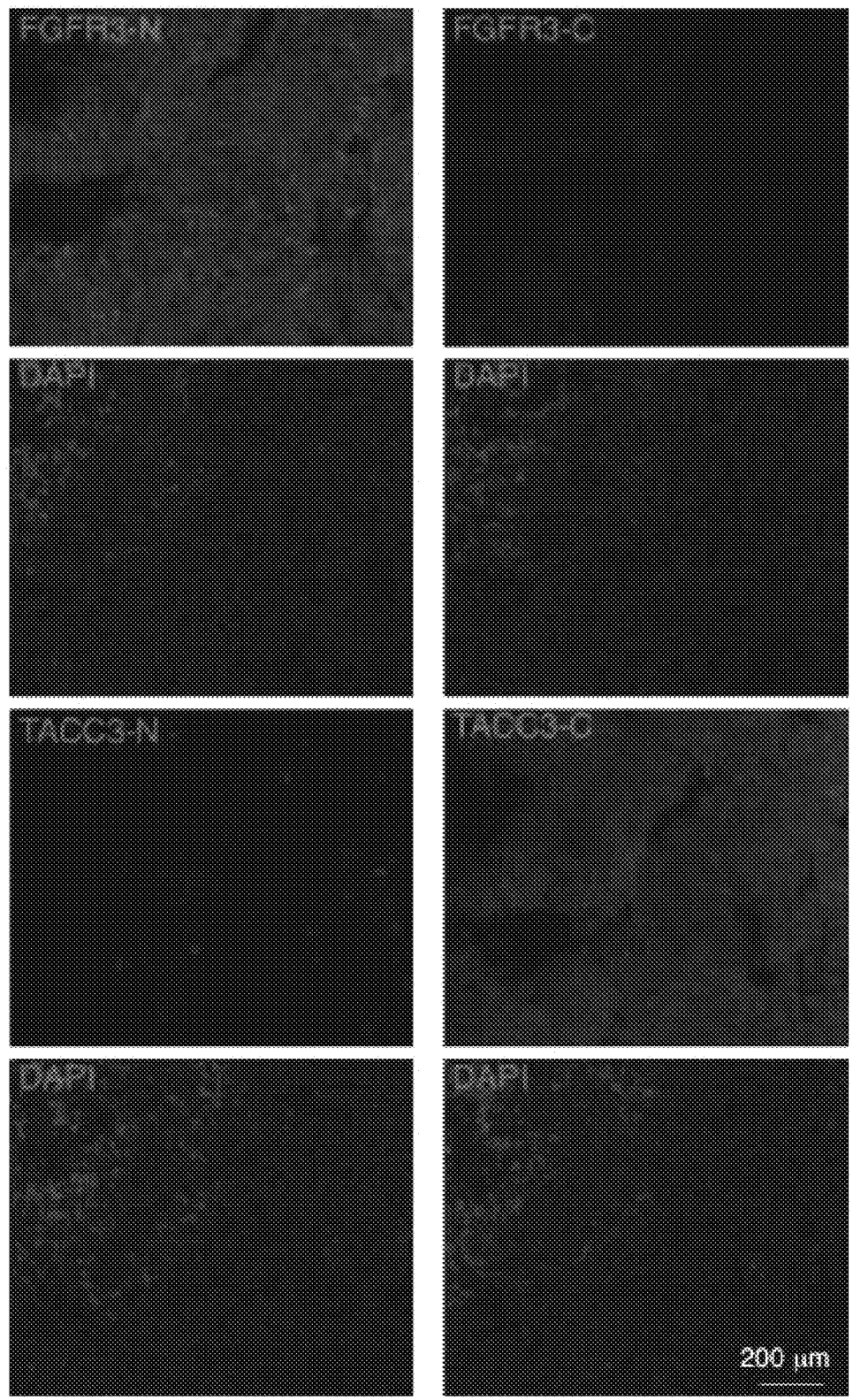
FIGS. 42A-B show evaluation of the expression of FGFR3-TACC3 fusion elements. (A) Microphotographs of immunofluorescence staining of a representative GBM harboring FGFR3-TACC3 fusion using antibodies that recognize the N- and C-termini of FGFR3 (FGFR3-N, FGFR3-C) and TACC3 (TACC3-N, TACC3-C), red. Nuclei are counterstained with DAPI, blue. (B) Quantitative RT-PCR of four representative GBM carrying FGFR3-TACC3 fusion and three negative controls using primer pairs that amplify FGFR3 and TACC3 regions included in or excluded from the fusion transcripts, as indicated in the diagram. OAW28: ovarian cystoadenocarcinoma cell line harboring wild type FGFR3 and TACC3 genes; GBM55 and GBM0822: GBM harboring wild type FGFR3 and TACC3 genes; GBM3808; GBM1133; GBM0826; GBM3048: GBM harboring FGFR3-TACC3 (F3-T3) fusion. Error bars are SD of triplicate samples.
Figure 42B:
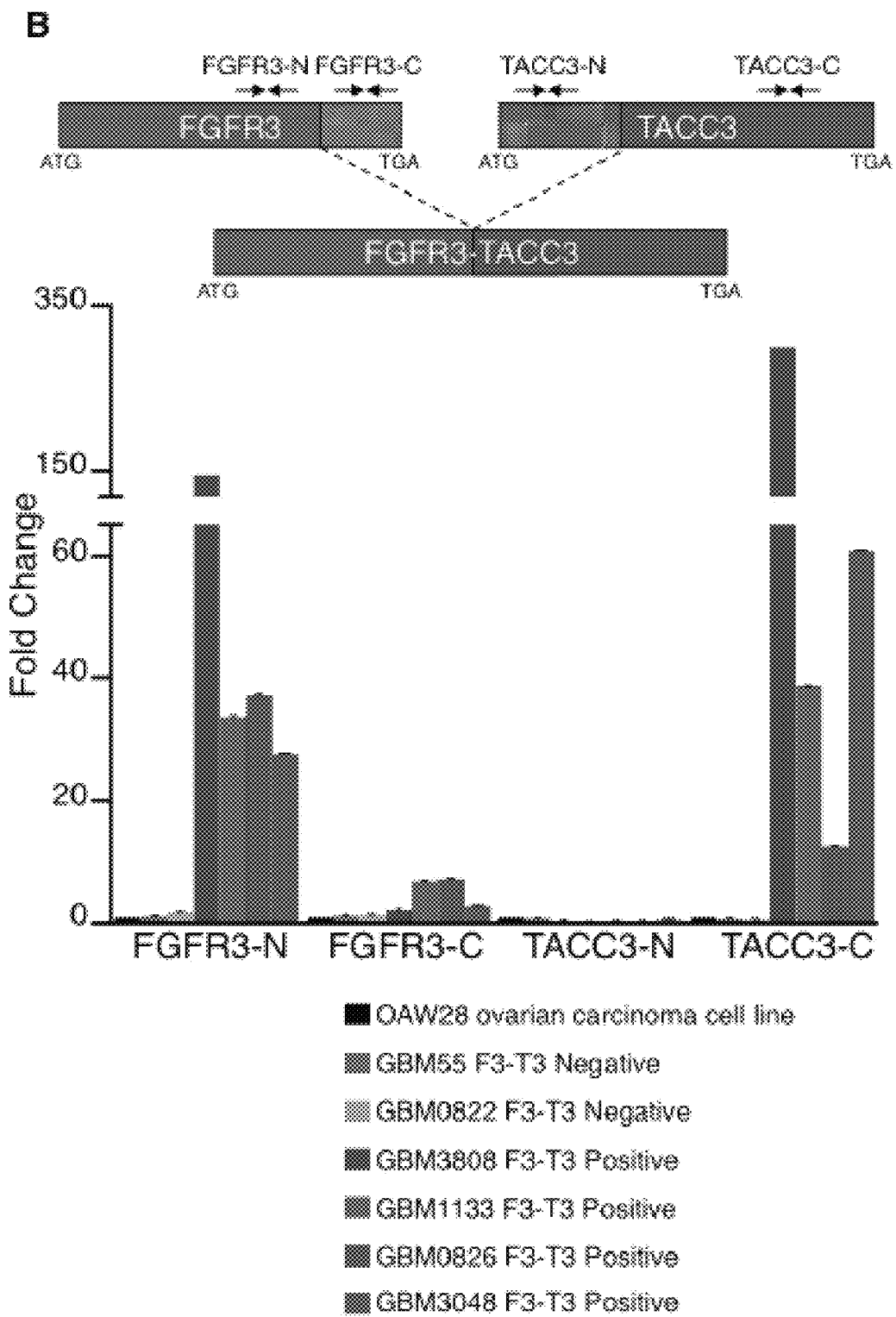

Immunostaining analysis of FGFR3-TACC3-positive tumors. The expression of the FGFR3 fusion protein was analyzed by IHC or IF using an antibody that recognizes the N-terminal region of FGFR3 (FGFR3-N) in 12 GBM and 3 lower grade glioma harboring FGFR3-TACC3 fusions for which sufficient tissue was available. Remarkably, each of the 15 positive tumors but none of those that had scored negative in the RT-PCR assay, displayed strong positivity for FGFR3 in the vast majority of tumor cells but not endothelial cells throughout the analyzed tumor section (FIGS. 37A-H). Notably, IF using an antibody that recognizes an epitope at the C-terminus of TACC3, which is invariably retained within FGFR3-TACC3 variants (TACC3-C), reproduced the staining pattern of the FGFR3-N antibody in FGFR3-TACC3 positive tumors. Conversely, negative or very weak staining was obtained in FGFR3-TACC3-positive tumors with antibodies recognizing the regions of FGFR3 (FGFR3 C-terminal region, FGFR3-C) and TACC3 (TACC3 N-terminal region, TACC3-N) constantly excluded from FGFR3-TACC3 fusion proteins (FIG. 42A). Consistently, quantitative RT-PCR of GBM harboring FGFR3-TACC3 fusions showed that the expression of the N-terminal coding region of FGFR3 and the C-terminal coding region of TACC3 (which are included in the fusion genes) is markedly higher than the expression of the C-terminal coding region of FGFR3 and the N-terminal coding region of TACC3, which are excluded from the fusion transcripts (FIG. 42B). One recurrent GBM from a patient whose tumor had been found positive for FGFR3-TACC3 at the initial diagnosis and who had recurred after concurrent radiotherapy and temozolomide treatment was analyzed. The recurrent tumor retained the same FGFR3-TACC3 fusion gene and protein that was present in the untreated GBM as determined by RT-PCR-sequencing and FGFR3 IF, respectively (FIG. 43A-C). Although this requires additional evaluation, the retained uniform positivity for FGFR3 in this recurrent GBM suggests that targeting the FGFR3-TACC3 fusion protein at relapse is a valid therapeutic strategy.

Figure 45:
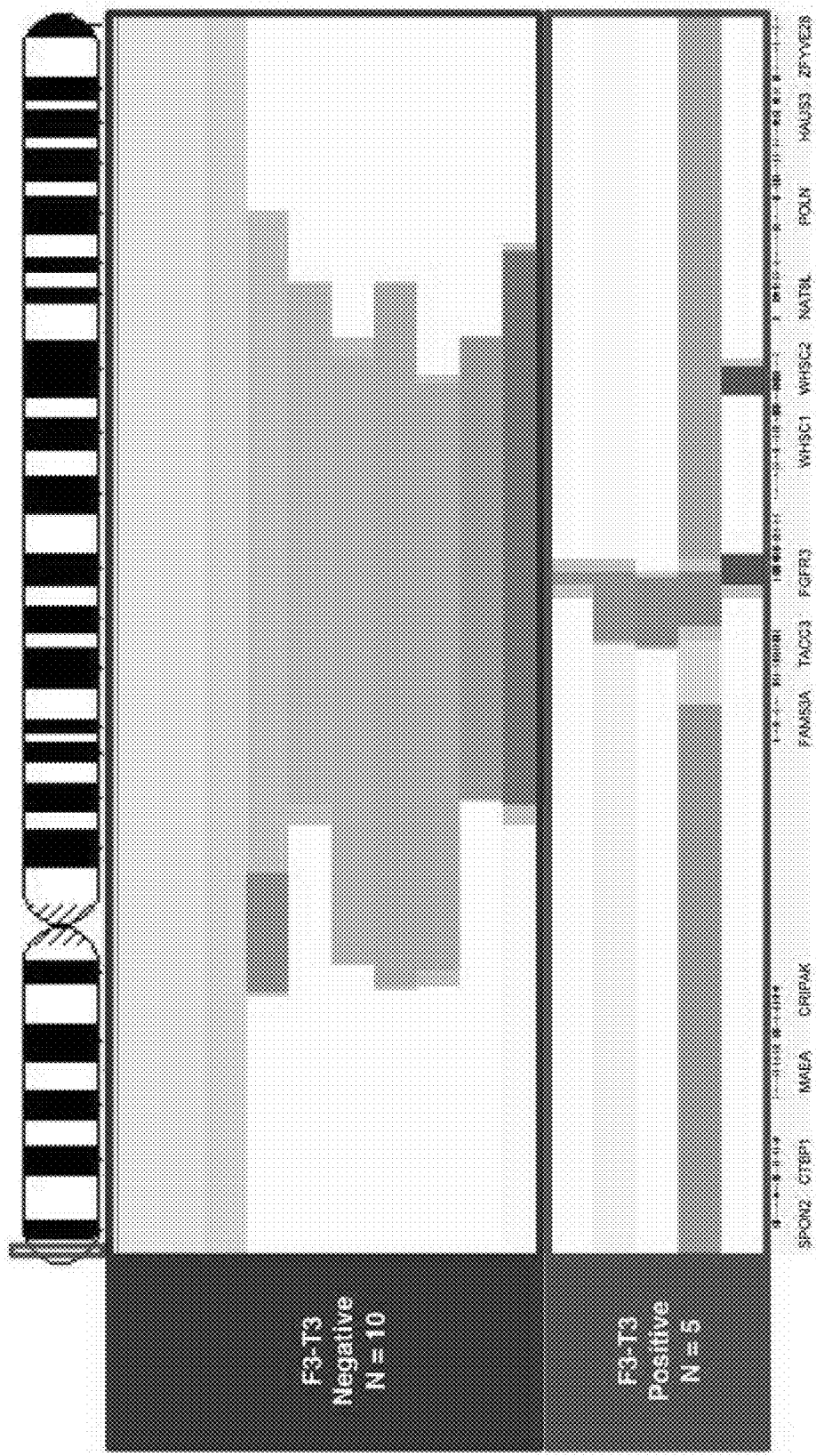
FIG. 45 shows analysis of SNP6.0 arrays of GBM harboring CNVs of FGFR3 and TACC3 genomic loci. CNVs of the FGFR3/TACC3 genomic loci in "gain labeled" (LRR>0.2) TCGA samples. The CNA magnitudes (expressed as log 2 ratio) were classified using simple thresholds: deletion (x<−1), loss (−1<x≤−0.2), gain (0.2≤x<1) or amplification (x>1). Gains are in gradient of red, loss in gradient of blue. Samples with uniform gains/amplification of FGFR3 and TACC3 lack FGFR3-TACC3 fusions. Samples harboring FGFR3-TACC3 fusions (F3-T3) show microamplifications involving the first FGFR3 exons, which are spliced in the fusion gene.

Clinical and molecular characteristics of glioma patients with FGFR3-TACC3 fusions. Clinical and molecular profiling data were available for 591 patients including 380 GBM (9 with FGFR3-TACC3 fusions) and all 211 lower grade glioma (3 with FGFR3-TACC3 fusions). Of these 12 patients 5 are males and 7 females, aged 48y to 82y (median=61y). The molecular profile of FGFR3-TACC3-positive glioma was determined. To do so, the analysis of CNVs and somatic mutations of key GBM genes in the dataset was combined with the SNP6.0 high-density genomic array analysis of 158 TCGA-derived GBM samples fully annotated for FGFR3-TACC3 fusion genes (the RNA-seq and/or RT-PCR analysis of these samples had revealed that 5 of them harbor FGFR3-TACC3 fusions) (6). Patients with FGFR3-TACC3 fusions displayed unique characteristics (Table 13). FGFR3-TACC3 fusions were mutually exclusive with EGFR amplification (0/16 vs. 166/411; p=0.0004, FDR q-value corrected for multiple comparisons=0.0012) and showed a clear trend against the presence of the EGFRvIII transcript variant (0/16 vs. 37/219; p=0.083). Conversely, CDK4 amplification was significantly more frequent in FGFR3-TACC3-positive tumors (7/16 vs 41/408, p=0.0008; FDR q-value=0.0024). A less significant association of FGFR3-TACC3 fusions was also seen with amplification of MDM2, which as CDK4, maps to chromosome 12q (4/16 vs 24/408, p=0.016; FDR q-value=0.048). No statistical association between FGFR3-TACC3 fusions and other genetic and epigenetic alterations that commonly occur in gliomas harboring wild type IDH genes was found (CDKN2A deletion, TERT promoter mutations, gain of chromosome 7p, loss of chromosome 10q and methylation of the MGMTpromoter, Table 13). When compared with the IDH wild type patient population of grade II and grade III glioma and GBM, there was no significant difference in progression free survival (PFS) or overall survival (OS) between patients positive or negative for FGFR3-TACC3 (FIGS. 44A-B). Finally, it was established whether the CNV analysis of the FGFR3 and TACC3 genomic loci could be used to predict positivity for FGFR3-TACC3 fusions. The analysis of high-density SNP6.0 arrays of the 158 GBM samples from the Atlas-TCGA revealed that 10 samples displayed different degrees of copy number gains encompassing the entire FGFR3 and TACC3 loci (FIG. 45). However, none of them harbored FGFR3-TACC3 fusions. Conversely, the 5 FGFR3-TACC3-positive samples in the dataset harbor micro-amplification events involving only the exons of the FGFR3 gene that are included in the fusion breakpoint. This finding suggests that any CNV survey that is less accurate than high-density SNP arrays, could fail to identify the genomic marks associated with true FGFR3-TACC3-positive cases.

growth inhibition of GIC-1123 tumor xenografts (FIGS. 38C-D) with a statistically significant tumor regression after two weeks (p-value of the slope calculated from the treatment starting point=0.04). The above findings provide a strong foundation for the treatment of GBM patients harboring FGFR-TACC rearrangements with JNJ-42756493.

Two patients with recurrent GBM harboring FGFR3-TACC3 fusions were treated with JNJ-42756493 in a first-in-man phase I trial. Patient 1, male aged 52, underwent partial surgical resection of a right parietal GBM, followed by fractionated radiotherapy and concomitant temozolomide (TMZ) as first line treatment (36). The RT-PCR-sequencing analysis of the GBM specimen revealed positivity for the FGFR3-TACC3 fusion (FGFR3-exon17-TACC3-exon 6, sample 4451, FIGS. 40 and 41) and the immunostaining using FGFR3 antibody on paraffin embedded sections showed strong positivity in a large fraction of tumor cells. After 5 cycles of TMZ, the patient presented with dizziness and headache and brain MRI revealed tumor progression

TABLE 13

Molecular alterations in IDH wild type glioma harboring FGFR3-TACC3 fusions. The table reports the absolute number and frequency (percentage) of individual glioma-specific molecular alterations in tumors scoring positive or negative for FGFR3-TACC3 fusions. The analysis is done on the Union dataset (TCGA and "Pitié-Salpêtrière Hospital" datasets, see methods for details). Statistically significant associations are indicated in bold (Fisher Exact test, q-values adjusted with FDR).

| | N of FGFR3-TACC3 Positive | % of FGFR3-TACC3 Positive | N of FGRR3-TACC3 Negative | % of FGFR3-TACC Negative | P-value (Fisher test) | q-value (FDR) |
|---|---|---|---|---|---|---|
| EGFR amplification | 0/16 | 0.0% | 166/411 | 40.4% | 4.E−04 | 0.0012 |
| CDK4 amplification | 7/16 | 43.7% | 41/408 | 10.0% | 8.E−04 | 0.0024 |
| MDM2 amplification | 4/16 | 25.0% | 24/408 | 5.9% | 0.016 | 0.048 |
| EGFRvIII | 0/16 | 0.0% | 37/219 | 16.9% | 0.063 | 0.25 |
| CDKN2A deletion | 4/16 | 25.0% | 188/411 | 45.7% | 0.13 | 0.39 |
| Chr. 7p gain | 12/15 | 80.0% | 242/374 | 64.7% | 0.28 | 0.84 |
| Chr. 10q deletion | 12/16 | 75.0% | 253/420 | 60.2% | 0.3 | 0.9 |
| TERT promoter mutation | 9/11 | 81.8% | 128/163 | 78.5% | 0.8 | 1 |
| MGMT promoter hypermethylation | 6/12 | 50.0% | 73/160 | 45.6% | 0.7 | 1 |

Preclinical and clinical relevance of targeting FGFR3-TACC3 fusions. JNJ-42756493 is a potent, oral pan-FGFR tyrosine kinase inhibitor with IC50 values in the low nanomolar range for all members of the FGFR family. It has demonstrated potent antitumor activities in nonclinical models with FGFR aberrations including squamous non-small cell lung cancer, gastric, breast, hepatocellular cancer (HCC), endometrial, and bladder (34, 35). To ask whether JNJ-42756493 is effective in targeting specifically FGFR-TACC-positive cells, mouse astrocytes expressing FGFR3-TACC3, FGFR3-TACC3 containing a mutation that inactivates the kinase activity of FGFR3 (FGFR3-TACC3-KD), or the empty vector were treated with JNJ-42756493. The effect of JNJ-42756493 on human glioma stem cells GIC-1123 that harbor the FGFR3-TACC3 gene fusion (6) was also studied. These experiments revealed that both mouse astrocytes and GIC-1123 that express FGFR3-TACC3 but not cells expressing the KD mutant fusion or the empty vector are highly sensitive to FGFR inhibition by JNJ-42756493 with an IC50 of 3.03 nM and 1.55 nM, respectively (FIGS. 38A-B). Next, the effect of oral treatment with JNJ-42756493 of mice bearing xenografts of human GIC-1123 affects tumor growth was tested. Mice were randomized to receive vehicle or JNJ-42756493 (12 mg/kg). Mirroring the in vitro results, JNJ-42756493 elicited a potent (FIG. 39A). At this time the patient was enrolled in the JNJ-42756493 trial and received JNJ-42756493 (12 mg/day administered in cycles of 7 days followed by 7 days off treatment). After 3 weeks the patient reported a marked clinical improvement (complete regression of dizziness and headache). On MRI, the sum of product diameters (RANO criteria, FIG. 39B) and volumetry (FIG. 39C) measured without excluding cystic and necrotic components showed disease stabilization. However, the tumor mass underwent significant decrease of the enhancing parenchyma (−44%) with formation of a cystic portion in the central core (33). The objective response was further corroborated by the marked reduction of the extent of tumor vascularity estimated by quantitative analysis of rCBV (relative cerebral blood volume) from dynamic susceptibility MR perfusion maps (37) (FIG. 39D). Stabilization lasted for 115 days. During JNJ-42756493 treatment mild and manageable toxicity was observed (grade I hyperphosphatemia, asthenia, dysgueusia, dry mouth, keratitis, and grade II nail changes). After 4 months, tumor progressed on MRI locally both on T1 contrast-enhanced area and T2/FLAIR hypersignal. The patient was re-operated and subsequently treated with CCNU. He is still alive, but in progression after 21 months from diagnosis and 287 days from the start of the anti-FGFR therapy.

Patient 2 is a 64 years old woman, affected by left parietal GBM, diagnosed by stereotactic biopsy. The tumor was positive for FGFR3-TACC3 gene fusion by RT-PCR-sequencing and showed diffuse FGFR3 expression in most tumor cells (FIGS. 37A, 37C, 37E, sample 4620). The patient received as first line treatment fractionated radiotherapy and TMZ according to the Stupp protocol (36), but after 2 cycles of monthly TMZ she presented with clinical deterioration including progressive headaches, right homonymous hemianopsia and memory impairment. Brain MRI performed 3 and 4 months after the completion of concomitant chemo-radiotherapy revealed tumor progression with increase of the left parietal mass and the appearance of a small contralateral lesion (FIG. 49E). The patient was thus enrolled in the JNJ-42756493 trial (12 mg/day administered in cycles of 7 days followed by 7 days off treatment) and showed clinical improvement after 4 weeks (regression of headaches, visual field defect and memory impairment). Best response was observed after 104 days of treatment with a 22% reduction of tumor size according to the RANO criteria (FIG. 39F) and 28% according to volumetry (FIG. 39G). Grade I hyperphosphatemia, nail changes, and mucositis were observed. Clinical status remained stable until disease progression occurring 134 days after the start of the anti-FGFR. The patient is still alive and is receiving a third-line chemotherapy with nitrosoureas and bevacizumab.

TABLE 14

Summary of FGFR-TACC fusion transcripts identified in all cancer types. FGFR3-TACC3 fusion variants are ranked according to their prevalence across any cancer type. The number of FGFR-TACC fusions identified in each tumor type, including those identified in the present study, is also indicated.

| FGFR-TACC Fusion Variants | | N Cases | Tumor Type |
|---|---|---|---|
| FGFR3-TACC3 | FGFR3exon17-TACC3exon11 | 30 | Brain Tumors, N = 10 (N = 2,[6]; N = 2,[9, 15]; N = 6, Present Study) Bladder Cancer, N = 6 (N = 3,[12, 15]; N = 3,[11]) Lung Cancer, N = 13 (N = 4,[12, 15]; N = 9,[10]) Renal Carcinoma, N = 1,[15] |
| | FGFR3exon17-TACC3exon10 | 18 | Brain Tumors, N = 5 (N = 1,[6]; N = 1,[9]; N = 3, Present Study) Oral Cancer, N = 1[12] Head and Neck Cancer, N = 2,[12, 15] Bladder Cancer, N = 3,[7] Lung Cancer, N = 7 (N = 4,[8]; N = 2,[10]; N = 1,[14]) |
| | FGFR3exon17-TACC3exon8 | 8 | Brain Tumors, N = 6 (N = 2,[6]; N = 4, Present Study) Lung Cancer, N = 2 (N = 1,[10]; N = 1,[14]) |
| | FGFR3exon17-TACC3exon4 | 4 | Brain Tumors, N = 2 (N = 1,[9]; N = 1,[13]) Bladder Cancer, N = 1[9] Lung Cancer, N = 1[14] |
| | FGFR3exon17-TACC3exon6 | 2 | Brain Tumors, N = 2, Present Study |
| | FGFR3exon18-TACCexon4 | 1 | Brain tumors, N = 1, Present study |
| | FGFR3exon17-TACC3exon9 INS63bp | 1 | Brain tumors, N = 1,[6] |
| | FGFR3exon18-TACC3exon9 INS66bp | 1 | Brain Tumors, N = 1, Present study |
| | FGFR3exon18-TACC3exon5 | 1 | Brain Tumors, N = 1, Present study |
| | FGFR3exon18-TACC3exon5 INS33bp INS71bp | 1 | Lung Cancer, N = 1,[10] |
| | FGFR3exon18-TACC3exon13 | 1 | Brain Tumors, N = 1, Present study |
| | FGFR3exon18-TACC3exon11 | 1 | Lung Cancer, N = 1,[10] |
| FGFR1-TACC1 | FGFR1exon17-TACC1exon7 | 5 | Brain Tumors, N = 5 (N = 1,[6]; N = 3,[13]; N = 1, Present study) |
| FGFR2-TACC2 | | 1 | Stomach Adenocarcinoma, N = 1[15] |

Discussion

FGFR-TACC fusions are potent oncogenic events that when present in brain tumor cells confer sensitivity to FGFR inhibitors (6). Since the original identification of recurrent FGFR-TACC fusions in GBM, small subgroups of patients harboring FGFR-TACC translocations have been identified in several other tumor types (7-15). Here, an unbiased RT-PCR-sequencing analysis for the identification of all possible functional FGFR-TACC fusion transcripts is reported. The screening of a large glioma dataset from multiple Institutions not only confirmed that FGFR-TACC rearrangements occur in ~3% of human GBM but also revealed that FGFR-TACC fusions are present in the subgroup of IDH wild type lower grade glioma (grade II-III) with prevalence similar to that of GBM. IDH wild type grade II and III glioma have a significantly worse clinical outcome than the IDH mutant glioma and manifests molecular and clinical features that resemble GBM (5). The finding that FGFR-TACC fusions occur in IDH wild type but not IDH mutant glioma provides an important clue for the molecular characterization of this glioma subtype. Furthermore, the clustering of such potent oncogenic events in IDH wild type glioma underscores the particularly aggressive nature of this group of glioma. While it was shown that FGFR-TACC fusions cluster within the poor clinical outcome subgroup of IDH wild type glioma, these translocations do not seem to carry prognostic value within the IDH wild type subgroup of glioma patients. Without being bound by theory, the sample size of patients harboring FGFR-TACC fusions is too small to draw definitive conclusions with respect to the impact on survival and larger studies may be necessary to clarify the prognostic role of FGFR-TACC fusions in IDH wild type glioma.

Beside mutual exclusivity between IDH1 mutations and FGFR-TACC fusions, the results showed that patients with FGFR3-TACC3 rearrangements lack EGFR amplification and EGFRvIII but are significantly enriched for amplification of CDK4 (and MDM2 to a lesser extent). Knowledge of these molecular characteristics will help select those patients who most likely harbor FGFR-TACC rearrangements and design combinatorial targeted therapies that might be more effective in the FGFR-TACC-positive glioma subgroup.

The molecular screen uncovered 6 new FGFR3-TACC3 fusion events. Together with the previously identified variants, 12 distinct isoforms of FGFR3-TACC3 have been reported, thus revealing a remarkable variability of FGFR3-

TACC3 transcripts in human cancer (see Table 14 summarizing the structure of all the FGFR-TACC variants identified to date). The structural heterogeneity of FGFR3-TACC3 fusions is yet more pronounced at the genomic level, whereby each fusion event harbors distinct genomic breakpoints, even for identical fusion transcripts. This finding underscores the notion that targeted genomic analyses are unlikely to be suitable approaches for the molecular diagnosis of FGFR3-TACC3 positivity. Conversely, the unbiased identification of FGFR3-TACC3-positive tumors with the RT-PCR-sequencing assay reported here overcomes the limitations of screening only for previously identified FGFR3-TACC3 fusions and provides a simple molecular diagnostic assay.

Rather than displaying uniform amplifications of the FGFR3 and TACC3 genomic loci, FGFR3-TACC3-positive samples harbor small, intragenic micro-amplification events typically encompassing only the exons of the FGFR3 and TACC3 genes included in the breakpoint (6). This finding is consistent with the notion that a "fusion breakpoint principle" sustains the CNVs of driver gene fusions such as FGFR3-TACC3 in which local CNVs target exclusively the breakpoint region (38). It is noted that such small and irregular CNVs may easily go undetected from CNV analyses performed using platforms less sensitive than the high-density SNP6.0 genomic arrays. Furthermore, the notion that FGFR3-TACC3-negative GBM may harbor uniform amplifications across the FGFR3 and TACC3 loci argues against the standard analysis of FGFR3 and/or TACC3 CNVs as a method for the selection of FGFR3-TACC3-positive tumors.

There is a growing body of evidence supporting the notion that GBM is a markedly heterogeneous tumor. The formidable degree of intra-tumor heterogeneity of GBM is a potential cause of failure of targeted therapies in these tumors. In particular, the intra-tumor heterogeneity of GBM has previously been recognized in light of the mosaic expression of the RTK genes EGFR, PDGFRA and MET by neighboring cells (16-19). Thus, in the majority of GBM, amplification or overexpression of individual RTK genes are present in a sub-clonal fraction of tumor cells and co-exist with amplification/expression of other RTK-coding genes within the tumor mass. Therefore, it was essential to determine whether such heterogeneity was also present in gliomas harboring FGFR-TACC translocations. The immunostaining of FGFR3-TACC3-positive tumors revealed that positive specimens manifest strong and uniform expression of the fusion protein, which is also retained after recurrence. This behavior is reminiscent of other driver chromosome translocations (BCR-ABL, EML4-ALK) and is compatible with the glioma-initiating functions of FGFR-TACC fusions (6). It is also the scenario expected for a driver oncogene whose activity remains essential for tumor maintenance regardless of secondary genetic alterations that occur during tumor progression. The strong antitumor effects obtained with JNJ-42756493 in glioma cells harboring FGFR3-TACC3 fusions have built a compelling rationale for the treatment of glioma patients positive for FGFR-TACC rearrangements. JNJ-42756493 is an oral ATP-competitive pan-FGFR selective inhibitor that inhibits tyrosine phosphorylation of activated FGFR at nanomolar concentrations (34, 35). The enrollment of two patients with recurrent FGFR3-TACC3-positive GBM in a phase I trial with JNJ-42756493 showed that this treatment has tolerable toxicity and clear anti-tumor activity, thus validating FGFR-TACC as a therapeutic target. Therefore, targeted inhibition of FGFR-TK in preselected IDH wild type FGFR-TACC-positive glioma may provide clinical benefits for patients with recurrent glioma who currently lack valuable therapeutic options. In conclusion, described herein is the importance and feasibility of prospective genotyping for FGFR-TACC fusions in glioma patients and provided a preliminary evidence of clinical response that warrants the investigation of the sensitivity of gliomas harboring FGFR-TACC rearrangements to FGFR kinase inhibition in clinical trials.

REFERENCES

1. Medves S, Demoulin J B. Tyrosine kinase gene fusions in cancer: translating mechanisms into targeted therapies. J Cell Mol Med 2012; 16:237-48.
2. Mitelman F, Johansson B, Mertens F. The impact of translocations and gene fusions on cancer causation. Nat Rev Cancer 2007; 7:233-45.
3. Weathers S P, Gilbert M R. Advances in treating glioblastoma. F1000Prime Rep. 2014; 6:46.
4. Omuro A, DeAngelis L M. Glioblastoma and other malignant gliomas: a clinical review. JAMA 2013; 310: 1842-50.
5. Sanson M, Marie Y, Paris S, Idbaih A, Laffaire J, Ducray F, et al. Isocitrate dehydrogenase lcodon 132 mutation is an important prognostic biomarker in gliomas. J Clin Oncol 2009; 27:4150-4.
6. Singh D, Chan J M, Zoppoli P, Niola F, Sullivan R, Castano A, et al. Transforming fusions of FGFR and TACC genes in human glioblastoma. Science 2012; 337: 1231-5.
7. Cancer Genome Atlas Research N. Comprehensive molecular characterization of urothelial bladder carcinoma. Nature 2014; 507:315-22.
8. Majewski I J, Mittempergher L, Davidson N M, Bosma A, Willems S M, Horlings H M, et al. Identification of recurrent FGFR3 fusion genes in lung cancer through kinome-centred RNA sequencing. J Pathol 2013; 230: 270-6.
9. Parker B C, Annala M J, Cogdell D E, Granberg K J, Sun Y, Ji P, et al. The tumorigenic FGFR3-TACC3 gene fusion escapes miR-99a regulation in glioblastoma. J Clin Invest 2013; 123:855-65.
10. Wang R, Wang L, Li Y, Hu H, Shen L, Shen X, et al. FGFR1/3 Tyrosine Kinase Fusions Define a Unique Molecular Subtype of Non-Small Cell Lung Cancer. Clin Cancer Res 2014; 20:4107-14.
11. Williams S V, Hurst C D, Knowles M A. Oncogenic FGFR3 gene fusions in bladder cancer. Hum Mol Genet 2013; 22:795-803.
12. Wu Y M, Su F, Kalyana-Sundaram S, Khazanov N, Ateeq B, Cao X, et al. Identification of targetable FGFR gene fusions in diverse cancers. Cancer Discov 2013; 3:636-47.
13. Zhang J, Wu G, Miller C P, Tatevossian R G, Dalton J D, Tang B, et al. Whole-genome sequencing identifies genetic alterations in pediatric low-grade gliomas. Nat Genet 2013; 45:602-12.
14. Capelletti M, Dodge M E, Ercan D, Hammerman P S, Park S I, Kim J, et al. Identification of Recurrent FGFR3-TACC3 Fusion Oncogenes from Lung Adenocarcinoma. Clin Cancer Res 2014, DOI: 10.1158/1078-0432.CCR-14-1337; in press.
15. Stransky N, Cerami E, Schalm S, Kim J L, Lengauer C. The landscape of kinase fusions in cancer. Nat Commun 2014; 5:4846.
16. Inda M M, Bonavia R, Mukasa A, Narita Y, Sah D W, Vandenberg S, et al. Tumor heterogeneity is an active process maintained by a mutant EGFR-induced cytokine circuit in glioblastoma. Genes Dev 2010; 24:1731-45.
17. Snuderl M, Fazlollahi L, Le L P, Nitta M, Zhelyazkova B H, Davidson C J, et al. Mosaic amplification of multiple receptor tyrosine kinase genes in glioblastoma. Cancer Cell 2011; 20:810-7.
18. Ene C I, Fine H A. Many tumors in one: a daunting therapeutic prospect. Cancer Cell 2011; 20:695-7.
19. Sottoriva A, Spiteri I, Piccirillo S G, Touloumis A, Collins V P, Marioni J C, et al. Intratumor heterogeneity in human glioblastoma reflects cancer evolutionary dynamics. Proc Natl Acad Sci USA 2013; 110:4009-14.
20. Kindich R, Florl A R, Jung V, Engers R, Muller M, Schulz W A, et al. Application of a modified real-time PCR technique for relative gene copy number quantification to the determination of the relationship between NKX3.1 loss and MYC gain in prostate cancer. Clin Chem 2005; 51:649-52.
21. Bulusu K C, Tym J E, Coker E A, Schierz A C, Al-Lazikani B. canSAR: updated cancer research and drug discovery knowledgebase. Nucleic Acids Res 2014; 42:D1040-7.
22. Reyes-Botero G, Giry M, Mokhtari K, Labussiere M, Idbaih A, Delattre J Y, et al. Molecular analysis of diffuse intrinsic brainstem gliomas in adults. J Neurooncol 2014; 116:405-11.
23. Labussiere M B B, Mokhtari K, Di Stefano A L, Rahimian A, Rossetto M, Ciccarino P, Saulnier O, Paterra R, Marie Y, Finocchiaro G, Sanson M. Combined analysis of TERT, EGFR and IDH status define distinct prognostic glioblastoma classes. Neurology 2014; 83:1200-6.
24. Quillien V, Lavenu A, Karayan-Tapon L, Carpentier C, Labussiere M, Lesimple T, et al. Comparative assessment of 5 methods (methylation-specific polymerase chain reaction, MethyLight, pyrosequencing, methylation-sensitive high-resolution melting, and immunohistochemistry) to analyze O6-methylguanine-DNA-methyltranferase in a series of 100 glioblastoma patients. Cancer 2012; 118:4201-11.
25. Idbaih A, Aimard J, Boisselier B, Marie Y, Paris S, Criniere E, et al. Epidermal growth factor receptor extracellular domain mutations in primary glioblastoma. Neuropathol Appl Neurobiol 2009; 35:208-13.
26. Idbaih A, Marie Y, Lucchesi C, Pierron G, Manie E, Raynal V, et al. BAC array CGH distinguishes mutually exclusive alterations that define clinicogenetic subtypes of gliomas. Int J Cancer 2008; 122:1778-86.
27. Gonzalez-Aguilar A, Idbaih A, Boisselier B, Habbita N, Rossetto M, Laurenge A, et al. Recurrent mutations of MYD88 and TBL1XR1 in primary central nervous system lymphomas. Clin Cancer Res 2012; 18:5203-11.
28. Olshen A B, Venkatraman E S, Lucito R, Wigler M. Circular binary segmentation for the analysis of array-based DNA copy number data. Biostatistics 2004; 5:557-72.
29. Hoang-Xuan K, He J, Huguet S, Mokhtari K, Marie Y, Kujas M, et al. Molecular heterogeneity of oligodendrogliomas suggests alternative pathways in tumor progression. Neurology 2001; 57:1278-81.
30. Houillier C, Lejeune J, Benouaich-Amiel A, Laigle-Donadey F, Criniere E, Mokhtari K, et al. Prognostic impact of molecular markers in a series of 220 primary glioblastomas. Cancer 2006; 106:2218-23.
31. Goldman M, Craft B, Swatloski T, Ellrott K, Cline M, Diekhans M, et al. The UCSC Cancer Genomics Browser: update 2013. Nucleic Acids Res 2013; 41:D949-54.
32. Brennan C W, Verhaak R G, McKenna A, Campos B, Noushmehr H, Salama S R, et al. The somatic genomic landscape of glioblastoma. Cell 2013; 155:462-77.
33. Wen P Y, Macdonald D R, Reardon D A, Cloughesy T F, Sorensen A G, Galanis E, et al. Updated response assessment criteria for high-grade gliomas: response assessment in neuro-oncology working group. J Clin Oncol 2010; 28:1963-72.
34. Bahleda R, Dienstmann R, Adamo B, Gazzah A, Infante J R, Zhong B, et al. Phase 1 study of JNJ-42756493, a pan-fibroblast growth factor receptor (FGFR) inhibitor, in patients with advanced solid tumors. J Clin Oncol 2014; 32:suppl; abstr 2501.
35. Squires M, Ward G, Saxty G, Berdini V, Cleasby A, King P, et al. Potent, selective inhibitors of fibroblast growth factor receptor define fibroblast growth factor dependence in preclinical cancer models. Mol Cancer Ther 2011; 10:1542-52.
36. Stupp R, Mason W P, van den Bent M J, Weller M, Fisher B, Taphoorn M J, et al. Radiotherapy plus concomitant and adjuvant temozolomide for glioblastoma. N Engl J Med 2005; 352:987-96.
37. Law M, Yang S, Babb J S, Knopp E A, Golfinos J G, Zagzag D, et al. Comparison of cerebral blood volume and vascular permeability from dynamic susceptibility contrast-enhanced perfusion M R imaging with glioma grade. AJNR Am J Neuroradiol 2004; 25:746-55.
38. Wang X S, Prensner J R, Chen G, Cao Q, Han B, Dhanasekaran S M, et al. An integrative approach to reveal driver gene fusions from paired-end sequencing data in cancer. Nat Biotechnol 2009; 27:1005-11.

SEQUENCE LISTING

```
<160> NUMBER OF SEQ ID NOS: 560

<210> SEQ ID NO 1
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(178)

<400> SEQUENCE: 1 g tgc tgg cat gcc gcg ccc tcc cag agg ccc acc ttc aag cag ctg gtg    49
```

```
 Cys Trp His Ala Ala Pro Ser Gln Arg Pro Thr Phe Lys Gln Leu Val
  1               5                  10                  15 gag gac ctg gac cgt gtc ctt acc gtg acg tcc acc gac ttt aag gag       97
Glu Asp Leu Asp Arg Val Leu Thr Val Thr Ser Thr Asp Phe Lys Glu
             20                  25                  30 tcg gcc ttg agg aag cag tcc tta tac ctc aag ttc gac ccc ctc ctg      145
Ser Ala Leu Arg Lys Gln Ser Leu Tyr Leu Lys Phe Asp Pro Leu Leu
             35                  40                  45 agg gac agt cct ggt aga cca gtg ccc gtg gcc                          178
Arg Asp Ser Pro Gly Arg Pro Val Pro Val Ala
             50                  55

<210> SEQ ID NO 2
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctttaaggag tcggccttga ggaagcagtc cttatacctc aagttcgacc ccctcctgag    60
ggacagtcct ggtagaccag tgcccgtggc c                                  91

<210> SEQ ID NO 3
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
actttaagga gtcggccttg aggaagcagt ccttatacct caagttcgac cccctcctga    60
gggacagtcc tggtagacca gtgcccgtgg g                                  91

<210> SEQ ID NO 4
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gactttaagg agtcggcctt gaggaagcag tccttatacc tcaagttcga ccccctcctg    60
agggacagtc ctggtagacc agtgcccgtg g                                  91

<210> SEQ ID NO 5
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgactttaag gagtcggcct tgaggaagca gtccttatac ctcaagttcg acccctcct    60 gagggacagt cctggtagac cagtgcccgt t                                  91

<210> SEQ ID NO 6
<211> LENGTH: 91
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 6
ccgactttaa ggagtcggcc ttgaggaagc agtccttata cctcaagttc gacccctcc    60 tgagggacag tcctggtaga ccagtgcccg g                                  91

<210> SEQ ID NO 7
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
accgacttta aggagtcggc cttgaggaag cagtccttat acctcaagtt cgacccctc    60 ctgagggaca gtcctggtag accagtgccc c                                  91

<210> SEQ ID NO 8
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caccgacttt aaggagtcgg ccttgaggaa gcagtcctta tacctcaagt tcgaccccct   60
cctgagggac agtcctggta gaccagtgcc c                                  91

<210> SEQ ID NO 9
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccaccgactt taaggagtcg gccttgagga agcagtcctt atacctcaag ttcgacccc    60 tcctgaggga cagtcctggt agaccagtgc c                                  91

<210> SEQ ID NO 10
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tccaccgact ttaaggagtc ggccttgagg aagcagtcct tatacctcaa gttcgacccc   60
ctcctgaggg acagtcctgg tagaccagtg g                                  91

<210> SEQ ID NO 11
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 11
gtccaccgac tttaaggagt cggccttgag gaagcagtcc ttatacctca agttcgaccc        60
cctcctgagg gacagtcctg gtagaccagt t        91

<210> SEQ ID NO 12
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgtccaccga ctttaaggag tcggccttga ggaagcagtc cttatgcctc aagttcggcc        60
ccctcctgag ggacagtcct ggtagaccag g        91

<210> SEQ ID NO 13
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gacgtccacc gactttaagg agtcggcctt gaggaagcag tccttatacc tcaagttcga        60 cccctcctg agggacagtc ctggtagacg        90

<210> SEQ ID NO 14
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgacgtccac cgactttaag gagtcggcct tgaggaagca gtccttatac ctcaagttcg        60
accccctcct gagggacagt cctggtagac c        91

<210> SEQ ID NO 15
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtgacgtcca ccgactttaa ggagtcggcc ttgaggaagc agtccttata cctcaagttc        60
gaccccctcc tgagggacag tcctggtaga a        91

<210> SEQ ID NO 16
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgtgacgtcc accgacttta aggagtcggc cttgaggaag cagtccttat acctcaagtt        60
cgaccccctc ctgagggaca gtcctggtag g                               91

<210> SEQ ID NO 17
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccgtgacgtc caccgacttt aaggagtcgg ccttgaggaa gcagtcctta tacctcaagt   60
tcgaccccct cctgagggac agtcctggta a                                91

<210> SEQ ID NO 18
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cttaccgtga cgtccaccga ctttaaggag tcggccttga ggaagcagtc cttatacctc   60
aagttcgacc ccctcctgag ggacagtcct t                                91

<210> SEQ ID NO 19
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtccttaccg tgacgtccac cgactttaag gagtcggcct tgaggaagca gtccttatac   60
ctcaagttcg accccctcct gagggacagt t                                91

<210> SEQ ID NO 20
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgtccttacc gtgacgtcca ccgactttaa ggagtcggcc ttgaggaagc agtccttata   60
cctcaagttc gaccccctcc tgagggacag g                                91

<210> SEQ ID NO 21
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgtccttac cgtgacgtcc accgacttta aggagtcggc cttgaggaag cagtccttat   60
acctcaagtt cgaccccctc ctgagggaca a                                91

```
<210> SEQ ID NO 22
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgtgtcctta ccgtgacgtc caccgacttt aaggagtcgg ccttgaggaa gcagtcctta    60
tacctcaagt tcgaccccct cctgagggac c                                   91

<210> SEQ ID NO 23
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
accgtgtcct taccgtgacg tccaccgact ttaaggagtc ggccttgagg aagcagtcct    60
tatacctcaa gttcgacccc ctcctgaggg g                                   91

<210> SEQ ID NO 24
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaccgtgtcc ttaccgtgac gtccaccgac tttaaggagt cggccttgag gaagcagtcc    60
ttatacctca agttcgaccc cctcctgagg g                                   91

<210> SEQ ID NO 25
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaccgtgtc cttaccgtga cgtccaccga ctttaaggag tcggccttga ggaagcagtc    60
cttatacctc aagttcgacc ccctcctgag g                                   91

<210> SEQ ID NO 26
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctggaccgtg tccttaccgt gacgtccacc gactttaagg agtcggcctt gaggaagcag    60
tccttatacc tcaagttcga ccccctcctg g                                   91

<210> SEQ ID NO 27
<211> LENGTH: 91
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 27
cctggaccgt gtccttaccg tgacgtccac cgactttaag gagtcggcct tgaggaagca    60
gtccttatac ctcaagttcg accccctcct t                                   91

<210> SEQ ID NO 28
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gacctggacc gtgtccttac cgtgacgtcc accgacttta aggagtcggc cttgaggaag    60
cagtccttat acctcaagtt cgaccccctc c                                   91

<210> SEQ ID NO 29
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggacctggac cgtgtcctta ccgtgacgtc caccgacttt aaggagtcgg ccttgaggaa    60
gcagtcctta tacctcaagt tcgaccccct t                                   91

<210> SEQ ID NO 30
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aggacctgga ccgtgtcctt accgtgacgt ccaccgactt taaggagtcg gccttgagga    60
agcagtcctt atacctcaag ttcgaccccc c                                   91

<210> SEQ ID NO 31
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gaggacctgg accgtgtcct taccgtgacg tccaccgact ttaaggagtc ggccttgagg    60
aagcagtcct tatacctcaa gttcgaccccc                                    90

<210> SEQ ID NO 32
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 32
ggaggacctg gaccgtgtcc ttaccgtgac gtccaccgac tttaaggagt cggccttgag     60
gaagcagtcc ttatacctca agttcgaccc                                      90

<210> SEQ ID NO 33
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tggaggacct ggaccgtgtc cttaccgtga cgtccaccga ctttaaggag tcggccttga     60
ggaagcagtc cttatacctc aagttcgacc                                      90

<210> SEQ ID NO 34
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtggaggacc tggaccgtgt ccttaccgtg acgtccaccg actttaagga gtcggccttg     60
aggaagcagt ccttatacct caagttcgac                                      90

<210> SEQ ID NO 35
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggtggaggac ctggaccgtg tccttaccgt gacgtccacc gactttaagg agtcggcctt     60
gaggaagcag tccttatacc tcaagttcga                                      90

<210> SEQ ID NO 36
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggtggagga cctggaccgt gtccttaccg tgacgtccac cgactttaag gagtcggcct     60
tgaggaagca gtccttatac ctcaagttcg                                      90

<210> SEQ ID NO 37
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctggtggagg acctggaccg tgtccttacc gtgacgtcca ccgactttaa ggagtcggcc     60

```
ttgaggaagc agtccttata cctctaatca                                          90

<210> SEQ ID NO 38
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gctggtggag gacctggacc gtgtccttac cgtgacgtcc accggcttta aggagtcggc         60
ctcgaggaag cagcccttt acctcaagtt                                           90

<210> SEQ ID NO 39
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agctggtgga ggacctggac cgtgtcctta ccgtgacgtc caccgacttt aaggagtcgg         60
ccttgaggaa gcagtcctta tacctcaagt                                          90

<210> SEQ ID NO 40
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cagctggtgg aggacctgga ccgtgtcctt accgtgacgt ccaccgactt taaggagtcg         60
gccttgagga agcagtcctt atacctcaag                                          90

<210> SEQ ID NO 41
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcagctggtg gaggacctgg accgtgtcct taccgtgacg tccaccgact ttaaggagtc         60
ggccttgagg aagcagtcct tatacctcaa                                          90

<210> SEQ ID NO 42
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agcagctggt ggaggacctg gaccgtgtcc ttaccgtgac gtccaccgac tttaaggagt         60
cggccttgag gaagcagtcc ttatacctca                                          90

<210> SEQ ID NO 43
```

<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aagcagctgg tggaggacct ggaccgtgtc cttaccgtga cgtccaccga ctttaaggag    60
tcggccttga ggaagcagtc cctatacccc                                     90

<210> SEQ ID NO 44
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
caagcagctg gtggaggacc tggaccgtgt ccttaccgtg acgtccaccg actttaagga    60
gtcggccttg aggaagcagt ccttatacct                                     90

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcaagcagct ggtggaggac ctggaccgtg tccttaccgt gacgtccacc gactttaagg    60
agtcggcctt gaggaagcag tccttatacc                                     90

<210> SEQ ID NO 46
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttcaagcagc tggtggagga cctggaccgt gtccttaccg tgacgtccac cgactttaag    60
gagtcggcct tgaggaagca gtccttatac                                     90

<210> SEQ ID NO 47
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cttcaagcag ctggtggagg acctggaccg tgtccttacc gtgacgtcca ccgactttaa    60
ggagtcggcc ttgaggaagc agtccttata                                     90

<210> SEQ ID NO 48
<211> LENGTH: 90
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 48
ccttcaagca gctggtggag gacctggacc gtgtccttac cgtgacgtcc accgacttta    60
aggagtcggc cttgaggaag cagtccttat                                     90

<210> SEQ ID NO 49
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
accttcaagc agctggtgga ggacctggac cgtgtcctta ccgtgacgtc caccgacttt    60
aaggagtcgg ccttgaggaa gcagtcctta                                     90

<210> SEQ ID NO 50
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caccttcaag cagctggtgg aggacctgga ccgtgtcctt accgtgacgt ccaccgactt    60
taaggagtcg gccttgagga agcagtcctt                                     90

<210> SEQ ID NO 51
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccaccttcaa gcagctggtg gaggacctgg accgtgtcct taccgtgacg tccaccgact    60
ttaaggagtc ggccttgagg aagcagtcct                                     90

<210> SEQ ID NO 52
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cccaccttca agcagctggt ggaggacctg gaccgtgtcc ttaccgtgac gtccaccgac    60
tttaaggagt cggccttgag gaagcagtcc                                     90

<210> SEQ ID NO 53
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
```

```
ggcccacctt caagcagctg gtggaggacc tggaccgtgt ccttaccgtg acgtccaccg    60
actttaagga gtcggccttg aggaagcagt                                    90

<210> SEQ ID NO 54
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aggcccacct tcaagcagct ggtggaggac ctggaccgtg tccttaccgt gacgtccacc    60
gactttaagg agtcggcctt gaggaagcag                                    90

<210> SEQ ID NO 55
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gaggcccacc ttcaagcagc tggtggagga cctggaccgt gtccttaccg tgacgtccac    60
cgactttaag gagtcggcct tgaggaagca                                    90

<210> SEQ ID NO 56
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agaggcccac cttcaagcag ctggtggagg tcctggaccg tgtccttacc gtgacgtcca    60
ccgactttaa ggagtcggcc ttgaggaagc                                    90

<210> SEQ ID NO 57
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cagaggccca ccttcaagca gctggtggag gacctggacc gtgtccttac cgtgacgtcc    60
accgacttta aggagtcggc cttgaggaag                                    90

<210> SEQ ID NO 58
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccagaggccc accttcaagc agctggtgga ggacctggac cgtgtcctta ccgtgacgtc    60
caccgacttt aaggagtcgg ccttgaggaa                                    90
```

<210> SEQ ID NO 59
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cccagaggcc caccttcaag cagctggtgg aggacctgga ccgtgtcctt accgtgacgt      60
ccaccgactt taaggagtcg gccttgagga                                      90

<210> SEQ ID NO 60
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tcccagaggc ccaccttcaa gcagctggtg gaggacctgg accgtgtcct taccgtgacg      60
tccaccgact ttaaggagtc ggccttgagg                                      90

<210> SEQ ID NO 61
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctcccagagg cccaccttca agcagctggt ggaggacctg gaccgtgtcc ttaccgtgac      60
gtccaccgac tttaaggagt cggccttgag                                      90

<210> SEQ ID NO 62
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cctcccagag gcccaccttc aagcagctgg tggaggacct ggaccgtgtc cttaccgtga      60
cgtccaccga ctttaaggag tcggccttga                                      90

<210> SEQ ID NO 63
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccctcccaga ggcccacctt caagcagctg gtggaggacc tggaccgtgt ccttaccgtg      60
acgtccaccg actttaagga gtcggccttg                                      90

<210> SEQ ID NO 64
<211> LENGTH: 90

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gcgccctccc agaggcccac cttcaagcag ctggtggagg acctggaccg tgtccttacc      60
gtgacgtcca ccgactttaa ggagtcggcc                                      90

<210> SEQ ID NO 65
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cgcgccctcc cagaggccca ccttcaagca gctggtggag gacctggacc gtgtccttac      60
cgtgacgtcc accgacttta aggagtcggc                                      90

<210> SEQ ID NO 66
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccgcgccctc ccagaggccc accttcaagc agctggtgga ggacctggac cgtgtcctta      60
ccgtgacgtc caccgacttt aaggagtcgg                                      90

<210> SEQ ID NO 67
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gccgcgccct cccagaggcc caccttcaag cagctggtgg aggacctgga ccgtgtcctt      60
accgtgacgt ccaccgactt taaggagtcg                                      90

<210> SEQ ID NO 68
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgccgcgccc tcccagaggc ccaccttcaa gcagctggtg gaggacctgg accgtgtcct      60
taccgtgacg tccaccgact ttaaggagtc                                      90

<210> SEQ ID NO 69
<211> LENGTH: 90
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 69
atgccgcgcc ctcccagagg cccaccttca agcagctggt ggaggacctg gaccgtgtcc    60
ttaccgtgac gtccaccgac tttaaggagt                                     90

<210> SEQ ID NO 70
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
catgccgcgc cctcccagag gcccaccttc aagcagctgg tggaggacct ggaccgtgtc    60
cttaccgtga cgtccaccga ctttaaggag                                     90

<210> SEQ ID NO 71
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcatgccgcg ccctcccaga ggcccacctt caagcagctg gtggaggacc tggaccgtgt    60
ccttaccgtg acgtccaccg actttaagga                                     90

<210> SEQ ID NO 72
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggcatgccgc gccctcccag aggcccacct tcaagcagct ggtggaggac ctggaccgtg    60
tccttaccgt gacgtccacc gactttaagg                                     90

<210> SEQ ID NO 73
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tggcatgccg cgccctccca gaggcccacc ttcaagcagc tggtggagga cctggaccgt    60
gtccttaccg tgacgtccac cgactttaag                                     90

<210> SEQ ID NO 74
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctggcatgcc gcgccctccc agaggcccac cttcaagcag ctggtggagg acctggaccg        60
tgtccttacc gtgacgtcca ccgactttaa                                          90

<210> SEQ ID NO 75
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gctggcatgc cgcgccctcc cagaggccca ccttcaagca gctggtggag gacctggacc        60
gtgtccttac cgtgacgtcc accgacttta                                          90

<210> SEQ ID NO 76
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgctggcatg ccgcgccctc ccagaggccc accttcaagc agctggtgga ggacctggac        60
cgtgtcctta ccgtgacgtc caccgacttt                                          90

<210> SEQ ID NO 77
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gtgctggcat gccgcgccct cccagaggcc caccttcaag cagctggtgg aggacctgga        60
ccgtgtcctt accgtgacgt ccaccgactt                                          90

<210> SEQ ID NO 78
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Cys Trp His Ala Ala Pro Ser Gln Arg Pro Thr Phe Lys Gln Leu Val
1               5                   10                  15

Glu Asp Leu Asp Arg Val Leu Thr Val Thr Ser Thr Asp Phe Lys Glu
            20                  25                  30

Ser Ala Leu Arg Lys Gln Ser Leu Tyr Leu Lys Phe Asp Pro Leu Leu
        35                  40                  45

Arg Asp Ser Pro Gly Arg Pro Val Pro Val Ala
    50                  55

<210> SEQ ID NO 79
<211> LENGTH: 1048
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400
```

```
Pro Pro Lys Lys Gly Leu Gly Ser Pro Thr Val His Lys Ile Ser Arg
            405                 410                 415
Phe Pro Leu Lys Arg Gln Val Ser Leu Glu Ser Asn Ala Ser Met Ser
        420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
        530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
Ala Ser Gln Lys Cys Ile His Arg Asp Leu Ala Ala Arg Asn Val Leu
        610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
            660                 665                 670
His Gln Ser Asp Val Trp Ser Phe Gly Val Leu Leu Trp Glu Ile Phe
            675                 680                 685
Thr Leu Gly Gly Ser Pro Tyr Pro Gly Ile Pro Val Glu Glu Leu Phe
        690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
            740                 745                 750
Thr Val Thr Ser Thr Asp Phe Lys Glu Ser Ala Leu Arg Lys Gln Ser
            755                 760                 765
Leu Tyr Leu Lys Phe Asp Pro Leu Leu Arg Asp Ser Pro Gly Arg Pro
        770                 775                 780
Val Pro Val Ala Thr Glu Thr Ser Ser Met His Gly Ala Asn Glu Thr
785                 790                 795                 800
Pro Ser Gly Arg Pro Arg Glu Ala Lys Leu Val Glu Phe Asp Phe Leu
                805                 810                 815
Gly Ala Leu Asp Ile Pro Val Pro Gly Pro Pro Pro Gly Val Pro Ala
```

Pro Gly Gly Pro Pro Leu Ser Thr Gly Pro Ile Val Asp Leu Leu Gln
            820                 825                 830
Tyr Ser Gln Lys Asp Leu Asp Ala Val Val Lys Ala Thr Gln Glu Glu
        835                 840                 845
Asn Arg Glu Leu Arg Ser Arg Cys Glu Glu Leu His Gly Lys Asn Leu
865                 870                 875                 880
Glu Leu Gly Lys Ile Met Asp Arg Phe Glu Glu Val Val Tyr Gln Ala
                885                 890                 895
Met Glu Glu Val Gln Lys Gln Lys Glu Leu Ser Lys Ala Glu Ile Gln
            900                 905                 910
Lys Val Leu Lys Glu Lys Asp Gln Leu Thr Thr Asp Leu Asn Ser Met
        915                 920                 925
Glu Lys Ser Phe Ser Asp Leu Phe Lys Arg Phe Glu Lys Gln Lys Glu
    930                 935                 940
Val Ile Glu Gly Tyr Arg Lys Asn Glu Glu Ser Leu Lys Lys Cys Val
945                 950                 955                 960
Glu Asp Tyr Leu Ala Arg Ile Thr Gln Glu Gly Gln Arg Tyr Gln Ala
                965                 970                 975
Leu Lys Ala His Ala Glu Glu Lys Leu Gln Leu Ala Asn Glu Glu Ile
            980                 985                 990
Ala Gln Val Arg Ser Lys Ala Gln  Ala Glu Ala Leu Ala  Leu Gln Ala
        995                 1000                1005
Ser Leu Arg Lys Glu Gln Met  Arg Ile Gln Ser Leu  Glu Lys Thr
    1010                1015                1020
Val Glu Gln Lys Thr Lys Glu  Asn Glu Glu Leu Thr  Arg Ile Cys
    1025                1030                1035
Asp Asp Leu Ile Ser Lys Met  Glu Lys Ile
    1040                1045

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 80 g acg tcc acc gac ttt aag gag tcg g                                26
  Thr Ser Thr Asp Phe Lys Glu Ser
  1               5

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 81 g acg tcc acc gac gta aag gcg aca ca                               27
  Thr Ser Thr Asp Val Lys Ala Thr
  1               5

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(27)

<400> SEQUENCE: 82 gcc gtc ccc ggc cat ccc tca gga cgt                              27
Ala Val Pro Gly His Pro Ser Gly Arg
1               5

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 83 g acc tcc aac cag ggg ctg ctg gag t                              26
  Thr Ser Asn Gln Gly Leu Leu Glu
  1               5

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 84 g acg tcc acc gac gtg cca ggc cca cc                             27
  Thr Ser Thr Asp Val Pro Gly Pro
  1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Ser Thr Asp Phe Lys Glu Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Thr Ser Thr Asp Val Lys Ala Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Val Pro Gly His Pro Ser Gly Arg
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Ser Asn Gln Gly Leu Leu Glu
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Ser Thr Asp Val Pro Gly Pro
1               5

<210> SEQ ID NO 90
<211> LENGTH: 806
<212> TYPE: PRT
<213> ORGANISM: Homo sapiens

<400> SEQUENCE: 90

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
```

```
                130               135               140
Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Ile Lys Leu Arg His
                195                 200                 205

Gln Gln Trp Ser Leu Val Met Glu Ser Val Val Pro Ser Asp Arg Gly
                210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
                290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
                355                 360                 365

Ala Gly Ser Val Tyr Ala Gly Ile Leu Ser Tyr Gly Val Gly Phe Phe
                370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
                435                 440                 445

Pro Thr Leu Ala Asn Val Ser Glu Leu Glu Leu Pro Ala Asp Pro Lys
                450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
                500                 505                 510

Asp Ala Thr Asp Lys Asp Leu Ser Asp Leu Val Ser Glu Met Glu Met
                515                 520                 525

Met Lys Met Ile Gly Lys His Lys Asn Ile Ile Asn Leu Leu Gly Ala
                530                 535                 540

Cys Thr Gln Gly Gly Pro Leu Tyr Val Leu Val Glu Tyr Ala Ala Lys
545                 550                 555                 560
```

```
Gly Asn Leu Arg Glu Phe Leu Arg Ala Arg Pro Pro Gly Leu Asp
                565                 570                 575

Tyr Ser Phe Asp Thr Cys Lys Pro Pro Glu Glu Leu Thr Phe Lys
                580                 585                 590

Asp Leu Val Ser Cys Ala Tyr Gln Val Ala Arg Gly Met Glu Tyr Leu
                595                 600                 605

Ala Ser Gln Lys Cys Ile His Arg Asp Leu Ala Ala Arg Asn Val Leu
                610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
                675                 680                 685

Thr Leu Gly Gly Ser Pro Tyr Pro Gly Ile Pro Val Glu Glu Leu Phe
                690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
                740                 745                 750

Thr Val Thr Ser Thr Asp Glu Tyr Leu Asp Leu Ser Ala Pro Phe Glu
                755                 760                 765

Gln Tyr Ser Pro Gly Gly Gln Asp Thr Pro Ser Ser Ser Ser Ser Gly
                770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 91
<211> LENGTH: 4304
<212> TYPE: DNA
<213> ORGANISM: Homo sapiens

<400> SEQUENCE: 91
gtcgcgggca gctggcgccg cgcggtcctg ctctgccggt cgcacggacg caccggcggg    60
ccgccggccg gagggacggg gcgggagctg ggcccgcgga cagcgagccg gagcgggagc   120
cgcgcgtagc gagccgggct ccggcgctcg ccagtctccc gagcggcgcc cgcctcccgc   180
cggtgcccgc gccgggccgt gggggcagc atgcccgcgc gcgctgcctg aggacgccgc   240
ggcccccgcc cccgccatgg gcgccccctgc ctgcgccctc gcgctctgcg tggccgtggc   300
catcgtggcc ggcgcctcct cggagtcctt ggggacggag cagcgcgtcg tggggcgagc   360
ggcagaagtc ccgggcccag agcccggcca gcaggagcag ttggtcttcg gcagcgggga   420
tgctgtggag ctgagctgtc cccgccggg gggtggtccc atgggcccca ctgtctgggt   480
caaggatggc acagggctgg tgccctcgga gcgtgtcctg gtgggccccc agcggctgca   540
ggtgctgaat gcctcccacg aggactccgg ggcctacagc tgccggcagc ggctcacgca   600
gcgcgtactg tgccacttca gtgtgcgggt gacagacgct ccatcctcgg gagatgacga   660
```

```
agacggggag gacgaggctg aggacacagg tgtggacaca ggggcccctt actggacacg    720
gcccgagcgg atggacaaga agctgctggc cgtgccggcc gccaacaccg tccgcttccg    780
ctgcccagcc gctggcaacc ccactccctc catctcctgg ctgaagaacg gcagggagtt    840
ccgcggcgag caccgcattg gaggcatcaa gctgcggcat cagcagtgga gcctggtcat    900
ggaaagcgtg gtgccctcgg accgcggcaa ctacacctgc gtcgtggaga caagtttgg    960 cagcatccgg cagacgtaca cgctggacgt gctggagcgc tccccgcacc ggcccatcct   1020
gcaggcgggg ctgccggcca accagacggc ggtgctgggc agcgacgtgg agttccactg   1080
caaggtgtac agtgacgcac agccccacat ccagtggctc aagcacgtgg aggtgaatgg   1140
cagcaaggtg ggcccggacg gcacacccta cgttaccgtg ctcaagacgg cgggcgctaa   1200
caccaccgac aaggagctag aggttctctc cttgcacaac gtcacctttg aggacgccgg   1260
ggagtacacc tgcctggcgg gcaattctat tgggttttct catcactctg cgtggctggt   1320
ggtgctgcca gccgaggagg agctggtgga ggctgacgag gcgggcagtg tgtatgcagg   1380
catcctcagc tacggggtgg gcttcttcct gttcatcctg gtggtggcgg ctgtgacgct   1440
ctgccgcctg cgcagccccc ccaagaaagg cctgggctcc ccaccgtgc acaagatctc   1500 ccgcttcccg ctcaagcgac aggtgtccct ggagtccaac gcgtccatga gctccaacac   1560
accactggtg cgcatcgcaa ggctgtcctc aggggagggc cccacgctgg ccaatgtctc   1620
cgagctcgag ctgcctgccg accccaaatg ggagctgtct cgggcccggc tgaccctggg   1680
caagcccctt ggggagggct gcttcggcca ggtggtcatg gcggaggcca tcggcattga   1740
caaggaccgg gccgccaagc ctgtcaccgt agccgtgaag atgctgaaag acgatgccac   1800
tgacaaggac ctgtcggacc tggtgtctga gatggagatg atgaagatga tcgggaaaca   1860
caaaaacatc atcaacctgc tgggcgcctg cacgcagggc gggcccctgt acgtgctggt   1920
ggagtacgcg gccaagggta acctgcggga gtttctgcgg gcgcggcggc ccccgggcct   1980
ggactactcc ttcgacacct gcaagccgcc cgaggagcag ctcaccttca aggacctggt   2040
gtcctgtgcc taccaggtgg cccggggcat ggagtacttg gcctcccaga gtgcatcca   2100 cagggacctg gctgcccgca atgtgctggt gaccgaggac aacgtgatga agatcgcaga   2160
cttcgggctg gcccgggacg tgcacaacct cgactactac aagaagacaa ccaacggccg   2220 gctgccgtg aagtggatgg cgcctgaggc cttgtttgac cgagtctaca ctcaccagag   2280
tgacgtctgg tcctttgggg tcctgctctg ggagatcttc acgctggggg ctccccgta   2340 ccccggcatc cctgtggagg agctcttcaa gctgctgaag gagggccacc gcatggacaa   2400
gcccgccaac tgcacacacg acctgtacat gatcatgcgg gagtgctggc atgccgcgcc   2460
ctcccagagg cccaccttca gcagctggt ggaggacctg gaccgtgtcc ttaccgtgac   2520
gtccaccgac gagtacctgg acctgtcggc gcctttcgag cagtactccc cgggtggcca   2580
ggacaccccc agctccagct cctcagggga cgactccgtg tttgcccacg acctgctgcc   2640
cccggcccca cccagcagtg ggggctcgcg gacgtgaagg gccactggtc cccaacaatg   2700
tgaggggtcc ctagcagccc accctgctgc tggtgcacag ccactccccg gcatgagact   2760
cagtgcagat ggagagacag ctacacagag ctttggtctg tgtgtgtgtg tgtgcgtgtg   2820
tgtgtgtgtg tgtgcacatc cgcgtgtgcc tgtgtgcgtg cgcatcttgc ctccaggtgc   2880
agaggtaccc tgggtgtccc cgctgctgtg caacggtctc ctgactggtg ctgcagcacc   2940
gaggggcctt tgttctgggg ggacccagtg cagaatgtaa gtgggcccac ccggtgggac   3000
ccccgtgggg cagggagctg ggcccgacat ggctccggcc tctgcctttg caccacggga   3060
```

```
catcacaggg tgggcctcgg cccctcccac acccaaagct gagcctgcag ggaagcccca    3120
catgtccagc accttgtgcc tggggtgtta gtggcaccgc ctccccacct ccaggctttc    3180
ccacttccca ccctgcccct cagagactga aattacgggt acctgaagat gggagccttt    3240 acctttatg caaaaggttt attccggaaa ctagtgtaca tttctataaa tagatgctgt     3300
gtatatggta tatatacata tatatatata acatatatgg aagaggaaaa ggctggtaca    3360
acggaggcct gcgaccctgg gggcacagga ggcaggcatg gccctgggcg gggcgtgggg    3420
gggcgtggag ggaggcccca gggggtctca cccatgcaag cagaggacca gggcctttc    3480 tggcaccgca gttttgtttt aaaactggac ctgtatattt gtaaagctat ttatgggccc    3540
ctggcactct tgttcccaca ccccaacact tccagcattt agctggccac atggcggaga    3600
gttttaattt ttaacttatt gacaaccgag aaggtttatc ccgccgatag agggacggcc    3660
aagaatgtac gtccagcctg ccccggagct ggaggatccc ctccaagcct aaaaggttgt    3720
taatagttgg aggtgattcc agtgaagata tttattttcc tttgtccttt ttcaggagaa    3780
ttagatttct ataggatttt tctttaggag atttattttt tggacttcaa agcaagctgg    3840
tattttcata caaattcttc taattgctgt gtgtcccagg cagggagacg gtttccaggg    3900
aggggccggc cctgtgtgca ggttccgatg ttattagatg ttacaagttt atatatatct    3960
atatatataa tttattgagt ttttacaaga tgtatttgtt gtagacttaa cacttcttac    4020
gcaatgcttc tagagtttta tagcctggac tgctaccttt caaagcttgg agggaagccg    4080
tgaattcagt tggttcgttc tgtactgtta ctgggccctg agtctgggca gctgtccctt    4140
gcttgcctgc agggccatgg ctcagggtgg tctcttcttg gggcccagtg catggtggcc    4200
agaggtgtca cccaaaccgg caggtgcgat tttgttaacc cagcgacgaa ctttccgaaa    4260
aataaagaca cctggttgct aacctggaaa aaaaaaaaa aaaa                     4304
```

<210> SEQ ID NO 92
<211> LENGTH: 838
<212> TYPE: PRT
<213> ORGANISM: Homo sapiens

<400> SEQUENCE: 92

```
Met Ser Leu Gln Val Leu Asn Asp Lys Asn Val Ser Asn Glu Lys Asn
1               5                   10                  15

Thr Glu Asn Cys Asp Phe Leu Phe Ser Pro Pro Glu Val Thr Gly Arg
            20                  25                  30

Ser Ser Val Leu Arg Val Ser Gln Lys Glu Asn Val Pro Pro Lys Asn
        35                  40                  45

Leu Ala Lys Ala Met Lys Val Thr Phe Gln Thr Pro Leu Arg Asp Pro
    50                  55                  60

Gln Thr His Arg Ile Leu Ser Pro Ser Met Ala Ser Lys Leu Glu Ala
65                  70                  75                  80

Pro Phe Thr Gln Asp Asp Thr Leu Gly Leu Glu Asn Ser His Pro Val
                85                  90                  95

Trp Thr Gln Lys Glu Asn Gln Gln Leu Ile Lys Glu Val Asp Ala Lys
            100                 105                 110

Thr Thr His Gly Ile Leu Gln Lys Pro Val Glu Ala Asp Thr Asp Leu
        115                 120                 125

Leu Gly Asp Ala Ser Pro Ala Phe Gly Ser Gly Ser Ser Glu Ser
    130                 135                 140

Gly Pro Gly Ala Leu Ala Asp Leu Asp Cys Ser Ser Ser Ser Gln Ser
```

```
                145                 150                 155                 160
        Pro Gly Ser Ser Glu Asn Gln Met Val Ser Pro Gly Lys Val Ser Gly
                        165                 170                 175

Ser Pro Glu Gln Ala Val Glu Glu Asn Leu Ser Ser Tyr Ser Leu Asp
                        180                 185                 190

Arg Arg Val Thr Pro Ala Ser Glu Thr Leu Glu Asp Pro Cys Arg Thr
                        195                 200                 205

Glu Ser Gln His Lys Ala Glu Thr Pro His Gly Ala Glu Glu Glu Cys
                        210                 215                 220

Lys Ala Glu Thr Pro His Gly Ala Glu Glu Cys Arg His Gly Gly
        225                 230                 235                 240

Val Cys Ala Pro Ala Ala Val Ala Thr Ser Pro Gly Ala Ile Pro
                        245                 250                 255

Lys Glu Ala Cys Gly Gly Ala Pro Leu Gln Gly Leu Pro Gly Glu Ala
                        260                 265                 270

Leu Gly Cys Pro Ala Gly Val Gly Thr Pro Val Pro Ala Asp Gly Thr
                        275                 280                 285

Gln Thr Leu Thr Cys Ala His Thr Ser Ala Pro Glu Ser Thr Ala Pro
                        290                 295                 300

Thr Asn His Leu Val Ala Gly Arg Ala Met Thr Leu Ser Pro Gln Glu
        305                 310                 315                 320

Glu Val Ala Ala Gly Gln Met Ala Ser Ser Ser Arg Ser Gly Pro Val
                        325                 330                 335

Lys Leu Glu Phe Asp Val Ser Asp Gly Ala Thr Ser Lys Arg Ala Pro
                        340                 345                 350

Pro Pro Arg Arg Leu Gly Glu Arg Ser Gly Leu Lys Pro Pro Leu Arg
                        355                 360                 365

Lys Ala Ala Val Arg Gln Gln Lys Ala Pro Gln Glu Val Glu Glu Asp
                        370                 375                 380

Asp Gly Arg Ser Gly Ala Gly Glu Asp Pro Pro Met Pro Ala Ser Arg
        385                 390                 395                 400

Gly Ser Tyr His Leu Asp Trp Asp Lys Met Asp Asp Pro Asn Phe Ile
                        405                 410                 415

Pro Phe Gly Gly Asp Thr Lys Ser Gly Cys Ser Glu Ala Gln Pro Pro
                        420                 425                 430

Glu Ser Pro Glu Thr Arg Leu Gly Gln Pro Ala Ala Glu Gln Leu His
                        435                 440                 445

Ala Gly Pro Ala Thr Glu Glu Pro Gly Pro Cys Leu Ser Gln Gln Leu
                        450                 455                 460

His Ser Ala Ser Ala Glu Asp Thr Pro Val Val Gln Leu Ala Ala Glu
        465                 470                 475                 480

Thr Pro Thr Ala Glu Ser Lys Glu Arg Ala Leu Asn Ser Ala Ser Thr
                        485                 490                 495

Ser Leu Pro Thr Ser Cys Pro Gly Ser Glu Pro Val Pro Thr His Gln
                        500                 505                 510

Gln Gly Gln Pro Ala Leu Glu Leu Lys Glu Glu Ser Phe Arg Asp Pro
                        515                 520                 525

Ala Glu Val Leu Gly Thr Gly Ala Glu Val Asp Tyr Leu Glu Gln Phe
                        530                 535                 540

Gly Thr Ser Ser Phe Lys Glu Ser Ala Leu Arg Lys Gln Ser Leu Tyr
        545                 550                 555                 560

Leu Lys Phe Asp Pro Leu Leu Arg Asp Ser Pro Gly Arg Pro Val Pro
                        565                 570                 575
```

```
Val Ala Thr Glu Thr Ser Ser Met His Gly Ala Asn Glu Thr Pro Ser
            580                 585                 590

Gly Arg Pro Arg Glu Ala Lys Leu Val Glu Phe Asp Phe Leu Gly Ala
        595                 600                 605

Leu Asp Ile Pro Val Pro Gly Pro Pro Gly Val Pro Ala Pro Gly
610                 615                 620

Gly Pro Pro Leu Ser Thr Gly Pro Ile Val Asp Leu Leu Gln Tyr Ser
625                 630                 635                 640

Gln Lys Asp Leu Asp Ala Val Val Lys Ala Thr Gln Glu Glu Asn Arg
                645                 650                 655

Glu Leu Arg Ser Arg Cys Glu Glu Leu His Gly Lys Asn Leu Glu Leu
            660                 665                 670

Gly Lys Ile Met Asp Arg Phe Glu Val Val Tyr Gln Ala Met Glu
        675                 680                 685

Glu Val Gln Lys Gln Lys Glu Leu Ser Lys Ala Glu Ile Gln Lys Val
    690                 695                 700

Leu Lys Glu Lys Asp Gln Leu Thr Thr Asp Leu Asn Ser Met Glu Lys
705                 710                 715                 720

Ser Phe Ser Asp Leu Phe Lys Arg Phe Glu Lys Gln Lys Glu Val Ile
                725                 730                 735

Glu Gly Tyr Arg Lys Asn Glu Glu Ser Leu Lys Lys Cys Val Glu Asp
            740                 745                 750

Tyr Leu Ala Arg Ile Thr Gln Glu Gly Gln Arg Tyr Gln Ala Leu Lys
        755                 760                 765

Ala His Ala Glu Glu Lys Leu Gln Leu Ala Asn Glu Glu Ile Ala Gln
    770                 775                 780

Val Arg Ser Lys Ala Gln Ala Glu Ala Leu Ala Leu Gln Ala Ser Leu
785                 790                 795                 800

Arg Lys Glu Gln Met Arg Ile Gln Ser Leu Glu Lys Thr Val Glu Gln
                805                 810                 815

Lys Thr Lys Glu Asn Glu Glu Leu Thr Arg Ile Cys Asp Asp Leu Ile
            820                 825                 830

Ser Lys Met Glu Lys Ile
        835

<210> SEQ ID NO 93
<211> LENGTH: 2847
<212> TYPE: DNA
<213> ORGANISM: Homo sapiens

<400> SEQUENCE: 93
gcgtttgaaa ctccggcgcg ccggcggcca tcaagggcta gaagcgcgac ggcggtagca      60
gctaggcttg gccccggcg tggagcagac gcggacccct ccttcctggc ggcggcggcg     120
cgggctcaga gcccggcaac gggcgggcgg cagaatgag tctgcaggtc ttaaacgaca     180
aaaatgtcag caatgaaaaa aatacagaaa attgcgactt cctgttttcg ccaccagaag     240
ttaccggaag atcgtctgtt cttcgtgtgt cacagaaaga aaatgtgcca cccaagaacc     300
tggccaaagc tatgaaggtg acttttcaga cacctctgcg ggatccacag acgcacagga     360
ttctaagtcc tagcatggcc agcaaacttg aggctccttt cactcaggat gacacccttg     420
gactggaaaa ctcacacccg gtctggacac agaaagagaa ccaacagctc atcaaggaag     480
tggatgccaa aactactcat ggaattctac agaaaccagt ggaggctgac accgacctcc     540
tgggggatgc aagcccagcc tttgggagtg cagctccag cgagtctggc ccaggtgccc     600
```

```
tggctgacct ggactgctca agctcttccc agagcccagg aagttctgag aaccaaatgg      660
tgtctccagg aaaagtgtct ggcagccctg agcaagccgt ggaggaaaac cttagttcct      720
attccttaga cagaagagtg acaccgcct ctgagaccct agaagaccct tgcaggacag       780
agtcccagca caaagcggag actccgcacg agccgagga agaatgcaaa gcggagactc       840
cgcacggagc cgaggaggaa tgccggcacg gtggggtctg tgctcccgca gcagtggcca      900
cttcgcctcc tggtgcaatc cctaaggaag cctgcggagg agcaccctg cagggtctgc       960 ctggcgaagc cctgggctgc cctgcgggtg tgggcacccc cgtgccagca gatggcactc     1020
agacccttac ctgtgcacac acctctgctc ctgagagcac agcccaacc aaccacctgg      1080 tggctggcag ggccatgacc ctgagtcctc aggaagaagt ggctgcaggc caaatggcca     1140
gctcctcgag gagcggacct gtaaaactag aatttgatgt atctgatggc gccaccagca     1200
aaagggcacc cccaccaagg agactgggag agaggtccgg cctcaagcct cccttgagga     1260
aagcagcagt gaggcagcaa aaggcccgc aggaggtgga ggaggacgac ggtaggagcg      1320
gagcaggaga ggaccccccc atgccagctt ctcggggctc ttaccacctc gactgggaca     1380
aaatggatga cccaaacttc atcccgttcg gaggtgacac caagtctggt tgcagtgagg     1440
cccagccccc agaaagccct gagaccaggc tgggccagcc agcggctgaa cagttgcatg     1500
ctgggcctgc cacggaggag ccaggtccct gtctgagcca gcagctgcat tcagcctcag     1560
cggaggacac gcctgtggtg cagttggcag ccgagacccc aacagcagag agcaaggaga     1620
gagccttgaa ctctgccagc acctcgcttc ccacaagctg tccaggcagt gagccagtgc     1680
ccacccatca gcagggcag cctgccttgg agctgaaaga ggagagcttc agagaccccg      1740
ctgaggttct aggcacgggc gcggaggtgg attacctgga gcagtttgga acttcctcgt     1800
ttaaggagtc ggccttgagg aagcagtcct tatacctcaa gttcgacccc ctcctgaggg     1860
acagtcctgg tagaccagtg cccgtggcca ccgagaccag cagcatgcac ggtgcaaatg     1920
agactccctc aggacgtccg cgggaagcca agcttgtgga gttcgatttc ttgggagcac     1980
tggacattcc tgtgccaggc ccaccccag gtgttcccgc gcctgggggc ccacccctgt      2040
ccaccggacc tatagtggac ctgctccagt acagccagag ggacctggat gcagtggtaa     2100
aggcgacaca ggaggagaac cgggagctga ggagcaggtg tgaggagctc acgggaaga     2160 acctggaact ggggaagatc atggacaggt tcgaagaggt tgtgtaccag gccatggagg     2220
aagttcagaa gcagaaggaa ctttccaaag ctgaaatcca gaaagttcta aagaaaaag     2280 accaacttac cacagatctg aactccatgg agaagtcctt ctccgacctc ttcaagcgtt     2340
ttgagaaaca gaaagaggtg atcgagggct accgcaagaa cgaagagtca ctgaagaagt     2400
gcgtggagga ttacctggca aggatcaccc aggagggcca gaggtaccaa gccctgaaggg    2460 cccacgcgga ggagaagctg cagctggcaa acgaggagat cgcccaggtc cggagcaagg     2520
cccaggcgga agcgttggcc ctccaggcca gcctgaggaa ggagcagatg cgcatccagt     2580
cgctggagaa gacagtggag cagaagacta aagagaacga ggagctgacc aggatctgcg     2640
acgacctcat ctccaagatg gagaagatct gacctccacg gagccgctgt ccccgccccc     2700
ctgctcccgt ctgtctgtcc tgtctgattc tcttaggtgt catgttctt tttctgtctt      2760 gtcttcaact tttttaaaaa ctagattgct ttgaaaacat gactcaataa aagtttcctt     2820
tcaatttaaa cactgaaaaa aaaaaaa                                         2847
```

<210> SEQ ID NO 94

<211> LENGTH: 3578
<212> TYPE: DNA
<213> ORGANISM: Homo sapiens

<400> SEQUENCE: 94

```
gtcgcgggca gctggcgccg cgcggtcctg ctctgccggt cgcacggacg caccggcggg      60
ccgccggccg gagggacggg gcgggagctg ggcccgcgga cagcgagccg gagcgggagc     120
cgcgcgtagc gagccgggct ccggcgctcg ccagtctccc gagcggcgcc cgcctcccgc     180
cggtgcccgc gccgggccgt gggggcagc atgcccgcgc gcgctgcctg aggacgccgc      240
ggccccgcc cccgccatgg gcgccccgc ctgcgccctc gcgctctgcg tggccgtggc       300
catcgtggcc ggcgcctcct cggagtcctt ggggacggag cagcgcgtcg tggggcgagc     360
ggcagaagtc ccgggcccag agcccggcca gcaggagcag ttggtcttcg gcagcgggga     420
tgctgtggag ctgagctgtc ccccgcccgg gggtggtccc atggggccca ctgtctgggt     480
caaggatggc acagggctgg tgccctcgga gcgtgtcctg gtgggccccc agcggctgca     540
ggtgctgaat gcctcccacg aggactccgg ggcctacagc tgccgcagc ggctcacgca      600
gcgcgtactg tgccacttca gtgtgcgggt gacagacgct ccatcctcgg agatgacga     660
agacggggag gacgaggctg aggacacagg tgtggacaca ggggcccctt actggacacg     720
gcccgagcgg atggacaaga agctgctggc cgtgccggcc gccaacaccg tccgcttccg     780
ctgcccagcc gctggcaacc ccactccctc catctcctgg ctgaagaacg gcaggagtt      840
ccgcggcgag caccgcattg gaggcatcaa gctgcggcat cagcagtgga gcctggtcat     900
ggaaagcgtg gtgccctcgg accgcggcaa ctacacctgc gtcgtggaga caagtttgg      960
cagcatccgg cagacgtaca cgctggacgt gctggagcgc tccccgcacc ggcccatcct    1020
gcaggcgggg ctgccggcca accagacggc ggtgctgggc agcgacgtgg agttccactg    1080
caaggtgtac agtgacgcac agccccacat ccagtggctc aagcacgtgg aggtgaatgg    1140
cagcaaggtg ggcccggacg gcacacccta cgttaccgtg ctcaagacgg cgggcgctaa    1200
caccaccgac aaggagctag aggttctctc cttgcacaac gtcacctttg aggacgccgg    1260
ggagtacacc tgcctggcgg gcaattctat tgggttttct catcactctg cgtggctggt    1320
ggtgctgcca gccgaggagg agctggtgga ggctgacgag gcgggcagtg tgtatgcagg    1380
catcctcagc tacgggtgg gcttcttcct gttcatcctg gtggtggcgg ctgtgacgct    1440
ctgccgcctg cgcagccccc caagaaagg cctgggctcc ccaccgtgc acaagatctc      1500
ccgcttcccg ctcaagcgac aggtgtccct ggagtccaac gcgtccatga gctccaacac    1560
accactggtg cgcatcgcaa ggctgtcctc aggggagggc cccacgctgg ccaatgtctc    1620
cgagctcgag ctgcctgccg acccccaaatg ggagctgtct cgggcccggc tgaccctggg    1680
caagccccctt ggggagggct gcttcggcca ggtggtcatg gcggaggcca tcggcattga    1740
caaggaccgg gccgccaagc ctgtcaccgt agccgtgaag atgctgaaag acgatgccac    1800
tgacaaggac ctgtcggacc tggtgtctga gatggagatg atgaagatga tcgggaaaca    1860
caaaaacatc atcaacctgc tgggcgcctg cacgcagggc gggccctgt acgtgctggt     1920
ggagtacgcg gccaagggta acctgcggga gtttctgcgg gcgcggcggc cccgggcct     1980
ggactactcc ttcgacacct gcaagccgcc cgaggagcag ctcaccttca aggacctggt    2040
gtcctgtgcc taccaggtgg cccgggggcat ggagtacttg gcctcccaga gtgcatcca    2100
cagggacctg gctgccgca atgtgctggt gaccgaggac aacgtgatga agatcgcaga    2160
cttcgggctg gcccgggacg tgcacaacct cgactactac aagaagacaa ccaacggccg    2220
```

```
gctgcccgtg aagtggatgg cgcctgaggc cttgtttgac cgagtctaca ctcaccagag   2280
tgacgtctgg tcctttgggg tcctgctctg ggagatcttc acgctggggg gctccccgta   2340
ccccggcatc cctgtggagg agctcttcaa gctgctgaag gagggccacc gcatggacaa   2400
gcccgccaac tgcacacacg acctgtacat gatcatgcgg gagtgctggc atgccgcgcc   2460
ctcccagagg cccaccttca agcagctggt ggaggacctg gaccgtgtcc ttaccgtgac   2520
gtccaccgac tttaaggagt cggccttgag gaagcagtcc ttatacctca agttcgaccc   2580
cctcctgagg gacagtcctg gtagaccagt gcccgtggcc accgagacca gcagcatgca   2640
cggtgcaaat gagactccct caggacgtcc gcgggaagcc aagcttgtgg agttcgattt   2700
cttgggagca ctggacattc ctgtgccagg cccaccccca ggtgttcccg cgcctggggg   2760
cccacccctg tccaccggac ctatagtgga cctgctccag tacagccaga aggacctgga   2820
tgcagtggta aaggcgacac aggaggagaa ccgggagctg aggagcaggt gtgaggagct   2880
ccacgggaag aacctggaac tggggaagat catggacagg ttcgaagagg ttgtgtacca   2940
ggccatggag gaagttcaga agcagaagga actttccaaa gctgaaatcc agaaagttct   3000
aaaagaaaaa gaccaactta ccacagatct gaactccatg gagaagtcct tctccgacct   3060
cttcaagcgt tttgagaaac agaaagaggt gatcgagggc taccgcaaga acgaagagtc   3120
actgaagaag tgcgtggagg attacctggc aaggatcacc caggagggcc agaggtacca   3180
agccctgaag gcccacgcgg aggagaagct gcagctggca aacgaggaga tcgcccaggt   3240
ccggagcaag gcccaggcgg aagcgttggc cctccaggcc agcctgagga aggagcagat   3300
gcgcatccag tcgctggaga agacagtgga gcagaagact aaagagaacg aggagctgac   3360
caggatctgc gacgacctca tctccaagat ggagaagatc tgacctccac ggagccgctg   3420
tccccgcccc cctgctcccg tctgtctgtc ctgtctgatt ctcttaggtg tcatgttctt   3480
ttttctgtct tgtcttcaac ttttttaaaa actagattgc tttgaaaaca tgactcaata   3540
aaagtttcct ttcaatttaa acactgaaaa aaaaaaaa                          3578
```

<210> SEQ ID NO 95
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
catcctgccc ccagagtgc tgaggtgtgg ggcgggcctt ctggggcaca gcctgggcac    60
agaggtggct gtgcgaaggt cgctgagggt ccaggcttcc acccagtgtc cccgcagtca   120 gctgccacc agcagcctcc ccgggactct cc                                  152
```

<210> SEQ ID NO 96
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

```
ggctgggcga agttcgctga gggtccaggc ttcctcccag tgtccccgca gtcagctgcc    60
caccagcagc ctccccc                                                   77
```

<210> SEQ ID NO 97
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
acagcctggg cacagaggtg gctgtgcgaa ggtcgctgag ggtccaggct tccacccagt    60
gtccccgcag tcagctt                                                  77

<210> SEQ ID NO 98
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggcacagcct gggcacagag gtggctgtgc gaaggtcgct gagggtccag gcttccaccc    60
agtgtccccg cagtcaa                                                  77

<210> SEQ ID NO 99
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ttctggggca cagcctgggc acagaggtgg ctgtgcgaag gtcgctgagg gtccaggctt    60
ccacccagtg tccccgg                                                  77

<210> SEQ ID NO 100
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cttctgtggc acagcctggc acagaggtg gctgtgcgaa ggtcgctgag ggtccaggct    60
tccacccagt gtccccc                                                  77

<210> SEQ ID NO 101
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gccttctggg gcacagcctg ggcacagagg tggctgtgcg aaggtcgctg agggtccagg    60
cttccaccca gtgtccc                                                  77

<210> SEQ ID NO 102
<211> LENGTH: 77
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 102
ggtgtggggc gggccggctg gggcacagcc ggggcacaga ggtggctgtg cgaaggtcgc    60
tgagggtcca ggcttcc                                                   77

<210> SEQ ID NO 103
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggtgtggggc gggccttctg gggcacagcc tgggcacaga ggtggctgtg cgaaggtcgc    60
tgagggtcca ggcttcc                                                   77

<210> SEQ ID NO 104
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgctgaggtg tggggcgggc cttctggggc acagcctggg cacagaggtg gctgtgcgaa    60
ggtcgctgag ggtccaa                                                   77

<210> SEQ ID NO 105
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
agtgctgagg tgtggggcgg gccttctggg gcacagcctg gcacagagg tggctgtgcg     60 aaggtcgctg agggtcc                                                   77

<210> SEQ ID NO 106
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cccagagtgc tgaggtgtgg ggcgggcctt ctggggcaca gcctgggcac agaggtggct    60
gtgcgaaggt cgctgaa                                                   77

<210> SEQ ID NO 107
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 107
cctgcccccc agagtgctga ggtgtggggc gggccttctg gggcacagcc tgggcacaga    60
ggtggctgtg cgaagg                                                    76

<210> SEQ ID NO 108
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gtgctggctc tggcctggtg ccacccgcct atgcccctcc ccctgccgtc cccggccatc    60
ctgcccccca gagtgccggg ggctaagggc cagggaggtc acctgcacac tcccaccccc   120
ggtcacccgc acactcccac ccccggtcac cca                                153

<210> SEQ ID NO 109
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
agagtgcagg gggctaaggg ccagggaggt cacctgcaca ctcccacccc cggtcacccg    60
cacactccca cccccg                                                    76

<210> SEQ ID NO 110
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggccatcctg ccccccagag tgcaggggc taagggccag ggaggtcccc tgcacactcc     60
ctcccccggt cacccg                                                    76

<210> SEQ ID NO 111
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tccccctgcc gtccccggcc atcctgcccc ccagagtgca gggggctaag ggccagggag    60
gtcacctgca cactcc                                                    76

<210> SEQ ID NO 112
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
tgacgtccac cgacgtgagt gctggctctg gcctggtgcc acccgcctat gcccctcccc    60
ctgccgtccc cggccatccc tcaggacgtc cgcgggaagc caagcttgtg gagttcgatt   120
tcttgggagc actggacatt cctgtaagtc ct                                 152
```

```
<210> SEQ ID NO 113
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
atccctcagg acgtccgcgg gaagccaagc ttgtggagtt cgatttcttg ggagcactgg    60
acattcctgt aagtcc                                                   76
```

```
<210> SEQ ID NO 114
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
catccctcag gacgtccgcg ggaagccaag cttgtggagt tcgatttctt gggagcactg    60
gacattcctg taagtc                                                   76
```

```
<210> SEQ ID NO 115
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
catccctcag gacgtccgcg ggaagccaag cttgtggagt tcgatttctt gggagcactg    60
gacattcctg taagtc                                                   76
```

```
<210> SEQ ID NO 116
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gccatccctc aggacgtccg cgggaagcca agcttgtgga gttcgatttc ttgggagcac    60
tggacattcc tgtaag                                                   76
```

```
<210> SEQ ID NO 117
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ccggccatcc ctcaggacgt ccgcgggaag ccaagcttgt ggagttcgat ttcttgggag    60
```
cactggacat tcctgt                                                         76

<210> SEQ ID NO 118
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cacggccatc ccggaggacg tccgcgggaa cccaagcttg tggagttcga tttcttggta        60
gcactggaca ttcctg                                                         76

<210> SEQ ID NO 119
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cccggccatc cctcaggacg tccgcgggaa gccaagcttg tggagttcga tttcttggga        60
gcactggaca ttcctg                                                         76

<210> SEQ ID NO 120
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tccccggcca tccctcagga cgtccgcggg aagccaagct tgtggagttc gatttcttgg        60
gagcactgga cattcc                                                         76

<210> SEQ ID NO 121
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 121
tccccggcca tccctcagga ngtccgcggg aagccaagct tgtggagttc gatttcttgg        60
gagcactgga cattcc                                                         76

<210> SEQ ID NO 122
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtccccggcc atccctcagg acgtccgcgg gaagccaagc ttgtggagtt cgatttcttg        60

```
ggagcactgg acattc                                                    76

<210> SEQ ID NO 123
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ccgtccccgg ccatccctca ggacgtccgc gggaagccaa gcttgtggag ttcgatttct   60
tgggagcact ggacat                                                    76

<210> SEQ ID NO 124
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124 tcccccctgcc gtccccggcc atccctcagg acgtccgcgg gaagccaagc ttgtggagtt   60
cgatttcttg ggagca                                                    76

<210> SEQ ID NO 125
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
atgcccctcc ccctgccgtc cccggccatc cctcaggacg tccgcgggaa gccaagcttg   60
tggagttcga tttctt                                                    76

<210> SEQ ID NO 126
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cctatgcccc tccccctgcc gccccggcc atccctcagg acgtccgcgg gaagccaagc    60
ttgtggagtt cgattt                                                    76

<210> SEQ ID NO 127
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ctggcctggt gccacccgcc tatgcccctc ccctgccgt ccccggccat ccctcaggac    60
gtccgcggga agccaa                                                    76
```

```
<210> SEQ ID NO 128
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gagctggcct ggtgccacac gcctatgccc ctcccctgc cgtccccggc gatccatcag    60
gaagtccgcg ggacga                                                  76

<210> SEQ ID NO 129
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(40)
<223> OTHER INFORMATION: a, c, t, g, unknown or other

<400> SEQUENCE: 129
ggctctggcc tggtgccacc cgcctatgcc cctccccctn ccgtccccgg ccatccctca    60
ggacgtccgc gggaag                                                   76

<210> SEQ ID NO 130
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gtgctggctc tggcctggtg ccacccgcct atgcccctcc cctgccgtc cccggccatc    60 cctcaggacg tccgcg                                                   76

<210> SEQ ID NO 131
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ccaccgacgt gagtgctggc tctggcctgg tgccacccgc ctatgcccct ccccctgccg    60
tccccggcca tccctc                                                   76

<210> SEQ ID NO 132
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
tggaccgtgt ccttaccgtg acgtccaccg acgtgagtgc tggctctggc ctggtgccac    60 cgcctatgc cctcccctg gcccttagcc cccgtgtgtg ttaggggatg gcagtcagac    120
ctgatcactt gccctcttgt ccccagttta a                                 151
```

<210> SEQ ID NO 133
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgcccctccc ctgcccttag ccccctgtg tgtgttaggg atggcagtc agacctgatc    60 acttgccctc ttgtccgtcc                                              80

<210> SEQ ID NO 134
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
atgcccctcc cctgcccttca gcccccctgt gtgtgttagg ggatggcagt cagacctgat    60
cacttgccct cttgtctgtc                                                80

<210> SEQ ID NO 135
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcctatgccc ctccctgcc cttagccccc ctgtgtgtgt tagggatgg cagtcagacc    60 tgatcacttg ccctctctct                                              80

<210> SEQ ID NO 136
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gtgccacccg cctatgcccc tccctgccc ttagccccc tgtgtgtgtt aggggatggc    60
agtcagacct gatcactcac                                              80

<210> SEQ ID NO 137
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gctctggcct ggtgccccc gcctatgccc ctccctgcc cttagccccc ctgtgtgtgt    60 tagggatgg cagtcagtca                                                80

<210> SEQ ID NO 138
<211> LENGTH: 80

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gctctggcct ggtgccgccc gcctatgccc ctccctgcc cttagccccc ctgtgtgtgt    60 tagggatgg cagtcagtca                                                 80

<210> SEQ ID NO 139
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gctgcctctg tcctggtgcc cccgcctat gccctcccc tgcccttagc ccccctgtgt      60
gtgttagggg atggcatggc a                                              81

<210> SEQ ID NO 140
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cacccgccgg gggtgcgggc tctggcctgg tgcccccgc ctatgcccct ccctgccct     60 tagccccct gtgtgttgtg t                                               81

<210> SEQ ID NO 141
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 cccccgacg tgagtgctgg ctcgggcctg gtcccccccg cctatgcccc tccctgccc      60 ttagccccc tgtgtgtgtg                                                 80

<210> SEQ ID NO 142
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gacgtccacc gacgtgagtg ctggctctgg cctggtgcca cccgcctatg cccctcccct    60
gcccttagac ccctgcccc tg                                              82

<210> SEQ ID NO 143
<211> LENGTH: 84
<212> TYPE: DNA
<213> ORGANISM: Artificial Sequence
<220> FEATURE:
<223> OTHER INFORMATION: Description of Artificial Sequence: Synthetic
```

-continued

```
         oligonucleotide

<400> SEQUENCE: 143
cttaccgtga cgtccaccga cgtgagtgct ggctctggcc tggtgccacc cgcctatgcc    60
cctcccctgc ccttaggccc ttag                                           84

<210> SEQ ID NO 144
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cccttcaggt ccccccccccc gacgtgagtg ctggctctgg cctggtgcca cccgcctatg    60
cccctcccct gcccttgccc tt                                             82

<210> SEQ ID NO 145
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tgtccttacc gtgacgtcca ccgacgtgag tgctggctct ggcctggtgc cacccgccta    60
tgcccctccc ctgcccctgc cc                                             82

<210> SEQ ID NO 146
<211> LENGTH: 820
<212> TYPE: PRT
<213> ORGANISM: Homo sapiens

<400> SEQUENCE: 146

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175
```

```
Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
            245                 250                 255

Leu Gln Ala Gly Leu Pro Ala Asn Lys Thr Val Ala Leu Gly Ser Asn
        260                 265                 270

Val Glu Phe Met Cys Lys Val Tyr Ser Asp Pro Gln Pro His Ile Gln
    275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
        340                 345                 350

Ser Ala Trp Leu Thr Val Leu Glu Ala Leu Glu Arg Pro Ala Val
    355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Ser Ala Asp Ser Ser
        420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
        500                 505                 510

Met Leu Lys Ser Asp Ala Thr Glu Lys Asp Leu Ser Asp Leu Ile Ser
    515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
            565                 570                 575

Pro Gly Leu Glu Tyr Cys Tyr Asn Pro Ser His Asn Pro Glu Glu Gln
        580                 585                 590

Leu Ser Ser Lys Asp Leu Val Ser Cys Ala Tyr Gln Val Ala Arg Gly
```

```
                595                 600                 605
Met Glu Tyr Leu Ala Ser Lys Lys Cys Ile His Arg Asp Leu Ala Ala
            610                 615                 620
Arg Asn Val Leu Val Thr Glu Asp Asn Val Met Lys Ile Ala Asp Phe
625                 630                 635                 640
Gly Leu Ala Arg Asp Ile His His Ile Asp Tyr Tyr Lys Lys Thr Thr
                645                 650                 655
Asn Gly Arg Leu Pro Val Lys Trp Met Ala Pro Glu Ala Leu Phe Asp
            660                 665                 670
Arg Ile Tyr Thr His Gln Ser Asp Val Trp Ser Phe Gly Val Leu Leu
            675                 680                 685
Trp Glu Ile Phe Thr Leu Gly Gly Ser Pro Tyr Pro Gly Val Pro Val
            690                 695                 700
Glu Glu Leu Phe Lys Leu Leu Lys Glu Gly His Arg Met Asp Lys Pro
705                 710                 715                 720
Ser Asn Cys Thr Asn Glu Leu Tyr Met Met Met Arg Asp Cys Trp His
                725                 730                 735
Ala Val Pro Ser Gln Arg Pro Thr Phe Lys Gln Leu Val Glu Asp Leu
            740                 745                 750
Asp Arg Ile Val Ala Leu Thr Ser Asn Gln Glu Tyr Leu Asp Leu Ser
            755                 760                 765
Met Pro Leu Asp Gln Tyr Ser Pro Ser Phe Pro Asp Thr Arg Ser Ser
770                 775                 780
Thr Cys Ser Ser Gly Glu Asp Ser Val Phe Ser His Glu Pro Leu Pro
785                 790                 795                 800
Glu Glu Pro Cys Leu Pro Arg His Pro Ala Gln Leu Ala Asn Gly Gly
                805                 810                 815
Leu Lys Arg Arg
            820

<210> SEQ ID NO 147
<211> LENGTH: 5895
<212> TYPE: DNA
<213> ORGANISM: Homo sapiens

<400> SEQUENCE: 147
agatgcaggg gcgcaaacgc caaaggagac caggctgtag gaagagaagg gcagagcgcc        60
ggacagctcg gcccgctccc cgtcctttgg ggccgcggct ggggaactac aaggcccagc       120
aggcagctgc aggggcgga ggcggaggag ggaccagcgc gggtgggagt gagagagcga       180
gccctcgcgc cccgccggcg catagcgctc ggagcgctct tgcggccaca ggcgcggcgt       240
cctcggcggc gggcggcagc tagcgggagc cgggacgccg gtgcagccgc agcgcgcgga       300
ggaacccggg tgtgccggga gctgggcggc cacgtccgga cgggaccgag acccctcgta       360
gcgcattgcg gcgacctcgc cttccccggc cgcgagcgcg ccgctgcttg aaaagccgcg       420
gaacccaagg actttctcc ggtccgagct cggggcgccc gcagggcgc acggtacccg       480 tgctgcagtc gggcacgccg cggcgccggg gcctccgcag ggcgatggag cccggtctgc       540
aaggaaagtg aggcgccgcc gctgcgttct ggaggagggg ggcacaaggt ctggagaccc       600
cgggtggcgg acgggagccc tccccccgcc ccgcctccgg ggcaccagct ccggctccat       660
tgttcccgcc cggctggag gcgccgagca ccgagcgccg ccgggagtcg agcgccggcc       720
gcggagctct tgcgacccg ccaggacccg aacagagccc gggggcggcg ggccggagcc       780
ggggacgcgg gcacacgccc gctcgcacaa gccacggcgg actctcccga ggcggaacct       840
```

```
ccacgccgag cgagggtcag tttgaaaagg aggatcgagc tcactgtgga gtatccatgg    900
agatgtggag ccttgtcacc aacctctaac tgcagaactg ggatgtggag ctggaagtgc    960
ctcctcttct gggctgtgct ggtcacagcc acactctgca ccgctaggcc gtccccgacc   1020
ttgcctgaac aagcccagcc ctggggagcc cctgtggaag tggagtcctt cctggtccac   1080
cccggtgacc tgctgcagct tcgctgtcgg ctgcgggacg atgtgcagag catcaactgg   1140
ctgcgggacg gggtgcagct ggcggaaagc aaccgcaccc gcatcacagg ggaggaggtg   1200
gaggtgcagg actccgtgcc cgcagactcc ggcctctatg cttgcgtaac cagcagcccc   1260
tcgggcagtg acaccaccta cttctccgtc aatgtttcag atgctctccc ctcctcggag   1320
gatgatgatg atgatgatga ctcctcttca gaggagaaag aaacagataa caccaaacca   1380
aaccgtatgc ccgtagctcc atattggaca tccccagaaa gatggaaaaa gaaattgcat   1440
gcagtgccgg ctgccaagac agtgaagttc aaatgccctt ccagtgggac cccaaacccc   1500
acactgcgct ggttgaaaaa tggcaaagaa ttcaaacctg accacagaat tggaggctac   1560
aaggtccgtt atgccacctg gagcatcata atggactctg tggtgccctc tgacaagggc   1620
aactacacct gcattgtgga gaatgagtac ggcagcatca accacacata ccagctggat   1680
gtcgtggagc ggtcccctca ccggcccatc ctgcaagcag ggttgcccgc caacaaaaca   1740
gtggccctgg gtagcaacgt ggagttcatg tgtaaggtgt acagtgaccc gcagccgcac   1800
atccagtggc taaagcacat cgaggtgaat gggagcaaga ttgggccaga caacctgcct   1860
tatgtccaga tcttgaagac tgctggagtt aataccaccg acaaagagat ggaggtgctt   1920
cacttaagaa atgtctcctt tgaggacgca ggggagtata cgtgcttggc gggtaactct   1980
atcggactct cccatcactc tgcatggttg accgttctgg aagccctgga agagaggccg   2040
gcagtgatga cctcgcccct gtacctggag atcatcatct attgcacagg ggccttcctc   2100
atctcctgca tggtggggtc ggtcatcgtc tacaagatga agagtggtac caagaagagt   2160
gacttccaca gccagatggc tgtgcacaag ctggccaaga gcatccctct gcgcagacag   2220
gtgtctgctg actccagtgc atccatgaac tctggggttc ttctggttcg gccatcacgg   2280
ctctcctcca gtgggactcc catgctagca ggggtctctg agtatgagct tcccgaagac   2340
cctcgctggg agctgcctcg ggacagactg gtcttaggca aacccctggg agagggctgc   2400
tttgggcagg tggtgttggc agaggctatc gggctggaca aggacaaacc caacgtgtg   2460
accaaagtgg ctgtgaagat gttgaagtcg gacgcaacag agaaagactt gtcagacctg   2520
atctcagaaa tggagatgat gaagatgatc gggaagcata gaatatcat caacctgctg   2580
ggggcctgca cgcaggatgg tccattgtat gtcatcgtgg agtatgcctc caagggcaac   2640
ctgcgggagt acctgcaggc ccggaggccc caggctgg aatactgcta caacccagc    2700
cacaacccag aggagcagct ctcctccaag gacctggtgt cctgcgccta ccaggtggcc   2760
cgaggcatga gtatctggc ctccaagaag tgcatacacc gagacctggc agccaggaat   2820
gtcctggtga cagaggacaa tgtgatgaag atagcagact ttggcctcgc acgggacatt   2880
caccacatcg actactataa aaagacaacc aacggccgac tgcctgtgaa gtggatggca   2940
cccgaggcat tatttgaccg gatctacacc accagagtg atgtgtggtc tttcggggtg   3000
ctcctgtggg agatcttcac tctgggcggc tccccatacc ccggtgtgcc tgtggaggaa   3060
cttttcaagc tgctgaagga gggtcaccgc atggacaagc ccagtaactg caccaacgag   3120
ctgtacatga tgatgcggga ctgctggcat gcagtgccct cacagagacc caccttcaag   3180
```

```
cagctggtgg aagacctgga ccgcatcgtg gccttgacct ccaaccagga gtacctggac    3240
ctgtccatgc ccctggacca gtactccccc agctttcccg acacccggag ctctacgtgc    3300
tcctcagggg aggattccgt cttctctcat gagccgctgc ccgaggagcc ctgcctgccc    3360
cgacacccag cccagcttgc caatggcgga ctcaaacgcc gctgactgcc acccacacgc    3420
cctccccaga ctccaccgtc agctgtaacc ctcacccaca gccctgctg ggcccaccac     3480 ctgtccgtcc ctgtcccctt tcctgctggc aggagccggc tgcctaccag gggccttcct    3540
gtgtggcctg ccttcacccc actcagctca cctctccctc cacctcctct ccacctgctg    3600
gtgagaggtg caaagaggca gatctttgct gccagccact tcatcccctc ccagatgttg    3660
gaccaacacc cctccctgcc accaggcact gcctggaggg cagggagtgg gagccaatga    3720
acaggcatgc aagtgagagc ttcctgagct ttctcctgtc ggtttggtct gttttgcctt    3780
cacccataag cccctcgcac tctggtggca ggtgccttgt cctcagggct acagcagtag    3840
ggaggtcagt gcttcgtgcc tcgattgaag gtgacctctg ccccagatag gtggtgccag    3900
tggcttatta attccgatac tagtttgctt tgctgaccaa atgcctggta ccagaggatg    3960
gtgaggcgaa ggccaggttg ggggcagtgt tgtggccctg gggcccagcc ccaaactggg    4020
ggctctgtat atagctatga agaaaacaca aagtgtataa atctgagtat atatttacat    4080 gtcttttaa aagggtcgtt accagagatt tacccatcgg gtaagatgct cctggtggct     4140
gggaggcatc agttgctata tattaaaaac aaaaaagaaa aaaaggaaa atgttttaa      4200 aaaggtcata tattttttgc tactttgct gttttatttt tttaaattat gttctaaacc     4260
tattttcagt ttaggtccct caataaaaat tgctgctgct tcatttatct atgggctgta    4320
tgaaaagggt gggaatgtcc actggaaaga agggacaccc acgggccctg ggctaggtc     4380 tgtcccgagg gcaccgcatg ctcccggcgc aggttccttg taacctcttc ttcctaggtc    4440
ctgcacccag acctcacgac gcacctcctg cctctccgct gcttttggaa agtcagaaaa    4500
agaagatgtc tgcttcgagg gcaggaaccc catccatgca gtagaggcgc tgggcagaga    4560
gtcaaggccc agcagccatc gaccatggat ggtttcctcc aaggaaaccg gtggggttgg    4620
gctggggagg gggcacctac ctaggaatag ccacggggta gagctacagt gattaagagg    4680
aaagcaaggg cgcggttgct cacgcctgta atcccagcac tttgggacac cgaggtgggc    4740
agatcacttc aggtcaggag tttgagacca gcctggccaa cttagtgaaa ccccatctct    4800
actaaaaatg caaaaattat ccaggcatgg tggcacacgc ctgtaatccc agctccacag    4860
gaggctgagg cagaatccct tgaagctggg aggcggaggt tgcagtgagc cgagattgcg    4920
ccattgcact ccagcctggg caacagagaa acaaaaagg aaaacaaatg atgaaggtct     4980
gcagaaactg aaacccagac atgtgtctgc cccctctatg tgggcatggt tttgccagtg    5040
cttctaagtg caggagaaca tgtcacctga ggctagtttt gcattcaggt ccctggcttc    5100
gtttcttgtt ggtatgcctc cccagatcgt ccttcctgta tccatgtgac cagactgtat    5160
ttgttgggac tgtcgcagat cttggcttct tacagttctt cctgtccaaa ctccatcctg    5220
tccctcagga acggggggaa aattctccga atgttttgg ttttttggct gcttggaatt     5280
tacttctgcc acctgctggt catcactgtc ctcactaagt ggattctggc tccccgtac    5340 ctcatggctc aaactaccac tcctcagtcg ctatattaaa gcttatattt tgctggatta    5400
ctgctaaata caaagaaag ttcaatatgt tttcatttct gtaggaaaa tgggattgct     5460 gctttaaatt tctgagctag ggattttttg gcagctgcag tgttggcgac tattgtaaaa    5520
ttctctttgt ttctctctgt aaatagcacc tgctaacatt acaatttgta tttatgttta    5580
```
aagaaggcat catttggtga acagaactag gaaatgaatt tttagctctt aaaagcattt    5640
gctttgagac cgcacaggag tgtctttcct tgtaaaacag tgatgataat ttctgccttg    5700
gccctacctt gaagcaatgt tgtgtgaagg gatgaagaat ctaaaagtct tcataagtcc    5760
ttgggagagg tgctagaaaa atataaggca ctatcataat tacagtgatg tccttgctgt    5820
tactactcaa atcacccaca aatttcccca aagactgcgc tagctgtcaa ataaaagaca    5880
gtgaaattga cctga                                                    5895

<210> SEQ ID NO 148
<211> LENGTH: 805
<212> TYPE: PRT
<213> ORGANISM: Homo sapiens

<400> SEQUENCE: 148

Met Ala Phe Ser Pro Trp Gln Ile Leu Ser Pro Val Gln Trp Ala Lys
1               5                   10                  15

Trp Thr Trp Ser Ala Val Arg Gly Gly Ala Ala Gly Glu Asp Glu Ala
            20                  25                  30

Gly Gly Pro Glu Gly Asp Pro Glu Glu Asp Ser Gln Ala Glu Thr
        35                  40                  45

Lys Ser Leu Ser Phe Ser Ser Asp Ser Glu Gly Asn Phe Glu Thr Pro
50                  55                  60

Glu Ala Glu Thr Pro Ile Arg Ser Pro Phe Lys Glu Ser Cys Asp Pro
65                  70                  75                  80

Ser Leu Gly Leu Ala Gly Pro Gly Ala Lys Ser Gln Glu Ser Gln Glu
                85                  90                  95

Ala Asp Glu Gln Leu Val Ala Glu Val Val Glu Lys Cys Ser Ser Lys
            100                 105                 110

Thr Cys Ser Lys Pro Ser Glu Asn Glu Val Pro Gln Gln Ala Ile Asp
        115                 120                 125

Ser His Ser Val Lys Asn Phe Arg Glu Glu Pro Glu His Asp Phe Ser
    130                 135                 140

Lys Ile Ser Ile Val Arg Pro Phe Ser Ile Glu Thr Lys Asp Ser Thr
145                 150                 155                 160

Asp Ile Ser Ala Val Leu Gly Thr Lys Ala Ala His Gly Cys Val Thr
                165                 170                 175

Ala Val Ser Gly Lys Ala Leu Pro Ser Ser Pro Asp Ala Leu Gln
            180                 185                 190

Asp Glu Ala Met Thr Glu Gly Ser Met Gly Val Thr Leu Glu Ala Ser
        195                 200                 205

Ala Glu Ala Asp Leu Lys Ala Gly Asn Ser Cys Pro Glu Leu Val Pro
    210                 215                 220

Ser Arg Arg Ser Lys Leu Arg Lys Pro Lys Pro Val Pro Leu Arg Lys
225                 230                 235                 240

Lys Ala Ile Gly Gly Glu Phe Ser Asp Thr Asn Ala Ala Val Glu Gly
                245                 250                 255

Thr Pro Leu Pro Lys Ala Ser Tyr His Phe Ser Pro Glu Glu Leu Asp
            260                 265                 270

Glu Asn Thr Ser Pro Leu Leu Gly Asp Ala Arg Phe Gln Lys Ser Pro
        275                 280                 285

Pro Asp Leu Lys Glu Thr Pro Gly Thr Leu Ser Ser Asp Thr Asn Asp
    290                 295                 300

Ser Gly Val Glu Leu Gly Glu Glu Ser Arg Ser Ser Pro Leu Lys Leu

```
            305                 310                 315                 320
        Glu Phe Asp Phe Thr Glu Asp Thr Gly Asn Ile Glu Ala Arg Lys Ala
                        325                 330                 335

Leu Pro Arg Lys Leu Gly Arg Lys Leu Gly Ser Thr Leu Thr Pro Lys
                        340                 345                 350

Ile Gln Lys Asp Gly Ile Ser Lys Ser Ala Gly Leu Glu Gln Pro Thr
                        355                 360                 365

Asp Pro Val Ala Arg Asp Gly Pro Leu Ser Gln Thr Ser Ser Lys Pro
            370                 375                 380

Asp Pro Ser Gln Trp Glu Ser Pro Ser Phe Asn Pro Phe Gly Ser His
        385                 390                 395                 400

Ser Val Leu Gln Asn Ser Pro Pro Leu Ser Ser Glu Gly Ser Tyr His
                        405                 410                 415

Phe Asp Pro Asp Asn Phe Asp Glu Ser Met Asp Pro Phe Lys Pro Thr
                        420                 425                 430

Thr Thr Leu Thr Ser Ser Asp Phe Cys Ser Pro Thr Gly Asn His Val
                        435                 440                 445

Asn Glu Ile Leu Glu Ser Pro Lys Lys Ala Lys Ser Arg Leu Ile Thr
            450                 455                 460

Ser Gly Cys Lys Val Lys His Glu Thr Gln Ser Leu Ala Leu Asp
        465                 470                 475                 480

Ala Cys Ser Arg Asp Glu Gly Ala Val Ile Ser Gln Ile Ser Asp Ile
                        485                 490                 495

Ser Asn Arg Asp Gly His Ala Thr Asp Glu Glu Lys Leu Ala Ser Thr
                        500                 505                 510

Ser Cys Gly Gln Lys Ser Ala Gly Ala Glu Val Lys Gly Glu Pro Glu
                        515                 520                 525

Glu Asp Leu Glu Tyr Phe Glu Cys Ser Asn Val Pro Val Ser Thr Ile
            530                 535                 540

Asn His Ala Phe Ser Ser Glu Ala Gly Ile Glu Lys Glu Thr Cys
        545                 550                 555                 560

Gln Lys Met Glu Glu Asp Gly Ser Thr Val Leu Gly Leu Leu Glu Ser
                        565                 570                 575

Ser Ala Glu Lys Ala Pro Val Ser Val Ser Cys Gly Gly Glu Ser Pro
                        580                 585                 590

Leu Asp Gly Ile Cys Leu Ser Glu Ser Asp Lys Thr Ala Val Leu Thr
                        595                 600                 605

Leu Ile Arg Glu Glu Ile Ile Thr Lys Glu Ile Glu Ala Asn Glu Trp
            610                 615                 620

Lys Lys Lys Tyr Glu Glu Thr Arg Gln Glu Val Leu Glu Met Arg Lys
        625                 630                 635                 640

Ile Val Ala Glu Tyr Glu Lys Thr Ile Ala Gln Met Ile Glu Asp Glu
                        645                 650                 655

Gln Arg Thr Ser Met Thr Ser Gln Lys Ser Phe Gln Gln Leu Thr Met
                        660                 665                 670

Glu Lys Glu Gln Ala Leu Ala Asp Leu Asn Ser Val Glu Arg Ser Leu
                        675                 680                 685

Ser Asp Leu Phe Arg Arg Tyr Glu Asn Leu Lys Gly Val Leu Glu Gly
            690                 695                 700

Phe Lys Lys Asn Glu Glu Ala Leu Lys Lys Cys Ala Gln Asp Tyr Leu
        705                 710                 715                 720

Ala Arg Val Lys Gln Glu Glu Gln Arg Tyr Gln Ala Leu Lys Ile His
                        725                 730                 735
```

```
Ala Glu Glu Lys Leu Asp Lys Ala Asn Glu Glu Ile Ala Gln Val Arg
            740                 745                 750

Thr Lys Ala Lys Ala Glu Ser Ala Ala Leu His Ala Gly Leu Arg Lys
        755                 760                 765

Glu Gln Met Lys Val Ser Leu Glu Arg Ala Leu Gln Gln Lys Asn
770                 775                 780

Gln Glu Ile Glu Glu Leu Thr Lys Ile Cys Asp Glu Leu Ile Ala Lys
785                 790                 795                 800

Leu Gly Lys Thr Asp
            805

<210> SEQ ID NO 149
<211> LENGTH: 7802
<212> TYPE: DNA
<213> ORGANISM: Homo sapiens

<400> SEQUENCE: 149
agctgatgcg cgccccgccg gccgggaggc gggagtccgc gagccgggag cgggagcagc      60
agaggtctag cagccgggcg ccgcgggccg ggggcctgag gaggccacag gacgggcgtc     120
ttcccggcta gtggagcccg cgcgcgggcc cgctgcggcc gcaccgtgag gggaggaggc     180
cgaggaggac gcagcgccgg ctgccggcgg gaggaagcgc tccaccaggg ccccgacgg      240 cactcgttta accacatccg cgcctctgct ggaaacgctt gctggcgcct gtcaccggtt     300
ccctccattt tgaaagggaa aaaggctctc cccacccatt cccctgcccc taggagctgg     360
agccggagga gccgcgctca tggcgttcag cccgtggcag atcctgtccc ccgtgcagtg     420
ggcgaaatgg acgtggtctg cggtacgcgg cggggccgcc ggcgaggacg aggctggcgg     480
gcccgagggc gaccccgagg aggaggattc gcaagccgag accaaatcct tgagtttcag     540
ctcggattct gaaggtaatt ttgagactcc tgaagctgaa accccgatcc gatcacccttt    600 caaggagtcc tgtgatccat cactcggatt ggcaggacct ggggccaaaa gccaagaatc     660
acaagaagct gatgaacagc ttgtagcaga agtggttgaa aaatgttcat ctaagacttg     720
ttctaaacct tcagaaaatg aagtgccaca gcaggccatt gactctcact cagtcaagaa     780
tttcagagaa gaacctgaac atgattttag caaaatttcc atcgtgaggc cattttcaat     840
agaaacgaag gattccacgg atatctcggc agtcctcgga acaaaagcag ctcatggctg     900
tgtaactgca gtctcaggca aggctctgcc ttccagcccg ccagacgccc tccaggacga     960
ggcgatgaca gaaggcagca tgggggtcac cctcgaggcc tccgcagaag ctgatctaaa    1020
agctggcaac tcctgtccag agcttgtgcc agcagaaga agcaagctga aaagcccaa     1080 gcctgtcccc ctgaggaaga aagcaattgg aggagagttc tcagacacca acgctgctgt    1140
ggagggcaca cctctcccca aggcatccta tcacttcagt cctgaagagt tggatgagaa    1200
cacaagtcct tgctaggag atgccaggtt ccagaagtct ccccctgacc ttaaagaaac     1260
tcccggcact ctcagtagtg acaccaacga ctcaggggtt gagctggggg aggagtcgag    1320
gagctcacct ctcaagcttg agtttgattt cacagaagat acaggaaaca tagaggccag    1380
gaaagccctt ccaaggaagc ttggcaggaa actgggtagc acactgactc ccaagataca    1440
aaaagatggc atcagtaagt cagcaggttt agaacagcct acagacccag tggcacgaga    1500
cgggcctctc tcccaaacat cttccaagcc agatcctagt cagtgggaaa gcccagcttt    1560
caaccccttt gggagccact ctgttctgca gaactcccca cccctctctt ctgagggctc    1620
ctaccacttt gacccagata actttgacga atccatggat cccttaaac caactacgac     1680
```

```
cttaacaagc agtgactttt gttctcccac tggtaatcac gttaatgaaa tcttagaatc    1740
acccaagaag gcaaagtcgc gtttaataac gagtggctgt aaggtgaaga agcatgaaac    1800
tcagtctctc gccctggatg catgttctcg ggatgaaggg gcagtgatct cccagatttc    1860
agacatttct aatagggatg gccatgctac tgatgaggag aaactggcat ccacgtcatg    1920
tggtcagaaa tcagctggtg ccgaggtgaa aggtgagcca gaggaagacc tggagtactt    1980
tgaatgttcc aatgttcctg tgtctaccat aaatcatgcg ttttcatcct cagaagcagg    2040
catagagaag gagacgtgcc agaagatgga agaagacggg tccactgtgc ttgggctgct    2100
ggagtcctct gcagagaagg cccctgtgtc ggtgtcctgt ggaggtgaga gcccctgga    2160 tgggatctgc ctcagcgaat cagacaagac agccgtgctc accttaataa gagaagagat    2220
aattactaaa gagattgaag caaatgaatg gaagaagaaa tacgaagaga cccggcaaga    2280
agttttggag atgaggaaaa ttgtagctga atatgaaaag actattgctc aaatgattga    2340
agatgaacaa aggacaagta tgacctctca gaagagcttc cagcaactga ccatggagaa    2400
ggaacaggcc ctggctgacc ttaactctgt ggaaaggtcc ctttctgatc tcttcaggag    2460
atatgagaac ctgaaaggtg ttctggaagg gttcaagaag aatgaagaag ccttgaagaa    2520
atgtgctcag gattacttag ccagagttaa acaagaggag cagcgatacc aggccctgaa    2580
aatccacgca gaagagaaac tggacaaagc caatgaagag attgctcagg ttcgaacaaa    2640
agcaaaggct gagagtgcag ctctccatgc tggactccgc aaagagcaga tgaaggtgga    2700
gtccctggaa agggccctgc agcagaagaa ccaagaaatt gaagaactga caaaaatctg    2760
tgatgagctg attgcaaagc tgggaaagac tgactgagac actccccctg ttagctcaac    2820
agatctgcat ttggctgctt ctcttgtgac cacaattatc ttgccttatc caggaataat    2880 tgccccttg cagagaaaaa aaaaaactta aaaaagcac atgcctactg ctgcctgtcc    2940
cgctttgctg ccaatgcaac agccctggaa gaaaccctag agggttgcat agtctagaaa    3000
ggagtgtgac ctgacagtgc tggagcctcc tagtttcccc ctatgaaggt tcccttaggc    3060
tgctgagttt gggtttgtga tttatcttta gtttgtttta aagtcatctt actttccca    3120 aatgtgttaa atttgtaact cctctttggg gtcttctcca ccacctgtct gattttttg    3180 tgatctgttt aatcttttaa ttttttagta tcagtggttt tatttaagga dacagtttgg    3240
cctattgtta cttccaattt ataatcaaga aggggctctg gatccccttt taaattacac    3300
acactctcac acacatacat gtatgtttat agatgctgct gctcttttcc ctgaagcata    3360
gtcaagtaag aactgctcta cagaaggaca tatttccttg gatgtgagac cctatttga    3420 aatagagtcc tgactcagaa caccaactta agaatttggg ggattaaaga tgtgaagacc    3480
acagtcttgg gttttcatat ctggagaaga ctatttgcca tgacgttttg ttgccctggt    3540
atttggacac tcctcagctt taatgggtgt ggccccttta gggttagtcc tcagactaat    3600
gatagtgtct gctttctgca tgaacggcaa tatgggactc cctccaagct agggtttggc    3660
aagtctgccc tagagtcatt tactctcctc tgcctccatt tgttaataca gaatcaacat    3720
ttagtcttca ttatctttt tttttttttt gagacagagt ttcgatctat tttaagtatg    3780
tgaagaaaat ctacttgtaa aaggctcaga tcttaattaa aaggtaattg tagcacatta    3840
ccaattataa ggtgaagaaa tgtttttttc ccaagtgtga tgcattgttc ttcagatgtt    3900
gaaaagaaag caaaaaatac cttctaactt aagacagaat tttaacaaa atgagcagta    3960 aaagtcacat gaaccactcc aaaaatcagt gcattttgca tattttttaaa caaagacagc    4020
```

```
ttgttgaata ctgagaagag gagtgcaagg agaaggtctg tactaacaaa gccaaattcc      4080
tcaagctctt actggactca gttcagagtg gtgggccatt aaccccaaca tggaattttt      4140
ccatataaat ctcaatgaat tcccttcat ttgaataggc aaacccaaat ccatgcaagt       4200
gttttaaagc actgtcctgt cttaatctta catgctgaaa gtcttcatgg tgatatgcac      4260
tatattcagt atacgtatgt tttcctactt ctcttgtaaa actgttgcat gatccaactt      4320
cagcaatgaa ttgtgcctag tggagaacct ctatagatct taaaaaatga attattcttt      4380
agcagtgtat tactcacatg ggtgcaatct ttagccccag ggaggtcaat aatgtctttt      4440
aaagccagaa gtcacatttt accaatatgc atttatcata attggtgctt aggctgtata     4500
ttcaagcctg ttgtcttaac attttgtata aaaagaaca acagaaatta tctgtcattt      4560
gagaagtggc ttgacaatca tttgagcttt gaaagcagtc actgtggtgt aatatgaatg     4620
ctgtcctagt ggtcatagta ccaagggcac gtgtctcccc ttggtataac tgatttcctt      4680
tttagtcctc tactgctaaa taagttaatt ttgcattttg cagaaagaaa cattgattgc      4740
taaatctttt tgctgctgtg ttttggtgtt ttcatgttta cttgttttat attgatctgt      4800
tttaagtatg agaggcttat agtgccctcc attgtaaatc catagtcatc ttttaagct       4860 tattgtgttt aagaaagtag ctatgtgtta acagaggtg atggcagccc ttccctagca      4920
cactggtgga agagacccct taagaacctg accccagtga atgaagctga tgcacaggga     4980
gcaccaaagg accttcgtta agtgataatt gtcctggcct ctcagccatg accgttatga     5040
ggaaatatcc cccattcgaa cttaacagat gcctcctctc caaagagaat taaaatcgta      5100
gcttgtacag atcaagagaa tatactgggc agaatgaagt atgtttgttt attttctttt      5160
aaaaataaag gattttggaa ctctggagag taagaatata gtatagagtt tgcctcaaca      5220
catgtgaggc ccaaataacc tgctagctag gcagtaataa actctgttac agaagagaaa      5280
aagggccggg cacagtggct tattcctgta atcccaacac tgtggaaggc cgaggcagga     5340
ggatcacttg agtccaggag tttgaaacct acctaggcaa catggtgaaa ccttgtctct      5400
accaaaataa aaattagctg ggcatggtgg cacgtgcctg tggtcccagc tacttgggag      5460
gctgaggtgg gagcctggga ggtcaaggct gcagtgagcc atgatcatgc cactgcactc      5520
catcctgggt gacagcaaga tcttgtctca aaaaaaaaaa aaaaaaaaaa aaaaccagga     5580
gtgaaaaagg aaagtagaag gcagctgctg gcctagatgt tggtttggga atattaggtg     5640
atcctgttga gattctggat ccagagcaat ttctttagct tttgactttg ccaaagtgta     5700
gatagccttt atccagcagt attttaagtg gggaatgcaa cgtgaggcca actgaacaat      5760
tccccccgtg gctgcccaga tagtcacagt caaggttgga gagtctcctt ccagccagtg     5820
acctacccaa acctttgtt ctgtaaaact gctctggaaa taccgggaag cccagttttc      5880
tcacgtggtt tctagcttct tcagactcag cccaaattag gaagtgcaga agcacatgat     5940
ggtgaaaaac ctaggatttg gcagccttcc agaatggtat ggaatctgag ggaagattta     6000
tgtttcgttt tggaggatag ctcaagttga attttctttc cagccagtta ccctttcaac      6060
ctacccatac tttgtacaac tcttacacaa atacttagat atttattaga tagccctgaa      6120
ttcactctaa ttataaacag gggagtgtaaa ctgcccccag atgttcctgg gctgggtaaa    6180
agcagctgga gtgaagcact catttccat aaaggtaaca aagggcagct cagtggttac       6240
tcaagctcaa aagggttttt ttaagagcaa gcattggtta agtctgtgta tactgagttg      6300
gaagtgattt cagcacattc ttttttagtg gagtgaaagt tctgaagccc ccttttaact      6360
tcctcttggt ttttcattat aattggtagc catctcatga actgtctctg actgttgtct      6420
```

```
ctttgtggtc atgtgattgt gagcttgctt tctgacttgc atttctgact ttatcctgtt   6480
gttaggaaga tagaaactag gttttgaaag attacatgat tcaagcgagg gattttaaag   6540
taaagatgta tttattctga agaatctaaa agataacaga ttatttgctt atgaaagaac   6600
aatatagtct gggaatccca gaatgtcaag ccaaaggtct aagaagtcat ctccttcaaa   6660
tactttaata aagaagtatt tcgaggagat atctgtccaa aaaggtttga ctggcctcca   6720
gattccagtt attttaaaa agcaacttac cactaaatcc ttgagtctcc atagagtaac   6780
agtaaagaaa ctgatgtaac agactctcct ctcaaaggat ctcctctgga agagactatc   6840
agcggcagca ttctccaggg aagacccatc ccctagtgcc agagcttgca tcctggagac   6900
taaagattgc actttttgt agttttttgt ccaaatgcaa tcccatttct gtgcctctta   6960
gcatgcagtt agatttggac aaacaagatt cctaaggaat gactttatta actataaat   7020
ggttacagct attatataaa tatatattct ggttatagtt ctaatatgga gatgttgtgt   7080
gcaatgctgg cctgtggtgg tctgtgtaat gctttaactt gtatggagga ggccaggctc   7140
agagctgaga tgtggcctga accttccctg tatcgatcct ttaatttaga actgtcaaga   7200
tgtcactttc tccccctctg cctttagtg gtatctgaca tatactcaaa acagtaattt   7260
cctggtcaca tcattaactg ctaattctgt atttataaag aattttcaga tggacatgta   7320
caaatttgaa ctcaaaccat ccccagtcca gatacagggc agcgtgtagg tgaccacacc   7380
agagcctcag cctcggtcct tctcagccgt cgggatagga tccaggcatt tcttttaaat   7440
ctcagaggta gcagtaaact tttcagtatt gctgttagca agtgtgtgtt tgccaataga   7500
tacccattat actaatgtgc caagtaaatg ttcattgcac atctgcttcc actgtgttcc   7560
cacgggtgcc atgaagtgtg tgaggagccc ctcatctgga gggatgagtg ctgcgttgac   7620
tactgctatc aggattgtgt tgtgtggaat attcatctac ataaattta tatgcacagt   7680
aatttccctt tttatatgtc aagtaactat ttgtaaaagt tatactcaca aattattata   7740
atgattacta atatatttt tccatgtttc attgcctgaa taaaaactgt ttaccactgt   7800
ta                                                                  7802
```

<210> SEQ ID NO 150
<211> LENGTH: 907
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
                20                  25                  30

Leu Pro Ser Ser Glu Asp Asp Asp Asp Asp Ser Ser Ser Glu
            35                  40                  45

Glu Lys Glu Thr Asp Asn Thr Lys Pro Asn Pro Val Ala Pro Tyr Trp
    50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
```

```
            100                 105                 110
Gly Gly Tyr Lys Val Arg Tyr Ala Thr Trp Ser Ile Ile Met Asp Ser
        115                 120                 125

Val Val Pro Ser Asp Lys Gly Asn Tyr Thr Cys Ile Val Glu Asn Glu
130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
                180                 185                 190

Gln Pro His Ile Gln Trp Leu Lys His Ile Glu Val Asn Gly Ser Lys
                195                 200                 205

Ile Gly Pro Asp Asn Leu Pro Tyr Val Gln Ile Leu Lys Thr Ala Gly
        210                 215                 220

Val Asn Thr Thr Asp Lys Glu Met Glu Val Leu His Leu Arg Asn Val
225                 230                 235                 240

Ser Phe Glu Asp Ala Gly Glu Tyr Thr Cys Leu Ala Gly Asn Ser Ile
                245                 250                 255

Gly Leu Ser His His Ser Ala Trp Leu Thr Val Leu Glu Ala Leu Glu
                260                 265                 270

Glu Arg Pro Ala Val Met Thr Ser Pro Leu Tyr Leu Glu Ile Ile Ile
                275                 280                 285

Tyr Cys Thr Gly Ala Phe Leu Ile Ser Cys Met Val Gly Ser Val Ile
        290                 295                 300

Val Tyr Lys Met Lys Ser Gly Thr Lys Lys Ser Asp Phe His Ser Gln
305                 310                 315                 320

Met Ala Val His Lys Leu Ala Lys Ser Ile Pro Leu Arg Arg Gln Val
                325                 330                 335

Thr Val Ser Ala Asp Ser Ser Ala Ser Met Asn Ser Gly Val Leu Leu
                340                 345                 350

Val Arg Pro Ser Arg Leu Ser Ser Ser Gly Thr Pro Met Leu Ala Gly
                355                 360                 365

Val Ser Glu Tyr Glu Leu Pro Glu Asp Pro Arg Trp Glu Leu Pro Arg
                370                 375                 380

Asp Arg Leu Val Leu Gly Lys Pro Leu Gly Glu Gly Cys Phe Gly Gln
385                 390                 395                 400

Val Val Leu Ala Glu Ala Ile Gly Leu Asp Lys Asp Lys Pro Asn Arg
                405                 410                 415

Val Thr Lys Val Ala Val Lys Met Leu Lys Ser Asp Ala Thr Glu Lys
                420                 425                 430

Asp Leu Ser Asp Leu Ile Ser Glu Met Glu Met Met Lys Met Ile Gly
                435                 440                 445

Lys His Lys Asn Ile Ile Asn Leu Leu Gly Ala Cys Thr Gln Asp Gly
                450                 455                 460

Pro Leu Tyr Val Ile Val Glu Tyr Ala Ser Lys Gly Asn Leu Arg Glu
465                 470                 475                 480

Tyr Leu Gln Ala Arg Arg Pro Pro Gly Leu Glu Tyr Cys Tyr Asn Pro
                485                 490                 495

Ser His Asn Pro Glu Glu Gln Leu Ser Ser Lys Asp Leu Val Ser Cys
                500                 505                 510

Ala Tyr Gln Val Ala Arg Gly Met Glu Tyr Leu Ala Ser Lys Lys Cys
                515                 520                 525
```

```
Ile His Arg Asp Leu Ala Ala Arg Asn Val Leu Val Thr Glu Asp Asn
    530                 535                 540
Val Met Lys Ile Ala Asp Phe Gly Leu Ala Arg Asp Ile His His Ile
545                 550                 555                 560
Asp Tyr Tyr Lys Lys Thr Thr Asn Gly Arg Leu Pro Val Lys Trp Met
                565                 570                 575
Ala Pro Glu Ala Leu Phe Asp Arg Ile Tyr Thr His Gln Ser Asp Val
            580                 585                 590
Trp Ser Phe Gly Val Leu Leu Trp Glu Ile Phe Thr Leu Gly Gly Ser
        595                 600                 605
Pro Tyr Pro Gly Val Pro Val Glu Glu Leu Phe Lys Leu Leu Lys Glu
    610                 615                 620
Gly His Arg Met Asp Lys Pro Ser Asn Cys Thr Asn Glu Leu Tyr Met
625                 630                 635                 640
Met Met Arg Asp Cys Trp His Ala Val Pro Ser Gln Arg Pro Thr Phe
                645                 650                 655
Lys Gln Leu Val Glu Asp Leu Asp Arg Ile Val Ala Leu Thr Ser Asn
            660                 665                 670
Gln Gly Leu Leu Glu Ser Ser Ala Glu Lys Ala Pro Val Ser Val Ser
        675                 680                 685
Cys Gly Gly Glu Ser Pro Leu Asp Gly Ile Cys Leu Ser Glu Ser Asp
    690                 695                 700
Lys Thr Ala Val Leu Thr Leu Ile Arg Glu Glu Ile Ile Thr Lys Glu
705                 710                 715                 720
Ile Glu Ala Asn Glu Trp Lys Lys Lys Tyr Glu Glu Thr Arg Gln Glu
                725                 730                 735
Val Leu Glu Met Arg Lys Ile Val Ala Glu Tyr Glu Lys Thr Ile Ala
            740                 745                 750
Gln Met Ile Glu Asp Glu Gln Arg Thr Ser Met Thr Ser Gln Lys Ser
        755                 760                 765
Phe Gln Gln Leu Thr Met Glu Lys Glu Gln Ala Leu Ala Asp Leu Asn
    770                 775                 780
Ser Val Glu Arg Ser Leu Ser Asp Leu Phe Arg Arg Tyr Glu Asn Leu
785                 790                 795                 800
Lys Gly Val Leu Glu Gly Phe Lys Lys Asn Glu Glu Ala Leu Lys Lys
                805                 810                 815
Cys Ala Gln Asp Tyr Leu Ala Arg Val Lys Gln Glu Glu Gln Arg Tyr
            820                 825                 830
Gln Ala Leu Lys Ile His Ala Glu Glu Lys Leu Asp Lys Ala Asn Glu
        835                 840                 845
Glu Ile Ala Gln Val Arg Thr Lys Ala Lys Ala Glu Ser Ala Ala Leu
    850                 855                 860
His Ala Gly Leu Arg Lys Glu Gln Met Lys Val Glu Ser Leu Glu Arg
865                 870                 875                 880
Ala Leu Gln Gln Lys Asn Gln Glu Ile Glu Glu Leu Thr Lys Ile Cys
                885                 890                 895
Asp Glu Leu Ile Ala Lys Leu Gly Lys Thr Asp
            900                 905

<210> SEQ ID NO 151
<211> LENGTH: 2989
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 151

```
atgtggagct ggaagtgcct cctcttctgg gctgtgctgg tcacagccac actctgcacc      60
gctaggccgt ccccgacctt gcctgaacaa gcccagccct ggggagcccc tgtggaagtg     120
gagtccttcc tggtccaccc cggtgacctg ctgcagcttc gctgtcggct gcgggacgat     180
gtgcagagca tcaactggct gcgggacggg gtgcagctgc ggaaagcaa ccgcacccgc      240
atcacagggg aggaggtgga ggtgcaggac tccgtgcccg cagactccgg cctctatgct     300
tgcgtaacca gcagccccct gggcagtgac accacctact tctccgtcaa tgtttcagat     360
gctctcccct cctcggagga tgatgatgat gatgatgact cctcttcaga ggagaaagaa     420
acagataaca ccaaaccaaa ccgtatgccc gtagctccat attggacatc cccagaaaag     480
atggaaaaga aattgcatgc agtgccggct gccaagacag tgaagttcaa atgcccttcc     540
agtgggaccc caaaccccac actgcgctgg ttgaaaaatg gcaaagaatt caaacctgac     600
cacagaattg gaggctacaa ggtccgttat gccacctgga gcatcataat ggactctgtg     660
gtgccctctg acaagggcaa ctacacctgc attgtggaga tgagtacgg cagcatcaac      720
cacacatacc agctggatgt cgtggagcgg tcccctcacc ggcccatcct gcaagcaggg     780
ttgcccgcca acaaaacagt ggccctgggt agcaacgtgg agttcatgtg taaggtgtac     840
agtgacccgc agccgcacat ccagtggcta aagcacatcg aggtgaatgg gagcaagatt     900
ggcccagaca acctgcctta tgtccagatc ttgaagactg ctggagttaa taccaccgac     960
aaagagatgg aggtgcttca cttaagaaat gtctcctttg aggacgcagg ggagtatacg    1020
tgcttggcgg gtaactctat cggactctcc catcactctg catggttgac cgttctggaa    1080
gccctggaag agaggccggc agtgatgacc tcgcccctgt acctggagat catcatctat    1140
tgcacagggg ccttcctcat ctcctgcatg gtggggtcgg tcatcgtcta caagatgaag    1200
agtggtacca agaagagtga cttccacagc cagatggctg tgcacaagct ggccaagagc    1260
atccctctgc gcagacaggt gtctgctgac tccagtgcat ccatgaactc tgggttctt    1320
ctggttcggc catcacggct ctcctccagt gggactccca tgctagcagg ggtctctgag    1380
tatgagcttc ccaagaccc tcgctgggag ctgcctcggg acagactggt cttaggcaaa    1440
cccctgggag agggctgctt tgggcaggtg gtgttggcag aggctatcgg gctggacaag    1500
gacaaaccca accgtgtgac caaagtggct gtgaagatgt tgaagtcgga cgcaacagag    1560
aaagacttgt cagacctgat ctcagaaatg gagatgatga aagatgatcgg gaagcataag    1620
aatatcatca acctgctggg ggcctgcacg caggatggtc ccttgtatgt catcgtggag    1680
tatgcctcca gggcaacct gcgggagtac ctgcaggccc ggaggccccc agggctggaa    1740
tactgctaca cccccagcca caacccagag gagcagctct cctccaagga cctggtgtcc    1800
tgcgcctacc aggtggcccg aggcatggag tatctggcct ccaagaagtg catacaccga    1860
gacctggcag ccaggaatgt cctggtgaca gaggacaatg tgatgaagat agcagacttt    1920
ggcctcgcac gggacattca ccacatcgac tactataaaa agacaaccaa cggccgactg    1980
cctgtgaagt ggatggcacc cgaggcatta tttgaccgga tctacaccca ccagagtgat    2040
gtgtggtctt tcggggtgct cctgtgggag atcttcactc tgggcggctc cccatacccc    2100
ggtgtgcctg tggaggaact tttcaagctg ctgaaggagg tcaccgcat ggacaagccc    2160
agtaactgca ccaacgagct gtacatgatg atgcgggact gctggcatgc agtgccctca    2220
```

```
cagagaccca ccttcaagca gctggtggaa gacctggacc gcatcgtggc cttgacctcc    2280
aaccagtggg ctgctggagt cctctgcaga gaaggcccct gtgtcggtgt cctgtggagg    2340
tgagagcccc ctggatggga tctgcctcag cgaatcagac aagacagccg tgctcacctt    2400
aataagagaa gagataatta ctaaagagat tgaagcaaat gaatggaaga agaaatacga    2460
agagacccgg caagaagttt tggagatgag gaaaattgta gctgaatatg aaaagactat    2520
tgctcaaatg attgaagatg aacaaaggac aagtatgacc tctcagaaga gcttccagca    2580
actgaccatg gagaaggaac aggccctggc tgaccttaac tctgtggaaa ggtcccttt c   2640 tgatctcttc aggagatatg agaacctgaa aggtgttctg gaagggttca gaagaatga     2700 agaagccttg aagaaatgtg ctcaggatta cttagccaga gttaaacaag aggagcagcg    2760
ataccaggcc ctgaaaatcc acgcagaaga gaaactggac aaagccaatg aagagattgc    2820
tcaggttcga acaaaagcaa aggctgagag tgcagctctc catgctggac tccgcaaaga    2880
gcagatgaag gtggagtccc tggaaagggc cctgcagcag aagaaccaag aaattgaaga    2940
actgacaaaa atctgtgatg agctgattgc aaagctggga aagactgac                2989
```

```
<210> SEQ ID NO 152
<211> LENGTH: 821
<212> TYPE: PRT
<213> ORGANISM: Homo sapiens

<400> SEQUENCE: 152
```

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240
```

-continued

```
Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Gly Gly
        260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
        370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
        450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
        500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
        530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
        610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
```

```
                        660                 665                 670
Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
            690                 695                 700

Pro Gly Ile Pro Val Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 153
<211> LENGTH: 4654
<212> TYPE: DNA
<213> ORGANISM: Homo sapiens

<400> SEQUENCE: 153
ggcggcggct ggaggagagc gcggtggaga gccgagcggg cgggcggcgg gtgcggagcg      60
ggcgagggag cgcgcgcggc cgccacaaag ctcgggcgcc gcgggctgc atgcggcgta     120 cctggcccgg cgcggcgact gctctccggg ctggcggggg ccggccgcga gccccggggg    180
ccccgaggcc gcagcttgcc tgcgcgctct gagccttcgc aactcgcgag caaagtttgg    240
tggaggcaac gccaagcctg agtccttcct cctctcgtt ccccaaatcc gagggcagcc     300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg gacaacaca ggtcgcggag     480 gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtccctggcc cggccctcct    720
tcagtttagt tgaggatacc acattagagc cagaagagcc accaaccaaa taccaaatct    780
ctcaaccaga agtgtacgtg gctgcgccag gggagtcgct agaggtgcgc tgcctgttga    840
aagatgccgc cgtgatcagt tggactaagg atgggtgca cttggggccc aacaatagga    900
cagtgcttat tggggagtac ttgcagataa agggcgccac gctagagac ccggcctct     960 atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg ccaacactg tcaagtttcg ctgcccagcc gggggggaacc   1200
```

```
caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga atgaatacgg gtccatcaat cacacgtacc    1380
acctggatgt tgtggagcga tcgcctcacc ggcccatcct ccaagccgga ctgccggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgcccta cctcaaggtt ctcaaggccg ccggtgttaa caccacggac aaagagattg    1620
aggttctcta tattcggaat gtaacttttg aggacgctgg ggaatatacg tgcttggcgg    1680
gtaattctat tgggatatcc tttcactctg catggttgac agttctgcca gcgcctggaa    1740
gagaaaagga gattacagct tccccagact acctggagat agccatttac tgcatagggg    1800
tcttcttaat cgcctgtatg gtggtaacag tcatcctgtg ccgaatgaag aacacgacca    1860
agaagccaga cttcagcagc cagccggctg tgcacaagct gaccaaacgt atcccctgc    1920 ggagacaggt aacagtttcg gctgagtcca gctcctccat gaactccaac accccgctgg    1980
tgaggataac aacacgcctc tcttcaacgg cagacacccc catgctggca ggggtctccg    2040
agtatgaact tccagaggac ccaaaatggg agtttccaag agataagctg acactgggca    2100 agccctggg agaaggttgc tttgggcaag tggtcatggc ggaagcagtg ggaattgaca    2160
aagacaagcc caaggaggcg gtcaccgtgg ccgtgaagat gttgaaagat gatgccacag    2220
agaaagacct ttctgatctg gtgtcagaga tggagatgat gaagatgatt gggaaacaca    2280
agaatatcat aaatcttctt ggagcctgca cacaggatgg gcctctctat gtcatagttg    2340
agtatgcctc taaaggcaac ctccgagaat acctccgagc ccggaggcca cccgggatgg    2400
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttaggggc tcgccctacc    2760 cagggattcc cgtggaggaa cttttttaagc tgctgaagga aggacacaga atggataagc    2820
cagccaactg caccaacgaa ctgtacatga tgatgaggga ctgttggcat gcagtgccct    2880
cccagagacc aacgttcaag cagttggtag aagacttgga tcgaattctc actctcacaa    2940
ccaatgagga atacttggac ctcagccaac tctcgaaca gtattcacct agttaccctg    3000
acacaagaag ttcttgttct tcaggagatg attctgtttt ttctccagac ccatgcctt    3060 acgaaccatg ccttcctcag tatccacaca taaacggcag tgttaaaaca tgaatgactg    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcacc    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
```

```
tatttacaag gagttatttt ttgtattgat tttaaatgga tgtcccaatg cacctagaaa    3600
attggtctct cttttttaa tagctatttg ctaaatgctg ttcttacaca taatttctta     3660
attttcaccg agcagaggtg gaaaaatact tttgctttca gggaaaatgg tataacgtta    3720
atttattaat aaattggtaa tatacaaaac aattaatcat ttatagttt ttttgtaatt     3780 taagtggcat ttctatgcag gcagcacagc agactagtta atctattgct tggacttaac   3840
tagttatcag atcctttgaa aagagaatat ttacaatata tgactaattt ggggaaaatg   3900 aagtttgat ttatttgtgt ttaaatgctg ctgtcagacg attgttctta gacctcctaa   3960
atgccccata ttaaaagaac tcattcatag gaaggtgttt cattttggtg tgcaaccctg   4020
tcattacgtc aacgcaacgt ctaactggac ttcccaagat aaatggtacc agcgtcctct   4080
taaaagatgc cttaatccat tccttgagga cagaccttag ttgaaatgat agcagaatgt   4140
gcttctctct ggcagctggc cttctgcttc tgagttgcac attaatcaga ttagcctgta   4200
ttctcttcag tgaatttga taatggcttc cagactcttt ggcgttggag acgcctgtta    4260
ggatcttcaa gtcccatcat agaaaattga acacagagt tgttctgctg atagttttgg    4320
ggatacgtcc atcttttaa gggattgctt tcatctaatt ctggcaggac ctcaccaaaa    4380
gatccagcct catacctaca tcagacaaaa tatcgccgtt gttccttctg tactaaagta   4440
ttgtgttttg ctttggaaac acccactcac tttgcaatag ccgtgcaaga tgaatgcaga   4500
ttacactgat cttatgtgtt acaaaattgg agaaagtatt taataaaacc tgttaatttt   4560
tatactgaca ataaaaatgt ttctacagat attaatgtta acaagacaaa ataaatgtca   4620
cgcaacttat ttttttaata aaaaaaaaaa aaaa                               4654
```

<210> SEQ ID NO 154
<211> LENGTH: 2948
<212> TYPE: PRT
<213> ORGANISM: Homo sapiens

<400> SEQUENCE: 154

Met Gly Asn Glu Asn Ser Thr Ser Asp Asn Gln Arg Thr Leu Ser Ala
1               5                   10                  15

Gln Thr Pro Arg Ser Ala Gln Pro Pro Gly Asn Ser Gln Asn Ile Lys
            20                  25                  30

Arg Lys Gln Gln Asp Thr Pro Gly Ser Pro Asp His Arg Asp Ala Ser
        35                  40                  45

Ser Ile Gly Ser Val Gly Leu Gly Gly Phe Cys Thr Ala Ser Glu Ser
    50                  55                  60

Ser Ala Ser Leu Asp Pro Cys Leu Val Ser Pro Glu Val Thr Glu Pro
65                  70                  75                  80

Arg Lys Asp Pro Gln Gly Ala Arg Gly Pro Glu Gly Ser Leu Leu Pro
                85                  90                  95

Ser Pro Pro Ser Gln Glu Arg Glu His Pro Ser Ser Ser Met Pro
            100                 105                 110

Phe Ala Glu Cys Pro Pro Glu Gly Cys Leu Ala Ser Pro Ala Ala Ala
        115                 120                 125

Pro Glu Asp Gly Pro Gln Thr Gln Ser Pro Arg Glu Pro Ala Pro
    130                 135                 140

Asn Ala Pro Gly Asp Ile Ala Ala Ala Phe Pro Ala Glu Arg Asp Ser
145                 150                 155                 160

Ser Thr Pro Tyr Gln Glu Ile Ala Val Pro Ser Ala Gly Arg Glu
                165                 170                 175

-continued

Arg Gln Pro Lys Glu Glu Gly Gln Lys Ser Ser Phe Ser Phe Ser Ser
                180                 185                 190

Gly Ile Asp Gln Ser Pro Gly Met Ser Pro Val Pro Leu Arg Glu Pro
            195                 200                 205

Met Lys Ala Pro Leu Cys Gly Glu Gly Asp Gln Pro Gly Gly Phe Glu
        210                 215                 220

Ser Gln Glu Lys Glu Ala Ala Gly Gly Phe Pro Pro Ala Glu Ser Arg
225                 230                 235                 240

Gln Gly Val Ala Ser Val Gln Val Thr Pro Glu Ala Pro Ala Ala Ala
                245                 250                 255

Gln Gln Gly Thr Glu Ser Ser Ala Val Leu Glu Lys Ser Pro Leu Lys
            260                 265                 270

Pro Met Ala Pro Ile Pro Gln Asp Pro Ala Pro Arg Ala Ser Asp Arg
        275                 280                 285

Glu Arg Gly Gln Gly Glu Ala Pro Pro Gln Tyr Leu Thr Asp Asp Leu
    290                 295                 300

Glu Phe Leu Arg Ala Cys His Leu Pro Arg Ser Asn Ser Gly Ala Ala
305                 310                 315                 320

Pro Glu Ala Glu Val Asn Ala Ala Ser Gln Glu Ser Cys Gln Gln Pro
                325                 330                 335

Val Gly Ala Tyr Leu Pro His Ala Glu Leu Pro Trp Gly Leu Pro Ser
            340                 345                 350

Pro Ala Leu Val Pro Glu Ala Gly Ser Gly Lys Glu Ala Leu Asp
        355                 360                 365

Thr Ile Asp Val Gln Gly His Pro Gln Thr Gly Met Arg Gly Thr Lys
    370                 375                 380

Pro Asn Gln Val Val Cys Val Ala Ala Gly Gly Gln Pro Glu Gly Gly
385                 390                 395                 400

Leu Pro Val Ser Pro Glu Pro Ser Leu Leu Thr Pro Thr Glu Glu Ala
                405                 410                 415

His Pro Ala Ser Ser Leu Ala Ser Phe Pro Ala Ala Gln Ile Pro Ile
            420                 425                 430

Ala Val Glu Glu Pro Gly Ser Ser Ser Arg Glu Ser Val Ser Lys Ala
        435                 440                 445

Gly Met Pro Val Ser Ala Asp Ala Ala Lys Glu Val Val Asp Ala Gly
    450                 455                 460

Leu Val Gly Leu Glu Arg Gln Val Ser Asp Leu Gly Ser Lys Gly Glu
465                 470                 475                 480

His Pro Glu Gly Asp Pro Gly Glu Val Pro Ala Pro Ser Pro Gln Glu
                485                 490                 495

Arg Gly Glu His Leu Asn Thr Glu Gln Ser His Glu Val Gln Pro Gly
            500                 505                 510

Val Pro Pro Pro Leu Pro Lys Glu Gln Ser His Glu Val Gln Pro
        515                 520                 525

Gly Ala Pro Pro Pro Leu Pro Lys Ala Pro Ser Glu Ser Ala Arg
    530                 535                 540

Gly Pro Pro Gly Pro Thr Asp Gly Ala Lys Val His Glu Asp Ser Thr
545                 550                 555                 560

Ser Pro Ala Val Ala Lys Glu Gly Ser Arg Ser Pro Gly Asp Ser Pro
                565                 570                 575

Gly Gly Lys Glu Glu Ala Pro Glu Pro Pro Asp Gly Asp Pro Gly
            580                 585                 590

Asn Leu Gln Gly Glu Asp Ser Gln Ala Phe Ser Ser Lys Arg Asp Pro

```
              595                 600                 605
Glu Val Gly Lys Asp Glu Leu Ser Lys Pro Ser Ser Asp Ala Glu Ser
610                 615                 620

Arg Asp His Pro Ser Ser His Ser Ala Gln Pro Pro Arg Lys Gly Gly
625                 630                 635                 640

Ala Gly His Thr Asp Gly Pro His Ser Gln Thr Ala Glu Ala Asp Ala
                645                 650                 655

Ser Gly Leu Pro His Lys Leu Gly Glu Glu Asp Pro Val Leu Pro Pro
                660                 665                 670

Val Pro Asp Gly Ala Gly Glu Pro Thr Val Pro Glu Gly Ala Ile Trp
            675                 680                 685

Glu Gly Ser Gly Leu Gln Pro Lys Cys Pro Asp Thr Leu Gln Ser Arg
690                 695                 700

Glu Gly Leu Gly Arg Met Glu Ser Phe Leu Thr Leu Glu Ser Glu Lys
705                 710                 715                 720

Ser Asp Phe Pro Pro Thr Pro Val Ala Glu Val Ala Pro Lys Ala Gln
                725                 730                 735

Glu Gly Glu Ser Thr Leu Glu Ile Arg Lys Met Gly Ser Cys Asp Gly
                740                 745                 750

Glu Gly Leu Leu Thr Ser Pro Asp Gln Pro Arg Gly Pro Ala Cys Asp
                755                 760                 765

Ala Ser Arg Gln Glu Phe His Ala Gly Val Pro His Pro Pro Gln Gly
770                 775                 780

Glu Asn Leu Ala Ala Asp Leu Gly Leu Thr Ala Leu Ile Leu Asp Gln
785                 790                 795                 800

Asp Gln Gln Gly Ile Pro Ser Cys Pro Gly Glu Gly Trp Ile Arg Gly
                805                 810                 815

Ala Ala Ser Glu Trp Pro Leu Leu Ser Ser Glu Lys His Leu Gln Pro
                820                 825                 830

Ser Gln Ala Gln Pro Glu Thr Ser Ile Phe Asp Val Leu Lys Glu Gln
                835                 840                 845

Ala Gln Pro Pro Glu Asn Gly Lys Glu Thr Ser Pro Ser His Pro Gly
850                 855                 860

Phe Lys Asp Gln Gly Ala Asp Ser Ser Gln Ile His Val Pro Val Glu
865                 870                 875                 880

Pro Gln Glu Asp Asn Asn Leu Pro Thr His Gly Gly Gln Glu Gln Ala
                885                 890                 895

Leu Gly Ser Glu Leu Gln Ser Gln Leu Pro Lys Gly Thr Leu Ser Asp
                900                 905                 910

Thr Pro Thr Ser Ser Pro Thr Asp Met Val Trp Glu Ser Ser Leu Thr
            915                 920                 925

Glu Glu Ser Glu Leu Ser Ala Pro Thr Arg Gln Lys Leu Pro Ala Leu
930                 935                 940

Gly Glu Lys Arg Pro Glu Gly Ala Cys Gly Asp Gly Gln Ser Ser Arg
945                 950                 955                 960

Val Ser Pro Pro Ala Ala Asp Val Leu Lys Asp Phe Ser Leu Ala Gly
                965                 970                 975

Asn Phe Ser Arg Lys Glu Thr Cys Cys Thr Gly Gln Gly Pro Asn Lys
                980                 985                 990

Ser Gln Gln Ala Leu Ala Asp Ala  Leu Glu Glu Gly Ser  Gln His Glu
            995                 1000                1005

Glu Ala  Cys Gln Arg His Pro  Gly Ala Ser Glu Ala  Ala Asp Gly
        1010                1015                1020
```

-continued

```
Cys Ser Pro Leu Trp Gly Leu Ser Lys Arg Glu Met Ala Ser Gly
1025                1030                1035

Asn Thr Gly Glu Ala Pro Pro Cys Gln Pro Asp Ser Val Ala Leu
1040                1045                1050

Leu Asp Ala Val Pro Cys Leu Pro Ala Leu Ala Pro Ala Ser Pro
1055                1060                1065

Gly Val Thr Pro Thr Gln Asp Ala Pro Glu Thr Glu Ala Cys Asp
1070                1075                1080

Glu Thr Gln Glu Gly Arg Gln Gln Pro Val Pro Ala Pro Gln Gln
1085                1090                1095

Lys Met Glu Cys Trp Ala Thr Ser Asp Ala Glu Ser Pro Lys Leu
1100                1105                1110

Leu Ala Ser Phe Pro Ser Ala Gly Glu Gln Gly Glu Ala Gly
1115                1120                1125

Ala Ala Glu Thr Gly Gly Ser Ala Gly Ala Gly Asp Pro Gly Lys
1130                1135                1140

Gln Gln Ala Pro Glu Lys Pro Gly Glu Ala Thr Leu Ser Cys Gly
1145                1150                1155

Leu Leu Gln Thr Glu His Cys Leu Thr Ser Gly Glu Glu Ala Ser
1160                1165                1170

Thr Ser Ala Leu Arg Glu Ser Cys Gln Ala Glu His Pro Met Ala
1175                1180                1185

Ser Cys Gln Asp Ala Leu Leu Pro Ala Arg Glu Leu Gly Gly Ile
1190                1195                1200

Pro Arg Ser Thr Met Asp Phe Ser Thr His Gln Ala Val Pro Asp
1205                1210                1215

Pro Lys Glu Leu Leu Leu Ser Gly Pro Pro Glu Val Ala Ala Pro
1220                1225                1230

Asp Thr Pro Tyr Leu His Val Asp Ser Ala Ala Gln Arg Gly Ala
1235                1240                1245

Glu Asp Ser Gly Val Lys Ala Val Ser Ser Ala Asp Pro Arg Ala
1250                1255                1260

Pro Gly Glu Ser Pro Cys Pro Val Gly Glu Pro Pro Leu Ala Leu
1265                1270                1275

Glu Asn Ala Ala Ser Leu Lys Leu Phe Ala Gly Ser Leu Ala Pro
1280                1285                1290

Leu Leu Gln Pro Gly Ala Ala Gly Gly Glu Ile Pro Ala Val Gln
1295                1300                1305

Ala Ser Ser Gly Ser Pro Lys Ala Arg Thr Thr Glu Gly Pro Val
1310                1315                1320

Asp Ser Met Pro Cys Leu Asp Arg Met Pro Leu Leu Ala Lys Gly
1325                1330                1335

Lys Gln Ala Thr Gly Glu Glu Lys Ala Ala Thr Ala Pro Gly Ala
1340                1345                1350

Gly Ala Lys Ala Ser Gly Glu Gly Met Ala Gly Asp Ala Ala Gly
1355                1360                1365

Glu Thr Glu Gly Ser Met Glu Arg Met Gly Glu Pro Ser Gln Asp
1370                1375                1380

Pro Lys Gln Gly Thr Ser Gly Gly Val Asp Thr Ser Ser Glu Gln
1385                1390                1395

Ile Ala Thr Leu Thr Gly Phe Pro Asp Phe Arg Glu His Ile Ala
1400                1405                1410
```

```
Lys Ile Phe Glu Lys Pro Val Leu Gly Ala Leu Ala Thr Pro Gly
1415                1420                1425

Glu Lys Ala Gly Ala Gly Arg Ser Ala Val Gly Lys Asp Leu Thr
1430                1435                1440

Arg Pro Leu Gly Pro Glu Lys Leu Leu Asp Gly Pro Pro Gly Val
1445                1450                1455

Asp Val Thr Leu Leu Pro Ala Pro Pro Ala Arg Leu Gln Val Glu
1460                1465                1470

Lys Lys Gln Gln Leu Ala Gly Glu Ala Glu Ile Ser His Leu Ala
1475                1480                1485

Leu Gln Asp Pro Ala Ser Asp Lys Leu Leu Gly Pro Ala Gly Leu
1490                1495                1500

Thr Trp Glu Arg Asn Leu Pro Gly Ala Gly Val Gly Lys Glu Met
1505                1510                1515

Ala Gly Val Pro Pro Thr Leu Arg Glu Asp Glu Arg Pro Glu Gly
1520                1525                1530

Pro Gly Ala Ala Trp Pro Gly Leu Glu Gly Gln Ala Tyr Ser Gln
1535                1540                1545

Leu Glu Arg Ser Arg Gln Glu Leu Ala Ser Gly Leu Pro Ser Pro
1550                1555                1560

Ala Ala Thr Gln Glu Leu Pro Val Glu Arg Ala Ala Ala Phe Gln
1565                1570                1575

Val Ala Pro His Ser His Gly Glu Ala Val Ala Gln Asp Arg
1580                1585                1590

Ile Pro Ser Gly Lys Gln His Gln Glu Thr Ser Ala Cys Asp Ser
1595                1600                1605

Pro His Gly Glu Asp Gly Pro Gly Asp Phe Ala His Thr Gly Val
1610                1615                1620

Pro Gly His Val Pro Arg Ser Thr Cys Ala Pro Ser Pro Gln Arg
1625                1630                1635

Glu Val Leu Thr Val Pro Glu Ala Asn Ser Glu Pro Trp Thr Leu
1640                1645                1650

Asp Thr Leu Gly Gly Glu Arg Arg Pro Gly Val Thr Ala Gly Ile
1655                1660                1665

Leu Glu Met Arg Asn Ala Leu Gly Asn Gln Ser Thr Pro Ala Pro
1670                1675                1680

Pro Thr Gly Glu Val Ala Asp Thr Pro Leu Glu Pro Gly Lys Val
1685                1690                1695

Ala Gly Ala Ala Gly Glu Ala Glu Gly Asp Ile Thr Leu Ser Thr
1700                1705                1710

Ala Glu Thr Gln Ala Cys Ala Ser Gly Asp Leu Pro Glu Ala Gly
1715                1720                1725

Thr Thr Arg Thr Phe Ser Val Val Ala Gly Asp Leu Val Leu Pro
1730                1735                1740

Gly Ser Cys Gln Asp Pro Ala Cys Ser Asp Lys Ala Pro Gly Met
1745                1750                1755

Glu Gly Thr Ala Ala Leu His Gly Asp Ser Pro Ala Arg Pro Gln
1760                1765                1770

Gln Ala Lys Glu Gln Pro Gly Pro Glu Arg Pro Ile Pro Ala Gly
1775                1780                1785

Asp Gly Lys Val Cys Val Ser Ser Pro Pro Glu Pro Asp Glu Thr
1790                1795                1800

His Asp Pro Lys Leu Gln His Leu Ala Pro Glu Glu Leu His Thr
```

-continued

```
            1805                1810                1815
Asp Arg Glu Ser Pro Arg Pro Gly Pro Ser Met Leu Pro Ser Val
            1820                1825                1830
Pro Lys Lys Asp Ala Pro Arg Val Met Asp Lys Val Thr Ser Asp
            1835                1840                1845
Glu Thr Arg Gly Ala Glu Gly Thr Glu Ser Ser Pro Val Ala Asp
            1850                1855                1860
Asp Ile Ile Gln Pro Ala Ala Pro Ala Asp Leu Glu Ser Pro Thr
            1865                1870                1875
Leu Ala Ala Ser Ser Tyr His Gly Asp Val Val Gly Gln Val Ser
            1880                1885                1890
Thr Asp Leu Ile Ala Gln Ser Ile Ser Pro Ala Ala Ala His Ala
            1895                1900                1905
Gly Leu Pro Pro Ser Ala Ala Glu His Ile Val Ser Pro Ser Ala
            1910                1915                1920
Pro Ala Gly Asp Arg Val Glu Ala Ser Thr Pro Ser Cys Pro Asp
            1925                1930                1935
Pro Ala Lys Asp Leu Ser Arg Ser Ser Asp Ser Glu Glu Ala Phe
            1940                1945                1950
Glu Thr Pro Glu Ser Thr Thr Pro Val Lys Ala Pro Pro Ala Pro
            1955                1960                1965
Pro Pro Pro Pro Pro Glu Val Ile Pro Glu Pro Glu Val Ser Thr
            1970                1975                1980
Gln Pro Pro Pro Glu Glu Pro Gly Cys Gly Ser Glu Thr Val Pro
            1985                1990                1995
Val Pro Asp Gly Pro Arg Ser Asp Ser Val Glu Gly Ser Pro Phe
            2000                2005                2010
Arg Pro Pro Ser His Ser Phe Ser Ala Val Phe Asp Glu Asp Lys
            2015                2020                2025
Pro Ile Ala Ser Ser Gly Thr Tyr Asn Leu Asp Phe Asp Asn Ile
            2030                2035                2040
Glu Leu Val Asp Thr Phe Gln Thr Leu Glu Pro Arg Ala Ser Asp
            2045                2050                2055
Ala Lys Asn Gln Glu Gly Lys Val Asn Thr Arg Arg Lys Ser Thr
            2060                2065                2070
Asp Ser Val Pro Ile Ser Lys Ser Thr Leu Ser Arg Ser Leu Ser
            2075                2080                2085
Leu Gln Ala Ser Asp Phe Asp Gly Ala Ser Ser Gly Asn Pro
            2090                2095                2100
Glu Ala Val Ala Leu Ala Pro Asp Ala Tyr Ser Thr Gly Ser Ser
            2105                2110                2115
Ser Ala Ser Ser Thr Leu Lys Arg Thr Lys Lys Pro Arg Pro Pro
            2120                2125                2130
Ser Leu Lys Lys Lys Gln Thr Thr Lys Lys Pro Thr Glu Thr Pro
            2135                2140                2145
Pro Val Lys Glu Thr Gln Gln Glu Pro Asp Glu Glu Ser Leu Val
            2150                2155                2160
Pro Ser Gly Glu Asn Leu Ala Ser Glu Thr Lys Thr Glu Ser Ala
            2165                2170                2175
Lys Thr Glu Gly Pro Ser Pro Ala Leu Leu Glu Glu Thr Pro Leu
            2180                2185                2190
Glu Pro Ala Val Gly Pro Lys Ala Ala Cys Pro Leu Asp Ser Glu
            2195                2200                2205
```

```
Ser Ala Glu Gly Val Val Pro Pro Ala Ser Gly Gly Gly Arg Val
    2210            2215            2220

Gln Asn Ser Pro Pro Val Gly Arg Lys Thr Leu Pro Leu Thr Thr
    2225            2230            2235

Ala Pro Glu Ala Gly Glu Val Thr Pro Ser Asp Ser Gly Gly Gln
    2240            2245            2250

Glu Asp Ser Pro Ala Lys Gly Leu Ser Val Arg Leu Glu Phe Asp
    2255            2260            2265

Tyr Ser Glu Asp Lys Ser Ser Trp Asp Asn Gln Gln Glu Asn Pro
    2270            2275            2280

Pro Pro Thr Lys Lys Ile Gly Lys Lys Pro Val Ala Lys Met Pro
    2285            2290            2295

Leu Arg Arg Pro Lys Met Lys Lys Thr Pro Glu Lys Leu Asp Asn
    2300            2305            2310

Thr Pro Ala Ser Pro Pro Arg Ser Pro Ala Glu Pro Asn Asp Ile
    2315            2320            2325

Pro Ile Ala Lys Gly Thr Tyr Thr Phe Asp Ile Asp Lys Trp Asp
    2330            2335            2340

Asp Pro Asn Phe Asn Pro Phe Ser Ser Thr Ser Lys Met Gln Glu
    2345            2350            2355

Ser Pro Lys Leu Pro Gln Gln Ser Tyr Asn Phe Asp Pro Asp Thr
    2360            2365            2370

Cys Asp Glu Ser Val Asp Pro Phe Lys Thr Ser Ser Lys Thr Pro
    2375            2380            2385

Ser Ser Pro Ser Lys Ser Pro Ala Ser Phe Glu Ile Pro Ala Ser
    2390            2395            2400

Ala Met Glu Ala Asn Gly Val Asp Gly Asp Gly Leu Asn Lys Pro
    2405            2410            2415

Ala Lys Lys Lys Lys Thr Pro Leu Lys Thr Asp Thr Phe Arg Val
    2420            2425            2430

Lys Lys Ser Pro Lys Arg Ser Pro Leu Ser Asp Pro Pro Ser Gln
    2435            2440            2445

Asp Pro Thr Pro Ala Ala Thr Pro Glu Thr Pro Pro Val Ile Ser
    2450            2455            2460

Ala Val Val His Ala Thr Asp Glu Glu Lys Leu Ala Val Thr Asn
    2465            2470            2475

Gln Lys Trp Thr Cys Met Thr Val Asp Leu Glu Ala Asp Lys Gln
    2480            2485            2490

Asp Tyr Pro Gln Pro Ser Asp Leu Ser Thr Phe Val Asn Glu Thr
    2495            2500            2505

Lys Phe Ser Ser Pro Thr Glu Glu Leu Asp Tyr Arg Asn Ser Tyr
    2510            2515            2520

Glu Ile Glu Tyr Met Glu Lys Ile Gly Ser Ser Leu Pro Gln Asp
    2525            2530            2535

Asp Asp Ala Pro Lys Lys Gln Ala Leu Tyr Leu Met Phe Asp Thr
    2540            2545            2550

Ser Gln Glu Ser Pro Val Lys Ser Ser Pro Val Arg Met Ser Glu
    2555            2560            2565

Ser Pro Thr Pro Cys Ser Gly Ser Ser Phe Glu Glu Thr Glu Ala
    2570            2575            2580

Leu Val Asn Thr Ala Ala Lys Asn Gln His Pro Val Pro Arg Gly
    2585            2590            2595
```

```
Leu Ala Pro Asn Gln Glu Ser His Leu Gln Val Pro Glu Lys Ser
            2600                2605                2610

Ser Gln Lys Glu Leu Glu Ala Met Gly Leu Gly Thr Pro Ser Glu
        2615                2620                2625

Ala Ile Glu Ile Thr Ala Pro Glu Gly Ser Phe Ala Ser Ala Asp
    2630                2635                2640

Ala Leu Leu Ser Arg Leu Ala His Pro Val Ser Leu Cys Gly Ala
2645                2650                2655

Leu Asp Tyr Leu Glu Pro Asp Leu Ala Glu Lys Asn Pro Pro Leu
    2660                2665                2670

Phe Ala Gln Lys Leu Gln Glu Glu Leu Glu Phe Ala Ile Met Arg
2675                2680                2685

Ile Glu Ala Leu Lys Leu Ala Arg Gln Ile Ala Leu Ala Ser Arg
    2690                2695                2700

Ser His Gln Asp Ala Lys Arg Glu Ala Ala His Pro Thr Asp Val
2705                2710                2715

Ser Ile Ser Lys Thr Ala Leu Tyr Ser Arg Ile Gly Thr Ala Glu
    2720                2725                2730

Val Glu Lys Pro Ala Gly Leu Leu Phe Gln Gln Pro Asp Leu Asp
2735                2740                2745

Ser Ala Leu Gln Ile Ala Arg Ala Glu Ile Ile Thr Lys Glu Arg
    2750                2755                2760

Glu Val Ser Glu Trp Lys Asp Lys Tyr Glu Glu Ser Arg Arg Glu
2765                2770                2775

Val Met Glu Met Arg Lys Ile Val Ala Glu Tyr Glu Lys Thr Ile
    2780                2785                2790

Ala Gln Met Ile Glu Asp Glu Gln Arg Glu Lys Ser Val Ser His
2795                2800                2805

Gln Thr Val Gln Gln Leu Val Leu Glu Lys Glu Gln Ala Leu Ala
    2810                2815                2820

Asp Leu Asn Ser Val Glu Lys Ser Leu Ala Asp Leu Phe Arg Arg
2825                2830                2835

Tyr Glu Lys Met Lys Glu Val Leu Glu Gly Phe Arg Lys Asn Glu
    2840                2845                2850

Glu Val Leu Lys Arg Cys Ala Gln Glu Tyr Leu Ser Arg Val Lys
2855                2860                2865

Lys Glu Glu Gln Arg Tyr Gln Ala Leu Lys Val His Ala Glu Glu
    2870                2875                2880

Lys Leu Asp Arg Ala Asn Ala Glu Ile Ala Gln Val Arg Gly Lys
2885                2890                2895

Ala Gln Gln Glu Gln Ala Ala His Gln Ala Ser Leu Arg Lys Glu
    2900                2905                2910

Gln Leu Arg Val Asp Ala Leu Glu Arg Thr Leu Glu Gln Lys Asn
2915                2920                2925

Lys Glu Ile Glu Glu Leu Thr Lys Ile Cys Asp Glu Leu Ile Ala
    2930                2935                2940

Lys Met Gly Lys Ser
2945

<210> SEQ ID NO 155
<211> LENGTH: 9706
<212> TYPE: DNA
<213> ORGANISM: Homo sapiens

<400> SEQUENCE: 155
```

-continued

```
gcctgctcca agggaaggat caggagagaa gaaacgcaaa tcccagaacc gtgccaacat      60
ataaaacccc acattaaggg ttgtacagtg cactgggatt tctcaagtca cccgcttggt     120
cctcttccaa gtatacttta cttccttcca ttcctctcta aaactttttt aaaaactttc     180
actcctgctc taaaagttat cttggtttct tactctacct tatgccccctt gggcgaattt    240 tttcctctga ggagggaaga atagagttgc tgctgcagac acatcagatt ccctactggt     300
aacagctgga gtgcgtcacc tctgacaaaa ttctgggac gctgggaaca ctgaatcaac      360
atgggcaatg agaacagcac ctcggacaac cagaggactt tatcagctca gactccaagg     420
tccgcgcagc cacccgggaa cagtcagaat ataaaaagga agcagcagga cacgcccgga     480
agccctgacc acagagacgc gtccagcatt ggcagcgttg ggcttggagg cttctgcacc     540
gcttctgaga gttctgccag cctggatcca tgccttgtgt ccccagaggt gactgagcca     600
aggaaggacc cacagggagc cagggggcca gaaggttctt tgctgcccag cccaccaccg     660
tcccaggagc gagagcaccc ctcgtcctcc atgccctttg ccgagtgtcc cccggaaggt     720
tgcttggcaa gtccagcagc ggcacctgaa gatggtcctc agactcagtc tcccaggagg     780
gaacctgccc caaatgcccc aggagacatc gcggcggcat ttcccgctga gggacagc      840 tctactccat accaagagat tgctgccgtc cccagtgctg aagagagag acagccgaag      900 gaagaaggac agaagtcctc cttctccttc tccagtggca tcgaccagtc acctggaatg     960
tcgccagtac ccctcagaga gccaatgaag gcaccgctgt gtggagaggg ggaccagcct    1020
ggtggttttg agtcccaaga gaaagaggct gcaggtggct ttccccctgc agagtccagg    1080 caggggtgg cttctgtgca agtgaccct gaggcccctg ctgcagccca gcagggcaca     1140
gaaagctcag cggtcttgga gaagtccccc ctaaaaccca tggccccgat cccacaagat    1200
ccagccccaa gagcctcaga cagagaaaga ggccaagggg aggcgccgcc tcagtattta    1260
acagatgact tggaattcct cagggcctgc catctcccta ggagcaattc aggggctgcc    1320
ccagaagcag aagtgaatgc cgcttcccag gagagctgcc agcagccagt gggagcatat    1380
ctgccgcacg cagagctgcc ctggggcttg ccaagtcctg ccctggtgcc agaggctggg    1440
ggctctggga aggaggctct ggacaccatt gatgttcagg gtcacccaca gacagggatg    1500
cgaggaacca agcccaatca agttgtctgt gtggcagcag gcggccagcc cgaaggggt     1560 ttgcctgtga gccctgaacc ttccctgctc actccgactg aggaagcaca tccagcttca    1620
agcctcgctt cattcccagc tgctcagatt cctattgctg tagaagaacc tggatcatca    1680
tccagggaat cagtttccaa ggctgggatg ccagttctg cagatgcagc caagaggtg      1740 gtggatgcag ggttggtggg actggagagg caggtgtcag atcttggaag caagggagag    1800
catccagaag gggaccctgg agaggttcct gccccatcac cccaggagag gggagagcac    1860
ttgaacacgg agcaaagcca tgaggtccaa ccaggagtac caccccctcc tcttcccaag    1920
gagcaaagcc atgaggtcca accaggagca ccacccccctc ctcttcccaa ggcaccaagt    1980
gaaagtgcca gagggccacc ggggccaacg gatggagcca aggtccatga agattccaca    2040
agcccagccg tggctaaaga aggaagcaga tcacctggtg acagccctgg aggaaaggag    2100 gaagcccag agccacctga tggtggagac ccagggaacc tgcaaggaga ggactctcag     2160
gctttcagca gcaagcgtga tccagaagta ggcaaagatg agctttcaaa gccaagcagt    2220
gatgcagaga gcagagacca tcccagctca cactcagcac agccacccag aaagggggt     2280 gctgggcaca cggacgggcc ccactctcag acagcagagg ctgatgcatc tggcctacca    2340
```

-continued

```
cacaagctgg gtgaggagga ccccgtcctg ccccctgtgc cagatggagc tggtgagccc    2400
actgttcccg aaggagccat ctgggagggg tcaggattgc agcccaaatg tcctgacacc    2460
cttcagagca gggaaggatt gggaagaatg gagtctttcc tgactttaga atcagagaaa    2520
tcagattttc caccaactcc tgttgcagag gttgcaccca aagcccagga aggtgagagc    2580
acattggaaa taaggaagat gggcagctgt gatggggagg gcttgctgac gtccccagat    2640
caaccccgcg ggccggcgtg tgatgcgtcg agacaggaat ttcatgctgg ggtgccacat    2700 ccccccagg gggagaactt ggcagcagac ctggggctca cggcactcat cctggaccaa     2760
gatcagcagg gaatcccatc ctgcccaggg gaaggctgga taagaggagc tgcatccgag    2820
tggcccctac tatcttctga gaagcatctc cagccatccc aggcacaacc agagacatcc    2880
atctttgacg tgctcaagga gcaggccag ccacctgaaa atgggaaaga gacttctcca      2940
agccatccag gttttaagga ccaggagca gattcttccc aaatccatgt acctgtggaa      3000
cctcaggaag ataacaactt gcccactcat ggaggacagg agcaggcttt gggatcagaa    3060
cttcaaagtc agctccccaa aggcaccctg tctgatactc caacttcatc tcccactgac    3120 atggttttggg agagttctct gacagaagag tcagaattgt cagcaccaac gagacagaag    3180
ttgcctgcac taggggagaa gcggccgag ggagcatgcg tgatggtca gtcctcgagg       3240 gtctcgcctc cagcagcaga tgtcttaaaa gacttttctc ttgcagggaa cttcagcaga    3300
aaggaaactt gctgcactgg gcaggggcca aacaagtctc aacaggcatt ggctgatgcc    3360
ttggaagaag gcagccagca tgaagaagca tgtcaaaggc atccaggagc ttctgaagca    3420
gctgatggtt gttccccact ctggggcttg agtaagaggg gatggcaag tggaaacaca     3480 ggggaggccc caccttgtca gcctgactca gtagctctcc tggatgcagt tccctgcctg    3540
ccagccctgg cgcccgccag ccccggagtc acacccaccc aggatgcccc agagacagag    3600
gcatgtgatg aaacccagga aggcaggcag caaccagtgc cggccccgca gcagaaaatg    3660
gagtgctggg ccacttcgga tgcagagtcc ccaaagcttc ttgcaagttt cccatcagct    3720
ggggagcaag gtggtgaagc cggggctgct gagactggtg gcagcgctgg tgcaggagac    3780
ccaggaaagc agcaggctcc ggagaaacct ggagaagcta cttttgagttg tggcctcctt    3840 cagactgagc actgccttac ctccggggag gaagcttcta cctctgccct acgtgagtcc    3900
tgccaagctg agcaccccat ggccagctgc caggatgcct tgctgccagc cagagagctg    3960
ggtgggattc ccaggagcac catggatttt tctacacacc aggctgtccc agacccaaag    4020
gagctcctgc tgtctggggcc accagaagtg gctgctcctg acacccctta cctgcatgtc    4080
gacagtgctg cccagagagg agcagaagac agtggagtga agctgtttc ctctgcagac     4140 cccagagctc ctggcgaaag cccctgtcct gtagggagc ccccacttgc cttgaaaat     4200 gctgcctcct tgaagctgtt tgctggctcc ctcgcccccc tgttgcaacc aggagctgca    4260 ggtgggaaa tccctgcagt gcaagccagc agtggtagtc ccaaagccag aaccactgag    4320
ggaccagtgg actccatgcc atgcctggac cggatgccac ttctggccaa gggcaagcag    4380
gcaacagggg aagagaaagc agcaacagct ccaggtgcag gtgccaaggc cagtggggag    4440
ggcatggcag gtgatgcagc aggagagaca gagggcagca tggagaggat gggagagcct    4500
tcccaggacc caaagcaggg cacatcaggt ggtgtggaca caagctctga gcaaatcgcc    4560
accctcactg gcttcccaga cttcaggga cacatcgcca agatcttcga gaagcctgtg      4620
ctcggagccc tggccacacc tggagaaaag gcaggagctg ggaggagtgc agtgggtaaa    4680
gacctcacca ggccattggg cccagagaag cttctagatg ggcctccagg agtggatgtc    4740
```

```
accccttctcc ctgcacctcc tgctcgactc caggtggaga agaagcaaca gttggctgga    4800
gaggctgaga tttcccatct ggctctgcaa gatccagctt cagacaagct tctgggtcca    4860
gcagggctga cctgggagcg gaacttgcca ggtgccggtg tggggaagga gatggcaggt    4920
gtcccaccca cactgaggga agacgagagg ccagaggggc ctgggcagc  ctggccaggc    4980 ctggaaggcc aggcttactc acagctggag aggagcaggc aggaattagc ttcaggtctt    5040
ccttcaccag cagctactca ggagctccct gtggagagag ctgctgcctt ccaggtggct    5100
ccccatagcc atggagaaga ggccgtggcc caagacagaa ttccttctgg aaagcagcac    5160
caggaaacat ctgcctgcga cagtccacat ggagaagatg gtcccgggga cttttgctcac   5220 acaggggttc caggacatgt gccaaggtcc acgtgtgccc cttctcctca gagggaggtt    5280
ttgactgtgc ctgaggccaa cagtgagccc tggacccttg acacgcttgg gggtgaaagg    5340
agacccggag tcactgctgg catcttggaa atgcgaaatg ccctgggcaa ccagagcacc    5400
cctgcaccac caactggaga agtggcagac actcccctgg agcctggcaa ggtggcaggc    5460
gctgctgggg aagcagaggg tgacatcacc ctgagcacag ctgagacaca ggcatgtgcg    5520
tccggtgatc tgcctgaagc aggtactacg aggacattct ccgttgtggc aggtgacttg    5580
gtgctgccag gaagctgtca ggacccagcc tgctctgaca aggctccggg gatggagggt    5640
acagctgccc ttcatgggga cagcccagcc aggcccagc aggctaagga gcagccaggg     5700
cctgagcgcc ccattccagc tggggatggg aaggtgtgcg tctcctcacc tccagagcct    5760
gacgaaactc acgacccgaa gctgcaacat ttggctccag aagagctcca cactgacaga    5820
gagagcccca ggcctggccc atccatgtta ccttcggttc ctaagaagga tgctccaaga    5880
gtcatggata aagtcacttc agatgagacc agaggtgcgg aaggaacaga aagttcacct    5940
gtggcagatg atatcatcca gcccgctgcc cccgcagacc tggaaagccc aaccttagct    6000
gcctcttcct accacggtga tgttgttggc caggtctcta cggatctgat agcccagagc    6060
atctccccag ctgctgccca tgcgggtctt cctccctcgg ctgcagaaca catagtttcg    6120
ccatctgccc cagctggtga cagagtagaa gcttccactc cctcctgccc agatccggcc    6180
aaggacctca gcaggagttc cgattctgaa gaggcatttg agaccccgga gtcaacgacc    6240
cctgtcaaag ctccgccagc tccacccccca ccacccccg aagtcatccc agaacccgag    6300
gtcagcacac agccacccccc ggaagaacca ggatgtggtt ctgagacagt ccctgtccct    6360
gatggcccac ggagcgactc ggtggaagga agtcccttcc gtccccgtc acactccttc     6420 tctgccgtct tcgatgaaga caagccgata gccagcagtg ggacttacaa cttgactttt    6480
gacaacattg agcttgtgga tacctttcag accttggagc ctcgtgcctc agacgctaag    6540
aatcaggagg gcaaagtgaa cacacggagg aagtccacgg attccgtccc catctctaag    6600
tctacactgt cccggtcgct cagcctgcaa gccagtgact tgatggtgc ttcttcctca     6660 ggcaatcccg aggccgtggc ccttgcccca gatgcatata gcacgggttc cagcagtgct    6720
tctagtaccc ttaagcgaac taaaaaaccg aggccgcctt ccttaaaaaa gaaacagacc    6780
accaagaaac ccacagagac ccccccagtg aaggagacgc aacaggagcc agatgaagag    6840
agccttgtcc ccagtgggga gaatctagca tctgagacga aaacggaatc tgccaagacg    6900
gaaggtccta gcccagcctt attggaggag acgccccttg agccgctgt ggggcccaaa      6960 gctgcctgcc ctctggactc agagagtgca gaaggggttg tcccccggc ttctggaggt     7020 ggcagagtgc agaactcacc ccctgtcggg aggaaaacgc tgcctcttac cacggccccg    7080
```

-continued

```
gaggcagggg aggtaacccc atcggatagc ggggggcaag aggactctcc agccaagggg      7140
ctctccgtaa ggctggagtt tgactattct gaggacaaga gtagttggga caaccagcag      7200 gaaaacccc ctcctaccaa aaagataggc aaaaagccag ttgccaaaat gcccctgagg       7260
aggccaaaga tgaaaaagac acccgagaaa cttgacaaca ctcctgcctc acctcccaga     7320
tcccctgctg aacccaatga catccccatt gctaaaggta cttacacctt tgatattgac     7380
aagtgggatg accccaattt taacccttt tcttccacct caaaaatgca ggagtctccc     7440
aaactgcccc aacaatcata aactttgac ccagacacct gtgatgagtc cgttgacccc      7500
tttaagacat cctctaagac ccccagctca ccttctaaat ccccagcctc ctttgagatc     7560
ccagccagtg ctatggaagc caatggagtg gacggggatg ggctaaacaa gcccgccaag     7620
aagaagaaga cgcccctaaa gactgacaca tttagggtga aaagtcgcc aaaacggtct      7680 cctctctctg atccaccttc ccaggacccc accccagctg ctacaccaga aacaccacca     7740
gtgatctctg cggtggtcca cgccacagat gaggaaaagc tggcggtcac caaccagaag     7800
tggacgtgca tgacagtgga cctagaggct gacaaacagg actacccgca gccctcggac     7860
ctgtccacct ttgtaaacga gaccaaattc agttcaccca ctgaggagtt ggattacaga     7920
aactcctatg aaattgaata tatggagaaa attggctcct ccttacctca ggacgacgat     7980
gccccgaaga agcaggcctt gtaccttatg tttgacactt ctcaggagag ccctgtcaag     8040
tcatctcccg tccgcatgtc agagtccccg acgccgtgtt cagggtcaag ttttgaagag     8100
actgaagccc ttgtgaacac tgctgcgaaa accagcatc ctgtcccacg aggactggcc      8160
cctaaccaag agtcacactt gcaggtgcca gagaaatcct cccagaagga gctggaggcc     8220
atgggcttgg gcacccctt agaagcgatt gaaattacag ctcccgaggg ctcctttgcc      8280
tctgctgacg ccctcctcag caggctagct cacccgtct ctctctgtgg tgcacttgac       8340
tatctggagc ccgacttagc agaaaagaac ccccactat tcgctcagaa actccaggag      8400
gagttagagt ttgccatcat gcggatagaa gccctgaagc tggccaggca gattgctttg     8460
gcttcccgca gccaccagga tgccaagaga gaggctgctc acccaacaga cgtctccatc     8520
tccaaaacag ccttgtactc ccgcatcggg accgctgagg tggagaaacc tgcaggcctt    8580
ctgttccagc agcccgacct ggactctgcc ctccagatcg ccagagcaga gatcataacc    8640
aaggagagag aggtctcaga atggaaagat aaatatgaag aaagcaggcg ggaagtgatg     8700
gaaatgagga aaatagtggc cgagtatgag aagaccatcg ctcagatgat agaggacgaa     8760
cagagagaga agtcagtctc ccaccagacg gtgcagcagc tggttctgga aaggagcaa      8820 gccctggccg acctgaactc cgtggagaag tctctggccg acctcttcag aagatatgag     8880
aagatgaagg aggtcctaga aggcttccgc aagaatgaag aggtgttgaa agatgtgcg      8940 caggagtacc tgtcccgggt gaagaaggag gagcagaggt accaggccct gaaggtgcac    9000
gcggaggaga aactggacag ggccaatgct gagattgctc aggttcgagg caaggcccag    9060
caggagcaag ccgccaccca ggccagcctg cggaaggagc agctgcgagt ggacgccctg    9120
gaaaggacgc tggagcagaa gaataaagaa atagaagaac tcaccaagat tgtgacgaa     9180 ctgattgcca aaatggggaa aagctaactc tgaaccgaat gttttggact taactgttgc    9240
gtgcaatatg accgtcggca cactgctgtt cctccagttc catggacagg ttctgttttc    9300 acttttcgt atgcactact gtatttcctt tctaaataaa attgatttga ttgtatgcag      9360
tactaaggag actatcagaa tttcttgcta ttggtttgca ttttcctagt ataattcata    9420
gcaagttgac ctcagagttc ctgtatcagg gagattgtct gattctctaa taaaagacac    9480
```

```
attgctgacc ttggccttgc cctttgtaca caagttccca gggtgagcag ctttttggatt    9540 taatatgaac atgtacagcg tgcataggga ctcttgcctt aaggagtgta aacttgatct    9600
gcatttgctg atttgttttt aaaaaaacaa gaaatgcatg tttcaaataa aattctctat    9660
tgtaaataaa attttttctt tggatcttgg caaaaaaaaa aaaaaa                    9706
```

<210> SEQ ID NO 156
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Gln Ala Glu Ala Leu Ala Leu Gln Ala Ser Leu Arg
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Asp Pro Leu Leu Arg
1               5

<210> SEQ ID NO 158
<211> LENGTH: 1048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys

-continued

```
                165                 170                 175
Pro Ala Ala Gly Asn Pro Thr Pro Ser Ile Ser Trp Leu Lys Asn Gly
            180                 185                 190
Arg Glu Phe Arg Gly Glu His Arg Ile Gly Gly Ile Lys Leu Arg His
            195                 200                 205
Gln Gln Trp Ser Leu Val Met Glu Ser Val Val Pro Ser Asp Arg Gly
            210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
            245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
            290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
            325                 330                 335
Tyr Thr Cys Leu Ala Gly Asn Ser Ile Gly Phe Ser His His Ser Ala
            340                 345                 350
Trp Leu Val Val Leu Pro Ala Glu Glu Leu Val Glu Ala Asp Glu
            355                 360                 365
Ala Gly Ser Val Tyr Ala Gly Ile Leu Ser Tyr Gly Val Gly Phe Phe
            370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
            405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
            435                 440                 445
Pro Thr Leu Ala Asn Val Ser Glu Leu Glu Leu Pro Ala Asp Pro Lys
            450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
            485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
            530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Gly Leu Asp
            565                 570                 575
Tyr Ser Phe Asp Thr Cys Lys Pro Pro Glu Glu Gln Leu Thr Phe Lys
            580                 585                 590
```

-continued

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Phe Lys Glu Ser Ala Leu Arg Lys Gln Ser
        755                 760                 765

Leu Tyr Leu Lys Phe Asp Pro Leu Leu Arg Asp Ser Pro Gly Arg Pro
    770                 775                 780

Val Pro Val Ala Thr Glu Thr Ser Ser Met His Gly Ala Asn Glu Thr
785                 790                 795                 800

Pro Ser Gly Arg Pro Arg Glu Ala Lys Leu Val Glu Phe Asp Phe Leu
                805                 810                 815

Gly Ala Leu Asp Ile Pro Val Pro Gly Pro Pro Gly Val Pro Ala
            820                 825                 830

Pro Gly Gly Pro Pro Leu Ser Thr Gly Pro Ile Val Asp Leu Leu Gln
        835                 840                 845

Tyr Ser Gln Lys Asp Leu Asp Ala Val Val Lys Ala Thr Gln Glu Glu
    850                 855                 860

Asn Arg Glu Leu Arg Ser Arg Cys Glu Glu Leu His Gly Lys Asn Leu
865                 870                 875                 880

Glu Leu Gly Lys Ile Met Asp Arg Phe Glu Glu Val Val Tyr Gln Ala
                885                 890                 895

Met Glu Glu Val Gln Lys Gln Lys Glu Leu Ser Lys Ala Glu Ile Gln
            900                 905                 910

Lys Val Leu Lys Glu Lys Asp Gln Leu Thr Thr Asp Leu Asn Ser Met
        915                 920                 925

Glu Lys Ser Phe Ser Asp Leu Phe Lys Arg Phe Glu Lys Gln Lys Glu
    930                 935                 940

Val Ile Glu Gly Tyr Arg Lys Asn Glu Glu Ser Leu Lys Lys Cys Val
945                 950                 955                 960

Glu Asp Tyr Leu Ala Arg Ile Thr Gln Glu Gly Gln Arg Tyr Gln Ala
                965                 970                 975

Leu Lys Ala His Ala Glu Glu Lys Leu Gln Leu Ala Asn Glu Glu Ile
            980                 985                 990

Ala Gln Val Arg Ser Lys Ala Gln Ala Glu Ala Leu Ala Leu Gln Ala
        995                 1000                1005

Ser Leu Arg Lys Glu Gln Met Arg Ile Gln Ser Leu Glu Lys Thr
    1010                1015                1020

Val Glu Gln Lys Thr Lys Glu Asn Glu Glu Leu Thr Arg Ile Cys
    1025                1030                1035

Asp Asp Leu Ile Ser Lys Met Glu Lys Ile
    1040                1045

<210> SEQ ID NO 159
<211> LENGTH: 1027
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

```
Leu Glu Val Leu Ser Leu His Asn Val Thr Phe Asp Ala Gly Glu
            325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
        370                 375                 380

Leu Phe Ile Leu Val Val Ala Val Thr Leu Cys Arg Leu Arg Ser
385                 390                 395                 400

Pro Pro Lys Lys Gly Leu Gly Ser Pro Thr Val His Lys Ile Ser Arg
            405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
        450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
        530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
            565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735
```

```
Gln Arg Pro Thr Phe Lys Gln Leu Val Glu Asp Leu Asp Arg Val Leu
            740                 745                 750

Thr Val Thr Ser Thr Asp Val Ser Ala Gly Ser Gly Leu Val Pro Pro
            755                 760                 765

Ala Tyr Ala Pro Pro Pro Ala Val Pro Gly His Pro Ser Gly Arg Pro
            770                 775                 780

Arg Glu Ala Lys Leu Val Glu Phe Asp Phe Leu Gly Ala Leu Asp Ile
785                 790                 795                 800

Pro Val Pro Gly Pro Pro Gly Val Pro Ala Pro Gly Pro Pro
                805                 810                 815

Leu Ser Thr Gly Pro Ile Val Asp Leu Leu Gln Tyr Ser Gln Lys Asp
            820                 825                 830

Leu Asp Ala Val Val Lys Ala Thr Gln Glu Glu Asn Arg Glu Leu Arg
            835                 840                 845

Ser Arg Cys Glu Glu Leu His Gly Lys Asn Leu Glu Leu Gly Lys Ile
            850                 855                 860

Met Asp Arg Phe Glu Glu Val Val Tyr Gln Ala Met Glu Glu Val Gln
865                 870                 875                 880

Lys Gln Lys Glu Leu Ser Lys Ala Glu Ile Gln Lys Val Leu Lys Glu
                885                 890                 895

Lys Asp Gln Leu Thr Thr Asp Leu Asn Ser Met Glu Lys Ser Phe Ser
            900                 905                 910

Asp Leu Phe Lys Arg Phe Glu Lys Gln Lys Glu Val Ile Glu Gly Tyr
            915                 920                 925

Arg Lys Asn Glu Glu Ser Leu Lys Lys Cys Val Glu Asp Tyr Leu Ala
            930                 935                 940

Arg Ile Thr Gln Glu Gly Gln Arg Tyr Gln Ala Leu Lys Ala His Ala
945                 950                 955                 960

Glu Glu Lys Leu Gln Leu Ala Asn Glu Glu Ile Ala Gln Val Arg Ser
                965                 970                 975

Lys Ala Gln Ala Glu Ala Leu Ala Leu Gln Ala Ser Leu Arg Lys Glu
            980                 985                 990

Gln Met Arg Ile Gln Ser Leu Glu  Lys Thr Val Glu Gln  Lys Thr Lys
            995                 1000                1005

Glu Asn Glu Glu Leu Thr Arg  Ile Cys Asp Asp Leu  Ile Ser Lys
    1010                1015                1020

Met Glu Lys Ile
    1025

<210> SEQ ID NO 160
<211> LENGTH: 984
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
            50                  55                  60
```

```
Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
                115                 120                 125

Pro Ser Ser Gly Asp Asp Glu Asp Gly Glu Asp Ala Glu Asp Thr
            130              135              140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
                435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480
```

```
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
            530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
            595                 600                 605
Ala Ser Gln Lys Cys Ile His Arg Asp Leu Ala Ala Arg Asn Val Leu
            610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
                660                 665                 670
His Gln Ser Asp Val Trp Ser Phe Gly Val Leu Leu Trp Glu Ile Phe
            675                 680                 685
Thr Leu Gly Gly Ser Pro Tyr Pro Gly Ile Pro Val Glu Glu Leu Phe
            690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
            740                 745                 750
Thr Val Thr Ser Thr Asp Val Pro Gly Pro Pro Gly Val Pro Ala
            755                 760                 765
Pro Gly Gly Pro Pro Leu Ser Thr Gly Pro Ile Val Asp Leu Leu Gln
            770                 775                 780
Tyr Ser Gln Lys Asp Leu Asp Ala Val Val Lys Ala Thr Gln Glu Glu
785                 790                 795                 800
Asn Arg Glu Leu Arg Ser Arg Cys Glu Glu Leu His Gly Lys Asn Leu
                805                 810                 815
Glu Leu Gly Lys Ile Met Asp Arg Phe Glu Glu Val Val Tyr Gln Ala
                820                 825                 830
Met Glu Glu Val Gln Lys Gln Lys Glu Leu Ser Lys Ala Glu Ile Gln
            835                 840                 845
Lys Val Leu Lys Glu Lys Asp Gln Leu Thr Thr Asp Leu Asn Ser Met
850                 855                 860
Glu Lys Ser Phe Ser Asp Leu Phe Lys Arg Phe Glu Lys Gln Lys Glu
865                 870                 875                 880
Val Ile Glu Gly Tyr Arg Lys Asn Glu Glu Ser Leu Lys Lys Cys Val
                885                 890                 895
Glu Asp Tyr Leu Ala Arg Ile Thr Gln Glu Gly Gln Arg Tyr Gln Ala
```

```
                    900                 905                 910
Leu Lys Ala His Ala Glu Glu Lys Leu Gln Leu Ala Asn Glu Glu Ile
            915                 920                 925

Ala Gln Val Arg Ser Lys Ala Gln Ala Glu Ala Leu Ala Leu Gln Ala
        930                 935                 940

Ser Leu Arg Lys Glu Gln Met Arg Ile Gln Ser Leu Glu Lys Thr Val
945                 950                 955                 960

Glu Gln Lys Thr Lys Glu Asn Glu Glu Leu Thr Arg Ile Cys Asp Asp
            965                 970                 975

Leu Ile Ser Lys Met Glu Lys Ile
            980

<210> SEQ ID NO 161
<211> LENGTH: 949
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270
```

-continued

```
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
        290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                    325                 330                 335
Tyr Thr Cys Leu Ala Gly Asn Ser Ile Gly Phe Ser His His Ser Ala
                340                 345                 350
Trp Leu Val Val Leu Pro Ala Glu Glu Leu Val Glu Ala Asp Glu
        355                 360                 365
Ala Gly Ser Val Tyr Ala Gly Ile Leu Ser Tyr Gly Val Gly Phe Phe
    370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
                420                 425                 430
Ser Asn Thr Pro Leu Val Arg Ile Ala Arg Leu Ser Ser Gly Glu Gly
            435                 440                 445
Pro Thr Leu Ala Asn Val Ser Glu Leu Glu Leu Pro Ala Asp Pro Lys
        450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
                500                 505                 510
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
        530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
                580                 585                 590
Asp Leu Val Ser Cys Ala Tyr Gln Val Ala Arg Gly Met Glu Tyr Leu
            595                 600                 605
Ala Ser Gln Lys Cys Ile His Arg Asp Leu Ala Ala Arg Asn Val Leu
        610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                    645                 650                 655
Pro Val Lys Trp Met Ala Pro Glu Ala Leu Phe Asp Arg Val Tyr Thr
                660                 665                 670
His Gln Ser Asp Val Trp Ser Phe Gly Val Leu Leu Trp Glu Ile Phe
            675                 680                 685
Thr Leu Gly Gly Ser Pro Tyr Pro Gly Ile Pro Val Glu Glu Leu Phe
```

```
                690                 695                 700
Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735

Gln Arg Pro Thr Phe Lys Gln Leu Val Glu Asp Leu Asp Arg Val Leu
            740                 745                 750

Thr Val Thr Ser Thr Asp Val Lys Ala Thr Gln Glu Glu Asn Arg Glu
            755                 760                 765

Leu Arg Ser Arg Cys Glu Glu Leu His Gly Lys Asn Leu Glu Leu Gly
            770                 775                 780

Lys Ile Met Asp Arg Phe Glu Glu Val Val Tyr Gln Ala Met Glu Glu
785                 790                 795                 800

Val Gln Lys Gln Lys Glu Leu Ser Lys Ala Glu Ile Gln Lys Val Leu
            805                 810                 815

Lys Glu Lys Asp Gln Leu Thr Thr Asp Leu Asn Ser Met Glu Lys Ser
            820                 825                 830

Phe Ser Asp Leu Phe Lys Arg Phe Glu Lys Gln Lys Glu Val Ile Glu
            835                 840                 845

Gly Tyr Arg Lys Asn Glu Glu Ser Leu Lys Lys Cys Val Glu Asp Tyr
            850                 855                 860

Leu Ala Arg Ile Thr Gln Glu Gly Gln Arg Tyr Gln Ala Leu Lys Ala
865                 870                 875                 880

His Ala Glu Glu Lys Leu Gln Leu Ala Asn Glu Glu Ile Ala Gln Val
            885                 890                 895

Arg Ser Lys Ala Gln Ala Glu Ala Leu Ala Leu Gln Ala Ser Leu Arg
            900                 905                 910

Lys Glu Gln Met Arg Ile Gln Ser Leu Glu Lys Thr Val Glu Gln Lys
            915                 920                 925

Thr Lys Glu Asn Glu Glu Leu Thr Arg Ile Cys Asp Asp Leu Ile Ser
            930                 935                 940

Lys Met Glu Lys Ile
945

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gtaacctgcg ggagtttctg                                              20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
acaccaggtc cttgaaggtg                                              20

<210> SEQ ID NO 164
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cctgagggac agtcctggta                                               20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
agtgctccca agaaatcgaa                                               20

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cgtgaagatg ctgaaagacg atg                                           23

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
aaacgcttga agaggtcgga g                                             21

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
atgctagcag gggtctctga                                               20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cccttccaga acacctttca                                               20

<210> SEQ ID NO 170
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 170
atgatcatgc gggagtgc                                                    18

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gggggtcgaa cttgaggtat                                                  20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cgcaggcttt ttgtagtgag                                                  20

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tgtaggcgcg aaaggaag                                                    18

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gaactcatcc ggacccctat                                                  20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gctttcccca ttgcactta                                                   20

<210> SEQ ID NO 176
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 176
gaggagagaa gcacgtggag                                                    20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ggcagacgtg tgaggtgtaa                                                    20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gtgatcagca gctggactgt                                                    20

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gagcctgggc atggatct                                                      18

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
agaggtgacc accaatcagc                                                    20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cgtgtcccac acagagacag                                                    20

<210> SEQ ID NO 182
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 182
tgcgtcgtgg agaacaagtt t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gttccactgc aaggtgtaca g                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gcacaacctc gactactaca a                                              21

<210> SEQ ID NO 185
<211> LENGTH: 822
<212> TYPE: PRT
<213> ORGANISM: Homo sapiens

<400> SEQUENCE: 185

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205
```

```
Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
                260                 265                 270

Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
                340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
                420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
                500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
                580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
    610                 615                 620
```

```
Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
            725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
            805                 810                 815

Gly Gly Leu Lys Arg Arg
            820

<210> SEQ ID NO 186
<211> LENGTH: 5917
<212> TYPE: DNA
<213> ORGANISM: Homo sapiens

<400> SEQUENCE: 186
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc aggggcgga ggcggaggag ggaccagcgc gggtgggagt gagagagcga     180
gccctcgcgc cccgccggcg catagcgctc ggagcgctct tgcggccaca ggcgcggcgt     240
cctcggcggc gggcggcagc tagcgggagc cgggacgccg gtgcagccgc agcgcgcgga     300
ggaacccggg tgtgccggga gctgggcggc cacgtccgga cgggaccgag acccctcgta     360
gcgcattgcg gcgacctcgc cttccccggc cgcgagcgcg ccgctgcttg aaaagccgcg     420
gaacccaagg acttttctcc ggtccgagct cggggcgccc cgcagggcgc acggtacccg     480
tgctgcagtc gggcacgccg cggcgccggg gcctccgcag ggcgatggag cccggtctgc     540
aaggaaagtg aggcgccgcc gctgcgttct ggaggagggg ggcacaaggt ctggagaccc     600
cgggtggcgg acgggagccc tccccccgcc ccgcctccgg ggcaccagct ccggctccat     660
tgttcccgcc cgggctggag gcgccgagca ccgagcgccg ccgggagtcg agcgccggcc     720
gcggagctct tgcgaccccg ccaggacccg aacagagccc gggggcggcg ggccggagcc     780
ggggacgcgg gcacacgccc gctcgcacaa gccacggcgg actctcccga ggcggaacct     840
ccacgccgag cgagggtcag tttgaaaagg aggatcgagc tcactgtgga gtatccatgg     900
agatgtggag ccttgtcacc aacctctaac tgcagaactg ggatgtggag ctggaagtgc     960
```

```
ctcctcttct gggctgtgct ggtcacagcc acactctgca ccgctaggcc gtccccgacc    1020
ttgcctgaac aagcccagcc ctggggagcc cctgtggaag tggagtcctt cctggtccac    1080
cccggtgacc tgctgcagct tcgctgtcgg ctgcgggacg atgtgcagag catcaactgg    1140
ctgcgggacg gggtgcagct ggcggaaagc aaccgcaccc gcatcacagg ggaggaggtg    1200
gaggtgcagg actccgtgcc cgcagactcc ggcctctatg cttgcgtaac cagcagcccc    1260
tcgggcagtg acaccaccta cttctccgtc aatgtttcag atgctctccc ctcctcggag    1320
gatgatgatg atgatgatga ctcctcttca gaggagaaag aaacagataa caccaaacca    1380
aaccgtatgc ccgtagctcc atattggaca tccccagaaa agatggaaaa gaaattgcat    1440
gcagtgccgg ctgccaagac agtgaagttc aaatgcccct tccagtggga cccaaacccc    1500
acactgcgct ggttgaaaaa tggcaaagaa ttcaaacctg accacagaat ggaggctac     1560 aaggtccgtt atgccacctg gagcatcata atggactctg tggtgccctc tgacaagggc    1620
aactacacct gcattgtgga gaatgagtac ggcagcatca ccacacata ccagctggat     1680 gtcgtggagc ggtcccctca ccggcccatc ctgcaagcag ggttgcccgc caacaaaaca    1740
gtggccctgg gtagcaacgt ggagttcatg tgtaaggtgt acagtgaccc gcagccgcac    1800
atccagtggc taaagcacat cgaggtgaat gggagcaaga ttggcccaga caacctgcct    1860
tatgtccaga tcttgaagac tgctggagtt ataccaccg acaaagagat ggaggtgctt     1920
cacttaagaa atgtctcctt tgaggacgca ggggagtata cgtgcttggc gggtaactct    1980
atcggactct cccatcactc tgcatggttg accgttctgg aagccctgga agagaggccg    2040
gcagtgatga cctcgcccct gtacctggag atcatcatct attgcacagg ggccttcctc    2100
atctcctgca tggtggggtc ggtcatcgtc tacaagatga agagtggtac caagaagagt    2160
gacttccaca gccagatggc tgtgcacaag ctggccaaga gcatccctct cgcagacag     2220 gtaacagtgt ctgctgactc cagtgcatcc atgaactctg gggttcttct ggttcggcca    2280
tcacggctct cctccagtgg gactcccatg ctagcagggg tctctgagta tgagcttccc    2340
gaagaccctc gctgggagct gcctcgggac agactggtct taggcaaacc cctgggagag    2400
ggctgctttg gcaggtggt gttggcagag gctatcgggc tggacaagga caaacccaac    2460
cgtgtgacca aagtggctgt gaagatgttg aagtcggacg caacagagaa agacttgtca    2520
gacctgatct cagaaatgga gatgatgaag atgatcggga gcataagaa tatcatcaac    2580 ctgctggggg cctgcacgca ggatggtccc ttgtatgtca tcgtggagta tgcctccaag    2640
ggcaacctgc gggagtacct gcaggccgg aggcccccag ggctggaata ctgctacaac    2700
cccagccaca cccagaggga gcagctctcc tccaaggacc tggtgtcctg cgcctaccag    2760
gtggcccgag gcatggagta tctggcctcc aagaagtgca tacaccgaga cctggcagcc    2820
aggaatgtcc tggtgacaga ggacaatgtg atgaagatag cagactttgg cctcgcacgg    2880
gacattcacc acatcgacta ctataaaaag acaaccaacg gccgactgcc tgtgaagtgg    2940
atggcacccg aggcattatt tgaccggatc tacacccacc agagtgatgt gtggtctttc    3000
ggggtgctcc tgtgggagat cttcactctg ggcggctccc catacccccgg tgtgcctgtg    3060 gaggaacttt tcaagctgct gaaggagggt caccgcatgg acaagcccag taactgcacc    3120
aacgagctgt acatgatgat gcgggactgc tggcatgcag tgccctcaca gagacccacc    3180
ttcaagcagc tggtggaaga cctggaccgc atcgtggcct tgacctccaa ccaggagtac    3240
ctggacctgt ccatgccct ggaccagtac tcccccagct ttcccgacac ccggagctct    3300
acgtgctcct caggggagga ttccgtcttc tctcatgagc cgctgcccga ggagcccctgc    3360
```

```
ctgccccgac acccagccca gcttgccaat ggcggactca aacgccgctg actgccaccc    3420
acacgccctc cccagactcc accgtcagct gtaaccctca cccacagccc ctgctgggcc    3480
caccacctgt ccgtccctgt cccctttcct gctggcagga gccggctgcc taccaggggc    3540
cttcctgtgt ggcctgcctt cacccactc agctcacctc tccctccacc tcctctccac     3600
ctgctggtga gaggtgcaaa gaggcagatc tttgctgcca gccacttcat cccctcccag    3660
atgttggacc aacaccccctc cctgccacca ggcactgcct ggagggcagg gagtgggagc   3720
caatgaacag gcatgcaagt gagagcttcc tgagctttct cctgtcggtt tggtctgttt    3780
tgccttcacc cataagcccc tcgcactctg gtggcaggtg ccttgtcctc agggctacag    3840
cagtagggag gtcagtgctt cgtgcctcga ttgaaggtga cctctgcccc agataggtgg    3900
tgccagtggc ttattaattc cgatactagt ttgctttgct gaccaaatgc ctggtaccag    3960
aggatggtga ggcgaaggcc aggttggggg cagtgttgtg gccctggggc ccagccccaa    4020
actgggggct ctgtatatag ctatgaagaa aacacaaagt gtataaatct gagtatatat    4080
ttacatgtct ttttaaaagg gtcgttacca gagatttacc catcgggtaa gatgctcctg    4140
gtggctggga ggcatcagtt gctatatatt aaaaacaaaa aagaaaaaaa aggaaaatgt    4200
ttttaaaaag gtcatatatt ttttgctact tttgctgttt tattttttta aattatgttc    4260
taaacctatt ttcagtttag gtccctcaat aaaaattgct gctgcttcat ttatctatgg    4320
gctgtatgaa aagggtggga atgtccactg gaaagaaggg acacccacgg gccctggggc    4380
taggtctgtc ccgagggcac cgcatgctcc cggcgcaggt tccttgtaac ctcttcttcc    4440
taggtcctgc acccagacct cacgacgcac ctcctgcctc tccgctgctt ttggaaagtc    4500
agaaaaagaa gatgtctgct tcagggcag gaacccatc catgcagtag aggcgctggg     4560
cagagagtca aggcccagca gccatcgacc atggatggtt tcctccaagg aaaccggtgg    4620
ggttgggctg gggagggggc acctacctag gaatagccac ggggtagagc tacagtgatt    4680
aagaggaaag caagggcgcg gttgctcacg cctgtaatcc cagcactttg ggacaccgag    4740
gtgggcagat cacttcaggt caggagtttg agaccagcct ggccaactta gtgaaacccc    4800
atctctacta aaaatgcaaa aattatccag gcatggtggc acacgcctgt aatcccagct    4860
ccacaggagg ctgaggcaga atcccttgaa gctgggaggc ggaggttgca gtgagccgag    4920
attgcgccat tgcactccag cctgggcaac agagaaaaca aaaagaaaa caaatgatga    4980 aggtctgcag aaactgaaac ccagacatgt gtctgccccc tctatgtggg catggttttg    5040
ccagtgcttc taagtgcagg agaacatgtc acctgaggct agttttgcat tcaggtccct    5100
ggcttcgttt cttgttggta tgcctcccca gatcgtcctt cctgtatcca tgtgaccaga    5160
ctgtatttgt tgggactgtc gcagatcttg gcttcttaca gttcttcctg tccaaactcc    5220
atcctgtccc tcaggaacgg ggggaaaatt ctccgaatgt ttttggtttt ttggctgctt    5280
ggaatttact tctgccacct gctggtcatc actgtcctca ctaagtggat tctggctccc    5340
ccgtacctca tggctcaaac taccactcct cagtcgctat attaaagctt atattttgct    5400
ggattactgc taaatacaaa agaaagttca atatgttttc atttctgtag ggaaaatggg    5460
attgctgctt taaatttctg agctagggat ttttggcag ctgcagtgtt ggcgactatt     5520
gtaaaattct ctttgtttct ctctgtaaat agcacctgct aacattacaa tttgtattta    5580
tgtttaaaga aggcatcatt tggtgaacag aactaggaaa tgaatttta gctcttaaaa     5640 gcatttgctt tgagaccgca caggagtgtc tttccttgta aaacagtgat gataatttct    5700
```

```
gccttggccc taccttgaag caatgttgtg tgaagggatg aagaatctaa aagtcttcat      5760
aagtccttgg gagaggtgct agaaaaatat aaggcactat cataattaca gtgatgtcct      5820
tgctgttact actcaaatca cccacaaatt tccccaaaga ctgcgctagc tgtcaaataa      5880
aagacagtga aattgacctg aaaaaaaaaa aaaaaa                                5917

<210> SEQ ID NO 187
<211> LENGTH: 76
<212> TYPE: DNA
<213> ORGANISM: Homo sapiens

<400> SEQUENCE: 187
gtgctggcat gccgcgccct cccagaggcc caccttcaag cagctggtgg aggacctgga      60
ccgtgtcctt accgtg                                                     76

<210> SEQ ID NO 188
<211> LENGTH: 76
<212> TYPE: DNA
<213> ORGANISM: Homo sapiens

<400> SEQUENCE: 188
atgcgggagt gctggcatga cgcgccctcc cagaggccca ccttcaagca gctggtggag      60
gacctggacc gtgtcc                                                     76

<210> SEQ ID NO 189
<211> LENGTH: 76
<212> TYPE: DNA
<213> ORGANISM: Homo sapiens

<400> SEQUENCE: 189
agctggtgga ggacctggac cgtgtcctta ccgtgacgtc caccgacgtg agtgctggct      60
ctggcctggt gccacc                                                     76

<210> SEQ ID NO 190
<211> LENGTH: 76
<212> TYPE: DNA
<213> ORGANISM: Homo sapiens

<400> SEQUENCE: 190
cccttaaaac aactcgttcc ctcagaccac acacaagaca gttcaagagg gactcaagga      60
cttacaggaa tgtcca                                                     76

<210> SEQ ID NO 191
<211> LENGTH: 76
<212> TYPE: DNA
<213> ORGANISM: Homo sapiens

<400> SEQUENCE: 191
aaccaaaggc tcagaccccc aggaatagaa aatataggcc cttaaaacaa ctcgttccct      60
cagaccacac acaaga                                                     76

<210> SEQ ID NO 192
<211> LENGTH: 76
<212> TYPE: DNA
<213> ORGANISM: Homo sapiens

<400> SEQUENCE: 192
tcaaggactt acaggaatgt ccagtgctcc caagaaatcg aactccacaa gcttggcttc      60
ccgcgcacgt cctgag                                                     76
```

<210> SEQ ID NO 193
<211> LENGTH: 76
<212> TYPE: DNA
<213> ORGANISM: Homo sapiens

<400> SEQUENCE: 193
ggacttacag gaatgtccag tgctcccaag aaatcgaact ccacaagctt ggcttcccgc    60
ggacgtcctg agggat    76

<210> SEQ ID NO 194
<211> LENGTH: 76
<212> TYPE: DNA
<213> ORGANISM: Homo sapiens

<400> SEQUENCE: 194
cagaccacac acaagacagt tcaagaggga ctcaaggact tacaggaatg tccagtgctc    60
ccaagaaatc gaactc    76

<210> SEQ ID NO 195
<211> LENGTH: 76
<212> TYPE: DNA
<213> ORGANISM: Homo sapiens

<400> SEQUENCE: 195
cttaccgtga cgtccaccga cgtgagtgct ggctctggcc tggtgccacc cgcctatgcc    60
cctcccctgc ccttag    76

<210> SEQ ID NO 196
<211> LENGTH: 76
<212> TYPE: DNA
<213> ORGANISM: Homo sapiens

<400> SEQUENCE: 196
aaacttgagg tataaggact gcttcctcaa ggccgactcc ttaaactggg acaagaggg    60 caagtgatca ggtctg    76

<210> SEQ ID NO 197
<211> LENGTH: 76
<212> TYPE: DNA
<213> ORGANISM: Homo sapiens

<400> SEQUENCE: 197
aacttgaggt ataaggactg cttcctcaag gccgactcct taaactgggg acaagagggc    60
aagtgatcag gtctga    76

<210> SEQ ID NO 198
<211> LENGTH: 76
<212> TYPE: DNA
<213> ORGANISM: Homo sapiens

<400> SEQUENCE: 198
gcccgcaggt acatgatcat gcgggagtgc tggcatgccg cgccctccca gaggcccacc    60
ttcaagcagc tggtgg    76

<210> SEQ ID NO 199
<211> LENGTH: 76
<212> TYPE: DNA
<213> ORGANISM: Homo sapiens

```
<400> SEQUENCE: 199
accgtgacgt ccaccgacgt gagtgctggc tctggcctgg tgcgacccgc cgatctctct    60
cccctgtcct tttcct                                                   76

<210> SEQ ID NO 200
<211> LENGTH: 76
<212> TYPE: DNA
<213> ORGANISM: Homo sapiens

<400> SEQUENCE: 200
tgggagggtg cggggggccg ggggggggag tgtgcaggtg agctccctgg cccttggccc    60
cctgccctct gggggg                                                   76

<210> SEQ ID NO 201
<211> LENGTH: 76
<212> TYPE: DNA
<213> ORGANISM: Homo sapiens

<400> SEQUENCE: 201
ctgggaatgg tggtgtctcg ggcagggttg tgggtgaccg ggggtgggag ggtgcggggg    60 accgggggg ggaggg                                                    76

<210> SEQ ID NO 202
<211> LENGTH: 76
<212> TYPE: DNA
<213> ORGANISM: Homo sapiens

<400> SEQUENCE: 202
agcgccctgc ccgcaggtac atgatcatgc gggagtgctg gcatgccgcg ccctcccaga    60
ggcccacctt caagca                                                   76

<210> SEQ ID NO 203
<211> LENGTH: 76
<212> TYPE: DNA
<213> ORGANISM: Homo sapiens

<400> SEQUENCE: 203
gccaacgcca tgcccaggcc ggagagtccc ggggaggctg ctggtgggca gctgactgcg    60
gggacactgg gtggaa                                                   76

<210> SEQ ID NO 204
<211> LENGTH: 76
<212> TYPE: DNA
<213> ORGANISM: Homo sapiens

<400> SEQUENCE: 204
aggccaccag aggccaacgc catgcccagg ccggagagtc ccggggaggc tgctggtggg    60
gaggcgaacg cgggga                                                   76

<210> SEQ ID NO 205
<211> LENGTH: 76
<212> TYPE: DNA
<213> ORGANISM: Homo sapiens

<400> SEQUENCE: 205
tgcccaggcc ggagagtccc ggggcggctg ctggggggga gctgactggg ggggcactgg    60
gggggagacc cgggcc                                                   76
```

```
<210> SEQ ID NO 206
<211> LENGTH: 76
<212> TYPE: DNA
<213> ORGANISM: Homo sapiens

<400> SEQUENCE: 206
taggccctta aaacaactcg ttccctcaga ccacacacaa gacagttcaa gagggactca      60
aggacttaca ggaatg                                                     76

<210> SEQ ID NO 207
<211> LENGTH: 76
<212> TYPE: DNA
<213> ORGANISM: Homo sapiens

<400> SEQUENCE: 207
actcaaggac ttacaggaat gtccagtgct cccaagaaat cgaactccac aagcttggct      60
tcccgcggac gtcctg                                                     76

<210> SEQ ID NO 208
<211> LENGTH: 76
<212> TYPE: DNA
<213> ORGANISM: Homo sapiens

<400> SEQUENCE: 208
aggcccttaa aacaactcgt tccctcagac cacacacaag acagttcaag agggactcaa      60
ggacttacag gaatgt                                                     76

<210> SEQ ID NO 209
<211> LENGTH: 76
<212> TYPE: DNA
<213> ORGANISM: Homo sapiens

<400> SEQUENCE: 209
gccctcccag aggcccacct tcaagcagct ggtggaggac ctggaccgtg tccttaccgt      60
gacgtccacc gacgtg                                                     76

<210> SEQ ID NO 210
<211> LENGTH: 76
<212> TYPE: DNA
<213> ORGANISM: Homo sapiens

<400> SEQUENCE: 210
gccgcgccct cccagaggcc caccttcaag cagctggtgg aggacctgga ccgtgtcctt      60
accgtgacgt ccaccg                                                     76

<210> SEQ ID NO 211
<211> LENGTH: 76
<212> TYPE: DNA
<213> ORGANISM: Homo sapiens

<400> SEQUENCE: 211
ggtggaggac ctggaccgtg accttaccgg gacgtccacc gacgggagtg ctggctctgg      60
cctggtgcca cccgcc                                                     76

<210> SEQ ID NO 212
<211> LENGTH: 76
<212> TYPE: DNA
<213> ORGANISM: Homo sapiens

<400> SEQUENCE: 212
```

```
gacgtccacc gacgtgagtg ctggctctgg cctggtgcca cccgcctatg cccctccccc    60
tgccgtcccc ggccat                                                    76

<210> SEQ ID NO 213
<211> LENGTH: 76
<212> TYPE: DNA
<213> ORGANISM: Homo sapiens

<400> SEQUENCE: 213
tgtccttacc gtgacgtcca ccgacgtgag tgctggctct ggcctggtgc acccgccta     60 tgcccctccc cctgcc                                                    76

<210> SEQ ID NO 214
<211> LENGTH: 76
<212> TYPE: DNA
<213> ORGANISM: Homo sapiens

<400> SEQUENCE: 214
tacctgctgg tctcggtggc cacgggcact ggtctaccag ggctgtccct ccggaggggg    60
tcaaacttga gggata                                                    76

<210> SEQ ID NO 215
<211> LENGTH: 76
<212> TYPE: DNA
<213> ORGANISM: Homo sapiens

<400> SEQUENCE: 215
ctggaccgtg tccttaccgt gacgtccacc gacgtgagtg ctggctctgg cctggtgcca    60
cccgcccatg cccctc                                                    76

<210> SEQ ID NO 216
<211> LENGTH: 76
<212> TYPE: DNA
<213> ORGANISM: Homo sapiens

<400> SEQUENCE: 216
tgtccttacc gtgacgtcca ccgacgtgag tgctggctct ggcctggtgc acccgccta     60 tgcccctccc ctgccc                                                    76

<210> SEQ ID NO 217
<211> LENGTH: 76
<212> TYPE: DNA
<213> ORGANISM: Homo sapiens

<400> SEQUENCE: 217
aaaagattta agtttagatc tttaatatac ctagaacggt ggctgtaacc agcaaggcag    60
gagccctttg tgttgg                                                    76

<210> SEQ ID NO 218
<211> LENGTH: 76
<212> TYPE: DNA
<213> ORGANISM: Homo sapiens

<400> SEQUENCE: 218
tgggtcaaac ttgaggtata aggactgctt cctcaaggcc gactccttat actggggaca    60
agagggcaag tgatca                                                    76

<210> SEQ ID NO 219
<211> LENGTH: 76
```

```
<212> TYPE: DNA
<213> ORGANISM: Homo sapiens

<400> SEQUENCE: 219
gagtgctggc tctggcctgg tgccacccgc ctatgcccct cccctggcg tccccggcca    60 tcctgccccc cagagt                                                   76

<210> SEQ ID NO 220
<211> LENGTH: 76
<212> TYPE: DNA
<213> ORGANISM: Homo sapiens

<400> SEQUENCE: 220
gagtgctggc tctggcctgg tgccacccgc ctatgcccct cccctgccg tccccggcca    60 tcctgccccc cagagt                                                   76

<210> SEQ ID NO 221
<211> LENGTH: 76
<212> TYPE: DNA
<213> ORGANISM: Homo sapiens

<400> SEQUENCE: 221
gccaacgcca tgcccaggcc ggagagtccc ggggaggctg ctggtgggga gctgacttcg    60
gggacactgg ggggaa                                                   76

<210> SEQ ID NO 222
<211> LENGTH: 76
<212> TYPE: DNA
<213> ORGANISM: Homo sapiens

<400> SEQUENCE: 222
catgcgggag tgctggcatg gcgcgccctc ccagcggccc accttcaagc agctggtggg   60
ggacctggac cgtgtc                                                   76

<210> SEQ ID NO 223
<211> LENGTH: 76
<212> TYPE: DNA
<213> ORGANISM: Homo sapiens

<400> SEQUENCE: 223
acgtgagtgc tggctctggc ctggtgccac ccgcctatgc ccctcccct gccgtccccg    60 gccatcctgc ccccca                                                   76

<210> SEQ ID NO 224
<211> LENGTH: 76
<212> TYPE: DNA
<213> ORGANISM: Homo sapiens

<400> SEQUENCE: 224
ccctcccaga ggcccacctt caagcagctg gtggaggacc tggaccgtgt ccttaccgtg    60
acgtccaccg acgtga                                                   76

<210> SEQ ID NO 225
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
```

```
ggacttacag gaatgtccag tgctcccaag aaatcgaact ccacaagctt ggcttcccgc      60
ggacgtcctg agggat                                                     76

<210> SEQ ID NO 226
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
catccctcag gacgtccgcg ggaagccaag cttgtggagt tcgatttctt gggagcactg      60
gacattcctg taagtc                                                     76

<210> SEQ ID NO 227
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
catccctcag gacgtccgcg ggaagccaag cttgtggagt tcgatttctt gggagcactg      60
gacattcctg taagtc                                                     76

<210> SEQ ID NO 228
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
catccctcag gacgtccgcg ggaagccaag cttgtggagt tcgatttctt gggagcactg      60
gacattcctg taagtc                                                     76

<210> SEQ ID NO 229
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gccatccctc aggacgtccg cgggaagcca agcttgtgga gttcgatttc ttgggagcac      60
tggacattcc tgtaag                                                     76

<210> SEQ ID NO 230
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ccggccatcc ctcaggacgt ccgcgggaag ccaagcttgt ggagttcgat ttcttgggag      60
cactggacat tcctgt                                                     76
```

<210> SEQ ID NO 231
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
caggaatgtc cagtgctacc aagaaatcga actccacaag cttgggttcc cgcggacgtc    60
ctccgggatg gccgtg                                                   76

<210> SEQ ID NO 232
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
caggaatgtc cagtgctccc aagaaatcga actccacaag cttggcttcc cgcggacgtc    60
ctgagggatg gccggg                                                   76

<210> SEQ ID NO 233
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tccccggcca tccctcagga cgtccgcggg aagccaagct tgtggagttc gatttcttgg    60
gagcactgga cattcc                                                   76

<210> SEQ ID NO 234
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 234
tccccggcca tccctcagga ngtccgcggg aagccaagct tgtggagttc gatttcttgg    60
gagcactgga cattcc                                                   76

<210> SEQ ID NO 235
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gtccccggcc atccctcagg acgtccgcgg gaagccaagc ttgtggagtt cgatttcttg    60
ggagcactgg acattc                                                   76

<210> SEQ ID NO 236
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ccgtccccgg ccatccctca ggacgtccgc gggaagccaa gcttgtggag ttcgatttct      60
tgggagcact ggacat                                                     76

<210> SEQ ID NO 237
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tgctcccaag aaatcgaact ccacaagctt ggcttcccgc ggacgtcctg agggatggcc      60
ggggacggca gggga                                                      76

<210> SEQ ID NO 238
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
aagaaatcga actccacaag cttggcttcc cgcggacgtc ctgagggatg gccggggacg      60
gcagggggag gggcat                                                     76

<210> SEQ ID NO 239
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
aaatcgaact ccacaagctt ggcttcccgc ggacgtcctg agggatggcc ggggcggca      60 gggggagggg catagg                                                     76

<210> SEQ ID NO 240
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ctggcctggt gccacccgcc tatgcccctc ccctgccgt ccccggccat ccctcaggac      60
gtccgcggga agccaa                                                     76

<210> SEQ ID NO 241
<211> LENGTH: 76

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tcgtcccgcg gacttcctga tggatcgccg gggacggcag ggggaggggc ataggcgtgt    60
ggcaccaggc cagctc                                                    76

<210> SEQ ID NO 242
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: a, c, t, g, unknown or other

<400> SEQUENCE: 242
cttcccgcgg acgtcctgag ggatggccgg ggacggnagg gggaggggca taggcgggtg    60
gcaccaggcc agagcc                                                    76

<210> SEQ ID NO 243
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gtgctggctc tggcctggtg ccacccgcct atgcccctcc cctgccgtc cccggccatc     60 cctcaggacg tccgcg                                                    76

<210> SEQ ID NO 244
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gagggatggc cggggacggc aggggggaggg gcataggcgg gtggcaccag gccagagcca    60
gcactcacgt cggtgg                                                    76

<210> SEQ ID NO 245
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggacaagagg gcaagtgatc aggtctgact gccatcccct aacacacaca gggggctaa     60 gggcagggga ggggca                                                    76

<210> SEQ ID NO 246
<211> LENGTH: 76

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ggacaagagg gcaagtgatc aggtctgact gccatcccct aacacacaca gggggggctaa    60 gggcagggga ggggca                                                     76

<210> SEQ ID NO 247
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
atgcccctcc cctgccctta gcccccctgt gtgtgttagg ggatggcagt cagacctgat    60
cacttgccct cttgtc                                                     76

<210> SEQ ID NO 248
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gcctatgccc ctcccctgcc cttagccccc ctgtgtgtgt taggggatgg cagtcagacc    60
tgatcacttg ccctct                                                     76

<210> SEQ ID NO 249
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gtgccacccg cctatgcccc tcccctgccc ttagcccccc tgtgtgtgtt aggggatggc    60
agtcagacct gatcac                                                     76

<210> SEQ ID NO 250
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tgactgccat cccctaacac acacaggggg gctaagggca ggggaggggc ataggcgggg    60
ggcaccaggc cagagc                                                     76

<210> SEQ ID NO 251
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 251
tgactgccat cccctaacac acacaggggg gctaagggca ggggaggggc ataggcgggg    60
ggcaccaggc cagagc    76

<210> SEQ ID NO 252
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
tgccatcccc taacacacac agggggggcta agggcagggg aggggcatag gcggggggca    60
ccaggacaga ggcagc    76

<210> SEQ ID NO 253
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cacacagggg ggctaagggc aggggagggg cataggcggg ggggaccagg cccgagccag    60
cactcacgtc gggggg    76

<210> SEQ ID NO 254
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gacgtccacc gacgtgagtg ctggctctgg cctggtgcca cccgcctatg cccctcccct    60
gcccttagac cccctg    76

<210> SEQ ID NO 255
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
cttaccgtga cgtccaccga cgtgagtgct ggctctggcc tggtgccacc cgcctatgcc    60
cctcccctgc ccttag    76

<210> SEQ ID NO 256
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256

```
tgtccttacc gtgacgtcca ccgacgtgag tgctggctct ggcctggtgc cacccgccta    60
tgcccctccc ctgccc                                                   76

<210> SEQ ID NO 257
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
cgggggtggg agtgtgcggg tgaccggggg tgggagtgtg caggtgacct ccctggccct    60 tagcccctg cactct                                                    76

<210> SEQ ID NO 258
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cgggtgaccg ggggagggag tgtgcagggg acctccctgg cccttagccc cctgcactct    60 gggggggcagg atggcc                                                  76

<210> SEQ ID NO 259
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggagtgtgca ggtgacctcc ctggccctta gccccctgca ctctgggggg caggatggcc    60
ggggacggca gggga                                                    76

<210> SEQ ID NO 260
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ggggaggctg ctggtgggca gctgactgcg gggacactgg gaggaagcct ggaccctcag    60
cgaacttcgc ccagcc                                                   76

<210> SEQ ID NO 261
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
acagcctggg cacagaggtg gctgtgcgaa ggtcgctgag ggtccaggct tccacccagt    60
gtccccgcag tcagct                                                   76
```

<210> SEQ ID NO 262
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tgactgcggg gacactgggt ggaagcctgg accctcagcg accttcgcac agccacctct      60
gtgcccaggc tgtgcc                                                      76

<210> SEQ ID NO 263
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
cggggacact gggtggaagc ctggaccctc agcgaccttc gcacagccac ctctgtgccc      60
aggctgtgcc ccagaa                                                      76

<210> SEQ ID NO 264
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ggggacactg ggtggaagcc tggaccctca gcgaccttcg cacagccacc tctgtggcca      60
ggctgtgcca cagaag                                                      76

<210> SEQ ID NO 265
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggacactggg tggaagcctg gaccctcagc gaccttcgca cagccacctc tgtgcccagg      60
ctgtgcccca gaaggc                                                      76

<210> SEQ ID NO 266
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gaagcctgga ccctcagcga ccttcgcaca gccacctctg tgccccggct gtgcccagc       60 cggcccgccc cacacc                                                      76

<210> SEQ ID NO 267
<211> LENGTH: 76
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 267
gaagcctgga ccctcagcga ccttcgcaca gccacctctg tgcccaggct gtgccccaga    60
aggcccgccc cacacc    76

<210> SEQ ID NO 268
<211> LENGTH: 76
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 268
tggaccctca gcgaccttcg cacagccacc tctgtgccca ggctgtgccc cagaaggccc    60
gccccacacc tcagca    76

<210> SEQ ID NO 269
<211> LENGTH: 76
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 269
gaccctcagc gaccttcgca cagccacctc tgtgcccagg ctgtgcccca gaaggcccgc    60
cccacacctc agcact    76

<210> SEQ ID NO 270
<211> LENGTH: 76
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 270
tcagcgacct tcgcacagcc acctctgtgc ccaggctgtg cccagaagg cccgccccac    60 acctcagcac tctggg    76

<210> SEQ ID NO 271
<211> LENGTH: 76
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 271
ccttcgcaca gccacctctg tgcccaggct gtgccccaga aggcccgccc cacacctcag    60
cactctgggg ggcagg    76

<210> SEQ ID NO 272
<211> LENGTH: 76
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 272
gacgtccacc gacgtgagtg ctggctctgg cctggtgcca cccgcctatg cccctccccc    60
tgccgtcccc ggccat    76

<210> SEQ ID NO 273
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
caagagggac tcaaggactt acaggaatgt ccagtgctcc caagaaatcg aactccacaa    60
gcttggcttc ccgcgg    76

<210> SEQ ID NO 274
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
caagagggac tcaaggactt acaggaatgt ccagtgctcc caagaaatcg aactccacaa    60
gcttggcttc ccgcgg    76

<210> SEQ ID NO 275
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ataggccctt aaaacaactc gttccctcag accacacaca agacagttca agagggactc    60
aaggacttac aggaat    76

<210> SEQ ID NO 276
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tcaagaggga ctcaaggact tacaggaatg tccagtgctc ccaagaaatc gaactccaca    60
agcttggctt cccgcg    76

<210> SEQ ID NO 277
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
accacacaca agacagttca agagggactc aaggacttac aggaatgtcc agtgctccca    60
agaaatcgaa ctccac                                                          76

<210> SEQ ID NO 278
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gagctggcct ggtgccacac gcctatgccc ctcccctgc cgtccccggc gatccatcag          60
gaagtccgcg ggacga                                                          76

<210> SEQ ID NO 279
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ccaccgacgt gagtgctggc tctggcctgg tgccaccgc ctatgcccct ccccctgccg          60
tccccggcca tccctc                                                          76

<210> SEQ ID NO 280
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
caagagcctc agacagtgca tgagggaccc gagacagtgc ggcgagggaa cagcacagcg          60
gccccatgcc cccaac                                                          76

<210> SEQ ID NO 281
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
caagagcctc agacagtgca tgagggaccc gagacagtgc ggcgagggaa cagcacaggg          60
gccccatgcc cccaac                                                          76

<210> SEQ ID NO 282
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
cgttccctca gaccacacac aagacagttc aagagggact caaggactta caggaatgtc        60
cagtgctccc aagaga                                                          76

```
<210> SEQ ID NO 283
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ccaggaatag aaaatatagg cccttaaaac aactcgttcc ctcagaccac acacaagaca    60
gttcaagagg gactca                                                   76

<210> SEQ ID NO 284
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(40)
<223> OTHER INFORMATION: a, c, t, g, unknown or other

<400> SEQUENCE: 284
ggctctggcc tggtgccacc cgcctatgcc cctccccctn ccgtcccgg ccatccctca    60 ggacgtccgc gggaag                                                   76

<210> SEQ ID NO 285
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gccctgcccg caggtacatg atcatgcggg agtgctggca tgccgcgccc tcccagaggc    60
ccaccttcaa gcagct                                                   76

<210> SEQ ID NO 286
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ctggcatgcc gcgccctccc agaggcccac ctttaagcag ctggtagagg gcctggaccg    60
tgtccttacc gtgacg                                                   76

<210> SEQ ID NO 287
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
taaaacaact cgttccctca gaccacacac aagacagttc aagagggact caaggactta    60
caggaatgtc cagtgc                                                   76
```

```
<210> SEQ ID NO 288
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cacggccatc ccggaggacg tccgcgggaa cccaagcttg tggagttcga tttcttggta    60
gcactggaca ttcctg                                                   76

<210> SEQ ID NO 289
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289 tcccccctgcc gtccccggcc atccctcagg acgtccgcgg gaagccaagc ttgtggagtt   60
cgatttcttg ggagca                                                   76

<210> SEQ ID NO 290
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
agaccacaca caagacagtt caagagggac tcaaggactt acaggaatgt ccagtgctcc    60
caagaaatcg aactcc                                                   76

<210> SEQ ID NO 291
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
cccggccatc cctcaggacg tccgcgggaa gccaagcttg tggagttcga tttcttggga    60
gcactggaca ttcctg                                                   76

<210> SEQ ID NO 292
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
ggcatgccgc gccctcccag aggcccacct tcaagcagct ggtggaggac ctggaccgtg    60
tccttaccgt gacgtc                                                   76

<210> SEQ ID NO 293
<211> LENGTH: 76
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 293
ggcatgccgc gccctcccag aggcccacct tcaagcagct ggtggaggac ctggaccgtg    60
tccttaccgt gacgtc                                                    76

<210> SEQ ID NO 294
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
cggcgcacat acctgctggt ctcggtggcc acgggcactg gtctaccagg actgtccctc    60 aggaggggt caaact                                                     76

<210> SEQ ID NO 295
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
atacctgctg gtctcggtgg ccacgggcac tggtctacca ggactgtccc tcaggagggg    60
gtcaaacttg aggtat                                                    76

<210> SEQ ID NO 296
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
aggtataagg actgcttcct caaggccgac tccttaaact ggggacaaga gggcaagtga    60
tcaggtctga ctgcca                                                    76

<210> SEQ ID NO 297
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
ggaggacctg gactgtgtcc ttaccgtgac gtccaccgac gtgagtgctg gctctggcct    60
ggtgccaccc gcctat                                                    76

<210> SEQ ID NO 298
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 298
ggaggacctg gaccgtgtcc ttaccgtgac gtccaccgac gtgagtgctg gctctggcct    60
ggtgccaccc gcctat    76

<210> SEQ ID NO 299
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
caagcagctg gtggaggacc tggaccgtgt ccttaccgtg acgtccaccg acgtgagtgc    60
tggctctggc ctggtg    76

<210> SEQ ID NO 300
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
accttcaagc agctggtgga ggacctggac cgtgtcctta ccgtgacgtc caccgacgtg    60
agtgctggct ctggcc    76

<210> SEQ ID NO 301
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
caaacttgag gtataaggac tgcttcctca aggccgactc cttaaactgg ggacaagagg    60
gcaagtgatc aggtct    76

<210> SEQ ID NO 302
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tacctgctgg tctcggtggc cacgggcact ggtctaccag ggctgtccct ccggaggggg    60
tcaaacttga gggata    76

<210> SEQ ID NO 303
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
aacttgaggt ataaggactg cttcctcaag gccgactcct aaactggggg acaagagggc    60
aagtgatcag gtctga                                                   76

<210> SEQ ID NO 304
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
agctggtgga ggacctggac cgtgtcctta ccgtgacgtc caccgacgtg agtgctggct    60
ctggcctggt gccacc                                                   76

<210> SEQ ID NO 305
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gcgccctccc agaggcccac cttcaagcag ctggtggagg acctggaccg tgtccttacc    60
gtgacgtcca ccgacg                                                   76

<210> SEQ ID NO 306
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gcgggagtgc tggcatgccg cgccctccca gaggcccacc ttcaagcagc tggtggagga    60
cctggaccgt gtcctt                                                   76

<210> SEQ ID NO 307
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cctccactgg gtcctcaggg gtggggtcc ctccggggct gggcggggga gggactggca     60
ggcctgcagg ggggtt                                                   76

<210> SEQ ID NO 308
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tcacggcagc aagaaccaca ctcactgctg caaggccacc agaggccaac gccatgccca    60
ggccggagag tcccgg                                                   76

<210> SEQ ID NO 309

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tacatgatca tgcgggaggg ctggcatgcc gcgccctccc agaggcccac cttcaagcag    60
ctggtggagg gccggg                                                   76

<210> SEQ ID NO 310
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
ggtgggaagc ggcggggctc actcctgagc gccctgcccg caggacatg atcatgcggg    60 ggtgctggcc ttgcgg                                                   76

<210> SEQ ID NO 311
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gcgccctccc agaggcccac cttcaagcag ctggtggagg acctggaccg tgtccttacc    60
gtgacgtcca ccgacg                                                   76

<210> SEQ ID NO 312
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312 cctgccccccc agagtgctga ggtgtggggc gggccttctg gggcacagcc tgggcacaga   60
ggtggctgtg cgaagg                                                   76

<210> SEQ ID NO 313
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gcaggtacat gatcatgcgg gagtgccggc atttcgggac cttccctcgg gccaccctct    60
tccggttgtt gtgggc                                                   76

<210> SEQ ID NO 314
<211> LENGTH: 76
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 314
gcaggtacat gatcatgcgg gagtgctggc atgccgcgcc ctccccgagg accaccttcc    60
agcagccggg ggaggg                                                    76

<210> SEQ ID NO 315
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
cccgaataag gtgggaagcg gcggggctca ctcctgagcg ccctgaccgc aggtacatga    60
gcatgcggga gtggcg                                                    76

<210> SEQ ID NO 316
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cgtgtcctta ccgtgacgtc caccgacgtg agtgctggct ctggcctggt gccacccgcc    60
tatgcccctc cccctg                                                    76

<210> SEQ ID NO 317
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
acatgatcat gcgggagtgc tggcatgccg cgccccccca gaggcccacc ttcaagcagc    60
tggtggagga cctgga                                                    76

<210> SEQ ID NO 318
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gccttctggg gcacagcctg ggcacagagg tggctgtgcg aaggtcgctg agggtccagg    60
cttccaccca gtgtcc                                                    76

<210> SEQ ID NO 319
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
```

<222> LOCATION: (2)..(25)

<400> SEQUENCE: 319

```
t ccg gat gaa ctg gtc cct gtc ctt cg                          27
  Pro Asp Glu Leu Val Pro Val Leu
  1               5
```

<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
Pro Asp Glu Leu Val Pro Val Leu
1               5
```

<210> SEQ ID NO 321
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(24)

<400> SEQUENCE: 321

```
ctg atc gac ctg gat gtc ccc gtc ga                            26
Leu Ile Asp Leu Asp Val Pro Val
1               5
```

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

```
Leu Ile Asp Leu Asp Val Pro Val
1               5
```

<210> SEQ ID NO 323
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(26)

<400> SEQUENCE: 323

```
at gct gtc aga ggg ttt tgt gat gaa                            26
   Ala Val Arg Gly Phe Cys Asp Glu
   1               5
```

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Ala Val Arg Gly Phe Cys Asp Glu
1               5

<210> SEQ ID NO 325
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (3)..(26)

<400> SEQUENCE: 325 ac tac gat aaa aga cat aac cag tgc g                           27
   Tyr Asp Lys Arg His Asn Gln Cys
     1               5

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Tyr Asp Lys Arg His Asn Gln Cys
1               5

<210> SEQ ID NO 327
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 327
cgggggtggc ccccctcgg gggacagcgc atgcccgctg cgcaccatca agagagtcca      60
gttcggagtc ctgagtccgg atgaactggt ccctgtcctt cgaatggtgg aaggtgatac    120
catctatgat tactgctggt attctctgat gtcctcagcc cagccagaca cctcct        176

<210> SEQ ID NO 328
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: Any amino acid

<400> SEQUENCE: 328

Gly Gly Gly Pro Pro Ser Gly Asp Ser Ala Cys Pro Leu Arg Thr Ile
1               5                   10                  15

Lys Arg Val Gln Phe Gly Val Leu Ser Pro Asp Glu Leu Val Pro Val
            20                  25                  30

Leu Arg Met Val Glu Gly Asp Thr Ile Tyr Asp Tyr Cys Trp Tyr Ser
        35                  40                  45

Leu Met Ser Ser Ala Gln Pro Asp Thr Ser Xaa
    50                  55

<210> SEQ ID NO 329
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tggtccctgt ccttcgaatg gtggaaggtg ataccatcta tgattactgc tggtattctc    60
tgatgtcctc agcccagcca gacacctcct                                     90

<210> SEQ ID NO 330
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
ctggtccctg tccttcgaat ggtggaaggt gataccatct atgattactg ctggtattct    60
ctgatgtcct cagcccggcc agacacctcc                                     90

<210> SEQ ID NO 331
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
actggtccct gtccttcgaa tggtggaagg tgataccatc tatgattact gctggtattc    60
tctgatgtcc tcagcccagc cagacaccac                                     90

<210> SEQ ID NO 332
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
aactggtccc tgtccttcga atggtggaag gtgataccat ctatgattac tgctggtatt    60
ctctgatgtc ctcagcccag ccagacacct                                     90

<210> SEQ ID NO 333
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gaactggtcc ctgtccttcg aatggtggaa ggtgatacca tctatgatta ctgctggtat    60
tctctgatgt cctcagccca gccagacacc                                     90

<210> SEQ ID NO 334
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tgaactggtc cctgtccttc gaatggtgga aggtgatacc atctatgatt actgctggta    60
ttctctgatg tcctcagccc agccagacac                                     90

<210> SEQ ID NO 335
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
atgaactggt ccctgtcctt cgaatggtgg aaggtgatac catctatgat tactgctgta    60
ttctctgatg tcctcagccc agccagacac c                                   91

<210> SEQ ID NO 336
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
gatgaactgg tccctgtcct tcgaatggtg gaaggtgata ccatctatga ttactgctgg    60
tattctctga tgtcctcagc ccagccagac                                     90

<210> SEQ ID NO 337
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ggatgaactg gtccctgtcc ttcgaatggt ggaaggtgat accatctatg attactgctg    60
gtattctctg atgtcctcag cccagccaga                                     90

<210> SEQ ID NO 338
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
cggatgaact ggtccctgtc cttcgaatgg tggaaggtga taccatctat gattactgct    60
ggtattctct gatgtcctca gcccagccag                                     90

<210> SEQ ID NO 339
<211> LENGTH: 90
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 339
ccggatgaac tggtccctgt ccttcgaatg gtggaaggtg ataccatcta tgattactgc    60
tggtattctc tgatgtcctc agcccagcca                                    90

<210> SEQ ID NO 340
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tccggatgaa ctggtccctg tccttcgaat ggtggaaggt gataccatct atgattactg    60
ctggtattct ctgatgtcct cagcccagcc                                    90

<210> SEQ ID NO 341
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gtccggagga actggtccct gtccttcgaa tggtggaagg tgataccatc tatgattgct    60
gctggtattc tctgatgtcc tcagcccagc                                    90

<210> SEQ ID NO 342
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
agtccggatg aactggtccc tgtccttcga atggtggaag gtgataccat ctatgattac    60
tgctggtatt ctctgatgtc ctcagcccag                                    90

<210> SEQ ID NO 343
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gagtccggat gaactggtcc ctgtccttcg aatggtggaa ggtgatacca tctatgatta    60
ctgctggtat tctctgatgt cctcagcccg                                    90

<210> SEQ ID NO 344
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tgagtccgga tgaactggtc cctgtccttc gaatggtgga aggtgatacc atctatgatt    60
actgctggta ttctctgatg tcctcagccc                                    90

<210> SEQ ID NO 345
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ctgagtccgg atgaactggt ccctgtcctt cgaatggtgg aaggtgatac catctatgat    60
tactgctggt attctctgat gtcctcagcc                                    90

<210> SEQ ID NO 346
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
cctgagtccg gatgaactgg tccctgtcct tcgaatggtg gaaggtgata ccatctatga    60
ttactgctgg tattctctga tgtcctcagc                                    90

<210> SEQ ID NO 347
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tcctgagtcc ggatgaactg gtccctgtcc ttcgaatggt ggaaggtgat accatctatg    60
attactgctg gtattctctg atgtcctcag                                    90

<210> SEQ ID NO 348
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gtcctgagtc cggatgaact ggtccctgtc cttcgaatgg tggaaggtga taccatctat    60
gattactgct ggtattctct gatgtcctca                                    90

<210> SEQ ID NO 349
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
agtcctgagt ccggatgaac tggtccctgt ccttcgaatg gtggaaggtg ataccatcta    60

```
tgattactgc tggtattctc tgatgtcctc                                      90
```

<210> SEQ ID NO 350
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350

```
gagtcctgag tccggatgaa ctggtccctg tccttcgaat ggtggaaggt gataccatct      60
atgattactg ctggtattct ctgatgtcct                                      90
```

<210> SEQ ID NO 351
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351

```
ggagtcctga gtccggatga actggtccct gtccttcgaa tggtggaagg tgataccatc      60
tatgattact gctggtattc tctgatgtcc                                      90
```

<210> SEQ ID NO 352
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352

```
cggagtcctg agtccggatg aactggtccc tgtccttcga atggtggaag gtgataccat      60
ctatgattac tgctggtatt ctctgatgtc                                      90
```

<210> SEQ ID NO 353
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353

```
tcggagtcct gagtccggat gaactggtcc ctgtccttcg aatggtggaa ggtgatacca      60
tctatgatta ctgctggtat tctctgatgt                                      90
```

<210> SEQ ID NO 354
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354

```
ttcggagtcc tgagtccgga tgaactggtc cctgtccttc gaatggtgga aggtgatacc      60
atctatgatt actgctggta ttctctgatg                                      90
```

<210> SEQ ID NO 355
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
gttcggagtc ctgagtccgg atgaactggt ccctgtcctt cgaatggtgg aaggtgatac      60
catctatgat tactgctggt attctctgat                                       90

<210> SEQ ID NO 356
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
cagttcggag tcctgagtcc ggatgaactg gtccctgtcc ttcgaatggt ggaaggtgat      60
accatctatg attactgctg gtattctctg                                       90

<210> SEQ ID NO 357
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
ccagttcgga gtcctgagtc cggatgaact ggtccctgtc cttcgaatgg tggaaggtga      60
taccatctat gattactgct ggtattctct                                       90

<210> SEQ ID NO 358
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tccagttcgg agtcctgagt ccggatgaac tggtccctgt ccttcgaatg gtggaaggtg      60
ataccatcta tgattactgc tggtattctc                                       90

<210> SEQ ID NO 359
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
gtccagttcg gagtcctgag tccggatgaa ctggtccctg tccttcgaat ggtggaaggt      60
gataccatct atgattactg ctggtattct                                       90

<210> SEQ ID NO 360
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gagtccagtt cggagtcctg agtccggatg aactggtccc tgtccttcga atggtggaag    60
gtgataccat ctatgattac tgctggtatt                                     90

<210> SEQ ID NO 361
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
agagtccagt tcggagtcct gagtccggat gaactggtcc ctgtccttcg aatggtggaa    60
ggtgatacca tctatgatta ctgctggtat                                     90

<210> SEQ ID NO 362
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gagagtccag ttcggagtcc tgagtccgga tgaactggtc cctgtccttc gaatggtgga    60
aggtgatacc atctatgatt actgctggta                                     90

<210> SEQ ID NO 363
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
agagagtcca gttcggagtc ctgagtccgg atgaactggt ccctgtcctt cgaatggtgg    60
aaggtgatac catctatgat tactgctggt                                     90

<210> SEQ ID NO 364
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
aagagagtcc agttcggagt cctgagtccg gatgaactgg tccctgtcct tcgaatggtg    60 gaagggata ccatctatga ttactgccgg                                      90

<210> SEQ ID NO 365
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 365
caagagagtc cagttcggag tcctgagtcc ggatgaactg gtccctgtcc ttcgaatggt    60
ggaaggtgat accatctatg attactgctg                                     90

<210> SEQ ID NO 366
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tcaagagagt ccagttcgga gtcctgagtc cggatgaact ggtccctgtc cttcgaatgg    60
tggaaggtga taccatctat gattactgct                                     90

<210> SEQ ID NO 367
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
atcaagagag tccagttcgg agtcctgagt ccggatgaac tggtccctgt ccttcgaatg    60
gtggaaggtg ataccatcta tgattactgc                                     90

<210> SEQ ID NO 368
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
caccatcaag agagtccagt tcggagtcct gagtccggat gaactggtcc ctgtccttcg    60
aatggtggaa ggtgatacca tctatgatta                                     90

<210> SEQ ID NO 369
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
cgcaccatca agagagtcca gttcggagtc ctgagtccgg atgaactggt ccctgtcctt    60
cgaatggtgg aaggtgatac catctatgat                                     90

<210> SEQ ID NO 370
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gcgcaccatc aagagagtcc agttcggagt cctgagtccg gatgaactgg tccctgtcct    60
```

```
tcgaatggtg aaggtgata ccatctatga                                        90
```

<210> SEQ ID NO 371
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371

```
gcccgctgcg caccatcaag agagtccagt tcggagtcct gagtccggat gaactggtcc     60
ctgtccttcg aatggtggaa ggtgatacca                                       90
```

<210> SEQ ID NO 372
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372

```
cgcatgcccg ctgcgcacca tcaagagagt ccagttcgga gtcctgagtc cggatgaact     60
ggtccctgtc cttcgaatgg tggaaggtga                                       90
```

<210> SEQ ID NO 373
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373

```
gcgcatgccc gctgcgcacc atcaagagag tccagttcgg agtcctgagt ccggatgaac     60
tggtccctgt ccttcgaatg gtggaaggtg                                       90
```

<210> SEQ ID NO 374
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374

```
agcgcatgcc cgctgcgcac catcaagaga gtccagttcg gagtcctgag tccggatgaa     60
ctggtccctg tccttcgaat ggtggaaggt                                       90
```

<210> SEQ ID NO 375
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375

```
cagcgcatgc ccgctgcgca ccatcaagag agtccagttc ggagtcctga gtccggatga     60
actggtccct gtccttcgaa tggtggaagg                                       90
```

<210> SEQ ID NO 376

```
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gggacagcgc atgcccgctg cgcaccatca agagagtcca gttcggagtc ctgagtccgg    60
atgaactggt ccctgtcctt cgaatggtgg                                     90

<210> SEQ ID NO 377
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
cgggggacag cgcatgcccg ctgcgcacca tcaagagagt ccagttcgga gtcctgagtc    60
cggatgaact ggtccctgtc cttcgaatgg                                     90

<210> SEQ ID NO 378
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
cccccctcgg gggacagcgc atgcccgctg cgcaccatca agagagtcca gttcggagtc    60
ctgagtccgg atgaactggt ccctgtcctt                                     90

<210> SEQ ID NO 379
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ccccccctcg ggggacagcg catgcccgct gcgcaccatc aagagagtcc agttcggagt    60
cctgagtccg gatgaactgg tccctgtcct                                     90

<210> SEQ ID NO 380
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380 ggcccccct cggggggacag cgcatgcccg ctgcgcacca tcaagagagt ccagttcgga    60
gtcctgagtc cggatgaact ggtccctgtc                                     90

<210> SEQ ID NO 381
<211> LENGTH: 90
<212> TYPE: DNA
<213> ORGANISM: Artificial Sequence
<220> FEATURE:
```

<223> OTHER INFORMATION: Description of Artificial Sequence: Synthetic
    oligonucleotide

<400> SEQUENCE: 381
ggggtggccc cccctcgggg dacagcgcat gcccgctgcg caccatcaag agagtccagt    60
tcggagtcct gagtccggat gaactggtcc                                    90

<210> SEQ ID NO 382
<211> LENGTH: 90
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 382
cgggggtggc cccccctcgg ggacagcgc atgcccgctg cgcaccatca agagagtcca    60
gttcggagtc ctgagtccgg atgaactggt                                    90

<210> SEQ ID NO 383
<211> LENGTH: 170
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (2)..(169)

<400> SEQUENCE: 383 g cag ctg gac tgt gcc ttg gac cta atg agg cgc ctg cct ccc cag caa    49
  Gln Leu Asp Cys Ala Leu Asp Leu Met Arg Arg Leu Pro Pro Gln Gln
  1               5                  10                  15 atc gag aaa aac ctc agc gac ctg atc gac ctg gat gtc ccc gtt gag    97
Ile Glu Lys Asn Leu Ser Asp Leu Ile Asp Leu Asp Val Pro Val Glu
            20                  25                  30 gcc ctc acc acg gtg aag cca tac tgc aat gag atc cat gcc cag gct    145
Ala Leu Thr Thr Val Lys Pro Tyr Cys Asn Glu Ile His Ala Gln Ala
        35                  40                  45 caa ctg tgg ctc aag aga gac ccc a                                  170
Gln Leu Trp Leu Lys Arg Asp Pro
    50                  55

<210> SEQ ID NO 384
<211> LENGTH: 56
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 384

Gln Leu Asp Cys Ala Leu Asp Leu Met Arg Arg Leu Pro Pro Gln Gln
1               5                  10                  15

Ile Glu Lys Asn Leu Ser Asp Leu Ile Asp Leu Asp Val Pro Val Glu
            20                  25                  30

Ala Leu Thr Thr Val Lys Pro Tyr Cys Asn Glu Ile His Ala Gln Ala
        35                  40                  45

Gln Leu Trp Leu Lys Arg Asp Pro
    50                  55

<210> SEQ ID NO 385

```
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tggatgtccc cgtgggggcc ctcaccacgg tgaagccata ctgcaatgag atccatgccc    60
aggctcaact gtggctcaag agagacccca                                    90

<210> SEQ ID NO 386
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ctggatctcc ccgtcgagcc cctcccacg gtgaagccat actgcaatga gatccatgcc     60
caggctcaac tgtggctcaa gagagacccc                                    90

<210> SEQ ID NO 387
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
caaggatgtc cccgttgagg ccctcaccac ggtgaagcca tactgcaatg agatccatgc    60
ccaggctcaa ctgtggctca agagagacct                                    90

<210> SEQ ID NO 388
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
acctggatgt ccccgtcgag gccctcccca cggtgaagcc atactgcaat gagatccatg    60
cccaggctca actgtggctc aagagagacc                                    90

<210> SEQ ID NO 389
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
gccctggatg tccccgtcga ggccctcacc acggtgaagc catactgcaa tgagatccat    60
gcccaggctc aactgtggct caagagagac                                    90

<210> SEQ ID NO 390
<211> LENGTH: 90
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 390
ccaccttgat gtccccgtcg aggccctcac cacggtgaag ccatactgca atgagatcca    60
tgcccaggct caactgtggc tcaagagaga                                     90

<210> SEQ ID NO 391
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gcgacctgga tgtccccgtc gaggccctcc ccacggtgaa gccatactgc aatgagatcc    60
atgcccaggc tcaactgtgg ctcaagagag                                     90

<210> SEQ ID NO 392
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
gatcgacctg gatgtccccg tcgaggccct caccacggtg aagccatact gcaatgagat    60
ccatgcccag gctcaactgt ggctcaagag                                     90

<210> SEQ ID NO 393
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
acctgatcga cctggatgtc cccgtcgagg ccctcaccac ggtgaagcca tactgcaatg    60
agatccatgc ccaggctcaa ctgtggctca                                     90

<210> SEQ ID NO 394
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
cgacctgatc gacctggatg tccccgtcga ggccctcacc acggtgaagc catactgcaa    60
tgagatccat gcccaggctc aactgtggct                                     90

<210> SEQ ID NO 395
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
```
ctcagcgacc tgatcgacct ggatgtcccc gtcgaggccc tcaccacggt gaagccatac    60
tgcaatgaga tccatgccca ggctcaactg                                      90

<210> SEQ ID NO 396
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
aaaacctcag cgacctgatc gacctggatg tccccgtcga ggccctcacc acggtgaagc    60
catactgcaa tgagatccat gcccaggctc                                     90

<210> SEQ ID NO 397
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397 gaaaacctc agcgacctga tcgacctgga tgtccccgtc gaggccctca ccacggtgaa     60
gccatactgc aatgagatcc atgcccaggc                                     90

<210> SEQ ID NO 398
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
agaaaaacct cagcgacctg atcgacctgg atgtccccgt cgaggccctc accacggtga    60
agccatactg caatgagatc catgcccagg                                     90

<210> SEQ ID NO 399
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cgagaaaaac ctcagcgacc tgatcgacct ggatgtcccc gtcgaggccc tcaccacggt    60
gaagccatac tgcaatgaga tccatgccca                                     90

<210> SEQ ID NO 400
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
tcgagaaaaa cctcagcgac ctgatcgacc tggatgtccc cgtcgaggcc ctcaccacgg    60
tgaagccata ctgcaatgag atccatgccc                                     90

<210> SEQ ID NO 401
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
atcgagaaaa acctcagcga cctgatcgac ctggatgtcc ccgtcgaggc cctcaccacg      60
gtgaagccat actgcaatga gatccatgcc                                      90

<210> SEQ ID NO 402
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
aatcgagaaa aacctcagcg acctgatcga cctggatgtc cccgtcgagg ccctcaccac      60
ggtgaagcca tactgcaatg agatccatgc                                      90

<210> SEQ ID NO 403
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
aaatcgaaaa aaacctcagc gacctgatcg acctggatgg ccccggcgag gccctcacca      60
cggtgaagcc atactgcaat gagatccatg                                      90

<210> SEQ ID NO 404
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
caaatcgaga aaaacctcag cgacctgatc gacctggatg tccccgtcga ggccctcacc      60
acggtgaagc catactgcaa tgagatccat                                      90

<210> SEQ ID NO 405
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gcaaatcgag aaaaacctca gcgacctgat cgacctggat gtccccgtcg aggccctcac      60
cacggtgaag ccatactgca atgagatcca                                      90

<210> SEQ ID NO 406
<211> LENGTH: 90

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
agcaaatcga gaaaaacctc agcgacctga tcgacctgga tgtccccgtc gaggccctca      60
ccacggtgaa gccatactgc aatgagatcc                                      90

<210> SEQ ID NO 407
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
cagcaaatcg agaaaaacct cagcgacctg atcgacctgg atgtccccgt cgaggccctc      60
accacggtga agccatactg caatgagatc                                      90

<210> SEQ ID NO 408
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ccccagcaaa tcgagaaaaa cctcagcgac ctgatcgacc tggatgtccc cgtcgaggcc      60
ctcaccacgg tgaagccata ctgcaatgag                                      90

<210> SEQ ID NO 409
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ctccccagca aatcgagaaa aacctcagcg acctgatcga cctggatgtc cccgtcgagg      60
ccctcaccac ggtgaagcca tactgcaatg                                      90

<210> SEQ ID NO 410
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
cctccccagc aaatcgagaa aaacctcagc gacctgatcg acctggatgt ccccgtcgag      60
gccctcacca cggtgaagcc atactgcaat                                      90

<210> SEQ ID NO 411
<211> LENGTH: 90
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 411
gcctccccag caaatcgaga aaaacctcag cgacctgatc gacctggatg tccccgtcga    60
ggccctcacc acggtgaagc catactgcaa                                    90

<210> SEQ ID NO 412
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
tgcctcccca gcaaatcgag aaaaacctca gcgacccgat cgacctggat gtccccgtcg    60
aggccctcac cacggtgaag ccatactgca                                    90

<210> SEQ ID NO 413
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ctgcctcccc agcaaatcga gaaaaacctc agcgacctga tcgacctgga tgtccccgtc    60
gaggccctca ccacggtgaa gccatactgc                                    90

<210> SEQ ID NO 414
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
cctgcctccc cagcaaatcg agaaaaacct cagcgacctg atcgacctgg atgtccccgt    60
cgaggccctc accacggtga agccatactg                                    90

<210> SEQ ID NO 415
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
cgcctgcctc cccagcaaat cgagaaaaac ctcagcgacc tgatcgacct ggatgtcccc    60
gtcgaggccc tcaccacggt gaagccatac                                    90

<210> SEQ ID NO 416
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416

```
ggcgcctgcc tccccagcaa atcgagaaaa acctcagcga cctgatcgac ctggatgtcc    60
ccgtcgaggc cctcaccacg gtgaagccat                                     90
```

<210> SEQ ID NO 417
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417

```
gcggtgcctg cctccccagc aaatcgagaa aaacctcagc gacctgatcg acctggatgt    60
ccccgtcgag gccctcacca cggtgaagcc                                     90
```

<210> SEQ ID NO 418
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418

```
tgaggcgcct gcctcccccag caaatcgaga aaaacctcag cgacctgatc gacctggatg    60
tccccgtcga ggccctcacc acggtgaagc                                     90
```

<210> SEQ ID NO 419
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419

```
atgaggcgcc tgcctcccca gcaaatcgag aaaaacctca gcgacctgat cgacctggat    60
gtccccgtcg aggccctcac cacggtgaag                                     90
```

<210> SEQ ID NO 420
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420

```
aatgaggcgc ctgcctcccc agcaaatcga gaaaaacctc agcgacctga tcgacctgga    60
tgtccccgtc gaggccctca ccacggtgaa                                     90
```

<210> SEQ ID NO 421
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421

```
taatgaggcg cctgcctccc cagcaaatcg agaaaaacct cagcgacctg atcgacctgg    60
atgtccccgt cgaggccctc accacggtga                                     90
```

<210> SEQ ID NO 422
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gacctaatga ggcgcctgcc tccccagcaa atcgagaaaa acctcagcga cctgatcgac    60
ctggatgtcc ccgtcgaggc cctcaccacg                                     90

<210> SEQ ID NO 423
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
ttggacctaa tgaggcgcct gcctccccag caaatcgaga aaaacctcag cgacctgatc    60
gacctggatg tccccgtcga ggccctcacc                                     90

<210> SEQ ID NO 424
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
ctgggaccta aggaggcgcc tgcctcccca gcaaatcgag aaaaacctca gcgacctgat    60
cgacctggat gtccccgtcg aggccctcac                                     90

<210> SEQ ID NO 425
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gccttggacc taatgaggcg cctgcctccc cagcaaatcg agaaaaacct cagcgacctg    60
atcgacctgg atgtccccgt cgaggccctc                                     90

<210> SEQ ID NO 426
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gtgccttgga cctaatgagg cgcctgcctc cccagcaaat cgagaaaaac ctcagcgacc    60
tgatcgacct ggatgtcccc gtcgaggccc                                     90

<210> SEQ ID NO 427
<211> LENGTH: 90
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 427
actgggcctg gggcctaatg aggcgcctgc ctccccagca aatcgagaaa aacctcagcg    60
acctgatcga cctggatgtc cccgtcgagg                                    90

<210> SEQ ID NO 428
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
gactgtgcct gggccctaag gaggcgcctg cctccccagc aaatcgagaa aaacctcagc    60
gacctgatcg acctggatgt ccccgtcgag                                    90

<210> SEQ ID NO 429
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
catggactgt gccttggacc taatgaggcg cctgcctccc cagcaaatcg agaaaaacct    60
cagcgacctg atcgacctgg atgtccccga                                    90

<210> SEQ ID NO 430
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gctggactgt gccttggacc taatgaggcc ccttcctccc cagcaaatcg agaaaaacct    60
cagcgacctg atcgacctgg atgtcccccg                                    90

<210> SEQ ID NO 431
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
agctggactg tgccttggac ctaatgaggc gcctgcctcc ccagcaaatc gagaaaaacc    60
ccagcgacct gatcgacctg gatgtccccg g                                  91

<210> SEQ ID NO 432
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gcagctggac tgtgccttgg acctaatgag gcgcctgcct ccccagcaaa tcgagaaaaa    60
cctcagcgac ctgatcgacc tggatgtccc c    91

<210> SEQ ID NO 433
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433
ggagtgggtt aatgcattaa tccttaagaa taaactgaaa gtgcgaactg cctatccgtc    60
attgagactt attcatgctg tcagagggtt ttgtgatgaa ggaacctgta cagataaagc   120
caatattctg tatgcctggg cgagaaatgc tccccctacc cggctcccca aggtg        176

<210> SEQ ID NO 434
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: Any amino acid

<400> SEQUENCE: 434

Glu Trp Val Asn Ala Leu Ile Leu Lys Asn Lys Leu Lys Val Arg Thr
1               5                   10                  15

Ala Tyr Pro Ser Leu Arg Leu Ile His Ala Val Arg Gly Phe Cys Asp
            20                  25                  30

Glu Gly Thr Cys Thr Asp Lys Ala Asn Ile Leu Tyr Ala Trp Ala Arg
        35                  40                  45

Asn Ala Pro Pro Thr Arg Leu Pro Lys Gly Xaa
    50                  55

<210> SEQ ID NO 435
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ggttttgtga tgaaggaacc tgtacagata aagccaatat tctgtatgcc tgggcgagaa    60
atgctccccc tacccggctc cccaaaggtg    90

<210> SEQ ID NO 436
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
tggttttgtg atgaaggaac ctgtacagat aaagccaata ttctgtatgc ctgggcgaga    60

```
aatgctcccc ctacccggct ccccaaaggt                                     90

<210> SEQ ID NO 437
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ctggttttgt gatgaaggaa cctgtacaga taaagccaat attctgtatg cctgggcgag    60
aaatgctccc cctacgcggc tccccaaagg                                     90

<210> SEQ ID NO 438
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
gagggttttg tgatgaagga acctgtacag ataaagccaa tattctgtat gcctgggcga    60
gaaatgctcc ccctacccgg ctccccaaag                                     90

<210> SEQ ID NO 439
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
gttactggtt ttgtgatgaa ggaacctgta cagataaagc caatattctg tatgcctggg    60
cgagaaatgc tcccctacc cggctcccca a                                    91

<210> SEQ ID NO 440
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gctgtcagag ggttttgtga tgaaggaacc tgtacagata aagccaatat tctgtatgcc    60
tgggcgagaa atgctccccc tacccggctc                                     90

<210> SEQ ID NO 441
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
tgctgtcaga gggttttgtg atgaaggaac ctgtacagat aaagccaata ttctgtatgc    60
ctgggcgaga aatgctcccc ctacccggcc c                                   91

<210> SEQ ID NO 442
```

```
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
atgctgtcag agggttttgt gatgaaggaa cctgtacaga taaagccaat attctgtatg    60
cctgggcgag aaatgctccc cctacccggc                                     90

<210> SEQ ID NO 443
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
catgctgtca gagggttttg tgatgaagga gcctgtacag ataaagccaa tattctgtat    60
gcctgggcga gaaatgctcc ccctacccgg                                     90

<210> SEQ ID NO 444
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tcatgctgtc agagggtttt gtgatgaagg aacctgtaca gataaagcca atattctgta    60
tgcctgggcg agaaatgctc cccctacccg                                     90

<210> SEQ ID NO 445
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
tattcatgct gtcagagggt tttgtgatga aggaacctgt acagataaag ccaatattct    60
gtatgcctgg gcgagaaatg ctcccccctac                                    90

<210> SEQ ID NO 446
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
cttattcatg ctgtcagagg ttttgtgat gaaggaacct gtacagataa agccaatatt    60
ctgtatgcct gggcgagaaa tactccccct                                     90

<210> SEQ ID NO 447
<211> LENGTH: 90
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 447
acttattcat gctgtcagag ggttttgtga tgaaggaacc tgtacagata aagccaatat    60
tctgtatgcc tgggcgagaa atgctccccc                                    90

<210> SEQ ID NO 448
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
gagacttatt catgctgtca gagggttttg tgatgaagga acctgtacag ataaagccaa    60
tattctgtat gcctgggcga gaaatgctcc                                    90

<210> SEQ ID NO 449
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
tgagacttat tcatgctgtc agagggtttt gtgatgaagg aacctgtaca gataaagcca    60
atattctgta tgcctgggcg agaaatgctc                                    90

<210> SEQ ID NO 450
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
ttgagactta ttcatgctgt cagagggttt tgtgatgaag gaacctgtac agataaagcc    60
aatattctgt atgcctgggc gagaaatgct                                    90

<210> SEQ ID NO 451
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
gtcattgaga cttattcatg ctgtcagagg gttttgtgat gaaggaacct gtacagataa    60
agccaatatt ctgtatgcct gggcgagaaa                                    90

<210> SEQ ID NO 452
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452

```
ccgtcattga gacttattca tgctgtcaga gggttttgtg atgaaggaac ctgtacagat    60
aaagccaata ttctgtatgc ctgggcgaga                                    90

<210> SEQ ID NO 453
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
tatccgtcat tgagacttat tcatgctgtc agagggtttt gtgatgaagg aacctgtaca    60
gataaagcca atattctgta tgcctgggcg                                    90

<210> SEQ ID NO 454
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
ctatccgtca ttgagactta ttcatgctgt cagagggttt tgtgatgaag gaacctgtac    60
agataaagcc aatattctgt atgcctgggc                                    90

<210> SEQ ID NO 455
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
cctatccgtc attgagactt attcatgctg tcagagggtt ttgtgatgaa ggaacctgta    60
cagataaagc caatattctg tatgcctggg                                    90

<210> SEQ ID NO 456
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
gcctatccgt cattgagact tattcatgct gtcagagggt tttgtgatga aggaacctgt    60
acagataaag ccaatattct gtatgcctgg                                    90

<210> SEQ ID NO 457
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
tgaaagtgcg aactgcctat ccgtcattga gacttattca tgctgtcaga gggttttgtg    60
atgaaggaac ctgtacagat aaagccaata                                    90
```

<210> SEQ ID NO 458
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 458
ctgaaagtgc gaactgccta tccgtcattg agacttattc atgctgtcag agggttttgt    60
gatgaaggaa cctgtacaga taaagccaat    90

<210> SEQ ID NO 459
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 459
aaactgaaag tgcgaactgc ctatccgtca ttgagactta ttcatgctgt cagagggttt    60
tgtgatgaag gaacctgtac agataaagcc    90

<210> SEQ ID NO 460
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 460
taaactgaaa gtgcgaactg cctatccgtc attgagactt attcatgctg tcagagggtt    60
ttgtgatgaa ggaacctgta cagataaagc    90

<210> SEQ ID NO 461
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 461
attaatcctt aagaataaac tgaaagtgcg aactgcctat ccgtcattga gacttattca    60
tgctgtcaga gggttttgtg atgaaggaac    90

<210> SEQ ID NO 462
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 462
gcattaatcc ttaagaataa actgaaagtg cgaactgcct atccgtcatt gagacttatt    60
catgctgtca gagggttttg tgatgaagga    90

<210> SEQ ID NO 463
<211> LENGTH: 90

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
ggagtgggtt aatgcattaa tccttaagaa taaactgaaa gtgcgaactg cctatccgtc    60
attgagactt attcatgctg tcagagggtt                                     90

<210> SEQ ID NO 464
<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 464
acacgatttt gtcttgtgtt gccaagtcta cctgtgccat caacaacacc ctcattgctt    60
tcttcatttt gactacgata aaagacataa ccagtgcggt gcaatccaag cgaagaaaat   120
ccaagtaaac aagcaggact gcgacttgat acttggaaat gtgtgtg                 167

<210> SEQ ID NO 465
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (56)..(56)
<223> OTHER INFORMATION: Any amino acid

<400> SEQUENCE: 465

His Asp Phe Val Leu Cys Cys Gln Val Tyr Leu Cys His Gln His
 1               5                  10                  15

Pro His Cys Phe Leu His Phe Asp Tyr Asp Lys Arg His Asn Gln Cys
                20                  25                  30

Gly Ala Ile Gln Ala Lys Lys Ile Gln Val Asn Lys Gln Asp Cys Asp
            35                  40                  45

Leu Ile Leu Gly Asn Val Cys Xaa
        50                  55

<210> SEQ ID NO 466
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ataaaagaca taaccagtgc ggtgcaatcc aagcgaagaa aatccaagta acaagcagg     60 actgcgactt gatacttgga aatgtgtgtg                                     90

<210> SEQ ID NO 467
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 467
ttgctttctt cattttgact acgataaaag acataaccag tgcggtgcaa tccaagcgaa    60
gaaaatccaa gtaaacaagc aggactgcga                                    90

<210> SEQ ID NO 468
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
cctcattgct ttcttcattt tgactacgat aaaagacata accagtgcgg tgcaatccaa    60
gcgaagaaaa tccaagtaaa caagcaggac                                    90

<210> SEQ ID NO 469
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ccctcattgc tttcttcatt ttgactacga taaaagacat aaccagtgcg gtgcaatcca    60
agcgaagaaa atccaagtaa acaagcagga                                    90

<210> SEQ ID NO 470
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
caccctcatt gctttcttca ttttgactac gataaaagac ataaccagtg cggtgcaatc    60
caagcgaaga aaatccaagt aaacaagcag                                    90

<210> SEQ ID NO 471
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
caacaccctc attgctttct tcattttgac tacgataaaa gacataacca gtgcggtgca    60
atccaagcga agaaaatcca agtaaacaag                                    90

<210> SEQ ID NO 472
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
caacaacacc ctcattgctt tcttcatttt gactacgata aaagacataa ccagtgcggt    60
gcaatccaag cgaagaaaat ccaagtaaac                                     90

<210> SEQ ID NO 473
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
atcaacaaca ccctcattgc tttcttcatt ttgactacga taaaagacat aaccagtgcg    60
gtgcaatcca agcgaagaaa atccaagtaa                                     90

<210> SEQ ID NO 474
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
catcaacaac accctcattg ctttcttcat tttgactacg ataaaagaca taaccagtgc    60
ggtgcaatcc aagcgaagaa aatccaagta                                     90

<210> SEQ ID NO 475
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gtgccatcaa caacccctc attgctttct tcattttgac tacgataaaa gacataacca    60
gtgcggtgca atccaagcga agaaaatcca                                     90

<210> SEQ ID NO 476
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gtctacctgt gccatcaaca acaccctcat tgctttcttc attttgacta cgataaaaga    60
cataaccagt gcggtgcaat ccaagcgaag                                     90

<210> SEQ ID NO 477
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
caagtctacc tgtgccatca acaacaccct cattgctttc ttcattttga ctacgataaa    60
agacataacc agtgcggtgc aatccaagcg                                     90

<210> SEQ ID NO 478
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 478
ccaagtctac ctgtgccatc aacaacaccc tcattgcttt cttcattttg actacgataa    60
aagacataac cagtgcggtg caatccaagc                                    90

<210> SEQ ID NO 479
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 479
gtcttgtgtt gccaagtcta cctgtgccat caacaacacc ctcattgctt tcttcatttt    60
gactacgata aagacataa ccagtgcggt                                     90

<210> SEQ ID NO 480
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 480
ttttcttgtg ttgccaagtc tacctgtgcc atcaacaaca ccctcattgc tttcttcatt    60
ttgactacga taaaagacat aaccagtgcg                                    90

<210> SEQ ID NO 481
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 481
attttgtctt gtgttgccaa gtctacctgt gccatcaaca cacccctcat tgctttcttc    60
attttgacta cgataaaaga cataaccagt                                    90

<210> SEQ ID NO 482
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 482
acacgatttt gtcttgtgtt gccaagtcta cctgtgccat caacaacacc ctcattgctt    60
tcttcatttt gactacgata aaagacataa                                    90

<210> SEQ ID NO 483
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 483
atttagagca cagtgatgag caagcagtaa taaagtctcc cttaaaatgc accctccttc    60
cacctggcca ggaatcagca ttgggaatgg taccacctcc cgaaaatgtc agaatgaatt   120
ctgttaattt caagaacatt ctacagtggg agtcacctgc ttttgc                  166

<210> SEQ ID NO 484
<211> LENGTH: 55
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (55)..(55)
<223> OTHER INFORMATION: Any amino acid

<400> SEQUENCE: 484

Leu Glu His Ser Asp Glu Gln Ala Val Ile Lys Ser Pro Leu Lys Cys
1               5                   10                  15

Thr Leu Leu Pro Pro Gly Gln Glu Ser Ala Leu Gly Met Val Pro Pro
            20                  25                  30

Pro Glu Asn Val Arg Met Asn Ser Val Asn Phe Lys Asn Ile Leu Gln
        35                  40                  45

Trp Glu Ser Pro Ala Phe Xaa
    50                  55

<210> SEQ ID NO 485
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 485
agcattggga atggtaccac ctcccgaaaa tgtcagaatg aattctgtta atttcaagaa    60
cattctacag tgggagtcac ctgcttttgc                                    90

<210> SEQ ID NO 486
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 486
gtcagcattg gaatggtac cacctcccga aaatgtcaga atgaattctg ttaatttcaa    60
gaacattcta cagtgggagt cacctgcttt                                    90

<210> SEQ ID NO 487
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 487

```
cagtaataaa gtctccctta aaatgcaccc tccttccacc tggccaggaa tcagcattgg    60
gaatggtacc acctcccgaa aatgtcagaa                                    90
```

<210> SEQ ID NO 488
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488

```
gtgatgagca agcagtaata aagtctccct taaaatgcac cctccttcca cctggccagg    60
aatcagcatt gggaatggta ccacctcccg                                    90
```

<210> SEQ ID NO 489
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489

```
acagtgatga gcaagcagta ataaagtctc ccttaaaatg caccctcctt ccacctggcc    60
aggaatcagc attgggaatg gtaccaccaa                                    90
```

<210> SEQ ID NO 490
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490

```
atttagagca cagtgatgag caagcagtaa taaagtctcc cttaaaatgc accctccttc    60
cacctggcca ggaatcagca ttgggaatgg                                    90
```

<210> SEQ ID NO 491
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

```
Leu Gln Leu Ala Asn Glu Glu Ile Ala Gln Val Arg
1               5                   10
```

<210> SEQ ID NO 492
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

```
Asp Gly Thr Gly Leu Val Pro Ser Glu Arg
1               5                   10
```

```
<210> SEQ ID NO 493
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Val Gly Pro Asp Gly Thr Pro Tyr Val Thr Val Leu Lys
1               5                   10

<210> SEQ ID NO 494
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Val Leu Val Gly Pro Gln Arg
1               5

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
cgtgaagatg ctgaaagacg atg                                         23

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
aaacgcttga agaggtcgga g                                           21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
tgcctgtgga ggaactttc a                                            21

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
cccaaactca gcagcctaag                                             20
```

<210> SEQ ID NO 499
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
tggaccgtgt ccttaccgt                                                  19

<210> SEQ ID NO 500
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
ggtcctttgg ggtcctgct                                                  19

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
cctctttcag ctccaaggca                                                 20

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
tctaccagga ctgtccctca g                                               21

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
gggagtctca tttgcaccgt                                                 20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
ctgcatccag gtccttctgg                                                 20

-continued

```
<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
ccagttccag gttcttcccg                                              20

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
caacctcttc gaacctgtcc a                                            21

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
aagacgatgc cactgacaag                                              20

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 508
cccagcaggt tgatgatgtt tttg                                         24

<210> SEQ ID NO 509
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 509
tccttctccg acctcttcaa gc                                           22

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 510
taatcctcca cgcacttctt cag                                          23

<210> SEQ ID NO 511
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
tacctggacc tgtcggcg                                                    18

<210> SEQ ID NO 512
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
tgggcaaaca cggagtcg                                                    18

<210> SEQ ID NO 513
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
ccacagacgc acaggattct aagtc                                            25

<210> SEQ ID NO 514
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 514
tgagtttccc agtccaaggg tg                                               22

<210> SEQ ID NO 515
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
gtgacgtcca ccgactttaa ggagtcggcc                                       30

<210> SEQ ID NO 516
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Val Thr Ser Thr Asp Phe Lys Glu Ser Ala
1               5                   10

<210> SEQ ID NO 517
```

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 517
gtgacgtcca ccgacgtaaa ggcgacacag                              30

<210> SEQ ID NO 518
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 518

Val Thr Ser Thr Asp Val Lys Ala Thr Gln
1               5                   10

<210> SEQ ID NO 519
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 519
gcgaagaggg gctcggtggt gcagttggca                              30

<210> SEQ ID NO 520
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 520
cctcccgcca gcaggagccc ccagcagcct                              30

<210> SEQ ID NO 521
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 521
gactcagtgc agatgttccc tcgccgcact                              30

<210> SEQ ID NO 522
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 522
gcctgggcac agagggtgtc cgagagcagc                              30

<210> SEQ ID NO 523

-continued

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
ccacccgcct atgccaggca attccgcgaa                                    30

<210> SEQ ID NO 524
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
tggacctgtc ggcgcaggag caacggcagc                                    30

<210> SEQ ID NO 525
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
gagtgctggc tctggcccgg gactctccgg                                    30

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
aggtggctgt gcgaaggtcg ctgagggtcc                                    30

<210> SEQ ID NO 527
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tgccgtcccc ggccatccct caggacgtcc g                                  31

<210> SEQ ID NO 528
<211> LENGTH: 2421
<212> TYPE: DNA
<213> ORGANISM: Homo sapiens

<400> SEQUENCE: 528
atgggcgccc ctgcctgcgc cctcgcgctc tgcgtggccg tggccatcgt ggccggcgcc   60
tcctcggagt ccttggggac ggagcagcgc gtcgtggggc gagcggcaga agtcccgggc  120
ccagagcccg gccagcagga gcagttggtc ttcggcagcg gggatgctgt ggagctgagc  180
tgtcccccgc ccgggggtgg tcccatgggg cccactgtct gggtcaagga tggcacaggg  240
```

```
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt tggcagcat ccggcagacg     720 tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag acgcgggcg ctaacaccac cgacaaggag      960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200 cccccaaga aaggcctggg ctcccccacc gtgcacaaga tctcccgctt cccgctcaag      1260
cgacaggtgt ccctggagtc caacgcgtcc atgagctcca acacaccact ggtgcgcatc    1320
gcaaggctgt cctcagggga gggccccacg ctggccaatg tctccgagct cgagctgcct    1380
gccgacccca atgggagct gtctcgggcc cggctgaccc tgggcaagcc ccttggggag     1440
ggctgcttcg gccaggtggt catggcggag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac     1620 ctgctgggcg cctgcacgca gggcgggccc ctgtacgtgc tggtggagta cgcggccaag    1680
ggtaacctgc gggagtttct gcgggcgcgg cggccccgg gcctggacta ctccttcgac      1740
acctgcaagc cgcccgagga gcagctcacc ttcaaggacc tggtgtcctg tgcctaccag    1800
gtggcccggg gcatggagta cttggcctcc agaagtgca tccacaggga cctggctgcc     1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctcccc cgtacccggg catccctgtg    2100
gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgccccggc cccacccagc    2400 agtgggggct cgcggacgtg a                                              2421
```

<210> SEQ ID NO 529
<211> LENGTH: 2517
<212> TYPE: DNA
<213> ORGANISM: Homo sapiens

<400> SEQUENCE: 529

```
atgagtctgc aggtcttaaa cgacaaaaat gtcagcaatg aaaaaaatac agaaaattgc    60
gacttcctgt tttcgccacc agaagttacc ggaagatcgt ctgttcttcg tgtgtcacag   120
aaagaaaatg tgccacccaa gaacctggcc aaagctatga aggtgacttt tcagacacct   180
ctgcgggatc cacagacgca caggattcta agtcctagca tggccagcaa acttgaggct   240
cctttcactc aggatgacac ccttggactg aaaaactcac acccggtctg gacacagaaa   300
gagaaccaac agctcatcaa ggaagtggat gccaaaacta ctcatggaat tctacagaaa   360
ccagtggagc tgacaccgga cctcctgggg gatgcaagcc cagcctttgg gagtggcagc   420
tccagcgagt ctggcccagg tgccctggct gacctggact gctcaagctc ttcccagagc   480
ccaggaagtt ctgagaacca aatggtgtct ccaggaaaag tgtctggcag ccctgagcaa   540
gccgtggagg aaaaccttag ttcctattcc ttagacagaa gagtgacacc cgcctctgag   600
accctagaag acccttgcag acagagtcc cagcacaaag cggagactcc gcacggagcc    660
gaggaagaat gcaaagcgga gactccgcac ggagccgagg aggaatgccg gcacggtggg   720
gtctgtgctc ccgcagcagt ggccacttcg cctcctggtg caatccctaa ggaagcctgc   780
ggaggagcac ccctgcaggg tctgcctggc gaagccctgg gctgccctgc gggtgtgggc   840
accccgtgc cagcagatgg cactcagacc cttacctgtg cacacacctc tgctcctgag    900
agcacagccc caaccaacca cctggtggct ggcagggcca tgaccctgag tcctcaggaa   960
gaagtggctg caggccaaat ggccagctcc tcgaggagcg acctgtaaa actagaattt   1020
gatgtatctg atggcgccac cagcaaaagg gcacccccac caaggagact gggagagagg   1080
tccggcctca gcctcccctt gaggaaagca gcagtgaggc agcaaaaggc cccgcaggag   1140
gtggaggagg acgacggtag gagcggagca ggagaggacc cccccatgcc agcttctcgg   1200
ggctcttacc acctcgactg gacaaaatg gatgacccaa acttcatccc gttcggaggt    1260
gacaccaagt ctggttgcag tgaggcccag cccccagaaa gccctgagac caggctgggc   1320
cagccagcgg ctgaacagtt gcatgctggg cctgccacgg aggagccagg tccctgtctg   1380
agccagcagc tgcattcagc ctcagcgag gacacgcctg tggtgcagtt ggcagccgag    1440
accccaacag cagagagcaa ggagagagcc ttgaactctg ccagcaccto gcttcccaca   1500
agctgtccag gcagtgagcc agtgcccacc catcagcagg ggcagcctgc cttgagctg    1560
aaagaggaga gcttcagaga ccccgctgag gttctaggca cgggcgcgga ggtggattac   1620
ctggagcagt ttggaacttc ctcgtttaag gagtcggcct tgaggaagca gtccttatac   1680
ctcaagttcg accccctcct gagggacagt cctggtagac cagtgcccgt ggccaccgag   1740
accagcagca tgcacggtgc aaatgagact ccctcaggac gtccgcggga agccaagctt   1800
gtggagttcg atttcttggg agcactggac attcctgtgc caggcccacc cccaggtgtt   1860
cccgcgcctg gggcccacc cctgtccacc ggacctatag tggacctgct ccagtacagc    1920
cagaaggacc tggatgcagt ggtaaaggcg acacaggagg agaaccggga gctgaggagc   1980
aggtgtgagg agctccacgg gaagaacctg gaactgggga gatcatggga caggttcgaa   2040
gaggttgtgt accaggccat ggaggaagtt cagaagcaga aggaactttc caaagctgaa   2100
atccagaaag ttctaaaaga aaagagccaa cttaccacag atctgaactc catggagaag   2160
tccttctccg acctcttcaa gcgttttgag aaacagaaag aggtgatcga gggctaccgc   2220
aagaacgaag agtcactgaa gaagtgcgtg gaggattacc tggcaaggat cacccaggag   2280
```

-continued

| | |
|---|---|
| ggccagaggt accaagccct gaaggcccac gcggaggaga agctgcagct ggcaaacgag | 2340 |
| gagatcgccc aggtccggag caaggcccag gcggaagcgt tggccctcca ggccagcctg | 2400 |
| aggaaggagc agatgcgcat ccagtcgctg gagaagacag tggagcagaa gactaaagag | 2460 |
| aacgaggagc tgaccaggat ctgcgacgac ctcatctcca agatggagaa gatctga | 2517 |

<210> SEQ ID NO 530
<211> LENGTH: 2850
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 530

| | |
|---|---|
| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg gccagcagga gcagttggtc ttcggcagcg gggatgctgt ggagctgagc | 180 |
| tgtcccccgc ccgggggtgg tcccatgggg cccactgtct gggtcaagga tggcacaggg | 240 |
| ctggtgccct cggagcgtgt cctggtgggg cccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctgg acgtgctgga cgctcccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga atggcagcaa ggtgggcccg | 900 |
| gacggcacac cctacgttac cgtgctcaag acggcgggcg ctaacaccac cgacaaggag | 960 |
| ctagaggttc tctccttgca caacgtcacc tttgaggacg ccggggagta cacctgcctg | 1020 |
| gcgggcaatt ctattgggtt ttctcatcac tctgcgtggc tggtggtgct gccagccgag | 1080 |
| gaggagctgg tggaggctga cgaggcgggc agtgtgtatg caggcatcct cagctacggg | 1140 |
| gtgggcttct tcctgttcat cctggtggtg cggctgtga cgctctgccg cctgcgcagc | 1200 |
| cccccaaga aaggcctggg ctcccccacc gtgcacaaga tctcccgctt cccgctcaag | 1260 |
| cgacaggtgt ccctggagtc caacgcgtcc atgagctcca acacaccact ggtgcgcatc | 1320 |
| gcaaggctgt cctcagggga gggcccacg ctggccaatg tctccgagct cgagctgcct | 1380 |
| gccgacccca atgggagct gtctcgggcc cggctgaccc tggcaagcc ccttggggag | 1440 |
| ggctgcttcg gccaggtggt catggcggag gccatcggca ttgacaagga ccgggccgcc | 1500 |
| aagcctgtca ccgtagccgt gaagatgctg aaagacgatg ccactgacaa ggacctgtcg | 1560 |
| gacctggtgt ctgagatgga gatgatgaag atgatcggga acacaaaaa catcatcaac | 1620 |
| ctgctgggcg cctgcacgca gggcgggccc ctgtacgtgc tggtggagta cgcggccaag | 1680 |
| ggtaacctgc gggagtttct gcgggcgcgg cggcccccgg gcctggacta ctccttcgac | 1740 |
| acctgcaagc cgcccgagga gcagctcacc ttcaaggacc tggtgtcctg tgcctaccag | 1800 |

| | |
|---|---|
| gtggcccggg gcatggagta cttggcctcc cagaagtgca tccacaggga cctggctgcc | 1860 |
| cgcaatgtgc tggtgaccga ggacaacgtg atgaagatcg cagacttcgg gctggcccgg | 1920 |
| gacgtgcaca acctcgacta ctacaagaag acgaccaacg gccggctgcc cgtgaagtgg | 1980 |
| atggcgcctg aggccttgtt tgaccgagtc tacactcacc agagtgacgt ctggtccttt | 2040 |
| ggggtcctgc tctgggagat cttcacgctg gggggctccc cgtaccccgg catccctgtg | 2100 |
| gaggagctct tcaagctgct gaaggagggc accgcatgg acaagcccgc caactgcaca | 2160 |
| cacgacctgt acatgatcat gcgggagtgc tggcatgccg cgccctccca gaggcccacc | 2220 |
| ttcaagcagc tggtgaagga cctggaccgt gtccttaccg tgacgtccac cgacgtaaag | 2280 |
| gcgacacagg aggagaaccg ggagctgagg agcaggtgtg aggagctcca cgggaagaac | 2340 |
| ctggaactgg ggaagatcat ggacaggttc gaagaggttg tgtaccaggc catggaggaa | 2400 |
| gttcagaagc agaaggaact ttccaaagct gaaatccaga aagttctaaa agaaaaagac | 2460 |
| caacttacca cagatctgaa ctccatggag aagtccttct ccgacctctt caagcgtttt | 2520 |
| gagaaacaga aagaggtgat cgagggctac cgcaagaacg aagagtcact gaagaagtgc | 2580 |
| gtggaggatt acctggcaag gatcacccag gagggccaga ggtaccaagc cctgaaggcc | 2640 |
| cacgcggagg agaagctgca gctggcaaac gaggagatcg cccaggtccg gagcaaggcc | 2700 |
| caggcggaag cgttggccct ccaggccagc ctgaggaagg agcagatgcg catccagtcg | 2760 |
| ctggagaaga cagtggagca agagactaaa gagaacgagg agctgaccag gatctgcgac | 2820 |
| gacctcatct ccaagatgga gaagatctga | 2850 |

<210> SEQ ID NO 531
<211> LENGTH: 3147
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 531

| | |
|---|---|
| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg gccagcagga gcagttggtc ttcggcagcg gggatgctgt ggagctgagc | 180 |
| tgtccccccgc ccggggtgg tcccatgggg cccactgtct gggtcaagga tggcacaggg | 240 |
| ctggtgccct cggagcgtgt cctggtgggg ccccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggccgga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctga cgtgctgga gcgctccccg caccggccca cctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga atggcagcaa ggtgggcccg | 900 |
| gacggcacac cctacgttac cgtgctcaag acggcgggcg ctaacaccac cgacaaggag | 960 |

```
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200 cccccccaaga aaggcctggg ctcccccacc gtgcacaaga tctcccgctt cccgctcaag    1260
cgacaggtgt ccctggagtc caacgcgtcc atgagctcca acacaccact ggtgcgcatc    1320
gcaaggctgt cctcagggga gggccccacg ctggccaatg tctccgagct cgagctgcct    1380
gccgacccca atgggagct gtctcgggcc cggctgaccc tgggcaagcc ccttggggag    1440
ggctgcttcg gccaggtggt catggcggag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggccccgg cctgacta ctccttcgac    1740 acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctccc cgtacccgg catccctgtg    2100 gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgactttaag    2280
gagtcggcct tgaggaagca gtccttatac ctcaagttcg accccctcct gagggacagt    2340
cctggtagac cagtgcccgt ggccaccgag accagcagca tgcacggtgc aaatgagact    2400
ccctcaggac gtccgcggga agccaagctt gtggagttcg atttcttggg agcactggac    2460
attcctgtgc caggcccacc cccaggtgtt cccgcgcctg ggggcccacc cctgtccacc    2520
ggacctatag tggacctgct ccagtacagc cagaaggacc tggatgcagt ggtaaaggcg    2580
acacaggagg agaaccggga gctgaggagc aggtgtgagg agctccacgg gaagaacctg    2640
gaactgggga agatcatgga caggttcgaa gaggttgtgt accaggccat ggaggaagtt    2700
cagaagcaga aggaactttc caaagctgaa atccagaaag ttctaaaaga aaagaccaa    2760 cttaccacag atctgaactc catggagaag tccttctccg acctcttcaa gcgtttggag    2820
aaacagaaag aggtgatcga gggctaccgc aagaacgaag agtcactgaa gaagtgcgtg    2880
gaggattacc tggcaaggat cacccaggag ggccagaggt accaagccct gaaggcccac    2940
gcggaggaga agctgcagct ggcaaacgag gagatcgccc aggtccggag caaggcccag    3000
gcggaagcgt tggccctcca ggccagcctg aggaaggagc agatgcgcat ccagtcgctg    3060
gagaagacag tggagcagaa gactaaagag aacgaggagc tgaccaggat ctgcgacgac    3120
ctcatctcca agatggagaa gatctga                                       3147
```

<210> SEQ ID NO 532
<211> LENGTH: 2955
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 532

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180
tgtccccgc ccgggggtgg tcccatgggg cccactgtct gggtcaagga tggcacaggg      240
ctggtgccct cggagcgtgt cctggtgggg ccccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct ccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg agaaacaagt tggcagcat ccggcagacg      720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag acggcgggcg ctaacaccac cgacaaggag     960
ctagaggttc tctccttgca aacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg cggctgtga cgctctgccg cctgcgcagc    1200
cccccaaga aaggcctggg ctcccccacc gtgcacaaga tctcccgctt cccgctcaag    1260
cgacaggtgt ccctggagtc caacgcgtcc atgagctcca acaccaccac ggtgcgcatc    1320
gcaaggctgt cctcagggga gggcccacg ctggccaatg tctccgagct cgagctgcct    1380
gccgacccca atgggagct gtctcggccc cggctgaccc tggcaagcc ccttggggag    1440
ggctgcttcg gccaggtggt catggcggag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggccccgg gcctggacta ctccttcgac    1740
acctgcaagc gccccgagga gcagctcacc ttcaaggacc tggtgtcctg tgcctaccag    1800
gtggcccggg gcatggagta cttggcctcc agaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctcccc cgtacccgg catccctgtg    2100
gaggagctct tcaagctgct gaaggagggc caccgcatgg acaagcccgc caactgcaca    2160
cacgacctgt acatgatcat gcgggagtgc tggcatgccg cgccctccca gaggcccacc    2220
```

```
ttcaagcagc tggtggagga cctggaccgt gtccttaccg tgacgtccac cgacgtgcca    2280
ggcccacccc caggtgttcc cgcgcctggg ggcccacccc tgtccaccgg acctatagtg    2340
gacctgctcc agtacagcca gaaggacctg gatgcagtgg taaaggcgac acaggaggag    2400
aaccgggagc tgaggagcag gtgtgaggag ctccacggga agaacctgga actggggaag    2460
atcatggaca ggttcgaaga ggttgtgtac caggccatgg aggaagttca gaagcagaag    2520
gaactttcca aagctgaaat ccagaaagtt ctaaaagaaa agaccaact taccacagat    2580 ctgaactcca tggagaagtc cttctccgac ctcttcaagc gttttgagaa acagaaagag    2640
gtgatcgagg gctaccgcaa gaacgaagag tcactgaaga agtgcgtgga ggattacctg    2700
gcaaggatca cccaggaggg ccagaggtac caagccctga aggcccacgc ggaggagaag    2760
ctgcagctgg caaacgagga gatcgcccag gtccggagca aggcccaggc ggaagcgttg    2820
gccctccagg ccagcctgag gaaggagcag atgcgcatcc agtcgctgga agacagtg     2880 gagcagaaga ctaaagagaa cgaggagctg accaggatct gcgacgacct catctccaag    2940
atggagaaga tctga                                                    2955
```

<210> SEQ ID NO 533
<211> LENGTH: 3330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 533

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180 tgtccccgc ccgggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga cggatggac     480 aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga cgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag acggcgggcg ctaacaccac cgacaaggag     960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
ccccccaaga aaggcctggg ctcccccacc gtgcacaaga tctcccgctt cccgctcaag    1260
```

```
cgacaggtgt ccctggagtc caacgcgtcc atgagctcca acacaccact ggtgcgcatc    1320
gcaaggctgt cctcagggga gggccccacg ctggccaatg tctccgagct cgagctgcct    1380
gccgacccca aatgggagct gtctcgggcc cggctgaccc tgggcaagcc ccttggggag    1440
ggctgcttcg gccaggtggt catggcgag gccatcggca ttgacaagga ccgggccgcc     1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac     1620 ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctcccc cgtacccegg catccctgtg    2100 gaggagctct tcaagctgct gaaggagggc caccgcatgg acaagccegc caactgcaca    2160 cacgacctgt acatgatcat gcgggagtgc tggcatgccg cgccctccca gaggcccacc    2220
ttcaagcagc tggtggagga cctggaccgt gtccttaccg tgacgtccac cgacgagaga    2280
gccttgaact ctgccagcac ctcgcttccc acaagctgtc caggcagtga gccagtgccc    2340
acccatcagc aggggcagcc tgccttggag ctgaaagagg agagcttcag agacccegct    2400 gaggttctag gcacgggcgc ggaggtggat tacctggagc agtttggaac ttcctcgttt    2460
aaggagtcgg ccttgaggaa gcagtcctta tacctcaagt tcgacccect cctgagggac    2520 agtcctggta gaccagtgcc cgtggccacc gagaccagca gcatgcacgg tgcaaatgag    2580
actccctcag gacgtccgcg ggaagccaag cttgtggagt tcgatttctt gggagcactg    2640
gacattcctg tgccagggcc accccaggt gttccgcgc ctgggggccc accectgtcc      2700 accggaccta tagtggacct gctccagtac agccagaagg acctggatgc agtggtaaag    2760
gcgacacagg aggagaaccg ggagctgagg agcaggtgtg aggagctcca cggaagaac    2820 ctggaactgg ggaagatcat ggacaggttc gaagaggttg tgtaccaggc catggaggaa   2880
gttcagaagc agaaggaact ttccaaagct gaaatccaga agttctaaa agaaaaagac    2940 caacttacca cagatctgaa ctccatggag aagtccttct ccgacctctt caagcgtttt    3000
gagaaacaga aagaggtgat cgagggctac cgcaagaacg aagagtcact gaagaagtgc    3060
gtggaggatt acctggcaag gatcacccag gagggccaga ggtaccaagc cctgaaggcc    3120
cacgcggagg agaagctgca gctggcaaac gaggagatcg cccaggtccg gagcaaggcc    3180
caggcggaag cgttggccct ccaggccagc ctgaggaagg agcagatgcg catccagtcg    3240
ctggagaaga cagtggagca gaagactaaa gagaacgagg agctgaccag gatctgcgac    3300
gacctcatct ccaagatgga gaagatctga                                     3330
```

<210> SEQ ID NO 534
<211> LENGTH: 2780
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 534
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtgtatg caggcatcct cagctacggg 1140
gtgggcttct tcctgttcat cctggtggtg gcggctgtga cgctctgccg cctgcgcagc 1200
ccccccaaga aaggcctggg ctcccccacc gtgcacaaga tctcccgctt cccgctcaag 1260
cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380
gccgacccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggga aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggcccccgg gcctggacta ctccttcgac 1740
acctgcaagc cgcccgagga gcagctcacc ttcaaggacc tggtgtcctg tgcctaccag 1800
gtggcccggg gcatggagta cttggcctcc cagaagtgca tccacaggga cctggctgcc 1860
cgcaatgtgc tggtgaccga ggacaacgtg atgaagatcg cagacttcgg gctggcccgg 1920
gacgtgcaca acctcgacta ctacaagaag acgaccaacg gccggctgcc cgtgaagtgg 1980
atggcgcctg aggccttgtt tgaccgagtc tacactcacc agagtgacgt ctggtccttt 2040
ggggtcctgc tctgggagat cttcacgctg gggggctccc cgtaccccgg catccctgtg 2100
gaggagctct tcaagctgct gaaggagggc caccgcatgg acaagcccgc caactgcaca 2160
cacgacctgt acatgatcat gcgggagtgc tggcatgccg cgccctccca gaggcccacc 2220
ttcaagcagc tggtggagga cctggaccgt gtccttaccg tgacgtccac cgacgagtac 2280

-continued

| | |
|---|---|
| ctggacctgt cggcgccttt cgagcagtac tccccgggtg gccaggacac ccccagaagc | 2340 |
| agaaggaact ttccaaagct gaaatccaga aagttctaaa agaaaaagac caacttacca | 2400 |
| cagatctgaa ctccatggag aagtccttct ccgacctctt caagcgtttt gagaaacaga | 2460 |
| aagaggtgat cgagggctac cgcaagaacg aagagtcact gaagaagtgc gtggaggatt | 2520 |
| acctggcaag gatcacccag gagggccaga ggtaccaagc cctgaaggcc cacgcggagg | 2580 |
| agaagctgca gctggcaaac gaggagatcg cccaggtccg gagcaaggcc caggcggaag | 2640 |
| cgttggccct ccaggccagc ctgaggaagg agcagatgcg catccagtcg ctggagaaga | 2700 |
| cagtggagca gaagactaaa gagaacgagg agctgaccag gatctgcgac gacctcatct | 2760 |
| ccaagatgga gaagatctga | 2780 |

<210> SEQ ID NO 535
<211> LENGTH: 3135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 535

| | |
|---|---|
| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg ccagcagga gcagttggtc ttcggcagcg gggatgctgt ggagctgagc | 180 |
| tgtccccgc ccggggtgg tcccatgggg cccactgtct gggtcaagga tggcacaggg | 240 |
| ctggtgccct cggagcgtgt cctggtgggg cccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt tggcagcat ccggcagacg | 720 |
| tacacgctgg acgtgctgga cgctccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga tggcagcaa ggtgggcccg | 900 |
| gacggcacac cctacgttac cgtgctcaag acggcgggcg ctaacaccac cgacaaggag | 960 |
| ctagaggttc tctccttgca aacgtcacc tttgaggacg ccggggagta cacctgcctg | 1020 |
| gcgggcaatt ctattgggtt ttctcatcac tctgcgtggc tggtggtgct gccagccgag | 1080 |
| gaggagctgg tggaggctga cgaggcgggc agtgtgtatg caggcatcct cagctacggg | 1140 |
| gtgggcttct tcctgttcat cctggtggtg gcggctgtga cgctctgccg cctgcgcagc | 1200 |
| cccccaaga aaggcctggg ctcccccacc gtgcacaaga tctcccgctt cccgctcaag | 1260 |
| cgacaggtgt cctggagtc caacgcgtcc atgagctcca cacaccact ggtgcgcatc | 1320 |
| gcaaggctgt cctcagggga gggcccacg ctggccaatg tctccgagct cgagctgcct | 1380 |
| gccgacccca atgggagct gtctcggggcc cggctgaccc tggcaagcc ccttgggag | 1440 |
| ggctgcttcg ccaggtggt catggcggag gccatcggca ttgacaagga ccgggccgcc | 1500 |

```
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc agaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctccc cgtacccgg catccctgtg     2100
gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgcagga gcaacggcag cctaccctcc agccacaggg ctgctgcctt    2340
gctggttaca gccaccgttt ctctagcatg cacggtgcaa atgagactcc ctcaggacgt    2400
ccgcgggaag ccaagcttgt ggagttcgat ttcttgggag cactggacat tcctgtgcca    2460
ggcccacccc caggtgttcc cgcgcctggg ggcccaccc tgtccaccgg acctatagtg     2520
gacctgctcc agtacagcca gaaggacctg gatgcagtgg taaaggcgac acaggaggag    2580
aaccgggagc tgaggagcag gtgtgaggag ctccacggga gaacctgga actggggaag     2640
atcatggaca ggttcgaaga ggttgtgtac caggccatgg aggaagttca gaagcagaag    2700
gaactttcca agctgaaat ccagaaagtt ctaaagaaa aagaccaact taccacagat      2760
ctgaactcca tggagaagtc cttctccgac ctcttcaagc gttttgagaa acagaaagag    2820
gtgatcgagg ctaccgcaa gaacgaagag tcactgaaga agtgcgtgga ggattacctg     2880
gcaaggatca cccaggaggg ccagaggtac caagccctga aggcccacgc ggaggagaag    2940
ctgcagctgg caaacgagga gatcgcccag gtccggagca aggcccaggc ggaagcgttg    3000
gccctccagg ccagcctgag gaaggagcag atgcgcatcc agtcgctgga agagacagtg    3060
gagcagaaga ctaaagagaa cgaggagctg accaggatct gcgacgacct catctccaag    3120
atggagaaga tctga                                                    3135
```

<210> SEQ ID NO 536
<211> LENGTH: 3396
<212> TYPE: DNA
<213> ORGANISM: Artificial Sequence
<220> FEATURE:
<223> OTHER INFORMATION: Description of Artificial Sequence: Synthetic
    polynucleotide <400> SEQUENCE: 536

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc    120
ccagagcccg ccagcagga gcagttggtc ttcggcagcg gggatgctgt ggagctgagc     180
tgtccccgc ccggggtgg tccatgggg cccactgtct gggtcaagga tggcacaggg      240
ctggtgccct cggagcgtgt cctggtgggg cccagcggc tgcaggtgct gaatgcctcc    300
cacgaggact ccggggccta cagctgccgg cagcggctca cgcagcgcgt actgtgccac     360
```

```
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt tggcagcat ccggcagacg     720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag acggcgggcg ctaacaccac cgacaaggag    960
ctagaggttc tctccttgca caacgtcacc tttgaggacg ccggggagta cacctgcctg   1020
gcgggcaatt ctattgggtt ttctcatcac tctgcgtggc tggtggtgct gccagccgag   1080
gaggagctgg tggaggctga cgaggcgggc agtgtgtatg caggcatcct cagctacggg   1140
gtgggcttct tcctgttcat cctggtggtg gcggctgtga cgctctgccg cctgcgcagc   1200
cccccaaga aaggcctggg ctcccccacc gtgcacaaga tctcccgctt cccgctcaag    1260
cgacaggtgt ccctggagtc caacgcgtcc atgagctcca acacaccact ggtgcgcatc   1320
gcaaggctgt cctcaggga gggccccacg ctggccaatg tctccgagct cgagctgcct   1380
gccgacccca atgggagct gtctcgggcc cggctgaccc tgggcaagcc ccttggggag    1440
ggctgcttcg gccaggtggt catggcgag gccatcggca ttgacaagga ccgggccgcc   1500
aagcctgtca ccgtagccgt gaagatgctg aaagacgatg ccactgacaa ggacctgtcg   1560
gacctggtgt ctgagatgga gatgatgaag atgatcggga acacaaaaa catcatcaac   1620
ctgctgggcg cctgcacgca gggcgggccc ctgtacgtgc tggtggagta cgcggccaag   1680
ggtaacctgc gggagtttct gcgggcgcgg cggccccgg gcctgactac tccttcgac   1740
acctgcaagc cgcccgagga gcagctcacc ttcaaggacc tggtgtcctg tgcctaccag   1800
gtggcccggg gcatggagta cttggcctcc cagaagtgca tccacaggga cctggctgcc   1860
cgcaatgtgc tggtgaccga ggacaacgtg atgaagatcg cagacttcgg gctggcccgg   1920
gacgtgcaca acctcgacta ctacaagaag acgaccaacg gccggctgcc cgtgaagtgg   1980
atggcgcctg aggccttgtt tgaccgagtc tacactcacc agagtgacgt ctggtccttt   2040
ggggtcctgc tctgggagat cttcacgctg ggggctccc cgtaccccgg catccctgtg   2100
gaggagctct tcaagctgct gaaggagggc caccgcatgg acaagcccgc caactgcaca   2160
cacgacctgt acatgatcat gcgggagtgc tggcatgccg cgccctccca gaggcccacc   2220
ttcaagcagc tggtggagga cctggaccgt gtccttaccg tgacgtccac cgacgagtac   2280
ctggacctgt cggcgcctgt ggtgcagttg gcagccgaga ccccaacagc agagagcaag   2340
gagagagcct tgaactctgc cagcacctcg cttcccacaa gctgtccagg cagtgagcca   2400
gtgcccaccc atcagcaggg gcagcctgcc ttggagctga agaggagag cttcagagac   2460
cccgctgagg ttctaggcac gggcgcgag gtggattacc tggagcagtt tggaacttcc   2520
tcgtttaagg agtcggcctt gaggaagcag tccttatacc tcaagttcga cccctcctg   2580
agggacagtc ctggtagacc agtgcccgtg gccaccgaga ccagcagcat gcacggtgca   2640
aatgagactc cctcaggacg tccgcgggaa gccaagcttg tggagttcga tttcttggga   2700
gcactggaca ttcctgtgcc aggcccaccc ccaggtgttc ccgcgcctgg gggcccaccc   2760
```

| | |
|---|---|
| ctgtccaccg gacctatagt ggacctgctc cagtacagcc agaaggacct ggatgcagtg | 2820 |
| gtaaaggcga cacaggagga gaaccgggag ctgaggagca ggtgtgagga gctccacggg | 2880 |
| aagaacctgg aactggggaa gatcatggaa aggttcgaag aggttgtgta ccaggccatg | 2940 |
| gaggaagttc agaagcagaa ggaactttcc aaagctgaaa tccagaaagt tctaaaagaa | 3000 |
| aaagaccaac ttaccacaga tctgaactcc atggagaagt ccttctccga cctcttcaag | 3060 |
| cgttttgaga aacagaaaga ggtgatcgag ggctaccgca agaacgaaga gtcactgaag | 3120 |
| aagtgcgtgg aggattacct ggcaaggatc acccaggagg ccagaggta ccaagccctg | 3180 |
| aaggcccacg cggaggagaa gctgcagctg caaacgagg agatcgccca ggtccggagc | 3240 |
| aaggcccagg cggaagcgtt ggccctccag gccagcctga ggaaggagca gatgcgcatc | 3300 |
| cagtcgctgg agaagacagt ggagcagaag actaaagaga cgaggagct gaccaggatc | 3360 |
| tgcgacgacc tcatctccaa gatggagaag atctga | 3396 |

<210> SEQ ID NO 537
<211> LENGTH: 3504
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 537

| | |
|---|---|
| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg ccagcagga gcagttggtc ttcggcagcg gggatgctgt ggagctgagc | 180 |
| tgtcccccgc ccgggggtgg tcccatgggg cccactgtct gggtcaagga tggcacaggg | 240 |
| ctggtgccct cggagcgtgt cctggtgggg cccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt tggcagcat ccggcagacg | 720 |
| tacacgctgg acgtgctgga gcgctcccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga tggcagcaa ggtgggcccg | 900 |
| gacggcacac cctacgttac cgtgctcaag acggcgggcg ctaacaccac cgacaaggag | 960 |
| ctagaggttc tctccttgca caacgtcacc tttgaggacg ccggggagta cacctgcctg | 1020 |
| gcgggcaatt ctattgggtt ttctcatcac tctgcgtggc tggtggtgct gccagccgag | 1080 |
| gaggagctgg tggaggctga cgaggcgggc agtgtgtatg caggcatcct cagctacggg | 1140 |
| gtgggcttct tcctgttcat cctggtggtg gcggctgtga cgctctgccg cctgcgcagc | 1200 |
| cccccaaga aaggcctggg ctcccccacc gtgcacaaga tctccgcctt cccgctcaag | 1260 |
| cgacaggtgt ccctggagtc caacgcgtcc atgagctcca acacaccact ggtgcgcatc | 1320 |
| gcaaggctgt cctcagggga gggcccacg ctggccaatg tctccgagct cgagctgcct | 1380 |

```
gccgacccca aatgggagct gtctcgggcc cggctgaccc tgggcaagcc ccttggggag    1440
ggctgcttcg gccaggtggt catggcggag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac     1620 ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctcccc gtacccggg catccctgtg     2100 gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac cccagctcc     2340 agctcctcag gggacgtgcg tgagccaccg cacccggcgt ttcctaggtc agcggaggac    2400
acgcctgtgg tgcagttggc agccgagacc ccaacagcag agagcaagga gagagccttg    2460
aactctgcca gcacctcgct tcccacaagc tgtccaggca gtgagccagt gcccacccat    2520 cagcagggc agcctgcctt ggagctgaaa gaggagagct tcagagaccc cgctgaggtt     2580
ctaggcacgg gcgcggaggt ggattacctg gagcagtttg gaacttcctc gtttaaggag    2640
tcggccttga ggaagcagtc cttataccc aagttcgacc ccctcctgag ggacagtcct     2700
ggtagaccag tgcccgtggc caccgagacc agcagcatgc acgtgcaaa tgagactccc     2760 tcaggacgtc cgcgggaagc caagcttgtg gagttcgatt tcttgggagc actggacatt    2820
cctgtgccag gcccaccccc aggtgttccc gcgcctgggg gcccaccct gtccaccgga     2880 cctatagtgg acctgctcca gtacagccag aaggacctgg atgcagtggt aaaggcgaca    2940
caggaggaga accgggagct gaggagcagg tgtgaggagc tccacgggaa gaacctggaa    3000
ctggggaaga tcatggacag gttcgaagag gttgtgtacc aggccatgga ggaagttcag    3060
aagcagaagg aactttccaa agctgaaatc cagaaagttc taaaagaaaa agaccaactt    3120
accacagatc tgaactccat ggagaagtcc ttctccgacc tcttcaagcg ttttgagaaa    3180
cagaaagagg tgatcgaggg ctaccgcaag aacgaagagt cactgaagaa gtgcgtggag    3240
gattacctgg caaggatcac ccaggagggc cagaggtacc aagccctgaa ggcccacgcg    3300
gaggagaagc tgcagctggc aaacgaggag atcgcccagg tccggagcaa ggcccaggcg    3360
gaagcgttgg ccctccaggc cagcctgagg aaggagcaga tgcgcatcca gtcgctggag    3420
aagacagtgg agcagaagac taaagagaac gaggagctga ccaggatctg cgacgacctc    3480
atctccaaga tggagaagat ctga                                          3504

<210> SEQ ID NO 538
<211> LENGTH: 3555
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 538

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180
tgtcccccgc ccgggggtgg tcccatgggg cccactgtct gggtcaagga tggcacaggg     240
ctggtgccct cggagcgtgt cctggtgggg ccccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt tggcagcat ccggcagacg      720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag acgcgggcg ctaacaccac cgacaaggag      960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
cccccaaga aaggcctggg ctcccccacc gtgcacaaga tctcccgctt cccgctcaag    1260
cgacaggtgt ccctggagtc caacgcgtcc atgagctcca acaccaccact ggtgcgcatc    1320
gcaaggctgt cctcagggga gggcccacg ctggccaatg tctccgagct cgagctgcct    1380
gccgacccca atgggagct gtctcggggc cggctgaccc tgggcaagcc ccttggggag    1440
ggctgcttcg gccaggtggt catggcgag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaaa catcatcaac    1620
ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc agaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag cgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg ggggctcccc cgtaccccgg catccctgtg    2100
gaggagctct tcaagctgct gaaggagggc caccgcatgg acaagccccg caactgcaca    2160
cacgacctgt acatgatcat gcgggagtgc tggcatgccg cgccctccca gaggcccacc    2220
```

```
ttcaagcagc tggtggagga cctggaccgt gtccttaccg tgacgtccac cgacgagtac    2280
ctggacctgt cggcgccttt cgagcagtac tccccgggtg ccaggacac  cccagaaagc    2340 cctgagacca ggctgggcca gccagcggct gaacagttgc atgctgggcc tgccacggag    2400
gagccaggtc cctgtctgag ccagcagctg cattcagcct cagcgagga  cacgcctgtg    2460 gtgcagttgg cagccgagac ccaacagca  gagagcaagg agagagcctt gaactctgcc    2520
agcacctcgc ttcccacaag ctgtccaggc agtgagccag tgcccaccca tcagcagggg    2580
cagcctgcct tggagctgaa agaggagagc ttcagagacc ccgctgaggt tctaggcacg    2640
ggcgcggagg tggattacct ggagcagttt ggaacttcct cgtttaagga gtcggccttg    2700
aggaagcagt ccttatacct caagttcgac cccctcctga gggacagtcc tggtagacca    2760
gtgcccgtgg ccaccgagac cagcagcatg cacggtgcaa atgagactcc ctcaggacgt    2820
ccgcgggaag ccaagcttgt ggagttcgat ttcttgggag cactggacat tcctgtgcca    2880
ggcccacccc caggtgttcc cgcgcctggg ggcccacccc tgtccaccgg acctatagtg    2940
gacctgctcc agtacagcca gaaggacctg gatgcagtgg taaaggcgac acaggaggag    3000
aaccgggagc tgaggagcag gtgtgaggag ctccacggga agaacctgga actggggaag    3060
atcatggaca ggttcgaaga ggttgtgtac caggccatgg aggaagttca gaagcagaag    3120
gaactttcca agctgaaaat ccagaaagtt ctaaaagaaa agaccaact  taccacagat    3180 ctgaactcca tggagaagtc cttctccgac ctcttcaagc gttttgagaa acagaaagag    3240
gtgatcgagg gctaccgcaa gaacgaagag tcactgaaga agtgcgtgga ggattacctg    3300
gcaaggatca cccaggaggg ccagaggtac caagccctga aggcccacgc ggaggagaag    3360
ctgcagctgg caaacgagga gatcgcccag gtccggagca aggcccaggc ggaagcgttg    3420
gccctccagg ccagcctgag gaaggagcag atgcgcatcc agtcgctgga agagacagtg    3480
gagcagaaga ctaaagagaa cgaggagctg accaggatct gcgacgacct catctccaag    3540
atggagaaga tctga                                                    3555

<210> SEQ ID NO 539
<211> LENGTH: 949
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
```

-continued

```
                115                 120                 125
Pro Ser Ser Gly Asp Asp Glu Asp Gly Glu Asp Glu Ala Glu Asp Thr
        130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
            180                 185                 190
Arg Glu Phe Arg Gly Glu His Arg Ile Gly Gly Ile Lys Leu Arg His
        195                 200                 205
Gln Gln Trp Ser Leu Val Met Glu Ser Val Val Pro Ser Asp Arg Gly
    210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
        275                 280                 285
Lys His Val Glu Val Asn Gly Ser Lys Val Gly Pro Asp Gly Thr Pro
    290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Glu Leu Val Glu Ala Asp Glu
        355                 360                 365
Ala Gly Ser Val Tyr Ala Gly Ile Leu Ser Tyr Gly Val Gly Phe Phe
    370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
    530                 535                 540
```

```
Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Val Lys Ala Thr Gln Glu Glu Asn Arg Glu
        755                 760                 765

Leu Arg Ser Arg Cys Glu Glu Leu His Gly Lys Asn Leu Glu Leu Gly
    770                 775                 780

Lys Ile Met Asp Arg Phe Glu Glu Val Val Tyr Gln Ala Met Glu Glu
785                 790                 795                 800

Val Gln Lys Gln Lys Glu Leu Ser Lys Ala Glu Ile Gln Lys Val Leu
                805                 810                 815

Lys Glu Lys Asp Gln Leu Thr Thr Asp Leu Asn Ser Met Glu Lys Ser
            820                 825                 830

Phe Ser Asp Leu Phe Lys Arg Phe Glu Lys Gln Lys Glu Val Ile Glu
        835                 840                 845

Gly Tyr Arg Lys Asn Glu Glu Ser Leu Lys Lys Cys Val Glu Asp Tyr
    850                 855                 860

Leu Ala Arg Ile Thr Gln Glu Gly Gln Arg Tyr Gln Ala Leu Lys Ala
865                 870                 875                 880

His Ala Glu Glu Lys Leu Gln Leu Ala Asn Glu Glu Ile Ala Gln Val
                885                 890                 895

Arg Ser Lys Ala Gln Ala Glu Ala Leu Ala Gln Ala Ser Leu Arg
            900                 905                 910

Lys Glu Gln Met Arg Ile Gln Ser Leu Glu Lys Thr Val Gln Lys
        915                 920                 925

Thr Lys Glu Asn Glu Glu Leu Thr Arg Ile Cys Asp Asp Leu Ile Ser
    930                 935                 940

Lys Met Glu Lys Ile
945
```

<210> SEQ ID NO 540
<211> LENGTH: 1048
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 540

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365
```

-continued

```
Ala Gly Ser Val Tyr Ala Gly Ile Leu Ser Tyr Gly Val Gly Phe Phe
    370             375             380
Leu Phe Ile Leu Val Val Ala Ala Val Thr Leu Cys Arg Leu Arg Ser
385             390             395             400
Pro Pro Lys Lys Gly Leu Gly Ser Pro Thr Val His Lys Ile Ser Arg
            405             410             415
Phe Pro Leu Lys Arg Gln Val Ser Leu Glu Ser Asn Ala Ser Met Ser
            420             425             430
Ser Asn Thr Pro Leu Val Arg Ile Ala Arg Leu Ser Ser Gly Glu Gly
            435             440             445
Pro Thr Leu Ala Asn Val Ser Glu Leu Glu Leu Pro Ala Asp Pro Lys
    450             455             460
Trp Glu Leu Ser Arg Ala Arg Leu Thr Leu Gly Lys Pro Leu Gly Glu
465             470             475             480
Gly Cys Phe Gly Gln Val Val Met Ala Glu Ala Ile Gly Ile Asp Lys
            485             490             495
Asp Arg Ala Ala Lys Pro Val Thr Val Ala Val Lys Met Leu Lys Asp
            500             505             510
Asp Ala Thr Asp Lys Asp Leu Ser Asp Leu Val Ser Glu Met Glu Met
    515             520             525
Met Lys Met Ile Gly Lys His Lys Asn Ile Ile Asn Leu Leu Gly Ala
    530             535             540
Cys Thr Gln Gly Gly Pro Leu Tyr Val Leu Val Glu Tyr Ala Ala Lys
545             550             555             560
Gly Asn Leu Arg Glu Phe Leu Arg Ala Arg Arg Pro Pro Gly Leu Asp
            565             570             575
Tyr Ser Phe Asp Thr Cys Lys Pro Pro Glu Glu Gln Leu Thr Phe Lys
            580             585             590
Asp Leu Val Ser Cys Ala Tyr Gln Val Ala Arg Gly Met Glu Tyr Leu
            595             600             605
Ala Ser Gln Lys Cys Ile His Arg Asp Leu Ala Ala Arg Asn Val Leu
    610             615             620
Val Thr Glu Asp Asn Val Met Lys Ile Ala Asp Phe Gly Leu Ala Arg
625             630             635             640
Asp Val His Asn Leu Asp Tyr Tyr Lys Lys Thr Thr Asn Gly Arg Leu
            645             650             655
Pro Val Lys Trp Met Ala Pro Glu Ala Leu Phe Asp Arg Val Tyr Thr
            660             665             670
His Gln Ser Asp Val Trp Ser Phe Gly Val Leu Leu Trp Glu Ile Phe
    675             680             685
Thr Leu Gly Gly Ser Pro Tyr Pro Gly Ile Pro Val Glu Glu Leu Phe
    690             695             700
Lys Leu Leu Lys Glu Gly His Arg Met Asp Lys Pro Ala Asn Cys Thr
705             710             715             720
His Asp Leu Tyr Met Ile Met Arg Glu Cys Trp His Ala Ala Pro Ser
            725             730             735
Gln Arg Pro Thr Phe Lys Gln Leu Val Glu Asp Leu Asp Arg Val Leu
            740             745             750
Thr Val Thr Ser Thr Asp Phe Lys Glu Ser Ala Leu Arg Lys Gln Ser
    755             760             765
Leu Tyr Leu Lys Phe Asp Pro Leu Leu Arg Asp Ser Pro Gly Arg Pro
    770             775             780
```

Val Pro Val Ala Thr Glu Thr Ser Ser Met His Gly Ala Asn Glu Thr
785                 790                 795                 800

Pro Ser Gly Arg Pro Arg Glu Ala Lys Leu Val Glu Phe Asp Phe Leu
            805                 810                 815

Gly Ala Leu Asp Ile Pro Val Pro Gly Pro Pro Gly Val Pro Ala
        820                 825                 830

Pro Gly Gly Pro Pro Leu Ser Thr Gly Pro Ile Val Asp Leu Leu Gln
        835                 840                 845

Tyr Ser Gln Lys Asp Leu Asp Ala Val Val Lys Ala Thr Gln Glu Glu
    850                 855                 860

Asn Arg Glu Leu Arg Ser Arg Cys Glu Leu His Gly Lys Asn Leu
865                 870                 875                 880

Glu Leu Gly Lys Ile Met Asp Arg Phe Glu Glu Val Val Tyr Gln Ala
                885                 890                 895

Met Glu Glu Val Gln Lys Gln Lys Glu Leu Ser Lys Ala Glu Ile Gln
            900                 905                 910

Lys Val Leu Lys Glu Lys Asp Gln Leu Thr Thr Asp Leu Asn Ser Met
        915                 920                 925

Glu Lys Ser Phe Ser Asp Leu Phe Lys Arg Phe Glu Lys Gln Lys Glu
    930                 935                 940

Val Ile Glu Gly Tyr Arg Lys Asn Glu Glu Ser Leu Lys Lys Cys Val
945                 950                 955                 960

Glu Asp Tyr Leu Ala Arg Ile Thr Gln Glu Gly Gln Arg Tyr Gln Ala
                965                 970                 975

Leu Lys Ala His Ala Glu Glu Lys Leu Gln Leu Ala Asn Glu Glu Ile
            980                 985                 990

Ala Gln Val Arg Ser Lys Ala Gln Ala Glu Ala Leu Ala Leu Gln Ala
        995                 1000                1005

Ser Leu Arg Lys Glu Gln Met Arg Ile Gln Ser Leu Glu Lys Thr
    1010                1015                1020

Val Glu Gln Lys Thr Lys Glu Asn Glu Glu Leu Thr Arg Ile Cys
    1025                1030                1035

Asp Asp Leu Ile Ser Lys Met Glu Lys Ile
    1040                1045

<210> SEQ ID NO 541
<211> LENGTH: 984
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 541

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

```
Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Ala Glu Asp Thr
130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
        290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
            325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
        370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
            500                 505                 510
```

```
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
            595                 600                 605
Ala Ser Gln Lys Cys Ile His Arg Asp Leu Ala Ala Arg Asn Val Leu
            610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
                660                 665                 670
His Gln Ser Asp Val Trp Ser Phe Gly Val Leu Leu Trp Glu Ile Phe
            675                 680                 685
Thr Leu Gly Gly Ser Pro Tyr Pro Gly Ile Pro Val Glu Glu Leu Phe
            690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
                740                 745                 750
Thr Val Thr Ser Thr Asp Val Pro Gly Pro Pro Gly Val Pro Ala
            755                 760                 765
Pro Gly Gly Pro Pro Leu Ser Thr Gly Pro Ile Val Asp Leu Leu Gln
770                 775                 780
Tyr Ser Gln Lys Asp Leu Asp Ala Val Val Lys Ala Thr Gln Glu Glu
785                 790                 795                 800
Asn Arg Glu Leu Arg Ser Arg Cys Glu Glu Leu His Gly Lys Asn Leu
                805                 810                 815
Glu Leu Gly Lys Ile Met Asp Arg Phe Glu Glu Val Val Tyr Gln Ala
            820                 825                 830
Met Glu Glu Val Gln Lys Gln Lys Glu Leu Ser Lys Ala Glu Ile Gln
            835                 840                 845
Lys Val Leu Lys Glu Lys Asp Gln Leu Thr Thr Asp Leu Asn Ser Met
850                 855                 860
Glu Lys Ser Phe Ser Asp Leu Phe Lys Arg Phe Glu Lys Gln Lys Glu
865                 870                 875                 880
Val Ile Glu Gly Tyr Arg Lys Asn Glu Glu Ser Leu Lys Lys Cys Val
                885                 890                 895
Glu Asp Tyr Leu Ala Arg Ile Thr Gln Glu Gly Gln Arg Tyr Gln Ala
            900                 905                 910
Leu Lys Ala His Ala Glu Glu Lys Leu Gln Leu Ala Asn Glu Glu Ile
            915                 920                 925
Ala Gln Val Arg Ser Lys Ala Gln Ala Glu Ala Leu Ala Leu Gln Ala
```

```
                    930             935             940
Ser Leu Arg Lys Glu Gln Met Arg Ile Gln Ser Leu Glu Lys Thr Val
945                 950             955             960

Glu Gln Lys Thr Lys Glu Asn Glu Glu Leu Thr Arg Ile Cys Asp Asp
                965             970             975

Leu Ile Ser Lys Met Glu Lys Ile
            980

<210> SEQ ID NO 542
<211> LENGTH: 1109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 542

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300
```

-continued

```
Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
```

```
                        725                 730                 735
    Gln Arg Pro Thr Phe Lys Gln Leu Val Glu Asp Leu Asp Arg Val Leu
                    740                 745                 750

Thr Val Thr Ser Thr Asp Glu Arg Ala Leu Asn Ser Ala Ser Thr Ser
                755                 760                 765

Leu Pro Thr Ser Cys Pro Gly Ser Glu Pro Val Pro Thr His Gln Gln
            770                 775                 780

Gly Gln Pro Ala Leu Glu Leu Lys Glu Ser Phe Arg Asp Pro Ala
    785                 790                 795                 800

Glu Val Leu Gly Thr Gly Ala Glu Val Asp Tyr Leu Glu Gln Phe Gly
                    805                 810                 815

Thr Ser Ser Phe Lys Glu Ser Ala Leu Arg Lys Gln Ser Leu Tyr Leu
                820                 825                 830

Lys Phe Asp Pro Leu Leu Arg Asp Ser Pro Gly Arg Pro Val Pro Val
            835                 840                 845

Ala Thr Glu Thr Ser Ser Met His Gly Ala Asn Glu Thr Pro Ser Gly
    850                 855                 860

Arg Pro Arg Glu Ala Lys Leu Val Glu Phe Asp Phe Leu Gly Ala Leu
    865                 870                 875                 880

Asp Ile Pro Val Pro Gly Pro Pro Gly Val Pro Ala Pro Gly Gly
                    885                 890                 895

Pro Pro Leu Ser Thr Gly Pro Ile Val Asp Leu Leu Gln Tyr Ser Gln
                900                 905                 910

Lys Asp Leu Asp Ala Val Val Lys Ala Thr Gln Glu Glu Asn Arg Glu
                915                 920                 925

Leu Arg Ser Arg Cys Glu Glu Leu His Gly Lys Asn Leu Glu Leu Gly
    930                 935                 940

Lys Ile Met Asp Arg Phe Glu Glu Val Val Tyr Gln Ala Met Glu Glu
    945                 950                 955                 960

Val Gln Lys Gln Lys Glu Leu Ser Lys Ala Glu Ile Gln Lys Val Leu
                    965                 970                 975

Lys Glu Lys Asp Gln Leu Thr Thr Asp Leu Asn Ser Met Glu Lys Ser
                980                 985                 990

Phe Ser Asp Leu Phe Lys Arg Phe  Glu Lys Gln Lys Glu  Val Ile Glu
            995                 1000                1005

Gly Tyr Arg Lys Asn Glu Glu  Ser Leu Lys Lys Cys  Val Glu Asp
        1010                1015                1020

Tyr Leu Ala Arg Ile Thr Gln  Glu Gly Gln Arg Tyr  Gln Ala Leu
        1025                1030                1035

Lys Ala His  Ala Glu Glu Lys  Leu Gln Leu Ala Asn  Glu Glu Ile
        1040                1045                1050

Ala Gln Val Arg Ser Lys Ala  Gln Ala Glu Ala Leu  Ala Leu Gln
        1055                1060                1065

Ala Ser  Leu Arg Lys Glu Gln  Met Arg Ile Gln Ser  Leu Glu Lys
        1070                1075                1080

Thr Val Glu Gln Lys Thr Lys  Glu Asn Glu Glu Leu  Thr Arg Ile
        1085                1090                1095

Cys Asp Asp Leu Ile Ser Lys  Met Glu Lys Ile
        1100                1105

<210> SEQ ID NO 543
<211> LENGTH: 926
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 543

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
        290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
```

-continued

```
               385                 390                 395                 400
        Pro Pro Lys Lys Gly Leu Gly Ser Pro Thr Val His Lys Ile Ser Arg
                        405                 410                 415

Phe Pro Leu Lys Arg Gln Val Ser Leu Glu Ser Asn Ala Ser Met Ser
                        420                 425                 430

Ser Asn Thr Pro Leu Val Arg Ile Ala Arg Leu Ser Ser Gly Glu Gly
                        435                 440                 445

Pro Thr Leu Ala Asn Val Ser Glu Leu Glu Leu Pro Ala Asp Pro Lys
                        450                 455                 460

Trp Glu Leu Ser Arg Ala Arg Leu Thr Leu Gly Lys Pro Leu Gly Glu
        465                 470                 475                 480

Gly Cys Phe Gly Gln Val Val Met Ala Glu Ala Ile Gly Ile Asp Lys
                        485                 490                 495

Asp Arg Ala Ala Lys Pro Val Thr Val Ala Val Lys Met Leu Lys Asp
                        500                 505                 510

Asp Ala Thr Asp Lys Asp Leu Ser Asp Leu Val Ser Glu Met Glu Met
                        515                 520                 525

Met Lys Met Ile Gly Lys His Lys Asn Ile Ile Asn Leu Leu Gly Ala
                        530                 535                 540

Cys Thr Gln Gly Gly Pro Leu Tyr Val Leu Val Glu Tyr Ala Ala Lys
        545                 550                 555                 560

Gly Asn Leu Arg Glu Phe Leu Arg Ala Arg Arg Pro Pro Gly Leu Asp
                        565                 570                 575

Tyr Ser Phe Asp Thr Cys Lys Pro Pro Glu Glu Gln Leu Thr Phe Lys
                        580                 585                 590

Asp Leu Val Ser Cys Ala Tyr Gln Val Ala Arg Gly Met Glu Tyr Leu
                        595                 600                 605

Ala Ser Gln Lys Cys Ile His Arg Asp Leu Ala Ala Arg Asn Val Leu
                        610                 615                 620

Val Thr Glu Asp Asn Val Met Lys Ile Ala Asp Phe Gly Leu Ala Arg
        625                 630                 635                 640

Asp Val His Asn Leu Asp Tyr Tyr Lys Lys Thr Thr Asn Gly Arg Leu
                        645                 650                 655

Pro Val Lys Trp Met Ala Pro Glu Ala Leu Phe Asp Arg Val Tyr Thr
                        660                 665                 670

His Gln Ser Asp Val Trp Ser Phe Gly Val Leu Leu Trp Glu Ile Phe
                        675                 680                 685

Thr Leu Gly Gly Ser Pro Tyr Pro Gly Ile Pro Val Glu Glu Leu Phe
                        690                 695                 700

Lys Leu Leu Lys Glu Gly His Arg Met Asp Lys Pro Ala Asn Cys Thr
        705                 710                 715                 720

His Asp Leu Tyr Met Ile Met Arg Glu Cys Trp His Ala Ala Pro Ser
                        725                 730                 735

Gln Arg Pro Thr Phe Lys Gln Leu Val Glu Asp Leu Asp Arg Val Leu
                        740                 745                 750

Thr Val Thr Ser Thr Asp Glu Tyr Leu Asp Leu Ser Ala Pro Phe Glu
                        755                 760                 765

Gln Tyr Ser Pro Gly Gly Gln Asp Thr Pro Ser Lys Gln Lys Glu Leu
                        770                 775                 780

Ser Lys Ala Glu Ile Gln Lys Val Leu Lys Glu Lys Asp Gln Leu Thr
        785                 790                 795                 800

Thr Asp Leu Asn Ser Met Glu Lys Ser Phe Ser Asp Leu Phe Lys Arg
                        805                 810                 815
```

-continued

```
Phe Glu Lys Gln Lys Glu Val Ile Glu Gly Tyr Arg Lys Asn Glu Glu
                820                 825                 830

Ser Leu Lys Lys Cys Val Glu Asp Tyr Leu Ala Arg Ile Thr Gln Glu
                835                 840                 845

Gly Gln Arg Tyr Gln Ala Leu Lys Ala His Ala Glu Glu Lys Leu Gln
                850                 855                 860

Leu Ala Asn Glu Glu Ile Ala Gln Val Arg Ser Lys Ala Gln Ala Glu
865                 870                 875                 880

Ala Leu Ala Leu Gln Ala Ser Leu Arg Lys Glu Gln Met Arg Ile Gln
                885                 890                 895

Ser Leu Glu Lys Thr Val Glu Gln Lys Thr Lys Glu Asn Glu Glu Leu
                900                 905                 910

Thr Arg Ile Cys Asp Asp Leu Ile Ser Lys Met Glu Lys Ile
                915                 920                 925

<210> SEQ ID NO 544
<211> LENGTH: 1043
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
```

```
                245                 250                 255
Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670
```

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
690                 695                 700

Lys Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Gln Glu Gln
            755                 760                 765

Arg Gln Pro Thr Leu Gln Pro Gln Gly Cys Cys Leu Ala Gly Tyr Ser
            770                 775                 780

His Arg Ser Ser Met His Gly Ala Asn Glu Thr Pro Ser Gly Arg Pro
785                 790                 795                 800

Arg Glu Ala Lys Leu Val Glu Phe Asp Phe Leu Gly Ala Leu Asp Ile
                805                 810                 815

Pro Val Pro Gly Pro Pro Gly Val Pro Ala Pro Gly Pro Pro
            820                 825                 830

Leu Ser Thr Gly Pro Ile Val Asp Leu Leu Gln Tyr Ser Gln Lys Asp
            835                 840                 845

Leu Asp Ala Val Val Lys Ala Thr Gln Glu Glu Asn Arg Glu Leu Arg
850                 855                 860

Ser Arg Cys Glu Glu Leu His Gly Lys Asn Leu Glu Leu Gly Lys Ile
865                 870                 875                 880

Met Asp Arg Phe Glu Glu Val Val Tyr Gln Ala Met Glu Glu Val Gln
                885                 890                 895

Lys Gln Lys Glu Leu Ser Lys Ala Glu Ile Gln Lys Val Leu Lys Glu
            900                 905                 910

Lys Asp Gln Leu Thr Thr Asp Leu Asn Ser Met Glu Lys Ser Phe Ser
            915                 920                 925

Asp Leu Phe Lys Arg Phe Glu Lys Gln Lys Glu Val Ile Glu Gly Tyr
            930                 935                 940

Arg Lys Asn Glu Glu Ser Leu Lys Lys Cys Val Glu Asp Tyr Leu Ala
945                 950                 955                 960

Arg Ile Thr Gln Glu Gly Gln Arg Tyr Gln Ala Leu Lys Ala His Ala
                965                 970                 975

Glu Glu Lys Leu Gln Leu Ala Asn Glu Glu Ile Ala Gln Val Arg Ser
            980                 985                 990

Lys Ala Gln Ala Glu Ala Leu Ala Leu Gln Ala Ser Leu Arg Lys Glu
            995                 1000                1005

Gln Met Arg Ile Gln Ser Leu Glu Lys Thr Val Glu Gln Lys Thr
            1010                1015                1020

Lys Glu Asn Glu Glu Leu Thr Arg Ile Cys Asp Asp Leu Ile Ser
            1025                1030                1035

Lys Met Glu Lys Ile
    1040

<210> SEQ ID NO 545
<211> LENGTH: 1131
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 545

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400
```

```
Pro Pro Lys Lys Gly Leu Gly Ser Pro Thr His Lys Ile Ser Arg
            405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
            435                 440                 445
Pro Thr Leu Ala Asn Val Ser Glu Leu Glu Leu Pro Ala Asp Pro Lys
        450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
                500                 505                 510
Asp Ala Thr Asp Lys Asp Leu Ser Asp Leu Val Ser Glu Met Glu Met
                515                 520                 525
Met Lys Met Ile Gly Lys His Lys Asn Ile Ile Asn Leu Leu Gly Ala
        530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
                580                 585                 590
Asp Leu Val Ser Cys Ala Tyr Gln Val Ala Arg Gly Met Glu Tyr Leu
                595                 600                 605
Ala Ser Gln Lys Cys Ile His Arg Asp Leu Ala Ala Arg Asn Val Leu
        610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
                660                 665                 670
His Gln Ser Asp Val Trp Ser Phe Gly Val Leu Leu Trp Glu Ile Phe
                675                 680                 685
Thr Leu Gly Gly Ser Pro Tyr Pro Gly Ile Pro Val Glu Glu Leu Phe
        690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
                740                 745                 750
Thr Val Thr Ser Thr Asp Glu Tyr Leu Asp Leu Ser Ala Pro Val Val
                755                 760                 765
Gln Leu Ala Ala Glu Thr Pro Thr Ala Glu Ser Lys Glu Arg Ala Leu
        770                 775                 780
Asn Ser Ala Ser Thr Ser Leu Pro Thr Ser Cys Pro Gly Ser Glu Pro
785                 790                 795                 800
Val Pro Thr His Gln Gln Gly Gln Pro Ala Leu Glu Leu Lys Glu Glu
                805                 810                 815
```

-continued

Ser Phe Arg Asp Pro Ala Glu Val Leu Gly Thr Gly Ala Glu Val Asp
              820                 825                 830

Tyr Leu Glu Gln Phe Gly Thr Ser Ser Phe Lys Glu Ser Ala Leu Arg
          835                 840                 845

Lys Gln Ser Leu Tyr Leu Lys Phe Asp Pro Leu Leu Arg Asp Ser Pro
      850                 855                 860

Gly Arg Pro Val Pro Val Ala Thr Glu Thr Ser Ser Met His Gly Ala
865                 870                 875                 880

Asn Glu Thr Pro Ser Gly Arg Pro Arg Glu Ala Lys Leu Val Glu Phe
                885                 890                 895

Asp Phe Leu Gly Ala Leu Asp Ile Pro Val Pro Gly Pro Pro Pro Gly
            900                 905                 910

Val Pro Ala Pro Gly Gly Pro Pro Leu Ser Thr Gly Pro Ile Val Asp
        915                 920                 925

Leu Leu Gln Tyr Ser Gln Lys Asp Leu Asp Ala Val Val Lys Ala Thr
    930                 935                 940

Gln Glu Glu Asn Arg Glu Leu Arg Ser Arg Cys Glu Glu Leu His Gly
945                 950                 955                 960

Lys Asn Leu Glu Leu Gly Lys Ile Met Asp Arg Phe Glu Glu Val Val
                965                 970                 975

Tyr Gln Ala Met Glu Glu Val Gln Lys Gln Lys Glu Leu Ser Lys Ala
            980                 985                 990

Glu Ile Gln Lys Val Leu Lys Glu  Lys Asp Gln Leu Thr  Thr Asp Leu
        995                 1000                1005

Asn Ser Met Glu Lys Ser Phe  Ser Asp Leu Phe Lys  Arg Phe Glu
    1010                1015                1020

Lys Gln Lys Glu Val Ile Glu  Gly Tyr Arg Lys Asn  Glu Glu Ser
    1025                1030                1035

Leu Lys Lys Cys Val Glu Asp  Tyr Leu Ala Arg Ile  Thr Gln Glu
    1040                1045                1050

Gly Gln Arg Tyr Gln Ala Leu  Lys Ala His Ala Glu  Glu Lys Leu
    1055                1060                1065

Gln Leu Ala Asn Glu Glu Ile  Ala Gln Val Arg Ser  Lys Ala Gln
    1070                1075                1080

Ala Glu Ala Leu Ala Leu Gln  Ala Ser Leu Arg Lys  Glu Gln Met
    1085                1090                1095

Arg Ile Gln Ser Leu Glu Lys  Thr Val Glu Gln Lys  Thr Lys Glu
    1100                1105                1110

Asn Glu Glu Leu Thr Arg Ile  Cys Asp Asp Leu Ile  Ser Lys Met
    1115                1120                1125

Glu Lys Ile
    1130

<210> SEQ ID NO 546
<211> LENGTH: 1166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (795)..(795)
<223> OTHER INFORMATION: Any amino acid

<400> SEQUENCE: 546

Met Gly Ala Pro Ala Cys Ala Leu Ala Leu Cys Val Ala Val Ala Ile

-continued

```
1               5                   10                  15
Val Ala Gly Ala Ser Ser Glu Ser Leu Gly Thr Glu Gln Arg Val Val
            20                  25                  30
Gly Arg Ala Ala Glu Val Pro Gly Pro Glu Pro Gly Gln Gln Glu Gln
            35                  40                  45
Leu Val Phe Gly Ser Gly Asp Ala Val Glu Leu Ser Cys Pro Pro Pro
50                      55                  60
Gly Gly Gly Pro Met Gly Pro Thr Val Trp Val Lys Asp Gly Thr Gly
65                      70                  75                  80
Leu Val Pro Ser Glu Arg Val Leu Val Gly Pro Gln Arg Leu Gln Val
                85                  90                  95
Leu Asn Ala Ser His Glu Asp Ser Gly Ala Tyr Ser Cys Arg Gln Arg
                100                 105                 110
Leu Thr Gln Arg Val Leu Cys His Phe Ser Val Arg Val Thr Asp Ala
                115                 120                 125
Pro Ser Ser Gly Asp Asp Glu Asp Gly Glu Asp Glu Ala Glu Asp Thr
                130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
                180                 185                 190
Arg Glu Phe Arg Gly Glu His Arg Ile Gly Gly Ile Lys Leu Arg His
                195                 200                 205
Gln Gln Trp Ser Leu Val Met Glu Ser Val Val Pro Ser Asp Arg Gly
                210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
                275                 280                 285
Lys His Val Glu Val Asn Gly Ser Lys Val Gly Pro Asp Gly Thr Pro
                290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
                340                 345                 350
Trp Leu Val Val Leu Pro Ala Glu Glu Leu Val Glu Ala Asp Glu
                355                 360                 365
Ala Gly Ser Val Tyr Ala Gly Ile Leu Ser Tyr Gly Val Gly Phe Phe
                370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
                420                 425                 430
```

```
Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Gly Leu Asp
            565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
        770                 775                 780

Val Arg Glu Pro Pro His Pro Ala Phe Pro Xaa Ser Ala Glu Asp Thr
785                 790                 795                 800

Pro Val Val Gln Leu Ala Ala Glu Thr Pro Thr Ala Glu Ser Lys Glu
            805                 810                 815

Arg Ala Leu Asn Ser Ala Ser Thr Ser Leu Pro Thr Ser Cys Pro Gly
            820                 825                 830

Ser Glu Pro Val Pro Thr His Gln Gln Gly Gln Pro Ala Leu Glu Leu
        835                 840                 845
```

Lys Glu Glu Ser Phe Arg Asp Pro Ala Glu Val Leu Gly Thr Gly Ala
    850                 855                 860

Glu Val Asp Tyr Leu Glu Gln Phe Gly Thr Ser Ser Phe Lys Glu Ser
865                 870                 875                 880

Ala Leu Arg Lys Gln Ser Leu Tyr Leu Lys Phe Asp Pro Leu Leu Arg
                885                 890                 895

Asp Ser Pro Gly Arg Pro Val Pro Val Ala Thr Glu Thr Ser Ser Met
            900                 905                 910

His Gly Ala Asn Glu Thr Pro Ser Gly Arg Pro Arg Glu Ala Lys Leu
        915                 920                 925

Val Glu Phe Asp Phe Leu Gly Ala Leu Asp Ile Pro Val Pro Gly Pro
930                 935                 940

Pro Pro Gly Val Pro Ala Pro Gly Gly Pro Leu Ser Thr Gly Pro
945                 950                 955                 960

Ile Val Asp Leu Leu Gln Tyr Ser Gln Lys Asp Leu Asp Ala Val Val
                965                 970                 975

Lys Ala Thr Gln Glu Glu Asn Arg Glu Leu Arg Ser Arg Cys Glu Glu
            980                 985                 990

Leu His Gly Lys Asn Leu Glu Leu Gly Lys Ile Met Asp Arg Phe Glu
        995                 1000                1005

Glu Val Val Tyr Gln Ala Met Glu Glu Val Gln Lys Gln Lys Glu
    1010                1015                1020

Leu Ser Lys Ala Glu Ile Gln Lys Val Leu Lys Glu Lys Asp Gln
    1025                1030                1035

Leu Thr Thr Asp Leu Asn Ser Met Glu Lys Ser Phe Ser Asp Leu
    1040                1045                1050

Phe Lys Arg Phe Glu Lys Gln Lys Glu Val Ile Glu Gly Tyr Arg
    1055                1060                1065

Lys Asn Glu Glu Ser Leu Lys Lys Cys Val Glu Asp Tyr Leu Ala
    1070                1075                1080

Arg Ile Thr Gln Glu Gly Gln Arg Tyr Gln Ala Leu Lys Ala His
    1085                1090                1095

Ala Glu Glu Lys Leu Gln Leu Ala Asn Glu Glu Ile Ala Gln Val
    1100                1105                1110

Arg Ser Lys Ala Gln Ala Glu Ala Leu Ala Leu Gln Ala Ser Leu
    1115                1120                1125

Arg Lys Glu Gln Met Arg Ile Gln Ser Leu Glu Lys Thr Val Glu
    1130                1135                1140

Gln Lys Thr Lys Glu Asn Glu Glu Leu Thr Arg Ile Cys Asp Asp
    1145                1150                1155

Leu Ile Ser Lys Met Glu Lys Ile
    1160                1165

<210> SEQ ID NO 547
<211> LENGTH: 1184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

-continued

```
Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445
```

```
Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Glu Ser Pro Glu Thr Arg
770                 775                 780

Leu Gly Gln Pro Ala Ala Glu Gln Leu His Ala Gly Pro Ala Thr Glu
785                 790                 795                 800

Glu Pro Gly Pro Cys Leu Ser Gln Gln Leu His Ser Ala Ser Ala Glu
                805                 810                 815

Asp Thr Pro Val Val Gln Leu Ala Ala Glu Thr Pro Thr Ala Glu Ser
            820                 825                 830

Lys Glu Arg Ala Leu Asn Ser Ala Ser Thr Ser Leu Pro Thr Ser Cys
        835                 840                 845

Pro Gly Ser Glu Pro Val Pro Thr His Gln Gly Gln Pro Ala Leu
850                 855                 860

Glu Leu Lys Glu Glu Ser Phe Arg Asp Pro Ala Glu Val Leu Gly Thr
```

```
                865                 870                 875                 880
Gly Ala Glu Val Asp Tyr Leu Glu Gln Phe Gly Thr Ser Ser Phe Lys
                    885                 890                 895
Glu Ser Ala Leu Arg Lys Gln Ser Leu Tyr Leu Lys Phe Asp Pro Leu
                    900                 905                 910
Leu Arg Asp Ser Pro Gly Arg Pro Val Pro Val Ala Thr Glu Thr Ser
                    915                 920                 925
Ser Met His Gly Ala Asn Glu Thr Pro Ser Gly Arg Pro Arg Glu Ala
                    930                 935                 940
Lys Leu Val Glu Phe Asp Phe Leu Gly Ala Leu Asp Ile Pro Val Pro
945                 950                 955                 960
Gly Pro Pro Pro Gly Val Pro Ala Pro Gly Gly Pro Pro Leu Ser Thr
                    965                 970                 975
Gly Pro Ile Val Asp Leu Leu Gln Tyr Ser Gln Lys Asp Leu Asp Ala
                    980                 985                 990
Val Val Lys Ala Thr Gln Glu Glu Asn Arg Glu Leu Arg Ser Arg Cys
                    995                 1000                1005
Glu Glu Leu His Gly Lys Asn Leu Glu Leu Gly Lys Ile Met Asp
                    1010                1015                1020
Arg Phe Glu Glu Val Val Tyr Gln Ala Met Glu Glu Val Gln Lys
                    1025                1030                1035
Gln Lys Glu Leu Ser Lys Ala Glu Ile Gln Lys Val Leu Lys Glu
                    1040                1045                1050
Lys Asp Gln Leu Thr Thr Asp Leu Asn Ser Met Glu Lys Ser Phe
                    1055                1060                1065
Ser Asp Leu Phe Lys Arg Phe Glu Lys Gln Lys Glu Val Ile Glu
                    1070                1075                1080
Gly Tyr Arg Lys Asn Glu Glu Ser Leu Lys Lys Cys Val Glu Asp
                    1085                1090                1095
Tyr Leu Ala Arg Ile Thr Gln Glu Gly Gln Arg Tyr Gln Ala Leu
                    1100                1105                1110
Lys Ala His Ala Glu Glu Lys Leu Gln Leu Ala Asn Glu Glu Ile
                    1115                1120                1125
Ala Gln Val Arg Ser Lys Ala Gln Ala Glu Ala Leu Ala Leu Gln
                    1130                1135                1140
Ala Ser Leu Arg Lys Glu Gln Met Arg Ile Gln Ser Leu Glu Lys
                    1145                1150                1155
Thr Val Glu Gln Lys Thr Lys Glu Asn Glu Glu Leu Thr Arg Ile
                    1160                1165                1170
Cys Asp Asp Leu Ile Ser Lys Met Glu Lys Ile
                    1175                1180

<210> SEQ ID NO 548
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 548
cttcggggag cagcgatgcg ac                                            22

<210> SEQ ID NO 549
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 549
ctgtccatcc agaggaggag ta                                              22

<210> SEQ ID NO 550
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
cgtgacgtcc accgacttta aggagtcggc ct                                   32

<210> SEQ ID NO 551
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
cgtgacgtcc accgacgtaa aggcgacaca gg                                   32

<210> SEQ ID NO 552
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
tgcgaagagg ggctcggtgg tgcagttggc ag                                   32

<210> SEQ ID NO 553
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
gcctcccgcc agcaggagcc cccagcagcc tt                                   32

<210> SEQ ID NO 554
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
agactcagtg cagatgttcc ctcgccgcac tg                                   32

<210> SEQ ID NO 555
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 555
agcctgggca cagagggtgt ccgagagcag cc                                      32

<210> SEQ ID NO 556
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
gccacccgcc tatgccaggc aattccgcga ag                                      32

<210> SEQ ID NO 557
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
ctggacctgt cggcgcagga gcaacggcag cc                                      32

<210> SEQ ID NO 558
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
gagtgctggc tctggcccgg gactctccgg cc                                      32

<210> SEQ ID NO 559
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gaggtggctg tgcgaaggtc gctgagggtc ca                                      32

<210> SEQ ID NO 560
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ctgccgtccc cggccatccc tcaggacgtc cgc                                     33
```

What is claimed is:

1. A method for treating a FGFR3-TACC3 fusion associated cancer in a subject in need thereof, the method comprising administering to the subject an effective amount of JNJ-42756493, wherein the subject has a FGFR3-TACC3 fusion associated cancer, wherein the FGFR3-TACC3 fusion comprises a tyrosine kinase domain of FGFR3 fused to the TACC domain of transforming acidic coiled-coil-containing (TACC)3.

2. The method of claim 1, wherein the subject has FGFR3-TACC3 fusion associated epithelial cancer, glioma, glioblastoma multiforme, breast cancer, lung cancer, prostate cancer, bladder carcinoma, squamous lung carcinoma, head and neck carcinoma or colorectal carcinoma.

3. The method of claim 1, wherein the subject has FGFR3-TACC3 fusion associated epithelial cancer.

4. The method of claim 1, wherein the subject has FGFR3-TACC3 fusion associated glioblastoma multiforme.

5. The method of claim 1, wherein the subject has FGFR3-TACC3 fusion associated glioma.

6. The method of claim 5, wherein the glioma is a grade II or III glioma.

7. The method of claim 4, wherein the subject does not have mutations in IDH1 or IDH2 genes.

8. The method of claim 4, wherein the subject does not have a gene amplification in EGFR.

9. The method of claim 4, wherein the subject does not express EGFRγIII transcript variant.

10. The method of claim 4, wherein the subject has a gene amplification of CDK4, MDM2, or both.

11. The method of claim 1, wherein the FGFR3-TACC3 fusion comprises SEQ ID NO: 85, 86, 87, or 89.

12. The method of claim 1, wherein the FGFR3-TACC3 fusion comprises SEQ ID NO: 85.

13. The method of claim 1, wherein the FGFR3-TACC3 fusion comprises SEQ ID NO: 87.

14. The method of claim 1, wherein the FGFR3-TACC3 fusion comprises SEQ ID NO: 158, 159, 160, or 161.

15. The method of claim 1, wherein the FGFR3-TACC3 fusion comprises SEQ ID NO: 542, 543, 544, 545, 546, or 547.

16. The method of claim 1, wherein the FGFR3-TACC3 fusion comprises a tyrosine kinase domain of FGFR3 transcript variant 1 fused to the TACC domain of TACC3.

17. The method of claim 1, wherein a nucleotide sequence encoding the FGFR3-TACC3 fusion comprises SEQ ID NO: 1-77, 80-82, or 84.

18. The method of claim 1, wherein a nucleotide sequence encoding the FGFR3-TACC3 fusion comprises SEQ ID NO: 519-527, or 530-538.

19. The method of claim 1, wherein a nucleotide sequence encoding the FGFR3-TACC3 fusion comprises SEQ ID NO: 533-538.

20. A method for diagnosing and treating a FGFR3-TACC3 fusion associated cancer in a subject in need thereof, the method comprising:
  a. obtaining a biological sample from the subject;
  b. detecting whether the subject has a FGFR3-TACC3 fusion is present in the biological sample, wherein the FGFR3-TACC3 fusion comprises a tyrosine kinase domain of FGFR3 fused to the TACC domain of transforming acidic coiled-coil-containing (TACC) 3; and
  c. diagnosing the subject with a FGFR3-TACC3 fusion associated cancer when the presence of the FGFR3-TACC3 fusion in the biological sample is detected; then
  d. administering to the subject an effective amount of JNJ-42756493.

21. The method of claim 6, wherein the subject does not have mutations in IDH1 or IDH2 genes.

22. The method of claim 6, wherein the subject does not have a gene amplification in EGFR.

23. The method of claim 6, wherein the subject does not express EGFRγIII transcript variant.

24. The method of claim 6, wherein the subject has a gene amplification of CDK4, MDM2, or both.

* * * * *